US 7,790,905 B2

(12) United States Patent
Tawa et al.

(10) Patent No.: US 7,790,905 B2
(45) Date of Patent: Sep. 7, 2010

(54) PHARMACEUTICAL PROPYLENE GLYCOL SOLVATE COMPOSITIONS

(75) Inventors: Mark Tawa, Brighton, MA (US); Örn Almarsson, Shrewsbury, MA (US); Julius Remenar, Framingham, MA (US)

(73) Assignee: McNeil-PPC, Inc., Skillman, NJ (US)

( * ) Notice: Subject to any disclaimer, the term of this patent is extended or adjusted under 35 U.S.C. 154(b) by 1554 days.

(21) Appl. No.: 10/747,742

(22) Filed: Dec. 29, 2003

(65) Prior Publication Data
US 2007/0015841 A1   Jan. 18, 2007

Related U.S. Application Data

(60) Provisional application No. 60/486,713, filed on Jul. 11, 2003, provisional application No. 60/459,501, filed on Apr. 1, 2003, provisional application No. 60/456,608, filed on Mar. 21, 2003, provisional application No. 60/456,027, filed on Mar. 18, 2003, provisional application No. 60/441,335, filed on Jan. 21, 2003, provisional application No. 60/437,516, filed on Dec. 30, 2002.

(51) Int. Cl.
C07D 231/12 (2006.01)
A61K 31/415 (2006.01)

(52) U.S. Cl. .................. 548/375.1; 514/406
(58) Field of Classification Search ............ 424/246; 514/220, 557, 406; 548/375.1
See application file for complete search history.

(56) References Cited

U.S. PATENT DOCUMENTS

| | | |
|---|---|---|
| 2,665,277 A | 1/1954 | Homeyer et al. |
| 2,711,411 A | 6/1955 | Holbert et al. |
| 3,028,420 A | 4/1962 | Petrow et al. |
| 3,598,123 A | 8/1971 | Zaffaroni |
| 3,845,770 A | 11/1974 | Theeuwes et al. |
| 3,916,899 A | 11/1975 | Theeuwes et al. |
| 3,970,651 A * | 7/1976 | Kaplan et al. ........... 540/226 |
| 4,008,321 A | 2/1977 | Kamishita et al. |
| 4,198,507 A | 4/1980 | Barry et al. |
| 4,267,179 A | 5/1981 | Heeres et al. |
| 4,368,197 A | 1/1983 | Shefter et al. |
| 4,513,006 A | 4/1985 | Maryanoff et al. |
| 4,764,604 A | 8/1988 | Muller |
| 4,853,379 A | 8/1989 | Shroot et al. |
| 4,916,134 A | 4/1990 | Heeres et al. |
| 4,925,674 A * | 5/1990 | Giannini et al. ........... 424/469 |
| 4,927,855 A | 5/1990 | Lafon |
| 4,994,604 A | 2/1991 | Tung et al. |
| 3,536,809 A | 4/1991 | Schaller et al. |
| 5,006,513 A | 4/1991 | Hector et al. |
| 5,023,092 A | 6/1991 | DuRoss |
| 5,059,595 A | 10/1991 | Le Grazie |
| 5,073,543 A | 12/1991 | Marshall et al. |
| 5,120,548 A | 6/1992 | McClelland et al. |
| 5,177,262 A | 1/1993 | Taylor et al. |
| 5,242,942 A | 9/1993 | Costanzo et al. |
| 5,273,760 A | 12/1993 | Oshlack et al. |
| 5,286,493 A | 2/1994 | Oshlack et al. |
| 5,324,351 A | 6/1994 | Oshlack et al. |
| 5,332,834 A | 7/1994 | Bhattacharya et al. |
| 5,338,644 A | 8/1994 | Taylor et al. |
| 5,354,556 A | 10/1994 | Sparks et al. |
| 5,356,467 A | 10/1994 | Oshlack et al. |
| 5,366,738 A | 11/1994 | Rork et al. |
| 5,380,867 A | 1/1995 | Bhattacharya et al. |
| 5,384,327 A | 1/1995 | Costanzo et al. |
| 5,412,094 A | 5/1995 | Amos et al. |
| 5,414,997 A | 5/1995 | Tailer |
| 5,466,823 A | 11/1995 | Talley et al. |
| 5,472,712 A | 12/1995 | Oshlack et al. |
| 5,474,997 A | 12/1995 | Gray et al. |
| 5,510,496 A | 4/1996 | Talley et al. |
| 5,521,207 A | 5/1996 | Graneto |
| 5,523,090 A | 6/1996 | Znaiden et al. |
| 5,563,165 A | 10/1996 | Talley et al. |
| 5,591,767 A | 1/1997 | Mohr et al. |
| 5,614,342 A | 3/1997 | Molaire et al. |
| 5,631,250 A | 5/1997 | Bunnell et al. |
| 5,633,015 A | 5/1997 | Gilis et al. |
| 5,633,272 A | 5/1997 | Talley et al. |
| 5,639,476 A | 6/1997 | Oshlack et al. |
| 5,641,512 A | 6/1997 | Cimiluca |
| 5,661,151 A | 8/1997 | Saksena et al. |
| 5,674,533 A | 10/1997 | Santus et al. |
| 5,703,232 A | 12/1997 | Bunnell et al. |

(Continued)

FOREIGN PATENT DOCUMENTS

EP   0310122 B1   4/1989

(Continued)

OTHER PUBLICATIONS

Gavezzotti, Acc. Chem. Res. 1994, 27, 309-314.*

(Continued)

*Primary Examiner*—Shaojia Anna Jiang
*Assistant Examiner*—Jonathan S Lau
(74) *Attorney, Agent, or Firm*—Saliwanchik, Lloyd & Saliwanchik; Laura A. Donnelly

(57) ABSTRACT

The invention relates to pharmaceutical compositions comprising propylene glycol solvates of APIs.

23 Claims, 29 Drawing Sheets

U.S. PATENT DOCUMENTS

| | | | |
|---|---|---|---|
| 5,707,975 A | 1/1998 | Francois et al. | |
| 5,733,566 A | 3/1998 | Lewis | |
| 5,736,541 A * | 4/1998 | Bunnell et al. | 514/220 |
| 5,753,688 A | 5/1998 | Talley et al. | |
| 5,753,693 A | 5/1998 | Shank | |
| 5,760,007 A | 6/1998 | Shank et al. | |
| 5,760,068 A * | 6/1998 | Talley et al. | 514/403 |
| 5,932,598 A | 8/1999 | Talley et al. | |
| 5,935,933 A | 8/1999 | Shank et al. | |
| 5,952,187 A | 9/1999 | Stenglein et al. | |
| 5,972,986 A | 10/1999 | Seibert et al. | |
| 5,985,902 A | 11/1999 | Talley et al. | |
| 5,998,380 A | 12/1999 | Ehrenberg et al. | |
| 5,998,413 A | 12/1999 | Heeres et al. | |
| 6,001,996 A | 12/1999 | Amos et al. | |
| 6,054,136 A * | 4/2000 | Farah et al. | 424/400 |
| 6,071,537 A | 6/2000 | Shank | |
| 6,132,420 A | 10/2000 | Dionne et al. | |
| 6,156,781 A | 12/2000 | Talley et al. | |
| 6,191,117 B1 | 2/2001 | Kozachuk | |
| 6,201,010 B1 | 3/2001 | Cottrell | |
| 6,245,357 B1 | 6/2001 | Edgren et al. | |
| 6,268,385 B1 | 7/2001 | Whittle et al. | |
| 6,270,787 B1 | 8/2001 | Ayer | |
| 6,283,953 B1 | 9/2001 | Ayer et al. | |
| 6,287,295 B1 | 9/2001 | Chen et al. | |
| 6,294,192 B1 | 9/2001 | Patel et al. | |
| 6,319,903 B1 | 11/2001 | Carrazana et al. | |
| 6,323,266 B2 | 11/2001 | Phillips | |
| 6,333,050 B2 | 12/2001 | Wong et al. | |
| 6,342,249 B1 | 1/2002 | Wong et al. | |
| 6,348,458 B1 | 2/2002 | Hamied et al. | |
| 6,365,185 B1 | 4/2002 | Ritschel et al. | |
| 6,368,626 B1 | 4/2002 | Bhatt et al. | |
| 6,375,978 B1 | 4/2002 | Kleiner et al. | |
| 6,384,034 B2 | 5/2002 | Simitchieva et al. | |
| 6,403,640 B1 | 6/2002 | Stoner et al. | |
| 6,413,965 B1 | 7/2002 | Mylari | |
| 6,420,394 B1 | 7/2002 | Supersaxo | |
| 6,488,962 B1 | 12/2002 | Berner et al. | |
| 6,503,884 B1 | 1/2003 | Ehrenberg et al. | |
| 6,559,293 B1 | 5/2003 | Almarsson et al. | |
| 6,570,036 B1 | 5/2003 | Reuter | |
| 6,579,895 B2 | 6/2003 | Karim et al. | |
| 6,613,790 B2 | 9/2003 | Carter | |
| 6,699,840 B2 | 3/2004 | Almarsson et al. | |
| 7,078,526 B2 | 7/2006 | Remenar et al. | |
| 7,132,570 B2 | 11/2006 | Neckebrock et al. | |
| 7,132,579 B2 | 11/2006 | Neckebrock et al. | |
| 7,172,769 B2 | 2/2007 | Kararli et al. | |
| 7,205,413 B2 | 4/2007 | Morissette et al. | |
| 7,446,107 B2 | 11/2008 | Remenar et al. | |
| 7,452,555 B2 | 11/2008 | Childs | |
| 7,459,449 B2 | 12/2008 | Keltjens | |
| 2002/0006951 A1 | 1/2002 | Hageman et al. | |
| 2002/0013357 A1 | 1/2002 | Nadkarni et al. | |
| 2002/0015735 A1 | 2/2002 | Hedden et al. | |
| 2002/0034542 A1 | 3/2002 | Thombre et al. | |
| 2002/0037925 A1 | 3/2002 | Dewey et al. | |
| 2002/0042446 A1 | 4/2002 | Dewey et al. | |
| 2002/0071857 A1 | 6/2002 | Kararli et al. | |
| 2002/0107250 A1 | 8/2002 | Hariharan et al. | |
| 2002/0119193 A1 | 8/2002 | Le et al. | |
| 2003/0069190 A1 | 4/2003 | Abdel-Magid et al. | |
| 2003/0072802 A1 | 4/2003 | Cutler | |
| 2003/0096014 A1 | 5/2003 | Sherman | |
| 2003/0162226 A1 | 8/2003 | Cima et al. | |
| 2003/0166581 A1 | 9/2003 | Almarsson et al. | |
| 2003/0224006 A1 | 12/2003 | Zaworotko et al. | |
| 2004/0019211 A1 | 1/2004 | Remenar et al. | |
| 2004/0029946 A1 | 2/2004 | Arora et al. | |
| 2004/0053853 A1 | 3/2004 | Almarsson et al. | |
| 2004/0106052 A1 | 6/2004 | Molaire | |
| 2004/0106053 A1 | 6/2004 | Molaire et al. | |
| 2004/0106055 A1 | 6/2004 | Molaire et al. | |
| 2004/0154890 A1 | 8/2004 | Liu | |
| 2004/0171062 A1 | 9/2004 | Hirth et al. | |
| 2004/0176335 A1 | 9/2004 | Childs | |
| 2004/0242640 A1 | 12/2004 | Desai et al. | |
| 2005/0070551 A1 | 3/2005 | Remenar et al. | |
| 2005/0169982 A1 | 8/2005 | Almarsson et al. | |
| 2005/0181041 A1 | 8/2005 | Goldman | |
| 2005/0252649 A1 | 11/2005 | Chiu et al. | |
| 2005/0256127 A1 | 11/2005 | Ku et al. | |
| 2006/0134198 A1 | 6/2006 | Tawa et al. | |
| 2006/0223794 A1 | 10/2006 | Hickey et al. | |
| 2007/0015841 A1 | 1/2007 | Tawa et al. | |
| 2007/0021510 A1 | 1/2007 | Hickey et al. | |
| 2007/0059356 A1 | 3/2007 | Almarsson et al. | |
| 2007/0293674 A1 | 12/2007 | Scoppettuolo et al. | |

FOREIGN PATENT DOCUMENTS

| | | |
|---|---|---|
| EP | 0283992 B1 | 9/1992 |
| EP | 413528 B1 | 11/1995 |
| EP | 1167355 A1 | 1/2002 |
| EP | 1364649 A1 | 11/2003 |
| FR | 769586 | 6/1934 |
| FR | 2849029 | 6/2004 |
| GB | 1 297 261 | 12/1972 |
| GB | 2 169 601 | 7/1986 |
| IN | 182620 | 12/1994 |
| IT | 01303251 | 11/2000 |
| JP | 46-33588 | 10/1971 |
| JP | 54-16494 | 2/1979 |
| JP | 54-095589 | 7/1979 |
| WO | WO 94/16733 A1 | 8/1994 |
| WO | WO 95/17407 A1 | 6/1995 |
| WO | WO 95/23596 | 9/1995 |
| WO | WO 96/07331 A1 | 3/1996 |
| WO | WO 96/33193 | 10/1996 |
| WO | WO 98/57967 A1 | 12/1998 |
| WO | WO 00/07583 A2 | 2/2000 |
| WO | WO 00/32189 A1 | 6/2000 |
| WO | WO 00/50020 A2 | 8/2000 |
| WO | WO 00/53283 A1 | 9/2000 |
| WO | WO 00/72841 A1 | 12/2000 |
| WO | WO 01/13904 A2 | 3/2001 |
| WO | WO 01/41536 A2 | 6/2001 |
| WO | WO 01/41760 A3 | 6/2001 |
| WO | WO 01/42221 A1 | 6/2001 |
| WO | WO 01/42222 A1 | 6/2001 |
| WO | WO 01/45706 | 6/2001 |
| WO | WO 01/51919 A2 | 7/2001 |
| WO | WO 01/78724 A1 | 10/2001 |
| WO | WO 01/91750 A1 | 12/2001 |
| WO | WO 01/97853 A1 | 12/2001 |
| WO | WO 02/00627 A1 | 1/2002 |
| WO | WO 02/10125 | 2/2002 |
| WO | WO 02/056878 A2 | 7/2002 |
| WO | WO 02/056915 | 7/2002 |
| WO | WO 02/062318 A2 | 8/2002 |
| WO | WO 02/102376 | 12/2002 |
| WO | WO 03/033462 A2 | 4/2003 |
| WO | WO 03/070738 A2 | 8/2003 |
| WO | WO 03/074474 A2 | 9/2003 |
| WO | WO 03/101392 A2 | 12/2003 |
| WO | WO 2004/054571 A1 | 7/2004 |
| WO | WO 2004/078161 A1 | 9/2004 |
| WO | WO 2004/078163 A2 | 9/2004 |
| WO | WO 2004/089313 A2 | 10/2004 |
| WO | WO 2005/023198 A2 | 3/2005 |
| WO | WO 2005/037424 A1 | 4/2005 |
| WO | WO 2005/053612 | 6/2005 |

| | | | |
|---|---|---|---|
| WO | WO 2005/055983 A2 | 6/2005 | |
| WO | WO 2005/060968 A1 | 7/2005 | |
| WO | WO 2005/089375 A2 | 9/2005 | |
| WO | WO 2005/094804 A1 | 10/2005 | |
| WO | WO 2006/024930 A1 | 3/2006 | |

OTHER PUBLICATIONS

Salem et. al. 5,736,541International Journal of Pharmaceutics, 141, 1996, 257-259.*
Brittain, HG. Polymorphism in Pharmaceutical Solids, 1999, Marcel Dekker, Inc., p. 183, 202-208, 219.*
Davidovich et al. American Pharmaceutical Review, 2004, 7(1) p. 10, 12, 14,16, 100.*
Definition of solvate, The Free Dictionary, http://www.thefreedictionary.com/solvate, accessed online on Jul. 21, 2009.*
Dean, J.A. Analytical Chemistry Handbook, 1995, McGraw-Hill, Inc., p. 10.24-10.26.*
US Pharmacopia #23, 1995, p. 1843.*
Rubino, J. T. et al. "Influence of solvent composition on the solubilities and solid-state properties of the sodium salts of some drugs" *International Journal of Pharmaceutics*, 1990, pp. 141-145, vol. 65, No. 1-2.
"Solvated cephalosporin antibiotic prodn.—i.e. 1,2-propylene glycol adduct of cefatrizine", Jul. 28, 1979, Database WPI, Section Ch, Week 197936, Derwent Publications Ltd., London, GB, XP002282989, abstract only.
Fung, H. L. at al. "Solvent Effects on Comparative Dissolution of Pharmaceutical Solvates" *Chemical and Pharmaceutical Bulletin*, 1974, pp. 454-458, vol. 22, No. 2.
Aakeröy, C. et al. "Crystal engineering of hydrogen-bonded assemblies—a progress report" *Aust. J. Chem.*, 2001, pp. 409-421, vol. 54.
Bingham, A. et al. "Over one hundred solvates of sulfathiazole" *Chem. Commun.*, 2001, pp. 603-604.
Byriel, K., et al. "Molecular cocrystals of carboxylic acids. IX Carboxylic acid interactions with organic heterocyclic bases. The crystal structures of the adducts of (2,4- dichlorophenoxy) acetic acid with 3-hydroxypyridine, 2,4,6,-trinitrobenzoic acid with 2-aminopyrimidine, and 4-nitrobenzoic acid with 3-amino-1,2,4-triazole" *Aust. J. Chem.*, 1992, pp. 969-981, vol. 45, No. 6.
Salmon, J. et al. "Supramolecular chemistry of boronic acids (Abstract)" 38th Midwest Regional Meeting of the American Chemical Society in Columbia, MO., Nov. 5-7, 2003, published by the American Chemical Society, Washington, D.C.
Urbina, J. et al. "Supramolecular design of inorganic/organic networks using flexible ligands with self-complementary hydrogen bonds (Abstract)" 38th Midwest Regional Meeting of the American Chemical Society in Columbia, MO., Nov. 5-7, 2003, published by the American Chemical Society, Washington, D.C.
Smith, D. et al. "Structure confirmation by single crystal X-ray diffraction of a series of new schiff bases and theoretical computations on 3-(N-2-α, α, α-triflourotoluylidene amino) tetrahydrothiophene-1, 1-dioxide (Abstract)" 216th ACS National Meeting in Boston, MA., Aug. 23-27, 1998, published by the American Chemical Society, Washington, D.C.
Desiraju, G. "Supramolecular synthons in crystal engineering—A new organic synthesis" *Angew. Chem. Int. Ed. Engl.*, 1995, pp. 2311-2327, vol. 34.
Fritchie, C. et al. "The configuration of phenothiazine in various molecular complexes" *Chem. Commun.*, 1968, pp. 833-834.
Huang, C.-M. et al. "Molecular packing modes. Part XI. Crystal structures of the 2:1 complexes of benzamide with succinic acid and furamide with oxalic acid" *J. Chem. Soc. Perkins Trans. 2: Physical Organic Chemistry*, 1973, pp. 503-508, vol. 5.
Jackisch, M. et al. "Structures of three related biphenyl compounds: 4,4'-biphenyldiol, 3,3',5,5'-tetra-*tert*-butyl-4,4'-biphenyldiol, and 3,3',5,5'- tetra-*tert*-butyl-1,1'-bicyclohexa-2,5- dienylidene-4,4'-dione" *Acta Cryst.*, 1990, pp. 919-922, vol. C46.
Kim, S. et al. "The structure of a crystalline complex containing one phenobarbital molecule and two adenine derivatives" *Proc. Natl. Acad. Sci. USA*, 1968, pp. 402-408, vol. 60.

Kobayashi, H. at al. "Sinusoidal structure of the 1:1 complex of phenothiazine and 7,7,8,8-tetracyanoquinodimethane, PTZ-TCNQ" *Acta Cryst.*, 1974, pp. 1010-1017, vol. B30.
Ermer, O. et al. "Molecular recognition among alcohols and amines: super-tetrahedral crystal architectures of linear diphenol-diamine complexes and aminophenols" *J. Chem. Soc. Perkins Trans. 2*, 1994, pp. 925-944.
Martin, R. et al. "Polyphenal-caffeine complexation" *J. Chem. Soc., Chem. Commun.*, 1986, pp. 105-106.
Lehn, J.-M. et al. "Molecular recognition directed self-assembly of ordered supramolecular strands by cocrystallization of complementary molecular components" *Chem. Soc., Chem. Commun.*, 1990, pp. 479-481.
Lynch, D. et al. "Molecular cocrystals of carboxylic acids. XV Preparation and characterization of heterocyclic base adducts with a series of carboxylic acids, and the crystal structures of the adducts of 2-aminopyrimidine with 2,6-dihydroxybenzoic acid, 4-aminobenzoic acid, phenoxyacetic acid, (2,4-dichlorophenoxy) acetic acid, (3,4- dichlorophenoxy)- acetic acid and salicylic acid, and 2-aminopyridmine with 2,6-dihydroxybenzoic acid" *Aust. J. Chem.*, 1994, pp. 1097-1115, vol. 47.
McIntosh, J. et al. "Chemotherapeutic drugs in anaerobic infections of wounds" *The Lancet*, Jun. 26, 1943, pp. 793-795.
McIntosh, J. et al. "Zinc peroxide, proflavine and penicillin in experimental *cl. welchii* infections" *The Lancet*, Dec. 26, 1942, pp. 750-752.
Smith, G. et al. "Molecular cocrystals of carboxylic acids. XXI the role of secondary group interactions in adduct formation between 2-aminopyramidine and substituted benzoic acids: the crystal structures of the adducts with *o*-phthalic acid, *o*-nitrobenzoic acid, *o*-aminobenzoic acid and *m*-aminobenzoic acid" *Aust. J. Chem.*, 1995, pp. 1151-1166, vol. 48.
Weissbuch, I. et al. "Crystal morphology control with tailor-made additives; a stereochemical approach" *Advances in Crystal Growth Research*, 2001, pp. 381-400.
McMahon, J. et al. "Crystal engineering of the composition of pharmaceutical phases. 3[1]. Primary amide supramolecular heterosynthons and their role in the design of pharmaceutical co-crystals" *Z. Kristallogr.*, 2005, pp. 340-350, vol. 220.
Meejoo, S. et al. "The interplay of aryl-perfluoroaryl stacking interactions and interstack hydrogen bonding in controlling the structure of a molecular cocrystal" *Chemphyschem*, 2003, pp. 766-769, vol. 4.
Mirmehrabi, M. et al. "Improving the filterability and solid density of ranitidine hydrochloride form 1" *Journal of Pharmaceutical Sciences*, Jul. 2004, pp. 1692-1700, vol. 93, No. 7.
Morris, K. et al. "Theoretical approaches to physical transformations of active pharmaceutical ingredients during manufacturing processes" *Advanced Drug Delivery Reviews*, 2001, pp. 91-114, vol. 48.
Nakanishi, I. et al. "X-ray structural studies on two forms of β-cyclodextrin barbital complexes" *Journal of Inclusion Phenomena*, 1984, pp. 689-699, vol. 2.
Nakao, S. et al. "The crystal and molecular structure of the 2:1 molecular complex of theophylline with phenobarbital" *Acta Cryst.*, 1977, pp. 1373-1378, vol. B33.
Natarajan, S. et al. "Reinvestigation of the crystal structure of diglycine hydrochloride" *Zeitschrift für Kristallographic*, 1992, pp. 265-270, vol. 198.
Olenik, B. et al. "Cooperative and anticooperative effects in the cocrystals of mono- and diazanaphthalenes with *meso*-1, 2-diphenyl-1,2-ethanediol" *Crystal Growth & Design*, 2003, pp. 175-181, vol. 3, No. 2.
Olenik, B. et al. "Supramolecular synthesis by cocrystallization of oxalic and fumaric acid with diazanaphthalenes" *Crystal Growth & Design*, 2003, pp. 183-188, vol. 3, No. 2.
Groth, P. "*d*-Glucose-sodium chloride-monohydrate (glucose-sodium chloride) = $2C_6H_{12}O_6 \cdot NaCl \cdot H_2O$" *Chemische Krystallographie*, 1910, pp. 438-439.
Oswald, I. et al. "Rationalisation of co-crystal formation through knowledge-mining" *Crystallography Reviews*, 2004, pp. 57-66, vol. 10, No. 1.

Ouyang, X. et al. "Single-crystal-to-single-crystal topochemical polymerizations of a terminal diacetylene: two remarkable transformations give the same conjugated polymer" *J. Am. Chem. Soc.*, 2003, pp. 12400-12401, vol. 125.

Patel, U. et al. "Structure of the 1:1 complex between 4-amino-*N*-(4,6-dimethyl-2- pyrimidinyl)- benzenesulfonamide (sulfadimidine) and 2-hydroxybenzoic acid (salicylic acid)" *Acta Cryst.*, 1988, pp. 1264-1267, vol. C44.

Reddy, L. et al. "Phenyl-perfluorophenyl synthon mediated cocrystallization of carboxylic acids and amides" *Crystal Growth & Design*, 2004, pp. 89-94, vol. 4., No. 1.

Remenar, J. et al. "Crystal engineering of novel cocrystals of a triazole drug with 1,4-dicarboxylic acids" *J. Am. Chem. Soc.*, 2003, pp. 8456-8457, vol. 125.

Schmidt, G. "Photodimerization in the solid state" *Pure Appl. Chem.*, 1971, pp. 647-678, vol. 27.

Shan, N. et al. "Co-crystal of 4,7-phenanthroline and coboxylic acids: synthon competition and prediction" *Tetrahedron Letter*, 2002, pp. 8721-8725, vol. 43.

Shan, N. et al. "Crystal engineering using 4,4'-bipyridyl with di- and tricarboxylic acids" *Crystal Engineering*, 2002, pp. 9-24, vol. 5.

Shan, N. et al. "Supramolecular synthons in the co-crystal structures of 2-aminopyrimdine with dils and carboxylic acids" *Tetrahedron Letters*, 2002, pp. 3101-3104, vol. 43.

McIntosh, J. et al. "Further observations on the chemotherapy of experimental gas gangrene: flavazole, marfanil, V187 and V335" *British Journal of Experimental Pathology*, 1946, pp. 46-54, vol. 27.

Shaviv, R. et al. "Magnetochemistry of the tetrahaloferrate (III) ions 6. Crystal structure and magnetic ordering in $[(pyH)_3Cl][FeCl_4]_2$" *Inorganica Chimica Acta*, 1992, pp. 613-621, vol. 198-200.

Shefter, E. "Structural studies on complexes IV: Crystal structure of a 1:1 5-chlorosalicylic acid and theophylline complex" *Journal of Pharmaceutical Sciences*, 1969, pp.710-714, vol. 58.

Shimizu, N. et al. "Structure of 2,4-diamino-5-(3,4,5-trimethoxybenzyl) pyrimidne-5,5-diethylbarbituric acid (1:1)" *Acta Cryst.*, 1982, pp. 2309-2311, vol. B38.

Singh, N. B. et al. "Solid state reaction between 8-hydroxyquinoline and *p*-nitrobenzoic acid" *Indian Journal of Chemistry*, May 1988, pp. 429-432, vol. 37B.

Smith, G. et al. "The 1:1 adduct of 4-aminobenzoic acid with 4-aminodensonitrile" *Acta Cryst.*, 2000, pp. 1155-1156, vol. C56.

Steiner, T. "Donor and acceptor strengths in C-H•••O hydrogen bonds quantified from crystallographic data of small solvent molecules" *New J. Chem.*, 1998, pp. 1099-1103.

Storey, R. et al. "Automation of solid form screening procedures in the pharmaceutical industry—how to avoid the bottlenecks" *Crystallography Reviews*, 2004, pp. 45-56, vol. 10, No. 1.

Szafran, M. et al, "Molecular structures and hydrogen bonding in the 1:1 and 1:2 complexes of pyridine betaine with 2,6-dichloro-4-nitrophenol; an example of strongly coupled hydrogen bonds, O-H•••O=C-O-H•••O-" *Journal of Molecular Structure*, 1997, pp. 145-160, vol. 416.

Takeuchi, M. et al. "Synchrotron radiation SAXS/WAXS study of polymorph-dependent phase behavior of binary mixtures of saturated monoacid triacylglycerols" *Crystal Growth & Design*, 2003, pp. 369-374, vol. 3, No. 3.

Tang, C. P. et al. "Reaction pathways in crystalline host-guest inclusion complexes: rotation by a net 180° of the acetyl group on photoaddition of guest- acetophenone and —m-Chloroacetophenone to the atom C5 of host deoxycholic acid" *J. Am. Chem. Soc.*, 1985, pp. 4058-4070, vol. 107.

Taylor, R. et al. "Rules governing the crystal packing of mono- and dialcohols" *Acta Crystallographica Section B, Structural Science*, 2001, pp. 815-827, vol. B57.

Thallapally, P. et al. "Polymorphism of 1,3,5-trinitrobenzene induced by a trisindane additive" *Angew. Chem. Int. Ed.*, 2004, pp. 1149-1155, vol. 43.

Timmerman, P. et al. "Noncovalent Assembly of functional groups on calix[4]arene molecular boxes" *Chem. Eur. J.*, 1997, pp. 1823-1832, vol. 3., No. 11.

Shan, N. et al. "Mechanochemistry and co-crystal formation: effect of solvent on reaction kinetics" *Chem. Commun.*, 2002, pp. 2372-2373.

Caira, M. et al. "X-ray structure and thermal analysis of a 1:1 complex between (*S*)-naproxen and heptakis (2,3,6-tri-*O*-methyl)-β-cyclodextrin" *Journal of Inclusion Phenomena and Molecular Recognition in Chemistry*, 1995, pp. 277-290, vol. 20.

Trask, A. et al. "Crystal engineering of organic cocrystals by the solid-state grinding approach" *Top Curr. Chem.*, 2005, pp. 41-70, vol. 254.

Trask, A. et al. "Pharmaceutical cocrystallization: engineering a remedy for caffeine hydration" *Crystal Growth & Design*, 2005, pp. 1013-1021, vol. 5, No. 3.

Trask, A. et al. "Solvent-drop grinding: green polymorph control of cocrystallisation" *Chem. Commun.*, 2004, pp. 890-891 in addition to supplemental materials.

Trowbridge, L. et al. "Composites for nonlinear optics: Crystal growth and polymorphism" *University of Sussex, Falmer Brighton UK, School of Chemistry and Molecular Sciences*, pp. 272. Abstr. Pap., Am. Chem. Soc. 1994, vol. 208.

Uno, T. et al. "Structure of 5,5-diphenylhydantoin-1-(4-bromophenyl)-4-dimethylamino-2,3-dimethyl-3-pyrazolin-5-one (1:1)" *Acta Cryst*, 1980, pp. 2794-2796, vol. B36.

Van Roey, P. et al. "Structure-activity studies of non-steroidal aromatase inhibitors: the crystal and molecular structures of CGS 16949A and CGS 18320B" *J. Enzyme Inhibition*, 1991, pp. 119-132, vol. 5.

Van Roey, P. et al. "Structure of *cis*-1-{[4-(1-imidazolylmethyl) cyclohexyl] methyl} imidazole- succinic acid complex" *Acta Cryst.*, 1991, pp. 1015-1018, vol. C47.

Vishweshwar, P. et al. "Crystal engineering of pharmaceutical co-crystals from polymorphic active pharmaceutical ingredients" *Chem. Commun.*, 2005, pp. 4601-4603.

Vishweshwar, P. et al. "Recurrence of carboxylic acid- pyridine supramolecular synthon in the crystal structures of some pyrazinecarboxylic acids" *J. Org. Chem.*, 2002, pp. 556-565, vol. 67.

Vishweshwar, P. et al. "Supramolecular synthons based on N-H•••N and C-H•••O hydrogen bonds. Crystal engineering of a helical structure with 5,5-diethylbarbituric acid" *Chem. Commun.*, 2002, pp. 1830-1831.

Vishweshwar, P. et al. "Supramolecular synthons in phenol-isonicotinamide adducts" *Cryst. Eng. Comm.* 2003, pp. 164-168, vol. 5, No. 31.

Voet, D. et al. "The crystal and molecular structure of the intermolecular complex 9- ethyladenine-5, 5-diethylbarbituric acid" *Journal of the American Chemical Society*, Nov. 15, 1972, pp. 8213-8222, vol. 94, No. 23.

Voet, D. et al. "The structure of an intermolecular complex between cytosine and 5-fluorouracil" *Journal of the American Chemical Society*, May 21, 1969, pp. 3069-3075, vol. 91, No. 11.

Stezowski, J. J. et al. "Characterization of a 1:1 complex of an unusual structure in the phenothiazine/phenazine binary phase diagram" *Zeitschrift fur Kristallographie* in *International Journal for Structural, Physical, Chemical Aspects of Crystalline Materials*, 1983, pp. 213-215, vol. 162, No. 1-4.

Wang, A. et al. "Crystal structure of 1:1 complex of barbital with 1-methylimidazole" *Journal of Pharmaceutical Sciences*, Mar. 1979, pp. 361-363, vol. 68, No. 3.

Alberola, S. et al. "Crystalline and Molecular Structure of Sulfanilimide-Antipyrine" *Acta Cryst.*, 1977, pp. 3337-3341, vol. B33.

Wood, R. A. et al. "2,5-O-methylene-D-mannitol sodium-chloride, $C_7H_{14}O_6 \cdot NaCl$" *Cryst. Struct. Comm.*, 1976, 207-210, vol. 5.

Xu, J. et al. "Effect of composition distribution on miscibility and co-crystallization phenomena in the blends of low density polyethylene with conventional and metallocene-based ethylene-butene copolymers" *Polymer*, 2001, pp. 3867-3874, vol. 42.

Yoo, J. et al. "Cocrystallization of a dinuclear platinum complex as a monomer and a one-dimensional polymer" *Polyhedron*, 2002, pp. 715-719, vol. 21.

Zaitu, S. et al. "A 2:1 molecular complex of theophylline and 5-fluorouracil as the monohydrate" *Acta Cryst.*, 1995, pp. 1857-1859, vol. C51.

Zaman, M. B. et al. "Linear hydrogen-bonded molecular tapes in the cocrystals of squaric acid with 4,4'-dipyridylacetylene and 1,2-bis(4-pyridyl) ethylene" *Acta Cryst.*, 2001, pp. 621-624, vol. C57.

Zerkowski, J. et al. "Design of organic structures in the solid state: hydrogen-bonded molecular "tapes"[1]" *J. Am. Chem. Soc.*, 1990, pp. 9025-9026, vol. 112.

Zerkowski, J. et al. "Investigations into the robustness of secondary and tertiary architecture of hydrogen-bonded crystalline tapes" *Chem. Mater.*, 1994, pp. 1250-1257, vol. 6.

Zerkowski, J. et al. "New varieties of crystalline architecture produced by small changes in molecular structure in tape complexes of melamines and barbiturates" *J. Am. Chem. Soc.*, 1994, pp. 4305-4315, vol. 116.

Zerkowski, J. et al. "Polymorphic packing arrangements in a class of engineered organic crystals" *Chem. Mater.*, 1997, pp. 1933-1941, vol. 9.

Zerkowski, J. et al. "Solid-state structures of "Rosette" and "Crinkled Tape" motifs derived from the cyanuric acid-melamine lattice" *J. Am. Chem. Soc.*, 1992, pp. 5473-5475, vol. 114.

Zhang, R. et al. "Atmospheric new particle formation enhanced by organic acids" *Science*, Jun. 4, 2004, pp. 1487-1490 with additional supporting online material, vol. 304.

Zhu, H. et al. "Influence of water activity in organic solvent + water mixtures on the nature of the crystallizing drug phase. 1. theophylline" *International Journal of Pharmaceutics*, 1996, pp. 151-160, vol. 135.

Chang, Y. et al. "An Approach to the Design of Molecular Solids. Strategies for Controlling the Assembly of Molecules into Two-Dimensional Layered Structures" *J. Am. Chem. Soc.*, 1993, pp. 5991-6000, vol. 115.

Cowan, J. A. et al. "Neutron diffraction studies of the 1:1 and 2:1 cocrystals of benzene-1,2,4,5-tetracarboxylic acid and 4,4'-bipyridine" *Acta Cryst.*, 2006, pp. o157-o161, vol. C62.

Davies, N. M. et al. "Clinical Pharmacokinetics and Pharmacodynamics of Celecoxib. A Selective Cyclo-Oxygenase-2 Inhibitor" *Clin. Pharmacokinet.*, Mar. 2000, pp. 225-242, vol. 38, No. 3.

Desiraju, G.R. "Solid-State Chemistry: Crystal Gazing: Structure Prediction and Polymorphism" *Science*, Oct. 17, 1997, pp. 404-405, vol. 278, No. 5337.

Doelker, E. "Physicochemical behavior of active substances. Consequences for the feasibility and stability of pharmaceutical forms" *STP Pharma Pratiques*, 1999, pp. 399-409, vol. 9, No. 5.

Doelker, E. "Cystalline modifications and polymorphism changes during drug manufacturing" *Annales Pharmaceutiques Francaises*, 2002, pp. 161-176, vol. 60, No. 3.

Dunitz, J. D. "Are crystal structures predictable?" *Chem Commun.*, 2003, pp. 545-548.

Feynman, R. P. "There's Plenty of Room at the Bottom" *Engineering and Science*, Feb. 1960, pp. 22-36.

Jain, N. K. et al. "Polymorphism in Pharmacy" *Indian Drugs*, 1986, pp. 315-329, vol. 23, No. 6.

Ball, P. "Scandal of crystal design. . ." *Nature*, Jun. 20, 1996, pp. 648-650, vol. 381.

Bastin, R. J. et al. "Salt Selection and Optimization Procedures for Pharmaceutical New Chemical Entities" *Organic Process Research & Development*, 2000, pp. 427-435, vol. 4, No. 5.

Bernstein, J. et al. "Concomitant Polymorphs" *Angew. Chem. Int. Ed.*, 1999, pp. 3440-3461, vol. 38.

Boucher, E. et al. "Use of Hydrogen Bonds to Control Molecular Aggregation. Behavior of Dipyridones and Pyridone-Pyrimidones Designed to Form Cyclic Triplexes" *J. Org. Chem.*, 1995, pp. 1408-1412, vol. 60.

Kirchner, M. T. et al., Co-crystals with Acetylene: Small is not Simple! *Chem. Eur. J.*, 2010, pp. 2131-2146, vol. 16.

Moulton, B. et al. "From Molecules to Crystal Engineering: Supramolecular Isomerism and Polymorphism in Network Solids" *Chem. Rev.*, 2001, pp. 1629-1658, vol. 101.

Muzaffar, N. A. et al. "Polymorphism and Drug Availability" *Journal of Pharmacy*, 1979, pp. 59-66, vol. 1, No. 1.

Osorio-Lozada, A. et al. "Synthesis and determination of the absolute stereochemistry of the enantiomers of adrafinil and modafinil" *Tetrahedron: Asymmetry*, 2004, pp. 3811-3815, vol. 15.

Otsuka, M. et al. "Effect of Polymorphic Forms of Bulk Powders on Pharmaceutical Properties of Carbamazepine Granules" *Chem. Pharm. Bull.*, 1999, pp. 852-856, vol. 47, No. 6.

Shattock, T. R. et al. "Hierarchy of Supramolecular Synthons: Persistent Carboxylic Acid•••Pyridine Hydrogen Bonds in Cocrystals That also Contain a Hydroxyl Moiety" *Cryst. Growth Des.*, 2008, pp. 4533-4545, vol. 8, No. 12.

Thayer, A. M. "Form and Function: The choice of pharmaceutical crystalline form can be used to optimize drug properties, and cocrystals are emerging as new alternatives" *Chemical & Engineering News*, Jun. 18, 2007, pp. 17-30, vol. 85, No. 25.

Villa, L. A. et al. "Central Nervous System Paracoccidioidomycosis. Report of a Case Successfully Treated with Itraconazol" *Rev. Inst. Med. Trop. S. Paulo*, Jul.-Aug. 2000, pp. 231-234, vol. 42, No. 4.

Zaworotko, M. J. "Crystal Engineering of Diamondoid Networks" *Chemical Society Reviews*, 1994, pp. 283-288, vol. 23.

Klein, C. L. et al. "Molecular Structure of Two Conformationally Restrained Fentanyl Analogues: cis- and trans-Isomers of N-{3-Methyl-1-[2-(1,2,3,4-tetrahydro)naphthyl]-4-piperidinyl}-N-phenylpropanamide" *Journal of Pharmaceutical Sciences*, Nov. 1985, pp. 1147-1151, vol. 74, No. 11.

Wunderlich, H. F. et al. "The Derivatives of carbamazepine with ammonium halogenides and formamide" *Pharmazie*, 1991, pp. 507-509, vol. 46, No. 7.

El-Nahhas, S. A. "Physico-chemical characteristics of carbamazepine-β-cyclodextrin inclusion compounds and carbamazepine-PEG solid dispersions" *Pharmazie*, 1996, pp. 960-963, vol. 51, No. 12.

Reynolds, J. E. F. (ed). Martindale, The Extra Pharmacopoeia, 1993, The Pharmaceutical Press, London, England, 13th edition, p. 1610.

Pedireddi, V. R. et al. "Layered Structures Formed by Dinitrobenzoic Acids" *Tetrahedron Letters*, 1998, pp. 9831-9834, vol. 39.

Zaman, M. B. et al. "Crystal Engineering Using Anilic Acids and Dipyridyl Compounds through a New Supramolecular Synthon" *J. Org. Chem.*, 2001, pp. 5987-5995, vol. 66.

Japanese Notice of Reasons for Rejection dated Oct. 8, 2009, Japanese Application No. 2003-572946.

Aakeröy, C. et al. "Aromatic dicarboxylic acids as building blocks of extended hydrogen-bonded architectures" *Supramolecular Chemistry*, 1998, pp. 127-135, vol. 9.

Aakeröy, C. et al. "Assembly of 2-D inorganic/organic lamellar structures through a combination of copper (I) coordination polymers and self-complimentary hydrogen bonds" *J. Chem. Soc., Dalton Trans.*, 2000, pp. 3869-3872.

Aakeröy, C. et al. "Building organic assemblies with 2-pyridone and dicarboxylic acids: relating molecular conformation and synthon stability to crystal structure" *Crystal Engineering*, 1998, pp. 225-241, vol. 1, No. 3-4.

Aakeröy, C. et al. "The C-H•••Cl hydrogen bond: does it exist?" *New J. Chem.*, 1999, pp. 145-152.

Aakeröy, C. et al. "Crystal engineering of ionic soloids" *Modular Chemistry* (ed. by Michl, J.), 1997, pp. 153-162, Kluwer Academic Publishers, The Netherlands.

Aakeröy, C. et al. "Crystal engineering: strategies and architectures" *Acta Cryst.*, 1997, pp. 569-586, vol. B53.

Aakeröy, C. et al. "Crystal engineering using intermolecular hydrogen-bonded connectors and classic coordination chemistry" *Transactions ACA*, 1998, pp. 97-103, vol. 33.

Aakeröy, C. et al. "The crystal structure of the molecular cocrystal L-malic acid L-tartaric acid (1/1)" *Supramolecular Chemistry*, 1996, pp. 153-156, vol. 7.

Aakeröy, C. et al. "Deliberate combination of coordination polymers and hydrogen bonds in a supramolecular design strategy for inorganic/organic hybrid networks" *Chem. Commun.*, 2000, pp. 935-936.

Akazome, M. et al. "Enantioselective inclusion of methyl phenyl sulfoxides and benzyl methyl sulfoxides by (R)-phenylglycyl-(R)-phenylglycine and the crystal structures of the inclusion cavities" *J. Org. Chem.*, 2000, pp. 68-76, vol. 65.

Akhtaruzzaman, M.D. et al. "One-dimensional hydrogen-bonded molecular tapes in 1, 4-bis[(4-pyridinio) ethynyl]benzene chloranilate" *Acta. Cryst.*, 2001, pp. o353-o355, vol. E57.

Allen, F. et al. "Systematic analysis of structural data as a research technique in organic chemistry" *Acc. Chem. Res.*, 1983, pp. 146-153, vol. 16.

Almarsson, Ö. et al. "Crystal engineering of the composition of pharmaceutical phases. Do pharmaceutical co-crystals represent a new path to improved medicines?" *Chem. Commun.*, 2004, pp. 1889-1896.

Amai, M. et al. "1:1 complex of octadecanoic acid and 3-pyridinecarboxamide" *Acta Cryst.*, 1998, pp. 1367-1369, vol. C54.

Anderson, N. et al. "Sulfonation with inversion by mitsunobu reaction: an improvement on the original conditions" *J. Org. Chem.*, 1996, pp. 7955-7958, vol. 61.

Aoki, K. etal. "A 1:1 complex of theophylline and *p*-nitrophenol" *Acta Cryst.*, 1978, pp. 2333-2336, vol. B34.

Ashton, P. et al. "Combining different hydrogen-bonding motifs to self-assemble interwoven superstructures" *Chem. Eur. J.*, 1998, pp. 577-589, vol. 4, No. 4.

Barker, P. A. et al. "Effect of crystallization temperature on the cocrystallization temperature on the cocrystallization of hydroxybutyrate/ hydroxyvalerate copolymers" *Polymer*, pp. 913-919, vol. 38, No. 4.

Berkovitch-Yellin, Z. et al. "Electron density distribution in cumulenes: an x-ray study of the complex allenedicarboxylic acid-acetamide (1:1) at −150° C" *Acta Cryst.*, 1977, pp. 3670-3677, vol. B33.

Berkovitch-Yellin, Z. et al. "The role played by C-H•••O and C-H•••N interactions in determining molecular packing and conformation" *Acta Cryst.*, 1984, pp. 159-165, vol. B40.

Berl, V. et al. "Induced fit selection of a barbiturate receptor from a dynamic structural and conformational/configurational library" *Eur. J. Org. Chem.*, 1999, pp. 3089-3094.

Bertolasi, V. et al. "Competition between hydrogen bonding and donor-acceptor interactions in co-crystals of 1,3-dimethylbarbituric acid with aromatic amines" *New J. Chem.*, 2001, pp. 408-415, vol. 25.

Bertolasi, V. et al. "General rules for the packing of hydrogen-bonded crystals as derived from the analysis of squaric acid anions: aminoaromatic nitrogen base co-crystals" *Acta Cryst.*, 2001, pp. 591-598, vol. B57.

Bettinetti, G. et al. "Structure and solid-state chemistry of anhydrous and hydrated crystal forms of the trimethoprim-sulfamethoxypyridazine 1:1 molecular complex" *Journal of Pharmaceutical Sciences*, Apr. 2000, pp. 478-489, vol. 89, No. 4.

Bettinetti, G. et al. "Thermal analysis of binary systems of the pharmaceuticals trimetoprim and benzoic acid" *Journal of Thermal Analysis*, 1983, pp. 285-294, vol. 28.

Bettis, J. et al. "Biopharmaceutics and dosage form design" *Amer. J. Hosp. Pharm.*, Mar. 1973, pp. 240-243, vol. 30.

Bolton, S. et al. "Complexes formed in solution by homologs of caffeine" *Journal of the American Pharmaceutical Association*, Jan. 1957, pp. 38-41, vol. XLVI, No. 1.

Bond, A. "*In situ* co-crystallisation as a tool for low-temperature crystal engineering" *Chem. Commun.*, 2003, pp. 250-251, vol. 2.

Bonin, M. et al. "Urotropin azelate: a rather unwilling co-crystal" *Acta Cryst.*, 2003, pp. 72-86, vol. B59.

Bosshard, C. et al. "Microscopic nonlinearities of two-component organic crystals" *J. Opt. Soc. Am. B*, Nov. 2001, pp. 1620-1626, vol. 18, No. 11.

Gluzman, M. Kh. et al. "Investigation of Eutectic Melting in Systems Composed of Organic Salts and Acids" *Journal of Physical Chemistry*, 1960, pp. 2742-2747, vol. 34.

Braga, D. et al. "Hydrogen bonding interactions between ions: a powerful tool in molecular crystal engineering" *Structure and Bonding*, 2004, pp. 1-32, vol. 111.

Brierley, C. et al. "Preparation and structure of the 1:2 π-molecular complex of phenothiazine with pyromellitic dianhydride" *J. Chem. Phys.*, Feb. 1, 1985, pp. 1522-1528, vol. 82, No. 1.

Burgi, H. et al. "Crystallisation of supramolecular materials" *Current Opinion in Solid State & Materials Science*, 1998, pp. 425-430, vol. 3.

Byrn, S. R. et al. "Solid-state pharmaceutical chemistry" *Chem. Mater.*, 1994, pp. 1148-1158, vol. 6.

Caira, M. "Molecular complexes of sulfonamides. Part 1. 1:1 complexes between sulfadimidine [4-amino-N-(4,6-dimethyl-2-pyrimidinyl) benzenesulfonamide] and 2- and 4- aminobenzoic acids" *Journal of Crystallographic and Spectroscopic Research*, 1991, pp. 641-648, vol. 21, No. 5.

Caira, M. "Molecular complexes of sulfonamides. Part 2. 1:1 complexes between drug molecules: sulfadimidine —acetylsalicylic acid and sulfadimidine-4-aminosalicylic acid" *Journal of Crystallographic and Spectroscopic Research*, 1992, pp. 193-200, vol. 22, No. 2.

Caira, M. "Molecular complexes of sulfonamides. 3. Structure of 5-methoxysulfadiazine (Form II) and its 1:1 complex with acetylsalicylic acid" *Journal of Chemical Crystallography*, 1994, pp. 695-701, vol. 24, No. 10.

Caira, M. et al. "Order-disorder enantiotropy, monotropy, and isostructurality in a tetroxoprim-sulfametrole 1:1 molecular complex: crystallographic and thermal studies" *Journal of Pharmaceutical Sciences*, Nov. 2003, pp. 2164-2167, vol. 92, No. 11.

Caira, M. et al. "Selective formation of hydrogen bonded cocrystals between a sulfonamide and aromatic carboxylic acids in the solid state" *J. Chem. Soc. Perkin Trans. 2*, 1995, pp. 2213-2216.

Caira, M. et al. "Structure of a 1:1 complex between the anthelmintic drug mebendazole and propionic acid" *Journal of Chemical Crystallography*, 1998, vol. 28, No. 1, pp. 11-15.

Camerman, A. et al. "Hydrogen bonding interaction of diphenylbarbituric acid and 9- ethyladenine. Crystal structure of a 1:1 complex" *Can. J. Chem.*, 2000, pp. 1045-1051, vol. 78.

Camerman, A. et al. "Molecular structure of acetylacetone. A crystallographic determination" *J. Am. Chem. Soc.*, 1983, pp. 1584-1586, vol. 105, No. 6.

Cannon, A. et al. "Noncovalent derivatization: green chemistry applications of crystal engineering" *Crystal Growth & Design*, 2002, pp. 255-257, vol. 2. No. 4.

Chinnakali, K. et al. "2-aminopyrimidine and *p*-phenylene-diacetic acid (1:1) co-crystal" *Acta Cryst.*, 1999, pp. 399-401, vol. C55.

Brader, M.L. et al. "Hybrid insulin cocrystals for controlled release delivery" *Nature Biotechnol.*, 2002, 20:800-804.

Fleischman, S.G. et al. "Crystal Engineering of the Composition of Pharmaceutiacal Phases: Multiple-Component Crystalline Solids Involving Carbamazepine" *Crystal Growth & Design.*, 2003, 3(6):909-919.

Choi, C. et al. "Cocrystallization of melaminium levulinate monohydrate" *Acta Cryst.*, 2004, pp. o295-o296, vol. C60.

Chow, Y. P. et al. "Complexation of acetaminophen with methyl xanthines" *Journal of Pharmaceutical Sciences*, 1972, pp. 1454-1458, vol. 61.

Christian, S. et al. "Activity coefficient effects in spectral and solubility studies of molecular complex equilibria" *Journal of the American Chemical Society.*, Sep. 20, 1972, pp. 6861-6862, vol. 94, No. 19, Communications to the editor.

Coll, M. et al. "Molecular structure of the complex formed between the anticancer drug cisplatin and d(pGpG): C222₁ crystal form" *Journal of Biomolecular Structure & Dynamics*, 1990, pp. 315-330, vol. 8, No. 2.

Copp, S. et al. "Supramolecular chemistry of [Mn(CO)$_3$ ($\mu_3$-OH)]$_4$: Assembly of a cubic hydrogen-bonded diamondoid network with 1,2-diamineothane" *J. Am. Chem. Soc.*, 1992, pp. 8719-8720, vol. 114.

Cordi, A. et al. "(*S*)-Spiro [(1, 3-diazacyclopent-1-ene)-5, 2' —(7'-methyl-1',2',3',4'- tetrahydronaphthalene)]: resolution, stereospecific synthesis, and preliminary pharmacological characterization as a partial α-adrenergic agonist" *J. Med. Chem.*, 1997, pp. 2931-2935, vol. 40.

Craven, M. et al. "The 2:1 crystal complex of 5, 5-diethylbarbituric acid (barbital) and caffeine" *Acta Cryst.*, 1974, pp. 1191-1195, vol. B30.

Craven, M. et al. "The crystal structures of two polymorphs of 5,5'-diethylbarbituric acid (barbital)" *Acta Cryst.*, 1969, pp. 1978-1993, vol. B25.

Cudney, B. et al. "Screening and optimization strategies for macromolecular crystal growth" *Acta Cryst.*, 1994, pp. 414-423, vol. D50.

Datta, S. et al. "Molecular complex formation between riboflavin and salicylate in an aqueous medium" *Bull. Chem. Soc. Jpn.*, 2003, pp. 1729-1734, vol. 76.

Davey, R. J. et al. "Crystal engineering- nucleation, the key step" *Cryst. Eng. Comm.*, 2002, pp. 257-264, vol. 4, No. 47.

Davey, R. J. et al. "Crystallisation in polymer films: control of morphology and kinetics of an organic dye in a polysilicone matrix" *J. Mater. Chem.*, 1997, pp. 237-241, vol. 7, No. 2.

Debernardis, J. et al. "Conformationally defined adrenergic agents. 5. Resolution, absolute configuration, and pharmacological characterization of the enantiomers of 2-(5,6- dihydroxy-1,2,3,4-tetrahydro-1-naphthyl) imidazoline: a potent agonist at $\alpha$-adrenoceptors" *J. Med. Chem.*, 1987, pp. 1011-1017, vol. 30.

Desiraju, G. et al. "Crystal and co-crystal" *Cryst. Eng. Comm.*, 2003, pp. 466-467, vol. 5, No. 82.

Desiraju, G. et al. "Crystal engineering: outlook and prospects" *Current Science*, Oct. 25, 2001, pp. 1038-1042, vol. 81, No. 8.

Duax, W. et al. "The structure of the crystalline complex estradiol. Urea (1:1)" *Acta Cryst.*, 1972, pp. 1864-1871, vol. B28.

Dunitz, J. "Crystal and co-crystal: a second opinion" *Cryst. Eng. Comm.*, 2003, pp. 506, vol. 5, No. 91.

Dunitz, J. "New light on an old story: the solid-state transformation on ammonium cyanate into urea" *J. Am. Chem. Soc.*, 1998, pp. 13274-13275, vol. 120.

Enright, G. at al. "Thermally programmable gas storage and release in single crystals of an organic van der Waals host" *J. Am. Chem. Soc.*, 2003, pp. 9896-9897, vol. 125.

Epstein, R. et al. "The x-ray crystal structure of the molecular complex 8-bromo-9- ethyladenine-5-allyl-5-isobutylbarbituric acid" *Acta Cryst.*, 1976, pp. 2180-2188, vol. B32.

Oswald, I.D.H. et al. "The formation of paracetamol (acetaminophen) adducts with hydrogen-bond acceptors" *Acta Cryst.*, 2002, B58:1057-1066.

Vishweshwar, P. et al. "Molecular complexes of homologous alkanedicarboxylic acids with isonicotinamide: X-ray crystal structures, hydrogen bond synthons, and melting point alternation" *Crystal Growth & Design*, 2003, pp. 783-790, vol. 3, No. 5.

Etter, M. "Encoding and decoding hydrogen-bond patterns of organic compounds" *Acc. Chem. Res.*, 1990, pp. 120-126, vol. 23.

Etter, M. et al. "Graph-set analysis of hydrogen-bond patterns in organic crystals" *Acta Cryst.*, 1990, pp. 256-262, vol. B46.

Etter, M. at al. "Hydrogen bond directed cocrystallization and molecular recognition properties of acyclic imides" *J. Am. Chem. Soc.*, 1991, pp. 2586-2598, vol. 113.

Etter, M. "Hydrogen bonds as design elements in organic chemistry" *J. Phys. Chem.*, 1991, pp. 4601-4610, vol. 95.

Fabian, L. et al. "Volumetric measure of isostructurality" *Acta Cryst.*, 1999, pp. 1099-1108, vol. B55.

Fallon III, L. "The crystal and molecular structure of 5-fluorouracil" *Acta Cryst.*, pp. 2549-2556, vol. B29.

Feibush, B. et al. "Chiral separation of heterocyclic drugs by HPLC: solute-stationary phase base-pair interactions" *J. Am. Chem. Soc.*, 1986, pp. 3310-3318, vol. 108.

Fifer, E. et al. "Fentanyl analogues 3. 2-(1,2,3,4-tetrahydro)-naphthyl substituted 4-anilidopiperidines" *Eur. J. Med. Chem.- Chim. Ther.*, 1984, pp. 519-524, vol. 19, No. 6.

Reck, G. et al. "Crystal structures of the carbamazepine/ammonium chloride and carbamazepine/ammonium bromide adducts and their transformation into carbamazepine dihydrate" *Pharmazie*, 1991, pp. 509-512, vol. 46, No. 7.

Foxman, B. M. et al. "Environmentally benign synthesis using crystal engineering: steric accommodation in non-covalent derivatives of hydroquinones" *Crystal Engineering*, 1998, pp. 109-118, vol. 1, No. 1.

Foxman, B. M. et al. "Noncovalent derivatives of hydroquinone: *BIS*-(*N,N*-dialkyl) bicyclo[2.2.2]octane-1,4-dicarboxamide complexes" *Crystal Engineering*, 1999, pp. 55-64, vol. 2. No. 1.

Fujii, S. et al. "Crystal and molecular structure of a 1:1 molecular complex of adenine and riboflavin" *Archives of Biochemistry and Biophysics*, 1977, pp. 363-370, vol. 181.

Gao, X. et al. "Supramolecular construction of molecular ladders in the solid state" *Angew. Chem. Int. Ed.*, 2004, pp. 232-236, vol. 43.

Gartland, G. L. et al. "Hydrogen bonding NH•••O=C of barbiturates: the (1:1) crystal complex of urea and 5,5-diethylbarbituric acid (barbital)" *Acta Cryst*, 1974, pp. 980-987, vol. B30.

Ghosh, M. "Structure and conformation of the 1:1 molecular complex sulfaproxyline-caffeine" *Acta Cryst.*, 1991, pp. 577-580, vol. C47.

Giuseppetti, G. P. et al. "The crystal structure of a sulfamethoxazole-trimethoprim 1:1 molecular compound" *II Farmaco- Ed. Sc.*, pp. 138-151, vol. 35.

Goswami, S. et al. "2-aminopyrimidine-fumaric acid cocrystal" *Acta Cryst.*, 1999, pp. 583585, vol. C55.

Haynes, D. "Supramolecular synthon competition in organic sulfonates: a CSD survey" *Cryst. Eng. Comm.*, 2004, pp. 584-588, vol. 6, No. 95.

Goswami, S. et al. "1:1 Hetero-assembly of 2-amino-pyramidine and (+)-camphoric acid" *Acta Cryst.*, 2000, pp. 477-478, vol. C56.

Goswami, S. et al. "Molecular recognition induced supramolecular array of 2- aminopyrimidine with terephthalic acid, 1,4-phenylenediacetic acid and furmaric acid in solid state via H-bonding and Π-stacking interactions" *Supramolecular Chemistry*, 1999, pp. 25-33, vol. 11.

Graja, A. et al. "Interplay of acceptor molecule shape, crystal structure and physical properties of a new molecular complex $C_{70} \cdot 2[(Ph_3P) AuCl]$" *Chemical Physics Letters*, Nov. 19, 1999, pp. 725-732. vol. 313.

Haixin, L. et al. "Structure of the 1:1 complex of 6,6'-diquinolyl ether with 5,5-diethylbarbituric acid" *Acta Cryst.*, 1992, pp. 2096-2098, vol. C48.

Henck, J. et al. "Disappearing and reappearing polymorphs. The benzocaine:picric acid system" *J. Am. Chem. Soc.*, 2001, pp. 1834-1841, vol. 123.

Higuchi, T. et al. "Complexation of organic substances in aqueous solution by hydroxyaromatic acids and their salts" *J. Pharm. Sci.*, 1961, pp. 905-909, vol. 50.

Hino, T. et al. "Assessment of nicotinamide polymorphs by differential scanning calorimetry" *Thermochimica Acta*, 2001, pp. 85-92, vol. 374.

Högberg, T. et al. "Crystallographic, theoretical and molecular modelling studies on the conformations of the salicylamide, raclopride, a selective dopamine-$D_2$ antagonist" *J. Pharm. Pharmacol.*, 1987, pp. 787-796, vol. 39.

Hsu, I. et al. "The 2:1 crystal complex of 2-aminopyridine and 5,5-diethylbarbituric acid (barbital)" *Acta Cryst.*, 1974, pp. 994-997, vol. B30.

Hsu, I. et al. "The 1:1 crystal complex of *N*-methyl-2-pyridone and 5,5-diethylbarbituric acid (barbital)" *Acta Cryst.*, 1974, pp. 998-1001, vol. B30.

Hsu, I. et al. "The crystalline complex (1:1) of salicylamide and 5-ethyl-5-isoamylbarbituric acid (amobarbital)" *Acta Cryst.*, 1974, pp. 843-846, vol. B30.

Hsu, I. et al. "The crystal structure of the 1:1 complex of acetamide with 5,5-diethylbarbituric acid (barbital)" *Acta Cryst.*, 1974, pp. 974-979, vol. B30.

Hsu, I. et al. "The crystal structure of the triclinic 1:2 complex of hexamethylphosphoramide with 5,5-diethylbarbituric acid (barbital)" *Acta Cryst.*, 1974, pp. 1299-1304, vol. B30.

Hsu, I. et al. "Hydrogen bonding NH. . . N of barbiturates: The 1:1 crystal complex of imidazole and 5,5-diethylbarbituric acid (barbital)" *Acta Cryst.*, 1974, pp. 988-993, vol. B30.

Ibragimov, B. "A simple correlation between the structures of different crystal modifications of a given host-guest complex and their crystallization temperatures" *Journal of Inclusion of Phenomena and Macrocyclic Chemistry*, 1999, pp. 345-353, vol. 34.

Ishida, T. et al. "Structural study of histamine $H_2$-receptor antagonists. Five 3-[2-(diamino- methyleneamino)-4-thiazolymethylthio] propionamidine and -amide derivatives" *Acta Cryst.*, 1989, pp. 505-512, vol. B45.

Katakai, R. et al. "Stepwise synthesis of oligopeptides with *N*-carboxy-$\alpha$-amino acid anhydrides. IV. Glycine NCA" *J. Org. Chem.*, 1972, pp. 327-329, vol. 37, No. 2.

Kawakami, Y. et al. "The rationale for E2020 as a potent acetylcholinesterase inhibitor" *Bioorganic & Medicinal Chemistry*, 1996, pp. 1429-1446, vol. 4, No. 9.

Kelders, H. et al. "Automated protein crystallization and a new crystal form of a subtilisin: eglin complex" *Protein Engineering*, 1987, pp. 301-303, vol. 1, No. 4.

Khalil, R. M. "Complexation of paracetamol with xanthine derivatives" *Egypt. J. Pharm. Sci.*, 1992, pp. 757-769, vol. 33, No. 5-6.

Kim, S. "Crystal structure of the 1:1 complex of 5-fluorouracil and 9-ethylhypoxanthine" *Science*, Nov. 24, 1967, pp. 1046-1048, vol. 158, No. 3804.

Kiryu, S. et al. "Crystal structure of a 1:1 aminopyrine-barbital complex" *Journal of Pharmaceutical Sciences*, May 1971, pp. 699-703, vol. 60, No. 5.

Kiryu, S. et al. "Crystal structure of a 1:1 aminopyrine-cyclobarbital complex" *Chem. Pham. Bull.*, 1974, pp. 1588-1592, vol. 22.

Klein, C. et al. "Molecular structure of two conformationally restrained fentanyl analogues: cis- and trans-isomers of N-{3-methyl-1-[1,2,3,4-tetrahydro) naphthyl]-4-piperidinyl}-Nphenylpropanamide" *Journal of Pharmaceutical Sciences*, Nov. 1985, pp. 1147-1151, vol. 74, No. 11.

Koshima, H. et al. "Photoreactivities of two kinds of bimolecular crystals formed from acridine and phenothiazine" *J. Chem. Soc., Perkins Trans. 2*, 1997, pp. 2033-2038.

Koshima, H. et al. "Polymorphs of a cocrystal with achiral and chiral structures prepared by pseudoseeding: tryptamine/hydrocinnamic acid" *Crystal Growth & Design*, 2001, pp. 355-357, vol. 1, No. 5.

Krishnamohan Sharma, C. V. et al. "X-ray crystal structure of $C_6H_3(CO_2H)_3$- 1,3,5•1.5(4,4'-bipy): a 'super trimesic acid' chicken-wire grid" *Chem. Commun.*, 1996, pp. 2655-2656.

Kuroda, R. et al. "Generation of a co-crystal phase with coloristic properties via solid state grinding procedures" *Chem. Commun.*, 2002, pp. 2848-2849.

Leiserowitz, L. et al. "The molecular packing modes and hydrogen-bonding properties of amide: dicarboxylic acid complexes" *Acta Cryst.*, 1977, pp. 2719-2733, vol. B33.

Leiserowitz, L. "Molecular packing modes. Carboxylic acids" *Acta Cryst.*, 1976, pp. 775-802, vol. B32.

Lynch, D. et al. "Molecular cocrystals of carboxylic acids. XXXI adducts of 2- aminopyrimidine and 3-amino-1,2,4-triazole with heterocyclic carboxylic acids" *Aust. J. Chem.*, 1998, pp. 403-408, vol. 51.

Macgillivray, L. et al. "Supramolecular control of reactivity in the solid state using linear molecular templates" *J. Am. Chem. Soc.*, 2000, pp. 7817-7818, vol. 122.

Mathias, J. et al. "Structural preferences of hydrogen-bonded networks in organic solution- the cyclic $CA_3• M_3$ 'rosette'" *J. Am. Chem. Soc.*, 1994, pp. 4316-4325, vol. 116.

Mastropaolo, D. et al. "Hydrogen bonding interaction of diphenylhydantoin and 9-ethyladenine" *Molecular Pharmacology*, 1983, pp. 273-277, vol. 23.

Maryanoff, B. "Stereochemistry in a medium-sized ring. Highly diastereoselective N-oxidation of a substituted 3-benzazonine. X-ray crystal structure of an unusual complex between an amine N-oxide and saccharin" *J. Org. Chem.*, 1990, pp. 760-764, vol. 55.

Martin, R. et al. "The caffeine-potassium chlorogenate molecular complex" *Phytochemistry*, 1987, pp. 273-279, vol. 26, No. 1.

Anderson, J. "Constitution of aurous compounds: Gold mirrors" *Nature*, Oct. 2, 1937, pp. 583-584, Letters to the Editor.

Robbins, A. H. et al. "The crystal structure of the 1:2 adduct of potassium triiodide and 5,5-diethylbarbituric acid (barbital)" *American Crystallographic Association- Series 2, Papers and Abstracts*, 1973, p. 87.

Beerges, P. et al. "Phenothiazine tetracyanoethylene" *Private Communication*, 1994.

Madarasz, J. et al. "Thermal, ftir and xrd study on some 1:1 molecular compounds of theophylline" *Journal of Thermal Analysis and Calorimetry*, 2002, pp. 281-290, vol. 69.

Caronna, T. et al. "Halogen bonding and Π•••Π stacking control reactivity in the solid state" *J. Am. Chem. Soc.*, 2004, pp. 4500-4501, vol. 126.

Zerkowski, J. et al. "Steric control of secondary, solid-state architecture in 1:1 complexes of melamines and barbiturates that crystallize as crinkled tapes" *J. Am. Chem. Soc.*, 1994, pp. 4298-4304, vol. 116.

Zaitu, S. et al. "1:1 Molecular complex of theophylline and p-nitroaniline" *Acta Cryst.*, 1995, pp. 2390-2392, vol. C51.

Kofler, L. et al., *Thermal micromethods for the study of organic compounds and their mixtures*, pp. 1-145, 148-351, 354-386, Innsbruck, Austria, 1980.

Quehenberger, H. "Concerning organic molecular compounds and their polymorphism" *Monatshefte für Chemie*, 1949, pp. 595-606, vol. 80, No. 5.

Wiedenfeld, H. et al. "The crystal structure of the theophylline-urea complex" *Arch. Pharm.*, 1986, pp. 654-659, vol. 319.

Bunick, G. et al, "The crystal and molecular structure of the complex 2,6-diamino-9- ethylpurine 5,5-diethylbarbituric acid" *American Crystallographic Association, Abstract Papers* Winter 1976, p. 30.

Buczak, G. et al. "Crystal structure and vibrational spectra of the 1:1 and 1:2 complexes of pyridine betaine with pentachlorophenol" *Journal of Molecular Structure*, 1997, pp. 143-151, vol. 436-437.

Tomura, M. et al. "One-dimensional zigzag chain structures with intermolecular C-H••• Π and C-H•••O interactions consisted of phthalic acid and pyridine derivatives" *Chemistry Letters*, 2001, pp. 532-533.

Zerkowski, J. et al. "Design of organic structures in the solid state: molecular tapes based on the network of hydrogen bonds present in the cyanuric acid•melamine complex" *J. Am. Chem. Soc.*, 1994, pp. 2382-2391, vol. 116.

Harkema, S. et al. "The crystal structure of urea oxalic acid (2:1)" *Acta Cryst.*, 1972, pp. 1646-1648, vol. B28.

Krantz, J. et al. "Sodium theophylline glycinate" *Journal of the American Pharmaceutical Association*, 1946, pp. 248-250.

Datta, S. et al. "Crystal structures of drugs: advances in determination, prediction and engineering" *Nature*, Jan. 2004, pp. 42-57, vol. 3.

Aakeröy, C. et at. "Charge-assisted hydrogen bonds and halogen-halogen interactions in organic salts: benzylammonium benzoates and pentaflourobenzoates" *Structural Chemistry*, 1999, pp. 229-242, vol. 10, No. 3.

Childs, S. et al. "Crystal engineering approach to forming cocrystals of amine hydrochlorides with organic acids. Molecular complexes of fluoxetine hydrochloride with benzoic, succinic, and fumaric acids" *J. Am. Chem. Soc.*, 2004, pp. 13335-13342, vol. 126.

Aakeröy, C. et al. "Modular supramolecular synthesis based on a dominance hierarchy of intermolecular interactions (Abstract)" 223rd ACS National Meeting in Orlando, FL., Apr. 7-11, 2002, published by the American Chemical Society, Washington, D.C.

Helfrich, B. et al. "Polymorphism as an indication of structural versatility (Abstract)" 223rd ACS National Meeting in Orlando, FL., Apr. 7-11, 2002, published by the American Chemical Society, Washington, D.C.

Weber, E. et al. "Synthesis of new Schiff bases: reaction of monofluorobenzaldehydes with 3-aminosulfolane hydrochloride (Abstract)" 216th ACS National Meeting in Boston, MA., Aug. 23-27, 1998, published by the American Chemical Society, Washington, D.C.

Scarbrough, F. et al. "Crystal structure of a complex between lumiflavin and 2,6- diamino-9-ethylpurine: a flavin adenine dinucleotide model exhibiting charge-transfer interactions" *Proc. Natl. Acad. Sci. USA*, Nov. 1976, pp. 3807-3811, vol. 73, No. 11.

Munn, R. et al. "A Model for resonance-assisted hydrogen bonding in crystals and its graph set analysis" *J. Phys. Chem. A*, 2001, pp. 6938-6942, vol. 105.

Lynch, D. et al. "1:1 Molecular complexes of 4-amino-N-(4,6-dimethylpyrimidin-2-yl) benzene-sulfonamide (sulfamethazine) with indole-2-carboxylic acid and 2,4-dinitrobenzoic acid" *Aust. J. Chem.*, 2000, pp. 383-387, vol. 53.

Aakeröy, C. et al. "Solid state, crystal engineering and hydrogen bonds" *Comprehensive Coordination Chemistry II* (ed. by McCleverty, J. et al.), pp. 679-688, Elsevier Ltd., Oxford, UK.

Levin, B. et al. "The not-so-trivial synthesis and characterization of heterocyclic boronic acids (Abstract)" 38th Midwest Regional Meeting of the American Chemical Society in Columbia, MO., Nov. 5-7, 2003, published by the American Chemical Society, Washington, D.C.

Smith, G. et al. "Interactions of aromatic carboxylic acids with quinolin-8-ol (oxine): Synthesis and the crystal structures of the proton-transfer compounds with the nitro-substituted benzoic acids" *Aust. J. Chem.*, 2001, pp. 171-175, vol. 54.

Stalker, R. et al. "Asymmetric synthesis of two new conformationally constrained lysine derivatives" *Tetrahedron*, 2002, pp. 4837-4849, vol. 58.

Voet, D. et al. "Barbiturates and adenine derivatives. Molecular structure of a hydrogen-bonded complex" *Journal of the American Chemical Society*, Aug. 9, 1972, pp. 5888-5891, vol. 94, No. 16.

Le Jeunne, C. et al. "Comparative efficacy and safety of calcium carbasalate plus metoclopramide versus ergotamine tartrate plus caffeine in the treatment of acute migraine attacks" *Eur. Neurol.*, 1999, pp. 37-43, vol. 41.

Aakeröy, C. et al. "Hydrogen-bonded layers of hydrogentartrate anions: two-dimensional building blocks for crystal engineering" *J. Mater. Chem.*, 1993, pp. 1129-1135, vol. 3, No. 11.

Hu, Z. et al. "Separation of 4-aminobenzoic acid by cocrystallization: Crystal structure of the complex of 4-aminobenzoic acid with (2R,3R)-tartaric acid" *Journal of Chemical Crystallography*, Dec. 2002, pp. 525-529, vol. 32, No. 12.

Guarrera, D. et al. "Molecular self-assembly in the solid state. The combined use of solid state NMR and differential scanning calorimetry for the determination of phase constitution" *Chem. Mater.*, 1994, pp. 1293-1296, vol. 6.

Doi, M. et al. "Conformational study of a potent human renin inhibitor: x-ray crystal structure of isopropyl (2R, 3S) -4-cyclohexyl-2-hydroxy-3-{N[(2R)-2-morpholinocarbonylmethy-3-(1-naphthyl) propionyl] —L-histidylamino}butyrate (KRI-1314), a pentapeptide analogue with amino acid sequence corresponding to the cleavage site of angiotensinogen" *J. Chem. Soc. Perkin Trans. 1*, 1991, pp. 1153-1158.

Crihfield, a. et al. "Crystal engineering through halogen bonding. 2. Complexes of diacetylene-linked heterocycles with organic iodides" *Crystal Growth & Design*, 2003, pp. 313-320, vol. 3, No. 3.

Aakeröy, C. et al. "A versatile route to porous solids: organic-inorganic hybrid materials assembled through hydrogen bonds" *Angew. Chem. Int. Ed.*, 1999, pp. 1815-1819, vol. 38, No. 12.

Shefter, E. et al., ACS, Abstr. Papers (Summer), 1970, 35, compound name: sulfathiazole-theophylline complex.

Shefter, E. et al., ACS, Abstr. Papers (Summer), 1970, 35, compound name: sulfathiazole-sulfanilamide complex.

Wiedenfeld, H. et al. "Solubilization of aminophenazone" *Arch. Pharm.*, 1982, pp. 633- 641, vol. 315.

Cacciapuoti, A. et al. "In vitro and in vivo activities of SCH 56592 (Posaconazole), a new triazole antifungal agent, against *Aspergillus* and *Candida*" *Antimicrobial Agents and Chemotherapy*, Aug. 2000, pp. 2017-2022, vol. 44, No. 8.

Callahan, J.C. et al. "Equilibrium moisture content of pharmaceutical excipients" *Drug Development and Industrial Pharmacy*, 1982, pp. 355-369, vol. 8, No. 3.

Dannaoui, E. et al. "Acquired itraconazole resistance in Aspergillus fumigatus" *Journal of Antimicrobial Chemotherapy*, 2001, pp. 333-340, vol. 47.

Denning, D. W. et al. "In vitro activity of Saperconazole (R66 905) compared with Amphotericin B and Itraconazole against *Aspergillus* species" *Eur. J. Clin. Microbial. Infect. Dis.*, 1990, pp. 693-697, vol. 9.

Dressman, J. B. et al. "Dissolution testing as a prognostic tool for oral drug absorption: immediate release dosage forms" *Pharmaceutical Research*, 1998, pp. 11-22, vol. 15, No. 1.

Ebert, W. R. "Soft elastic gelatin capsules: a unique dosage form" *Pharmaceutical Technology*, Oct. 1977, pp. 44-50, vol. 1, No. 5.

Gascon, M.—P. et al. "In vitro forecasting of drugs which may interfere with the biotransformation of midazolam" *Eur J. Clin. Pharmacol.*, 1991, pp. 573-578, vol. 41.

Heeres, J. et al. "Antimycotic azoles. 7. Synthesis and antifungal properties of a series of novel triazol-3-ones" *J. Med. Chem.*, 1984, pp. 894-900, vol. 27.

Honig, P. K. et al. "Itraconazole affects single-dose Terfenadine pharmacokinetics and cardiac repolarization pharmacodynamics" *J. Clin. Pharmacol.*, 1993, pp. 1201-1206, vol. 33.

Imai, T. et al. "Successful treatment of cerebral Aspergillosis with a high oral dose of Itraconazole after excisional surgery" *Internal Medicine*, Oct. 1999, pp. 829-832, vol. 38, No. 10.

Kovacs, J. et al. "New type of bridged monoamino-β-cyclodextrins" *Journal of Inclusion Phenomena and Molecular Recognition in Chemistry*, 1996, pp. 53-56, vol. 25.

Lavrijsen, A. P. M. et al. "Hepatic injury associated with itraconazole" *The Lancet*, Jul. 25, 1992, pp. 251-252, vol. 340.

Neuvonen, P. J. et al. "Itraconazole drastically increases plasma concentrations of lovastatin and lovastatin acid" *Clinical Pharmacology & Therapeutics*, 1996, pp. 54-61, vol. 60, No. 1.

Nomeir, A. A. et al. "Pharmacokinetics of SCH 56592, a new azole broad-spectrum antifungal agent, in mice, rats, rabbits, dogs, and cynomolgus monkeys" *Antimicrobial Agents and Chemotherapy*, Mar. 2000, pp. 727-731, vol. 44, No. 3.

Odds, F. C. "Antifungal activity of saperconazole (R 66 905) in vitro" *Journal of Antimicrobial Chemotherapy*, 1989, pp. 533-537, vol. 24.

Saksena, A. K. et al. "Advances in the chemistry of novel broad-spectrum orally active azole antifungals: recent studies leading to the discovery of SCH 56592" in *Advances in the Chemistry of Novel Broad-Spectrum Orally Active Azole Antifungals* (Royal Soc. Chem., Cambridge), 1997, pp. 180-199.

Saksena, A. K. et al. "Concise asymmetric routes to 2,2,4-trisubstituted tetrahydrofurans via chiral titanium imide enolates: key intermediates towards synthesis of highly active azole antifungals SCH 51048 and SCH 56592" *Tetrahedron Letters*, 1996, pp. 5657-5660, vol. 37, No. 32.

Hepperle, M. et al. "Mono N-arylation of piperazine(III): metal-catalyzed N-arylation and its application to the novel preparations of the antifungal posaconazole and its advanced intermediate" *Tetrahedron Letters*, 2002, pp. 3359-3363, vol. 43.

Van Cutsem, J. V. et al. "Oral and parenteral therapy with saperconazole (R 66905) of invasive aspergillosis in normal and immunocompromised animals" *Antimicrobial Agents and Chemotheraphy*, Dec. 1989, pp. 2063-2068, vol. 33, No. 12.

West, A. R., "Solid Solutions" In: *Solid State Chemistry and its Applications*, 1988, pp. 358-365, Wiley, NY.

Aronhime, J. et al. "Crystalline forms of pharmaceuticals and characterization thereof", Oral Presentation, Mar. 8, 2005, USPTO, Alexandria, VA.

Desiraju, G. R. "Chemistry beyond the molecule" *Nature*, Jul. 26, 2001, pp. 397-400, vol. 412.

Physician's Desk Reference, 56th Ed., pp. 1800-1804, 2002.

Kim, H. et al. "High-performance liquid chromatographic analysis of the anti-fungal agent SCH 56592 in dog serum" *Journal of Chromatography B*, 2000, pp. 93-98, vol. 738.

Vippagunta, S. R. et al. "Crystalline solids" *Advanced Drug Delivery Reviews*, 2001, pp. 3-26, vol. 48.

McCrone, W. C. "Polymorphism", In: *The Physics and Chemistry of the Organic Solid State*, vol. II, Fox, D. et al. (eds.), 1965, pp. 725-767, Interscience, New York.

Leger, J.M. et al. "Crystal Structure of the 1:1 Sulfacetamide-Caffeine Complex" *Acta Cryst.*, 1977, pp. 1455-1459, vol. B33.

Simonov, Y. et al. "Structure of the caffeine-copper(II) acetate additional compound", *Izvestiya Akademli Nauk Moldayskoi SSR, Seriya Fiziko-Tekhnicheskikh i Matematicheskikh Nauk*, 1972, vol. 3, pp. 83-84, abstract only.

Weissbuch, I. et al. "Understanding and control of nucleation, growth, habit, dissolution and structure of two- and three-dimensional crystals using 'tailor-made' auxiliaries" *Acta Cryst.*, 1995, B51:115-148.

Faught, E. et al. "Topiramate Dose-Ranging Trial in Refractory Partial Epilepsy", *Amer. Epilepsy Soc. Proc.*, (1995), p. 33, vol. 36, Supp. 4.

Privitera, M. et al. "Dose-Ranging Trial with Higher Doses of Topiramate in Patients with Resistant Partial Seizures", *Amer. Epilepsy Soc. Proc.*, 1995, p. 33, vol. 36, Supp. 4.

Sachdeo, S. K. et al. "Topiramate: Double-Blind Trial as Monotherapy", *Amer. Epilepsy Soc. Proc.*, 1995, p. 33, vol. 36, Supp. 4.

Press Release. "Clinical Development of Topiramate for Obesity Extended to Simplify Dosing, Improve Tolerability". http://www.orthomcneil.com/news/article020402.html (Feb. 4, 2002), N.J.

Rosenfeld, W. E. "Topiramate: A Review of Preclinical, Pharmacokinetic, and Clinical Data", *Clinical Therapeutics*, 1997, pp. 1294-1308, vol. 19, No. 6.

Physician's Desk Reference, 56th Edition, 2002, pp. 2590-2595.

Database WPI, Section Ch, Week 197936, Derwent Publishing Ltd., London, Great Britain, Class B02, AN 1979-65538B, XP002282989 and JP 54 095589A (Sumitomo) 1979 Abstract.

Fitzgerald, G. A. "The Coxibs, Selective Inhibitors of Cyclooxygenase-2", *New England Journal of Medicine*, vol. 345, No. 6, Aug. 9, 2001, pp. 433-442.

Aakeröy, C. et al. "Low-dimensional architectures of silver coordination compounds assembled via amide-amide hydrogen bonds" *Crystal Engineering*, 1998, pp. 39-49, vol. 1, No. 1.

Aakeröy, C. et al. "Molecular mechanics and crystal engineering" *Crystal Engineering* (ed. by Seddon, K. R. et al.), 1999, pp. 69-82, Kluwer Academic Publishers, The Netherlands.

Aakeröy, C. et al. "New building blocks for crystal engineering. Syntheses and crystal structures of oxime-substituted pyridines" *Cryst. Eng. Comm.*, 2000, pp. 1-6, vol. 27.

Aakeröy, C. et al. "Novel colorless composite materials for nonlinear optics" *Adv. Mater.*, 1993, pp. 364-367, vol. 5, No. 5.

Aakeröy, C. et al. "Organic assemblies of 2-pyridones with dicarboxylic acids" *Tetrahedron*, 2000, pp. 6693-6699, vol. 56.

Aakeröy, C. et al. "Pitfalls in the supramolecular assembly of silver(I) coordination compounds" *Journal of Molecular Structure*, 1999, pp. 91-101, vol. 474.

Aakeröy, C. et al. "A structural study of 2-amino-5-nitropyridine and 2-amino-3-nitropyridine: intermolecular forces and polymorphism" *J. Mater. Chem.*, 1998, pp. 1385-1389, vol. 8, No. 6.

Aakeröy, C. et al. "Supramolecular assembly of low-dimensional silver (I) architectures via amide-amide hydrogen bonds" *Chem. Commun.*, 1998, pp. 1067-1068.

Aakeröy, C. et al. "'Total synthesis' supramolecular style: design and hydrogen-bond-directed assembly of ternary supermolecules" *Angew. Chem. Int. Ed.*, 2001, pp. 3240-3242, vol. 40, No. 17.

Aakeröy, C. et al. "Two-fold interpenetration of 3-D nets assembled via three-co-ordinate silver(I) ions and amide-amide hydrogen bonds" *J. Chem. Soc., Dalton Trans.*, 1998, pp. 1943-1945.

Ahn, S. et al. "Polymorphs of a 1:1 cocrystal with tunnel and layer structures: p,p'- biphenol/dimethyl sulfoxide" *Crystal Growth & Design*, 2001, pp. 107-111, vol. 1, No. 2.

Aakeröy, C. at al. "Hydrogen-bonding in solids" *Crystal Engineering* (ed. by Seddon, K. R. et al.), 1999, pp. 303-324, Kluwer Academic Publishers, The Netherlands.

Aakeröy, C. et al. "Di-hydroxy malonic acid as a building block of hydrogen-bonded 3-dimensional architectures" *Journal of Chemical Crystallography*, 1998, pp. 111-117, vol. 28, No. 2.

Aakeröy, C. et al. "Do polymorphic compounds make good cocrystallizing agents? A structural case study that demonstrates the importance of synthon flexibility" *Crystal Growth & Design*, 2003, pp. 159-165, vol. 3, No. 2.

Aakeröy, C. et al. "Heteromeric intermolecular interactions as synthetic tools for the formation of binary co-crystals" *Cryst. Eng. Comm.*, 2004, pp. 19-24, vol. 6, No. 5.

Aakeröy, C. et al. "Hydrogen-bond assisted assembly of organic and organic-inorganic solids" *Crystal Engineering: From Molecules and Crystals to Materials*, 1999, pp. 89-106, Kluwer Academic Publishers, The Netherlands.

Aakeröy, C. et al. "A high-yielding supramolecular reaction" *J. Am. Chem. Soc.*, 2002, 14425-14432, vol. 124.

Aakeröy, C. et al. "The hydrogen bond and crystal engineering" *Chemical Society Reviews*, 1993, pp. 397-407.

Ammar, H. O. et al. "Effect of Aromatic Hydrotropes on the Solubility of Carbamazepine. Part II: Effect of Nicotinamide, Sodium Salts of Benzoic, Naphthoic and Nicotinic Acids" *Egypt. J. Pharm. Sci.*, 1994, pp. 209-223, vol. 35, No. 1-6.

De Jong, E. M. G. J. et al. "Dystrophic Psoriatic Fingernails Treated with 1% 5-Fluorouracil in a Nail Penetration-Enhancing Vehicle: A Double-Blind Study" *Dermatology*, 1999, pp. 313-318, vol. 199, No. 4.

Dvorkin et al. "Crystal and Molecular Structure of a Complex 18-crown-6 with 6-chloro-7- sulfamido-3,4-dihydro-1,2,4-benzothiadiazine-1, 1-dioxide (hypothiazide) of 1:1 Composition" *Kristallagrafiya*, 1990, pp. 682-686, vol. 35, No. 3 (with English abstract).

Walsh, R. D. et al. "Crystal Engineering of the Composition of Pharmaceutical Phases" *Chem. Commun.*, 2003, pp. 186-187.

* cited by examiner

PHARMACEUTICAL PROPYLENE GLYCOL SOLVATE COMPOSITIONS

This application claims the benefit of U.S. Provisional Application No. 60/486,713, filed Jul. 11, 2003, U.S. Provisional Application No. 60/459,501, filed Apr. 1, 2003, U.S. Provisional Application No. 60/456,608, filed Mar. 21, 2003, U.S. Provisional Application No. 60/456,027, filed Mar. 18, 2003, U.S. Provisional Application No. 60/441,335, filed Jan. 21, 2003, and U.S. Provisional Application No. 60/437,516, filed Dec. 30, 2002. The content of each of these applications is hereby incorporated by reference in its entirety.

FIELD OF THE INVENTION

The present invention relates to drug-containing compositions, pharmaceutical compositions comprising such drugs, and methods for preparing same.

BACKGROUND OF THE INVENTION

Drugs in pharmaceutical compositions can be prepared in a variety of different forms. Such drugs can be prepared so as to have a variety of different chemical forms including chemical derivatives or salts. Such drugs can also be prepared to have different physical forms. For example, the drugs may be amorphous or may have different crystalline polymorphs, perhaps existing in different solvation or hydration states. By varying the form of a drug, it is possible to vary the physical properties thereof. For example, crystalline polymorphs typically have different solubilities from one another, such that a more thermodynamically stable polymorph is less soluble than a less thermodynamically stable polymorph. Pharmaceutical polymorphs can also differ in properties such as shelf-life, bioavailability, morphology, vapor pressure, density, color, and compressibility. Accordingly, variation of the solvation state of a drug is one of many ways in which to modulate the physical properties thereof.

A solvate may be defined as a compound formed by solvation, for example as a combination of solvent molecules with molecules or ions of a solute. Well known solvent molecules include water, alcohols and other polar organic solvents. Alcohols include methanol, ethanol, n-propanol, isopropanol, n-butanol, isobutanol, and t-butanol. Alcohols also include polymerized alcohols such as polyalkylene glycols (e.g., polyethylene glycol, polypropylene glycol). The best-known and preferred solvent is typically water, and solvate compounds formed by solvation with water are termed hydrates.

Propylene glycol (1,2-propanediol) is a known substance which is a liquid at ambient temperature. As far as the applicants are aware, propylene glycol is not generally well-known for use in the formation of solvates. U.S. Pat. No. 3,970,651 does disclose the use of propylene glycol in the formation of a crystalline cephalosporin derivative. According to this disclosure a propylene glycolate derivative of a specific cephalosporin zwitterion may be formed in the presence of propylene glycol at acidic pH. This disclosure indicates that the propylene glycol derivative is more stable in solid form than the corresponding ethanolate, especially having excellent colour stability and thermal stability. No other solvates are disclosed in this US patent other than the specific solvate of cephalosporin.

In pharmaceutical formulations certain chemical classes of drugs pose particular problems in preparing pharmaceutical formulations for medical use. One such problem arises in the case of hygroscopic drugs, which tend to absorb water from the air. This is disadvantageous because it makes storage of the drug difficult and can cause degradation of the drug in some cases. Such compounds must be handled in controlled humidity environments during manufacture in order to prevent potency errors due to the changing weight of the drug. The final product must be packaged in individual moisture resistant blisters in order to prevent changes in or degradation of the product. Another problem arises from variable hydration states: molecules may change to a more or less stable form as water, a volatile liquid, is lost. Such changes have been known to cause some hydrates to become amorphous. Likewise, absorption of water by a hygroscopic molecule can plasticize the system and lead to recrystallization as a less stable polymorph.

SUMMARY OF THE INVENTION

Solvates are rarely used in pharmaceuticals because the solvents are usually volatile thus making it difficult to maintain the solvent in the crystal. If one were to desolvate a pharmaceutical solvate or if it desolvated due to storage conditions or otherwise, it could lead to the formation of multiple polymorphs or complete collapse of the crystal structure, forming an amorphous compound with different physical properties. Obviously, this batch-to-batch variability and questionable shelf life is undesired. Typically people find solvates of common solvents, such as propanol and ethanol. Propylene glycol is similar in structure to propanol, but is not thought of as a solvent. Propylene glycol solvates of the present invention desolvate only at considerably higher temperatures and harsher conditions than traditional solvates. Propylene glycol solvates are also pharmaceutically acceptable in much larger amounts than one would expose people to with a traditional solvate. Thus, the propylene glycol solvates of the present invention have characteristics that are vastly superior to traditional solvates.

It has now been found that amorphous, crystalline, hygroscopic, or poorly soluble drugs can be made more soluble, more stable, and less hygroscopic and can be prepared simply, reliably and inexpensively.

In a first aspect, the present invention provides a pharmaceutical composition comprising a propylene glycol solvate of a drug which is hygroscopic or has low aqueous solubility. It has surprisingly been found that by using propylene glycol to form a solvate of a hygroscopic drug, the hygroscopicity of the drug is decreased and/or the stability and aqueous solubility is increased. The drug is therefore much easier to formulate and store than its counterpart untreated or hydrated form.

A number of advantages have been found from the use of propylene glycol in this way. First of all, a higher temperature is required to remove propylene glycol as compared with water or ethanol. This therefore results in an increased thermal stability. Thus the invention further relates to methods of making a pharmaceutical solvate more stable at high temperatures by making a PG solvate of the drug. Secondly, propylene glycol solvates are generally more pharmaceutically acceptable than other common solvates, including those formed from alcohols other than ethanol. It has further been found that the PG solvates of the present invention have fewer solvation states than hydration states. This is beneficial because production and quality of a drug can be more predictable and consistent. Thus an aspect of the present invention relates to methods of reducing the number of hydration states by making a PG solvate of a drug. PG solvates are also beneficial in addressing the problem of polymorphism. Thus an aspect of the present invention relates to methods of reducing the rate and extent a drug changes form and methods of reducing the chance of making an unwanted form because the PG solvates drive production of a single form. Another aspect of the present invention relates to changing the crystal habit of the drug crystal and preventing a drug crystalline habit from changing to a different habit.

The invention relates to making a pharmaceutical that can be made as a hydrate, more soluble or stable by forming a PG solvate of the drug.

The invention further relates to making a pharmaceutical more stable in a humid environment by making a PG solvate of the drug.

The invention further relates to making a crystalline compound from a pharmaceutical that does not readily crystallize by making a crystalline PG solvate of the drug.

The invention further relates to increasing the solubility of a crystalline pharmaceutical by making a PG solvate of the drug.

The invention further relates to methods of lowering the amount of drug solvation during wet granulation by making a PG solvate of the drug.

A particularly important aspect of the present invention is the realization that formation of propylene glycol solvates is applicable in a general way to drugs whereby the above advantages may be conferred. For example, the invention further relates to reducing the level of hygroscopicity of a pharmaceutical metal salt (crystalline, amorphous, solvate (e.g., hydrate)) by forming a PG solvate of the salt. Surprisingly, it has been found that the invention is particularly applicable to those drugs that are in the form of metal salts, such as alkali metal or alkaline earth metal salts. This is especially the case where the metal is selected from sodium, potassium, lithium, calcium and magnesium. Such salts can be hygroscopic and it has hitherto been difficult to find a suitable general means of formulation for these drugs.

Generally, the molar ratio of propylene glycol to drug in the solvate is in the range 0.5 to 2, (e.g., 0.5, 1.0, 1.5, 2.0). Depending on the nature of the drug, the ratio of propylene glycol to drug in the solvate may be approximately 0.25, 0.33, 0.5, 0.67, 0.75, 1.0, 1.5, 2.0 or 3.0.

The composition may further comprise a pharmaceutically-acceptable diluent, excipient or carrier and details of pharmaceutical compositions are also set out in further detail below. The solvate of the pharmaceutical composition according to the present invention is preferably in a crystalline form.

Advantageously, the powder X-ray diffraction (PXRD) spectrum of the composition according to the invention differs from the corresponding powder X-ray diffraction spectrum of unsolvated drug by at least one property selected from:

(i) a loss of at least one peak;
(ii) shifting of more than half the peaks at the 2-theta angle by at least 0.2, 0.3, 0.4, or 0.5 degrees; or
(iii) formation of at least one new peak.

It is preferred that the solvate is stable to temperatures of up to 50 degrees C. under a stream of nitrogen gas in a thermogravimetric analysis apparatus.

The PXRD could be the same if their were a host-guest relationship and the PG was not completely frozen out. This would be an inclusion compound rather than a true solvate, but it may still be less hygroscopic than a hydrate, less prone to solvent loss than an inclusion with ethanol, less prone to being filled by some toxic co-solvent if PG fits well, and less prone to polymorphism to a less soluble form due to instability caused by a vacated void in the structure. The DSC transitions are likely to occur at different temperatures and have different intensities than for the parent molecule and it's other hydrates/solvates.

In one aspect of the invention, the drug is a hygroscopic drug, including hygroscopic metal salts. A non-exhaustive list of hygroscopic drugs is set out in Table 1, along with their suppliers and routes of administration.

TABLE 1

Hygroscopic Drugs

| Product (company) | Active ingredient | Hygroscopic | Route(s) of Administration |
|---|---|---|---|
| Solu-Medrol (P&U) | Methyl prednisolone succinate ester | X | Intravenous |
| Primaxin IV and IM (Merck) | Imipenem/cilastatin | X (cilastatin) | Intravenous/ Intramuscular |
| Vitravene Injection (CIBA) | Fomivirsen sodium | X | Intravenous |
| Baycol (Bayer) | Cerivastatin sodium | X | Oral |
| Synercid IV (Aventis) | Dalfopristin/ Quinopristin | X | Intravenous |
| Factrel (Wyeth) | Gonadorelin HCl (decapeptide) | X | Intravenous/ Subcutaneous |
| Clindets Pledgets (Stiefel) | Clindamycin phosphate (ester prodrug) | X | Topical |
| Famvir (SKB) | Famciclovir | X | Oral |
| Nascobal Gel (Schwarz) | Cyanocobalamin | X | Intranasal |
| Tasmar (Roche) | Tolcapone | X | Oral |
| Ellence Injection (P&U) | Epirubicin HCl | X | Intravenous |
| Colestid (P&U) | Colestipol HCl (anion excluded) | X | Oral |
| Pfizerpen Injection (Pfizer) | Penicillin G potassium | X | Intravenous |
| Bacitracin Injection (Paddock) | Bacitracin (peptide) | X | Intravenous |
| Lescol (Novartis) | Fluvastatin sodium | X | Oral |
| Voltaren XR (Novartis) | Diclofenac sodium | X | Oral |
| Salagen (MGI) | Pilocarpine HCl | X | Oral |
| Urecholine injection (Merck) | Bethanechol chloride | X | Intravenous |
| Syprine (Merck) | Trientine 2(HCl) | X | Oral |
| Singulair chewable (Merck) | Montelukast sodium | X | Oral |
| Mustargen injection (Merck) | Mechlorethamine HCl | X | Intravenous |
| Hydrocortone phosphate injection (Merck) | Hydrocortisone phosphate ester | X | Intravenous |
| Decadron phosphate injection (Merck) | Dexamethasone phosphate ester | X | Intravenous |
| Gastrocrom (Medeva) | Chromolyn sodium | X | Oral |
| Mestinon (ICN) | Pyridostigmine bromide | X | Oral |
| Adipex-P (Gate) | Phentermine HCl | X | Oral |
| Micardis (Boehringer-Ingelh.) | Telmisartan | X | Oral |
| Cerubidine injection (Bedford) | Daunorubicin HCl | X | Intravenous |
| Biltricide (Bayer) | Praziquantel | X | Oral |
| Elmiron (Alza) | Pentosan polysulfate sodium | X | Oral |

In one embodiment, the formulation comprises celecoxib. Although the invention is not limited to this particular drug, celecoxib provides a suitable example of the efficacy of the invention. Further details of celecoxib are set out below. In a further embodiment, the drug comprises naproxen, further details of which are also set out below.

In another aspect of the invention, the drug has low aqueous solubility. Typically, low aqueous solubility in the present application refers to a compound having a solubility in water which is less than or equal to 10 mg/ml, when measured at 37 degrees C., and preferably less than or equal to 5 mg/ml or 1 mg/ml. "Low aqueous solubility" can further be defined as less than or equal to 900, 800, 700, 600, 500, 400, 300, 200 150 100, 90, 80, 70, 60, 50, 40, 30, 20 micrograms/ml, or further 10, 5 or 1 micrograms/ml, or further 900, 800, 700, 600, 500, 400, 300, 200 150, 100 90, 80, 70, 60, 50, 40, 30, 20, or 10 ng/ml, or less than 10 ng/ml when measured at 37 degrees C. Aqueous solubility can also be specified as less than 500, 400, 300, 200, 150, 100, 75, 50 or 25 mg/ml. As embodiments of the present invention, solubility can be increased 2, 3, 4, 5, 7, 10, 15, 20, 25, 50, 75, 100, 200, 300, 500, 750, 1000, 5000, or 10,000 times by making a PG solvate of the neutral (crystalline or amorphous), salt, or solvate form (e.g., hydrate, ethanolate, methanolate, isopropanolate, etc.). Further aqueous solubility can be measured in simulated gastric fluid (SGF) rather than water. SGF (non-diluted) of the present invention is made by combining 1 g/L Triton X-100 and 2 g/L NaCl in water and adjusting the pH with 200 mM HCl to obtain a solution with a final pH=1.7.

PG solvates of steroids are also included as embodiments of the present invention. Steroids are an important class of drugs which have low aqueous solubility. Particularly important steroids include acetoxypregnenolone, alclometasone dipropionate, aldosterone, anagestone, norethynodrel, androsterone, betamethasone, budesonide, chlormadinone, chloroprednisone, corticosterone, cortisone, cyclosporine, desogestrel, desoximethasone, desoxycorticosterone, dexamethasone, dichlorisone, dimethisterone, equilenin, equilin, estradiol, estriol, estrogens, estrone, ethisterone, ethynodiol di, ethynyl estradiol, fludrocortisone, fludrocortisone, flunsolide, fluocinolone acetonide, fluorohydrocortisone, fluorometholone, fluoxymesterone, fluprednisolone, flurandrenolide, flurandrenolone, flurogestone, fluticasone propionate, hydrocortisone, hydroxydion, hydroxymethylprogesterone, hydroxyprogesterone, leuprolide, levonorgestrel, loteprednol etabonate, medroxyprogesterone, melengestrol, mesalamine, mestranol, methandrostenolone, methazolamide, methyl testosterone, methylandrostenediol, methylprednisolone, mometasone furoate, norelgestromin, norethandrolone, norethindrone, norethindrone, norethisterone, norgestimate, norgestrel, normethisterone, ondansetron hydrochloride, oxandrolone, oxymetholone, paramethasone, paramethasone, prednisolone, prednisolone, prednisone, pregnenolone, progesterone, prometholone, spironolactone, testosterone, testosterone enanthate, triamcinolone, triamcinolone acetonide, triamcinolone acetonide, vetamethasone disodium phosphate (for some steroids alternative names are included). Formulating steroid drugs presents a problem because of their low aqueous solubility. Embodiments of the present invention are methods of increasing the solubility of steroids by making a PG solvate. Solubility can be specified as discussed above. It is difficult to make crystals of steroids because of their planar structure. Crystallization can be facilitated by making PG solvates. Thus, crystalline PG solvates of steroids and methods of making the same are included in embodiments of the present invention. Steroids generally tend to form non-stoichiometric channel hydrates in which water molecules are trapped in channels between planar steroid regions. Thus, embodiments of the present invention include inhibiting channel formation in steroids by making a PG solvate. Metal salts of steroid drugs can be made and are another example of hygroscopic drugs. Thus, steroid PG solvates are in accordance with one aspect of the present invention. Steroid drugs, whether hygroscopic or not, surprisingly and advantageously form stoichiometric solvates with propylene glycol. Further, the dissolution rate and solubility can be increased with propylene glycol solvates. Thus, the steroid solvates have surprisingly new properties that make them more favourable for pharmaceutical use and are easier to handle than other forms such as hydrates.

In a further aspect, the present invention provides a method for preparing a propylene glycol solvate of a drug, which method comprises:

(a) contacting propylene glycol with a drug in solution;
(b) crystallizing a propylene glycol solvate of the drug from the solution; and
(c) isolating the solvate. (the drug may be, for example, a hygroscopic drug or a drug of low aqueous solubility).

In a further aspect, the present invention provides a method for decreasing the hygroscopicity of a drug, which method comprises (a) contacting the drug with propylene glycol in solution;
(b) crystallizing a propylene glycol solvate of the drug from the solution; and
(c) isolating the solvate, wherein the solvate has decreased hygroscopicity as compared to the drug.

In a further aspect, the present invention provides a method for increasing the aqueous solubility of a drug, which method comprises (a) contacting the drug with propylene glycol in solution;
(b) crystallizing a propylene glycol solvate of the drug from the solution; and
(c) isolating the solvate, wherein the solvate has increased aqueous solubility as compared to the drug.

Typically, conditions for making a solvate are the same as for preparing the corresponding non-solvated form of the drug: the solvate of neutral compound would not be pH controlled; the solvate of an acid addition salt would be prepared by including PG with the drug and the acid; and the solvate of a base addition salt would involve adding the drug, the desired base, and the PG. Different co-solvent systems, anti-solvents, or temperature conditions may be used to encourage PG solvate formation. Seed crystals may be added if they have previously been prepared and isolated.

The step of isolating the solvate may include separating the solution phase from the solvate. Any common method of separation may be employed, including filtration and decanting. The crystalline solvate may be rinsed one or more times with an appropriate solvent following filtration or decanting. The crystalline solvate is preferably dried to remove excess solution phase. Drying may be carried out by thermal processing, vacuum, blowing a stream of gas such as air, nitrogen, argon or another inert gas, or a combination of any or all of these methods. The intention of the rinsing and drying steps is to remove impurities including residual co-solvents and excess PG, acid, or base if used.

The invention will now be described in further detail, by way of example only, with reference to the accompanying drawings.

DETAILED DESCRIPTION OF THE INVENTION

Figure 1:
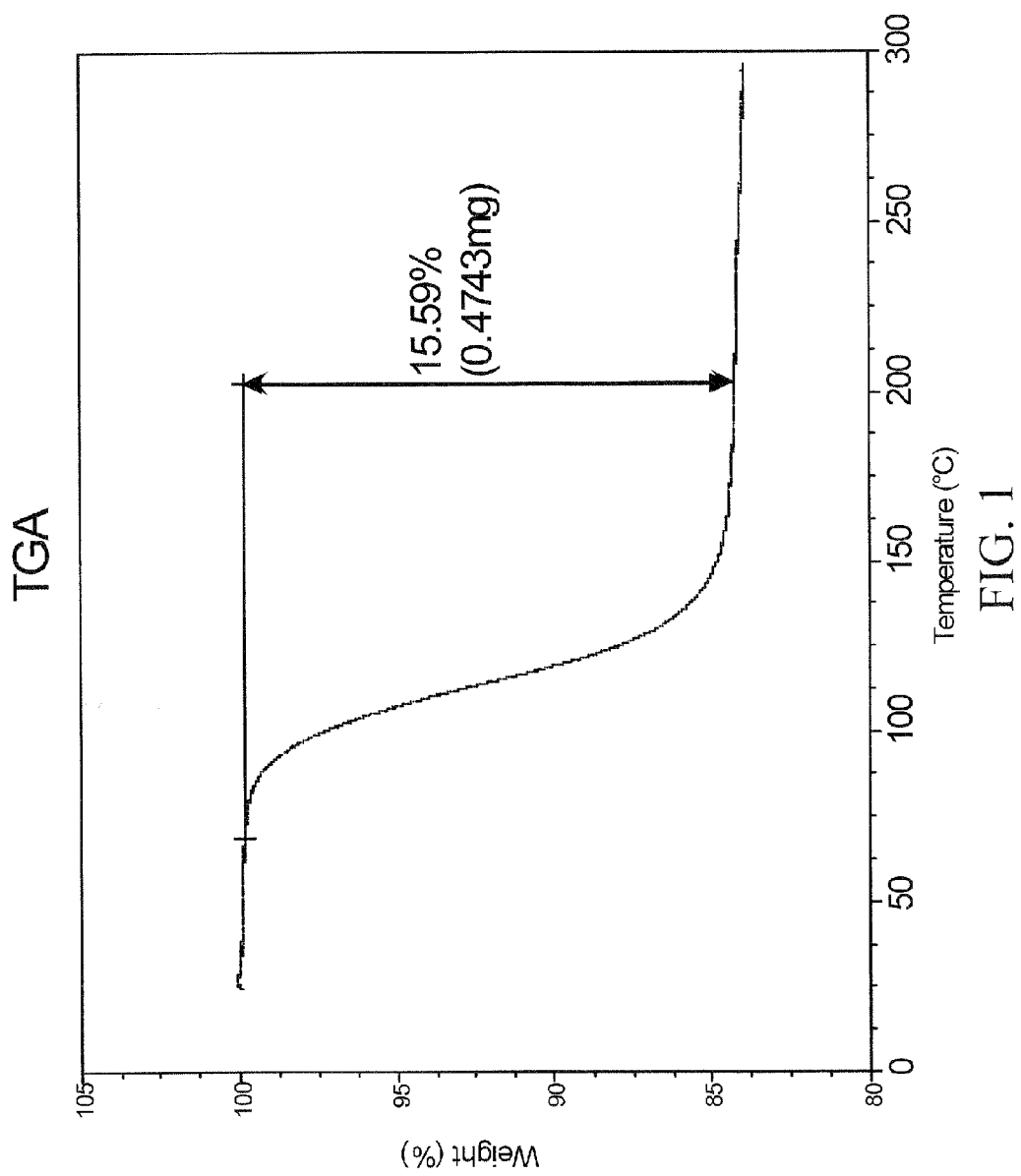
FIG. 1 shows a thermogravimetric analysis of a propylene glycol solvate of a celecoxib sodium salt.

The present invention relates to propylene glycol solvate forms, preferably stoichiometric, of certain drugs, including those which are hygroscopic or have low aqueous solubility. Whilst the invention is applicable to any such drugs in general, metal salts of the non-steroidal anti-inflammatory drug celecoxib serve to illustrate the present invention by way of example. Unlike traditional non-steroidal anti-inflammatory drugs (NSAIDs), celecoxib is a selective inhibitor of cyclooxygenase II (COX-2) which causes fewer side effects when administered to a subject. The present applicants have identified new forms of celecoxib that have improved properties, particularly as oral formulations. The applicants have found that a stable, crystalline sodium salt of celecoxib can be synthesised which is significantly more soluble in water than the neutral celecoxib on the market. This sodium salt, or other metal salts can subsequently be improved according to the present invention by the production of a propylene glycol solvate thereof.

Salts of celecoxib are formed by reaction of celecoxib with an acceptable base. Acceptable bases include, but are not limited to, metal hydroxides and alkoxides with sufficiently high $pK_a$'s (e.g., $pK_a$'s greater than about 11 to about 12).

Naproxen is a further API which may be used to illustrate the present invention. Naproxen is a member of the ibufenac group of NSAIDs. This API is practically insoluble in water. Other examples of illustrations of the present invention include olanzapine and cortisone acetate.

An aspect of the present invention provides a pharmaceutical composition comprising a propylene glycol solvate of a drug that is less hygroscopic than the amorphorous, neutral crystalline, or salt crystalline form, and/or has greater aqueous solubility. Hygroscopicity should be assessed by dynamic vapor sorption analysis, in which 5-50 mg of the compound is suspended from a Cahn microbalance. The compound being analyzed should be placed in a non-hygroscopic pan and its weight should be measured relative to an empty pan composed of identical material and having nearly identical size, shape, and weight. Ideally, platinum pans should be used. The pans should be suspended in a chamber through which a gas, such as air or nitrogen, having a controlled and known percent relative humidity (% RH) is flowed until eqilibrium criteria are met. Typical equilibrium criteria include weight changes of less than 0.01% change over 3 minutes at constant humidity and temperature. The relative humidity should be measured for samples dried under dry nitrogen to constant weight (<0.01% change in 3 minutes) at 40 degrees C. unless doing so would de-solvate or otherwise convert the material to an amorphous compound. In one aspect, the hygroscopicity of a dried compound can be assessed by increasing the RH from 5 to 95% in increments of 5% RH and then decreasing the RH from 95 to 5% in 5% increments to generate a moisture sorption isotherm. The sample weight should be allowed to equilibrate between each change in % RH. If the compound deliquesces or becomes amorphous between above 75% RH, but below 95% RH, the experiment should be repeated with a fresh sample and the relative humidity range for the cycling should be narrowed to 5-75% RH or 10-75% RH instead of 5-95% RH. If the sample cannot be dried prior to testing due to lack of form stability, than the sample should be studied using two complete humidity cycles of either 10-75% RH or 5-95% RH, and the results of the second cycle should be used if there is significant weight loss at the end of the first cycle.

Hygroscopicity can be defined using various parameters. For purposes of the present invention, a non-hygroscopic molecule should not gain or lose more than 1.0%, or more preferably, 0.5% weight at 25 degrees C. when cycled between 10 and 75% RH (relative humidity at 25 degrees C.). The non-hygroscopic molecule more preferably should not gain or lose more than 1.0%, or more preferably, 0.5% weight when cycled between 5 and 95% RH at 25 degrees C., or more than 0.25% of its weight between 10 and 75% RH. Most preferably, a non-hygroscopic molecule will not gain or lose more than 0.25% of its weight when cycled between 5 and 95% RH.

Alternatively, for purposes of the present invention, hygroscopicity can be defined using the parameters of Callaghan et al., *Equilibrium moisture content of pharmaceutical excipients*, in Drug Dev. Ind. Pharm., Vol. 8, pp. 335-369 (1982). Callaghan et al. classified the degree of hygroscopicity into four classes.

| | |
|---|---|
| Class 1: Non-hygroscopic | Essentially no moisture increases occur at relative humidities below 90%. |
| Class 2: Slightly hygroscopic | Essentially no moisture increases occur at relative humidities below 80%. |
| Class 3: Moderately hygroscopic | Moisture content does not increase more than 5% after storage for 1 week at relative humidities below 60%. |
| Class 4: Very hygroscopic | Moisture content increase may occur at relative humidities as low as 40 to 50%. |

Alternatively, for purposes of the present invention, hygroscopicity can be defined using the parameters of the European Pharmacopoeia Technical Guide (1999, p. 86) which has defined hygrospocity, based on the static method, after storage at 25 degrees C. for 24 h at 80% RH:

Slightly hygroscopic: Increase in mass is less than 2 percent m/m and equal to or greater than 0.2 percent m/m.

Hygroscopic: Increase in mass is less than 15 percent m/m and equal to or greater than 0.2 percent m/m.

Very hygroscopic: Increase in mass is equal to or greater than 15 percent m/m.

Deliquescent: Sufficient water is absorbed to form a liquid.

PG solvates of the present invention can be set forth as being in Class 1, Class 2, or Class 3, or as being Slightly hygroscopic, Hygroscopic, or Very hygroscopic. PG solvates of the present invention can also be set forth based on their ability to reduce hygroscopicity. Thus, preferred PG solvates of the present invention are less hygroscopic than the non-PG solvated reference compound, e.g., the reference compound of a celecoxib sodium salt PG solvate is celecoxib sodium salt. Further included in the present invention are PG solvates that do not gain or lose more than 1.0% weight at 25 degrees C. when cycled between 10 and 75% RH, wherein the reference compound gains or loses more than 1.0% weight under the same conditions. Further included in the present invention are PG solvates that do not gain or lose more than 0.5% weight at 25 degrees C. when cycled between 10 and 75% RH, wherein the reference compound gains or loses more than 0.5% or more than 1.0% weight under the same conditions. Further included in the present invention are PG solvates that do not gain or lose more than 1.0% weight at 25 degrees C. when cycled between 5 and 95% RH, wherein the reference compound gains or loses more than 1.0% weight under the same conditions. Further included in the present invention are PG solvates that do not gain or lose more than 0.5% weight at 25 degrees C. when cycled between 5 and 95% RH, wherein the reference compound gains or loses more than 0.5% or more than 1.0% weight under the same conditions. Further included in the present invention are PG solvates that do not gain or lose more than 0.25% weight at 25 degrees C. when cycled between 5 and 95% RH, wherein the reference compound gains or loses more than 0.5% or more than 1.0% weight under the same conditions.

Further included in the present invention are PG solvates that have a hygroscopicity (according to Callaghan et al.) that is at least one class lower than the reference compound or at least two classes lower than the reference compound. Non-limiting examples include; a Class 1 PG solvate of a Class 2 reference compound, a Class 2 PG solvate of a Class 3 reference compound, a Class 3 PG solvate of a Class 4 reference compound, a Class 1 PG solvate of a Class 3 reference compound, a Class 1 PG solvate of a Class 4 reference compound, or a Class 2 PG solvate of a Class 4 reference compound.

Further included in the present invention are PG solvates that have a hygroscopicity (according to the European Pharmacopoeia Technical Guide) that is at least one class lower than the reference compound or at least two classes lower than the reference compound. Non-limiting examples include; a Slightly hygroscopic PG solvate of a Hygroscopic reference compound, a Hygroscopic PG solvate of a Very Hygroscopic reference compound, a Very hygroscopic PG solvate of a Deliquescent reference compound, a Slightly hygroscopic PG solvate of a Very Hygroscopic reference compound, a Slightly hygroscopic PG solvate of a Deliquescent reference compound, a Hygroscopic PG solvate of a Deliquescent reference compound.

In another aspect of the present invention, the dissolution profile of the API (active pharmaceutical ingredient) (e.g. celecoxib) is modulated whereby the aqueous dissolution rate or the dissolution rate in simulated gastric fluid (SGF) or in simulated intestinal fluid (SIF), or in a solvent or plurality of solvents is increased. Dissolution rate is the rate at which API solids dissolve in a dissolution medium. For APIs whose absorption rates are faster than the dissolution rates (e.g., steroids), the rate-limiting step in the absorption process is often the dissolution rate. Because of a limited residence time at the absorption site, APIs that are not dissolved before they are removed from the intestinal absorption site are considered useless. Therefore, the rate of dissolution has a major impact on the performance of APIs that are poorly soluble. Because of this factor, the dissolution rate of APIs in solid dosage forms is an important, routine, quality control parameter used in the API manufacturing process.

$$\text{Dissolution rate} = K\,S(C_s - C) \tag{1}$$

where K is dissolution rate constant, S is the surface area, $C_s$ is the apparent solubility, and C is the concentration of API in the dissolution media. For rapid API absorption, $C_s - C$ is approximately equal to $C_s$. The dissolution rate of APIs may be measured by conventional means known in the art.

The increase in the dissolution rate of a composition of the present invention, as compared to the unsolvated form, may be specified, such as by 10, 20, 30, 40, 50, 60, 70, 80, 90, or 100%, or by 2, 3, 4, 5, 6, 7, 8, 9, 10, 15, 20, 25, 30, 40, 50, 75, 100, 125, 150, 175, 200, 250, 300, 350, 400, 500, 1000, 10,000, or 100,000 fold greater than the unsolvated form in the same solution. Conditions under which the dissolution rate is measured are discussed above. The increase in dissolution may be further specified by the time the composition remains supersaturated. Examples of above embodiments include: compositions with a dissolution rate, at 37 degrees C. and a pH of 7.0, that is increased at least 5 fold over the unsolvated form, compositions with a dissolution rate in SGF that is increased at least 5 fold over the unsolvated form, compositions with a dissolution rate in SIF that is increased at least 5 fold over the unsolvated form.

The present invention demonstrates that the length of time in which celecoxib or other APIs remains in solution can be increased to a surprising high degree by using a PG solvate form as discussed herein. The presence of propylene glycol allows the formation of a supersaturated solution of the API and a high concentration of API will remain in solution for an extended period of time. Celecoxib, for example, has a solubility in water of less than 1 microgram/mL and cannot be maintained as a supersaturated solution for any appreciable time. The present invention has drawn compositions that can be maintained for a period of time (e.g., 15, 30, 45, 60, minutes and longer) as supersaturated solutions at concentrations 2, 3, 5, 7, 10, 20, 30, 40, 50, 60, 70, 80, 90, or 100%, or by 3, 4, 5, 6, 7, 8, 9, 10, 15, 20, 25, 30, 40, 50, 75, 100, 125, 150, 175, 200, 250, 300, 350, 400, 500, 1000, 10,000, or 100,000 fold greater than the solubility of the unsolvated form in the same solution (e.g., water or SGF).

The methods of the present invention can be used to make a pharmaceutical API formulation with greater solubility, dissolution, bioavailability, AUC, reduced time to $T_{max}$, the average time from administration to reach peak blood serum levels, higher $C_{max}$, the average maximum blood serum concentration of API following administration, and longer $T_{1/2}$, the average terminal half-life of API blood serum concentration following $T_{max}$, when compared to the unsolvated form.

AUC is the area under the plot of plasma concentration of API (not logarithm of the concentration) against time after API administration. The area is conveniently determined by the "trapezoidal rule": the data points are connected by straight line segments, perpendiculars are erected from the abscissa to each data point, and the sum of the areas of the triangles and trapezoids so constructed is computed. When the last measured concentration ($C_n$, at time $t_n$) is not zero, the AUC from $t_n$ to infinite time is estimated by $C_n/k_{el}$.

The AUC is of particular use in estimating bioavailability of drugs, and in estimating total clearance of drugs ($Cl_T$). Following single intravenous doses, AUC=D/$Cl_T$, where D is the dose, for single compartment systems obeying first-order elimination kinetics; alternatively, AUC=$C_0/k_{el}$, where $k_{el}$ is the drug elimination rate constant. With routes other than the intravenous AUC=F·D/$Cl_T$, where F is the bioavailability of the drug.

Thus, in a further aspect, the present invention provides a process for modulating the bioavailability of an API when administered in its normal and effective dose range, whereby the AUC is increased, the time to $T_{max}$ is reduced, or $C_{max}$ is increased, which process comprises the preparation of a PG solvate.

Examples of the above embodiments include: compositions with a time to $T_{max}$ that is reduced by at least 10% as compared to the neutral free form, compositions with a time to $T_{max}$ that is reduced by at least 20% over the free form, compositions with a time to $T_{max}$ that is reduced by at least 40% over the free form, compositions with a time to $T_{max}$ that is reduced by at least 50% over the free form, compositions with a $T_{max}$ that is reduced by at least 60% over the free form, compositions with a $T_{max}$ that is reduced by at least 70% over the free form, compositions with a $T_{max}$ that is reduced by at least 80% over the free form, compositions with a $C_{max}$ that is increased by at least 20% over the free form, compositions with a $C_{max}$ that is increased by at least 30% over the free form, compositions with a $C_{max}$ that is increased by at least 40% over the free form, compositions with a $C_{max}$ that is increased by at least 50% over the free form, compositions with a $C_{max}$ that is increased by at least 60% over the free form, compositions with a $C_{max}$ that is increased by at least 70% over the free form, compositions with a $C_{max}$ that is increased by at least 80% over the free form, compositions with a $C_{max}$ that is increased by at least 2 times the free form, compositions with a $C_{max}$ that is increased by at least 3 times the free form, compositions with a $C_{max}$ that is increased by at least 4 times the free form, compositions with a $C_{max}$ that is increased by at least 5 times the free form, compositions with a $C_{max}$ that is increased by at least 6 times the free form, compositions with a $C_{max}$ that is increased by at least 7 times the free form, compositions with a $C_{max}$ that is increased by at least 8 times the free form, compositions with a $C_{max}$ that is increased by at least 9 times the free form, compositions with a $C_{max}$ that is increased by at least 10 times the free form, compositions with an AUC that is increased by at least 10% over the free form, compositions with an AUC that is increased by at least 20% over the free form, compositions with an AUC that is increased by at least 30% over the free form, compositions with an AUC that is increased by at least 40% over the free form, compositions with an AUC that is increased by at least 50% over the free form, compositions with an AUC that is increased by at least 60% over the free form, compositions with an AUC that is increased by at least 70% over the free form, compositions with an AUC that is increased by at least 80% over the free form, compositions with an AUC that is increased by at least 1 times the free form, compositions with an AUC that is increased by at least 2 times the free form, compositions with an AUC that is increased by at least 3 times the free form, or compositions with an AUC that is increased by at least 4 times the free form.

The uptake of a drug by a subject can also be assessed in terms of maximum blood serum concentration and time to reach maximum blood serum concentration. Pharmaceutical compositions with a more rapid onset to therapeutic effect typically reach a higher maximum blood serum concentration ($C_{max}$) a shorter time after oral administration ($T_{max}$). Preferably, compositions of the present invention have a higher $C_{max}$ and/or a shorter $T_{max}$ than in the unsolvated form. The $T_{max}$ for the compositions of the present invention occurs within about 60 minutes, 55 minutes, 50 minutes, 45 minutes, 40 minutes, 35 minutes, 30 minutes, 25 minutes, 20 minutes, 15 minutes, 10 minutes, or within about 5 minutes of administration (e.g., oral administration). Even more preferably, the therapeutic effects of compositions of the present invention begin to occur within about 60 minutes, 55 minutes, 50 minutes, 45 minutes, 40 minutes, 35 minutes, 30 minutes, within about 25 minutes, within about 20 minutes, within about 15 minutes, within about 10 minutes, or within about 5 minutes of administration (e.g., oral administration).

Compositions of the present invention have a bioavailability greater than their respective unsolvated forms. In other embodiments, the compositions of the present invention have a bioavailability of at least 50%, 60%, 65%, 70%, 75%, 80%, 85%, 87%, 90%, 91%, 92%, 93%, 94%, 95%, 96%, 97%, 98%, or 99%.

In a particular embodiment of the present invention, administration of celecoxib PG solvate to a subject may result in effective pain relief. Pain relief can be attained by inter alia reaching an appropriate blood serum concentration of a suitable analgesic. In the case of the selective COX-2 inhibitor celecoxib, about 250 ng/mL is an appropriate concentration for the relief of pain of various causes. Any standard pharmacokinetic protocol can be used to determine blood serum concentration profile in humans following oral administration of a celecoxib formulation, and thereby establish whether that formulation meets the pharmacokinetic criteria set out herein. The prior art includes many examples of pharmacokinetic studies and as such U.S. Pat. No. 6,579,895 and WO 01/91750 are hereby included as references in their entirety.

In a further aspect the present invention provides a process for improving the dose response of an API by making a composition of the present invention. Dose response is the quantitative relationship between the magnitude of response and the dose inducing the response and may be measured by conventional means known in the art. The curve relating therapeutic effect (as the dependent variable) to dose (as the independent variable) for an API-cell system is the "dose-response curve". Typically, the dose-response curve is the measured response to an API plotted against the dose of the API (mg/kg) given. The dose response curve can also be a curve of AUC against the dose of the API given.

The dose-response curve for many APIs (e.g. presently-marketed celecoxib (CELEBREX™)) is nonlinear. Preferably, the dose-response curves for the PG solvate compositions of the present invention are linear or contain a larger linear region than presently-marketed celecoxib. A preferred embodiment of the present invention may incorporate a dose-response curve with a linear slope that is steeper than that of celecoxib. This would allow a faster-onset of therapeutic relief from a smaller dosage of API. An initially steep dose-response curve which gradually levels out could be employed to generate a controlled-release formulation. Also, the absorption or uptake of many APIs (e.g. presently-marketed celecoxib) depends in part on food effects, such that uptake of the API increases when taken with food, especially fatty food. Preferably, uptake of the PG solvates of the present invention exhibit a decreased dependence on food, such that the difference in uptake of the PG solvates when taken with food and when not taken with food is less than the difference in uptake of the unsolvated form.

The compositions of the present invention, including the active pharmaceutical ingredient (API) and formulations comprising the API, are suitably stable for pharmaceutical use. Preferably, the API or formulations thereof of the present invention are stable such that when stored at 30 degrees C. for 2 years, less than 0.2% of any one degradant is formed. The term degradant refers herein to product(s) of a single type of chemical reaction. For example, if a hydrolysis event occurs that cleaves a molecule into two products, for the purpose of the present invention, it would be considered a single degradant. More preferably, when stored at 40 degrees C. for 2 years, less than 0.2% of any one degradant is formed. Alternatively, when stored at 30 degrees C. for 3 months, less than 0.2% or 0.15%, or 0.1% of any one degradant is formed, or when stored at 40 degrees C. for 3 months, less than 0.2% or 0.15%, or 0.1% of any one degradant is formed. Further alternatively, when stored at 60 degrees C. for 4 weeks, less than 0.2% or 0.15%, or 0.1% of any one degradant is formed. The relative humidity (RH) may be specified as ambient (RH), 75% (RH), or as any single integer between 1 to 99%.

APIs prepared in the form of propylene glycol solvates have several important advantages over other solvates and their free form counterparts. In general, solvates are more commonly formed with water, methanol, ethanol, or other alcohols than with propylene glycol. These more common solvates are more easily removed from the crystal matrix by elevated temperatures than propylene glycol. PG solvates have an increased thermal stability over those of more traditional solvates. Also, PG solvates are generally more pharmaceutically acceptable than other common solvates, including those formed from alcohols other than ethanol. Investigations of the PG solvates of the present invention have shown fewer solvation states than hydration states. Reference compounds for PG solvates can be unsolvated free acid, unsolvated free base, zwitter ions, hydrates, or other solvates (e.g. methanol, ethanol, etc.). This decrease in form diversity associated with PG solvates can lead to more predictability and more consistent results during production and quality control. Stabilization of a desired solvate or polymorph can be achieved by causing the less desirable forms (e.g. solvates, polymorphs, hydrates) to be energetically less favorable than the desired form. In this way, PG solvates can aid in the production of pharmaceutical formulations with increased form stability.

The present invention further relates to methods of making a pharmaceutical solvate more stable at elevated temperatures (e.g. 30, 40, 50 degrees C.) by producing a PG solvate of the drug. The present invention further relates to methods of making a more pharmaceutically acceptable solvate of many APIs by employing propylene glycol rather than more biologically harmful solvents (e.g. methanol). The present invention further relates to methods of reducing the number of forms (e.g. hydration states, solvation states, polymorphs, etc.) possible for a pharmaceutical solvate.

Pharmaceutically acceptable PG solvates can be administered by controlled- or delayed-release means. Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. (Kim, Cherng-ju, Controlled Release Dosage Form Design, Technomic Publishing, Lancaster, Pa.: 2000).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under dosing a drug (i.e., going below the minimum therapeutic levels) as well as exceeding the toxicity level for the drug.

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the PG solvates of the present invention. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed salt forms and thus effect controlled delivery of the drug. Examples of specific anion exchangers include, but are not limited to, Duolite® A568 and Duolite® AP143 (Rohm & Haas, Spring House, Pa. USA).

One embodiment of the invention encompasses a unit dosage form which comprises a pharmaceutically acceptable PG solvate, or a polymorph, solvate, hydrate, dehydrate, co-crystal, anhydrous, or amorphous form thereof, and one or more pharmaceutically acceptable excipients or diluents, wherein the pharmaceutical composition or dosage form is formulated for controlled-release. Specific dosage forms utilize an osmotic drug delivery system.

A particular and well-known osmotic drug delivery system is referred to as OROS® (Alza Corporation, Mountain View, Calif. USA). This technology can readily be adapted for the delivery of compounds and compositions of the invention. Various aspects of the technology are disclosed in U.S. Pat. Nos. 6,375,978 B1; 6,368,626 B1; 6,342,249 B1; 6,333,050 B2; 6,287,295 B1; 6,283,953 B1; 6,270,787 B1; 6,245,357 B1; and 6,132,420; each of which is incorporated herein by reference. Specific adaptations of OROS® that can be used to administer compounds and compositions of the invention include, but are not limited to, the OROS® Push-Pull™, Delayed Push-Pull™, Multi-Layer Push-Pull™, and Push-Stick™ Systems, all of which are well known. See, e.g., http://www.alza.com.

Additional OROS® systems that can be used for the controlled oral delivery of compounds and compositions of the invention include OROS®-CT and L-OROS®. Id.; see also, Delivery Times, vol. II, issue II (Alza Corporation).

Conventional OROS® oral dosage forms are made by compressing a drug powder (e.g., celecoxib sodium PG solvate) into a hard tablet, coating the tablet with cellulose derivatives to form a semi-permeable membrane, and then drilling an orifice in the coating (e.g., with a laser). (Kim, Cherng-ju, Controlled Release Dosage Form Design, Technomic Publishing, Lancaster, Pa.: 2000). The advantage of such dosage forms is that the delivery rate of the drug is not influenced by physiological or experimental conditions. Even a drug with a pH-dependent solubility can be delivered at a constant rate regardless of the pH of the delivery medium. But because these advantages are provided by a build-up of osmotic pressure within the dosage form after administration, conventional OROS® drug delivery systems cannot be used to effectively deliver drugs with low water solubility. Because PG solvates and complexes of this invention (e.g., celecoxib sodium PG solvate) are far more soluble in water than unsolvated forms, they are well suited for osmotic-based delivery to patients.

A specific dosage form of the invention comprises: a wall defining a cavity, the wall having an exit orifice formed or formable therein and at least a portion of the wall being semipermeable; an expandable layer located within the cavity remote from the exit orifice and in fluid communication with the semipermeable portion of the wall; a dry or substantially dry state drug layer located within the cavity adjacent to the exit orifice and in direct or indirect contacting relationship with the expandable layer; and a flow-promoting layer interposed between the inner surface of the wall and at least the external surface of the drug layer located within the cavity, wherein the drug layer comprises a PG solvate, or a polymorph, solvate, hydrate, dehydrate, co-crystal, anhydrous, or amorphous form thereof. See U.S. Pat. No. 6,368,626, the entirety of which is incorporated herein by reference.

Another specific dosage form of the invention comprises: a wall defining a cavity, the wall having an exit orifice formed or formable therein and at least a portion of the wall being semipermeable; an expandable layer located within the cavity remote from the exit orifice and in fluid communication with the semipermeable portion of the wall; a drug layer located within the cavity adjacent the exit orifice and in direct or indirect contacting relationship with the expandable layer; the drug layer comprising a liquid, active agent formulation absorbed in porous particles, the porous particles being adapted to resist compaction forces sufficient to form a compacted drug layer without significant exudation of the liquid, active agent formulation, the dosage form optionally having a placebo layer between the exit orifice and the drug layer, wherein the active agent formulation comprises a PG solvate, or a polymorph, solvate, hydrate, dehydrate, co-crystal, anhydrous, or amorphous form thereof. See U.S. Pat. No. 6,342, 249, the entirety of which is incorporated herein by reference.

Excipients employed in pharmaceutical compositions of the present invention can be solids, semi-solids, liquids or combinations thereof. Compositions of the invention containing excipients can be prepared by any known technique of pharmacy that comprises admixing an excipient with a drug or therapeutic agent. A pharmaceutical composition of the invention contains a desired amount of API per dose unit and, if intended for oral administration, can be in the form, for example, of a tablet, a caplet, a pill, a hard or soft capsule, a lozenge, a cachet, a dispensable powder, granules, a suspension, an elixir, a dispersion, a liquid, or any other form reasonably adapted for such administration. Presently preferred are oral dosage forms that are discrete dose units each containing a predetermined amount of the drug, such as tablets or capsules.

Non-limiting examples follow of excipients that can be used to prepare pharmaceutical compositions of the invention.

Pharmaceutical compositions of the invention optionally comprise one or more pharmaceutically acceptable carriers or diluents as excipients. Suitable carriers or diluents illustratively include, but are not limited to, either individually or in combination, lactose, including anhydrous lactose and lactose monohydrate; starches, including directly compressible starch and hydrolyzed starches (e.g., Celutab™ and Emdex™); mannitol; sorbitol; xylitol; dextrose (e.g., Cerelose™ 2000) and dextrose monohydrate; dibasic calcium phosphate dihydrate; sucrose-based diluents; confectioner's sugar; monobasic calcium sulfate monohydrate; calcium sulfate dihydrate; granular calcium lactate trihydrate; dextrates; inositol; hydrolyzed cereal solids; amylose; celluloses including microcrystalline cellulose, food grade sources of alpha- and amorphous cellulose (e.g., RexcelJ), powdered cellulose, hydroxypropylcellulose (HPC) and hydroxypropylmethylcellulose (HPMC); calcium carbonate; glycine; bentonite; block co-polymers; polyvinylpyrrolidone; and the like. Such carriers or diluents, if present, constitute in total about 5% to about 99%, preferably about 10% to about 85%, and more preferably about 20% to about 80%, of the total weight of the composition. The carrier, carriers, diluent, or diluents selected preferably exhibit suitable flow properties and, where tablets are desired, compressibility.

Lactose, mannitol, dibasic sodium phosphate, and microcrystalline cellulose (particularly Avicel PH microcrystalline cellulose such as Avicel PH 101), either individually or in combination, are preferred diluents. These diluents are chemically compatible with celecoxib. The use of extragranular microcrystalline cellulose (that is, microcrystalline cellulose added to a granulated composition) can be used to improve hardness (for tablets) and/or disintegration time. Lactose, especially lactose monohydrate, is particularly preferred. Lactose typically provides compositions having suitable release rates of celecoxib, stability, pre-compression flowability, and/or drying properties at a relatively low diluent cost. It provides a high density substrate that aids densification during granulation (where wet granulation is employed) and therefore improves blend flow properties and tablet properties.

Pharmaceutical compositions of the invention optionally comprise one or more pharmaceutically acceptable disintegrants as excipients, particularly for tablet formulations. Suitable disintegrants include, but are not limited to, either individually or in combination, starches, including sodium starch glycolate (e.g., Explotab™ of PenWest) and pregelatinized corn starches (e.g., National™ 1551 of National Starch and Chemical Company, National™ 1550, and Colorcon™ 1500), clays (e.g., Veegum™ HV of R.T. Vanderbilt), celluloses such as purified cellulose, microcrystalline cellulose, methylcellulose, carboxymethylcellulose and sodium carboxymethylcellulose, croscarmellose sodium (e.g., Ac-Di-Sol™ of FMC), alginates, crospovidone, and gums such as agar, guar, locust bean, karaya, pectin and tragacanth gums.

Disintegrants may be added at any suitable step during the preparation of the composition, particularly prior to granulation or during a lubrication step prior to compression. Such disintegrants, if present, constitute in total about 0.2% to about 30%, preferably about 0.2% to about 10%, and more preferably about 0.2% to about 5%, of the total weight of the composition.

Croscarmellose sodium is a preferred disintegrant for tablet or capsule disintegration, and, if present, preferably constitutes about 0.2% to about 10%, more preferably about 0.2% to about 7%, and still more preferably about 0.2% to about 5%, of the total weight of the composition. Croscarmellose sodium confers superior intragranular disintegration capabilities to granulated pharmaceutical compositions of the present invention.

Pharmaceutical compositions of the invention optionally comprise one or more pharmaceutically acceptable binding agents or adhesives as excipients, particularly for tablet formulations. Such binding agents and adhesives preferably impart sufficient cohesion to the powder being tableted to allow for normal processing operations such as sizing, lubrication, compression and packaging, but still allow the tablet to disintegrate and the composition to be absorbed upon ingestion. Such binding agents may also prevent or inhibit crystallization or recrystallization of a celecoxib salt of the present invention once the salt has been dissolved in a solution. Suitable binding agents and adhesives include, but are not limited to, either individually or in combination, acacia; tragacanth; sucrose; gelatin; glucose; starches such as, but not limited to, pregelatinized starches (e.g., National™ 1511 and National™ 1500); celluloses such as, but not limited to, methylcellulose and carmellose sodium (e.g., Tylose™); alginic acid and salts of alginic acid; magnesium aluminum silicate; PEG; guar gum; polysaccharide acids; bentonites; povidone, for example povidone K-15, K-30 and K-29/32; polymethacrylates; HPMC; hydroxypropylcellulose (e.g., Klucel™ of Aqualon); and ethylcellulose (e.g., Ethocel™ of the Dow Chemical Company). Such binding agents and/or adhesives, if present, constitute in total about 0.5% to about 25%, preferably about 0.75% to about 15%, and more preferably about 1% to about 10%, of the total weight of the pharmaceutical composition.

Many of the binding agents are polymers comprising amide, ester, ether, alcohol or ketone groups and, as such, are preferably included in pharmaceutical compositions of the present invention. Polyvinylpyrrolidones such as povidone K-30 are especially preferred. Polymeric binding agents can have varying molecular weight, degrees of crosslinking, and grades of polymer. Polymeric binding agents can also be copolymers, such as block co-polymers that contain mixtures of ethylene oxide and propylene oxide units. Variation in these units' ratios in a given polymer affects properties and performance. Examples of block co-polymers with varying compositions of block units are Poloxamer 188 and Poloxamer 237 (BASF Corporation).

Pharmaceutical compositions of the invention optionally comprise one or more pharmaceutically acceptable wetting agents as excipients. Non-limiting examples of surfactants that can be used as wetting agents in pharmaceutical compositions of the invention include quaternary ammonium compounds, for example benzalkonium chloride, benzethonium chloride and cetylpyridinium chloride, dioctyl sodium sulfosuccinate, polyoxyethylene alkylphenyl ethers, for example nonoxynol 9, nonoxynol 10, and octoxynol 9, poloxamers (polyoxyethylene and polyoxypropylene block copolymers), polyoxyethylene fatty acid glycerides and oils, for example polyoxyethylene (8) caprylic/capric mono- and diglycerides (e.g., Labrasol™ of Gattefosse), polyoxyethylene (35) castor oil and polyoxyethylene (40) hydrogenated castor oil; polyoxyethylene alkyl ethers, for example polyoxyethylene (20) cetostearyl ether, polyoxyethylene fatty acid esters, for example polyoxyethylene (40) stearate, polyoxyethylene sorbitan esters, for example polysorbate 20 and polysorbate 80 (e.g., Tween™ 80 of ICI), propylene glycol fatty acid esters, for example propylene glycol laurate (e.g., Lauroglycol™ of Gattefosse), sodium lauryl sulfate, fatty acids and salts thereof, for example oleic acid, sodium oleate and triethanolamine oleate, glyceryl fatty acid esters, for example glyceryl monostearate, sorbitan esters, for example sorbitan monolaurate, sorbitan monooleate, sorbitan monopalmitate and sorbitan monostearate, tyloxapol, and mixtures thereof. Such wetting agents, if present, constitute in total about 0.25% to about 15%, preferably about 0.4% to about 10%, and more preferably about 0.5% to about 5%, of the total weight of the pharmaceutical composition.

Wetting agents that are anionic surfactants are preferred. Sodium lauryl sulfate is a particularly preferred wetting agent. Sodium lauryl sulfate, if present, constitutes about 0.25% to about 7%, more preferably about 0.4% to about 4%, and still more preferably about 0.5% to about 2%, of the total weight of the pharmaceutical composition.

Pharmaceutical compositions of the invention optionally comprise one or more pharmaceutically acceptable lubricants (including anti-adherents and/or glidants) as excipients. Suitable lubricants include, but are not limited to, either individually or in combination, glyceryl behapate (e.g., Compritol™ 888 of Gattefosse); stearic acid and salts thereof, including magnesium, calcium and sodium stearates; hydrogenated vegetable oils (e.g., Sterotex™ of Abitec); colloidal silica; talc; waxes; boric acid; sodium benzoate; sodium acetate; sodium fumarate; sodium chloride; DL-leucine; PEG (e.g., Carbowax™ 4000 and Carbowax™ 6000 of the Dow Chemical Company); sodium oleate; sodium lauryl sulfate; and magnesium lauryl sulfate. Such lubricants, if present, constitute in total about 0.1% to about 10%, preferably about 0.2% to about 8%, and more preferably about 0.25% to about 5%, of the total weight of the pharmaceutical composition.

Magnesium stearate is a preferred lubricant used, for example, to reduce friction between the equipment and granulated mixture during compression of tablet formulations.

Suitable anti-adherents include, but are not limited to, talc, cornstarch, DL-leucine, sodium lauryl sulfate and metallic stearates. Talc is a preferred anti-adherent or glidant used, for example, to reduce formulation sticking to equipment surfaces and also to reduce static in the blend. Talc, if present, constitutes about 0.1% to about 10%, more preferably about 0.25% to about 5%, and still more preferably about 0.5% to about 2%, of the total weight of the pharmaceutical composition.

Glidants can be used to promote powder flow of a solid formulation. Suitable glidants include, but are not limited to, colloidal silicon dioxide, starch, talc, tribasic calcium phosphate, powdered cellulose and magnesium trisilicate. Colloidal silicon dioxide is particularly preferred.

Other excipients such as colorants, flavors and sweeteners are known in the pharmaceutical art and can be used in pharmaceutical compositions of the present invention. Tablets can be coated, for example with an enteric coating, or uncoated. Compositions of the invention can further comprise, for example, buffering agents.

Optionally, one or more effervescent agents can be used as disintegrants and/or to enhance organoleptic properties of pharmaceutical compositions of the invention. When present in pharmaceutical compositions of the invention to promote dosage form disintegration, one or more effervescent agents are preferably present in a total amount of about 30% to about 75%, and preferably about 45% to about 70%, for example about 60%, by weight of the pharmaceutical composition.

According to a particularly preferred embodiment of the invention, an effervescent agent, present in a solid dosage form in an amount less than that effective to promote disintegration of the dosage form, provides improved dispersion of the celecoxib in an aqueous medium. Without being bound by theory, it is believed that the effervescent agent is effective to accelerate dispersion of the drug, such as celecoxib, from the dosage form in the gastrointestinal tract, thereby further enhancing absorption and rapid onset of therapeutic effect. When present in a pharmaceutical composition of the invention to promote intragastrointestinal dispersion but not to enhance disintegration, an effervescent agent is preferably present in an amount of about 1% to about 20%, more preferably about 2.5% to about 15%, and still more preferably about 5% to about 10%, by weight of the pharmaceutical composition.

An "effervescent agent" herein is an agent comprising one or more compounds which, acting together or individually, evolve a gas on contact with water. The gas evolved is generally oxygen or, most commonly, carbon dioxide. Preferred effervescent agents comprise an acid and a base that react in the presence of water to generate carbon dioxide gas. Preferably, the base comprises an alkali metal or alkaline earth metal carbonate or bicarbonate and the acid comprises an aliphatic carboxylic acid.

Non-limiting examples of suitable bases as components of effervescent agents useful in the invention include carbonate salts (e.g., calcium carbonate), bicarbonate salts (e.g., sodium bicarbonate), sesquicarbonate salts, and mixtures thereof. Calcium carbonate is a preferred base.

Non-limiting examples of suitable acids as components of effervescent agents and/or solid organic acids useful in the invention include citric acid, tartaric acid (as D-, L-, or D/L-tartaric acid), malic acid, maleic acid, fumaric acid, adipic acid, succinic acid, acid anhyrides of such acids, acid salts of such acids, and mixtures thereof. Citric acid is a preferred acid.

In a preferred embodiment of the invention, where the effervescent agent comprises an acid and a base, the weight ratio of the acid to the base is about 1:100 to about 100:1, more preferably about 1:50 to about 50:1, and still more preferably about 1:10 to about 10:1. In a further preferred embodiment of the invention, where the effervescent agent comprises an acid and a base, the ratio of the acid to the base is approximately stoichiometric.

Excipients which solubilize metal salts of drugs like celecoxib typically have both hydrophilic and hydrophobic regions, or are preferably amphiphilic or have amphiphilic regions. One type of amphiphilic or partially-amphiphilic excipient comprises an amphiphilic polymer or is an amphiphilic polymer. A specific amphiphilic polymer is a polyalkylene glycol, which is commonly comprised of ethylene glycol and/or propylene glycol subunits. Such polyalkylene glycols can be esterified at their termini by a carboxylic acid, ester, acid anhyride or other suitable moiety. Examples of such excipients include poloxamers (symmetric block copolymers of ethylene glycol and propylene glycol; e.g., poloxamer 237), polyalkyene glycolated esters of tocopherol (including esters formed from a di- or multi-functional carboxylic acid; e.g., d-alpha-tocopherol polyethylene glycol-1000 succinate), and macrogolglycerides (formed by alcoholysis of an oil and esterification of a polyalkylene glycol to produce a mixture of mono-, di- and tri-glycerides and mono- and di-esters; e.g., stearoyl macrogol-32 glycerides). Such pharmaceutical compositions are advantageously administered orally.

Solid dosage forms of the invention can be prepared by any suitable process, not limited to processes described herein.

An illustrative process comprises (a) a step of blending a celecoxib salt of the invention with one or more excipients to form a blend, and (b) a step of tableting or encapsulating the blend to form tablets or capsules, respectively.

In a preferred process, solid dosage forms are prepared by a process comprising (a) a step of blending a drug salt such as a celecoxib salt of the invention with one or more excipients to form a blend, (b) a step of granulating the blend to form a granulate, and (c) a step of tableting or encapsulating the blend to form tablets or capsules respectively. Step (b) can be accomplished by any dry or wet granulation technique known in the art, but is preferably a dry granulation step. A salt of the present invention is advantageously granulated to form particles of about 1 micrometer to about 100 micrometer, about 5 micrometer to about 50 micrometer, or about 10 micrometer to about 25 micrometer. One or more diluents, one or more disintegrants and one or more binding agents are preferably added, for example in the blending step, a wetting agent can optionally be added, for example in the granulating step, and one or more disintegrants are preferably added after granulating but before tableting or encapsulating. A lubricant is preferably added before tableting. Blending and granulating can be performed independently under low or high shear. A process is preferably selected that forms a granulate that is uniform in drug content, that readily disintegrates, that flows with sufficient ease so that weight variation can be reliably controlled during capsule filling or tableting, and that is dense enough in bulk so that a batch can be processed in the selected equipment and individual doses fit into the specified capsules or tablet dies.

In an alternative embodiment, solid dosage forms are prepared by a process that includes a spray drying step, wherein a celecoxib salt is suspended with one or more excipients in one or more sprayable liquids, preferably a non-protic (e.g., non-aqueous or nonalcoholic) sprayable liquid, and then is rapidly spray dried over a current of warm air.

A granulate or spray dried powder resulting from any of the above illustrative processes can be compressed or molded to prepare tablets or encapsulated to prepare capsules. Conventional tableting and encapsulation techniques known in the art can be employed. Where coated tablets are desired, conventional coating techniques are suitable.

Excipients for tablet compositions of the invention are preferably selected to provide a disintegration time of less than about 30 minutes, preferably about 25 minutes or less, more preferably about 20 minutes or less, and still more preferably about 15 minutes or less, in a standard disintegration assay.

Celecoxib dosage forms of the invention preferably comprise celecoxib in a daily dosage amount of about 10 mg to about 1000 mg, more preferably about 25 mg to about 400 mg, and most preferably about 50 mg to about 200 mg.

In a further embodiment the PG solvate comprises an API from Table 3. For APIs in Table 3 listed as salts, solvates, hydrates, and the like, the PG solvate can either be of the form listed in Table 3 or a PG solvate of the free form, or a PG solvate of another form that is not listed. Table 3 includes the CAS number, chemical name or a PCT or patent reference (each incorporated herein in their entireties). In another embodiment, any one or more of the APIs of Table 3 may be specifically excluded from the present invention. Any APIs currently known in the art may also be specifically excluded from the present invention. For example, azithromycin and cephalosporin may be specifically excluded from the present invention.

Exemplification

Procedure for Raman Acquisition

Acquisition

The sample was either left in the glass vial in which it was processed or an aliquot of the sample was transferred to a glass slide. The glass vial or slide was positioned in the sample chamber. The measurement was made using an Almega™ Dispersive Raman (Almega™ Dispersive Raman, Thermo-Nicolet, 5225 Verona Road, Madison, Wis. 53711-4495) system fitted with a 785 nm laser source. The sample was manually brought into focus using the microscope portion of the apparatus with a 10× power objective (unless otherwise noted), thus directing the laser onto the surface of the sample. The spectrum was acquired using the parameters outlined in Table 1. (Exposure times and number of exposures may vary; changes to parameters will be indicated for each acquisition.)

TABLE 2

Raman Spectral acquisition parameters

| Parameter | Setting Used |
| --- | --- |
| Exposure time (s) | 2.0 |
| Number of exposures | 10 |
| Laser source wavelength (nm) | 785 |
| Laser power (%) | 100 |
| Aperture shape | pin hole |
| Aperture size (um) | 100 |
| Spectral range | 104-3428 |
| Grating position | Single |
| Temperature at acquisition (degrees C.) | 24.0 |

Procedure for Powder X-Ray Diffraction (PXRD)

All powder x-ray diffraction patterns were obtained using the D/Max Rapid X-ray Diffractometer (D/Max Rapid, Contact Rigaku/MSC, 9009 New Trails Drive, The Woodlands, Tex., USA 77381-5209) equipped with a copper source (Cu/K$_\alpha$ 1.5406 Å), manual x-y stage, and 0.3 mm collimator, unless otherwise indicated. The sample was loaded into a 0.3 mm boron rich glass capillary tube (e.g., Charles Supper Company, 15 Tech Circle, Natick Mass. 01760-1024) by sectioning off one end of the tube and tapping the open, sectioned end into a bed of the powdered sample or into the sediment of a slurried precipitate. Note, precipitate can be amorphous or crystalline. The loaded capillary was mounted in a holder that was secured into the x-y stage. A diffractogram was acquired (e.g., Control software: RINT Rapid Control Software, Rigaku Rapid/XRD, version 1.0.0, © 1999 Rigaku Co.) under ambient conditions at a power setting of 46 kV at 40 mA in reflection mode, while oscillating about the omega-axis from 0-5 degrees at 1 degree/s and spinning about the phi-axis at 2 degrees/s. The exposure time was 15 minutes unless otherwise specified. The diffractogram obtained was integrated over 2-theta from 2-60 degrees and chi (1 segment) from 0-360 degrees at a step size of 0.02 degrees using the cyllnt utility in the RINT Rapid display software (Analysis software: RINT Rapid display software, version 1.18, Rigaku/MSC.) provided by Rigaku with the instrument. The dark counts value was set to 8 as per the system calibration (System set-up and calibration by Rigaku); normalization was set to average; the omega offset was set to 180°; and no chi or phi offsets were used for the integration. The analysis software JADE XRD Pattern Processing, versions 5.0 and 6.0 (([8]1995-2002, Materials Data, Inc. was also used.

The relative intensity of peaks in a diffractogram is not necessarily a limitation of the PXRD pattern because peak intensity can vary from sample to sample, e.g., due to crystalline impurities. Further, the angles of each peak can vary by about +/−0.1 degrees, preferably +/−0.05. The entire pattern or most of the pattern peaks may also shift by about +/−0.1 degree due to differences in calibration, settings, and other variations from instrument to instrument and from operator to operator. The above limitations result in a PXRD error of +/−0.1 degrees 2-theta for each diffraction peak.

Procedure for Differential Scanning Calorimetry (DSC)

An aliquot of the sample was weighed into an aluminum sample pan. (e.g., Pan part # 900786.091; lid part # 900779.901; TA Instruments, 109 Lukens Drive, New Castle, Del. 19720) The sample pan was sealed either by crimping for dry samples or press fitting for wet samples (e.g., hydrated or solvated samples). The sample pan was loaded in to the apparatus (DSC: Q1000 Differential Scanning Calorimeter, TA Instruments, 109 Lukens Drive, New Castle, Del. 19720), which is equipped with an autosampler, and a thermogram was obtained by individually heating the sample (e.g., Control software: Advantage for QW-Series, version 1.0.0.78, Thermal Advantage Release 2.0, © 2001 TA instruments-Water LLC) at a rate of 10 degrees C./min from T$_{min}$ (typically 20 degrees C.) to T$_{max}$ (typically 300 degrees C.) (Heating rate and temperature range may vary, changes to these parameters will be indicated for each sample) using an empty aluminum pan as a reference. Dry nitrogen (e.g., Compressed nitrogen, grade 4.8, BOC Gases, 575 Mountain Avenue, Murray Hill, N.J. 07974-2082) was used as a sample purge gas and was set at a flow rate of 50 mL/min. Thermal transitions were viewed and analyzed using the analysis software (Analysis Software: Universal Analysis 2000 for Windows 95/95/2000/NT, version 3.1E; Build 3.1.0.40, © 1991-2001TA instruments-Water LLC) provided with the instrument.

Procedure for Thermogravimetric Analysis (TGA)

An aliquot of the sample was transferred into a platinum sample pan. (Pan part # 952019.906; TA Instruments, 109 Lukens Drive, New Castle, Del. 19720) The pan was placed on the loading platform and was then automatically loaded in to the apparatus (TGA: Q500 Thermogravimetric Analyzer, TA Instruments, 109 Lukens Drive, New Castle, Del. 19720) using the control software (Control software: Advantage for QW-Series, version 1.0.0.78, Thermal Advantage Release 2.0, (D 2001 TA instruments-Water LLC). Thermograms were obtained by individually heating the sample at 10 degrees C./min from 25 degrees C. to 300 degrees C. (Heating rate and temperature range may vary, changes in parameters will be indicated for each sample) under flowing dry nitrogen (e.g., Compressed nitrogen, grade 4.8, BOC Gases, 575 Mountain Avenue, Murray Hill, N.J. 07974-2082), with a sample purge flow rate of 60 mL/min and a balance purge flow rate of 40 mL/min. Thermal transitions (e.g. weight changes) were viewed and analyzed using the analysis software (Analysis Software: Universal Analysis 2000 for Windows 95/95/2000/NT, version 3.1E; Build 3.1.0.40, © 1991-2001TA instruments-Water LLC) provided with the instrument.

EXAMPLE 1

Celecoxib Sodium Salt PG Solvate

A propylene glycol solvate of the sodium salt of celecoxib was prepared. To a solution of celecoxib (312 mg; 0.818 mmol) in diethyl ether (6 mL) was added propylene glycol (0.127 mL, 1.73 mmol). To the clear solution was added sodium ethoxide in ethanol (21%, 0.275 mL, 0.817 mmol). After 1 minute, crystals began to form. After 5 minutes, the solid had completely crystallized. The solid was collected by filtration and was washed with additional diethyl ether (10 mL). The off-white solid was then air-dried and collected. The crystalline salt form was identified as a 1:1 solvate of propylene glycol. The solid was characterized by TGA and PXRD. The results are depicted in FIGS. 1 and 2A.

Figure 2A:
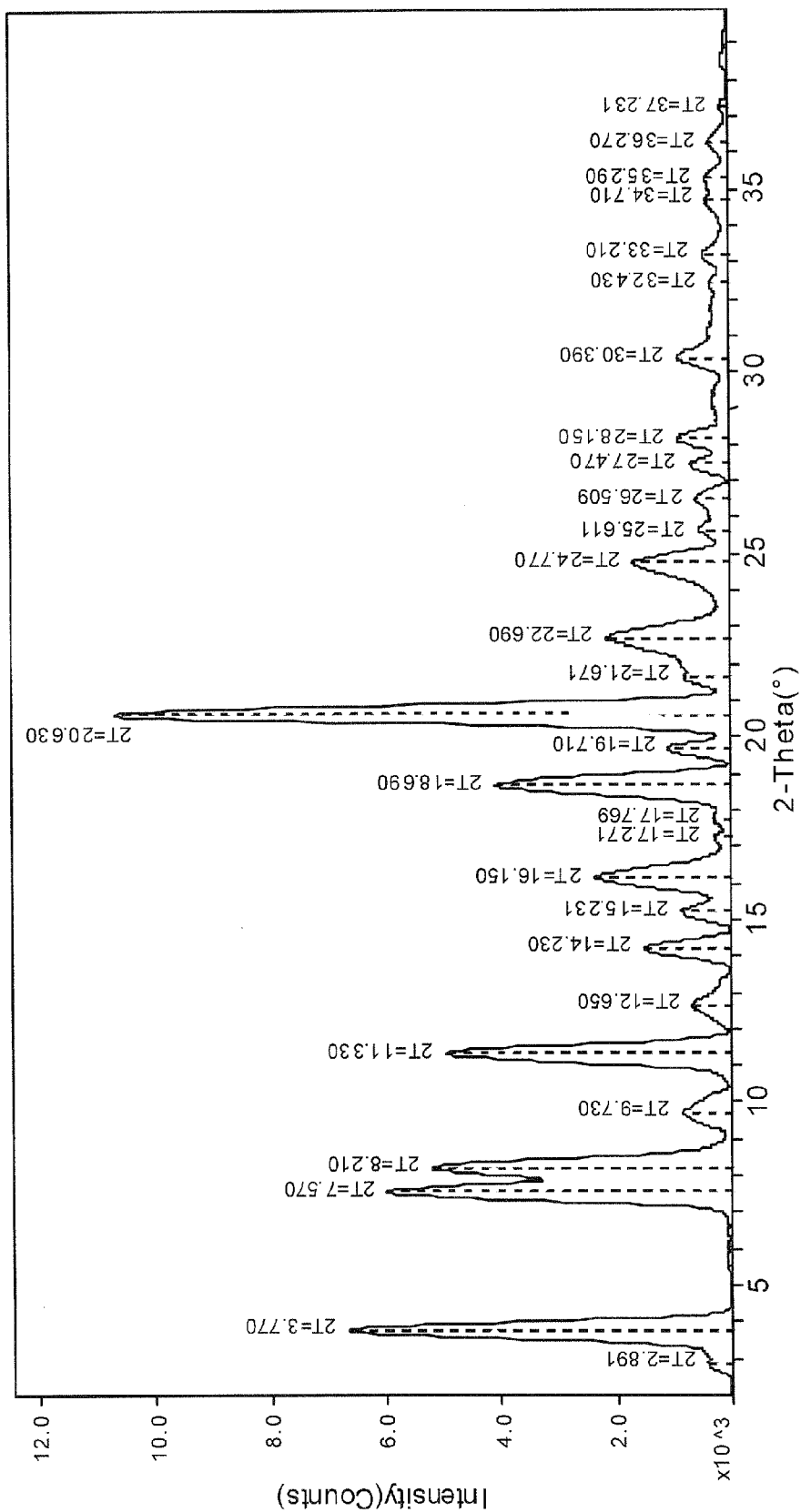
FIG. 2A-D shows the PXRD pattern of a propylene glycol solvate of a celecoxib sodium salt.

FIG. 1 shows the results of TGA. A weight loss of about 15.6% was observed between about 65 and 200 degrees C. which represents 1 molar equivalent of propylene glycol to celecoxib Na salt. FIG. 2A shows the results of PXRD. Peaks, in 2-theta angles, that can be used to characterize the solvate include any 1, 2, 3, 4, 5, 6, 7, 8, 9, or 10 of the following: 3.77, 7.57, 8.21, 11.33, 14.23, 16.13, 18.69, 20.65, 22.69 and 24.77 degrees or any one or any combination of 1, 2, 3, 4, 5, 6, 7, 8, 9, 10, or more peaks of FIG. 2A. The TGA thermogram or PXRD diffractogram data may be used alone or in any combination to characterize the solvate. A 0.8 mm collimator was used during acquisition of the diffractogram.

Figure 2B:
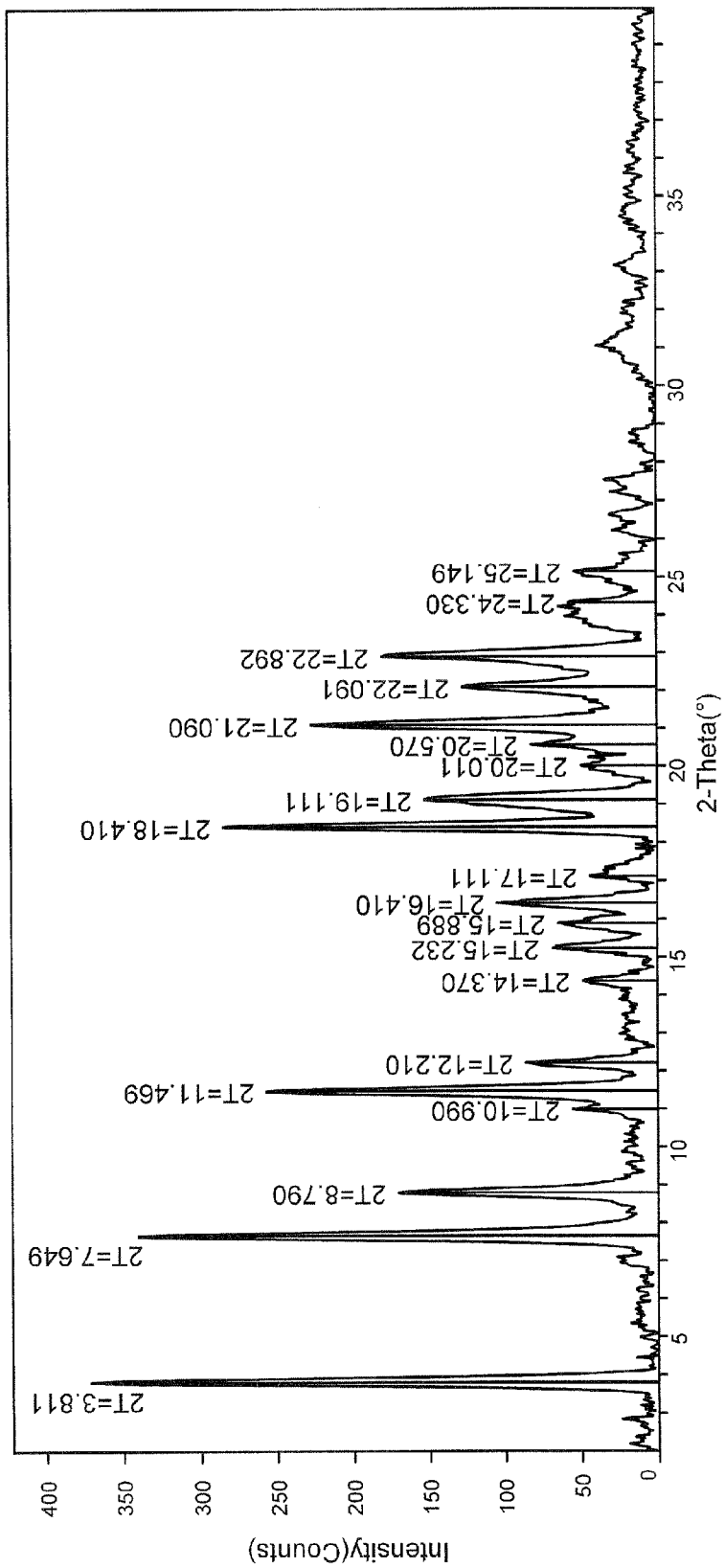
Figure 2C:
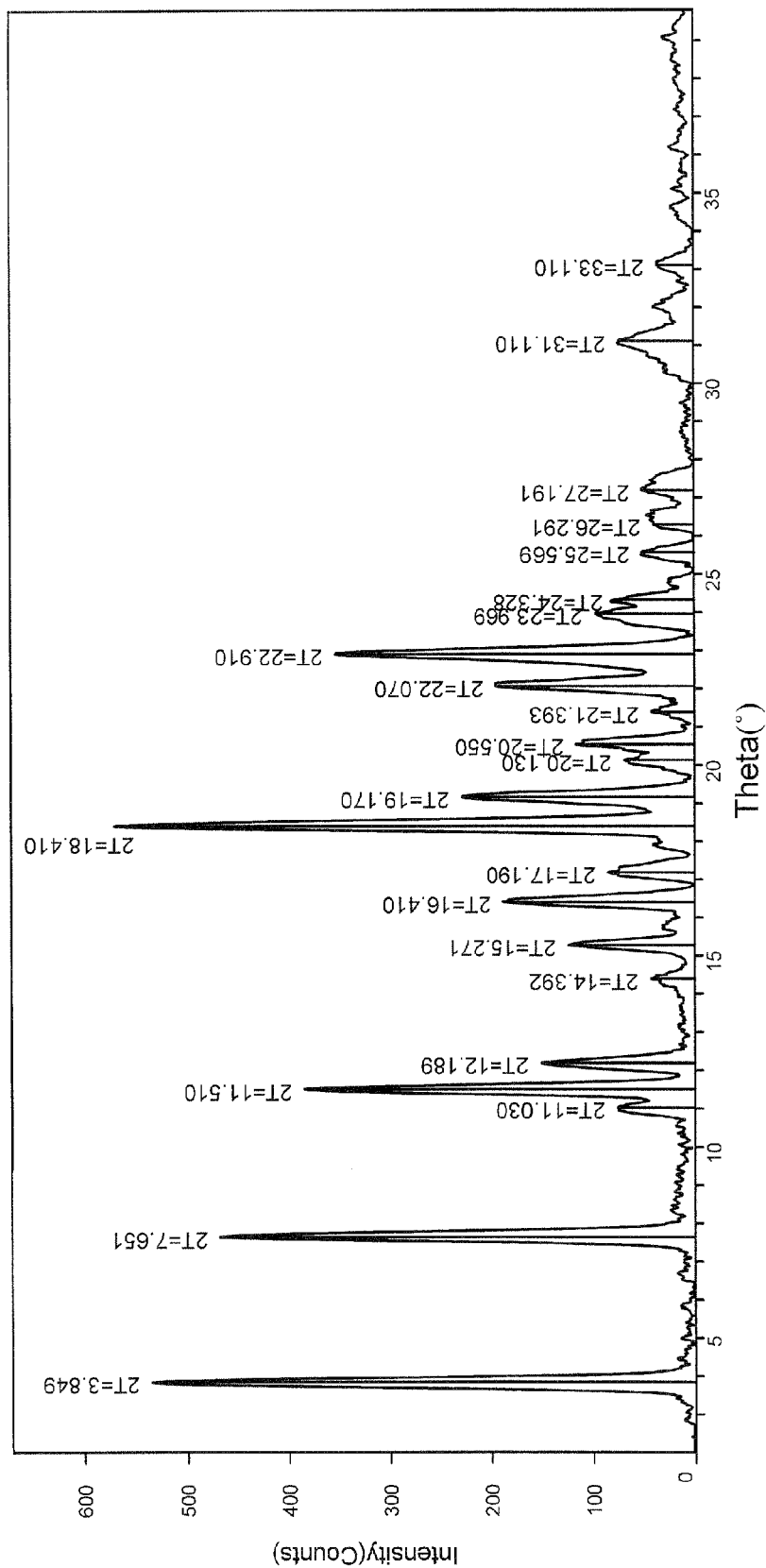
Figure 2D:
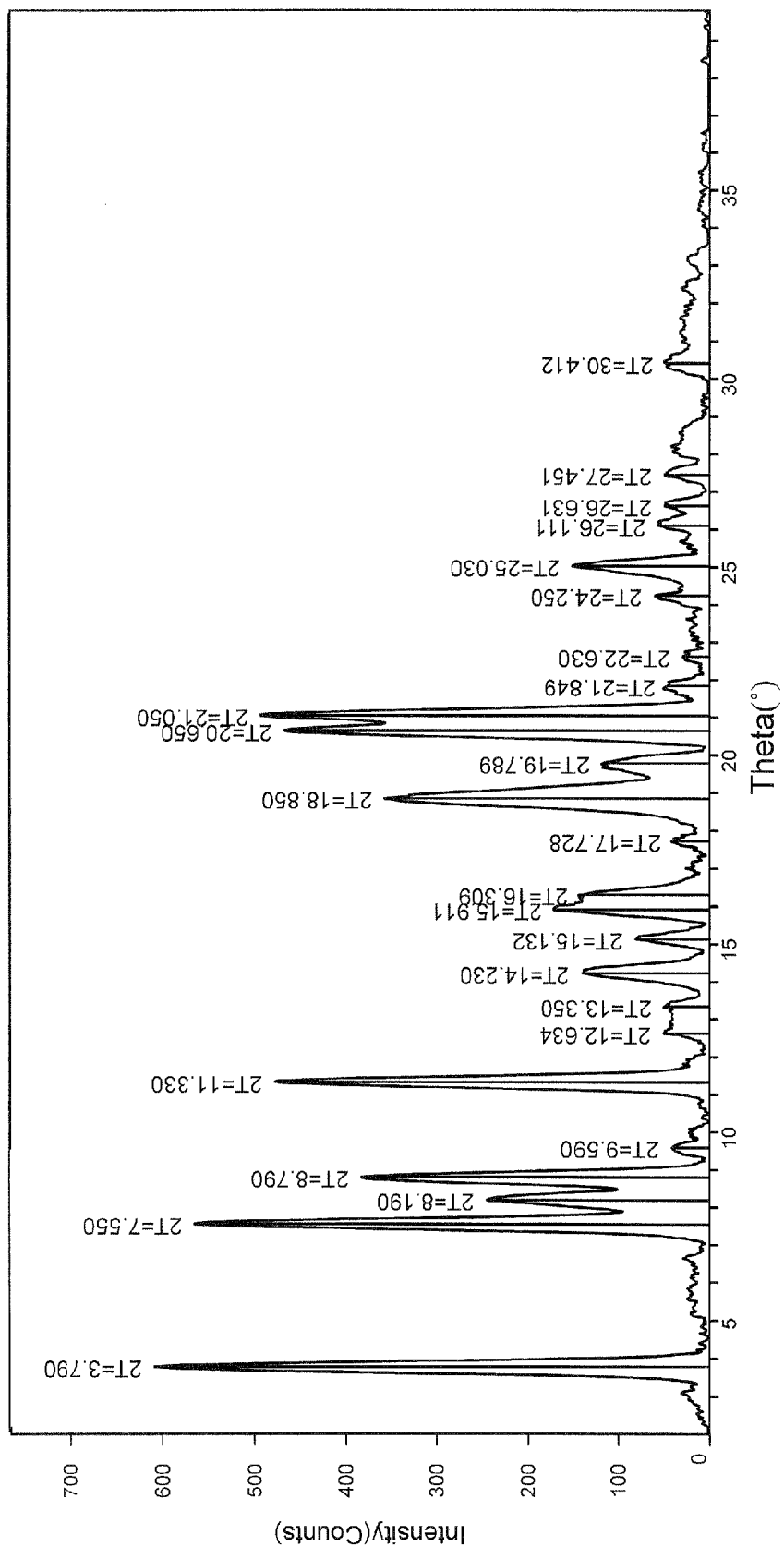

Several closely related, yet distinguishable, PXRD diffractograms have been obtained by performing the above synthesis several times. FIGS. 2B, 2C, and 2D are additional diffractograms of the propylene glycol solvate of celecoxib sodium salt. A comparison of these diffractograms yields a number of noticeable differences. For example, the peak at 8.21 degrees 2-theta in FIG. 2A is not present in FIG. 2B or 2C. Another peak at 8.79 degrees 2-theta, present in FIGS. 2B and 2D, is not found in FIG. 2A or 2C. Other distinctions can also be found between the four diffractograms. Such distinctions in otherwise similar diffractograms suggest the existence of polymorphism or perhaps a variable hydrate.

In another embodiment of the present invention, a PG solvate of an API can give rise to distinct PXRD diffractograms. This can be caused by polymorphism, a variable hydrate, a different environmental condition, etc. In one embodiment, the propylene glycol solvate of celecoxib sodium salt can yield a PXRD pattern with the absence or presence of a peak at 8.21 degrees 2-theta. In another embodiment, the propylene glycol solvate of celecoxib sodium salt can yield a PXRD pattern with the absence or presence of a peak at 8.79 degrees 2-theta.

EXAMPLE 2

Celecoxib Potassium Salt PG Solvate

A propylene glycol solvate of the potassium salt of celecoxib was prepared. To a solution of celecoxib (253 mg, 0.664 mmol) in diethyl ether (6 mL) was added propylene glycol (0.075 mL, 1.02 mmol). To the clear solution was added potassium t-butoxide in tetrahydrofuran (THF) (1 M, 0.66 mL, 0.66 mmol). Crystals immediately began to form. After 5 minutes, the solid had completely crystallized. The solid was collected by filtration and was washed with additional diethyl ether (10 mL). The white solid was then air-dried and collected. The crystalline salt form was found to be a 1:1 propylene glycol solvate of celecoxib K salt. The solid was characterized by TGA and PXRD. The results are depicted in FIGS. 3 and 4.

Figure 3:
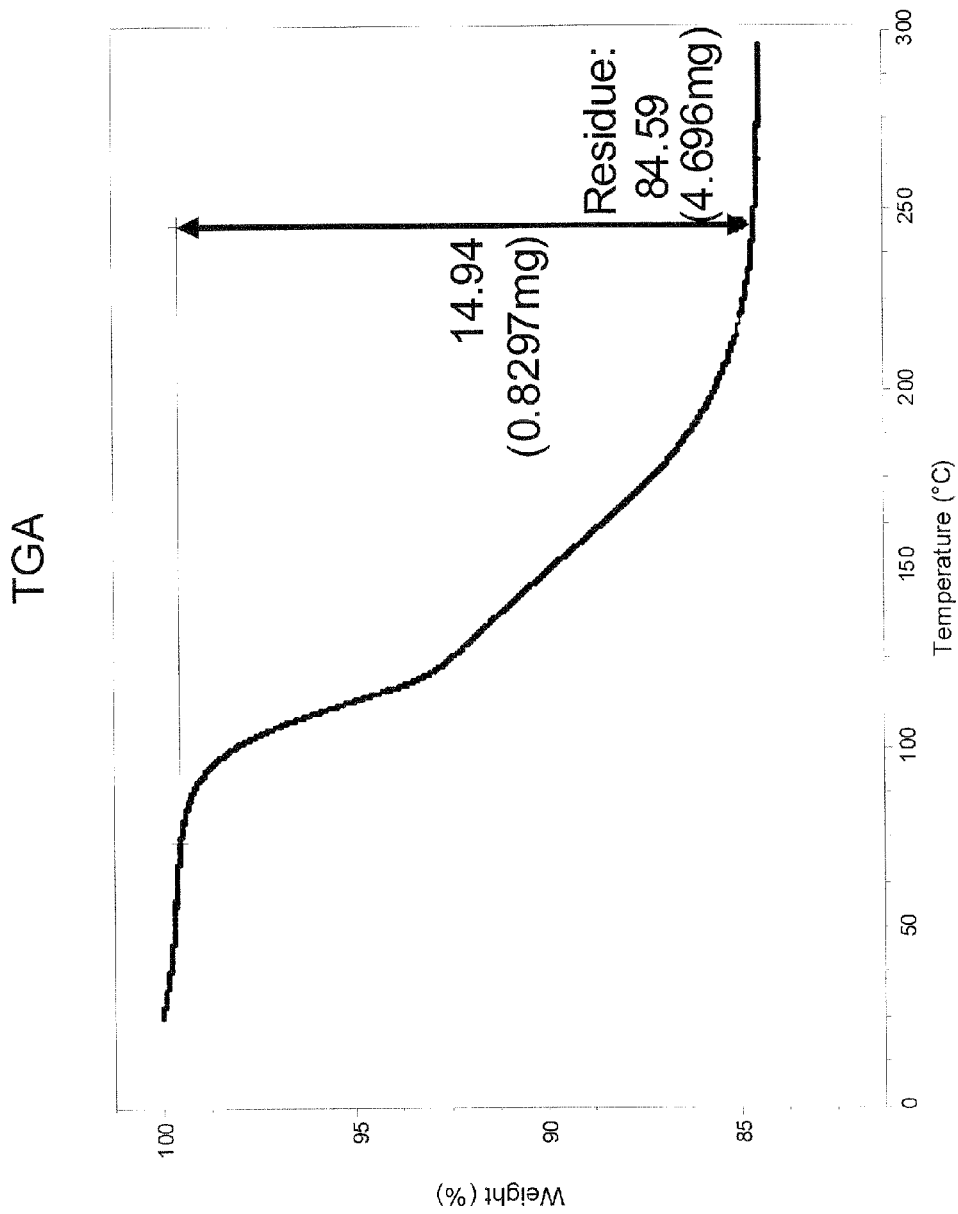
FIG. 3 shows a thermogravimetric analysis of a propylene glycol solvate of a celecoxib potassium salt.
Figure 4:
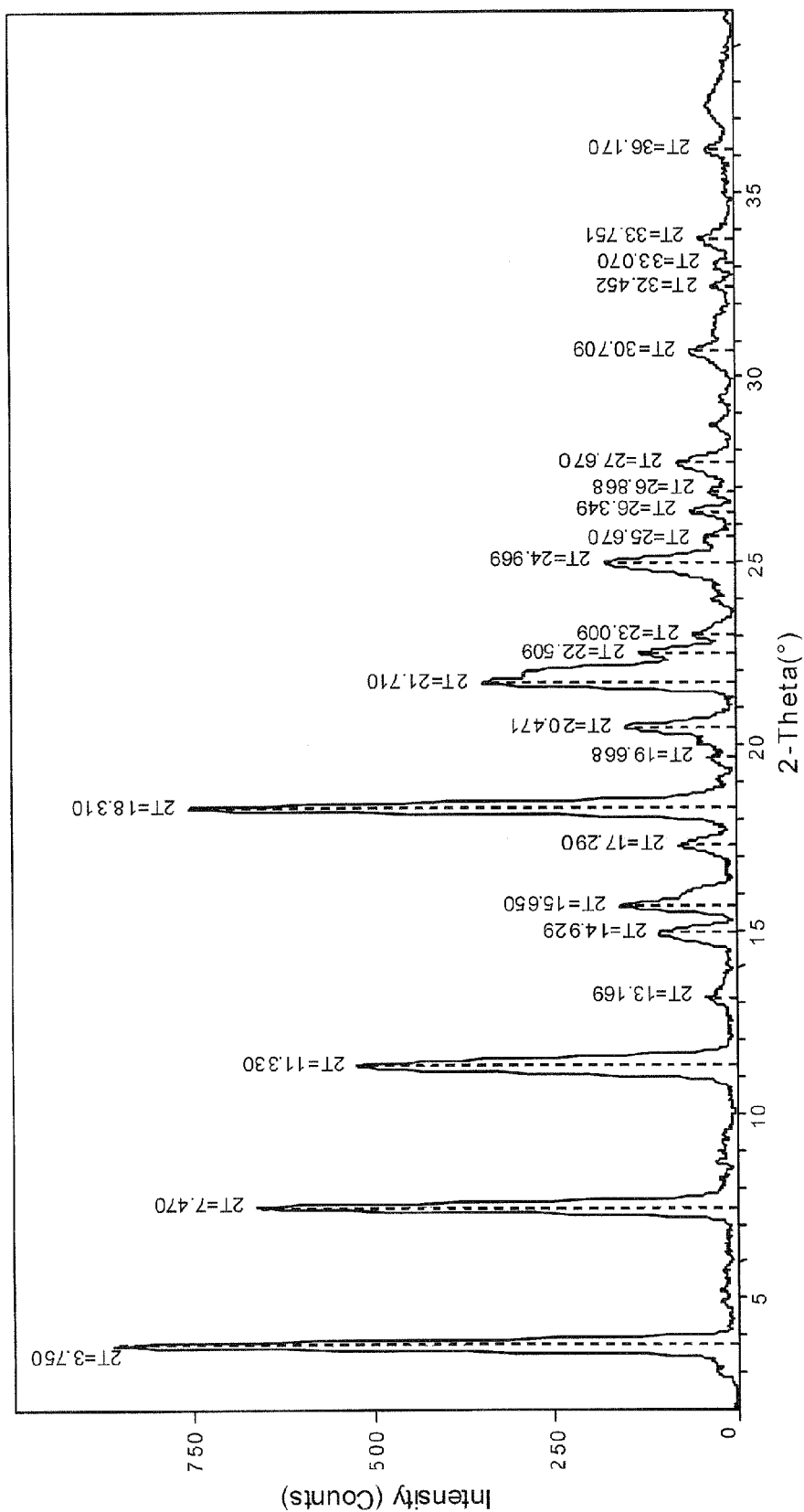
FIG. 4 shows the PXRD pattern of a propylene glycol solvate of a celecoxib potassium salt.

FIG. 3 shows the results of TGA. A weight loss of about 14.94% was observed between about 65 and about 250 degrees C. which is consistent with 1 molar equivalent of propylene glycol to celecoxib K. FIG. 4 shows the results of PXRD. Peaks, in 2-theta angles, that can be used to characterize the solvate include any 1, 2, 3, 4, 5, 6, 7, 8, 9, or 10 of the following: 3.75, 7.47, 11.33, 14.89, 15.65, 18.31, 20.49, 21.73, 22.51, and 24.97 degrees or any one or any combination of 1, 2, 3, 4, 5, 6, 7, 8, 9, 10, or more peaks of FIG. 4.

EXAMPLE 3

Celecoxib Lithium Salt PG Solvate

A propylene gly solvate of the lithium salt of celecoxib was prepared. To a solution of celecoxib (264 mg, 0.693 mmol) in diethyl ether (8 mL) was added propylene glycol (0.075 mL, 1.02 mmol). To the clear solution was added t-butyl lithium in pentane (1.7 M, 0.40 mL, 0.68 mmol). A brown solid formed immediately but dissolved within one minute which subsequently yielded a white fluffy solid. The white solid crystallized completely after 10 minutes. The solid was collected by filtration and was washed with additional diethyl ether (10 mL). The white solid was then air-dried and collected. The crystalline salt form was found to be a 1:1 propylene glycol solvate of celecoxib Li. The solid was characterized by TGA and PXRD.

Figure 5:
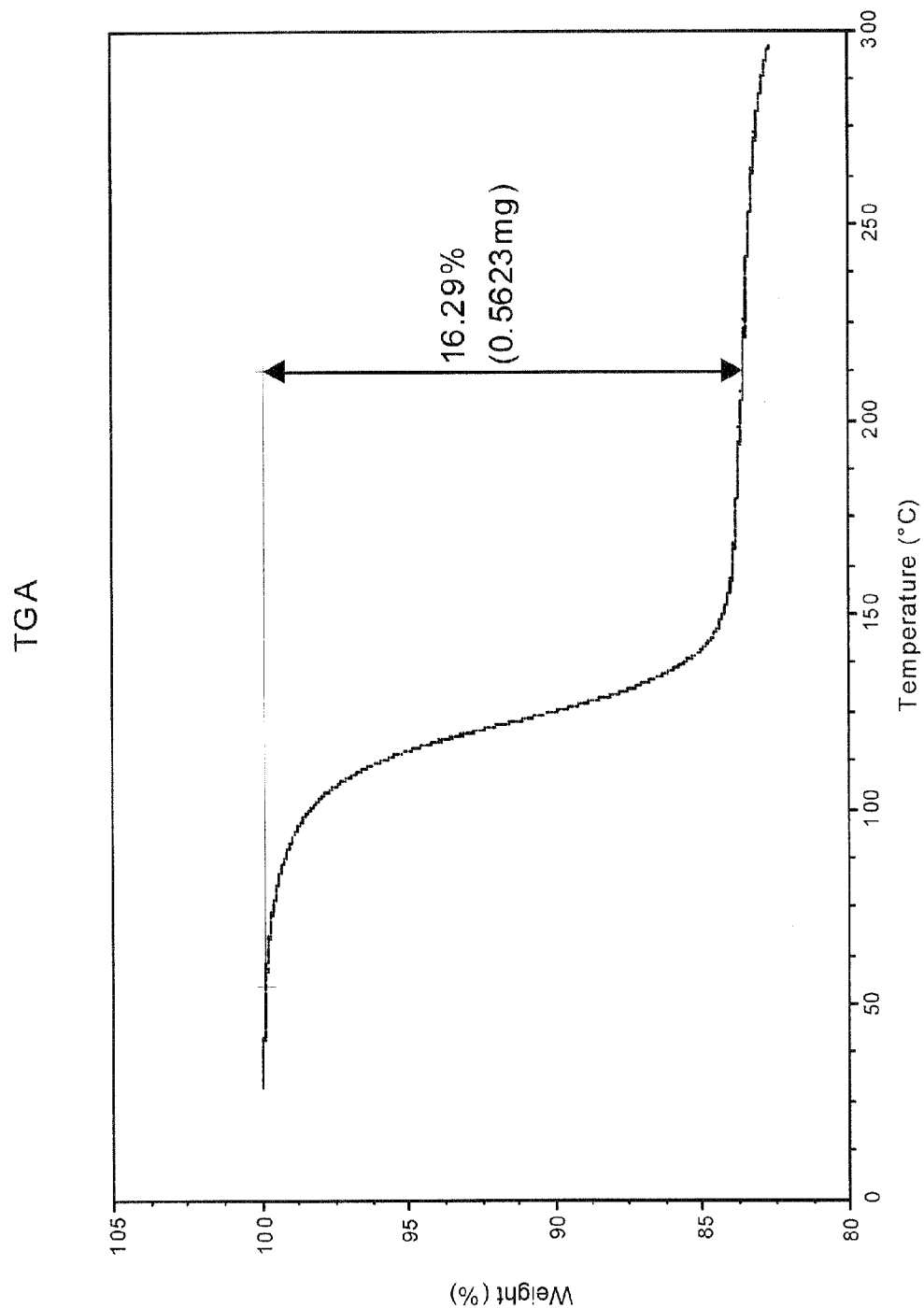
FIG. 5 shows a thermogravimetric analysis of a propylene glycol solvate of a celecoxib lithium salt.
Figure 6:
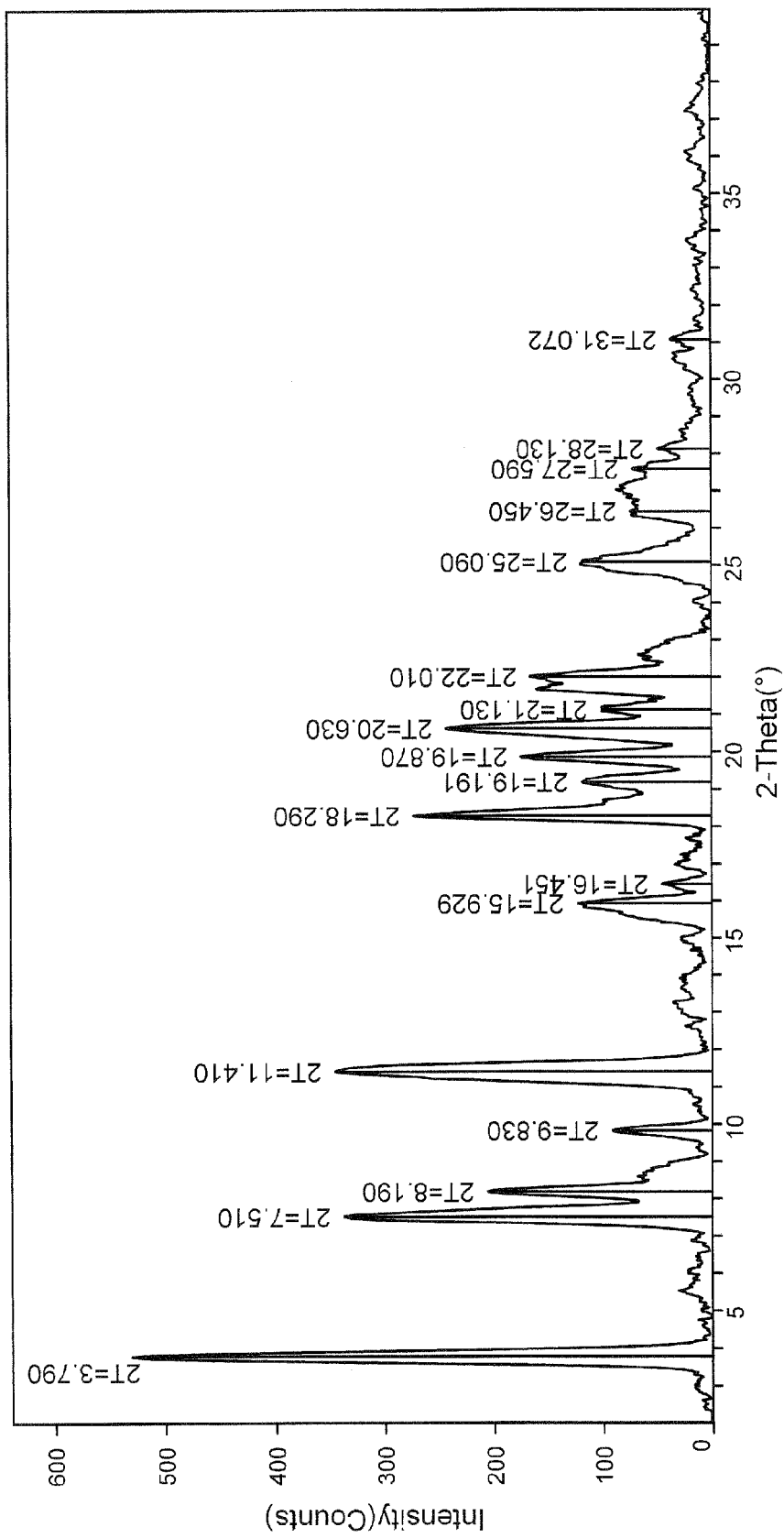
FIG. 6 shows the PXRD pattern of a propylene glycol solvate of a celecoxib lithium salt.

The results of TGA are depicted in FIG. 5 and show a weight loss of about 16.3% between 50 degrees C. and 210 degrees C. which is consistent with 1 molar equivalent of propylene glycol to celecoxib Li. The results of PXRD are shown in FIG. 6. Characteristic peaks of 2-theta angles that can be used to characterize the salt include any one, or combination of any 2, 3, 4, 5, 6, 7, 8, 9, 10, 11, or 12 of 3.79, 7.51, 8.19, 9.83, 11.41, 15.93, 18.29, 19.19, 19.87, 20.63, 22.01, or 25.09 degrees or any one or any combination of peaks of FIG. 6.

EXAMPLE 4

Naproxen Sodium Salt PG Solvate

Figure 7:
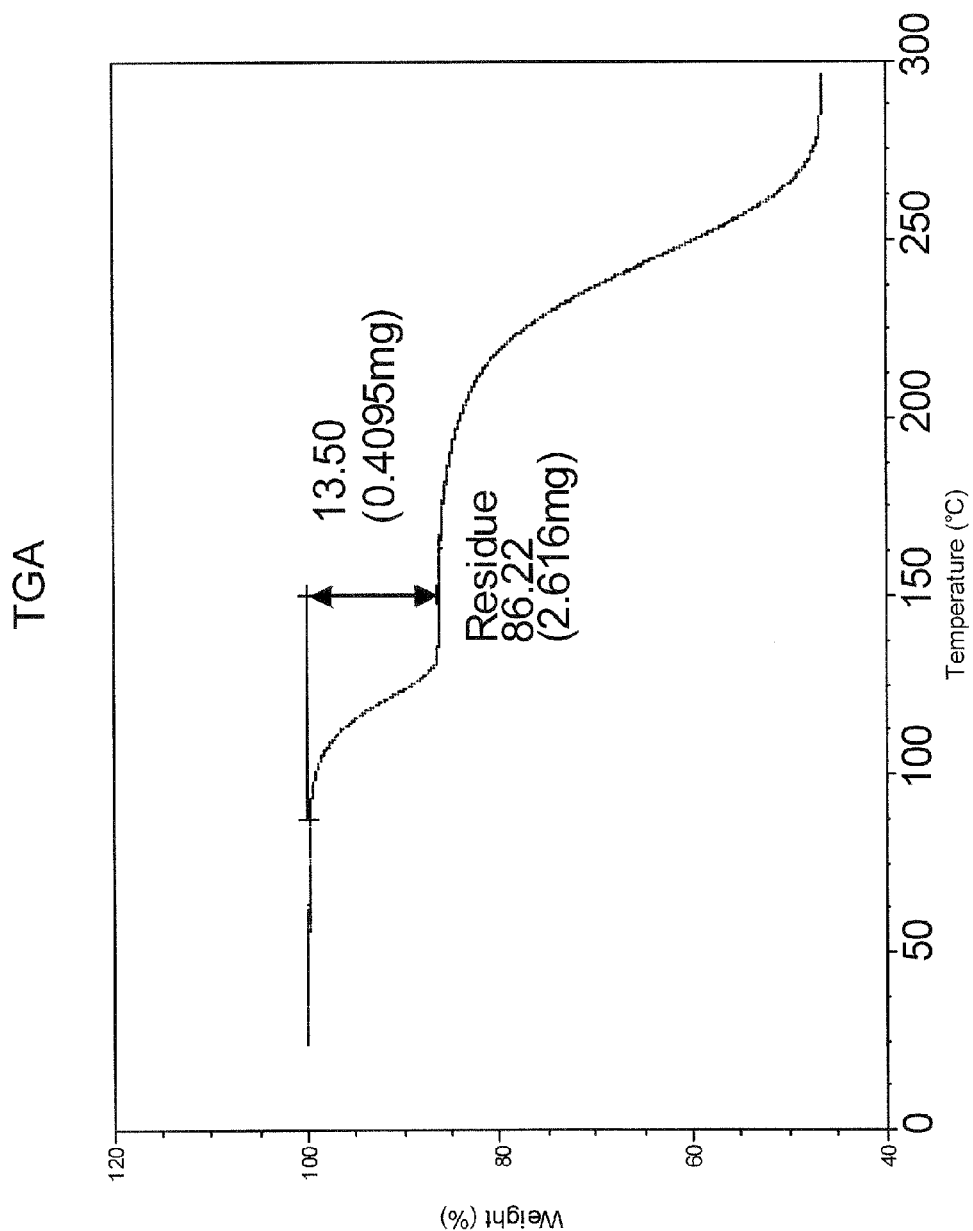
FIG. 7 shows the thermogravimetric analysis of a propylene glycol solvate of naproxen sodium salt.
Figure 8:
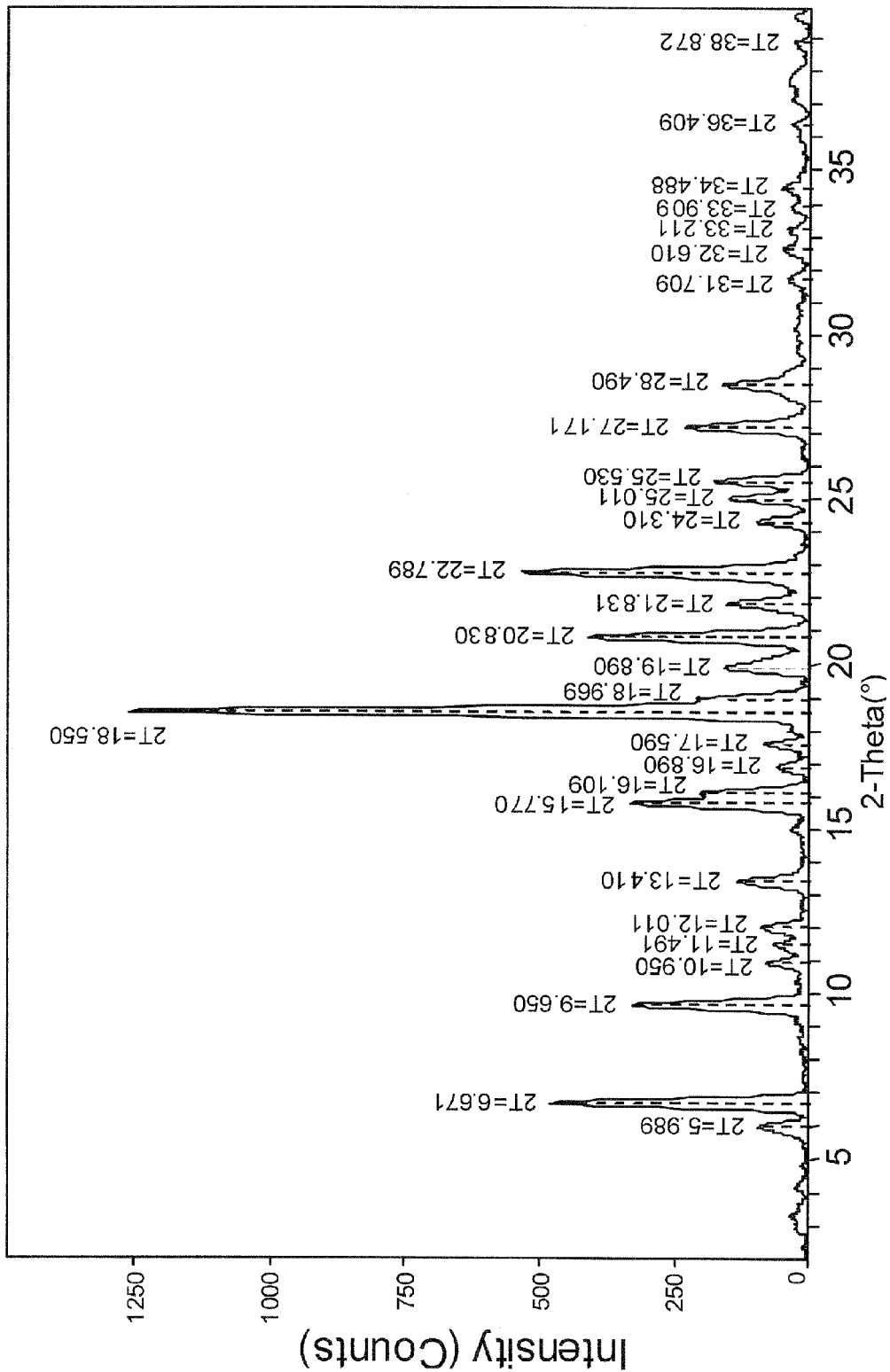
FIG. 8 shows a PXRD pattern of a propylene glycol solvate of naproxen sodium salt.

A propylene glycol solvate of a sodium salt of naproxen was prepared. To a solution of naproxen (348 mg, 1.51 mmol) in diethyl ether (10 mL) was added propylene glycol (0.200 ml, 2.72 mmol). To the clear solution was added sodium ethoxide in ethanol (21%, 0.750 mL, 2.01 mmol). The solution became slightly yellow due to the sodium ethoxide. After 1 minute, crystals began to form. After 5 minutes, the solid had completely crystallized. The solid was collected by filtration and was washed with diethyl ether (10 mL). The product was then air-dried and collected. The solvate was 2:1 naproxen Na:propylene glycol. The solid was characterized by TGA and PXRD. The TGA thermogram of naproxen sodium salt PG solvate is shown in FIG. 7, and indicates a 13.5 percent weight loss between about 75 and 150 degrees C. This weight loss is consistent with a 2:1 naproxen Na:propylene glycol solvate. The PXRD diffractogram of naproxen sodium salt PG solvate is shown in FIG. 8, and shows peaks at 2-theta angles, including but not limited to, 6.67, 9.65, 13.41, 15.77, 18.55, 20.83, 22.79, and 27.17 degrees. Any one, any two, any three, any four, any five, any six, any seven, or all eight of the above peaks or any one or any combination of peaks in FIG. 8 can be used to characterize naproxen sodium salt PG solvate.

EXAMPLE 5

Preparation of Olanzapine PG Solvate

Olanzapine PG solvate was prepared by dissolving 1.05 g of olanzapine form I in 8 mL of isopropylacetate and 2.0 mL of propylene glycol with heating. The hot liquid was filtered through a 0.2 micrometer nylon syringe filter. Crystallization occurred after cooling to room temperature. The addition of a small amount of seed crystals from a previous reaction followed by sonication for 10 seconds also facilitated crystallization. Olanzapine PG solvate was isolated by suction filtration, rinsed with isopropylacetate and allowed to air dry. The product was a fine yellow powder. The crystals grew in three dimensions, yielding chunks.

A second preparation of olanzapine form I PG solvate was completed by dissolving 16.2 mg of olanzapine form I in 0.05 ml of propylene glycol and 0.05 ml of isopropylacetate with heating. The sample was cooled to room temperature and a single crystal from a previous preparation was added. The sample was allowed to sit undisturbed for 2 days during which an aggregate clump of several large crystals grew. The crystals were transferred to filter paper, rinsed with a single drop of isopropylacetate, and dried by dabbing with the filter paper. The rinse procedure was repeated a total of four times with fresh filter paper. Characterization of the product has been achieved via TGA, DSC, PXRD, and Raman spectroscopy.

Figure 9:
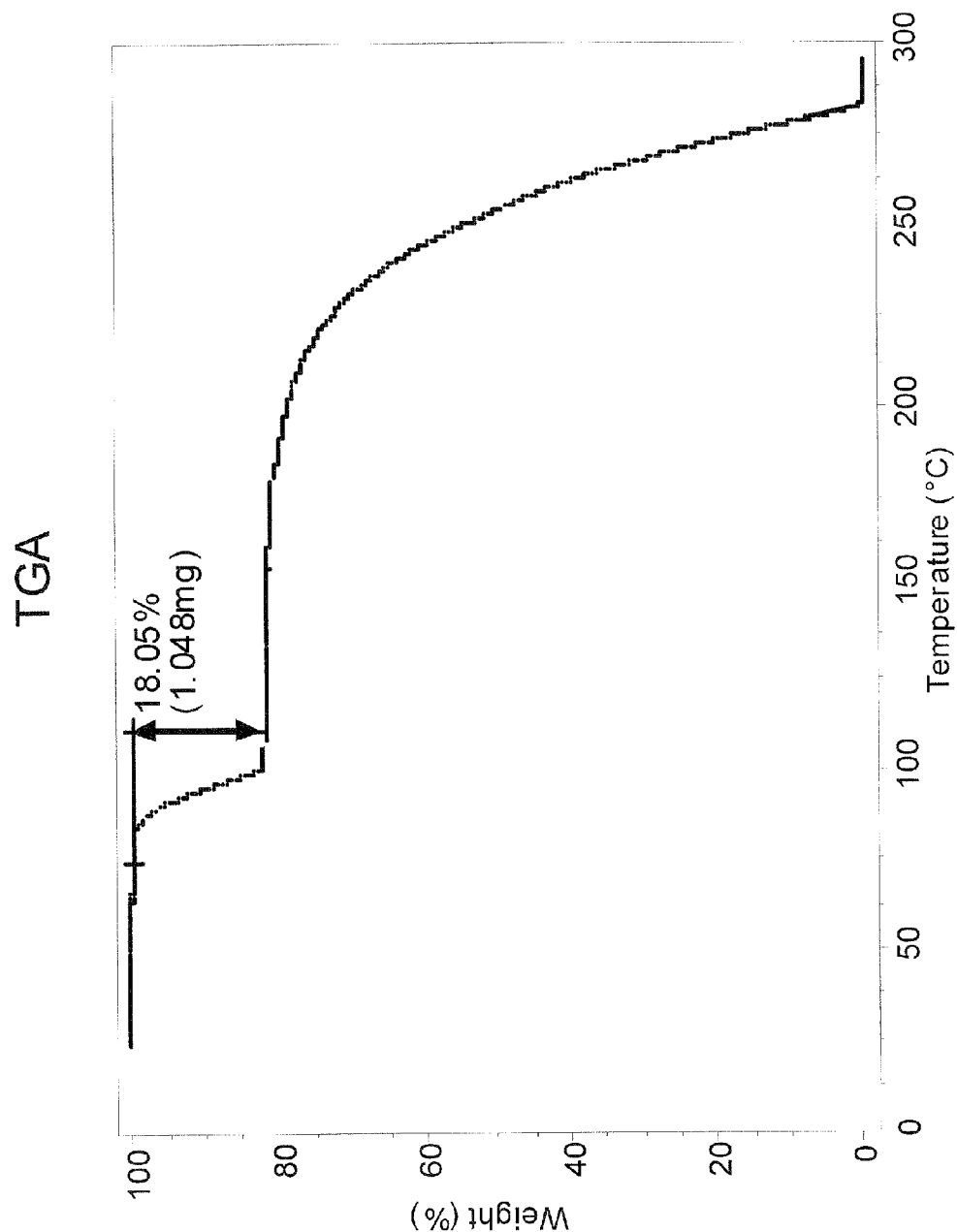
FIG. 9 shows the thermogravimetric analysis of a propylene glycol solvate of olanzapine form I.
Figure 10:
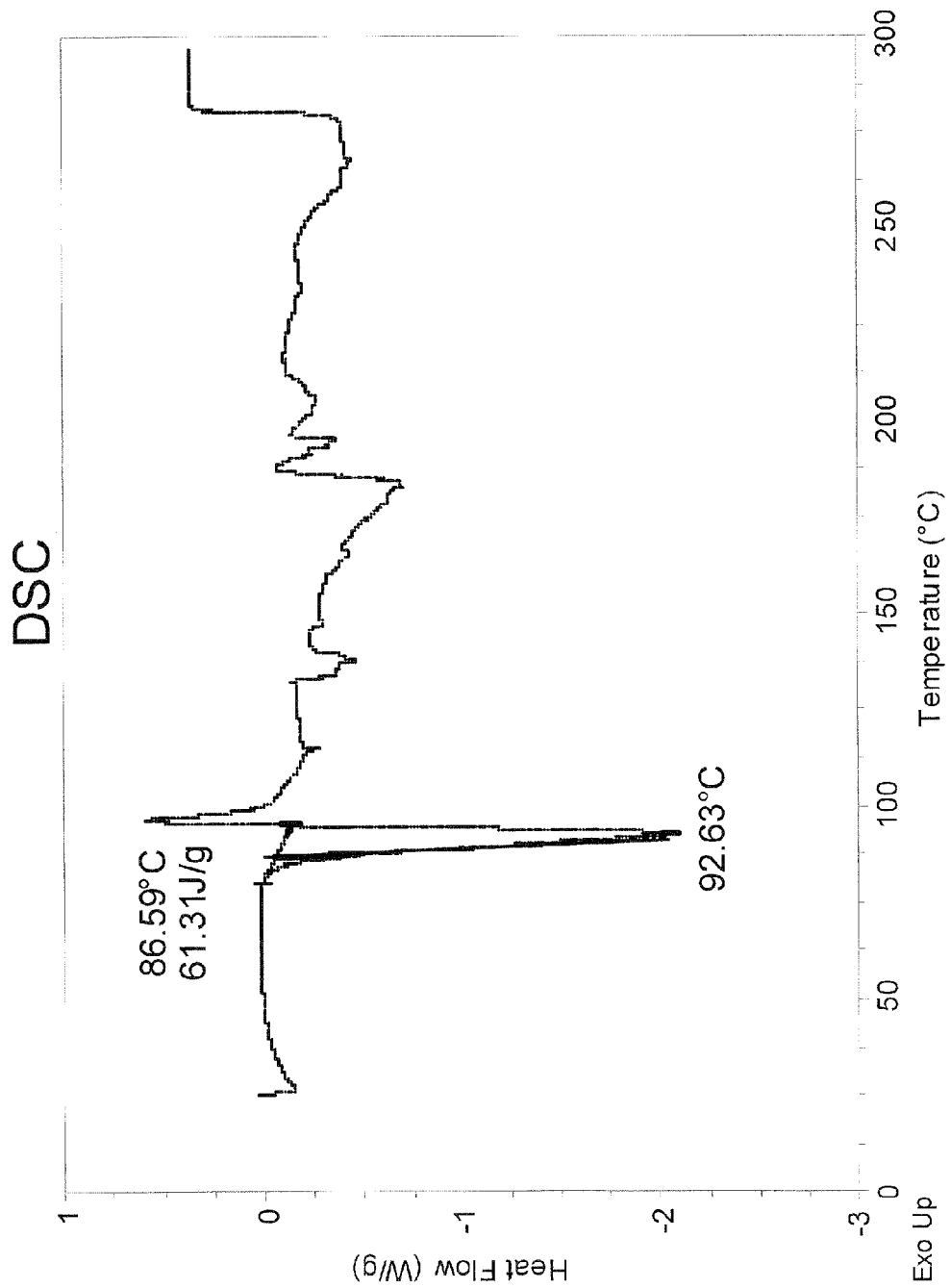
FIG. 10 shows the differential scanning calorimetry thermogram of a propylene glycol solvate of olanzapine form I.

Results from TGA analysis show an 18.05% weight loss representing loss of about 1 equivalent of propylene glycol (FIG. 9). Results from DSC show a peak endothermic transition at 92.63 degrees C. (FIG. 10).

Figure 11A:
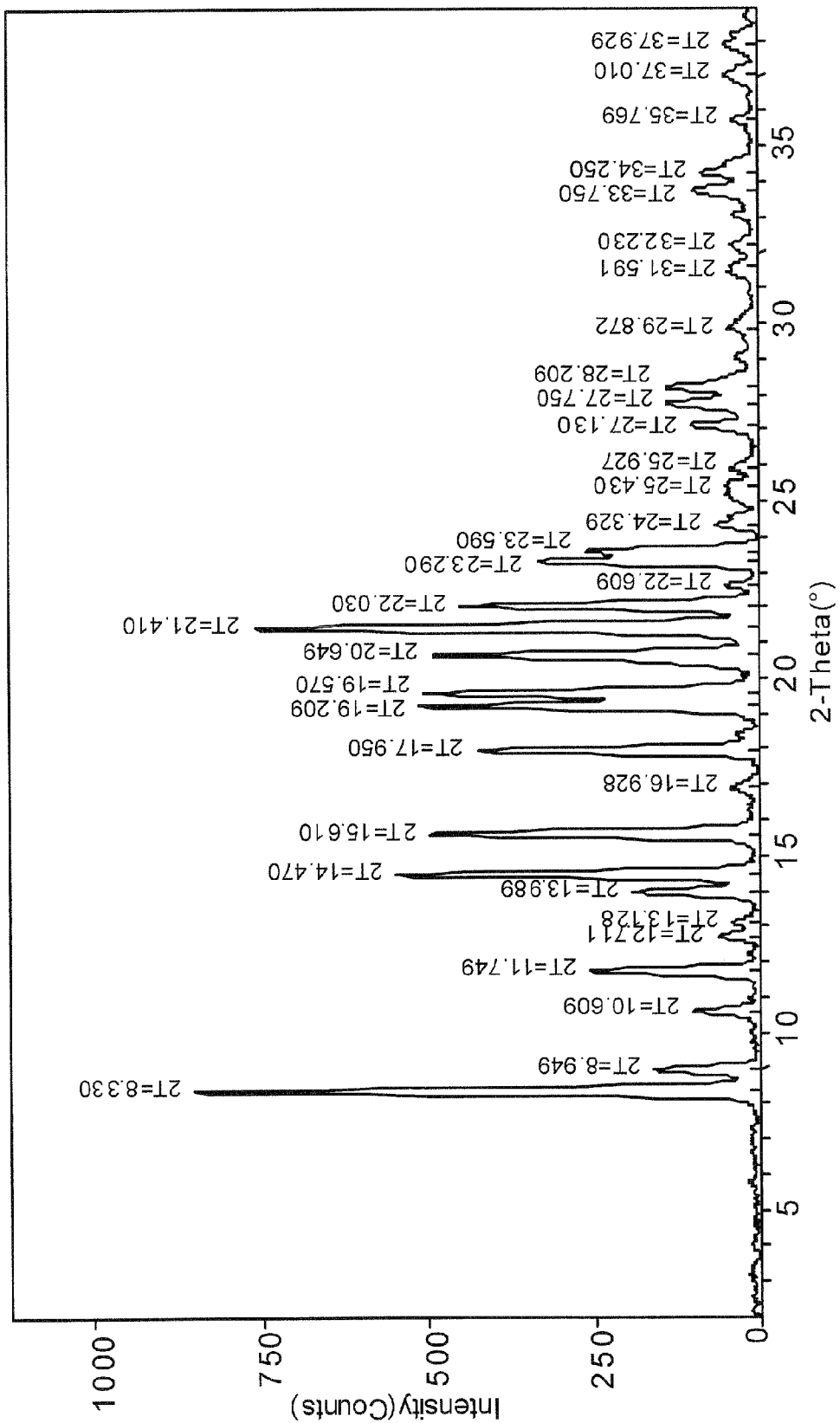
FIG. 11A-B shows PXRD patterns of a propylene glycol solvate of olanzapine form I.
Figure 11B:
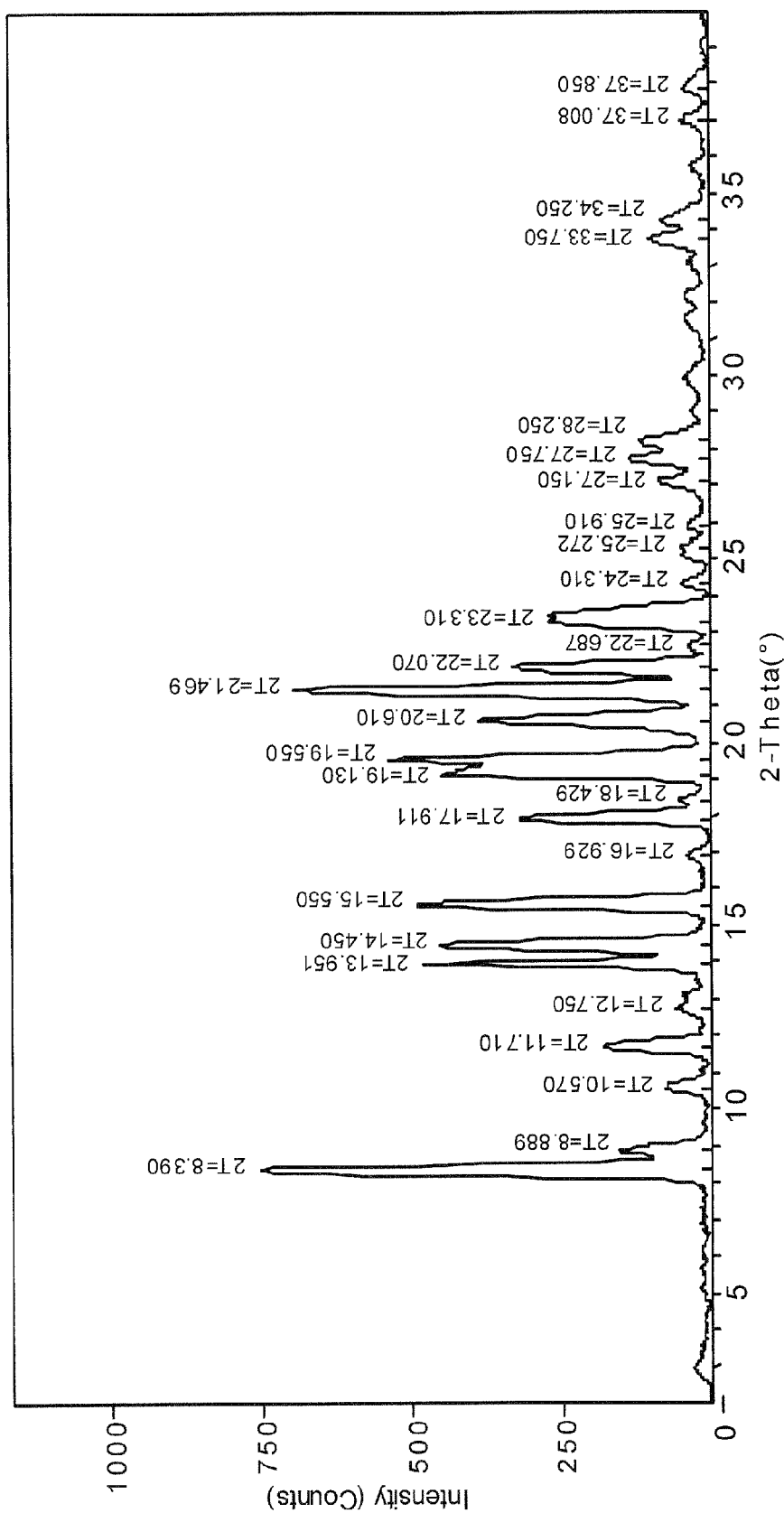

The PXRD pattern has characteristic peaks as shown for two sample preparations in FIGS. 11A and 11B. Peaks can be seen at 2-theta angles including but not limited to 8.33, 8.95, 11.75, 14.47, 15.61, 17.95, 19.21, 19.57, 20.65, 21.41, 22.03, and 23.29 in FIG. 11A. The crystal can be characterized by any one, any two, any three, any four, any 5, any 6, any 7, any 8, any 9, any 10, any 11, or all 12 of the peaks above or one or a combination of peaks in FIG. 11A. In the second representative sample, peaks can be seen at 2-theta angles including, but not limited to, 8.39, 8.89, 13.95, 14.45, 15.55, 17.91, 19.13, 19.55, 20.61, 21.47, 22.07, and 23.31 in FIG. 11B. The crystal can be characterized by any one, any two, any three, any four, any 5, any 6, any 7, any 8, any 9, any 10, any 11, or all 12 of the peaks above or one or a combination of peaks in FIG. 11B.

Figure 12:
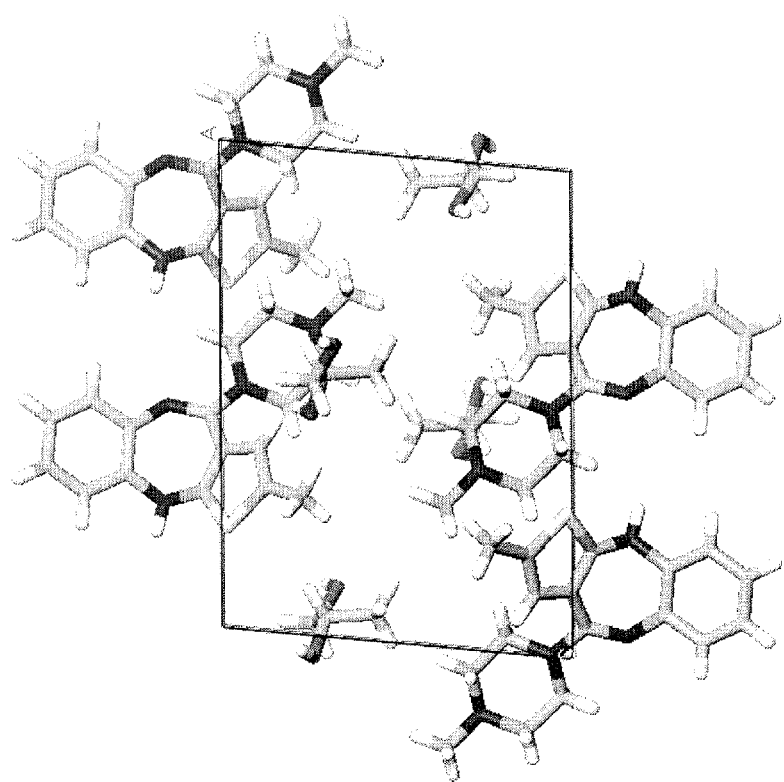
FIG. 12 shows a packing diagram of olanzapine form I PG solvate.

Single-crystal x-ray studies of olanzapine form I PG solvate were also completed. FIG. 12 shows a packing diagram of the single-crystal structure of olanzapine form I PG solvate. The unit cell data are as follows: space group P2(1)/c, A=10.4264(9), B=13.3916(11), C=14.4424(12), Alpha=90, Beta=95.503(2), Gamma=90, Volume=2007.2(3).

EXAMPLE 6

Preparation of Cortisone Acetate PG Solvate

Cortisone acetate PG solvate was prepared by dissolving 9.7 mg cortisone acetate in 0.6 mL propylene glycol with heating. Needle-like crystals formed upon cooling, followed by the conversion to large, very thin, rectangular plates over a couple hours.

A second preparation of cortisone acetate PG solvate was completed by dissolving 11.9 mg cortisone acetate in 0.7 mL isopropylacetate with heating to reflux. Upon crystal formation, 0.05 mL propylene glycol was added, heated to reflux to dissolve, and crystals again formed. The resultant crystals were collected and analyzed by PXRD, TGA, and DSC.

A third preparation of cortisone acetate PG solvate was completed by dissolving 65.8 mg cortisone acetate in 7.0 mL isopropylacetate and 0.05 mL propylene glycol with heating. The mixture was cooled slightly and seed crystals from a previous reaction (second preparation above) were added. The resultant crystals form rods, or long rectangular plates that are birefringent when viewed by plane polarized microscopy. Crystals were harvested after 30 minutes and analyzed by single crystal x-ray. Prior to PXRD measurement, the sample was ground, transferred to a vial, and left open to the atmosphere for 4 days.

Figure 13:
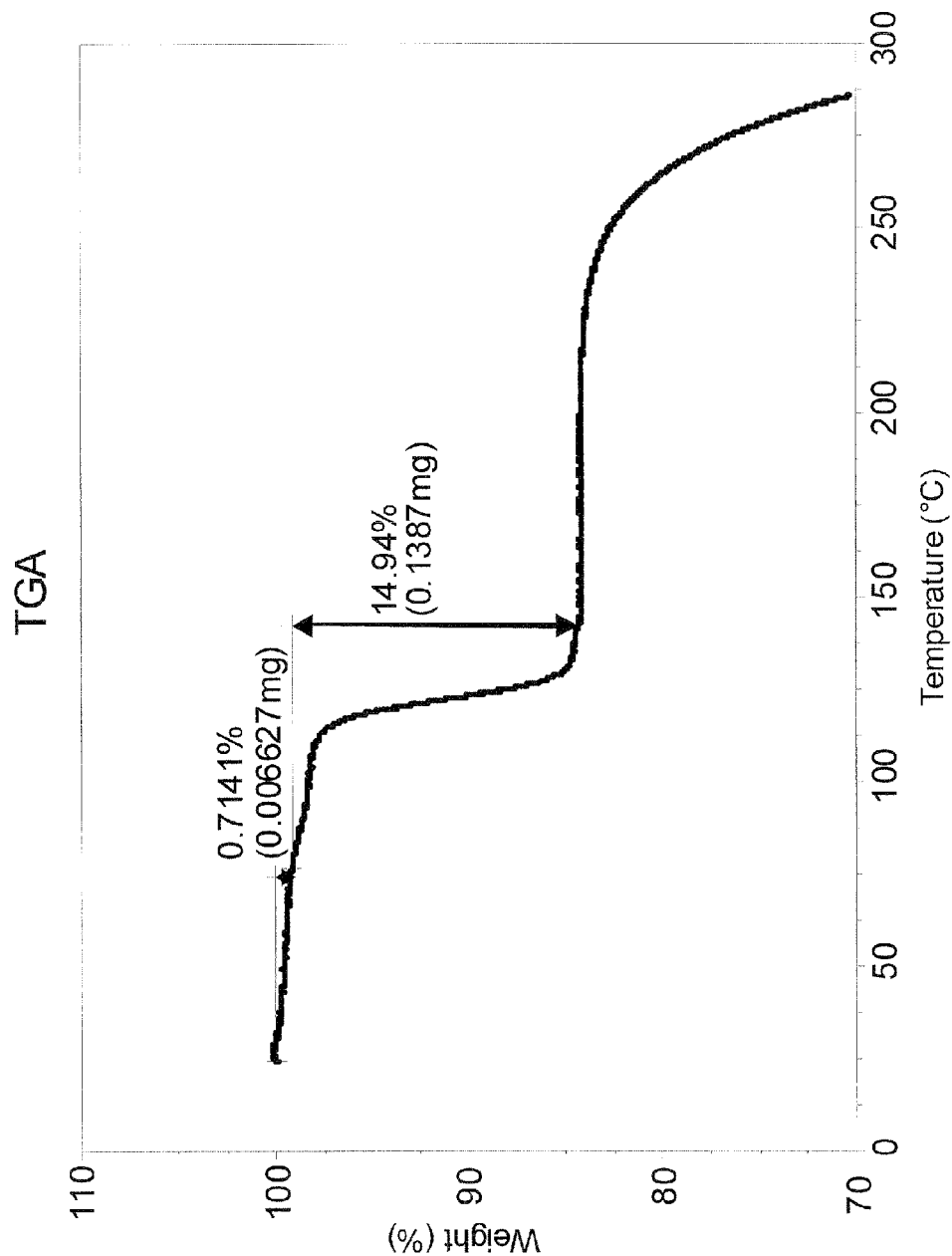
FIG. 13 shows the thermogravimetric analysis of a propylene glycol solvate of cortisone acetate.
Figure 14:
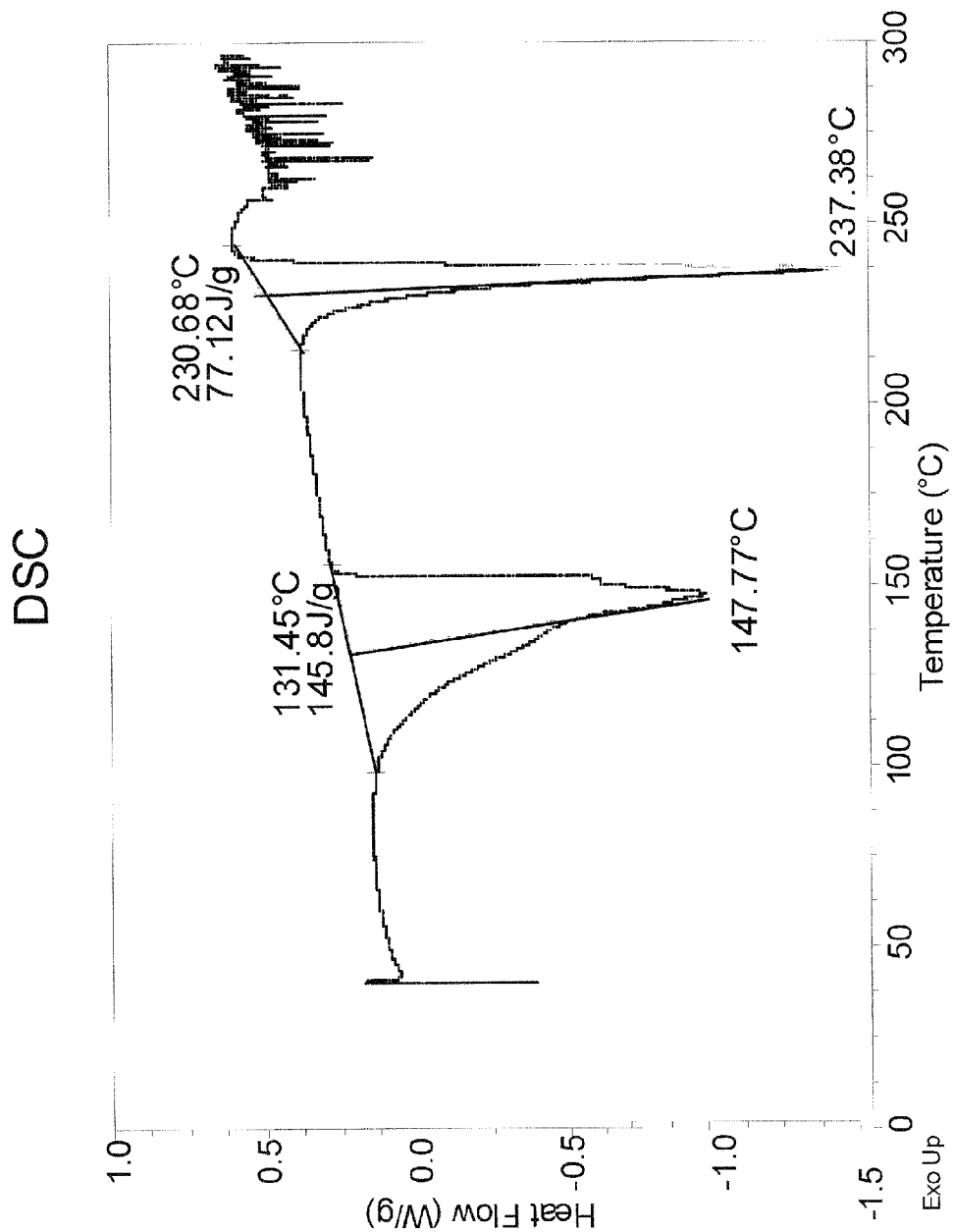
FIG. 14 shows the differential scanning calorimetry thermogram of a propylene glycol solvate of cortisone acetate.

Results from TGA analysis show a 15.9% weight loss at temperatures up to 150 degrees C. (FIG. 13). 14.9% weight loss occured between 70 and 150 degrees C. while up to 1.2% weight loss occurred at lower temperatures. This weight loss is representative of a cortisone acetate PG solvate with 1.0 equivalents of propylene glycol. DSC was completed in a closed, not sealed aluminium pan from room temperature to 300 degrees C. at 10 degrees/minute (FIG. 14). The compound was discovered to have two endothermic transitions, one at 148 degrees C. with an intensity of 146 J/g, and the second at 237 degrees C. with an intensity of 77 J/g.

Figure 15A:
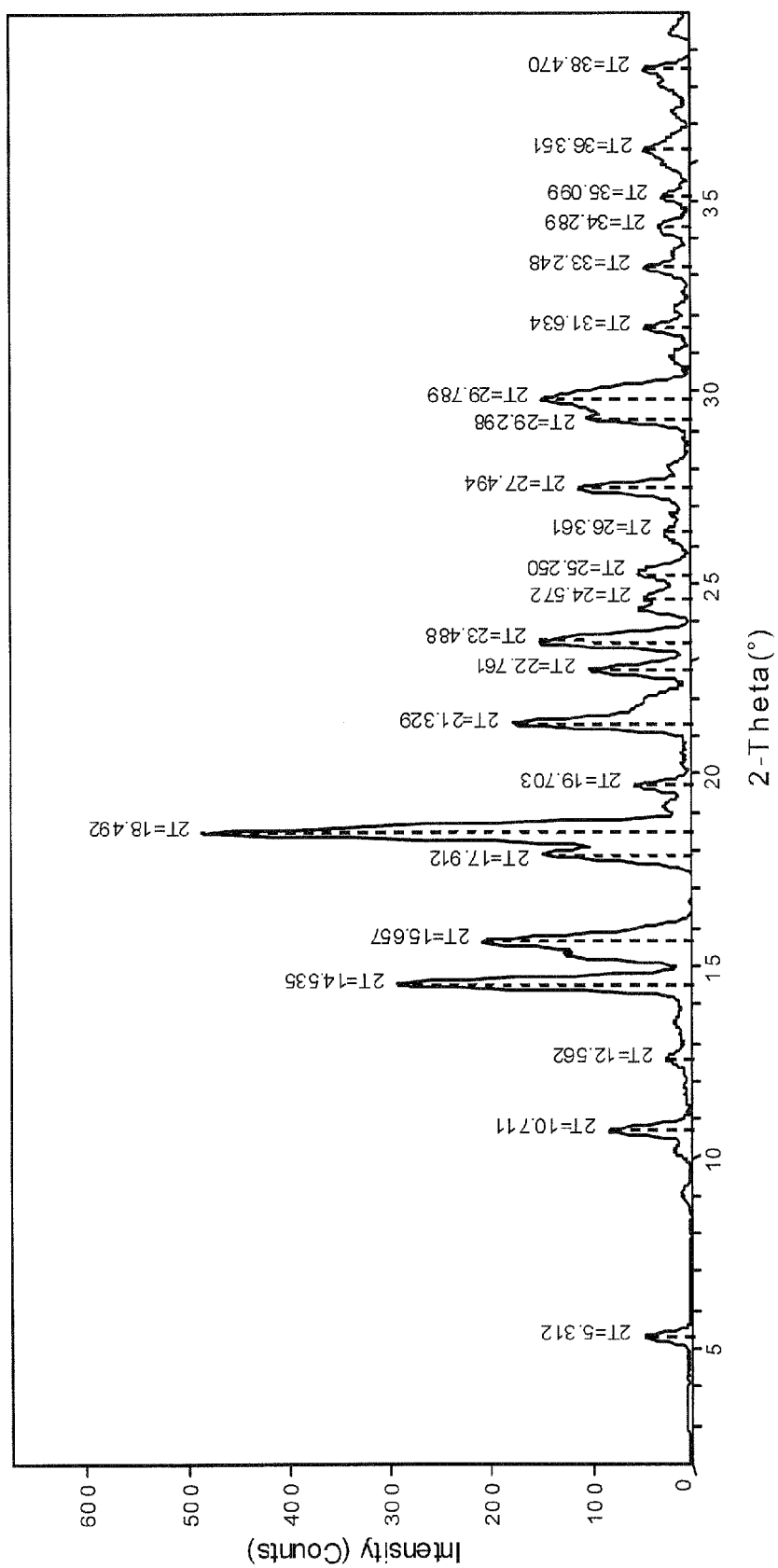
FIG. 15A-B shows PXRD patterns of a propylene glycol solvate of cortisone acetate.
Figure 15B:
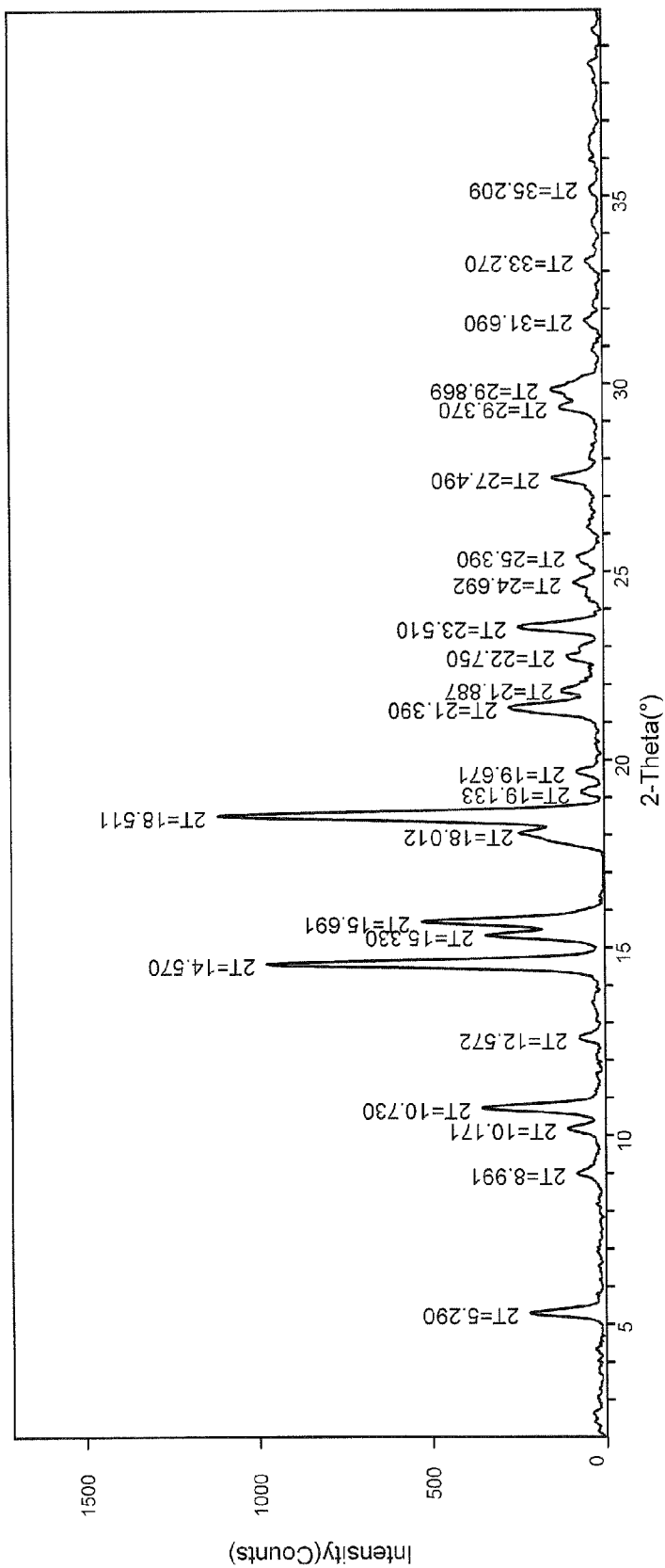
Figure 16:
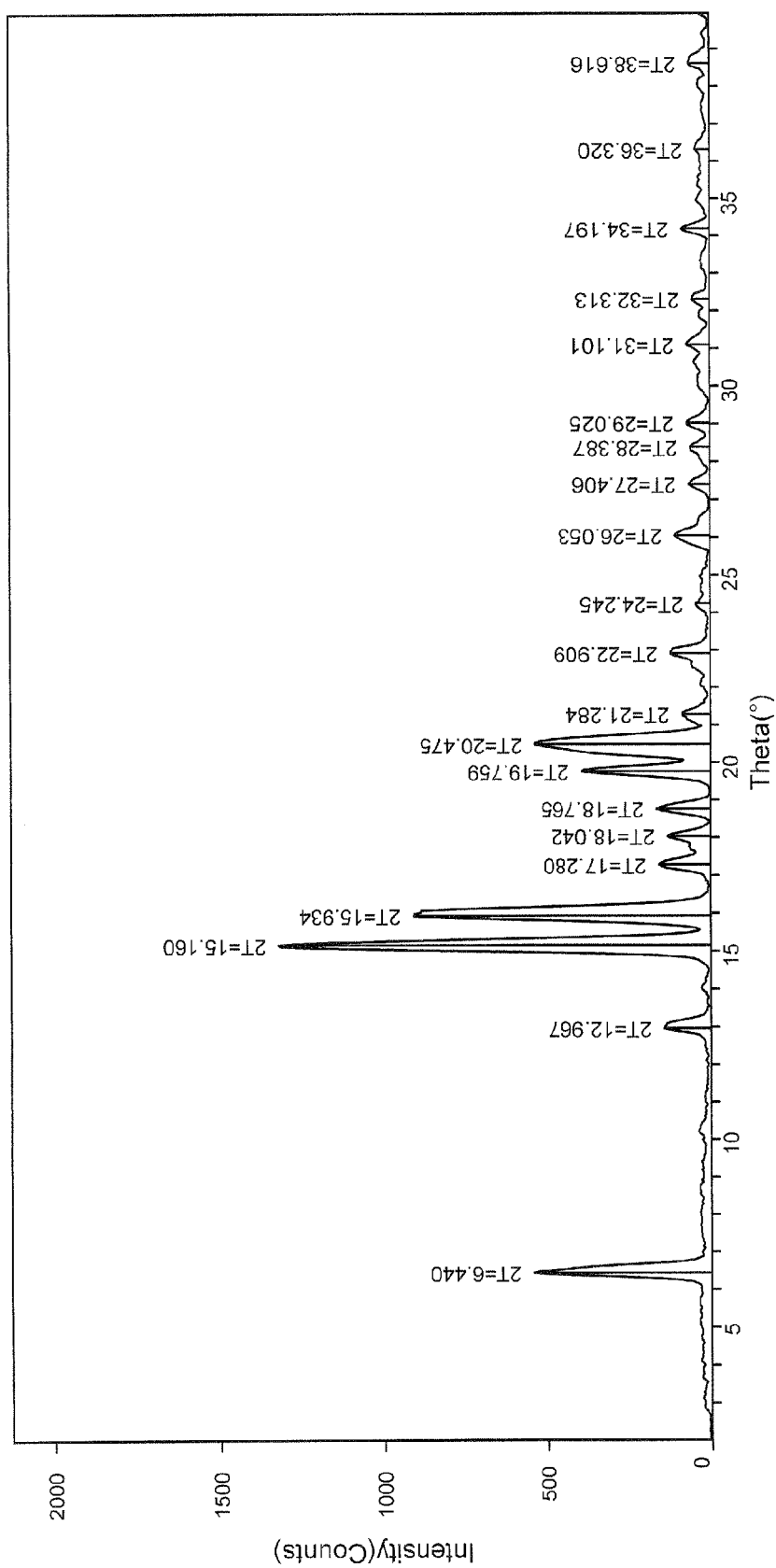
FIG. 16 shows a PXRD pattern of cortisone acetate.

The PXRD of cortisone acetate PG solvate crystallized from isopropylacetate/propylene glycol solution is shown in two diffractograms in FIG. 15A and FIG. 15B. Peaks can be seen at 2-theta angles including, but not limited to, 5.31, 10.71, 14.54, 15.66, 18.49, 21.33, and 23.49 degrees. The crystal can be characterized by any one, any two, any three, any four, any five, any six, or any seven, or any combination of the peaks listed above or one or a combination of peaks listed in FIG. 15A. In the second representative sample, peaks can be seen at 2-theta angles including, but not limited to, 5.29, 10.73, 14.57, 15.69, 18.51, 21.39, 23.51, and 27.49 in FIG. 15B. The crystal can be characterized by any one, any two, any three, any four, any 5, any 6, any 7, or all 8 of the peaks above or one or a combination of peaks in FIG. 15B. FIG. 16 shows a PXRD diffractogram of material crystallized from isopropylacetate alone. This is provided only to differentiate the PG solvate from the unsolvated form of the API.

Single-crystal x-ray studies of cortisone acetate PG solvate were also completed.

Figure 17:
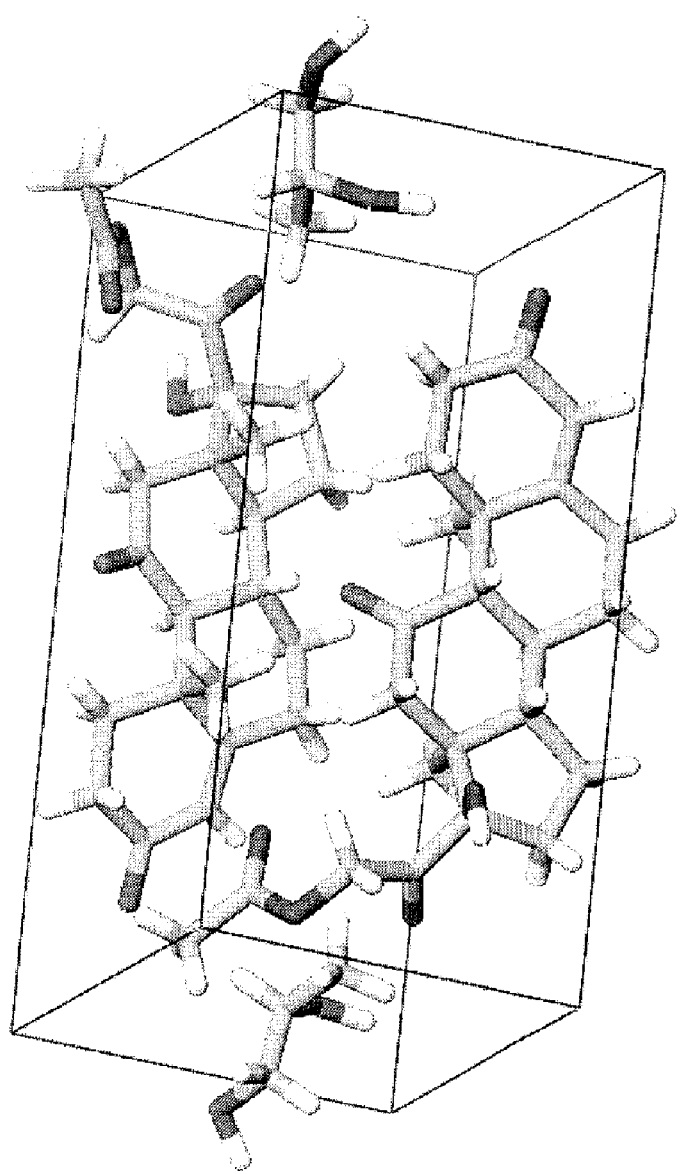
FIG. 17 shows a packing diagram of cortisone acetate PG solvate.

FIG. 17 shows a packing diagram of the single-crystal structure of cortisone acetate PG solvate. The unit cell data are as follows: space group P2(1), A=9.728(2), B=7.6306(15), C=16.454(3), Alpha=90, Beta=92.568(4), Gamma=90, Volume=1220.2(4).

EXAMPLE 7

Celecoxib Sodium PG Solvate Trihydrate

Preparation:

Celecoxib Na propylene glycol trihydrate was formed by allowing the celecoxib sodium salt propylene glycol solvate to sit at 60% RH and 20 degrees C. for 3 days. (Note: Formation of the trihydrate at 75% and 40 degrees C. occurs as well). The trihydrate begins to form somewhere between 31 and 40% RH at room temperature.

Figure 18:
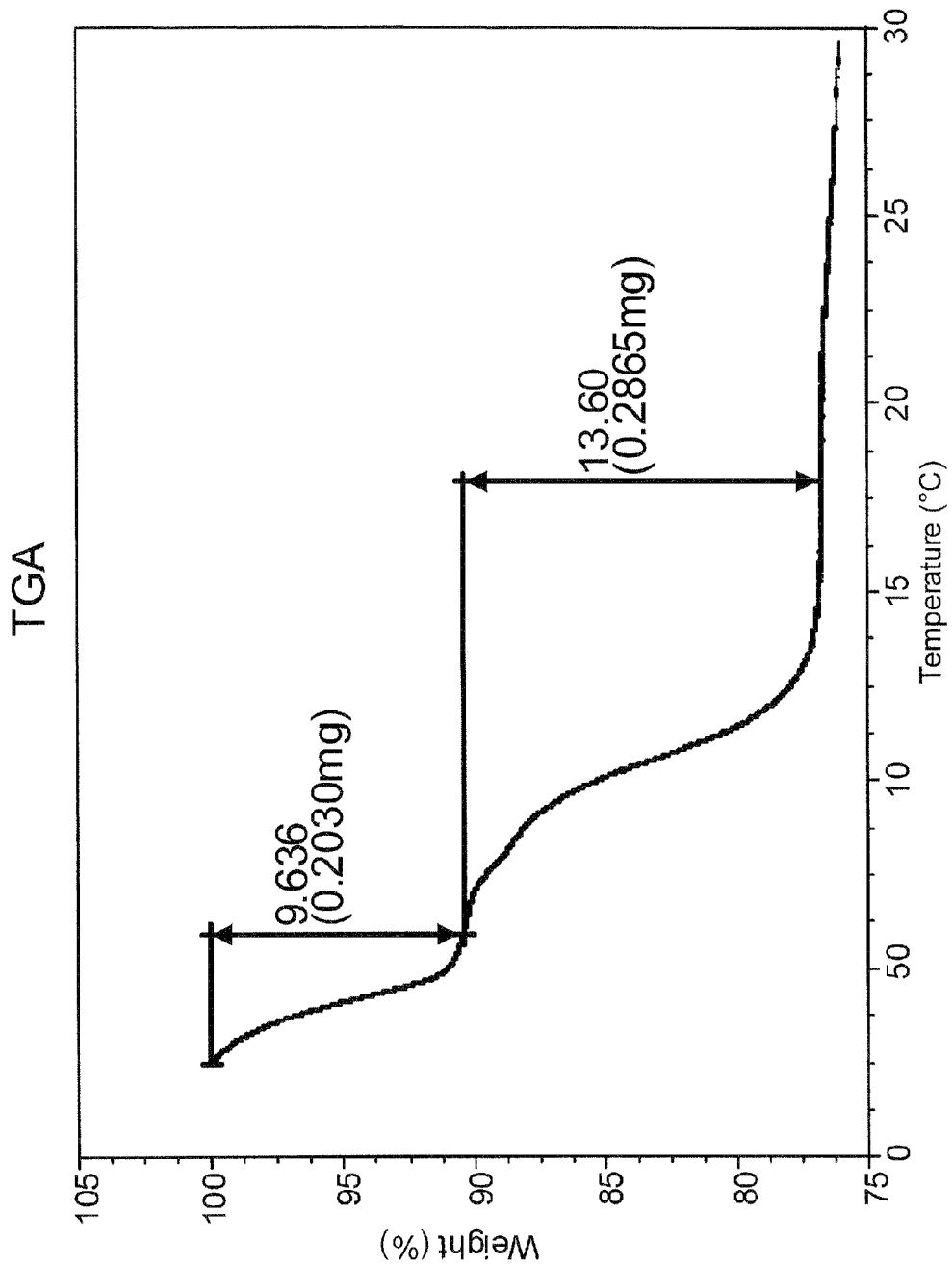
FIG. 18 shows the thermogravimetric analysis of a trihydrate of celecoxib sodium PG solvate.
Figure 19:
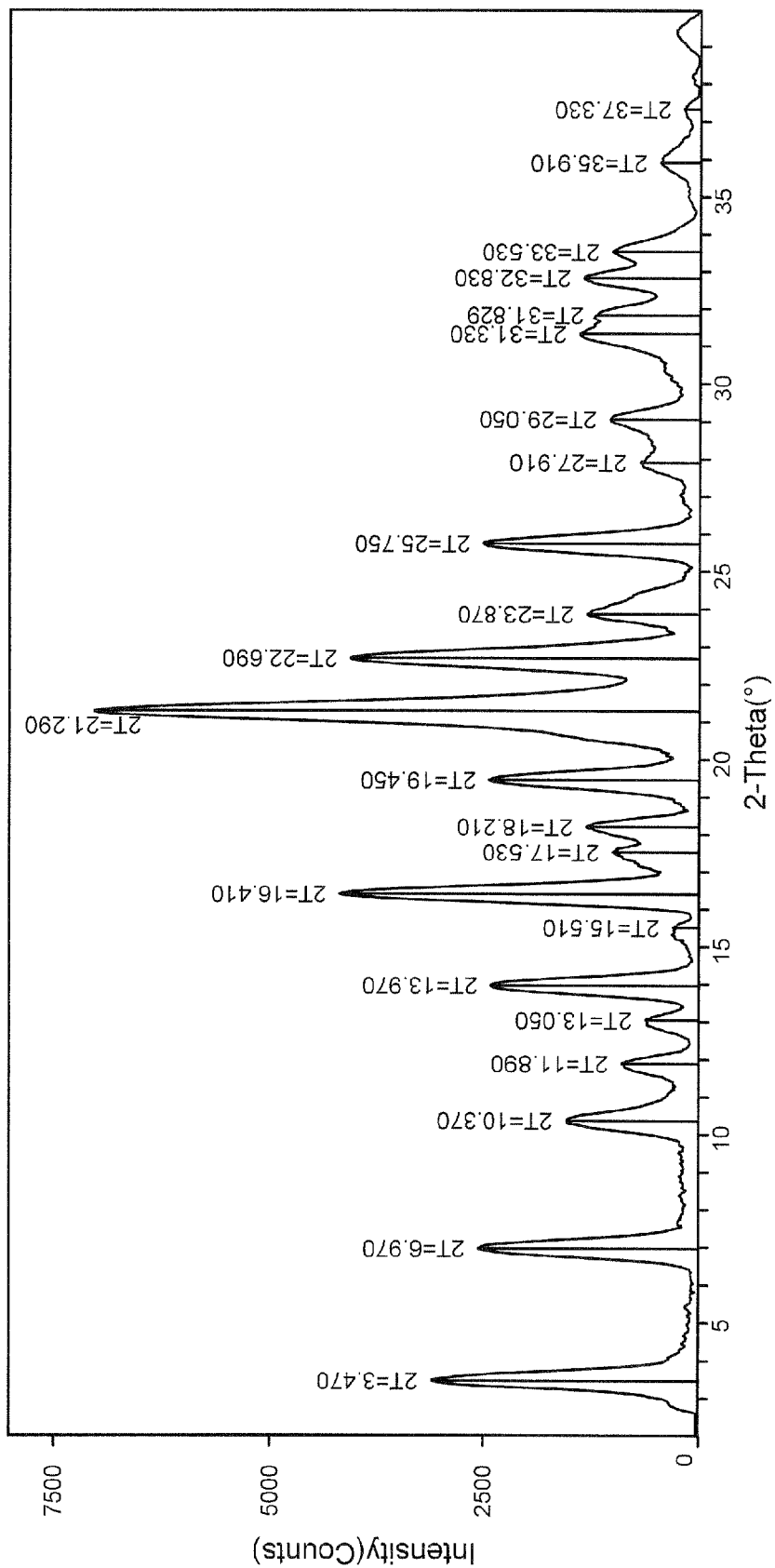
FIG. 19 shows the PXRD pattern of a trihydrate of celecoxib sodium PG solvate.

The solid was characterized by TGA and PXRD, which are shown in FIGS. 18 and 19, respectively. FIG. 18 shows the results of the TGA where 9.64% weight loss was observed between room temperature and 60 degrees C. and 13.6% weight loss was observed between 60 degrees C. and 175 degrees C. The PXRD pattern has characteristic peaks at 2-theta angles shown in FIG. 19. Any 1, 2, 3, 4, 5, 6, 7, 8, 9, 10, or more peaks can be used to characterize the trihydrate, including for example, peaks at 3.47, 6.97, 10.37, 13.97, 16.41, 19.45, 21.29, 22.69, 23.87, and 25.75 degrees. A 0.8 mm collimator was used during acquisition of the diffractogram.

The trihydrate can also be formed by crystallization of celecoxib Na propylene glycol solvate in the presence of H$_2$O. To a solution of celecoxib (136.2 mg; 0.357 mmol) in diethyl ether (6.0 mL), water (0.025 mL; 1.39 mmol), and propylene glycol (0.030 mL; 0.408 mmol) was added sodium ethoxide in ethanol (21 wt. %; 0.135 mL; 0.362 mmol). A solid formed within one minute and was isolated via filtration. The solid was then washed with additional diethyl ether (2.0 mL) and allowed to air dry. This procedure gives essentially the same PXRD pattern but there is a slight excess of water, which is probably surface water.

Figure 20:
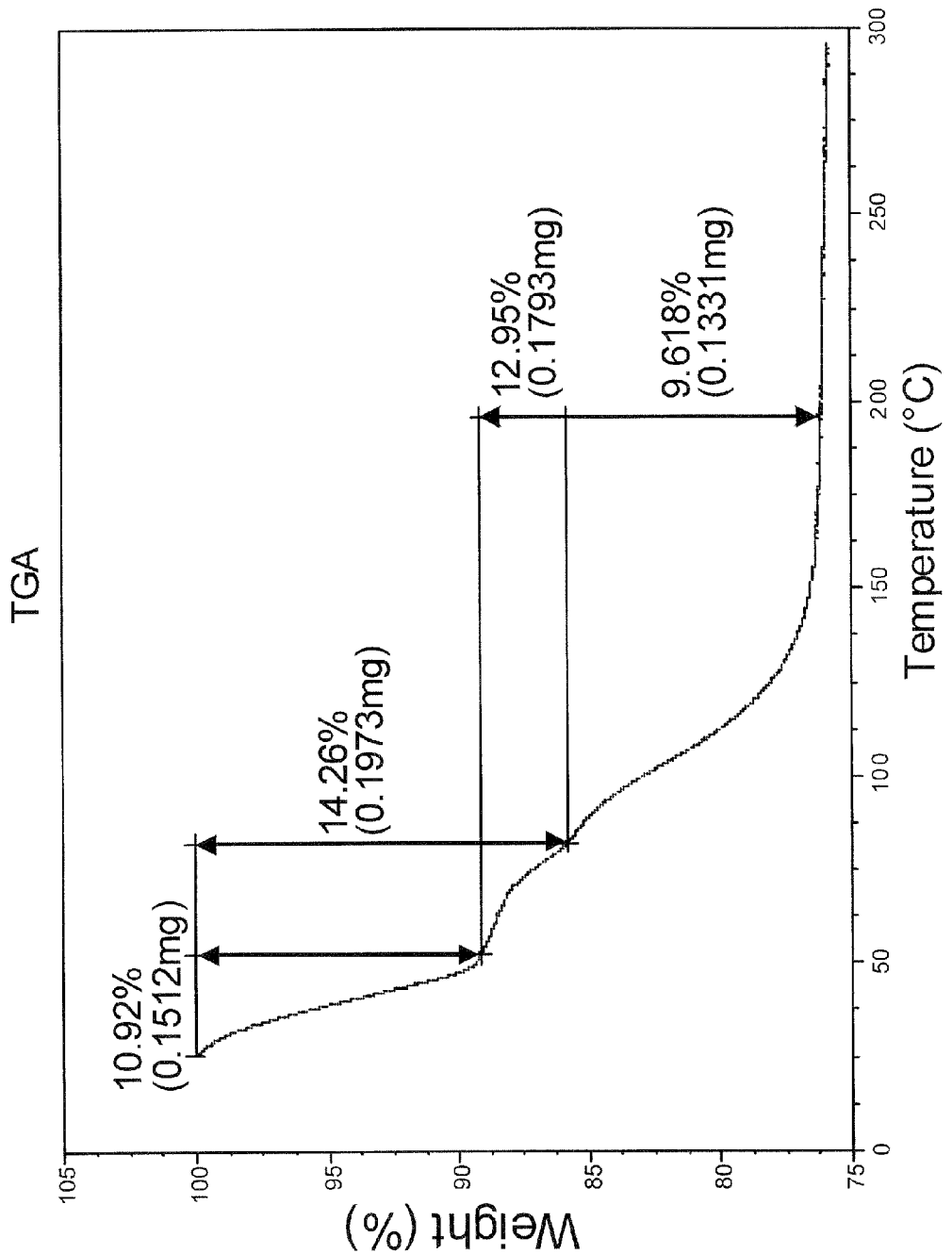
FIG. 20 shows the thermogravimetric analysis of a trihydrate of celecoxib sodium PG solvate.
Figure 21:
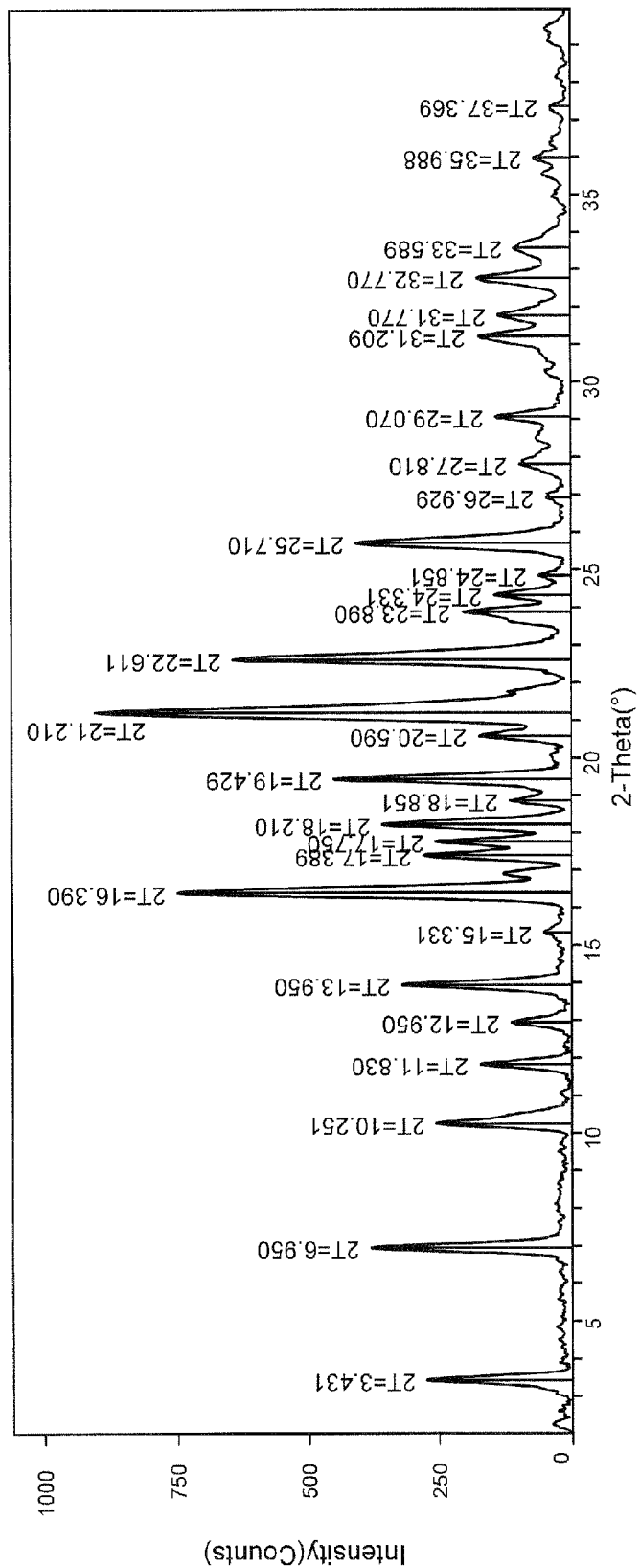
FIG. 21 shows the PXRD pattern of a trihydrate of celecoxib sodium PG solvate.

The solid was characterized by TGA and PXRD, which are shown in FIGS. 20 and 21, respectively. FIG. 20 shows the results of TGA where 10.92% weight loss was observed between room temperature and 50 degrees C. and 12.95% weight loss was observed between 50 degrees C. and 195 degrees C. The PXRD pattern has characteristic peaks at 2-theta angles shown in FIG. 21. Any 1, 2, 3, 4, 5, 6, 7, 8, 9, 10, 11, 12, or more peaks can be used to characterize the trihydrate, including for example, peaks at 3.43, 6.95, 10.25, 13.95, 16.39, 17.39, 17.75, 18.21, 19.43, 21.21, 22.61, and 25.71 degrees. A 0.8 mm collimator was used during acquisition of the diffractogram.

Figure 22:
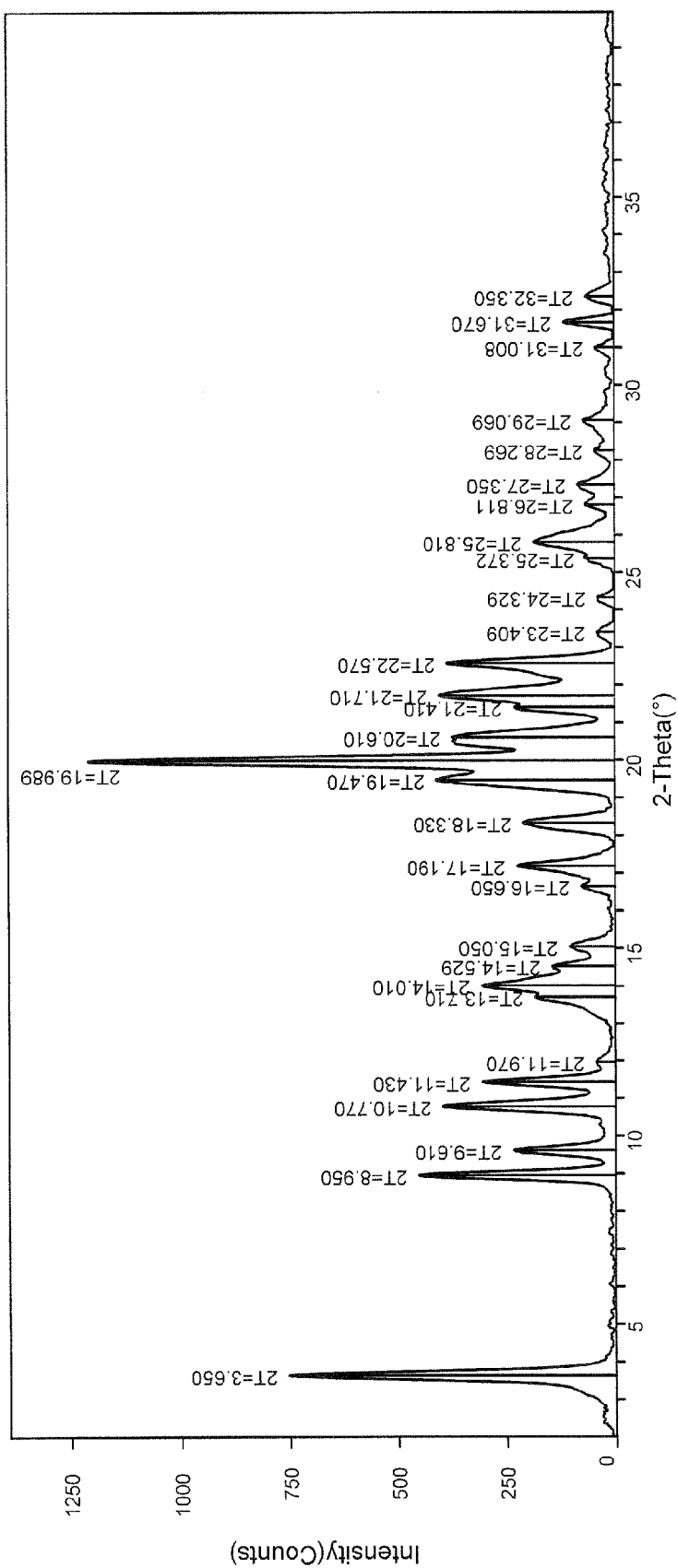
FIG. 22 shows the PXRD pattern of celecoxib sodium salt.
Figure 23:
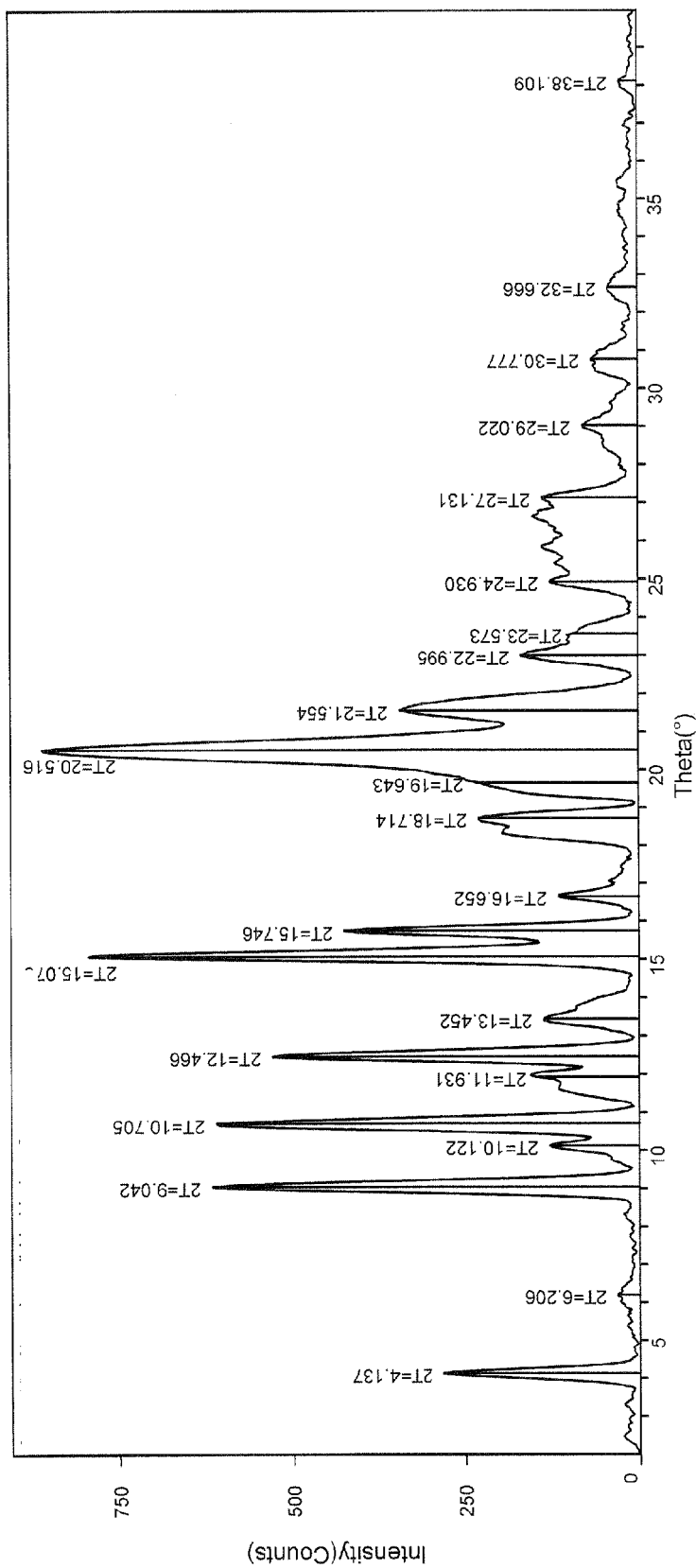
FIG. 23 shows the PXRD pattern of celecoxib lithium salt.
Figure 24:
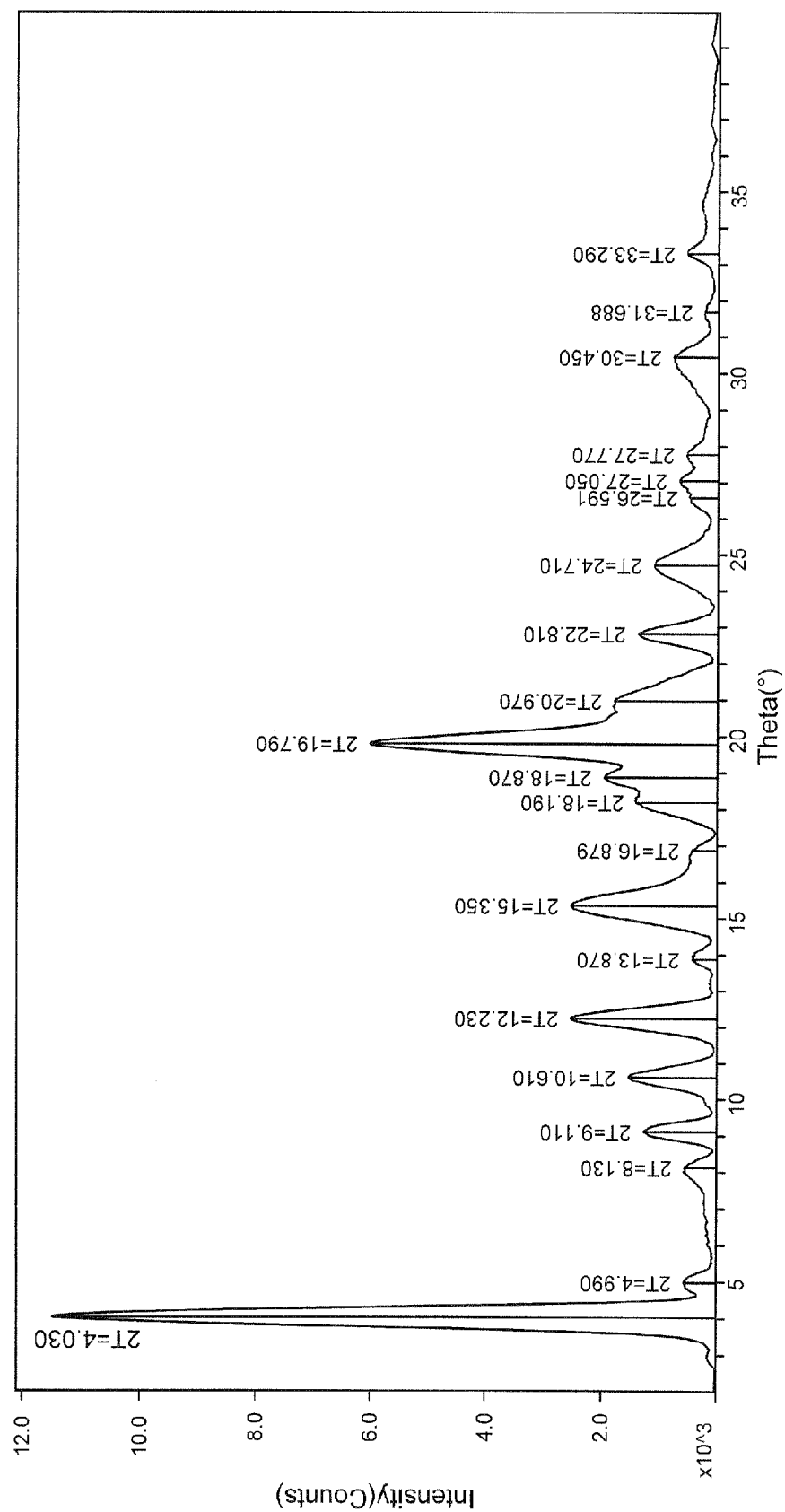
FIG. 24 shows the PXRD pattern of celecoxib potassium salt.

FIGS. 22-24 have been included as reference PXRD diffractograms. FIG. 22 shows the PXRD diffractogram of celecoxib sodium salt. FIG. 23 shows the PXRD diffractogram of celecoxib lithium salt. FIG. 24 shows the PXRD diffractogram of celecoxib potassium salt. Dynamic moisture sorption studies of several embodiments of the present invention have been discussed in PCT/US03/41273 filed on Dec. 24, 2003, entitled "Pharmaceutical Compositions With Improved Dissolution" by Tawa et al, which is hereby incorporated by reference, in its entirety. Dynamic moisture sorption studies can be used to illustrate important characteristics of the solvates of the present invention, such as decreased hygroscopicity or increased form stability.

While this invention has been particularly shown and described with references to preferred embodiments thereof, it will be understood by those skilled in the art that various changes in form and details may be made therein without departing from the scope of the invention encompassed by the appended claims.

TABLE 3

| API Generic Name | API Chemical Name | CAS No. | Patent Reference | | Example of Therapeutic Use | Example of Indication |
|---|---|---|---|---|---|---|
| (−)-amlodipine | 3,5-Pyridinedicarboxylic acid, 2-((2-aminoethoxy)methyl)-4-(2-chlorophenyl)-1,4-dihydro-6-methyl-, 3-ethyl-5-methyl ester, (S)-[CAS] | 103129-82-4 | WO | 9310779 | Antihypertensive, other | Hypertension, general |
| (−)-halofenate | (−)-Benzeneacetic acid, 4-chloro-Alpha-[3-(trifluoromethyl)-phenoxy]-, 2-(acetylamino)ethyl ester | | U.S. | 6,262,118 | Antidiabetic | Diabetes, Type II |
| (R)-salbutamol | 1,3-Benzenedimethanol, Alpha1-(((1,1-dimithylethyl)amino)methyl)-4-hydroxy-[CAS] | | | | Formulation, modified-release, <=24 hr | Asthma |
| (R)-salbutamol | 1,3-Benzenedimethanol, Alpha1-(((1,1-dimethylethyl)amino)methyl)-4-hydroxy-[CAS] | 34391-04-3 | U.S. | 5,547,994 | Antiasthma | Asthma |
| (R,R)-formoterol | Formamide, N-(2-hydroxy-5-(1-hydroxy-2-((2-(4-methoxyphenyl)-1-methylethyl)amino)ethyl)phenyl)- (R-(R*,R*))-[CAS] | 67346-49-0 | U.S. | 5,795,564 | Antiasthma | Asthma |
| (S)-doxazosin | (S)-1-(4-amino-6,7-dimethoxy-2-quinazolinyl)-4-(1,4-benzodioxan-2-yl carbonyl)piperazine | 70918-18-2 | WO | 9409785 | Prostate disorders | Benign prostatic hyperplasia |
| (S)-fluoxetine | Benzenepropanamide, N-methyl-Gamma-(4-(trifluoromethyl)phenoxy)-(S) | | | | Antimigraine | Migraine |
| (S)-oxybutynin | Benzeneacetic acid, Alpha-cyclohexyl-Alpha-hydroxy-, 4-(diethylamino)-2-butynyl ester, (S)-[CAS] | 119618-22-3 | | | Urological | Incontinence |
| 1,2-Naphthoquinone | | 524-42-5 | | | | |
| 17a-Hydroxyprogesterone | | 68-96-2 | | | | |
| 17-Methyltestosterone | | 58-18-4 | | | | |
| 195mPt-cisplatin | Platinum-195m, diamminedichloro, (SP-4-2)- | | U.S. | 6,074,626 | Anticancer, alkylating | Cancer, liver |
| 1a-Hydroxycholecalciferol | | 41294-56-8 | | | | |
| 1-Naphthyl Salicylate | | 550-97-0 | | | | |

TABLE 3-continued

| API Generic Name | API Chemical Name | CAS No. | Patent Reference | Example of Therapeutic Use | Example of Indication |
|---|---|---|---|---|---|
| 1-Naphthyl-amine-4-sulfonic Acid | | 84-86-6 | | | |
| 1-Theobromine-acetic Acid | | 5614-56-2 | | | |
| 2,4,6-Tribromo-m-cresol | | 4619-74-3 | | | |
| 2,6-Diamino-2¢-butyloxy-3,5¢-azopyridine | | 617-19-6 | | | |
| 21-Acetoxy-pregnenolone | | 566-78-9 | | | |
| 2-Amino-4-picoline | | 695-34-1 | | | |
| 2-Aminothiazole | | 96-50-4 | | | |
| 2-ethoxybenzoic acid | 2-Ethoxybenzoic acid | | DE 5134001 | Analgesic, NSAID | Pain, general |
| 2-Naphthol | | 135-19-3 | | | |
| 2-Naphthyl Benzoate | | 93-44-7 | | | |
| 2-Naphthyl Lactate | | 93-43-6 | | | |
| 2-Naphthyl Salicylate | | 613-78-5 | | | |
| 2-p-Sulfanilyl-anilinoethanol | | 80-02-4 | | | |
| 2-Thiouracil | | 141-90-2 | | | |
| 3¢,3¢¢,5¢,5¢¢-Tetrabromophenol-phthalein | | 76-62-0 | | | |
| 3-Amino-4-hydroxybutyric Acid | | 589-44-6 | | | |
| 3-Bromo-d-camphor | | 76-29-9 | | | |
| 3-Hydroxy-camphor | | 10373-81-6 | | | |
| 3-O-Lauroylpyridoxol Diacetate | | 1562-13-6 | | | |
| 3-Pentadecyl-catechol | | 492-89-7 | | | |
| 3-Quinuclidinol | | 1619-34-7 | | | |
| 4,4¢-Oxydi-2-butanol | | 821-33-0 | | | |
| 4,4¢-Sulfinyldianiline | | 119-59-5 | | | |
| 4-Amino-3-hydroxybutyric Acid | | 352-21-6 | | | |
| 4-Amino-3-phenylbutyric Acid | | 1078-21-3 | | | |
| 4-aminosali-cylic acid | Benzoic acid, 4-amino-2-hydroxy-[CAS] | 65-49-6 | | GI inflammatory/bowel disorders | inflammatory bowel disease |
| 4-Chloro-m-cresol | | 59-50-7 | | | |
| 4-Hexytresorcinol | | 136-77-6 | | | |
| 4-Salicyloyl-morpholine | | 3202-84-4 | | | |
| 5¢-Nitro-2¢-propoxy-acetanilide | | 553-20-8 | | | |
| 5-aminolevulinic acid, | Pentanoic acid, 5-amino-4-oxo-[CAS] | 106-60-5 | | Dermatological | Keratosis |
| 5-azacitidine | 1,3,5-Triazin-2(1H)-one, 4-amino-1-β-D-ribofuranosyl-[CAS] | 320-67-2 | | Anticancer, antimetabolite | Mylodysplastic syndrome |
| 5-Bromosalicyl-hydroxamic Acid | | 5798-94-7 | | | |

TABLE 3-continued

| API Generic Name | API Chemical Name | CAS No. | Patent Reference | | Example of Therapeutic Use | Example of Indication |
|---|---|---|---|---|---|---|
| 5F-DF-203 | 2-(4-Amino-3-methylphenyl)-6-hydroxybenzothiazole | | | | Anticancer, other | Cancer, breast |
| 5-FU | 2,4(1H,3H)-Pyrimidinedione, 5-fluoro [CAS] | 51-21-8 | | | Formulation, parenteral, targeted | Cancer, general |
| 5-HT3 antagonists | | | U.S. | 6,037,360 | Male sexual dysfunction | Premature ejaculation |
| 6-Azauridine | | 54-25-1 | | | | |
| 6-Mercapto-purine | | 50-44-2 | | | | |
| 8-Hydroxy-quinoline | | 148-24-3 | | | | |
| 9-Amino-camptothecin | | 91421-43-1 | | | | |
| A-151892 | N-[2-(2,2,2-Trifluoro-1-hydroxy-1-trifluoromethyl-ethyl)-naphthalen-1-yl]amide | | | | Urological | Overactive bladder |
| a1-Antitrypsin | | 9041-92-3 | | | | |
| A-5021 | 6H-Purin-6-one, 2-amino-9-(((1S,2R)-1,2-bis(hydroxymethyl)cyclopropyl)methyl)-1,9-dihydro-[CAS] | 145512-85-2 | | | Antiviral, other | Infection, varicella zoster virus |
| abacavir | 2-Cyclopentene-1-methanol, 4-(2-amino-6-(cyclopropylamino)-9H-purin-9-yl)-, (1S-cis)-[CAS] | 136470-78-5 188062-50-2 | EP | 434450 | Antiviral, anti-HIV | Infection, HIV/AIDS |
| abaperidone | 7-[3-[4-(6-Fluoro-1,2-benzisoxazol-3-yl)piperidin-1-yl]propoxy]-3-(hydroxymethyl)chromen-4-one | 183849-43-6 | WO | 9632389 | Neuroleptic | Schizophrenia |
| abarelix | D-Alaninamide, N-acetyl-3-(2-naphthalenyl)-D-alanyl-4-chloro-D-phenylalanyl-3-(3-pyridinyl)-D-alanyl-L-seryl-N-methyl-L-tyrosyl-D-asparaginyl-L-leucyl-N6-(1-methylethyl)-L-lysyl-L-prolyl-[CAS] | 183552-38-7 | U.S. | 5,843,902 | Anticancer, hormonal | Cancer, prostate |
| Abciximab | | 143653-53-6 | | | | |
| Abecarnil | | 111841-85-1 | | | | |
| abetimus | | 169147-32-4 | U.S. | 5,552,391 | Immunosuppressant | Lupus erythematosus, systemic |
| abiraterone | Androsta-5,16-dien-3-ol, 17-(3-pyridinyl)-, acetate (ester), (3β)-[CAS] | 154229-18-2 | GB | 2265624 | Anticancer, hormonal | Cancer, prostate |
| a-Bisabolol | | 515-69-5 | | | | |
| ABLC | Amphotericin B [CAS] | 1397-89-3 30652-87-0 | | | Formulation, conjugate, carbohydrate | Infection, *Candida*, general |
| ABT-751 | Benzenesulfonamide, N-[2-[(4-hydroxyphenyl)amino]-3-pyridinyl]-4-methoxy-[CAS] | 141430-65-1 | EP | 472053 | Anticancer, other | Cancer, general |
| AC-5216 | N-benzyl-N-ethyl-2-(7,8-dihydro-7-methyl-8-oxo-2-phenyl-9H-purin-9-yl)acetamide | 2627-69-2 | | | Anxiolytic | Anxiety, general |
| Acadesine | | 2627-69-2 | | | | |
| acamprosate | 1-Propanesulfonic acid, 3-(acetylamino)-[CAS] | 77337-76-9 | GB | 2051789 | Dependence treatment | Addiction, alcohol |
| Acamprosate | | 77337-73-6 | | | | |
| Acarbose | | 56180-94-0 | | | | |
| acebrophylline | 7H-Purine-7-acetic acid, 1,2,3,6-tetrahydro-1,3-dimethyl-2,6-dioxo-, compd. with trans-4-[[(2-amino-3,5-dibromophenyl)methyl]amino]cyclohexanol (1:1) [CAS] | 96989-76-3 | DE | 3425007 | Antiasthma | Asthma |
| acebutolol | Butanamide, N-[3-acetyl-4-[2-hydroxy-3-[(1-methylethyl)amino]propoxy]phenyl]-, (+/−)-[CAS] | 34381-68-5 37517-30-9 | U.S. | 3,726,919 | Antihypertensive, adrenergic | |
| Acecainide | | 32795-44-1 | | | | |
| Acecarbromal | | 77-66-7 | | | | |
| aceclofenac | Benzeneacetic acid, 2[(2,6-dichlorophenyl)amino]-, carboxymethyl ester [CAS] | 89796-99-6 | EP | 119932 | Anti-inflammatory | Pain, musculoskeletal |
| Acedapsone | | 77-46-3 | | | | |
| Acediasulfone | | 80-03-5 | | | | |
| Acefylline | | 652-37-9 | | | | |
| Aceglutamide | | 2490-97-3 | | | | |
| aceglutamide | Aluminum, pentakis(N2-acetyl-L-glutaminato)tetrahydroxytri-[CAS] | 12607-92-0 | DE | 2127176 | Antiulcer | Ulcer, GI, general |
| acemetacin | 1H-Indole-3-acetic acid, 1-(4-chlorobenzoyl)-5-methoxy-2-methyl-, carboxymethyl ester [CAS] | 53164-05-9 | U.S. | 3,910,952 | Anti-inflammatory | |

TABLE 3-continued

| API Generic Name | API Chemical Name | CAS No. | Patent Reference | Example of Therapeutic Use | Example of Indication |
|---|---|---|---|---|---|
| Acenocoumarol | | 152-72-7 | | | |
| Acetal | | 105-57-7 | | | |
| Acetamido-eugenol | | 305-13-5 | | | |
| Acetaminophen | | 103-90-2 | | | |
| Acetaminosalol | | 118-57-0 | | | |
| Acetanilide | | 103-84-4 | | | |
| Acetarsone | | 97-44-9 | | | |
| Acetazolamide | | 59-66-5 | | | |
| Acetiamine | | 299-89-8 | | | |
| Acetohexamide | | 968-81-0 | | | |
| Acetohydroxamic Acid | | 546-88-3 | | | |
| Acetophenazine | | 2751-68-0 | | | |
| Acetophenone | | 98-86-2 | | | |
| Acetosulfone | | 128-12-1 | | | |
| acetoxolone | Olean-12-en-30-oic acid, 3β-hydroxy-11-oxo-acetate, aluminium salt [CAS] | 29728-34-5 6277-14-1 | U.S. | 3,764,618 Antiulcer | |
| Acetrizoate | | 129-63-5 | | | |
| Acetyl Sulfamethoxy-pyrazine | | 3590-05-4 | | | |
| Acetylcarnitine | | 14992-62-2 | | | |
| Acetylcholine | | 66-23-9 | | | |
| Acetylcholine | | 60-31-1 | | | |
| Acetylcysteine | | 616-91-1 | | | |
| Acetylleucine Mono-ethanolamine | | 149-90-6 | | | |
| Acetyl-pheneturide | | 13402-08-9 | | | |
| acetylsalicylic acid | Benzoic acid, 2-(acetyloxy)-[CAS] | 50-78-2 | | Formulation, optimized, microencapsulate | Pain, general |
| a-Chloralose | | 530-75-6 | | | |
| | | 15879-93-3 | | | |
| aciclovir | 6H-Purin-6-one, 2-amino-1,9-dihydro-9-[(2-hydroxyethoxy)methyl]-[CAS] | 59277-89-3 | | Formulation, dermal, topical | Infection, herpes simplex virus |
| Acifran | | 72420-38-3 | | | |
| acipimox | Pyrazinecarboxylic acid, 5-methyl-, 4-oxide [CAS] | 51037-30-0 | GB | 1361967 Hypolipaemic/Antiatherosclerosis | Hyperlipidaemia, general |
| acitazanolast | Acetic acid, oxo[[3-(1H-tetrazol-5-yl)phenyl]amino]-[CAS] | 114607-46-4 | EP | 256507 Ophthalmological | Conjunctivitis |
| acitretin | 2,4,6,8-Nonatetraenoic acid, 9-(4-methoxy-2,3,6-trimethylphenyl)-3,7-dimethyl-, (all-E)-[CAS] | 55079-83-9 | GB | 1468401 Antipsoriasis | Psoriasis |
| aclarubicin | | 57576-44-0 | U.S. | 3,988,315 Anticancer, antibiotic | |
| | | 75443-99-1 | | | |
| Aclatonium Napadisilate | | 55077-30-0 | | | |
| Aconitine | | 302-27-2 | | | |
| Acranil ® | | 1684-42-0 | | | |
| Acriflavine | | 8048-52-0 | | | |
| Acrisorcin | | 7527-91-5 | | | |
| acrivastine | 2-Propenoic acid, 3-[6-[1-(4-methylphenyl)-3-(1-pyrrolidinyl)-1-propenyl]-2-pyridinyl]-, (E,E)-[CAS] | 87848-99-5 | EP | 85959 Antipruritic/inflamm, allergic | Rhinitis, allergic, general |
| acrivastine + pseudo-ephedrine | Benzenemethanol, Alpha-[1-(methylamino)ethyl]-, hydrochloride, [S-(R*,R)]-, mixtwith 2-Propenoic acid, 3-[6-[1-(4-methylphenyl)-3-(1-pyrrolidinyl)-1-propenyl]-2-pyridinyl]-, (E,E)- | | | Antiallergic, non-asthma | Rhinitis, allergic, seasonal |
| actagardine derivative | 3,3-dimethyl-1-propylamide HCl monocarboxamide actagardine | | | Peptide antibiotic | Infection, general |
| Actarit | | 18699-02-0 | | | |
| ACTH | | 9002-60-2 | | | |
| Acyclovir | | 59277-89-3 | | | |
| adapalene | 2-Naphthalenecarboxylic acid, 6-(4-methoxy-3-tricyclo[3.3.1.13,7]dec-1-ylphenyl)-[CAS] | 106685-40-9 | EP | 199636 Antiacne | Acne |
| ADCON-L | GL 402 [CAS] | 137802-74-5 | | Formulation, other | Fibrosis, epidural |
| Adefovir | | 106941-25-7 | | | |
| adefovir dipivoxil | Propanoic acid, 2,2-dimethyl-, (((2-(-6-amino-9H-purin-9-yl)ethoxy)methyl)phosphinylidene)bis(oxymethylene)ester-[CAS] | 142340-99-6 | EP | 205826 Antiviral, other | Infection, hepatitis-B virus |
| Adenoscan | 6-Amino-9-β-D-nbofuranosyl-9H-purine [CAS] | 58-61-7 | | Imaging agent | Diagnosis, coronary |

TABLE 3-continued

| API Generic Name | API Chemical Name | CAS No. | Patent Reference | Example of Therapeutic Use | Example of Indication |
|---|---|---|---|---|---|
| Adenosine Triphosphate | | 56-65-5 | | | |
| ADEPT | | 156079-88-8 | | Immunoconjugate, other | Cancer, colorectal |
| Adinazolam | | 37115-32-5 | | | |
| Adiphenine | | 64-95-9 | | | |
| ADL-10-0101 | | | WO | 9732857 Analgesic, other | Pain, general |
| Adrafinil | | 63547-13-7 | | | |
| Adrenalone | | 99-45-6 | | | |
| Adrenochrome | | 54-06-8 | | | |
| adrogolide | Benzo(f)thieno(2,3-c)quinoline-9,10-diol, 4,5,5a,6,7,11b-hexahydro-2-propyl-, diacetate (ester), hydrochloride (5aR-trans)-[CAS] | 166591-11-3 171752-56-0 | U.S. | 5,597,832 Dependence treatment | Addiction, cocaine |
| AEOL-10150 | | | U.S. | 6,103,714 Neuroprotective | Unspecified |
| AET | | 56-10-0 | | | |
| a-Ethylbenzyl Alcohol | | 93-54-9 | | | |
| AF-2259 | Benzeneacetic acid, Alpha-methyl-4-(2-methylpropyl)-, 2-methoxyphenyl ester [CAS] | 66332-77-2 | DE | 2726435 Anti-inflammatory | Inflammation, general |
| Afloqualone | | 56287-74-2 | | | |
| AG-041R | 1H-Indole-3-acetamide, 1-(2,2-diethoxyethyl)-2,3-dihydro-N-(4-methylphenyl)-3-((((4-methylphenyl)amino)carbonyl)amino)-2-oxo-, (3R)-[CAS] | 199800-49-2 | WO | 9419322 Alimentary/Metabolic, other | Unspecified |
| AG-2037 | N-(5-[2-(2-amino-4(3H)-oxo-5,6,7,8-tetrahydropyrido[2,3-d]pyrimidin-6-yl)ethy]-4-methylthieno-2-yl)glutamic acid | | | Anticancer, antimetabolite | Cancer, general |
| a-Glucose-1-phosphate | | 59-56-3 | | | |
| AGN-194310 | Benzoic acid, 4-((4-(4-ethylphenyl)-2,2-dimethyl-2H-1-benzothiopyran-6-yl)ethynyl)-[CAS] | 229961-45-9 | WO | 9709297 Dermatological | Psoriasis |
| agomelatine | Acetamide, N-(2-(7-methoxy-1-naphthalenyl)ethyl)-[CAS] | 138112-76-2 | EP | 447285 Antidepressant | Sleep disorder, general |
| Ahistan | | 518-61-6 | | | |
| AHL-157 | | | U.S. | 5,411,972 Hypolipaemic/ Antiatherosclerosis | Atherosclerosis |
| AIT-034 | 9H-Purine-9-propanamide, 1,6-dihydro-6-oxo-N-(3-(2-oxo-1-pyrrolidinyl)propyl)-[CAS] | 138117-48-3 | U.S. | 5,447,939 Cognition enhancer | Dementia, senile, general |
| AIT-202 | N-(2-(5-Hydroxy-1H-indol-3-yl)ethyl)-3-(6-oxo-6,9-dihydro-1H-purin-9-yl)propionamide | | WO | 9957120 Antidepressant | Unspecified |
| AJ-9677 | Acetic acid, ((3-((2R)-2-(((2R)-2-(3-chlorophenyl)-2-hydroxyethyl)amino)propyl)-1H-indol-7-yl)oxy)-[CAS] | 244081-42-3 | | Antidiabetic | Diabetes, Type II |
| AJG-049 | | | WO | 9733885 Gastroprokinetic | Motility dysfunction, GI, general |
| Ajmaline | | 12/07/4360 | | | |
| Alacepril | | 74258-86-9 | | | |
| albaconazole | 4(3H)-Quinazolinone, 7-chloro-3-[(1R,2R)-2-(2,4-difluorophenyl)-2-hydroxy-1-methyl-3-(1H-1,2,4-triazol-1-yl)propyl]-[CAS] | 187949-02-6 | WO | 9705131 Antifungal | Infection, *Candida*, general |
| albendazole | Carbamic acid, [5-(propylthio)-1H-benzimidazol-2-yl]-, methyl ester [CAS] | 54029-12-8 54965-21-8 | GB | 1464326 Anthelmintic | Infection, helminth, general |
| Albuterol | | 18559-94-9 | | | |
| Albutoin | | 830-89-7 | | | |
| alclofenac | Benzeneacetic acid, 3-chloro-4-(2-propenyloxy)-[CAS] | 22131-79-9 | GB | 1174535 Anti-inflammatory | |
| alclometasone | Pregna-1,4-diene-3,20-dione, 7-chloro-11-hydroxy-16-methyl-17,21-bis(1-oxopropoxy)-, (7Alpha,11β,16Alpha)-[CAS] | 66734-13-2 67452-97-5 | U.S. | 4,124,707 Antipruritic/inflamm, allergic | Inflammation, dermal |
| Alcuronium | | 23214-96-2 | | | |
| Aldioxa | | 5579-81-7 | | | |
| Aldol | | 107-89-1 | | | |
| Aldosterone | | 52-39-1 | | | |
| alendronate | Phosphonic acid, (4-amino-1-hydroxybutylidene)bis-[CAS] | 121268-17-5 129318-43-0 | GB | 2118042 Osteoporosis treatment | Osteoporosis |
| Alendronic Acid | | 66376-36-1 | | | |

TABLE 3-continued

| API Generic Name | API Chemical Name | CAS No. | Patent Reference | Example of Therapeutic Use | Example of Indication |
|---|---|---|---|---|---|
| Alexidine | | 22573-93-9 | | | |
| alfacalcidol | 9,10-Secocholesta-5,7,10(19)-triene-1,3-diol, (1Alpha,3β,5Z,7E)-[CAS] | 41294-56-8 | | Osteoporosis treatment | Osteodystrophy |
| Alfadolone | | 23930-37-2 | | | |
| Alfaxalone | | 23930-19-0 | | | |
| Alfentanil | | 71195-58-9 | | | |
| alfimeprase | | 259074-76-5 | | Fibrinolytic | Peripheral vascular disease |
| alfuzosin | 2-Furancarboxamide, N-[3-[(4-amino-6,7-dimethoxy-2-quinazolinyl)methylamino]propyl]tetrahydro-[CAS] | 81403-68-1 | GB | 2013679 Prostate disorder | Benign prostatic hyperplasia |
| alfuzosin | 2-Furancarboxamide, N-[3-[(4-amino-6,7-dimethoxy-2-quinazolinyl)methylamino]propyl]tetrahydro-[CAS] | 81403-80-7 81403-68-1 81403-80-7 | | Formulation, modivied-release, other | Benign prostatic hyperplasia |
| Algestone | | 595-77-7 | | | |
| Algestone Acetophenide | | 24356-94-3 | | | |
| Algin | | 9005-38-3 | | | |
| Alglucerase | | 143003-46-7 | | | |
| Alibendol | | 26750-81-2 | | | |
| aliskiren | (2S,4S,5S,7S)-5-Amino-N-(2-carbamoyl-2-methylpropyl)-4-hydroxy-2-isopropyl-7-[4-methoxy-3-(3-methoxypropoxy)benzyl]-8-methylnonanamide | 173334-57-1 | | Antihypertensive, renin system | Hypertension, general |
| alitretinoin | 9-cis retinoic acid | 03/08/5300 | | Antipruritic/inflamm, allergic | Eczema, general |
| alizapride | 1H-Benzotriazoie-5-carboxamide, 6-methoxy-N-[[1-(2-propenyl)-2-pyrrolidinyl)methyl]-[CAS] | 59338-93-1 | GB | 1475234 Antiemetic | Nausea and vomiting, general |
| Alkannin | | 517-88-4 | | | |
| Alkofanone | | 7527-94-8 | | | |
| Allantoin | | 97-59-6 | | | |
| Allobarbital | | 52-43-7 | | | |
| Allopurinol | | 315-30-0 | | | |
| Allyl Isothiocyanate | | 57-06-7 | | | |
| Allylestrenol | | 432-60-0 | | | |
| almagate | Magnesium, [carbonato(2-)]heptahydroxy(aluminum)tri-, dihydrate [CAS] | 66827-12-1 72526-11-5 | U.S. | 4,447,417 Antacid/Antiflatulent | |
| alminoprofen | Benzeneacetic acid, Alpha-methyl-4-[(2-methyl-2-propenyl)amino]-[CAS] | 39718-89-3 | U.S. | 3,957,850 Analgesic, NSAID | |
| almitrine | 1,3,5-Triazine-2,4-diamine, 6-[4-[bis(4-fluorophenyl)methyl]-1-piperazinyl]-N,N'-di-2-propenyl-, dimethanesulfonate [CAS] | 27469-53-0 29608-49-9 | GB | 1256513 Respiratory | |
| almotriptan | Pyrrolidine, 1-(((3-(2-(dimethylamino)ethyl)-1H-indol-5-yl)methyl)sulfonyl)-[CAS] | 154323-57-6 | WO | 9402460 Antimigraine | Migraine |
| Aloe-Emodin | | 481-72-1 | | | |
| Aloin | | 5133-19-7 | | | |
| alosetron | 2,3,4,5-Tetrahydro-5-methyl-2-[(5-methyl-1H-imidazol-4-yl)methyl]-1H-pyrido[4,3-b]indol-1-one [CAS] | 122852-42-0 122852-69-1 132414-02-9 | EP | 306323 GI inflammatory/bowel disorders | Irritable bowel syndrome |
| alovudine | Thymidine, 3'-deoxy-3'-fluoro-[CAS] | 25526-93-6 | EP | 470355 Antiviral, anti-HIV | Infection, HIV/AIDS |
| Aloxiprin | | 9014-67-9 | | | |
| Alpha-1 protease inhibitor | | | U.S. | 5,780,014 Formulation, inhalable, topical | Emphysema, alpha-1 antitrypsin deficiency |
| Alpha-dihydroergocryptine | Ergocryptine, 9,10-dihydro-methanesulfonate (salt)-[CAS] | 29261-93-6 | | Formulation, other | Parkinson's disease |
| Alphaprodine | | 77-20-3 | | | |
| Alpidem | | 82626-01-5 | | | |
| Alpiropride | | 81982-32-3 | | | |
| alprazolam | 4H-[1,2,4]Triazolo[4,3-al][1,4]benzodiazepine, 8-chloro-1-methyl-6-phenyl-[CAS] | 28981-97-7 | U.S. | 3,987,052 Anxiolytic | Anxiety, general |
| Alprenolol | | 13655-52-2 | | | |
| alsactide | Alpha1-17-Corticotropin, 1-β-alanine-17-[N-(4-aminobutyl)-L-lysinamide]-[CAS] | 34765-96-3 | U.S. | 3,749,704 ACTH | Arthritis, rheumatoid |

TABLE 3-continued

| API Generic Name | API Chemical Name | CAS No. | Patent Reference | | Example of Therapeutic Use | Example of Indication |
|---|---|---|---|---|---|---|
| ALT-711 | Thiazolium, 4,5-dimethyl-3-(2-oxo-2-phenylethyl)-, bromide [CAS] | 181069-80-7 | WO | 9622095 | Symptomatic antidiabetic | Hypertension, general |
| Althiazide | | 5588-16-9 | | | | |
| altinicline | Pyridine, 3-ethynyl-5-((2S)-1-methyl-2-pyrrolidinyl)-[CAS] | 179120-92-4 | U.S. | 5,594,011 | Antiparkinsonian | Parkinson's disease |
| altretamine | 1,3,5-Triazine-2,4,6-triamine, N,N,N',N',N'',N''-hexamethyl-[CAS] | 645-05-6 | U.S. | 3,424,752 | Anticancer, alkylating | Cancer, ovarian |
| aluminium chloride hexahydrate | Aluminium chloride, hexahydrate | 7446-70-0 | | | Dermatological | Hyperhidrosis |
| Aluminon | | 7784-13-6 | | | | |
| Aluminon | | 569-58-4 | | | | |
| Aluminum Acetate Solution | | 8006-13-1 | | | | |
| Aluminum Chlorate | | 15477-33-5 | | | | |
| Aluminum Hydroxy-chloride | | 1327-41-9 | | | | |
| Aluminum Potassium Sulfate | | 10043-67-1 | | | | |
| Aluminum Sodium Sulfate | | 10102-71-3 | | | | |
| alusulf | Aluminum hydroxide sulfate (Al7(OH)17(SO4)2), dodecahydrate [CAS] | 61115-28-4 | DE | 2510663 | Urological | Hyperphosphataemia |
| Alverine | | 150-59-4 | | | | |
| alvimopan | Glycine, N-[(2S)-2-[[(3R,4R)-4-(3-hydroxyphenyl)-3,4-dimethyl-1-piperidinyl]methyl]-1-oxo-3-phenylpropyl]-[CAS] | 156053-89-3 | EP | 657428 | GI inflammatory/bowel disorders | Ileus |
| alvocidib | 4H-1-Benzopyran-4-one, 2-(2-chlorophenyl)-5,7-dihydroxy-8-(3-hydroxy-1-methyl-4-piperidinyl)-, cis-(−)-[CAS] | 131740-09-5 146426-40-6 | | | Anticancer, other | Cancer, renal |
| ALX-0646 | | | WO | 9506638 | Antimigraine | Migraine |
| AM-24 | 2,4,6-Triiodophenol | 609-23-4 | | | GI inflammatory/bowel disorders | Crohn's disease |
| AM-36 | 1-Piperazineethanol, 4-[[3,5-bis(1,1-dimethylethyl)-4-hydroxyphenyl]methyl]-Alpha-(4-chlorophenyl)-[CAS] | 199467-52-2 | | | Neuroprotective | Unspecified |
| AM-477 | 2-Methoxyoestradiol | | | | Antiasthma | Asthma |
| Amantadine | | 768-94-5 | | | | |
| amantanium | 1-Decanaminium, N,N-dimethyl-N-[2-[(tricyclo[3.3.1.13,7]dec-1-ylcarbonyl)oxy]ethyl]-, bromide [CAS] | 58158-77-3 | U.S. | 4,288,609 | Antifungal | Infection, general |
| Ambazone | | 539-21-9 | | | | |
| Ambenonium | | 115-79-7 | | | | |
| ambrisentan | (+)-(2S)-2-[(4,6-dimethylpyrimidin-2-yl)oxy]-3-methoxy-3,3-diphenylpropanoic acid | 177036-94-1 | | | Vasodilator, peripheral | Heart failure |
| ambroxol | Cyclohexanol, 4-[[(2-amino-3,5-dibromophenyl)methyl]amino]-, trans-[CAS] | 23828-92-4 18683-91-5 | GB | 1178034 | COPD treatment | Bronchitis, chronic |
| Ambucaine | | 119-29-9 | | | | |
| Ambuphylline | | 5634-34-4 | | | | |
| Ambuside | | 3754-19-6 | | | | |
| Ambutonium Bromide | | 115-51-5 | | | | |
| amcinonide | Pregna-1,4-diene-3,20-dione, 21-(acetyloxy)-16,17-[cyclopentylidenebis(oxy)]-9-fluoro-11-hydroxy-, (11β, 16Alpha)-[CAS] | 51022-69-6 | DE | 2437847 | Antipsoriasis | |
| AMD-3100 | 1,4,8,11-Tetraazacyclotetradecane, 1,11-(1,4-phenylenebis(methylene))bis-, octahydrochloride [CAS] | 155148-31-5 | U.S. | 5,612,478 | Haematological | Chemotherapy-induced injury, bone marrow, leocopenia |
| Amdinocillin | | 32887-01-7 | | | | |
| Amdinociilin Pivoxil | | 32886-97-8 | | | | |
| amdoxovir | 1,3-Dioxolane-2-methanol, 4-(2,6-diamino-9H-purin-9-yl)-(2R-cis)-[CAS] | 145514-04-1 | EP | 656778 | Antiviral, anti-HIV | Infection, HIV/AIDS |

TABLE 3-continued

| API Generic Name | API Chemical Name | CAS No. | Patent Reference | Example of Therapeutic Use | Example of Indication |
|---|---|---|---|---|---|
| amelubant | Carbamic acid, ((4-((3-((4-(1-(4-hydroxyphenyl)-1-methylethyl)phenoxy)methyl)phenyl)methoxy)phenyl)iminomethyl)-ethyl ester [CAS] | 346735-24-8 | DE 10000907 | COPD treatment | Chronic obstructive pulmonary disease |
| Americaine | Benzenemethanaminium, N,N-dimethyl-N-[2-[2-[4-(1,1,3,3-tetramethylbutyl)phenoxy]ethoxy]ethyl]-, chloride, mixt. with ethyl 4-aminobenzoate [CAS] | 129128-13-8 | | Formulation, inhalable, other | Pain, general |
| Amezinium | | 30578-37-1 | | | |
| Amfenac | | 51579-82-9 | | | |
| Amidephrine | | 3354-67-4 | | | |
| Amidinomycin | | 3572-60-9 | | | |
| amifostine | Ethanethiol, 2-[(3-aminopropyl)amino]-, dihydrogen phosphate (ester)-[CAS] | 20537-88-6 63717-27-1 | EP 131500 | Radio/chemoprotective | Chemotherapy-induced injury, renal |
| amiglumide | Pentanoic acid, 5-(dipentylamino)-4-((2-naphthalenylcarbonyl)amino)-5-oxo-(R)-[CAS] | 119363-62-1 | WO 8805774 | GI inflammatory/bowel disorders | Pancreatitis |
| amikacin | | 37517-28-5 39831-55-5 | | Formulation, optimized, microencapsulate | Infection, general |
| Amiloride | | 2609-46-3 | | | |
| Aminacrine | | 90-45-9 | | | |
| amineptine | Heptanoic acid, 7-[(10,11-dihydro-5H-dibenzo[a,d]cyclohepten-5-yl)amino]-[CAS] | 30272-08-3 57574-09-1 | U.S. 3,758,528 | Antidepressant | |
| Aminitrozole | | 140-40-9 | | | |
| Amino Acid Preparations | | | | | |
| Aminocaproic Acid | | | | | |
| amino-glutethimide | 2,6-Piperidinedione, 3-(4-aminophenyl)-3-ethyl-[CAS] | 125-84-8 | U.S. 3,944,671 | Anticancer, hormonal | Cancer, breast |
| Aminoguanidine | 79-17-4 | | | | |
| Aminohippurate | | | | | |
| Aminometradine | | 642-44-4 | | | |
| Aminopentamide | | 60-46-8 | | | |
| aminophylline | 1H-Purine-2,6-dione, 3,7-dihydro-1,3-dimethyl-, compd. with 1,2-ethanediamine (2:1) [CAS] | 317-34-0 | | Formulation, modified-release, other | Asthma |
| Aminopromazine | | 58-37-7 | | | |
| Aminopyrine | | 58-15-1 | | | |
| Aminoquinuride | | 3811-56-1 | | | |
| Aminorex | | 2207-50-3 | | | |
| amiodarone | Methanone, (2-butyl-3-benzofuranyl)[4-[2-(diethylamino)ethoxy]-3,5-diiodophenyl]-[CAS] | 1951-25-3 19774-82-4 | U.S. 3,248,401 | Antiarrhythmic | Arrhythmia, general |
| Amiphenazole | | 490-55-1 | | | |
| Amiprilose | | 56824-20-5 | | | |
| amisulpride | Benzamide, 4-amino-N-[(1-ethyl-2-pyrrolidinyl)methyl]-5-(ethylsulfonyl)-2-methoxy-[CAS] | 71675-85-9 | U.S. 4,401,822 | Neuroleptic | Schizophrenia |
| Amitriptyline | | 50-48-6 | | | |
| amitriptyline + ketamine | 1-Propanamine,3-(10,11-dihydro-5H-dibenzo[a,d]cyclohepten-5-ylidene)-N,N-dimethyl + cyclohexanone,2-(2-chlorophenyl)-2-(methylamino) | | | Formulation, fixed-dose combinations | Pain, neuropathic |
| Amitriptylin-oxide | | 4317-14-0 | | | |
| amlexanox | 5H-[1]Benzopyrano[2,3-b]pyridine-3-carboxylic acid, 2-amino-7-(1-methylethyl)-5-oxo-[CAS] | 68302-57-8 | U.S. 4,299,963 | Antiasthma | Asthma |
| amlodipine | 3,5-Pyridinedicarboxylic acid, 2-[(2-aminoethoxy)methyl]-4-(2-chlorophenyl)-1,4-dihydro-6-methyl-, 3-ethyl 5-methyl ester [CAS] | 111470-99-6 88150-42-9 88150-47-4 | EP 89167 | Antianginal | Hypertension, general |
| Ammoniacum | | 03/07/9000 | | | |
| Ammonium Benzoate | | 1863-63-4 | | | |
| Ammonium Mandelate | | 530-31-4 | | | |
| Ammonium Salicylate | | 528-94-9 | | | |

TABLE 3-continued

| API Generic Name | API Chemical Name | CAS No. | Patent Reference | Example of Therapeutic Use | Example of Indication |
|---|---|---|---|---|---|
| Ammonium Valerate | | 42739-38-8 | | | |
| Amobarbital | | 57-43-2 | | | |
| Amocarzine | | 36590-19-9 | | | |
| Amodiaquin | | 86-42-0 | | | |
| amorolfine | Morpholine, 4-[3-[4-(1,1-dimethylpropyl)phenyl]-2-methylpropyl]-2,6-dimethyl-, cis-[CAS] | 78613-35-1<br>78613-38-4 | EP | 24334 Antifungal | Infection, fungal, general |
| Amoscanate | | 26328-53-0 | | | |
| amosulalol | Benzenesulfonamide, 5-[1-hydroxy-2-[[2-(2-methoxyphenoxy)ethyl]amino]ethyl]-2-methyl-, (+/−)-[CAS] | 70958-86-0<br>85320-68-9 | EP | 136103 Antihypertensive, adrenergic | Hypertension, general |
| Amotriphene | | 5585-64-8 | | | |
| amoxapine | Dibenz[b,f][1,4]oxazepine, 2-chloro-11-(1-piperazinyl)-[CAS] | 14028-44-5 | GB | 1192812 Antidepressant | Depression, general |
| amoxicillin | 4-Thia-1-azobicyclo[3,2,0]heptane-2-carboxylic acid, 6-[[amino(4-hydroxyphenyl)acetyl]amino]-3,3-dimethyl-7-oxo-,[2S-[2Alpha,5Alpha,6β(S*)]] [CAS] | 26787-78-0<br>61336-70-7 | | Formulation, modified-release, other | Infection, general |
| amoxicillin + potassium clavulan | | 74469-00-4 | GB | 1508977 Formulation, fixed-dose combinations | Infection, respiratory tract, general |
| AMPAlex | Piperidine, 1-(6-quinoxalinylcarbonyl)-[CAS] | 154235-83-3 | U.S. | 5,650,409 Psychostimulant | Attention deficit disorder |
| Amphetamine | | 300-62-9 | | | |
| Amphetaminil | | 17590-01-1 | | | |
| amphotericin B | Amphotericin B compd. with (3β)-cholest-5-en-3-yl hydrogen sulfate (1:1) [CAS] | 120895-52-5<br>1397-89-3 | U.S. | 4,822,777 Formulation, optimized, liposomes | Infection, general |
| ampicillin | 4-Thia-1-azabicyclo[3.2.0]heptane-2-carboxylic acid, 6-[(aminophenylacetyl)amino]-3,3-dimethyl-7-oxo-, [2S-[2Alpha,5Alpha,6β(S*)]] | 69-53-4<br>7177-48-2 | | Formulation, fixed-dose combinations | Infection, general |
| Ampirox-icam | | 99464-64-9 | | | |
| Ampligen | | 38640-92-5 | | | |
| amprenavir | Carbamic acid, (3-(((4-aminophenyl)sulfonyl)(2-methylpropyl)amino)-2-hydroxy-1-(phenylmethyl)propyl)-, tetrahydro-3-furanyl ester, (3S-(3R*(1R*,2S*)))-[CAS] | 161814-49-9 | U.S. | 5,783,701 Antiviral, anti-HIV | Infection, HIV/AIDS |
| amrinone | [3,4'-Bipyridin]-6(1H)-one, 5-amino-[CAS] | 60719-84-8<br>75898-90-7 | U.S. | 4,004,012 Cardiostimulant | |
| amrubicin | 5,12-Naphthacenedione, 9-acetyl-9-amino-7-[(2-deoxy-β-D-erythro-pentopyranosyl)oxy]-7,8,9,10-tetrahydro-6,11-dihydroxy-, hydrochloride, (7S-cis)-[CAS] | 92395-36-3 | EP | 107486 Anticancer, antibiotic | Cancer, lung, non-small cell |
| amsacrine | Methanesulfonamide, N-(4-(9-acridinylamino)-3-methoxyphenyl)-[CAS] | 51264-14-3 | | Anticancer, other | Cancer, leukaemia, acute lymphocytic |
| amtolmetin guacil | Glycine, N-[[1-methyl-5-(4-methylbenzoyl)-1H-pyrrol-2-yl]acetyl]-, 2-methoxyphenyl ester [CAS] | 87344-06-7 | GB | 2115417 Analgesic, NSAID | Arthritis, rheumatoid |
| Amylocaine | | 532-59-2 | | | |
| AN-152 | | | WO | 9719954 Anticancer, antibiotic | Cancer, prostate |
| anabolic steroids | | | WO | 9848812 Cardiovascular | Heart failure |
| Anagestone | | 2740-52-5 | | | |
| anagrelide | Imidazo[2,1-b]quinazolin-2(3H)-one, 6,7-dichloro-1,5-dihydro-, monohydrochloride [CAS] | 58579-51-4<br>68475-42-3 | GB | 1418822 Haematological | Thrombocytosis |
| anastrozole | 1,3-Benzenediacetonitrile, Alpha,Alpha,Alpha,Alpha'-tetramethyl-5-(1H-1,2,4-triazol-1-ylmethyl)-[CAS] | 120511-73-1 | EP | 296749 Anticancer, hormonal | Cancer, breast |
| Anazolene | | 3861-73-2 | | | |
| Ancitabine | | 31698-14-3 | | | |
| Ancrod | | 9046-56-4 | | | |
| andolast | N-4'-[5-Tetrazolyl]-phenyl-4-(5-tetrazolyl)-benzamide | 132640-22-3 | EP | 460083 Antiasthma | Asthma |
| Androisoxazole | | 360-66-7 | | | |
| Androstenediol | | 521-17-5 | | | |

TABLE 3-continued

| API Generic Name | API Chemical Name | CAS No. | Patent Reference | | Example of Therapeutic Use | Example of Indication |
|---|---|---|---|---|---|---|
| anecortave | 21-(Acetyloxy)-17-hydroxypregna-4,9(11)-diene-3,20-dione | 7753-60-8 | | | Ophthalmological | Macular degeneration |
| Anethole | | 4180-23-8; 104-46-1 (unspecified) | | | | |
| Anethole Trithione | | 532-11-6 | | | | |
| Angiogenix | | | U.S. | 6,417,205 | Cardiovascular | Cardiomyopathy, ischaemic |
| Angiotensin | | 1407-47-2 | | | | |
| anhydro-vinblastine | Vincaleukoblastine, 3',4'-didehydro-4'-deoxy-[CAS] | 38390-45-3 | U.S. | 6,011,041 | Anticancer, other | Cancer, general |
| anidulafungin | Echinocandin B, 1-((4R,5R)-4,5-dihydroxy-N2-((4''-(pentyloxy)(1,1':4',1''-terphenyl)-4-yl)carbonyl)-L-ornithine)-[CAS] | 166663-25-8 | U.S. | 6,384,013 | Antifungal | Infection, *Candida*, general |
| Anileridine | | 144-14-9 | | | | |
| Aniracetam | | 72432-10-1 | | | | |
| Anisindione | | 117-37-3 | | | | |
| Anisomycin | | 22862-76-6 | | | | |
| Anisotropine Methylbromide | | 80-50-2 | | | | |
| anistreplase | Anistreplase [CAS] | 81669-57-0 | EP | 28489 | Fibrinolytic | Infarction, myocardial |
| Antazoline | | 91-75-8 | | | | |
| Anthiolimine | | 305-97-5 | | | | |
| Anthralin | | 1143-38-0 | | | | |
| Anthramycin | | 4803-27-4 | | | | |
| Anthrarobin | | 577-33-3 | | | | |
| anthrax inhibitor | | | U.S. | 6,436,933 | Anti-infective, other | Infection, anthrax |
| antiangiogenic dendrimers | | | U.S. | 6,426,067 | Anticancer, other | Cancer, general |
| Anticort | L-Ascorbic acid, mixt with 2-(diethylamino)ethyl 4-aminobenzoate monohydrochloride, disodium hydrogen phosphate, potassium benzoate and zinc sulfate (1:1) [CAS] | 186646-39-9 | WO | 9640038 | Anabolic | Cachexia |
| antidepressants | | | U.S. | 5,898,036 | Antidepressant | Depression, general |
| anti-invasins | | | U.S. | 6,303,302 | Antifungal | Infection, fungal, general |
| Antimony Potassium Tartrate | | 28300-74-5 | | | | |
| Antimony Sodium Thioglycollate | | 539-54-8 | | | | |
| Antimony Thioglycoll-amide | | 6533-78-4 | | | | |
| Antiprogestin | 19-Norpregna-4,9-dien-3-one,(acetylphenyl)-20,20,21,21,21-pentafluoro-17-hydroxy-(11β,17Alpha)[CAS] | 211254-73-8 | DE | 19706061 | Anticancer, hormonal | Cancer, breast |
| Antipyrine | | 60-80-0 | | | | |
| Antipyrine Salicylate | | 520-07-0 | | | | |
| antithrombin III | Antithrombin, III [CAS] | 9000-94-6 90170-80-2 | | | Blood fraction | Antithrombin III deficiency |
| anxiolytics | | | U.S. | 5,756,538 | Anxiolytic | Anxiety, general |
| AP-521 | N-Piperonyl-2-amino-1,2,3,4-tetrahydrobenzo(b)thieno(2,3-c)pyridine-3-carbamide | 151227-08-6 | WO | 9321189 | Anxiolytic | Anxiety, general |
| AP-5280 | | | U.S. | 5,965,118 | Anticancer, alkylating | Cancer, general |
| Apalcillin | | 63469-19-2 | | | | |
| apaziquone | 1H-Indole-4,7-dione, 5-(1-aziridinyl)-3-(hydroxymethyl)-2-(3-hydroxy-1-propenyl)-1-methyl-, (E)-[CAS] | 114560-48-4 | WO | 8706227 | Anticancer, alkylating | Cancer, breast |
| Apazone | | 13539-59-8 | | | | |
| a-Phenyl-butyramide | | 90-26-6 | | | | |
| Apocodeine | | 641-36-1 | | | | |
| apomine | Phosphonic acid, (2-(3,5-bis(1,1-dimethylethyl)-4-hydroxyphenyl)ethylidene)bis-tetrakis(1-methylethyl) ester [CAS] | 126411-13-0 | | | Anticancer, other | Cancer, prostate |

TABLE 3-continued

| API Generic Name | API Chemical Name | CAS No. | Patent Reference | Example of Therapeutic Use | Example of Indication |
|---|---|---|---|---|---|
| apomorphine | 4H-Dibenzo[de,g]quinoline-10,11-diol, 5,6,6a,7-tetrahydro-6-methyl-, hydrochloride | 314-19-2 58-00-4 | | Formulation, transmucosal, nasal | Impotence |
| apraclonidine | 1,4-Benzenediamine, 2,6-dichloro-N1-(4,5-dihydro-1H-imidazol-2-yl)-[CAS] | 66711-21-5 73218-79-8 | U.S. 4,517,199 | Antiglaucoma | Glaucoma |
| aprepitant | 3H-1,2,4-Triazol-3-one, 5-[[[(2R,3S)-2-[(1R)-1-[3,5-bis(trifluoromethyl)phenyl]ethoxy]-3-(4-fluorophenyl)-4-morpholinyl]methyl]-1,2-dihydro-[CAS] | 170729-80-3 | U.S. 5,719,147 | Antiemetic | Chemotherapy-induced nausea and vomiting |
| aprindine | 1,3-Propanediamine, N-(2,3-dihydro-1H-inden-2-yl)-N',N'-diethyl-N-phenyl-[CAS] | 33237-74-0 37640-71-4 | GB 1321424 | Antiarrhythmic | |
| Aprobarbital | | 77-02-1 | | | |
| Apronalide | | 528-92-7 | | | |
| Aprotinin | | 9087-70-1 | | | |
| Aptiganel | | 137159-92-3 | | | |
| AQ4N | 9,10-Anthracenedione, 1,4-bis((2-(dimethyloxidoamino)ethyl)amino)-5,8-dihydroxy-[CAS] | 136470-65-0 | U.S. 5,132,327 | Anticancer, other | Cancer, general |
| Aquavan | | | U.S. 6,204,257 | Anaesthetic, injectable | Anaesthesia |
| AR-116081 | | | U.S. 6,107,324 | Neuroleptic | Unspecified |
| AR-A2 | (R)-N-[5-methyl-8-(4-methylpiperazin-1-yl)-1,2,3,4-tetrahydro-2-naphthyl]-4-morpholinobenzamide | | | Anxiolytic | Anxiety, general |
| Arachidonic Acid | | 506-32-1 | | | |
| aranidipine | 3,5-Pyridinedicarboxylic acid, 1,4-dihydro-2,6-dimethyl-4-(2-nitrophenyl)-, methyl 2-oxopropyl ester-[CAS] | 86780-90-7 | GB 2111978 | Antihypertensive, other | Hypertension, general |
| arbekacin | D-Streptamine, O-3-amino-3-deoxy-Alpha-D-glucopyranosyl-(1-6)-O-[2,6-diamino-2,3,4,6-tetradeoxy-Alpha-D-erythro-hexopyranosyl-(1-4)]-N1-(4-amino-2-hydroxy-1-oxobutyl)-2-deoxy-, (S)-[CAS] | 51025-85-5 75282-65-4 | U.S. 4,001,208 | Aminoglycoside antibiotic | Infection, general |
| Arbidol | 1H-indole-3-carboxylic acid, 6-bromo-4 ((dimethylamino)methyl)-5-hydroxy-1-methyl-2-((phenylthio)methyl)-, ethylester, monohydrochloride [CAS] | 131707-23-8 | WO 9008135 | Immunostimulant, other | Infection, influenza virus |
| arbutamine | 1,2-Benzenediol, 4-[1-hydroxy-2-[[4-(4-hydroxyphenyl)butyl]amino]ethyl]-, (R)-[CAS] | 128470-16-6 | WO 9220324 | Diagnostic | Diagnosis, coronary |
| Arcitumomab | | 154361-48-5 | | | |
| ardeparin | Heparin [CAS] | 9005-49-6 | | Anticoagulant | Thrombosis, venous |
| arecoline | 1,2,5,6-Tetrahydro-1-methyl-3-pyridine carboxylic acid methyl ester | | | Formulation, transdermal, patch | Alzheimer's disease |
| argatroban | 2-Piperidinecarboxylic acid, 1-[5-[(aminoiminomethyl)amino]-1-oxo-2-[[(1,2,3,4-tetrahydro-3-methyl-8-quinolinyl)sulfonyl]amino]pentyl]-4-methyl-[CAS] | 74863-84-6 | EP 8746 | Anticoagulant | Thrombosis, arterial |
| Arginine | | 74-79-3 | | | |
| Ariflo ® | | 153259-65-5 | | | |
| aripiprazole | 2(1H)-Quinolinone, 7-[4-[4-(2,3-dichlorophenyl)-1-piperazinyl]butoxy]-3,4-dihydro-[CAS] | 129722-12-9 | EP 367141 | Neuroleptic | Schizophrenia |
| arofylline | 1H-Purine-2,6-dione, 3-(4-chlorophenyl)-3,7-dihydro-1-propyl-[CAS] | 136145-07-8 | EP 435811 | COPD treatment | Chronic obstructive pulmonary disease |
| arotinolol | 2-Thiophenecarboxamide, 5-[2-[[3-[(1,1-dimethylethyl)amino]-2-hydroxypropyl]thio]-4-thiazolyl]-, (±)-[CAS] | 104766-23-6 68377-92-4 | U.S. 3,932,400 | Antihypertensive, adrenergic | Hypertension, general |
| Arsacetin | | 618-22-4 | | | |
| arsenic trioxide | Arsenic oxide (As2O3) [CAS] | 1327-53-3 | | Anticancer, other | Cancer, leukaemia, acute myelogenous |
| Arsphenamine | | 139-93-5 | | | |
| Arsthinol | | 119-96-0 | | | |
| Arteether | | 75887-54-6 | | | |
| Arteflene | | 123407-36-3 (Z-form) | | | |

TABLE 3-continued

| API Generic Name | API Chemical Name | CAS No. | Patent Reference | Example of Therapeutic Use | Example of Indication |
|---|---|---|---|---|---|
| Artemether | | 71963-77-4 | | | |
| Artemisinin | | 63968-64-9 | | | |
| artemotil | 3,12-Epoxy-12H-pyrano[4,3-j]-1,2-benzodioxepin, 10-ethoxydecahydro-3,6,9-trimethyl-, [3R-(3Alpha,5aβ,6β,8aβ,9aAlpha,10Alpha,12+62,12aR*)]-[CAS] | 75887-54-6 | | Antimalarial | Infection, malaria |
| artesunate | Butanedioic acid mono-[(3R,5aS,6R,8aS,9R,10R,12R,12aR)-decahydro-3,6,9-trimethyl-3,12-epoxy-12H-pyrano[4,3-j]-1,2-benzodioxepin-10-yl]ester | 88495-63-0 | | Formulation, transmucosal, systemic | Infection, malaria |
| arzoxifene | Benzo(b)thiophene-6-ol,2-(4-methoxyphenyl)-3-(4-(2-(1-piperidinyl)ethoxy)phenoxy)-[CAS] | 182133-27-3 | WO | 9609041 Anticancer, hormonal | Cancer, breast |
| AS-3201 | Spiro(pyrrolidine-3,4'(1'H)-pyrrolo(1,2-a)pyrazine)-1',2,3',5(2'H)-tetrone, 2'-((4-bromo-2-fluorophenyl)methyl)-, (3'R)-[CAS] | 147254-64-6 | EP | 520320 Symptomatic antidiabetic | Diabetic complication, general |
| ASA | Benzoic acid, 2-(acetyloxy)-[CAS] | 50-78-2 | | Formulation, modified-release, other | Pain, general |
| a-Santonin | | 56449-07-1 | | | |
| Ascaridole | | 481-06-1 | | | |
| Ascorbic Acid | | 512-85-6 | | | |
| | | 50-81-7 | | | |
| asenapine | 1H-Dibenz[2,3:6,7]oxepino[4,5-c]pyrrole, 5-chloro-2,3,3a,12b-tetrahydro-2-methyl-, trans-, (Z)-2-butenedioate (1:1) [CAS] | 85650-56-2 | WO | 9523600 Neuroleptic | Psychosis, general |
| asimadoline | Benzeneacetamide, N-[2-(3-hydroxy-1-pyrrolidinyl)-1-phenylethyl]-N-methyl-Alpha-phenyl-, [S-(R*,R*)]-[CAS] | 153205-46-0 | DE | 4215213 GI inflammatory/bowel disorders | Irritable bowel syndrome |
| asoprisnil | 11β-[4-(Hydroxyiminomethyl)phenyl]-17β-methoxy-17Alpha-(methoxymethyl)estra-4,9-dien-3-one | 199396-76-4 | EP | 0648778 Menstruation disorders | Endometriosis |
| Asoxime | | 34433-31-3 | | | |
| Aspartic Acid | | 56-84-8 | | | |
| Aspidin | | 584-28-1 | | | |
| Aspidinol | | 519-40-4 | | | |
| Aspirin | | 50-78-2 | | | |
| Aspirin, Dipyridamole | | | | | |
| aspoxicillin | Glycinamide, N-methyl-D-asparaginyl-N-(2-carboxy-3,3-dimethyl-7-oxo-4-thia-1-azabicyclo[3.2.0]hept-6-yl)-D-2-(4-hydroxyphenyl)-, [2S-(2Alpha,5Alpha,6β)]-[CAS] | 63358-49-6 | GB | 1533413 Penicillin, injectable | Infection, respiratory tract, general |
| AST-120 | AST 120 [CAS] | 90597-58-3 | | Urological | Renal failure |
| Astemizole | | 68844-77-9 | | | |
| asulacrine | 4-Acridinecarboxamide, 9-[[2-methoxy-4-[(methylsulfonyl)amino]phenyl]amino]-N,5-dimethyl-[CAS] | 80841-47-0 80841-48-1 | EP | 39224 Anticancer, other | Cancer, general |
| AT-1015 | (N-[2-[4-(5H-Dibenzo[a,d]cyclohepten-5-ylidene)-piperidino]ethyl]-1-formyl-4-piperidinecarboxamide monohydrochloride monohydrate | | | Antithrombotic | Thrombosis, general |
| atamestane | Androsta-1,4-diene-3,17-dione, 1-methyl-[CAS] | 96301-34-7 | DE | 3338212 Anticancer, hormonal | Cancer, breast |
| atazanavir | 2,5,6,10,13-Pentaazatetradecanedioic acid, 3,12-bis(1,1-dimethylethyl)-8-hydroxy-4,11-dioxo-9-(phenylmethyl)-6-((4-(2-pyridinyl)phenyl)methyl)-dimethyl ester, (3S,8S,9S,12S)-, sulfate (1:1) (salt) [CAS] | 229975-97-7 | | Antiviral, anti-HIV | Infection, HIV/AIDS |
| atenolol | Benzeneacetamide, 4-[2-hydroxy-3-[(1-methylethyl)amino]propoxy]-[CAS] | 29122-68-7 73677-19-7 | GB | 1285038 Antihypeertensive, adrenergic | Hypertension, general |
| atenolol + chlorthalidone | Benzeneacetamide, 4-[2-hydroxy-3-[(1-methylethyl)amino]propoxy]-, mixt. with 2-chloro-5-(2,3-dihydro-1-hydroxy-3-oxo-1H-isoindol-1-yl)benzenesulfonamide [CAS] | 73677-19-7 | U.S. | 3,836,671 Formulation, fixed-dose combinations | Hypertension, general |
| atenolol + nifedipine | Benzeneacetamide, 4-[2-hydroxy-3-[(1-methylethyl)amino]propoxy]- + 4-(2'-nitrophenyl)-2,6-dimethyl-3,5-dicarbomethoxy-1,4-dihydropyridine | | | Formulation, fixed-dose combinations | Hypertension, general |

TABLE 3-continued

| API Generic Name | API Chemical Name | CAS No. | Patent Reference | | Example of Therapeutic Use | Example of Indication |
|---|---|---|---|---|---|---|
| a-Terpineol | | 98-55-5 | | | | |
| Atevirdine | | 136816-75-6 | | | | |
| atipamezole | 1H-Imidazole, 4-(2-ethyl-2,3-dihydro-1H-inden-2-yl)-[CAS] | 104054-27-5 | EP | 183492 | Reproductive/gonadal, general | Sexual dysfunction, female |
| atiprimod dimaleate | 2-Azaspivo[4.5]decane-2-propanamine, N,N-diethyl-8,8-dipropyl, dimaleate | 130065-61-1 | U.S. | 5,744,495 | Antiarthritic, immunological | Arthritis, rheumatoid |
| ATL-146e | | | U.S. | 6,232,297 | Imaging agent | Unspecified |
| a-Tocopherol | | 59-02-9 | | | | |
| atomoxetine | Benzenepropanamine, N-methyl-Gamma-(2-methylphenoxy)-, (R)-[CAS] | 82248-59-7 83015-26-3 | EP | 52492 | Neurological | Attention deficit disorder |
| atorvastatin | 1H-Pyrrole-1-heptanoic acid, 2-(4-fluorophenyl)-β,delta-dihydroxy-5-(1-methylethyl)-3-phenyl-4-[(phenylamino)carbonyl]-[CAS] | 134523-03-8 134523-00-5 | EP | 409281 | Hypolipaemic/ Antiatherosclerosis | Hypercholesterol-aemia |
| atosiban | Oxytocin, 1-(3-mercaptopropanoic acid)-2-(O-ethyl-D-tyrosine)-4-L-threonine-8-L-ornithine-[CAS] | 90779-69-4 | EP | 112809 | Labour inhibitor | Labour, preterm |
| atovaquone | 1,4-Naphthalenedione, 2-[4-(4-chlorophenyl)cyclohexyl]-3-hydroxy-, trans-[CAS] | 95233-18-4 | EP | 123238 | Antifungal | Infection, Pneumocystis jiroveci |
| atovaquone + proguanil | 1,4-Naphthalenedione,2-[4-(4-chlorophenyl)cyclohexyl]-3-hydroxy-, trans + N-(4-chloro-phenyl)-N-(1-methylethyl)imidiodicarbonimidic diamide | | | | Antimalarial | Infection, malaria |
| atracurium | Isoquinolinium, 2,2'-[1,5-pentanediylbis[oxy(3-oxo-3,1-propanediyl)]]bis[1-[(3,4-dimethoxyphenyl)methyl]-1,2,3,4-tetrahydro-6,7-dimethoxy-2-methyl-[CAS] | 64228-81-5 | U.S. | 4,179,557 | Muscle relaxant | Surgery adjunct |
| atrasentan | 3-Pyrrolidinecarboxylic acid, 4-(1,3-benzodioxol-5-yl)-1-[2-(dibutylamino)-2-oxoethyl]-2-(4-methoxyphenyl)-, (2R,3R,4S)-[CAS] | 173937-91-2 | WO | 9730045 | Anticancer, other | Cancer, prostate |
| Atrial Natriuretic Peptide | | 85637-73-6 | | | | |
| Atrolactamide | | 2019-68-3 | | | | |
| Atropine | | 51-55-8 | | | | |
| Augmentin | | 74469-00-4 | | | Formulation. modified-release, other | Infection, respiratory tract, general |
| auranofin | Gold, (1-thio-β-D-glucopyranose 2,3,4,6-tetraacetato-S)(triethylphosphine)-[CAS] | 34031-32-8 | U.S. | 3,708,579 | Antiarthritic, other | Arthritis, rheumatoid |
| Aurothio-glucose | | 12192-57-3 | | | | |
| avasimibe | Sulfamic acid, [[2,4,6-tris(1-methylethyl)phenyl]acetyl]-, 2,6-bis(1-methylethyl)phenyl ester [CAS] | 166518-60-1 | U.S. | 5,491,172 | Hypolipaemic/ Antiatherosclerosis | Atherosclerosis |
| Avobenzone | | 70356-09-1 | | | | |
| AWD-12-281 | AWD 12-281 [CAS] | 257892-33-4 | | | Antiallergic, non-asthma | Rhinitis, allergic, general |
| Azacitidine | | 320-67-2 | | | | |
| Azacyclonol | | 115-46-8 | | | | |
| azanidazole | 2-Pyrimidinamine, 4-[2-(1-methyl-5-nitro-1H-imidazol-2-yl)ethenyl]-,(E)-[CAS] | 62973-76-6 | U.S. | 3,882,105 | Antibacteria, other | Infection, trichomoniasis |
| azapropazone | 1H-Pyrazolo[1,2-a][1,2,4]benzotriazine-1,3(2H)-dione, 5-(dimethylamino)-9-methyl-2-propyl-[CAS] | 13539-59-8 | FR | 1440629 | Anti-inflammatory | |
| Azaserine | | 115-02-6 | | | | |
| azasetron | 2H-1,4-Benzoxazine-8-carboxamide, N-1-azabicyclo[2.2.2]oct-3-yl-6-chloro-3,4-dihydro-4-methyl-3-oxo-, monohydrochioride-[CAS] | 123040-16-4 123040-94-8 123040-96-0 123040-69-7 | EP | 313393 | Antiemetic | Nausea and vomiting general |
| Azatadine | | 3964-81-6 | | | | |
| azathioprine | 6-[(1-Methyl-4-nitro-1H-imidazol-5-yl)thio]-1H-purine | 446-86-6 | | | Formulation, oral, other | Transplant rejection, bone marrow |
| AZD-4282 | glycine | | | | Analgesic, other | Pain, neuronpathic |
| AZD-6140 | 3,4 Difluorophenylcyclopropylamine | | | | Antithrombotic | Thrombosis, arterial |

TABLE 3-continued

| API Generic Name | API Chemical Name | CAS No. | Patent Reference | Example of Therapeutic Use | Example of Indication |
|---|---|---|---|---|---|
| azelaic acid | Nonanedioic acid [CAS] | 123-99-9 | | Antiacne | Acne |
| azelastine | 1(2H)-Phthalazinone, 4-[(4-chlorophenyl)methyl]-2-(hexahydro-1-methyl-1H-azepin-4-yl)-, monohydrochloride [CAS] | 58581-89-8 79307-93-0 | GB 1377231 | Antiasthma | Asthma |
| azelnidipine | 3,5-Pyridinedicarboxylic acid, 2-amino-1,4-dihydro-6-methyl-4-(3-nitrophenyl)-, 3-[1-(diphenylmethyl)-3-azetidinyl] 5-(1-methylethyl)ester, (+/−)-[CAS] | 123524-52-7 | EP 266922 | Antihypertensive, other | Hypertension, general |
| Azidamfenicol | | 13838-08-9 | | | |
| Azidocillin | | 17243-38-8 | | | |
| Azimilide | | 149908-53-2 | | | |
| Azintamide | | 1830-32-6 | | | |
| azithromycin | 9-deoxo-9a-aza-9a-methyl-9a-homoerythromycin-A | 76801-85-9 83905-01-5 92395-24-9 | U.S. 4,328,334 | Macrolide antibiotic | Infection, respiratory tract, lower |
| aziocillin | 4-Thia-1-azabicyclo[3.2.0]heptane-2-carboxylic acid, 3,3-dimethyl-7-oxo-6-[[[[(2-oxo-1-imidazolidinyl)carbonyl]amino]phenyl-acetyl]amino]-, [2S-[2.alpha.,5Alpha,6β(S*)]]-[CAS] | 37091-65-9 37091-66-0 | GB 1392849 | Penicillin, injectable | Infection, general |
| Azosemide | | 27589-33-9 | | | |
| aztreonam | Propanoic acid, 2-[[[1-(2-amino-4-thiazolyl)-2-[(2-methyl-4-oxo-1-sulfo-3-azetidinyl)amino]-2-oxoethylidene]amino]oxy]-2-methyl-, [2S-[2Alpha,3β(Z)]]-[CAS] | 104184-69-2 78110-38-0 | GB 2071650 | Beta-lactam antibiotic | Infection, general |
| azulene | Sodium 5-isopropyl-3,8-dimethyl-1-azulene sulfonate | 6223-35-4 | EP 88958 | Formulation, modified-release, other | Inflammation, general |
| bacampicillin | 4-Thia-1-azabicyclo[3.2.0]heptane-2-carboxylic acid, 6-[(aminophenylacetyl)amino]-3,3-dimethyl-7-oxo-, 1-[(ethoxycarbonyl)oxy]ethyl ester, [2S-[2Alpha,5Alpha,6β(S*)]]-[CAS] | 37661-08-8 50972-17-3 | GB 1363506 | Penicillin, oral | Infection, general |
| Bacitracin | | 1405-87-4 | | | |
| baclofen | β-(Aminomethyl)-4-chlorobenzenepropanoic acid [CAS] | 1134-47-0 | | Formulation, implant | Spastic paralysis |
| Baicalein | | 491-67-8 | | | |
| balofloxacin | 3-Quinolinecarboxylic acid, 1-cyclopropyl-6-fluoro-1,4-dihydro-8-methoxy-7-[3-(methylamino)-1-pipendinyl]-4-oxo-[CAS] | 127294-70-6 | EP 342675 | Quinolone antibacterial | Infection, urinary tract |
| balsalazide | Benzoic acid, 5-[[4-[[(2-carboxyethyl)amino]carbonyl]phenyl]azo]-2-hydroxy-, (E)-[CAS] | 80573-04-2 | U.S. 4,412,992 | GI inflammatory/bowel disorders | Colitis, ulcerative |
| bambuterol | Carbamic acid, dimethyl-, 5-[2-[(1,1-dimethylethyl)amino]-1-hydroxyethyl]-1,3-phenylene ester, monohydrochloride [CAS] | 81732-46-9 81732-65-2 | EP 43807 | Antiasthma | Asthma |
| Bamethan | | 3703-79-5 | | | |
| Bamifylline | | 2016-63-9 | | | |
| Bamipine | | 4945-47-5 | | | |
| Barbital | | 57-44-3 | | | |
| bamidipine | 3,5-Pyridinedicarboxylic acid, 1,4-dihydro-2,6-dimethyl-4-(3-nitrophenyl)-, methyl-1-(phenylmethyl)-3-pyrrolidinyl ester, [S-(R*,R*)]- | 104713-75-9 104757-53-1 71863-56-4 | U.S. 4,220,649 | Antihypertensive, other | Hypertensive, general |
| BAS-118 | N-Methyl-3-[2-(2-napthyl)acetylamino]benzamide | | | Antibacterial, other | Infection, *Helicobacter pylori* |
| Basic Aluminum Carbonate Gel | | 1339-92-0 | | | |
| Basiliximab | | 179045-86-4 | | | |
| Batimastat | | 130370-60-4 | | | |
| Batroxobin | | 9039-61-6 | | | |
| Bay-41-2272 | 5-cyclopropyl-2-[1 (2-fluoro-benzyl)-1H-pyrazolo[3,4-b]pyridine-3-yl]pyrimidin-4ylamine | | | Male sexual dysfunction | Sexual dysfunction, male, general |
| Bay-41-8543 | 2-[1-(2-Fluorobenzyl)-1H-pyrazolo[3,4-b]pyridin-3-yl]-5-(4-mopholinyl)pyrimidine-4,6-diamine | | | Cardiovascular | Unspecified |

TABLE 3-continued

| API Generic Name | API Chemical Name | CAS No. | Patent Reference | | Example of Therapeutic Use | Example of Indication |
|---|---|---|---|---|---|---|
| BAY-43-9006 | N-(4-chloro-3-(trifluoromethyl)phenyl)-N'-(4-(2-(N-methylcarbamoyl)-4-pyridyloxy)phenyl)urea | | | | Anticancer, other | Cancer, liver |
| BAY-57-1293 | N-[5(aminosulfonyl)-4-methyl-1,3-thiazol-2-yl]-N-methyl-2-[4-(2-pyridinyl)phenyl]acetamide | | | | Antiviral, other | Infection, herpes simplex virus |
| bazedoxifen | TSE 424 [CAS] | 198481-33-3 | EP | 802183 | Osteoporosis treatment | Osteoporosis |
| b-Benzal-butyramide | | 7236-47-7 | | | | |
| BBR-3464 | Platinum(4+), hexaaminedichlorobis(μ-(1,6-hexanediamine-N:N'))tri-stereoisomer, tetranitrate [CAS] | 172903-00-3 | U.S. | 5,744,497 | Anticancer, alkylating | Cancer, lung, non-small cell |
| BBR-3576 | | | U.S. | 5,519,029 | Anticancer, antibiotic | Cancer, prostate |
| BBR-3610 | | | U.S. | 6,060,616 | Anticancer, alkylating | Cancer, general |
| b-Carotene | | 7235-40-7 | | | | |
| BCH-1868 | (−)-2-R-dihydroxyphosphinyol-5-(S)-(guanin-9-yl-methyl)tetrahydrofuran | | | | Anticancer, antimetabolite | Cancer, general |
| Bebeerine | | 477-60-1 | | | | |
| Beclamide | | 501-68-8 | | | | |
| beclometasone | Pregna-1,4-diene-3,20-dione, 9-chloro-11β,17,21-trihydroxy-16β-methyl, [CAS] | 5534-09-8 4419-39-0 | WO | 0006132 | Formulation, inhalable, solution | Asthma |
| Befloxatone | | 134564-82-2 | | | | |
| befunolol | Ethanone, 1-[7-[2-hydroxy-3-[(1-methylethyl)amino]propoxy]-2-benzofuranyl]-[CAS] | 39543-79-8 39552-01-7 | | | Antiglaucoma | |
| Bemegride | | 64-65-3 | | | | |
| Benactyzine | | 302-40-9 | | | | |
| benazepril | 1H-1-Benzazepine-1-acetic acid, 3-[[1-(ethoxycarbonyl)-3-phenylpropyl]amino] 2,3,4,5-tetrahydro-2-oxo-, [S-(R*,R*)]-[CAS] | 86541-74-4 86541-75-5 86541-78-8 | EP | 72352 | Antihypertensive, renin system | Hypertension, general |
| bencyclane | 1-Propanamine, N,N-dimethyl-3-[[1-(phenylmethyl)cycloheptyl]oxy]-, (E)-2-butenedloate (1:1) [CAS] | 14286-84-1 2179-37-5 | WO | 9829409 | Vasodilator, peripheral | |
| bendazac | L-Lysine, mono[[[1-(phenylmethyl)-1H-indazol-3-yl]oxy]acetate] [CAS] | 81919-14-4 20187-55-7 | GB | 2081708 | Ophthalmological | |
| Bendro-flumethiazide | | 73-48-3 | | | | |
| Benexate | | 78718-25-9 | | | | |
| benfluorex | Ethanol, 2-[[1-methyl-2-[3-(trifluoromethyl)phenyl]ethyl]amino]-, benzoate (ester) [CAS] | 23602-78-0 23642-66-2 | GB | 1175516 | Hypolipaemic/Antiatherosclerosis | |
| Benfotiamine | | 22457-89-2 | | | | |
| Benfurodil | | 3447-95-8 | | | | |
| benidipine | 3,5-Pyridinedicarboxylic acid, 1,4-dihydro-2,6-dimethyl-4-(3-nitrophenyl)-, methyl 1-(phenylmethyl)-3-piperidinyl ester, monohydrochloride (R*,R*)-(+/−)-[CAS] | 105979-17-7 91599-74-5 | EP | 63365 | Antihypertensive, other | Hypertension, general |
| Benorylate | | 5003-48-5 | | | | |
| Benoxaprofen | | 67434-14-4 | | | | |
| Benoxinate | | 99-43-4 | | | | |
| Benperidol | | 2062-84-2 | | | | |
| Benproperine | | 2156-27-6 | | | | |
| Benserazide | | 322-35-0 | | | | |
| bentazepam | 2H-[1]Benzothieno[2,3-e]-1,4-diazepin-2-one, 1,3,6,7,8,9-hexahydro-5-phenyl[CAS] | 29462-18-8 | DE | 2005276 | Anxiolytic | |
| Bentiromide | | 37106-97-1 | | | | |
| Bentoquatam | | 1340-69-8 | | | | |
| Benzalkonium | | 8001-54-5 | | | | |
| Benzarone | | 1477-19-6 | | | | |
| benzbromarone | Methanone, (3,5-dibromo-4-hydroxyphenyl)(2-ethyl-3-benzofuranyl) [CAS] | 3562-84-3 | U.S. | 3,012,042 | Antigout | |
| Benzethonium | | 121-54-0 | | | | |
| Benzetimide | | 14051-33-3 | | | | |
| Benzilonium | | 1050-48-2 | | | | |
| Benziodarone | | 68-90-6 | | | | |
| benznidazole | N-benzyl-2-nitroimidazole-1-acetamide | 22994-85-0 | GB | 1138529 | Protozoacide | |
| benzocaine | Benzoic acid, 4-amino-, ethyl ester | 94-09-7 | | | Formulation, fixed-dose combinations | Pain, musculoskeletal |
| Benzoctamine | | 17243-39-9 | | | | |
| Benzonatate | | 104-31-4 | | | | |
| Benzoxonium | | 19379-90-9 | | | | |

TABLE 3-continued

| API Generic Name | API Chemical Name | CAS No. | Patent Reference | Example of Therapeutic Use | Example of Indication |
|---|---|---|---|---|---|
| Chloride | | | | | |
| benzoyl peroxide | Peroxide, dibenzoyl [CAS] | 94-36-0 | | Formulation, other | Acne |
| Benzoylpas | | 13898-58-3 | | | |
| Benzphetamine | | 156-08-1 | | | |
| Benzpiperylon | | 53-89-4 | | | |
| Benzquinamide | | 63-12-7 | | | |
| Benzthiazide | | 91-33-8 | | | |
| Benztropine | | 132-17-2 | | | |
| benzydamine | 1-Propanamine, N,N-dimethyl-3-[[1-(phenylmethyl)-1H-indazol-3-yl]oxy]-[CAS] | 132-69-4 642-72-8 | | Stomatologic reproductive, inflammatory | |
| Benzyl Benzoate | | 120-51-4 | | | |
| Benzylhydro-chlorothiazide | | 1824-50-6 | | | |
| Benzylmorphine | | 14297-87-1 | | | |
| Bephenium Hydroxy-naphthoate | | 3818-50-6 | | | |
| bepotastine | 1-Piperidinebutanoic acid, 4-((4-chlorophenyl)-2-pyridinylmethoxy)-, (S)-, monobenzenesulfonate [CAS] | 190786-44-8 190786-43-7 | WO | 9829409 Antiallergic, non-asthma | Allergy, general |
| bepridil | 1-Pyrrolidineethanamine, β-[(2-methylpropoxy)methyl]-N-phenyl-N-(phenylmethyl)-[CAS] | 64706-54-3 74764-40-2 74764-75-3 | EP | 146155 Antianginal | Angina, general |
| beraprost | 1H-Cyclopenta[b]benzofuran-5-butanoic acid, 2,3,3a,8b-tetrahydro-2-hydroxy-1-(3-hydroxy-4-methyl-1-octen-6-ynyl)-[CAS] | 88475-69-8 88430-50-6 | U.S. | 4,474,802 Prostaglandin | Peripheral vascular disease |
| Berberine | | 2086-83-1 | | | |
| Bergapten | | 484-20-8 | | | |
| Bermoprofen | | 78499-27-1 | | | |
| Besipirdine | | 119257-34-0 | | | |
| betahistine | 2-Pyridineethanamine, N-methyl-, dihydrochloride | 5579-84-0 5638-76-6 | | Formulation, modified-release, <=24 hr | Maniere's disease |
| betaine | Betaine-[CAS] | 107-43-7 | | Metabolic and enzyme disorders | Homocystinuria |
| betamethasone | Pregna-1,4-diene-3,20-dione, 9-fluoro-11,17,21-trihydroxy-16-methyl-, (11β,16β)-[CAS] | 378-44-9 | | Formulation, dermal, topical | Psoriasis |
| Betamipron | | 3440-28-6 | | | |
| Betasine | | 3734-24-5 | | | |
| betaxolol | 2-Propanol, 1-[4-[2-(cyclopropylmethoxy)ethyl]phenoxy]-3-[(1-methylethyl)amino]-[CAS] | 63659-18-7 63659-19-8 | U.S. | 4,252,984 Antihypertensive, adrenergic | Hypertension, general glaucoma |
| Betazole | | 105-20-4 | | | |
| Bethanechol | | 590-63-6 | | | |
| Bethanidine | | 55-73-2 | | | |
| Betoxycaine | | 3818-62-0 | | | |
| b-Eucaine | | 500-34-5 | | | |
| bevantolol | 2-Propanol, 1-[[2-(3,4-dimethoxyphenyl)ethyl]amino]-3-(3-methylphenoxy)-[CAS] | 42864-78-8 59170-23-9 | U.S. | 3,857,891 Antihypertensive, adrenergic | Hypertension, general |
| Bevonium | | 5205-82-3 | | | |
| bexarotene | Benzoic acid, 4-(1-(5,6,7,8-tetrahydro-3,5,5,8,8-pentamethyl-2-naphthalenyl)ethenyl)-[CAS] | 153559-49-0 | WO | 9321146 Anticancer, other | Cancer, lymphoma, T-cell |
| bezafibrate | Propanoic acid, 2-[4-[2-[(4-chlorobenzoyl)amino]ethyl]phenoxy]-2-methyl-[CAS] | 41859-67-0 | GB | 1359264 Hypolipaemic/Antiatherosclerosis | |
| Bezitramide | | 15301-48-1 | | | |
| BG-9928 | | 166374-48-7 | | Cardiostimulant | Heart failure |
| BIA-2-024 | 10,11-dihydro-10-hydroxyimino-5H-dibenz/b,f/azepine-5-carboxamide | 199997-15-4 | WO | 9745416 Antiepileptic | Epilepsy, general |
| BIA-2-093 | (S)-(−)-10-acetoxy-10,11-dihydro-5H-dibenzo/b,f/azepine-5-carboxamide-[CAS] | 236395-14-5 | | Antiepileptic | Epilepsy, general |
| BIA-3-202 | 1-(3,4-dihydroxy-5-nitrophenyl)-2-phenyl-ethanone | 274925-86-9 | EP | 1010688 Antiparkinsonian | Parkinson's disease |
| Bialamicol | | 493-75-4 | | | |
| biapenem | 5H-Pyrazolo[1,2-a][1,2,4]triazol-4-ium, 6-[[2-carboxy-6-(1-hydroxyethyl)-4-methyl-7-oxo-1-azabicyclo[3.2.0]hept-2-en-3-yl]thio]-6,7-dihydro-, hydroxide, inner salt, [4R-[4Alpha,5β,6β(R*)]]-[CAS] | 120410-24-4 | EP | 289801 Beta-lactam antibic | Infection, beta-lactamase resistant |
| Bibenzonium | | 15585-70-3 | | | |

TABLE 3-continued

| API Generic Name | API Chemical Name | CAS No. | Patent Reference | Example of Therapeutic Use | Example of Indication |
|---|---|---|---|---|---|
| Bibrocathol | | 6915-57-7 | | | |
| bicalutamide | Propanamide, N-[4-cyano-3-(trifluoromethyl)phenyl]-3-[(4-fluorophenyl)sulfonyl]-2-hydroxy-2-methyl-, (+/−)-[CAS] | 90357-06-5 | EP 100172 | Anticancer, hormonal | Cancer, prostate |
| bicifadine | 3-Azabicyclo[3.1.0]hexane, 1-(4-methylphenyl)-, (+/−)-[CAS] | 66504-75-4 71195-57-8 | DE 2740562 | Analgesic, other | Pain, general |
| bicyclic monoter-penediols | | | U.S. 6,294,585 | Dermatological | Unspecified |
| Bidisomide | | 116078-65-0 | | | |
| Betamiverine | | 479-81-2 | | | |
| Bietanautine | | 6888-11-5 | | | |
| Bietaserpine | | 53-1 8-9 | | | |
| bifemelane | 1-Butanamine, N-methyl-4-[2-(phenylmethyl)phenoxy]-, hydrochloride [CAS] | 62232-46-6 90293-01-9 | GB 1512880 | Cognition enhancer | Attention deficit disorder |
| Bifluranol | | 34633-34-6 | | | |
| bifonazole | 1H-Imidazole, 1-([1,1-biphenyl]-4-ylphenylmethyl)-[CAS] | 60628-96-8 60629-08-5 60629-09-6 | U.S. 4,118,487 | Antifungal | Infection, fungal, general |
| bimatoprost | 5-Heptenamide, 7-(3,5-dihydroxy-2-(3-hydroxy-5-phenyl-1-pentenyl)cyclopentyl)-N-ethyl (1R-(1Alpha(Z)2β(1E,3S,3Alpha,5Alpha)) [CAS] | 155206-00-1 | U.S. 5,688,819 | Prostaglandin | Glaucoma |
| bimoclomol | N-[2-hydroxy-3-(1-piperidinyl)propoxy]-3-pyridinecarboximidoyl chloride, (Z)-2-butanedioate (1:1) | 130493-04-8 | U.S. 5,147,874 | Symptomatic antidiabetic | Neuropathy, diabetic |
| bimosiamose | (1,1-Biphenyl)-3-acetic acid, 3',3'''-(1,6-hexanediyl)bis(6-Alpha-D-mannopyranosyloxy)-, [CAS] | 187269-40-5 | U.S. 5,444,050 | Antiasthma | Asthma |
| Binifibrate | | 69047-39-8 | | | |
| binodenoson | Adenosine, 2-((cyclohexylmethylene)hydrazino)-[CAS] | 144348-08-3 | | Vasodilator, coronary | Diagnosis, coronary |
| Biomed-101 | | | U.S. 6,423,744 | Anticancer, other | Cancer, renal |
| Biotin | | 58-85-5 | | | |
| Biperiden | | 514-65-8 | | | |
| biricodar | 2-Piperidinecarboxylic acid, 1-(oxo(3,4,5-trimethoxyphenyl)acetyl)-,4-(3-pyridinyl)-1-(3-(3-pyridinyl)propyl)butyl ester, (S)-, 2-hydroxy-1,2,3-propanetricarboxylate (1:2) [CAS] | 174254-13-8 159997-94-1 | | Radio/chemosensitizer | Cancer, breast |
| biriperone | 1-Butanone, 1-(4-fluorophenyl)-4-(3,4,6,7,12,12a-hexahydropyrazino[1',2':1,6]pyrido[3,4-b]indol-2(1H)-yl)-[CAS] | 42021-34-1 | DE 2333922 | Neuroleptic | |
| Bisacodyl | | 603-50-9 | | | |
| Bisantrene | | 78186-34-2 | | | |
| Bisbentiamine | | 2667-89-2 | | | |
| Bisdequalinium | | 52951-36-7 | | | |
| Bismuth Aluminate | | 12284-76-3 | | | |
| Bismuth Butylthiolaurate | | 53897-25-9 | | | |
| Bismuth Ethyl Camphorate | | 52951-37-8 | | | |
| Bismuth Iodosubgallate | | 138-58-9 | | | |
| Bismuth Sodium Iodide | | 53778-50-0 | | | |
| Bismuth Sodium Triglycollamate | | 5798-43-6 | | | |
| Bismuth Subcarbonate | | 5892-10-4 | | | |
| Bismuth Subgallate | | 22650-86-8 | | | |
| Bismuth Subnitrate | | 1304-85-4 | | | |
| Bismuth Subsalicylate | | 14882-18-9 | | | |
| Bismuth Tribromophenate | | 5175-83-7 | | | |

TABLE 3-continued

| API Generic Name | API Chemical Name | CAS No. | Patent Reference | | Example of Therapeutic Use | Example of Indication |
|---|---|---|---|---|---|---|
| bisoprolol | 2-Propanol, 1-[4-[[2-(1-methylethoxy)ethoxy]methyl]phenoxy]-3-[(1-methylethyl)amino]-[CAS] | 104344-23-2 66722-44-9 | GB | 1532380 | Antihypertensive, adrenergic | Heart failure |
| bisoprolol + HCTZ | 2-Propanol, 1-[4-[[2-(1-methylethoxy)ethoxy)methyl]phenoxy]-3-[(1-methylethyl)amino] mixt. with 6-chloro-3,4-dihydro-2H-1,2,4-benzothiadiazine-7-sulfonamide 1,1-dioxide | | | | Formulation, fixed dose combinations | Hypertension, general |
| bisoprolol + trichloro-methiazide | 2-Propanol, 1-[4-[[2-(1-methylethoxy)ethoxyjmethyl]phenoxy]-3-[(1-methylethyl)amino] mixt. with 6-chloro-3-(dichloromethyl)-3,4-dihydro-2H-1,2,4-benzothiadiazine-7-sulfonamide 1,1-dioxide | | | | Formulation, fixed-dose combinations | Hypertension, general |
| Bisoxatin | | 14008-48-1 | | | | |
| Bithionol | | 97-18-7 | | | | |
| Bitolterol | | 30392-40-6 | | | | |
| Bitoscanate | | 4044-65-9 | | | | |
| BL-3875 | | | WO | 0218378 | Anti-inflammatory | Unspecified |
| bleomycin | Bleomycin [CAS] | 11056-06-7 9041-93-4 | | | Formulation, transdermal, enhanced | Cancer, head and neck |
| blonanserin | Cycloocta[b]pyridine, 2-(4-ethyl-1-piperazinyl)-4-(4-fluorophenyl)-5,6,7,8,9,10-hexahydro-[CAS] | 132810-10-7 | EP | 385237 | Neuroleptic | Schizophrenia |
| BMS-184476 | | | EP | 639577 | Anticancer, other | Cancer, breast |
| BMS-387032 | cis-(+/−)-2-(Ethylthio)-5,7-dihydroxy-8-(3-hydroxy-1-methyl-4-piperidinyl)-4H-1 benzopyran-4-one | | WO | 9742949 | Anticancer, other | Cancer, general |
| BN-82451 | 4-[2-(aminomethyl)-1,3-thiazol-4-yl]-2,6-di-tert-butylphenol, dihydrochloride | | | | Neuroprotective | Unspecified |
| BNP-7787 | Ethanesulfonic acid, 2,2'-dithiobis-, disodium salt [CAS] | 16208-51-8 | | | Radio/chemoprotective | Chemotherapy-induced nausea and vomiting |
| BO-653 | 5-Benzofuranol, 4,6-bis(1,1-dimethylethyl)-2,3-dihydro-2,2-dipentyl-[CAS] | 157360-23-1 | WO | 9408930 | Hypolipaemic/ Antiatherosclerosis | Antherosclerosis |
| Bolandiol | | 19793-20-5 | | | | |
| Bolasterone | | 1605-89-6 | | | | |
| Boldenone | | 846-48-0 | | | | |
| bopindolol | 2-Propanol, 1-[(1,1-dimethylethyl)amino]-3-[(2-methyl-1H-indol-4-yl)oxy]-, benzoate (ester), (+/−)-[CAS] | 62658-63-3 82857-38-3 | U.S. | 4,340,541 | Antihypertensive, adrenergic | Hypertension, general |
| Bornyl Chloride | | 464-41-5 | | | | |
| Bornyl Salicylate | | 560-88-3 | | | | |
| bortezomib | Boronic acid, [(1R)-3-methyl-1-[[(2S)-1-oxo-3-phenyl-2-[(pyrazinyl-carbonyl)amino]propyl]amino]butyl]-[CAS] | 179324-69-7 | U.S. | 6,271,199 | Anticancer, other | Cancer, myeloma |
| bosentan | Benzenesulfonamide, 4-(1,1-dimethylethyl)-N-[6-(2-hydroxyethoxy)-5-(2-methoxyphenoxy)[2,2-bipynmidin]4-yl]-[CAS] | 147536-97-8 | EP | 633259 | Vasodilator, peripheral | Hypertension, pulmonary |
| BP2.94 | Phenol, 2-[[[(1R)-2-(1H-imidazol-4-yl)-1-methylethyl]imino]phenylmethyl] [CAS] | 139191-80-3 | WO | 9117146 | Respiratory | Rhinitis, general |
| BP4.897 | N-[4-[4-(2-methoxyphenyl)-1-piperazinyl]butyl]naphthalene-2-carboxamide | | EP | 779284 | Dependence treatment | Addiction, cocaine |
| b-Propiolactone | | 57-57-8 | | | | |
| Bradycor | | 140661-97-8 | | | | |
| Brain Natriuretic Peptide | | 114471-18-0 | | | | |
| Brallobarbital | | 561-86-4 | | | | |
| brasofensine | 8-Azabicyclo(3.2.1)octane-2-carboxaldehyde, 3-(3,4-dichlorophenyl)-8-methyl-, O-methyloxime, (1R-(1Alpha,2β(E),3Alpha,5Alpha))-[CAS] | 171655-91-7 | WO | 9528401 | Antiparkinsonian | Parkinson's disease |
| Brequinar | | 96187-53-0 | | | | |
| Bretylium | | 61-75-6 | | | | |
| Brilliant Green | | 633-03-4 | | | | |
| brimonidine | 6-Quinoxalinamine, 5-bromo-N-(4,5-dihydro-1H-imidazol-2-yl)-[CAS] | 59803-98-4 | DE | 2538620 | Antiglaucoma | Glaucoma |

TABLE 3-continued

| API Generic Name | API Chemical Name | CAS No. | Patent Reference | Example of Therapeutic Use | Example of Indication |
|---|---|---|---|---|---|
| brinzolamide | 2H-Thieno(3,2-e)-1,2-thiazine-6-sulfonamide, 4-(ethylamino)-3,4-dihydro-2-(3-methoxypropyl)-, 1,1-dioxide, (R)-[CAS] | 138890-62-7 | U.S. 5,378,703 | Antiglaucoma | Glaucoma |
| brivudin | Uridine, 5-(2-bromoethenyl)-2-deoxy, (E)-[CAS] | 69304-47-8 | | Antiviral, other | Infection, varicella zoster virus |
| Brodimoprim | | 56518-41-3 | | | |
| Bromazepam | | 1812-30-2 | | | |
| bromfenac | Benzeneacetic acid, 2-amino-3-(4-bromobenzoyl)-[CAS] | 91714-93-1 91714-94-2 | | Formulation, mucosal, topical | Inflammation, ocular |
| Bromhexine | | 3572-43-8 | | | |
| Bromindione | | 1146-98-1 | | | |
| Bromisovalum | | 496-67-3 | | | |
| Bromocriptine | | 25614-03-3 | | | |
| Bromodiphen-hydramine | | 118-23-0 | | | |
| Bromoform | | 75-25-2 | | | |
| Bromopride | | 4093-35-0 | | | |
| Bromosalicyl-chloranilide | | 3679-64-9 | | | |
| bromperidol | 1-Butanone, 4-[4-(4-bromophenyl)-4-hydroxy-1-piperidinyl]-1-(4-fluorophenyl)-[CAS] | 10457-90-6 | U.S. 3,438,991 | Neuroleptic | Psychosis, general |
| Bromphen-iramine | | 86-22-6 | | | |
| Broparoestrol | | 479-68-5 | | | |
| Bropirimine | | 56741-95-8 | | | |
| brostallicin | 4-(2-Bromoacrylamido)-N'''-(2-guanidinoethyl)-1,1',1'',1'''-tetramethyl-N,4':N',4'':N'',4'''-quater-[pyrrole-2-carboxamide] [CAS] | | | Anticancer, other | Cancer, general |
| brotizolam | 6H-Thieno[3,2-f][1,2,4]triazolo[4,3-a][1,4]diazepine, 2-bromo-4-(2-chlorophenyl)-9-methyl-[CAS] | 57801-81-7 | U.S. 4,094,984 | Hypnotic/Sedative | |
| Brovincamine | | 57475-17-9 | | | |
| Broxuridine | | 59-14-3 | | | |
| Broxyquinoline | | 521-74-4 | | | |
| Brucine | | 357-57-3 | | | |
| b-Sitosterol | | 83-46-5 | | | |
| Bucetin | | 1083-57-4 | | | |
| Bucillamine | | 65002-17-7 | | | |
| Bucindolol | | 71119-11-4 | | | |
| bucladesine | Adenosine, N-(1-oxobutyl)-, cyclic 3',5'-(hydrogen phosphate) 2-butanoate [CAS] | 362-74-3 | JP 51113896 | Cardiostimulant | Wound healing |
| Buclizine | | 82-95-1 | | | |
| Buclosamide | | 575-74-6 | | | |
| Bucolome | | 841-73-6 | | | |
| bucricaine | 9-Acridinamine, N-butyl-1,2,3,4-tetrahydro-, monohydrochloride [CAS] | 82636-28-0 | | Anaesthetic, local | |
| Bucumolol | | 58409-59-9 | | | |
| budesonide | Pregna-1,4-diene-3,20-dione, 16,17-[butylidenebis(oxy)]-11,21-dihydroxy-, (11β,16Alpha)-[CAS] | 51333-22-3 | GB 1429922 | Antiasthma | Asthma |
| budesonide + formoterol | Pregna-1,4-diene-3,20-dione, 16,17-[butylidenebis(oxy)]-11,21-dihydroxy-, (11β,1bAlpha) + formamide, N-[2-hydroxy-5-[1-hydroxy-2-[[2-(4-methoxyphenol)-1-methylethyl]amino]ethyl]phenyl]-(R*,R*)-(±) | | | Formulation, fixed-dose combinations | Asthma |
| budipine | Piperidine, 1-(1,1-dimethylethyl)-4,4-diphenyl-[CAS] | 57982-78-2 63661-61-0 | DE 2825322 | Antiparkinsonian | Parkinson's disease |
| Budralazine | | 36798-79-5 | | | |
| Bufeniode | | 22103-14-6 | | | |
| Bufetolol | | 53684-49-4 | | | |
| bufexamac | p-butoxyacetohydroxamic acid | 2438-72-4 | U.S. 3,479,396 | Anti-inflammatory | |
| buflomedil | 1-Butanone, 4-(1-pyrrolidinyl)-1-(2,4,6-trimethoxyphenyl)-[CAS] | 35543-24-9 55837-25-7 | GB 1325192 | Vasodilator, peripheral | |
| Buformin | | 692-13-7 | | | |
| Bufuralol | | S4340-62-4 | | | |
| Bumadizon | | 3583-64-0 | | | |
| bumetanide | Benzoic acid, 3-(aminosulfonyl)-5-(butylamino)-4-phenoxy-[CAS] | 28395-03-1 | U.S. 3,806,534 | Antihypertensive, diuretic | Hypertension, general |
| bunaftine | 1-Naphthalenecarboxamide, N-butyl-N-[2-(diethylamino)ethyl]-[CAS] | 32421-46-8 | DE 2009894 | Antiarrhythmic | |

TABLE 3-continued

| API Generic Name | API Chemical Name | CAS No. | Patent Reference | Example of Therapeutic Use | Example of Indication |
|---|---|---|---|---|---|
| Bunamiodyl Sodium | | 1923-76-8 | | | |
| bunazosin | 1H-1,4-Diazepine, 1-(4-amino-6,7-dimethoxy-2-quinazolinyl)hexahydro-4-(1-oxobutyl)-[CAS] | 52712-76-2 80755-51-7 | GB 1398455 | Antihypertens | |
| bunitrolol | Benzonitrile, 2-[3-[(1,1-dimethylethyl)amino]-2-hydroxypropoxy]-[CAS] | 34915-68-9 | U.S. 3,940,489 | Antihypertensive, adrenergic | |
| bupivacaine | 2-Piperidinecarboxamide, 1-butyl-N-(2,6-dimethylphenyl)-[CAS] | 38396-39-3 2180-92-9 | | Formulation, modified-release >24 hr | Anaesthesia |
| Bupranolol | | 14556-46-8 | | | |
| buprenorphine | 6,14-Ethenomorphinan-7-methanol, 17-(cyclopropylmethyl)-Alpha-(1,1-dimethylethyl)-4,5-epoxy-18,19-dihydro-3-hydroxy-6-methoxy-Alpha-methyl-, [5Alpha,7Alpha(S)]-[CAS] | 52485-79-7 53152-21-9 | U.S. 3,433,791 | Analgesic, other | |
| bupropion | 1-Propanone, 1-(3-chlorophenyl)-2-[(1,1-dimethylethyl)amino]-, (+/−)-[CAS] | 31677-93-7 34911-55-2 | U.S. 4,425,363 | Antidepressant | Depression, general |
| Buramate | | 4663-83-6 | | | |
| buserelin | Luteinizing hormone-releasing factor (pig), 6-[O-(1,1-dimethylethyl)-D-serine] 9-(N-ethyl-L-prolinamide)-10-deglycinamide-[CAS] | 57982-77-1 68630-75-1 | GB 1523623 | Releasing hormones | Cancer, prostate |
| buspirone | 8-Azaspiro[4.5]decane-7,9-dione, 8-[4-[4-(2-pyrimidinyl)-1-piperazinyl]butyl]-[CAS] | 36505-84-7 | EP 276536 | Anxiolytic | Anxiety, general |
| busulfan | 1,4-Butanediol, dimethanesulfonate [CAS] | 55-98-1 | | Formulation, optimized microparticles | Cancer, general |
| busulfan | 1,4-Butanediol, dimethanesulfonate-[CAS] | 55-98-1 | | Formulation, parenteral, other | Cancer, leukaemia, acute myelogenous |
| Butabarbital | | 143-81-7 | | | |
| Butacaine | | 149-16-6 | | | |
| Butacetin | | 2109-73-1 | | | |
| Butalamine | | 22131-35-7 | | | |
| Butalbital | | 77-26-9 | | | |
| Butallylonal | | 1142-70-7 | | | |
| butamben | 4-Aminobenzoic acid butyl ester [CAS] | 94-25-7 | | Formulation, modified-release, other | Pain, cancer |
| butamirate | Benzeneacetic acid, Alpha-ethyl-, 2-[2-(diethylamino)ethoxy]ethylester, 2-hydroxy-1,2,3-propanetricarboxylate (1:1) [CAS] | 18109-80-3 18109-81-4 | | Antitussive | Cough |
| Butanilicaine | | 3785-21-5 | | | |
| Butaperazine | | 653-03-2 | | | |
| Butaverine | | 55837-14-4 | | | |
| Butazolamide | | 16790-49-1 | | | |
| Butedronic Acid | | 51395-42-7 | | | |
| butenafine | 1-Naphthalenemethanamine, N-((4-(1,1-dimethylethyl)phenyl)methyl)-N-methyl-[CAS] | 101827-46-7 101828-21-1 | EP 164697 | Antifungal | Infection, dermatological |
| Butethal | | 77-28-1 | | | |
| Butethamate | | 14007-64-8 | | | |
| Butethamine | | 2090-89-3 | | | |
| Buthalital | | 510-90-7 | | | |
| Buthiazide | | 2043-38-1 | | | |
| Butibufen | | 55837-18-8 | | | |
| Butidrine | | 1506-12-3 | | | |
| butobendine | benzoic acid, 3,4,5-trimethoxy-, 1,2-ethanediylbis[(methylimino)(2-ethyl-2,1-ethanediyl)] ester, [S-(R*,R*)]-[CAS] | 55769-64-7 55769-65-8 | U.S. 4,021,473 | Antiarrhythmic | Arrhythmia, general |
| butoconazole | 1H-Imidazole, 1-[4-(4-chlorophenyl)-2-[(2,6-dichlorophenyl)thio]butyl]-, (+/−)-[CAS] | 64872-76-0 64872-77-1 | GB 1567431 | Antifungal | Infection, Candida, general |
| Butoctamide | | 32838-26-9 | | | |
| Butofilolol | | 64552-17-6 | | | |
| butorphanol | Morphinan-3,14-diol, 17-(cyclobutylmethyl)-, [S-(R*,R*)]-2,3-dihydroxybutanedioate (1:1) (salt) [CAS] | 42408-82-2 58786-99-5 | GB 1412129 | Analgesic, other | |
| Butoxycaine | | 3772-43-8 | | | |
| Butriptyline | | 35941-65-2 | | | |
| Butropium | | 29025-14-7 | | | |
| Buzepide | | 3691-21-2 | | | |
| BVT-5182 | | | WO 0208178 | Anorectic/Antiobesity | Obesity |

TABLE 3-continued

| API Generic Name | API Chemical Name | CAS No. | Patent Reference | | Example of Therapeutic Use | Example of Indication |
|---|---|---|---|---|---|---|
| BXT-51072 | 2H-1,2-Benzoselenazine, 3,4-dihydro-4,4-dimethyl-[CAS] | 173026-17-0 | | | GI inflammatory/bowel disorders | Colitis, ulcerative |
| C-1311 | 6H-Imidazo[4,5,1-de]acridin-6-one, 5-[[2-(diethylamino)ethyl]amino]-8-hydroxy-, 2HCl, 2H2O | | | | Anticancer, other | Cancer, general |
| cabergoline | Ergoline-8-carboxamide, N-[3-(dimethylamino)propyl]-N-[(ethylamino)carbonyl]-6-(2-propenyl)-, (8β)-[CAS] | 81409-90-7 85329-89-1 | GB | 2103603 | Antiprolactin | Galactorrhoea |
| Cabergoline | | 81409-90-7 | | | | |
| Cacodylic Acid | | 75-60-5 | | | | |
| Cactinomycin | | 8052-16-2 | | | | |
| cadexomer iodine | Cadexomer iodine [CAS] | 94820-09-4 | | | Anti-infective, other | Ulcer, venostasis |
| Cadmium Salicylate | | 19010-79-8 | | | | |
| Cadralazine | | 64241-34-5 | | | | |
| Cafaminol | | 30924-31-3 | | | | |
| caffeine | 1,2,3,-Propanetricarboxylic acid, 2-hydroxy- mixt. with 3,7-dihydro-1,3,7-trimethyl-1H-purine-2,6-dione [CAS] | 69-22-7 58-08-2 | | | Respiratory | Apnoea |
| Calcifediol | | 19356-17-3 | | | | |
| Calcipotriene | | 112965-21-6 | | | | |
| calcipotriol | 9,10-Secochola-5,7,10(19),22-tetraene-1,3,24-triol, 24-cyclopropyl-, (1Alpha,3β,5Z,7E,22E)-[CAS] | 112965-21-6 | WO | 8700834 | Antipsoriasis | Psoriasis |
| calcipotriol + beclometasone | 9,10-Secochola-5,7,10(19),22-tetraene-1,3,24-triol, 24-cyclopropyl-, (1Alpha,3β,5Z,7E,22E) + Pregna-1,4-diene-3,20-dione, 9-chloro-11β,17,21-trihydroxy-16β-methyl, 17,21-dipropionate | | | | Formulation, fixed-dose combinations | Psoriasis |
| calcitriol | 9,10-Secocholesta-5,7,10(19)-triene-1,3,25-triol, (1Alpha,3β,5Z,7E)-[CAS] | 32222-06-3 | | | Antipsoriasis | Psoriasis |
| Calcium 3-Aurothio-2-propanol-1-sulfonate | | 5743-29-3 | | | | |
| Calcium Acetylsalicylate | | 69-46-5 | | | | |
| Calcium Bromolactobionate | | 33659-28-8 | | | | |
| Calcium Carbonate | | 471-34-1 | | | | |
| Calcium Gluconate | | 299-28-5 | | | | |
| Calcium Glycerophosphate | | 27214-00-2 | | | | |
| calcium hopantothenate | Calcium D-(+)-4-(2,4-dihydroxy-3,3-dimethylbutyramido)butyrate (hemihydrate) [CAS] | 17097-76-6 | EP | 117260 | Neurological | Attention deficit disorder |
| Calcium Iodobehenate | | 1319-91-1 | | | | |
| Calcium Iodostearate | | 1301-16-2 | | | | |
| Calcium Lactate | | 814-80-2 | | | | |
| Calcium Levulinate | | 591-64-0 | | | | |
| Calciuhi Mesoxalate | | 21085-60-9 | | | | |
| Calcium N-Carbamoyl-aspartate | | 16649-79-9 | | | | |
| calcium polycarbophil | Polycarbophil, calcium salt-[CAS] | 126040-58-2 9003-97-8 | | | GI inflammatory/bowel disorders | Irritable bowel syndrome |
| Calcium Propionate | | 4075-81-4 | | | | |
| Calcium Succinate | | 140-99-8 | | | | |
| caldaret | 5-methyl-2-(1-piperazinyl)-benzenesulfonic acid monohydrate | 133804-44-1 | | | Cardiostimulant | Heart failure |

TABLE 3-continued

| API Generic Name | API Chemical Name | CAS No. | Patent Reference | Example of Therapeutic Use | Example of Indication |
|---|---|---|---|---|---|
| Calusterone | | 17021-26-0 | | | |
| Camazepam | | 36104-80-0 | | | |
| camostat | Benzeneacetic acid, 4-[[4-[(aminoiminomethyl)amino]benzoyl]oxy]-, 2-(dimethylamino)-2-oxoethyl ester, monomethanesulfonate [CAS] | 59721-28-7 59721-29-8 71079-09-9 | U.S. | 4,021,472 GI inflammatory/bowel disorders | Pancreatitis |
| Camphor | | 76-22-2 | | | |
| Camphotamide | | 4876-45-3 | | | |
| camptothecin | 4-Ethyl-4-hydroxy-1H-pyrano-[I3'4':6,7]indolizinol[1,2-b;]quinoline-3,14(4H,12H)-dione microemulsion | | | Formulation, optimized microemulsion | Cancer, general |
| Candesartan | | 139481-59-7 | | | |
| candesartan cilexetil | 1H-Benzimidazole-7-carboxylic acid, 2-ethoxy-1-[[2'-(1H-tetrazol-5-yl)[1,1'-biphenyl]-4-yl]methyl]-, 1-[[(cyclohexyloxy)carbonyl]oxy]ethyl ester, (+/−)-[CAS] | 145040-37-5 | EP | 520423 Antihypertensive, renin system | Hypertension, general |
| Candoxatril | | 123122-55-4 | | | |
| canertinib | N-[4-(3-(Chloro-4-fluoro-phenylamino)-7-(3-morpholin-4-yl-propoxy)-quinazolin 6-yl]-acrylamide | 289499-45-2 | | Anticancer, other | Cancer, lung, non-small cell |
| Canrenone | | 976-71-6 | | | |
| Cantharidin | | 56-25-7 | | | |
| cantuzumab mertansine | Maytansine, N2-deacetyl-N2-(3-mercapto-1-oxopropyl)-, conjugated humanized C242 monoclonal antibody | 139504-50-0 | | Immunotoxin | Cancer, colorectal |
| capecitabine | Cytidine, 5-deoxy-5-fluoro-N-[(pentyloxy)carbonyl]-[CAS] | 154361-50-9 | EP | 602454 Anticancer, antimetabolite | Cancer, breast |
| Capobenic Acid | | 21434-91-3 | | | |
| capravirine | 1H-imidazole-2-methanol, 5-(3,5-dichlorophenyl)thio-4-(1-methylethyl)-1-(4-pyridinyl)methyl carbamate (ester) [CAS] | 178979-85-6 | | Antiviral, anti-HIV | Infection, HIV/AIDS |
| Capromab | | 151763-64-3 | | | |
| capsaicin cream | N-[(4-hydroxy-3-methoxyphenyl)methyl] 8-methyl-, (E)-[CAS] | 404-86-4 | | Formulation, dermal, topical | Pain, post-herpetic |
| Captodiamine | | 486-17-9 | | | |
| captopril | L-Proline, 1-(3-mercapto-2-methyl-1-oxopropyl)-, (S)-[CAS] | 62571-86-2 | U.S. | 4,105,776 Antihypertensive, renin system | Hypertension, general |
| captopril + HCTZ | L-Proline, 1-(3-mercapto-2-methyl-1-oxopropyl)-, (S)-, mixt. with 6-chloro-3,4-dihydro-2H-1,2,4-benzothiadiazine-7-sulfonamide 1,1-dioxide [CAS] | 110075-07-5 | U.S. | 4,217,347 Antihypertensive, renin system | Hypertension, general |
| Capuride | | 5579-13-5 | | | |
| carabersat | Benzamide, N-(6-acetyl-3,4-dihydro-3-hydroxy-2,2-dimethyl-2H-1-benzopyran-4-yl)-4-fluoro, (3R-trans)-[CAS] | 184653-84-7 | WO | 9811890 Antiepileptic | Epilepsy, general |
| Caramiphen | | 77-22-5 | | | |
| carazolol | 2-Propanol, 1-(9H-carbazol-4-yloxy)-3-[(1-methylethyl)amino]-[CAS] | 57775-29-8 | DE | 2240599 Antihypertensive, adrenergic | |
| Carbachol | | 51-83-2 | | | |
| carbamazepine | 5H-Dibenz[b,f]azepine-5-carboxamide [CAS] | 298-46-4 | | Formulation, modified-release, other | Epilepsy, general |
| Carbamide Peroxide | | 124-43-6 | | | |
| Carbarsone | | 121-59-5 | | | |
| Carbaryl | | 63-25-2 | | | |
| Carbazochrome | | 13051-01-9 51460-26-5 | | | |
| carbendazim | Methyl-2-benzimidazolecarbamate | | | Anticancer, other | Cancer, general |
| Carbenicillin | | 4697-36-3 | | | |
| Carbenoxolone | | 5697-56-3 | | | |
| Carbetapentane | | 77-23-6 | | | |
| Carbicarb | Carbonic acid disodium salt, mixt. with monosodium salt-[CAS] | 72227-05-5 | | Alimentary/Metabolic, other | Acidosis |
| Carbidopa | | 28860-95-9 | | | |
| carbidopa + levodopa-1 | S-Alpha Hydrazino-3,4-dihydroxy-Alpha methyl benzene propanoic acid monohydrate + 3-hydroxy-L-tyrosine | | | Formulation, fixed-dose combinations | Parkinson's disease |
| Carbimazole | | 22232-54-8 | | | |
| Carbinoxamine | | 486-16-8 | | | |
| Carbocloral | | 541-79-7 | | | |
| carbocysteine | | 151756-26-2 638-23-3 | EP | 546272 Cystic fibrosis treatment | Cystic fibrosis |

TABLE 3-continued

| API Generic Name | API Chemical Name | CAS No. | Patent Reference | Example of Therapeutic Use | Example of Indication |
|---|---|---|---|---|---|
| Carbon Tetrachloride | | 56-23-5 | | | |
| carboplatin | Platinum, diammine[1,1-cyclobutanedicarboxylato(2-)]-, (SP-4-2)-[CAS] | 41575-94-4 | | Anticancer, alkylating | Cancer, ovarian |
| Carboprost | | 35700-23-3 | | | |
| carboprost trometamol | Prosta-5,13-dien-1-oic acid, 9,11,15-trihydroxy-15-methyl-, (5Z,9.alpha.,11Alpha,13E,15S)-, compd. with 2-amino-2-(hydroxymethyl)-1,3-propanediol(1:1) [CAS] | 58551-69-2 74849-93-7 | U.S. | 3,728,382 Prostaglandin | Abortion |
| Carboquone | 2,5-Cyclohexadiene-1,4-dione, 2-[2-[(aminocarbonyl)oxy]-1-methoxyethyl]-3,6-bis(1-aziridinyl)-5-methyl-[CAS] | 24279-91-2 | DE | 1905224 Anticancer, antibiotic | |
| Carbromal | | 77-65-6 | | | |
| Carbubarb | | 960-05-4 | | | |
| Carbutamide | | 339-43-5 | | | |
| Carbuterol | | 34866-47-2 | | | |
| Carfimate | | 3567-38-2 | | | |
| carglumic acid | N-Carbamoyl-L-glutamic acid | 1188-38-1 | | Metabolic and enzyme disorders | Hyperammonaemia |
| Cargutocin | | 33605-67-3 | | | |
| Carindacillin | | 35531-88-5 | | | |
| cariporide | Benzamide, N-(aminoiminomethyl)-4-(1-methylethyl)-3-(methylsulfonyl)-[CAS] | 159138-80-4 159138-81-5 | EP | 589336 Antianginal | Angina, general |
| Cariporide | | 159138-80-4 | | | |
| Carisoprodol | | 78-44-4 | | | |
| carmofur | 1(2H)-Pyrimidinecarboxamide, 5-fluoro-N-hexyl-3,4-dihydro-2,4-dioxo-[CAS] | 61422-45-5 | U.S. | 4,071,519 Anticancer, antimetabolite | |
| Carmoxirole | | 98323-83-2 | | | |
| carmustine | Urea, N,N-bis(2-chloroethyl)-N-nitroso-[CAS] | 154-93-8 | | Formulation, implant | Cancer, brain |
| Carnitine | | 461-06-3 | | | |
| Caroverine | | 23465-76-1 | | | |
| Caroxazone | | 18464-39-6 | | | |
| Carphenazine | | 2622-30-2 | | | |
| Carpipramine | | 5942-95-0 | | | |
| carprofen | 9H-Carbazole-2-acetic acid, 6-chloro-Alpha-methyl-, (+/−)-[CAS] | 53716-49-7 | U.S. | 3,896,145 Anti-inflammatory | |
| Carsalam | | 2037-95-8 | | | |
| carteolol | 2(1H)-Quinolinone, 5-[3-[(1,1-dimethylethyl)amino]-2-hydroxypropoxy]-3,4-dihydro-, monohydrochloride [CAS] | 51781-06-7 51781-21-6 | U.S. | 3,910,924 Antihypertensive, adrenergic | Glaucoma |
| Carticaine | | 23964-58-1 | | | |
| Carubicin | | 50935-04-1 | | | |
| Carumonam | | 87638-04-8 | | | |
| Carvacrol | | 499-75-2 | | | |
| carvedilol | 2-Propanol, 1-(9H-carbazol-4-yloxy)-3-[[2-(2-methoxyphenoxy)ethyl]amino]-[CAS] | 72956-09-3 | EP | 4920 Antihypertensive, adrenergic | Hypertension, general |
| Carvone | | 99-49-0 | | | |
| Cascarillin | | 10118-56-6 | | | |
| caspofungin | Pneumocandin B0, 1-((4R,5S)-5-((2-aminoethyl)amino)-N2-(10,12-dimethyl-1-oxotetradecyl)-4-hydroxy-L-ornithine) 5-(threo-3-hydroxy-L-ornithine)-, diacetate (salt) [CAS] | 162808-62-0 179463-17-3 | WO | 9421677 Antifungal | Infection, *Aspergillus* |
| Catechin | | 154-23-4 | | | |
| cathepsin K inhibitors | N-(1-benzothien-2-ylcarbonyl)-N-[2-(2-fluorophenyl)-4-oxo-1,2,3,4-tetrahydropyrimidin-5-yl]-L-leucinamide | | WO | 9613523 Osteoporosis treatment | Osteoporosis |
| cathepsin S inhibitors | N-(1-benzothien-2-ylcarbonyl)-N-[2-(2-fluorophenyl)-4-oxo-1,2,3,4-tetrahydropyrimidin-5-yl]-L-leucinamide | | | Antiasthma | Asthma |
| CC-401 | | | U.S. | 6,342,595 Immunosuppressant | Arthritis, rheumatoid |
| CCI-779 | Rapamycin 42-(3-hydroxy-2-(hydroxymethyl)-2-methylpropanoate) [CAS] | 162635-04-3 | | Anticancer, antibiotic | Cancer, renal |
| CCR5 antagonists | | | WO | 9732019 Antiviral, anti-HIV | Infection, HIV/AIDS |
| CDC-394 | | | U.S. | 634,061 Anticancer, other | Cancer, myeloma |
| CDC-801 | | | U.S. | 5,605,914 GI inflammatory/bowel disorders | Crohn's disease |

TABLE 3-continued

| API Generic Name | API Chemical Name | CAS No. | Patent Reference | Example of Therapeutic Use | Example of Indication |
|---|---|---|---|---|---|
| CEE-03-310 | 1H-3-Benzazepin-7-ol, 5-(2,3-dihydro-7 benzofuranyl)- 2,3,4,5,-tetrahydro-3-methyl-8-nitro, (5S)-[CAS] | 128022-68-4 | EP 347672 | Dependence treatment | Addiction, alcohol |
| cefaclor | 5-Thia-1-azabicyclo[4.2.0]oct-2-ene-2-carboxylic acid, 7-[(aminophenylacetyl)amino]-3-chloro-8-oxo-, [6R-[6Alpha,7β(R*)]]-[CAS] | 53994-73-3 70356-03-5 | GB 1461323 | Cephalosporin, oral | Infection, *Haemophilus influenzae* prophylaxis |
| cefadroxil | 5-Thia-1-azabicyclo[4.2.0]oct-2-ene-2-carboxylic acid, 7-[[amino(4-hydroxyphenyl)acetyl]amino]-3-methyl-8-oxo-, [6R-[6Alpha,7β(R*)]]-[CAS] | 50370-12-2 66592-87-8 | GB 1240687 | Cephalosporin, oral | Infection, general |
| cefalexin | 5-Thia-1-azabicyclo[4.2.0]oct-2-ene-2-carboxylic acid, 7-[(aminophenylacetyl)amino]-3-methyl-oxo-, [CAS] | 8105879-42-3 15686-71-2 | U.S. 4,775,751 | Cephalosporin, oral | Infection, respiratory tract, upper |
| cefalexin pivoxil | 5-Thia-1-azabicyclo[4.2.0]oct-2-ene-2-carboxylic acid, 7-[(aminophenylacetyl)amino]-3-methyl-8 oxo-, (2,2-dimethyl-1-oxopropoxy)methyl ester, monohydrochloride, [6R-[6Alpha,7β(R*)]]-[CAS] | 27726-31-4 | | Cephalosporin, oral | Infection, general |
| cefamandole | 7-D-mandeiamido-3[[(1-methyl-1H-tetrazol-5-yl)thio]methyl-3-cephem-4-carboxylic acid | 34444-01-4 | U.S. 3,641,021 | Cephalosporin, injectable | Infection, general |
| cefatrizine | 5-Thia-1-azabicyclo[4.2.0]oct-2-ene-2-carboxylic acid, 7-[[amino(4-hydroxyphenyl)acetyl]amino]-8-oxo-3-[(1H-1,2,3-triazol-4-ylthio)methyl]-, [6R-[6Alpha,7β(R*)]]-[CAS] | 51627-14-6 | GB 1460914 | Cephalosporin, oral | Infection, general |
| Cefazedone | | 56187-47-4 | | | |
| Cefazolin | | 25953-19-9 | | | |
| Cefbuper-azone | | 76610-84-9 | | | |
| cefcapene pivoxil | 7β-[(Z)-2-(2-amino-4-thiazolyl)-2-pentenoylamino]-3-carbamoyloxymethyl-3-cephem-4-carboxylic acid, pivaloyloxymethyl ester HCl-[CAS] | 105889-45-0 105889-46-1 | GB 2173194 | Cephalosporin, oral | Infection, respiratory tract, general |
| Cefclidin | | 105239-91-6 | | | |
| cefdinir | 5-Thia-1-azabicyclo(4.2.0)oct-2-ene-2-carboxylic acid, 7-[[(2-amino-4-thiazolyl)(hydroxyimino)acetyl]amino]-3-ethenyl-8-oxo-, [6R-[6Alpha,7β(Z)]]-[CAS] | 91832-40-5 | EP 105459 | Cephalosporin, oral | Infection, dermatological |
| cefditoren pivoxil | 5-Thia-1-azabicyclo[4.2.0]oct-2-ene-2-carboxylic acid, 7-[[(2-amino-4-thiazolyl)(methoxyimino)acetyl]amino]-3-[2-(4-methyl-5-thiazolyl)ethenyl]-8-oxo-, (2,2-dimethyl-1-oxopropoxy)methyl ester, [6R-[3(Z),6Alpha,7β(Z)]]-[CAS] | 104145-95-1 104146-53-4 117467-28-4 | JP 61178991 | Cephalosporin, oral | Infection, general |
| cefepime | Pyrrolidinium, 1-[[7-[[(2-amino-4-thiazolyl)(methoxyimino)acetyl]amino]-2-carboxy-8-oxo-5-thia-1-azabicyclo[4.2.0]oct-2-en-3-yl]methyl]-1-methyl-, hydroxide, inner salt, [6R-[6Alpha,7β(Z)]]-[CAS] | 107648-80-6 123171-59-5 88040-23-7 | EP 531981 | Cephalosporin, injectable | Infection, respiratory tract, lower |
| Cefetamet | | 65052-63-3 | | | |
| cefetamet pivoxil | 5-Thia-1-azabicyclo[4.2.0]oct-2-ene-2-carboxylic acid, 7-[[(2-amino-4-thiazolyl)(methoxyimino)acetyl]amino]-3-methyl-8-oxo-, (2,2-dimethyl-1-oxopropoxy)methyl ester, monohydrochloride, [6R-[6Alpha,7β(Z)]]-[CAS] | 111696-23-2 | GB 1581854 | Cephalosporin, oral | Infection, general |
| cefixime | 5-Thia-1-azabicyclo[4.2.0]oct-2-ene-2-carboxylic acid, 7-[[(2-amino-4-thiazolyl)[(carboxymethoxy)imino]acetyl]amino]-3-ethenyl-8-oxo-, [6R-[6Alpha,7β(Z)]]-[CAS] | 79350-37-1 | EP 30630 | Cephalosporin, oral | Infection, general |
| cefmenoxime | 5-Thia-1-azabicyclo[4.2.0]oct-2-ene-2-carboxylic acid, 7-[[(2-amino-4-thiazolyl)(methoxyimino)acetyl]amino]- | 65085-01-0 75738-58-8 | GB 1536281 | Cephalosporin, injectable | Infection, ocular |

TABLE 3-continued

| API Generic Name | API Chemical Name | CAS No. | Patent Reference | Example of Therapeutic Use | Example of Indication |
|---|---|---|---|---|---|
| cefmetazole | 3-[[(1-methyl-1H-tetrazol-5-yl)thio]methyl]-8-oxo-, [6R-[6Alpha,7β(Z)]]-[CAS] 5-Thia-1-azabicyclo[4.2.0]oct-2-ene-2-carboxylic acid, 7-[[[(cyanomethyl)thio]acetyl]amino]-7-methoxy-3-[[(1-methyl-1H-tetrazol-5-yl)thso]methyl]-8-oxo-, (6R-cis)-[CAS] | 56796-20-4 56796-39-5 | GB 1449420 | Cephalosporin, injectable | Infection, general |
| cefminox | 5-Thia-1-azabicyclo[4.2.0]oct-2-ene-2-carboxylic acid, 7-[[[(2-amino-2-carboxyethyl)thio]acetyl]amino]-7-methoxy-3-[[(1-methyl-1H-tetrazol-5-yl)thio]methyl]-8-oxo-, [6R-[6Alpha,7Alpha,7(S*)]]-[CAS] | 84305-41-9 | EP 24879 | Cephalosporin, injectable | Infection, urinary tract |
| cefodizime | 5-Thia-1-azabicyclo[4.2.0]oct-2-ene-2-carboxylic acid, 7-[[(2-amino-4-thiazolyl)(methoxyimino)acetyl]amino]-3-[[[5-(carboxymethyl)-4-methyl-2-thiazolyl]thio]methyl]-8-oxo-, [6R-[6Alpha,7β(Z)]]-[CAS] | 69739-16-8 86329-79-5 | U.S. 4,590,267 | Cephalosporin, injectable | Infection, respiratory tract, lower |
| cefonicid | 5-Thia-1-azabicyclo[4.2.0]oct-2-ene-2-carboxylic acid, 7-[(hydroxyphenylacetyl)amino]-8-oxo-3-[[[1-(sulfomethyl)-1H-tetrazol-5-yl]thio]methyl]-, disodium salt, [6R-[6Alpha,7B(R)]]-[CAS] | 61270-78-8 61270-58-4 | GB 1547473 | Cephalosporin, injectable | Infection, general |
| cefoperazone | 5-Thia-1-azabicyclo[4.2.0]oct-2-ene-2-carboxylic acid, 7-[[[[(4-ethyl-2,3-dioxo-1-piperazinyl)carbonyl]amino](4-hydroxyphenyl)acetyl]amino]-3-[[(1-methyl-1H-tetrazol-5-yl)thio]methyl]-8-oxo-, [6R-[6Alpha,7β(R*)]]]-[CAS] | 62893-19-0 | GB 1508071 | Cephalosporin, injectable | Infection, general |
| cefoperazone + sulbactam | | 92739-15-6 | U.S. 4,234,579 | Antibiotic, other | Infection, general |
| Ceforanide | | 60925-61-3 | | | |
| cefoselis | 5-Thia-1-azabicyclo[4.2.0]oct-2-ene-2-carboxylic acid, 7-[[(2-amino-4-thiazolyl)(methoxyimino)acetyl]amino]-3-[[2,3-dihydro-2-(2-hydroxyethyl)-3-imino-1H-pyrazol-1-yl]methyl]-8-oxo-, [6R-[6Alpha,7β(Z)]] | 122841-12-7 122841-10-5 | EP 307804 | Cephalosporin, injectable | Infection, general |
| cefotaxime | (6R,7R)-7-[[(2-amino-4-thiazolyl)(methoxyimino)acetyl]amino]cephalsporanic acidsodium salt | 64485-93-4 63527-52-6 | GB 1580621 | Cephalosporin, injectable | Infection, general |
| Cefotetan | | 69712-56-7 | | | |
| cefotiam | 5-Thia-1-azabicyclo[4.2.0]oct-2-ene-2-carboxylic acid, 7-[[(2-amino-4-thiazolyl)acetyl]amino]-3-[[[1-[2-(dimethylamino)ethyl]-1H-tetrazol-5-yl]thio]methyl]-8-oxo-, (6R-trans)-[CAS] | 61622-34-2 66309-69-1 | U.S. 4,080,498 | Cephalosporin, injectable | Infection, general |
| cefotiam hexetil | 1-(cyclohexyloxycarbonyloxy)ethyl 7β-[2-(2-aminothiazol-4-yl)acetamido]-3-[[[1-(2-dimethylaminoethyl)-1H-tetrazol-5-yl]thio]methyl]ceph-3-em-4-carboxylate 2HCl [CAS] | 95789-30-3 | EP 128029 | Cephalosporin, oral | Infection, respiratory tract, lower |
| cefoxitin | 5-Thia-1-azabicyclo(4.2.0)oct-2-ene-2-carboxylic acid, 3-(((aminocarbonyl)oxy)methyl)-7-methoxy-8-oxo-7-((2-thienylacetyl)amino)-, monosodium salt, (6R-cis)-[CAS] | 33564-30-6 35607-66-0 | GB 1348984 | Cephalosporin, oral | Infection, general |
| cefozopran | Imidazo[1,2-b]pyridazinium, 1-[[7-[[(5-amino-1,2,4-thiadiazol-3-yl)(methoxyimino)acetyl]amino]-2-carboxy-8-oxo-5-thia-1-azabicyclo[4.2.0]oct-2-en-3-yl]methyl]-, hydroxide, inner salt, [6R-[6Alpha,7β(Z)]]-[CAS] | 113359-04-9 | EP 203271 | Cephalosporin, injectable | Infection, general |
| cefpimizole | Pyridinium, 1-[[2-carboxy-7-[[[[(5-carboxy-1H-imidazol-4-yl)carbonyl]amino]phenylacetyl]amino]-8-oxo-5-thia-1-azabicyclo[4.2.0]oct-2-en-3-yl]methyl]-4-(2-sulfoethyl)-, hydroxide, inner salt, [6R-[6Alpha,7β4R*)]]-[CAS] | 84880-03-5 85287-61-2 | EP 60028 | Cephalosporin, injectable | Infection, respiratory tract, general |

TABLE 3-continued

| API Generic Name | API Chemical Name | CAS No. | Patent Reference | Example of Therapeutic Use | Example of Indication |
|---|---|---|---|---|---|
| cefpiramide | 5-Thia-1-azabicyclo[4.2.0]oct-2-ene-2-carboxylic acid, 7-[[[[(4-hydroxy-6-methyl-3-pyridinyl)carbonyl]amino](4-hydroxyphenyl)acetyl]amino]-3-[[(1-methyl-1H-tetrazol-5-yl)thio]methyl]-8-oxo-, [6R-[6Alpha,7β(R*)]]-[CAS] | 70797-11-4 | U.S. 4,156,724 | Cephalosporin, injectable | Infection, general |
| cefpirome | 5H-1-Pyrindinium, 1-[[7-[[(2-amino-4-thiazolyl)(methoxyimino)acetyl]amino]-2-carboxy-8-oxo-5-thia-1-azabicyclo[4.2.0]oct-2-en-3-yl]methyl]-6,7-dihydro-,hydroxide, inner salt, [6R-[6Alpha,711(Z)]]-[CAS] | 84957-29-9 98753-19-6 | EP 64740 | Cephalosporin, injectable | Infection, respiratory tract, lower |
| Cefpodoxime Proxetil | | 87239-81-4 | | | |
| cefprozil | 5-Thia-1-azabicyclo[4.2.0]oct-2-ene-2-carboxylic acid, 7-[[amino(4-hydroxyphenyl)acetyl]amino]-8-oxo-3-(1-propenyl)-, [6R-[6Alpha,7β(R*)]]-[CAS] | 92665-29-7 121123-17-9 | GB 2173798 | Cephalosporin, oral | Infection, dermatological |
| cefroxadine | 5-Thia-1-azabicyclo[4.2.0]oct-2-ene-2-carboxytic acid, 7-[(amino-1,4-cyciohexadien-1-ylacetyl)amino]-3-methoxy-8-oxo-, [6R-[6Alpha,7β(R*)]]-[CAS] | 51762-05-1 | GB 143511 | Cephalosporin, oral | Infection, general |
| cefsulodin | Pyridinium, 4-(aminocarbonyl)-1-([2-carboxy-8-oxo-7-[(phenylsulfoacetyl)amino]-5-thia-1-azabicyclo[4.2.0]oct-2-en-3-yl]methyl]-, hydroxide, inner salt, [6R-[6Alpha,7β(R*)]]-[CAS] | 52152-93-9 62587-73-9 | GB 138765 | Cephalosporin, injectable | Infection, pseudomonal |
| ceftazidime | Pyridinium, 1-[[7-[[(2-amino-4-thiazolyl)[(1-carboxy-1-methylethoxy)imino]acetyl]amino]-2-carboxy-8-oxo-5-thia-1-azabicyclo[4.2.0]oct-2-en-3-yl]methyl]-, hydroxide, inner salt, [6R-[6Alpha,7β(Z)]]-[CAS] | 72558-82-8 | GB 202539 | Cephalosporin, injectable | Infection, respiratory tract, upper |
| Cefteram | | 82547-58-8 | | | |
| Ceftezole | | 26973-24-0 | | | |
| ceftibuten | 5-Thia-1-azabicyclo[4.2.0]oct-2-ene-2-carboxylic acid, 7-[[2-(2-amino-4-thiazolyl)-4-carboxy-1-oxo-2-butenyl]amino]-8-oxo-, [6R-[6Alpha,7β(Z)]]-[CAS] | 97519-39-6 | EP 136721 | Cephalosporin, oral | Infection, respiratory tract, lower |
| ceftizoxime | 5-Thia-1-azabicyclo[4.2.0]oct-2-ene-2-carboxylic acid, 7-[[(2-amino-4-thiazolyl)(methoxyimino)acetyl]amino]-8-oxo-, [6R-[6Alpha,7β(Z)]]-[CAS] | 68401-81-0 68401-82-1 | GB 1600735 | Cephalosporin, injectable | Infection, general |
| ceftizoxime alapivoxil | 5-Thia-1-azabicyclo[4.2.0]oct-2-ene-2-carboxylic acid, 7-[[[2-[(2-amino-1-oxopropyl)amino]-4-thiazolyl](methoxyimino)acetyl]amino]-8 oxo-, (2,2-dimethyl-1-oxopropoxy)methyl ester, monohydrochloride, [6R-[6Alpha,7β(Z(S*))]]-[CAS] | 113812-94-5 135767-36-1 | JP 62209112 | Cephalosporin, oral | Infection, general |
| ceftriaxone | 5-Thia-1-azabicyclo[4.2.0]oct-2-ene-2-carboxylic acid, 7-[[(2-amino-4-thiazolyl)(methoxyimino)acetyl]amino]-8-oxo-3-[[(1,2,5,6-tetrahydro-2-methyl-5,6-dioxo-1,2,4-triazin-3-yl)thio]methyl]-, [6R-[6Alpha,7β(Z)]]-[CAS] | 73384-59-5 74578-69-1 | GB 2022090 | Cephalosporin, injectable | Infection, respiratory tract,lower |
| cefuroxime axetil | 5-Thia-1-azabicyclo[4.2.0]oct-2-ene-2-carboxylic acid, 3-([(aminocarbonyl)oxy]methyl]-7-[(2-furanyl(methoxyimino)acetyl]amino]-8-oxo-, 1-(acetyloxy)ethyl ester, [6R-[6Alpha,7β(Z)]]-[CAS] | 15686-71-2 64544-07-6 | GB 1571683 | Cephalosporin, oral | Infection, respiratory tract, upper |
| cefuroxime | 5-Thia-1-azabicyclo[4.2.0]oct-2-ene-2-carboxylic acid, 3-[[(aminocarbonyl)oxy]methyl]-7-[[2-furanyl(methoxyimino)acetyl]amino]-8-oxo-, [6R-[6Alpha,7β(Z)]]-[CAS] | 55268-75-2 56238-63-2 | GB 1453049 | Cephalosporin, injectable | Infection, general |

TABLE 3-continued

| API Generic Name | API Chemical Name | CAS No. | Patent Reference | Example of Therapeutic Use | Example of Indication |
|---|---|---|---|---|---|
| Cefuzonam | | 82219-78-1 | | | |
| celecoxib | Benzenesulfonamide, 4-(5-(4-methylphenyl)-3-(trifluoromethyl)-1H-pyrazol-1-yl)-[CAS] | 169590-42-5 | U.S. 5,760,068 | Antiarthritic, other | Arthritis, rheumatoid |
| celgosivir | Butanoic acid, octahydro-1,7,8-trihydroxy-6-indolizinyl ester, [1S-(1Alpha,6β,7Alpha,8β,8aβ)]-[CAS] | 121104-96-9 | U.S. 5,017,563 | Antiviral, other | Infection, hepatitis virus, general |
| celiprolol | Urea, N'-[3-acetyl-4-[3-[(1,1-dimethylethyl)amino]-2-hydroxypropoxy]phenyl]-N,N-diethyl-[CAS] | 56980-93-9 57470-78-7 | GB 1441359 | Antihypertensive, adrenergic | Angina, unstable |
| Cellulose Ethyl Hydroxyethyl Ether | | 9004-58-4 | | | |
| Centchroman | | 31477-60-8 | | | |
| CEP-1347 | 9,12-Epoxy-1H-diindolo[1,2,3-fg:3',2',1'-kl]pyrrolo[3,4-i][1,6]benzodiazocine-10-carboxylic acid, 5,16-bis((ethylthio)methyl)-2,3,9,10,11,12-hexahydro-10-hydroxy-9-methyl-1-oxo-, methyl ester, (9S,10R,12R)-[CAS] | 156177-65-0 | WO 9731002 | Antiparkinsonian | Parkinson's disease |
| CEP-701 | 9,12-Epoxy-1H-diindolo[1,2,3-fg:3',2', 1'-kl]pyrrolo[3,4-i][1,6]benzodiazocin-1-one, 2,3,9,10,11,12-hexahydro-10-hydroxy-10-(hydroxymethyl)-9-methyl-, (9S,10S,12R)-[CAS] | 111358-88-4 | | Anticancer, antimetabolite | Cancer, prostate |
| Cephacetrile | | 23239-41-0 | | | |
| Cephaeline | | 483-17-0 | | | |
| Cephalexin | | 15686-71-2 | | | |
| Cephaloglycin | | 3577-1-3 | | | |
| Cephaloridine | | 50-59-9 | | | |
| Cephalosporin C | | 61-24-5 | | | |
| Cephalothin | | 153-61-7 | | | |
| Cephapirin | | 24356-60-3 | | | |
| Cephradine | | 38821-53-3 | | | |
| Cerivastatin | | 145599-86-6 | | | |
| Ceronapril | | 111223-26-8 | | | |
| certoparin | Heparin [CAS] | 9005-49-6 | | Anticoagulant | Thrombosis, venous |
| Ceruletide | | 17650-98-5 | | | |
| Cerviprost | Prosta-5,13-dien-1-oic acid, 11,15-dihydroxy-9-oxo-, (5Z,11Alpha,13E,-15S)-[CAS] | 363-24-6 | | Formulation, dermal, topical | |
| Cetalkonium | | 122-18-9 | | | |
| Cetamolol | | 34919-98-7 | | | |
| Cethexonium | | 1794-74-7 | | | |
| cethromycin | 2H-Oxacyclotetradecino(4,3-d)oxazole-2,6,8,14(1H,7H,9H)-tetrone 4-ethyloctahydro-3a,7,9,11,13,15-hexamethyl-11-((3-(3-quinolinyl)-2-propenyl)oxy)-10-((3,4,6-trideoxy-3-(dimethylamino)-β-D-xylo-hexapyranosyl)oxy)-,(3aS, 4R,7R,9R,10R,11R,13R,15R,15aR)-[CAS] | 205110-48-1 | EP 929563 | Macrolide antibiotic | Infection, respiratory tract, general |
| Cetiedil | | 14176-10-4 | | | |
| Cetirizine | | 83881-51-0 | | | |
| cetirizine | Acetic acid, [2-[4-[(4-chlorophenyl)phenylmethyl]-1-piperazinyl]ethoxy]-, [CAS] | 83881-51-0 83881-52-1 | EP 58146 | Antiallergic, non-asthma | Allergy, general |
| cetirizine + pseudo-ephedrine | Acetic acid, [2-[4-[(4-chlorophenyl)phenylmethyl]-1-piperazinyl]ethoxy]-, dihydrochloride, Benzenemethanol, Alpha-[1-(methylamino)ethyl]-, hydrochloride, [S-(R*R*)]- | 83881-52-1 90-82-4 | | Formulation, optimized, microencapsulate | Allergy, general |
| Cetotiamine | | 137-76-8 | | | |
| Cetoxime | | 25394-78-9 | | | |
| cetraxate | Benzenepropanoic acid, 4-[[[4-(aminomethyl)cyclohexyl]carbonyl]oxy]-, trans-[CAS] | 27724-96-5 34675-84-8 | JP 48075547 | Antiulcer | |
| Cetrimonium | | 57-09-0 | | | |
| Cetrorelix | | 120287-85-6 | | | |
| Cetyldimethyl-ethylammonium | | 124-03-8 | | | |
| Cetylpyridinium | | 123-03-5 | | | |

TABLE 3-continued

| API Generic Name | API Chemical Name | CAS No. | Patent Reference | | Example of Therapeutic Use | Example of Indication |
|---|---|---|---|---|---|---|
| cevimeline | Spiro[1-azabicyclo[2.2.2]octane-3,5'-[1,3]oxathiolane], 2-methyl-, cis-[CAS] | 107220-27-9 107233-08-9 | EP | 205247 | Stomatological | Sjogren's syndrome |
| CG-1521 | 7-phenyl-2,4,6-heptatrienoythydroxamic acid | | | | Anticancer, other | Cancer, general |
| Chaulmoogric Acid | | 29106-32-9 | | | | |
| Chenodiol | | 474-25-9 | | | | |
| CHF-3381 | | | EP | 951465 | Analgesic, other | Pain, neuropathic |
| Chlophedianol | | 791-35-5 | | | | |
| Chloracizine | | 800-22-6 | | | | |
| chloral | 1,1-Ethanediol, 2,2,2-trichloro-[CAS] | 302-17-0 2218-68-0 515-82-2 | | | Formulation, transmucosal, systemic | Insomnia |
| Chlorambucil | | 305-03-3 | | | | |
| Chloramine-B | | 127-52-6 | | | | |
| Chloramine-T | | 127-65-1 | | | | |
| Chloramino-phenamide | | 121-30-2 | | | | |
| Chloramphenicol | | 56-75-7 | | | | |
| Chlorazanil | | 500-42-5 | | | | |
| Chlor-benzoxamine | | 522-18-9 | | | | |
| Chlorbetamide | | 97-27-8 | | | | |
| Chlorcyclizine | | 82-93-9 | | | | |
| Chlordantoin | | 5588-20-5 | | | | |
| Chlordiazepoxide | | 58-25-3 | | | | |
| Chlorguanide | | 500-92-5 | | | | |
| Chlorhexadol | | 3563-58-4 | | | | |
| chlorhexidine | 2,4,11,13-Tetraazatetradecanediimidamide, N,N''-bis(4-chlorophenyl)-3,12-diimino-[CAS] | 55-56-1 | | | Formulation, other | Xerostomia, Periodontitis |
| Chlorisondamine | | 69-27-2 | | | | |
| Chlormadinone | | 302-22-7 | | | | |
| Chlormerodrin | | 62-37-3 | | | | |
| Chlormezanone | | 80-77-3 | | | | |
| Chlormidazole | | 3689-76-7 | | | | |
| Chlornaphazine | | 494-03-1 | | | | |
| Chloroazodin | | 502-98-7 | | | | |
| Chlorophyll | | 1406-65-1 | | | | |
| Chloroprednisone | | 52080-57-6 | | | | |
| Chloroprocaine | | 3858-89-7 | | | | |
| Chloropyramine | | 59-32-5 | | | | |
| Chloroquine | | 54-05-7 | | | | |
| Chlorothen | | 148-65-2 | | | | |
| Chlorothiazide | | 58-94-6 | | | | |
| Chlorotrianisene | | 569-57-3 | | | | |
| Chloroxine | | 773-76-2 | | | | |
| Chloroxylenol | | 88-04-0 | | | | |
| Chlornzotocin | | 54749-90-5 | | | | |
| chlorphenamine | 2-Pyridinepropanamine, Gamma-(4-chlorophenyl)-N,N-dimethyl-[CAS] | 132-22-9 | | | Formulation, modified-release, other | Allergy, general |
| Chlorphenesin | | 104-29-0 886-74-8 | | | | |
| Chlorpheniramine | | 132-22-9 | | | | |
| Chlorphenoxamide | | 3576-64-5 | | | | |
| Chlorphenoxamine | | 77-38-3 | | | | |
| Chlorphentermine | | 461-78-9 | | | | |
| Chlorproethazine | | 84-01-5 | | | | |
| Chlorproguanil | | 537-21-3 | | | | |
| chlorproguanil + dapsone | 4,4'-Sulfonyldianiline + 1-(3,4-Dichlorophenyl)5-isopropylbiguanide | 537-21-3 80-08-0 | | | Antimalarial | Infection, malaria |
| Chlorpromazine | | 50-53-3 | | | | |
| Chlorpropamide | | 94-20-2 | | | | |
| Chlorprothixene | | 113-59-7 | | | | |
| Chlorquinaidol | | 72-80-0 | | | | |
| Chlortetracycline | | 57-62-5 | | | | |
| Chlorthalidone | | 77-36-1 | | | | |
| Chlorthenoxazin(e) | | 132-89-8 | | | | |
| Chlorzoxazone | | 95-25-0 | | | | |

TABLE 3-continued

| API Generic Name | API Chemical Name | CAS No. | Patent Reference | Example of Therapeutic Use | Example of Indication |
|---|---|---|---|---|---|
| Cholic Acid | | 81-25-4 | | | |
| Choline | | 67-48-1 | | | |
| | | 2016-36-6 | | | |
| | | 28319-77-9 | | | |
| choline theophyllinate | Ethanaminium, 2-hydroxy-N,N,N-trimethyl-, salt with 3,7-dihydro-1,3-dimethyl-1H-purine-2,6-dione (1:1) [CAS] | 4499-40-5 | | Formulation, modified-release, other | |
| choline-L-alfoscerate | Ethanaminium, 2-[[(2,3-dihydroxypropoxy)hydroxyphosphinyl]xy]-N,N,N-trimethyl-, hydroxide, inner salt, (R)-[CAS] | 28319-77-9 | JP | 55028955 Cognition enhancer | Amnesia |
| Chromocarb | | 4940-39-0 | | | |
| Chromonar | | 804-10-4 | | | |
| Chrysoidine | | 532-82-1 | | | |
| CHS-828 | Guanidine, N-[6-(4-chlorophenoxy)hexyl]-N'-cyano-N''-4-pyridinyl-[CAS] | 200484-11-3 | U.S. | 5,696,140 Anticancer, other | Cancer, general |
| Ci-1031 | Glycine, N-[2-[5-(aminoiminomethyl)-2-hydroxyphenoxy]-6-[3-(4,5-dihydro-1-methyl-1H-imidazol-2-yl)phenoxy]-3,5-difluoro-4-pyridinyl]-N-methyl-[CAS] | 183305-24-0 | WO | 9638421 Antianginal | Angina, unstable |
| Ci-1040 | Benzamide, 2-[(2-chloro-4-iodophenyl)amino]-N-(cyclopropylmethoxy)-3,4-difluoro-[CAS] | 212631-79-3 | WO | 9837881 Anticancer, other | Cancer, general |
| cibenzoline | 1H-Imidazole, 2-(2,2-diphenylcyclopropyl)-4,5-dihydro-[CAS] | 53267-01-9 | GB | 1417174 Antiarrhythmic | Arrhythmia, general |
| ciclesonide | Pregna-1,4-diene-3,20-dione 16,17-((cyclohexylmethylene)bis(oxy))-11-hydroxy-21-(2-methyl-1-oxopropoxy) (11β,16Alpha) [CAS] | 126544-47-6 | DE | 4129535 Antiasthma | Asthma |
| cicletanine | Furo[3,4-c]pyridin-7-ol, 3-(4-chlorophenyl)-1,3-dihydro-6-methyl-, (+/--)-[CAS] | 82747-56-6 89943-82-8 | U.S. | 4,383,998 Antihypertensive, other | |
| ciclonicate | 3-Pyridinecarboxylic acid, 3,3,5-trimethylcyclohexyl ester, trans-[CAS] | 53449-58-4 | DE | 1910481 Vasodilator, peripheral | Cancer, lung, small cell |
| ciclopirox | 2(1H)-Pyridinone, 6-cyclohexyl-1-hydroxy-4-methyl-, [CAS] | 41621-49-2 29342-05-0 | U.S. | 3,883,545 Antifungal | Infection, fungal, general |
| Ciclosidomine | | 66564-16-7 | | | |
| ciclosporin A | Cyclosporin A-[CAS] | 59865-13-3 | | Formulation, optimized, microemulsion | Transplant rejection, general |
| cidofovir | Phosphonic acid, [[2-(4-amino-2-oxo-1(2H)-pyrimidinyl)-1-(hydroxymethyl)ethoxy]methyl]-, (S)-[CAS] | 113852-37-2 | EP | 253412 Antiviral, other | Infection, cytomegalovirus |
| Cifenline | | 53267-01-9 | | | |
| cilansetron | 4H-Pyrido[3,2,1-jk]carbazol-11(8H)-one, 5,6,9,10-tetrahydro-10-[(2-methyl-1H-imidazol-1-yl)methyl]-, (R)-[CAS] | 120635-74-7 | EP | 297651 GI inflammatory/bowel disorders | Irritable bowel syndrome |
| Cilastatin | | 82009-34-5 | | | |
| cilazapril | 6H-Pyridazino[1,2-a][1,2]diazepine-1-carboxylic acid, 9-[[1-(ethoxycarbonyl)-3-phenylpropyl]amino]octahydro-10-oxo-, [1S-[1Alpha,9Alpha(R*)]]-[CAS] | 88768-40-5 90139-06-3 | GB | 2128984 Antihypertensive, renin system | Hypertension, general |
| cilengitide | Cyclo(L-arginylglycyl-L-Alpha-aspartyl-D-phenylalanyl-N-methyl-L-valyl) [CAS] | 188968-51-6 | EP | 770622 Anticancer, other | Cancer, lung, non-small cell |
| cilnidipine | 3,5-Pyridinedicarboxylic acid, 1,4-dihydro-2,6-dimethyl-4-(3-nitrophenyl)-, 2-methoxyethyl 3-phenyl-2-propenyl ester-[CAS] | 102106-21-8 132203-70-4 | EP | 161877 Antihypertensive, other | Hypertension, general |
| cilomilast | Cis-4-cyano-4-[3-(cyclopentyloxy)-4-methoxyphenyl]cyclohexane-1-carboxylic acid | 153259-65-5 | U.S. | 5,602,157 COPD treatment | Chronic obstructive pulmonary disease |
| cilostazol | 2(1H)-Quinolinone, 6-[4-(1-cyclohexyl-1H-tetrazol-5-yl)butoxy]-3,4-dihydro-[CAS] | 73963-72-1 | GB | 2033893 Antithrombotic | Peripheral vascular disease |
| Cimetidine | | 51481-61-9 | | | |
| cimetropium | 3-Oxa-9-azoniatricyclo[3.3.1.02,4]nonane, 9-(cyclopropylmethyl)-7-(3-hydroxy-1-oxo-2-phenylpropoxy)-9-methyl-, [7(S)-(1Alpha,2β,4β,5Alpha,7β)]-[CAS] | 51598-60-8 | U.S. | 3,853,886 Antispasmodic | Muscle spasm, general |

TABLE 3-continued

| API Generic Name | API Chemical Name | CAS No. | Patent Reference | Example of Therapeutic Use | Example of Indication |
|---|---|---|---|---|---|
| cinacalcet | 1-napthalenemethanamine,Alpha-methyl-N-[3-[3-(trifluoromethyl)phenyl]propyl]-, (AlphaR)-, | 364782-34-3 | | Hormone | Hyperparathyroidism |
| Cinchonidine | | 485-71-2 | | | |
| Cinchonine | | 118-10-5 | | | |
| Cinchophen | | 132-60-5 | | | |
| Cinepazet | | 23887-41-4 | | | |
| Cinepazide | | 23887-46-9 | | | |
| cinepazide | Piperazine, 1-[2-oxo-2-(1-pyrrolidinyl)ethyl]-4-[1-oxo-3-(3,4,5-trimethoxyphenyl)-2-propenyl]-, (Z)-2-butenedioate (1:1) [CAS] | 26328-04-1 | GB | 1218591 Vasodilator, peripheral | Peripheral vascular disease |
| Cinitapride | | 66564-14-5 | | | |
| Cinmetacin | | 20168-99-4 | | | |
| Cinnamedrine | | 90-86-8 | | | |
| Cinnarizine | | 298-57-7 | | | |
| cinolazepam | 1H-1,4-Benzodiazepine-1-propanenitrile, 7-chloro-5-(2-fluorophenyl)-2,3-dihydro-3-hydroxy-2-oxo-[CAS] | 75696-02-5 | DE | 2950235 Hypnotic/Sedative | Insomnia |
| cinoxacin | [1,3]Dioxolo[4,5-g]cinnoline-3-carboxylic acid, 1-ethyl-1,4-dihydro-4-oxo-[CAS] | 28657-80-9 | GB | 1296753 Quinolone antibacterial | Infection, urinary tract |
| Cinoxate | | 104-28-9 | | | |
| Cinromide | | 58473-74-8 | | | |
| Cioteronel | | 89672-11-7 | | | |
| cipamfylline | 1H-Purine-2,6-dione, 8-amino-1,3-bis(cyclopropylmethyl)-3,7-dihydro-[CAS] | 132210-43-6 | EP | 389282 Antipruritic/inflamm, allergic | Eczema, atopic |
| cipralisant | 1H-Imidazole, 4-[(1R,2R)-2-(5,5-dimethyl-1-hexynyl)cyclopropyl]-[CAS] | 213027-19-1 | U.S. | 6,008,240 Psychostimulant | Attention deficit disorder |
| ciprofibrate | Propanoic acid, 2-[4-(2,2-dichlorocyclopropyl)phenoxy]-2-methyl-[CAS] | 52214-84-3 | GB | 1385828 Hypolipaemic/Antiatherosclerosis | Hyperlipidaemia, general |
| ciprofloxacin | 3-Quinolinecarboxylic acid, 1-cyclopropyl-6-fluoro-1,4-dihydro-4-oxo-7-(1-piperazinyl)-[CAS] | 85721-33-1 | U.S. | 4,670,444 Quinolone antibacterial | Infection, general |
| ciprofloxacin + fluocinolone, SAL | 3-Quinolinecarboxylic acid, 1-cyclopropyl-6-fluoro-1,4-dihydro-4-oxo-7-(1-piperazinyl)- + (6Alpha, 11β, 16Alpha)-6,9-Difluoro-11,21-dihydroxy-16,17-[(1-methylethylidene)bis-(oxy)]-pregna-1,4-diene-3,20-dione | | | Formulation, fixed-dose combinations | Otitis |
| Ciramadol | | 63269-31-8 | | | |
| cisapride | Benzamide, 4-amino-5-chloro-N-[1-[3-(4-fluorophenoxy)propyl]-3-methoxy-4-piperidinyl]-2-methoxy-, cis-[CAS] | 81098-60-4 | EP | 76530 Gastroprokinetic | |
| cisatracurium | Isoquinolinium, 2,2'-[1,5-pentanediylbis[oxy(3-oxo-3,1-propanediyl)]]bis[1-[(3,4-dimethoxyphenyl)methyl]]-1,2,3,4-tetrahydro-6,7-dimethoxy-2-methyl-, [1R-[1Alpha,2Alpha(1'R*,2'R*)]]-, [CAS] | 96946-42-8 | U.S. | 5,453,510 Muscle relaxant | Surgery adjunct |
| cispiatin | Platinum, diamminedichloro-, (SP-4-2)-[CAS] | 15663-27-1 | U.S. | 4,177,263 Anticancer, alkylating | |
| citalopram | 5-Isobenzofurancarbonitrile, 1-[3-(dimethylamino)propyl]-1-(4-fluorophenyl)-1,3-dihydro-[CAS] | 59729-32-7 59729-33-8 | GB | 1526331 Antidepressant | Depression, general |
| citicoline | Cytidine 5-(trihydrogen diphosphate), P'-[2-(trimethylammonio)ethyl]ester, hydroxide, inner salt [CAS] | 987-78-0 | JP | 39006541 Cognition enhancer | Infarction, cerebral |
| Citiolone | | 1195-16-0 | | | |
| Citric Acid | | 77-92-9 | | | |
| Citrulline | | 372-75-8 | | | |
| cizolirtine | Ethanamine, N,N-dimethyl-2-[(1-methyl 1H-pyrazol-5-yl)phenylmethoxy]-, 2-hydroxy-1,2,3-propanetricarboxylate [CAS] | 142155-44-0 | | Urological | Incontinence |
| CJ-13610 | 4-(3-[4-(2-Methyl-imidazol-1-yl)-phenylsulfanyl]-phenyl)-tetrahydro-pyran-4-carboxylic acid amide | | | COPD treatment | Chronic obstructive pulmonary disease |

TABLE 3-continued

| API Generic Name | API Chemical Name | CAS No. | Patent Reference | | Example of Therapeutic Use | Example of Indication |
|---|---|---|---|---|---|---|
| CKD-602 | 1H-Pyrano[3',4':6,7]indolizino[1,2-b]quinoline-3,14(4H,12H)-dione, 4-ethyl-4-hydroxy-11-[2-[(1-methylethyl)amino]ethyl]-, monohydrochloride, (4S)-[CAS] | 213819-48-8 | WO | 9902530 | Anticancer, other | Cancer, ovarian |
| cladribine | Adenosine, 2-chloro-2'-deoxy-[CAS] | 4291-63-8 | EP | 173059 | Anticancer, antimetabolite | Cancer, leukaemia, hairy cell |
| Clanobutin | | 30544-61-7 | | | | |
| clarithromycin | Erythromycin, 6-O-methyl-[CAS] | 81103-11-9 | EP | 41355 | Macrolide antibiotic | Infection, respiratory tract, lower |
| Clavulanate, Disodium | | | | | | |
| Clavulanic Acid | | 58001-44-8 | | | | |
| Clebopride | | 55905-53-8 | | | | |
| Clemastine | | 15686-51-8 | | | | |
| Clemizole | | 442-52-4 | | | | |
| Clenbuterol | | 37148-27-9 | | | | |
| Clentiazem | | 96125-53-0 | | | | |
| clevidipine | 3,5-Pyridinedicarboxylic acid, 4-(2,3-dichlorophenyl)-1,4-dihydro-2,6-dimethyl-, methyl (1-oxobutoxy)methyl ester (±) [CAS] | 167221-71-8 | WO | 9512578 | Antihypertensive, other | Hypertension, general |
| clevudine | 2,4(1H,3H)-Pyrimidinedione, 1-(2-deoxy-2-fluoro-β-L-arabinofuranosyl)-5-methyl-[CAS] | 163252-36-6 | | | Antiviral, other | Infection, hepatitis-B virus |
| Clidanac | | 28968-07-2 | | | | |
| Clidinium | | 3485-62-9 | | | | |
| Clinafloxacin | | 105956-97-6 | | | | |
| Clindamycin | | 18323-44-9 | | | | |
| clindamycin + tretinoin | L-threo-Alpha-D-galacto-Octopyranoside, methyl 7-chloro-6,7,8-trideoxy-6-[[(1-methyl-4-propyl-2-pyrrolidinyl)carbonyl]amino]-1-thio-, (2S-trans)- + retinoic acid | | | | Formulation, fixed-dose combinations | Acne |
| clindamycin | L-Threo-Alpha-D-galacto octopyranoside, methyl 7-chloro-6,7,8-trideoxy-6-[[(1-methyl-4-propyl-2-pyrrolidinyl)carbonyl]amino]-1-thio-, 2-(dihydrogen phosphate), (2S-trans)- | 18323-44-9 24729-96-2 | | | Formulation, parenteral, other | Infection, gynaecological |
| Clinofibrate | | 30299-08-2 | | | | |
| Clinprost | | 88931-51-5 | | | | |
| clobazam | 1H-1,5-Benzodiazepine-2,4(3H,5H)-dione, 7-chloro-1-methyl-5-phenyl-[CAS] | 22316-47-8 | GB | 1214662 | Anxiolytic | |
| Clobenfurol | | 3611-72-1 | | | | |
| Clobenoside | | 29899-95-4 | | | | |
| Clobenzepam | | 1159-93-9 | | | | |
| Clobenzorex | | 13364-32-4 | | | | |
| Clobenztropine | | 5627-46-3 | | | | |
| clobetasol | Pregna-1,4-diene-3,20-dione, 21-chloro-9-fluoro-11,17-dihydroxy-16-methyl-, (11β,16β)-[CAS] | 25122-41-2 | | | Formulation, dermal, topical | Psoriasis |
| clobetasone | Pregna-1,4-diene-3,11,20-trione, 21-chloro-9-fluoro-16-methyl-17-(1-oxobutoxy)-, (16β)-[CAS] | 25122-57-0 54063-32-0 | GB | 1253831 | Antipruritic/inflamm, allergic | |
| Clobutinol | | 14860-49-2 | | | | |
| Clocapramine | | 47739-98-0 | | | | |
| Clocinizine | | 298-55-5 | | | | |
| Cloconazole | | 77175-51-0 | | | | |
| Clocortolone | | 4828-27-7 | | | | |
| clodronate | Phosphonic acid, (dichloromethylene)bis-[CAS] | 22560-50-5 | | | Osteoporosis treatment, Anticancer, hormonal | Pain, cancer, Hypercalcaemia of malignancy |
| Clodronic Acid | | 10596-23-3 | | | | |
| clofarabine | 2-chloro-9-(2-deoxy-2-fluoro-β-D-arabinofurasonyl)adenine | | | | Anticancer, antimetabolite | Cancer, leukaemia, chronic lymphocytic |
| clofazimine | 3-(p-chloroanilo)-10-(p-chlorophenyl)-2,10-dihydro-2-(isopropylimino)-phenazine | 2030-63-9 | | | Formulation, optimized, microencapsulate | Infection, tuberculosis |
| Clofenamide | | 671-95-4 | | | | |
| Clofibrate | | 637-07-0 | | | | |
| Clofibric Acid | | 882-09-7 | | | | |

TABLE 3-continued

| API Generic Name | API Chemical Name | CAS No. | Patent Reference | Example of Therapeutic Use | Example of Indication |
|---|---|---|---|---|---|
| Cloflucarban | | 369-77-7 | | | |
| Clofoctol | | 37693-01-9 | | | |
| Cloforex | | 14261-75-7 | | | |
| Clomacran | | 5310-55-4 | | | |
| Clomestrone | | 4091-75-2 | | | |
| Clometacin | | 25803-14-9 | | | |
| Clomethiazole | | 533-45-9 | | | |
| Clometocillin | | 1926-49-4 | | | |
| Clomiphene | | 911-45-5 | | | |
| Clomipramine | | 303-49-1 | | | |
| Clomocycline | | 1181-54-0 | | | |
| clonazepam | 2H-1,4-Benzodiazepin-2-one, 5-(2-chlorophenyl)-1,3-dihydro-7-nitro-[CAS] | 1622-61-3 | U.S. 4,316,897 | Antiepileptic | Epilepsy, general |
| clonidine | 1H-Imidazol-2-amine, N-(2,6-dichlorophenyl)-4,5-dihydro-[CAS] | 4205-90-7 | U.S. 4,060,084 | Formulation, transdermal, patch | Hypertension, general |
| Clonitazene | | 3861-76-5 | | | |
| Clonitrate | | 2612-33-1 | | | |
| Clonixin | | 17737-65-4 | | | |
| Clopamide | | 636-54-4 | | | |
| Clopenthixol | | 982-24-1 | | | |
| Cloperastine | | 3703-76-2 | | | |
| clopidogrel | Thieno[3,2-c]pyridine-5(4H)-acetic acid, Alpha-(2-chlorophenyl)-6,7-dihydro-, methyl ester, (S)-[CAS] | 120202-48-4 90055-48-4 113665-84-2 | EP 99802 | Antithrombotic | Infarction, myocardia |
| Clopirac | | 42779-82-8 | | | |
| Cloprednol | | 5251-34-3 | | | |
| cloranolol | 2-Propanol, 1-(2,5-dichlorophenoxy)-3-[(1,1-dimethylethyl)amino]-[CAS] | 39563-28-5 54247-25-5 | U.S. 4,310,549 | Antihypertensive, adrenergic | |
| Clorazepic Acid | | 23887-31-2 | | | |
| Clorexolone | | 2127-1-7 | | | |
| cloricromene | Acetic acid, [[8-chloro-3-[2-(diethylamino)ethyl]-4-methyl-2-oxo-2H-1-benzopyran-7-yl]oxy]-, ethyl ester [CAS] | 68206-94-0 | U.S. 4,349,566 | Vasodilator, coronary | Peripheral vascular disease |
| Clorindione | | 1146-99-2 | | | |
| Clorprenaline | | 3811-25-4 | | | |
| Clortermine | | 10389-73-8 | | | |
| Clospirazine | | 24527-27-3 | | | |
| Clostebol | | 1093-58-9 | | | |
| Clothiapine | | 2058-52-8 | | | |
| clotiazepam | 2H-Thieno[2,3-e]-1,4-diazepin-2-one, 5-(2-chlorophenyl)-7-ethyl-1,3-dihydro-1-methyl-[CAS] | 33671-46-4 | U.S. 3,849,405 | Anxiolytic | Anxiety, general |
| clotrimazole | 1-[(2-chlorophenyl)diphenylmethyl]-1H-imidazole | 23593-75-1 | U.S. 3,705,172 | Antifungal | |
| clotrimazole + betamethasone | Pregna-1,4-diene-3,20-dione, 9-fluoro-11-hydroxy-16-methyl-17,21-bis(1-oxopropoxy)-, (11β,16β)-, mixt. with 1-[(2-chlorophenyl)diphenylmethyl]-1H-imidazole [CAS] | 92522-91-3 | | Formulation, fixed-dose combinations | Infection, fungal, general |
| Cloxacillin | | 61-72-3 | | | |
| cloxazolam | Oxazolo[3,2-d][1,4]benzodiazepin-6(5H)-one, 10-chloro-11b-(2-chlorophenyl)-2,3,7,11b-tetrahydro-[CAS] | 24166-13-0 | U.S. 3,772,371 | Anxiolytic | |
| Cloxotestosterone | | 53608-96-1 | | | |
| Cloxyquin | | 130-16-5 | | | |
| clozapine | 5H-Dibenzo[b,e] 1,4]diazepine, 8-chloro-11-(4-methyl-1-piperazinyl)-[CAS] | 5786-21-0 | U.S. 3,539,573 | Neuroleptic | Schizophrenia |
| CMI-392 | Trans-2-[3-methoxy-4-(2-p-chlorophenylthio)ethoxy-5-(N-methyl-N'-hydroxyureidyl)methylphenyl]-5-(3,4,5-trimethoxyphenyl)tetrahydrofuran | 193739-23-0 | U.S. 5,648,486 | Antipsoriasis | Psoriasis |
| CMT-3 | 2-Naphthacenecarboxamide, 1,4,4a,5,5a,6,11,12a-octahydro-3,10,12,12a-tetrahydroxy-1,11-dioxo-, (4a5,5aR,12a5)-[CAS] | 15866-90-7 | U.S. 5,837,696 | Anticancer, other | Cancer, sarcoma, Kaposi's |
| CNI-1493 | Decanediamide, N,N-bis[3,5-bis[1-[(aminoiminomethyl)hydrazono]ethyl]phenyl]-, tetrahydrochloride [CAS] | 164301-51-3 | U.S. 5,750,573 | Anti-inflammatory | Psoriasis |

TABLE 3-continued

| API Generic Name | API Chemical Name | CAS No. | Patent Reference | | Example of Therapeutic Use | Example of Indication |
|---|---|---|---|---|---|---|
| CNS-5161 | N-[2-chloro-5-(methylthio)phenyl]-N-methyl-N-[3-(methylthio)phenyl]guanidine [CAS] | 160754-76-7 | WO | 9427591 | Analgesic, other | Pain, neuropathic |
| Cobamamide | | 13870-90-1 | | | | |
| Cocaethylene | | 529-38-4 | | | | |
| Cocaine | | 50-36-2 | | | | |
| Codeine | | 76-57-3 | | | | |
| | | 52-28-8 | | | | |
| CoFactor | 5,10 methylene - tetrahydrofolate | | | | Anticancer, antimetabolite | Cancer, colorectal |
| Colchicine | | 64-86-8 | | | | |
| colesevelam | 1-Hexanaminium, N,N,N-trimethyl-6-(2-propenylamino)-, polymer with (chloromethyl)oxirane, 2-propen-1-amine and N-2-propenyl-1-decanamine, hydrochloride [CAS] | 182815-44-7 | U.S. | 5,607,669 | Hypolipaemic/ Antiatherosclerosis | Hyperlipidaemia, general |
| colestilan | 1H-Imidazole, 2-methyl-, polymer with (chloromethyl)oxirane [CAS] | 95522-45-5 | JP | 59155421 | Hypolipaemic/ Antiatherosclerosis | Hypercholesterol-aemia |
| Colestipol | | 26658-42-4 | | | | |
| colforsin daropate | 6-(3-dimethylaminopropionyl)forskolin- [CAS] | 138605-00-2 | EP | 222413 | Cardiostimulant | Heart failure |
| colfosceril | 3,5,9-Trioxa-4-phosphapentacosan-1-aminium, 4-hydroxy-N,N,N-trimethyl-10 oxo-7-[(1-oxohexadecyl)oxy]-, hydroxide, inner salt, 4-oxide, (R)-[CAS] | 63-89-8 99732-49-7 | U.S. | 4826821 | Lung Surfactant | Respiratory distress syndrome, infant |
| Collagraft | | 138331-02-9 | | | Formulation, implant | Regeneration, bone |
| Colocynthin | | 1398-78-3 | | | | |
| Colpormon | | 1247-71-8 | | | | |
| coluracetam | 1-Pyrrolidineacetamide, 2-oxo-N-(5,6,7,8-tetrahydro-2,3-dimethylfuro[2,3-b]quinolin-4-yl)-[CAS] | 135463-81-9 | EP | 427636 | Cognition enhancer | Alzheimer's disease |
| combretastatin A-4 prodrug | disodium combretastatin-A-4-3-O-phosphate | | | | Anticancer, other | Cancer, thyroid |
| compound B, Pharmacor | | | U.S. | 6,362,165 | Antiviral, anti-HIV | Infection, HIV/AIDS |
| conivaptin | [1,1'-Biphenyl]-2-carboxamide, N-[4-[(4,5-dihydro-2-methylimidazo[4,5-d][1-benzazepin-6(1H)-yl)carbonyl]phenyl]-, [CAS] | 168626-94-6 | WO | 9503305 | GI inflammatory/ bowel disorders | Hyponatraemia |
| Connettivina | Hyaluronic acid [CAS] | 9004-61-9 | | | Vulnerary | |
| Convallatoxin | | 508-75-8 | | | | |
| Coparaffinate | | 8001-60-3 | | | | |
| Corticorelin Ovine Triflutate | | | | | | |
| Corticosterone | | 50-22-6 | | | | |
| Cortisone | | 53-06-5 | | | | |
| Cortivazol | | 1110-40-3 | | | | |
| Cosyntropin | | 16960-16-0 | | | | |
| Cotarnine | | 82-54-2 | | | | |
| Cotinine | | 486-56-6 | | | | |
| co-trimazine | Benzenesulfonamide, 4-amino-N-2-pyrimidinyl-, mixt. with 5-[(3,4,5-trimethoxyphenyl)methyl]-2,4-pyrimidinediamine [CAS] | 39474-58-3 | | | Trimethoprim and analogues | Infection, urinary tract |
| Coumetarol | | 4366-18-1 | | | | |
| CP-248 | 1H-Indene-3-acetamide, 5-fluoro-2-methyl-N-(phenylmethyl)-1-[(3,4,5-trimethoxyphenyl)methylene]-, (1Z)-[CAS] | 200803-37-8 | WO | 9747303 | Anticancer, other | Barrett's oesophagus |
| CP-461 | | | U.S. | 5,948,779 | Anticancer, other | |
| CPC-211 | Acetic acid, dichloro-, sodium salt [CAS] | 2156-56-1 | | | Neuroprotective | Acidosis, lactic |
| CPI-1189 | CPI 1189 [CAS] | 210475-67-5 | WO | 9631462 | Cognition enhancer | Dementia, AIDS-related |
| CRA-0450 | | | WO | 0202549 | Anxiolytic | Unspecified |
| creatinol-O-phosphate | Guanidine, N-methyl-N-[2-(phosphonooxy)ethyl]-[CAS] | 6903-79-3 | | | Antianginal | |
| CRL-5861 | Oxirane, methyl-, polymer with oxirane, block [CAS] | 106392-12-5 | U.S. | 4,837,014 | Antisickling | |
| crobenetine | (2R,6S)-3-[2-(S)-Benzyloxypropyl]-6,11,11-trimethyl-1,2,3,4,5,6,-hexahydro-2,6-methano-3-benzocin-10-ol | | WO | 9914199 | Neuroprotective | Ischaemia, cerebral |

TABLE 3-continued

| API Generic Name | API Chemical Name | CAS No. | Patent Reference | | Example of Therapeutic Use | Example of Indication |
|---|---|---|---|---|---|---|
| croconazole | 1H-Imidazole, 1-[1-[2-[(3-chlorophenyl)methoxy]phenyl]ethenyl]-[CAS] | 77175-51-0 | DE | 3021467 | Antifungal | Infection, funcal, general |
| cromoglicic acid | 4H-1-Benzopyran-2-carboxylic acid, 5,5'-[(2-hydroxy-1,3-propanediyl)bis(oxy)]bs4-oxo-[CAS] | 53736-52-0 | | | Formulation, mucosal, topical | Conjunctivitis |
| cromolyn | 4H-1-Benzopyran-2-carboxylic acid, 5,5'-[(2-hydroxy-1,3-propanediyl)bis(oxy)]bis[4-oxo-, [CAS] | 15826-37-6 16110-51-3 | | | Formulation, inhalable, solution | Asthma |
| Cropropamide | | 633-47-6 | | | | |
| Crotamiton | | 483-63-6 | | | | |
| Crotethamide | | 6168-76-9 | | | | |
| Crystacide | | | U.S. | 4,557,935 | Formulation, dermal, topical | Infection, dermatological |
| CS-502 | ☐ | | EP | 799823 | Analgesic, other | Pain, general |
| CS-758 | 4-[(1E,3E)-4-[trans-5-[[1R,2R)-2-(2,4-difluorophenyl)-2-hydroxy-1-methyl-3-(1H-1,2,4-triazol-1-yl)propyl]thio]-1,3-dioxan-2-yl]-1,3-butadienyl]-3-fluorobenzonitrile | | | | Antifungal | Infection, fungal, general |
| CS-834 | 1-Azabicyclo[3.2.0]hept-2-ene-2-carboxylic acid, 6-[(1R)-1-hydroxyethyl]-4-methyl-7-oxo-3-[[(3R)-5-oxo-3-pyrrolidinyl]thio]-, (2,2-dimethyl-1-oxopropoxy)methyl ester, (4R,5S,6S)-[CAS] | 157542-49-9 | EP | 599512 | Beta-lactam antibiotic | Infection, general |
| CT-052923 | [(2H-benzo[d]1,3-dioxalan-5-methyl)amino][4-(6,7-dimethoxyquinazolin-4-yl)piperazinyl]methane-1-thione | | | | Cardiovascular | Restenosis |
| CT-32228 | N-(4-bromophenyl)-6-(5-chloro-2-methylphenyl)-[1,3,5]triazine-2,4-diamine | | | | Anticancer, other | Cancer, general |
| Cupric Citrate | | 866-82-0 | | | | |
| Cuproxoline | | 13007-93-7 | | | | |
| CVT-2584 | Ethanol, 2,2'-[[6-[[(4-methoxyphenyl)methyl]amino]-9-(1-methylethyl)-9H-purin-2-yl]imino]bis-[CAS] | 199986-75-9 | WO | 9805335 | Cardiovascular | Restenosis |
| CX-659S | ((S)-6-amino-5-(6-hydroxy-2,5,7,8-tetramethylchroman-2-carboxamido)-3-methyl-1-phenyl-2,4-(1H,3H)-pyrmidinedione | | | | Dermatological | Eczema, general |
| Cyacetacide | | 140-87-4 | | | | |
| Cyamemazine | | 3546-03-0 | | | | |
| Cyanidin | | 528-58-5 | | | | |
| CYC400 | | | WO | 00172745 | Anticancer, other | Cancer, general |
| Cyclacillin | | 3485-14-1 | | | | |
| Cyclandelate | | 456-59-7 | | | | |
| Cyclazocine | | 3572-80-3 | | | | |
| Cyclexanone | | 15301-52-7 | | | | |
| Cyclexedrine | | 532-52-5 | | | | |
| cyclidrol | 3-Cyclohexene-1-methanol, 5-hydroxy-Alpha,Alpha,4-trimethyl-[CAS] | 498-71-5 | | | COPD treatment, Respiratory | Bronchitis, chronic |
| cyclin D1 inhibitors | | | U.S. | 6,033,843 | Anticancer, hormonal | Cancer, breast |
| Cyclizine | | 82-92-8 | | | | |
| Cyclobarbital | | 52-31-3 | | | | |
| Cyclobendazole | | 31431-43-3 | | | | |
| cyclobenzaprine | 1-Propanamine, 3-(5H-dibenzo[a,d]cyclohepten-5-ylidene)-N,N-dimethyl-[CAS] | 303-53-7 | | | Formulation, modified-release, other | Muscle spasm, general |
| Cyclobutyrol | | 512-16-3 | | | | |
| Cyclocumarol | | 518-20-7 | | | | |
| Cyclodrine | | 52109-93-0 | | | | |
| Cyclofenil | | 2624-43-3 | | | | |
| Cycloguanil | | 516-21-2 | | | | |
| Cyclomethy-caine | | 139-62-8 | | | | |
| Cyclonium Iodide | | 6577-41-9 | | | | |
| Cyclopent-amine | | 102-45-4 | | | | |
| Cyclopen-thiazide | | 742-20-1 | | | | |

TABLE 3-continued

| API Generic Name | API Chemical Name | CAS No. | Patent Reference | Example of Therapeutic Use | Example of Indication |
|---|---|---|---|---|---|
| Cyclopentobarbital | | 76-68-6 | | | |
| Cyclopentolate | | 512-15-2 | | | |
| cyclophosphamide | N,N-Bis(2-chloroethyl)tetrahydro-2H-1,3,2-oxazaphosphorin-2-amine-2-oxide monohydrate | 50-18-0 6055-19-2 | | Formulation, parenteral, targeted | Cancer, general |
| cyclopiroxalamine | 2(1H)-Pyridinone, 6-cyclohexyl-1-hydroxy-4-methyl-, cmpd with 2-aminoethanol(1:1) [CAS] | 41621-49-2 | | Formulation, transdermal, other | Vaginitis |
| Cycloserine | | 68-41-7 | | | |
| Cyclothiazide | | 2259-96-3 | | | |
| Cyclovalone | | 579-23-7 | | | |
| Cymarin | | 508-77-0 | | | |
| cymserine | Carbamic acid, [4-(1-methylethyl)phenyl]-, (3aS,8aR)-1,2,3,3a,8,8a-hexahydro-1,3a,8-trimethylpyrrolo[2,3-b]indol-5-yl ester [CAS] | 145209-39-8 | WO | 9902154 Cognition enhancer | Alzheimer's disease |
| Cynarin(e) | | 30964-13-7 | | | |
| CYP26 inhibitors | | | U.S. | 6,063,606 Dermatological | Unspecified |
| Cyproheptadine | | 129-03-3 | | | |
| cyproterone | (1β,2β)-6-Chloro-1,2-dihydro-17-hydroxy-3H-cyclopropa[1,2]pregna-1,4,6-triene-3,20-dione [CAS] | 2098-66-0 | | Radio/chemoprotective | Chemotherapy-induced injury, general |
| Cysteamine | | 60-23-1 | | | |
| cystic fibrosis ther | [[4-[[3-[[4-[1-(4-hydroxyphenyl)-1-methyl-ethyl]phenoxy]methyl]phenyl]methoxy]-phenyl]iminomethyl]-, ethyl ester | | | Cystic fibrosis treatment | Cystic fibrosis |
| cytarabine | 2(1H)-Pyrimidinone, 4-amino-1-[5-O-[hydroxy(octadecyloxy)phosphinyl]-β-D-arabinofuranosyl]-, [CAS] | 65093-40-5 147-94-4 | EP | 239015 Anticancer, antimetabolite | Myelodysplastic syndrome |
| D-24851 | N-(Pyridin-4-yl)-(1-(4-chlorobenzyl)-indol-3-yl)-glyoxyl-amide | | | Anticancer, other | Cancer, general |
| D-4418 | 8-Methoxyquinoline-5-[N-(2,5-dichloropyridin-3-yl)]carboxamide | | | Antiasthma | Asthma |
| DA-5018 | Benzeneacetamide, 4-(2-aminoethoxy)-N-(3-(3,4-dimethylphenyl)propyl)-3-methoxy-, monohydrochloride [CAS] | 174661-97-3 | U.S. | 5,242,944 Analgesic, other | Pain, musculoskeletal |
| DA-6034 | | | U.S. | 6,025,387 GI inflammatory/bowel disorders | Crohn's disease |
| DA-7867 | | | KR | 9957803 Antibacterial, other | Infection, general |
| DA-7911 | | | KR | 56034 Antiarthritic, other | Arthritis, rheumatoid |
| DA-8159 | 3-(1-Methyl-7-oxo-3-propyl-6,7-dihydro-1H-pyrazolo-[4,3-d]pyrimidin-5-yl)-N-[2-(1-methylpyrrolidin-2-yl)ethyl]-4-propoxybenzenesulfonamide | | KR | 353014 Male sexual dysfunction, | Sexual dysfunction, male, general |
| Dacarbazine | | 4342-3-4 | | | |
| Daclizumab | | 152923-56-3 | | | |
| Dactinomycin | | 50-76-0 | | | |
| dalbavancin | 5,31-Dichloro-38-de(methoxycarbonyl)-7-demethyl-1 9-deoxy-56-O-[2-deoxy-2-(10-methylundecanamido)-β-D-glucopyranurosyl]-38-[N-[3-(dimethylamino)propyl]carbamoyl]-42-O-Alpha-D-mannopyranosyl-N15-methylristomycin A aglycone | 171500-79-1 | | Peptide antibiotic | Infection, dermatological |
| Dalfopristin | | 112362-50-2 | | | |
| dalfopristin + quinupristin | Virginiamycin M1, 26-((2-(diethylamino)ethyl)sulfonyl)-26,27-dihydro-, (26R,27S)-, mixt with 4-(4-(dimethylamino)-N-methyl-L-phenylalanine)-5-(5-((1-azabicyclo(2.2.2)oct-3-ylthio)methyl)-4-oxo-L-2-pipendinecarboxylic acid) virginiamycin S1-[CAS] | 126602-89-9 | EP | 248703 Antibiotic, other | Infection, respiratory tract, general |
| dalteparin | Heparin-, [CAS] | 9041-08-1 | U.S. | 4,303,651 Anticoagulant | Thromboprophylaxis |
| Daltroban | | 79094-20-5 | | | |
| d-Aminolevulinic Acid | | 106-60-5 | | | |
| danaparoid | | | EP | 66908 Anticoagulant | Thrombosis, venous |
| danazol | Pregna-2,4-dien-20-yno[2,3-d]isoxazol-17-ol, (17Alpha)-[CAS] | 17230-88-5 | GB | 905844 Menstruation disorders | |

TABLE 3-continued

| API Generic Name | API Chemical Name | CAS No. | Patent Reference | Example of Therapeutic Use | Example of Indication |
|---|---|---|---|---|---|
| Danthron | | 117-10-2 | | | |
| Dantrolene | | 7261-97-4 | | | |
| dapiprazole | 1,2,4-Triazolo[4,3-a]pyridine, 5,6,7,8-tetrahydro-3-[2-[4-(2-methylphenyl)-1-piperazinyl]ethyl]-[CAS] | 72822-12-9 72822-13-0 | U.S. | 4,252,721 Ophthalmological | Glaucoma |
| dapivirine | 4-[[4-(2,4,6-trimethylphenyl)amino]pyrimidin-2-yl]amino]benzonitrile | 244767-67-7 | | Antiviral, anti-HIV | Infection, HIV/AIDS |
| dapoxetine | (+)-(S)-N,N-dimethyl-Alpha-[2-(1-naphthyl-oxy)ethyl]benzylamine HCl | 119356-77-3 | EP | 288188 Male sexual dysfunction | Premature ejaculation |
| dapsone | 4,4'-Sulfonyldianiline | 80-08-0 | | Formulation, dermal, topical | Acne |
| daptomycin | Daptomycin [CAS] | 103060-53-3 | EP | 178152 Peptide antibiotic | Infection, dermatological |
| Darbepoetin Alfa | | | | | |
| darifenacin | 3-Pyrrolidineacetamide, 1-[2-(2,3-dihydro-5-benzofuranyl)ethyl]-Alpha,Alpha-diphenyl-, (S)-[CAS] | 133099-04-4 | EP | 388054 Urological | Overactive bladder |
| daunorubicin | 5,12-Naphthacenedione, 8-acetyl-10-[(3-amino-2,3,6-trideoxy-Alpha-L-lyxo-hexopyranosyl)oxy]-7,8,9,10-tetrahydro-6,8,11-trihydroxy-1-methoxy-, (8S-cis)-[CAS] | 20830-81-3 | U.S. | 5,441,745 Formulation, optimized, liposomes | Cancer, sarcoma, Kaposi's |
| DAX, SciClone | 3-diallyl-8-cyclohexylxanthine | | | Cystic fibrosis treatment | Cystic fibrosis |
| DB-67 hydroxy-camptothecin | 7-tert-Butyldimethylsiiyl-10- | | | Anticancer, other | Cancer, general |
| d-Camphocarbo-xylic Acid | | 18530-30-8 | | | |
| DCF-987 | Dextran | | U.S. | 5,514,665 Formulation, other | Cystic fibrosis |
| DDT | | 50-29-3 | | | |
| Deamino-oxytocin | | 113-78-0 | | | |
| Deanol | | 108-01-0 | | | |
| Debrisoquin | | 1131-64-2 | | | |
| Decamethonium | | 541-22-0 | | | |
| Decimemide | | 14817-09-5 | | | |
| decitabine | 1,3,5-Triazin-2(1H)-one, 4-amino-1-(2-deoxy-β-D-erythro-pentofuranosyl)-[CAS] | 23339-46-0 2353-33-5 | | Anticancer, antimetabolite | Myelodysplastic syndrome |
| declopramide | Benzamide, 4-amino-3-chloro-N-(2-(diethylamino)ethyl)-[CAS] | 891-60-1 | WO | 9732582 Anticancer, other | Cancer, colorectal |
| Deferiprone | | 30652-11-0 | | | |
| Deferoxamine | | 70-51-9 | | | |
| deflazacort | 5'H-Pregna-1,4-dieno[17,16-d]oxazole-3,20-dione, 21-(acetyloxy)-11-hydroxy-2'-methyl-, (11β,16β)-[CAS] | 14484-47-0 74712-90-6 | GB | 1077393 Hormone | Asthma |
| Defosfamide | | 3733-81-1 | | | |
| degarelix | N-acetyl-3-(naphtalen-2-yl)-D-alanyl-4-chloro-D-phenylalanyl-3-(pyridin-3-yl)-D-alanyl-L-seryl-4-[[[(4S)-2,6-dioxohexahydropyrimidin-4-yl]carbonyl]amino]-L-phenylalanyl-4-(carbamoylamino)-D-phenylalanyl-L-leucyl-N6-(1-methylethyl)-L-lysyl-L-prolyl-D-alaninamide | 214766-78-6 | | Anticancer, hormonal | Cancer, prostate |
| dehydro-ascorbic acid | L-threo-2,3-Hexodiulosonic acid gamma-lactone | 490-83-5 | | Cognition enhancer | Alzheimer's disease |
| Dehydro-cholic Acid | | 81-23-2 | | | |
| Dehydro-emetine | | 4914-30-1 | | | |
| delapril | Glycine, N-(2,3-dihydro-1H-inden-2-yl)-N-[N-[1-(ethoxycarbonyl)-3-phenylpropyl]-L-alanyl]-, (S)-[CAS] | 83435-66-9 83435-67-0 | EP | 51391 Antihypertensive, renin system | Hypertension, general |
| delapril + manidipine | Glycine, N-(2,3-dihydro-1H-inden-2-yl)-N-[N-[1-(ethoxycarbonyl)-3-phenylpropyl]-L-alanyl]-, (S)-, 3,5-Pyridinedicarboxylic acid, 1,4-dihydro-2,6-dimethyl-4-(3-nitrophenyl)-, 2-[4-(diphenylmethyl)-1-piperazinyl]ethyl methyl ester [CAS] | | FR | 2733911 Formulation, fixed-dose combinations | Hypertension, general |

TABLE 3-continued

| API Generic Name | API Chemical Name | CAS No. | Patent Reference | Example of Therapeutic Use | Example of Indication |
|---|---|---|---|---|---|
| delavirdine | Piperazine, 1-[3-[(1-methylethyl)amino]-2-pyridinyl]-4-[[5-[(methylsulfonyl)amino]-1H-indol-2-yl]carbonyl]-[CAS] | 136817-59-9 | WO 9109849 | Antiviral, anti-HIV | Infection, HIV/AIDS |
| Delmadinane | | 13698-49-2 | | | |
| Delmopinol | | 79874-76-3 | | | |
| delorazepam | 2H-1,4-Benzodiazepin-2-one, 7-chloro-5-(2-chlorophenyl)-1,3-dihydro-[CAS] | 2894-67-9 | CH 408029 | Anxiolytic | |
| delucemine | 3,3-Bis-(m-fluorophenyl)-N-methylpropylamine [CAS] | 186495-99-8 | | Neuroprotective | Ischaemia, cerebral |
| Demanyl | | 6909-62-2 | | | |
| Demecarium | | 56-94-0 | | | |
| demeclocycline | 2-Naphthacenecarboxamide, 7-chloro-4-(dimethylamino)-1,4,4a,5,5a,6,11,12a-octahydro-3,6,10,12,12a-pentahydroxy-1,11-dioxo-, [4S-(4Alpha,4aAlpha,5aAlpha,6a,12aAlpha)]-[CAS] | 127-33-3 | | Formulation, modified-release, <=24 hr | Infection, general |
| Demecolcine | | 477-30-5 | | | |
| Demegestone | | 10116-22-0 | | | |
| Demexiptiline | | 24701-51-7 | | | |
| denaverine | Benzeneacetic acid, Alpha-(2-ethylbutoxy)-Alpha-phenyl-, 2-(dimethylamino)ethyl ester, [CAS] | 3321-06-0 | DE 4133785 | Analgesic, NSAID | Pain, musculoskeletal |
| Denileukin Diftitox | | 173146-27-5 | | | |
| Denopamine | | 71771-90-9 | | | |
| Denopterin | | 22006-84-4 | | | |
| Deoxycholic Acid | | 83-44-3 | | | |
| Deoxycorticosterone | | 64-85-7 56-47-3 | | | |
| Deoxydihydrostreptomycin | | 26086-49-7 | | | |
| Deoxyepinephrine | | 501-15-5 | | | |
| Depreotide | | 161982-62-3 | | | |
| depsipeptide | L-Valine, N-[(3S,4E)-3-hydroxy-7-mercapto-1-oxo-4-heptenyl]-D-valyl-D-cysteinyl-(2Z)-2-amino-2-butenoyl-, (4-1)-lactone, cyclic (1-2)-disulfide [CAS] | 128517-07-7 | EP 352646 | Anticancer, antibiotic | Cancer, general |
| Deptropine | | 604-51-3 | | | |
| Dequalinium | | 522-51-0 | | | |
| dersalazine | Benzoic acid, 2-hydroxy-5-[[4-[3-[4-(2-methyl-1H-imidazol[4,5-c]pyridin-1-yl]methyl]-1-piperidinyl]-3-oxo-1-phenyl-1-propenyl]phenyl]azo] (Z) [CAS] | 188913-57-7 188913-58-8 | U.S. 5,747,477 | Anti-inflammatory | |
| Deserpidine | | 131-01-1 | | | |
| desferrioxamine | Butanediamide, N'-[5-[[4-[[5-(acetylhydroxyamino)pentyl]amino]-1,4-dioxobutyl]hydroxyamino]pentyl]-N-(5-aminopentyl)-N-hydroxy-[CAS] | 70-51-9 | | Antidote | Poisoning, metal |
| Desflurane | | 57041-67-5 | | | |
| Desipramine | | 50-47-5 | | | |
| Deslanoside | | 17598-65-1 | | | |
| desloratadine | 5H-Benzo(5,6)cyclohepta(1,2-b)pyridine, 8-chloro-6, 11-dihydro-11-(4-piperidinylidene)-[CAS] | 100643-71-8 | U.S. 5,595,997 | Antiallergic, non-asthma | Rhinitis, allergic, perennial |
| deslorelin | Luteinizing hormone-releasing factor (pig), 6-D-tryptophan-9-(N-ethyl-L-prolinamide)-10-deglycinamide-[CAS] | 57773-65-6 | U.S. 4,034,082 | Releasing hormone | Cancer, prostate |
| desmopressin | Vasopressin, 1-(3-mercaptopropanoic acid)-8-D-arginine-[CAS] | 16679-58-6 | DE 2948345 | Hormone | Enuresis |
| Desogestrel | | 54024-22-5 | | | |
| desogestrel + estradiol | Estra-1,3,5(10)-triene-3,17-diol (17β)-, mixt. with (17Alpha)-13-ethyl-11-methylene-18,19-dinorpregn-4-en-20-yn-17-ol [CAS] | 122364-17-4 | | Menopausal disorders | Hormone replacement therapy |
| desogestrel, Akzo Nobel | 18,19-Dinorpregn-4-en-20-yn-17-ol, 13-ethyl-11-methylene-, (17Alpha)-[CAS] | 54024-55-5 | | Formulation, oral, other | Contraceptive, female |
| desogestrel + ethinylestrad (1) | 18,19-Dinorpregn-4-en-20-yn-17-ol, 13-ethyl-11-methylene-, (17Alpha)-[CAS] | 54024-22-5 71138-35-7 | U.S. 3,927,046 | Formulation, oral, other | Contraceptive, female |
| Desomorphine | | 427-00-9 | | | |
| Desonide | | 638-94-8 | | | |

TABLE 3-continued

| API Generic Name | API Chemical Name | CAS No. | Patent Reference | Example of Therapeutic Use | Example of Indication |
|---|---|---|---|---|---|
| Desoxi-metasone | | 382-67-2 | | | |
| Detaxtran | | 9015-73-0 | | | |
| Devacade | | | WO 9308176 | Analgesic, other | Pain, general |
| dexamethasone | Pregna-1,4-diene-3,20-dione,9-fluoro-11,17,21-trihydroxy-16-methyl-, (11β,16Alpha)-[CAS] | 50-02-2 2392-39-4 312-93-6 | | Formulation, other | Inflammation, ocular |
| dexanabinol | 6H-Dibenzo[b,d]pyran-9-methanol, 3-(1,1-dimethylheptyl)-6a,7,10,10a-tetrahydro-1-hydroxy-6,6-dimethyl-, (6aS-trans)-[CAS] | 112924-45-5 | EP 427518 | Neuroprotective | Head trauma |
| dexecadotril | Glycine, N-[2-[(acetylthio)methyl]-1-oxo-3-phenylpropyl]-, phenylmethyl ester, (R)-[CAS] | 112573-72-5 | EP 318377 | Alimentary/ Metabolic, other | Unspecified |
| dexefaroxan | 1H-Imidazole, 2-(2-ethyl-2,3-dihydro-2-benzofuranyl)-4,5-dihydro-[CAS] | 89197-00-2 89197-32-0 | EP 71368 | Cognitive enhancer | Alzheimer's disease |
| Dexetimide | | 21888-98-2 | | | |
| dexibuprofen | Benzeneacetic acid, Alpha-methyl-4-(2-methylpropyl)-, (AlphaS)-[CAS] | 51146-56-6 | | Analgesic, NSAID | Pain, general |
| dexketoprofen | Benzeneacetic acid, 3-benzoyl-Alpha-methyl-, (S)-[CAS] | 22161-81-5 | | Anti-inflammatory | Inflammation, general |
| dexloxiglumide | Pentanoic acid, 4-[(3,4-dichlorobenzoyl)amino]-5-[(3-methoxypropyl)pentylamino]-5-oxo-, (R)-[CAS] | 119817-90-2 | EP 0344184 | GI inflammatory/ bowel disorders | Irritable bowel syndrome |
| dexmedeto-midine | 1H-Imidazole, 4-[1-(2,3-dimethylphenyl)ethyl]-, (R)-[CAS] | 113775-47-6 86347-15-1 | EP 187471 | Hypnotic/Sedative | Anaesthesia |
| dexmethyl-phenidate | 2-Piperidineacetic acid, Alpha-phenyl-, methyl ester, (AlphaR,2R)- | 19262-68-1 | | Psychostimulant | Attention deficit disorder |
| Dexpanthenol | | 81-13-0 | | | |
| dexrazoxane | 2,6-Piperazinedione, 4,4'-(1-methyl-1,2-ethanediyl)bis-, (S)-[CAS] | 24584-09-6 | DE 1910283 | Radio/ chemoprotective | Chemotherapy-induced injury, general |
| Dextran-1 | Dextran [CAS] | 9004-54-0 | | Plasma substitute | |
| Dextranomer | | 56087-11-7 | | | |
| Dextroam-phetamine | | 51-64-9 | | | |
| dextro-methorphan | Morphinan, 3-methoxy-17-methyl-, (9Alpha,13Alpha,14Alpha)-, | 6700-34-1 125-71-3 357-56-2 | U.S. 4,221,788 | Formulation, oral, other | Cough, Emotional lability |
| Dextro-moramide | | | | | |
| dextropro-poxyphene | Benzeneethanol, Alpha-[2-(dimethylamino)-1-methylethyl]-Alpha-phenyl-, propanoate (ester), [S-(R,S*)]-[CAS] | 469-62-5 | | Formulation, modified-release, other | Pain, general |
| Dezocine | | 53648-55-8 | | | |
| DF-1012 | N-Tropyl 7-azaindol-3-ylcarboxamide | 163220-65-3 | WO 9504742 | Respiratory | Respiratory disease, general |
| DFA-IV | di-D-fructofuranose 2,6':6,2' dianhydride | | U.S. 5,700,832 | Antianaemic | anaemia, aplastic |
| d-Fenchone | | 4695-62-9 | | | |
| D-Glucurono-lactone | | 32449-92-6 | | | |
| Diab II | Diab II | 309956-85-2 | U.S. 6,153,632 | Antidiabetic | Diabetes, Type II |
| diacerein | 2-Anthracenecarboxylic acid, 4,5-bis(acetyloxy)-9,10-dihydro-9,10-dioxo-[CAS] | 13739-02-1 | U.S. 4,244,968 | Antiarthritic, other | Arthritis, rheumatioid |
| Diampromide | | 552-25-0 | | | |
| Diamthazole | | 136-96-9 | | | |
| Diathy-mosulfone | | 5964-62-5 | | | |
| Diatrizoate | | 737-31-5 | | | |
| diazepam | 2H-1,4-Benzodiazepin-2-one, 7-chloro-1,3-dihydro-1-methyl-5-phenyl-[CAS] | 439-14-5 | | Formulation, transmucosal, systemic | Anxiety, epilepsy, general |
| Diaziquone | | 57998-68-2 | | | |
| Diazoxide | | 364-98-7 | | | |
| dibekacin | D-Streptamine, O-3-amino-3-deoxy-Alpha-D-glucopyranosyl-(1-6)-O-[2,6-diamino-2,3,4,6-tetradeoxy-Alpha-D-erythro-hexopyranosyl-(1-4)]-2-deoxy-, sulfate (salt)[CAS] | 34493-98-6 58580-55-5 | GB 1349302 | Aminoglycoside antibiotic | Infection, general |
| Dibenzepin | | 4498-32-2 | | | |
| Dibromo-propamidine | | 496-00-4 | | | |

TABLE 3-continued

| API Generic Name | API Chemical Name | CAS No. | Patent Reference | Example of Therapeutic Use | Example of Indication |
|---|---|---|---|---|---|
| Dibucaine | | 61-12-1 | | | |
| Dichloral-phenazone | | 480-30-8 | | | |
| Dichlor-amine T | | 473-34-7 | | | |
| Dichlorisone | | 7008-26-6 | | | |
| Dichloro-benzyl Alcohol | | 1777-82-8 | | | |
| Dichlorophen | | 97-23-4 | | | |
| Dichloro-phenarsine | | 536-29-8 | | | |
| Dichlorphen-amide | | 120-97-8 | | | |
| diclofenac + HA | Hyaluronic acid + benzeneacetic acid, 2-[(2,6-dichlorophenyl)amino]-[CAS] | | | Formulation, transdermal, systemic | Keratosis |
| diclofenac | Benzeneacetic acid, 2-[(2,6-dichlorophenyl)amino]-, [CAS] | 15307-79-6 15307-86-5 15307-81-0 | | Formulation, modified-release, <=24 hr | Pain, general |
| Dicloxacillin | | 3116-76-5 | | | |
| Dicumarol | | 66-76-2 | | | |
| Dicyclomine | | 77-19-0 | | | |
| didanosine | Inosine, 2',3'-dideoxy-[CAS] | 69655-05-6 | U.S. 4,861,759 | Antiviral, anti-HIV | Infection, HIV/AIDS |
| Dideoxy-adenosine | | 4097-22-7 | | | |
| didox | Benzamide, N,3,4-trihydroxy-[CAS] | 69839-83-4 | U.S. 4,263,322 | Anticancer, antimetabolite | Cancer, general |
| Dienestrol | | 84-17-3 | | | |
| dienogest | 19-Norpregna-4,9-diene-21-nitrile, 17-hydroxy-3-oxo-, (17Alpha)-[CAS] | 65928-58-7 | GB 1524917 | Menstruation disorders | Endometriosis |
| dienogest + estradiol | 19-Norpregna-4,9-diene-21-nitrile, 17-hydroxy-3-oxo-,(17Alpha) + Estra-1,3,5(10)-triene-3,17-diol(17β) | | | Formulation, fixed-dose combinations | Contraceptive, female |
| Diethadione | | 702-54-5 | | | |
| Diethazine | | 60-91-3 | | | |
| Diethylbromo-acetamide | | 511-70-6 | | | |
| Diethyl-carbamazine | | 90-89-1 | | | |
| diethyl-propion | 1-Propanone, 2-(diethylamino)-1-phenyl-[CAS] | 90-84-6 | | Formulation, modified-release, <=24 hr | Obesity |
| Diethyl-stilbestrol | | 56-53-1 | | | |
| Difemerine | | 80387-96-8 | | | |
| Difenamizole | | 20170-20-1 | | | |
| Difenoxin | | 28782-42-5 | | | |
| Difenpiramide | | 51484-40-3 | | | |
| diflomotecan | (5R)-5-Ethyl-9,10-difluoro-1,4,5,13-tetrahydro-5-hydroxy-3H,15H-oxepino[3',4':6,]indolizino[1,2-b]quinoline-3,15-dione | 220997-97-7 | | Anticancer, other | Cancer, general |
| diflorasone | Pregna-1,4-diene-3,20-dione, 17,21-bis(acetyloxy)-6,9-difluoro-11-hydroxy-16-methyl-, (6Alpha,11β,16β)-[CAS] | 33564-31-7 2557-49-5 | U.S. 3,980,778 | Antipsoriasis | |
| Difloxacin | | 98106-17-3 | | | |
| Diflucortolone | | 2607-6-9 | | | |
| diflunisal | 2',4'-difluoro-4-hydroxy[1,1'-biphenyl]-3-carboxylic acid | 23674-86-4 22494-42-4 | GB 1175212 | Analgesic, NSAID | Pain, post operative |
| Difluprednate | | 23674-86-4 | | | |
| Digitalin | | 752-61-4 | | | |
| Digitoxin | | 71-63-6 | | | |
| digoxin | Card-20(22)-enolide, 3-[(O-2,6-dideoxy-β-D-ribo-hexopyranosyl-(1-4)-O-2,6-dideoxy-β-D-ribo-hexopyranosyl-(1-4)-2,6-dideoxy-β-D-ribo-hexopyranosyl)oxy]-12,14-dihydroxy-, (3β,5β,12β)-[CAS] | 20830-75-5 | U.S. 4,088,750 | Formulation, oral, enteric-coated | Heart failure |
| Dihexy-verine | | 561-77-3 | | | |
| Dihydral-azine | | 484-23-1 | | | |
| Dihydro-codeine | | 125-28-0 | | | |

TABLE 3-continued

| API Generic Name | API Chemical Name | CAS No. | Patent Reference | Example of Therapeutic Use | Example of Indication |
|---|---|---|---|---|---|
| Dihydro-codeinone | | 466-90-0 | | | |
| Enol dihydroergocryptine | Ergocryptine, dihydro-[CAS] | 25447-66-9 | | Formulation, other | Depression, general |
| dihydroer-gotamine | Ergotaman-3',6', 18-trione, 9,10-dihydro 12'-hydroxy-2'-methyl-5'-(phenylmethyl)-, (5'Alpha, 10Alpha)-[CAS] | 511-12-6 | | 6495535 Formulation, modified-release, other | Migraine |
| Dihydro-morphine | | 509-60-4 | | | |
| Dihydrostre-ptomycin | | 128-46-1 | | | |
| Dihydrota-chysterol | | 67-96-9 | | | |
| Dihydroxy-aluminum | | 13682-92-3 | | | |
| | | 539-68-4 | | | |
| Diisopromine | | 5966-41-6 | | | |
| Diisopropyl Paraoxon | | 3254-66-8 | | | |
| Diisapropyl-amine | | 660-27-5 | | | |
| dilazep | Benzoic acid, 3,4,5-trimethoxy-, (tetrahydro-1H-1,4-diazepine-1,4(5H)-diyl)di-3,1-propanediyt ester [CAS] | 35898-87-4 | JP | 51095086 Vasodilator, coronary | |
| Dilevalol | | 75659-07-3 | | | |
| diloxanide | 2-Furancarboxylic acid, 4-[(dichloroacetyl)methylamino]phenyl ester [CAS] | 3736-81-0 579-38-4 | | Amoebicide | |
| diltiazem | 1,5-Benzothiazepin-4(5H)-one, 3-(acetyloxy)-5-[2-(dimethylamino)ethyl]-2,3-dihydro-2-(4-methoxyphenyl)-, (2S-cis)-[CAS] | 33286-22-5 42399-41-7 | U.S. U.S. EP | 4,721,619 Antianginal 5,529,791 322277 | Angina, hypertension, general |
| Dimecrotic Acid | | 7706-67-4 | | | |
| Dim efline | | 1165-48-6 | | | |
| Dimemorfan | | 36309-01-0 | | | |
| Dimenhydrinate | | 523-87-5 | | | |
| Dimenoxadol | | 509-78-4 | | | |
| Dimepheptanol | | 545-90-4 | | | |
| Dimercaprol | | 59-52-9 | | | |
| Dimetacrine | | 4757-55-5 | | | |
| Dimethadione | | 695-53-4 | | | |
| Dimethazan | | 519-30-2 | | | |
| Dimethindene | | 5636-83-9 | | | |
| Dimethisoquin | | 86-80-6 | | | |
| Dimethisterone | | 79-64-1 | | | |
| Dimethocaine | | 94-15-5 | | | |
| Dimethoxanate | | 477-93-0 | | | |
| Dimethyl Sulfoxide | | 67-68-5 | | | |
| Dimethyl-thiambutene | | 524-84-5 | | | |
| Dimetofrine | | 22950-29-4 | | | |
| Dimorphol-amine | | 119-48-2 | | | |
| dinoprostone | Prosta-5,13-dien-1-oic acid, 11,15-dihydroxy-9-oxa-, (5Z, 11 Alpha, 13E, 155)-[CAS] | 363-24-6 | | Formulation, modified-release, <=24 hr | Labour, induction |
| diosmectite | Smecta-[CAS] | 110070-78-5 | FR | 2770778 Antidiarrhoeal | Diarrhoea, general |
| diosmin | 4H-1-Benzopyran-4-one, 7-[[6-O-(6-deoxy-Alpha-L-mannopyranosyl)-.beta.-D-glucopyranosyl]oxy]-5-hydroxy-2-(3-hydroxy-4-methoxyphenyl)-. [CAS] | 520-27-4 | DE | 2602314 Vasoprotect, systemic | |
| Dioxadrol | | 6495-46-1 | | | |
| Dioxaphetyl | | 467-86-7 | | | |
| Dioxethedmne | | 497-75-6 | | | |
| Dioxybenzone | | 131-53-3 | | | |
| Diphemanil | | 62-97-5 | | | |
| Diphenadione | | 82-66-6 | | | |
| Diphencyprone | | 886-38-4 | | | |
| Diphenhydramine | | 58-73-1 | | | |
| Diphenidol | | 972-02-1 | | | |
| Diphenoxylate | | 915-30-0 | | | |
| Diphenylpyraline | | 147-20-6 | | | |

TABLE 3-continued

| API Generic Name | API Chemical Name | CAS No. | Patent Reference | | Example of Therapeutic Use | Example of Indication |
|---|---|---|---|---|---|---|
| Diphetarsone | | 515-76-4 | | | | |
| Diphtheria & Tetanus Toxoids And Acellular Pertussis Vaccine Adsorbed | | | | | | |
| Dipipanone | | 467-83-4 | | | | |
| dipivefrin | Propanoic acid, 2,2-dimethyl-, 4-[1-hydroxy-2-(methylamino)ethyl]-1,2-phenylene ester, (+/−)-[CAS] | 52365-63-6 | U.S. | 3,809,714 | Antiglaucoma | Glaucoma |
| Dipyridamole | | 58-32-2 | | | | |
| Dipyrocetyl | | 486-79-3 | | | | |
| Dipyrone | | 5907-38-0 | | | | |
| diquafosol | Uridine 5'-(pentahydrogen tetraphosphate)-5'-ester with uridine, [CAS] | 211427-08-6 | | | Ophthalmological | Dry eye syndrome |
| dirithromycin | Erythromycin, 9-deoxo-11-deoxy-9,11-[imino[2-(2-methoxyethoxy)ethylidene]oxy]-, [9S(R)]-[CAS] | 62013-04-1 | DE | 2515075 | Macrolide antibiotic | Tonsillitis |
| disodium pamidronate | Phosphonic acid, (3-amino-1-hydroxypropylidene)bis-, disodium salt [CAS] | 57248-88-1 | EP | 177443 | Osteoporosis treatment | Hypercalcaemia of malignancy |
| Disofenin | | 65717-97-7 | | | | |
| disopyramide | 2-Pyridineacetamide, Alpha-[2-[bis(1-methylethyl)amino]ethyl]-Alpha-phenyl-[CAS] | 3737-09-5 | | | Formulation, modified-release, <=24 hr | Arrythmia, general |
| Dastigmine | | 15876-67-2 | | | | |
| Disulfamide | | 671-88-5 | | | | |
| Disulfiram | | 97-77-8 | | | | |
| Ditazol | | 18471-20-0 | | | | |
| Dithiazanine | | 514-73-8 | | | | |
| dithranol | 9(10H)-Anthracenone, 1,8-dihydroxy-[CAS] | 1143-38-0 | | | Formulation, dermal, topical | Psoriasis |
| Ditiocarb | | 148-18-5 | | | | |
| Dixanthogen | | 502-55-6 | | | | |
| Dixyrazine | | 2470-73-7. | | | | |
| DJ-927 | | | WO | 01027115 | Anticancer, other | Cancer, general |
| DK-507k | (−)-7-[(7S)-7-Amino-5-azaspiro[2,4]heptan-5-yl]-6-fluoro-1-[(1R,2S)-2-fluoro-1-cyclopropyl]-1,4-dihydro-8-methoxy-4-oxo-3-quinolinecarboxylic acid hydrochloride monohydrate | | | | Quinolone antibacterial | Infection, general |
| DL-Lactic Acid | | 598-82-3 | | | | |
| DMDC | Cytidine, 2'-deoxy-2'-methylene-, monohydrochloride [CAS] | 113648-25-2 | WO | 8807049 | Anticancer, antimetabolite | Cancer, general |
| DMXAA | 5,6-dimethylxanthenone-4-acetic acid | | | | Anticancer, other | Cancer, lung, general |
| DNA Stealth Nucleosides | | | U.S. | 6,132,776 | Antiviral, anti-HIV | Infection, HIV/AIDS |
| Dobesilate | | 20123-80-2 | | | | |
| dobutamine | 1,2-Benzenediol, 4-[2-[[3-(4-hydroxyphenyl)-1-methylpropyl]amino]ethyl]-, (+/−)-[CAS] | 34368-04-2 49745-95-1 | U.S. | 3,987,200 | Cardiostimulant | |
| Docarpamine | | 74639-40-0 | | | | |
| docetaxel | (2R,3S)-N-Carboxy-3-phenylisoserine, N-tert-butyl ester, 13-ester with 5β,20-epoxy-1,2Alpha,4,7β, 10β, 13Alpha-hexahydroxytax-11-en-9-one 4-acetate 2-benzoate-[CAS] | 114977-28-5 148408-66-6 | EP | 253738 | Anticancer, other | Cancer, breast |
| docosahexaenoic acid | | | EP | 707487 | Hypolipaemic/ Antiatherosclerosis | Hyperlipidaemia, general |
| docosanol | 1-Docosanol [CAS] | 661-19-8 | EP | 469064 | Antiviral, other | Infection, herpes simplex virus |
| docusate | | 128-49-4 577-11-7 | U.S. | 4,752,617 | Formulation, derm | Infection, herpes simplex virus prophylaxis |
| dofetilide | Methanesulfonamide, N-[4-[2-[methyl[2-[4-[(methylsulfonyl)amino]phenoxy]ethyl]amino]ethyl]phenyq-[CAS] | 115256-11-6 | EP | 245997 | Antiarrhythmic | Fibrillation, atrial |

TABLE 3-continued

| API Generic Name | API Chemical Name | CAS No. | Patent Reference | | Example of Therapeutic Use | Example of Indication |
|---|---|---|---|---|---|---|
| dolasetron mesilate | 1H-lndole-3-carboxylic acid, octahydro-3-oxo-2,6-methano-2H-quinolizin-8-yl ester, (2Alpha,6Alpha,8Alpha,9Alphaβ)-, monomethanesulfonate-[CAS] | 115956-13-3 115956-12-2 | EP | 266730 | Antiemetic | Chemotherapy-induced nausea and vomiting |
| Domiodoi | | 61869-07-6 | | | | |
| Domiphen | | 538-71-6 | | | | |
| Domitroban | | 112966-96-8 | | | | |
| domperidone | 2H-Benzimidazol-2-one, 5-chloro-1-[1-[3-(2,3-dihydro-2-oxo-1H-benzimidazol-1-yl)propyl]-4-piperidinyl]-1,3-dihydro-[CAS] | 57808-66-9 | U.S. | 4,066,772 | Antiemetic | |
| donepezil | 1H-Inden-1-one, 2,3-dihydro-5,6-dimethoxy-2-((1-(phenylmethyl)-4-piperidinyl)methyl)-, [CAS] | 120011-70-3 120014-06-4 | EP | 296560 | Cognition enhance | Alzheimer's disease |
| donitriptan | Piperazine, 1-(((3-(2-aminoethyl)-1H-indol-5-yl)oxy)acetyl)-4-(4-cyanophenyl)-[CAS] | 170912-52-4 | | | Antimigraine | Migraine |
| Dopamine | | 51-61-6 | | | | |
| Dopexamine | | 86197-47-9 | | | | |
| doramapimod | urea, N-[3-(1,1-dimethylethyl)-1-(4-methylphenyl)-1H-pyrazol-5-yl]-N'-[4-[2-(4-morpholinyl)ethoxy]-1-napthalenyl] | 285983-48-4 | | | Antiarthritic, immunological | Arthritis, rheumatoid |
| doranidazole | (±)-1,2,4-Butanetriol, 3-((2-nitro-1H-imidazol-1-yl)methoxy)-[CAS] | 137339-64-1 | WO | 9414778 | Radio/chemosensitizer | Surgery adjunct |
| doripenem | (1R,5S,6S)-2-[(3S,5S)-5-(sulfamoylaminomethyl)pyrrolidin-3-yl]thio-6-[(1R)-1-hydroxyethyl]-1-methylcarbapen-2-em-3-carboxylic acid | 148016-81-3 | EP | 528678 | Beta-lactam antibiotic | Infection, urinary tract |
| darzolamide | 4H-Thieno(2,3-b)thiopyran-2-sulfonamide, 4-(ethylamino)-5,6-dihydro-6-methyl-,7,7-dioxide (4S-trans)-[CAS] | 120279-96-1 | EP | 296879 | Antiglaucoma | Glaucoma |
| dorzolamide + timolol | 4H-Thieno(2,3-b)thiopyran-2-sulfonamide, 4-(ethylamino)-5,6-dihydro-6-methyl-7,7-dioxide (45-trans) + ethyl 2-propanol, 1-[(1,1-dimethyl)amino]-3-[[4-(4-morpholinyl)-1,2,5-thiadiazol-3-yl]oxy]-, (5), (Z)-2-butenedioate (1:1) (salt) [CAS] | 120279-96-1 26839-75-8 26921-17-5 | | | Formulation, fixed-dose combinations | Glaucoma |
| dosmalfate | Aluminium, (µ7-(7-((6-O-(6-deoxy-2,3,4-tri-O-sulfo-Alpha-L-mannosylpyranosyl)-2,3,4-tri-O-sulfo-β-D-glucopyranosyl)oxy)-5-hydroxy-2-(4-methoxy-3-(sulfooxy)phenyl-4H-1-benzopyran-4-onato(7-)))tetradeca-µ-hydroxyheneicosahydroxytetradeca-[CAS] | 122312-55-4 | | | Antiulcer | Ulcer, gastric |
| dosulepine | 1-Propanamine, 3-dibenzo[b,e]thiepin-11(6H)-ylidene-N,N-dimethyl-[CAS] | 113-53-1 | | | Antidepressant | |
| Dotarizine | | 84625-59-2 | | | | |
| Dothiepin | | 113-53-1 | | | | |
| Doxacurium | | 106819-53-8 | | | | |
| Doxapram | | 309-29-5 | | | | |
| doxazosin | Piperazine, 1-(4-amino-6,7-dimethoxy-2-quinazolinyl)-4-[(2,3-dihydro-1 4-benzodioxin-2-yl)carbonyl]-[CAS] | 74191-85-8 | GB | 2007656 | Antihypertensive, adrenergic | Hypertension, general |
| Doxefazepam | | 40762-15-0 | | | | |
| Doxenitoin | | 3254-93-1 | | | | |
| doxepin | 1-Propanamine, 3-dibenz[b,e]oxepin-11(6H)-ylidene-N,N-dimethyl- | 1668-19-5 | | | Formulation, dermal, topical | Pruritus |
| doxercalciferol | 9,10-secoergosta-5,7,10(19),22-tetraene-1,3-diol (1Alpha, 3β, 5Z, 7E, 22E) [CAS] | 54573-75-0 | U.S. | 5,104,854 | Hormone | Hyperpara-thyroidism |
| doxifluridine | Uridine, 5'-deoxy-5-fluoro-[CAS] | 3094-09-5 | U.S. | 4,071,680 | Anticancer, antimetabolite | Cancer, colorectal |
| doxofylline | 1H-Purine-2,6-dione, 7-(1,3-dioxolan-2-ylmethyl)-3,7-dihydro-1,3-dimethyl-[CAS] | 69975-86-6 | U.S. | 4,187,308 | Antiasthma | Asthma |
| doxorubicin | 5,12-Naphthacenedione, 10-[(3-amino-2,3,6-trideoxy-Alpha-L-Iyxo-hexopyranosyl)oxy]-7,8,9,10-tetrahydro 6,8,11-trihydroxy-8-(hydroxyacetyl)-1-methoxy-, (8S-cis)-[CAS] | 23214-92-8 | EP | 191824 | Formulation, optimized, liposomes | Cancer, general |

TABLE 3-continued

| API Generic Name | API Chemical Name | CAS No. | Patent Reference | Example of Therapeutic Use | Example of Indication |
|---|---|---|---|---|---|
| doxycycline | 2-Naphthacenecarboxamine, 4-(dimethylamino)-1,4,4a,5,5a,6,11,12a-octahydro-3,5,10,12,12a-pentahydroxy-6-methyl-1,11-dioxo-[4S-(4Alpha,4aAlpha,5Alpha,5aAlpha,6Alpha,12aAlpha)]-[CAS] | 564-25-0 17086-28-1 | | Formulation, modified-release, immediate | Periodontitis |
| doxylamine | N,N-Dimethyl-2-[1-phenyl-1-(2-pyridinyl)ethoxy]ethanamine | 469-21-6 | | Formulation, transmucosal systemic | Rhinitis, allergic, general |
| DPC-817 | β-D-2',3'-didehydro-2',3'-dideoxy-5-fluorocytidine | | | Antiviral, anti-HIV | Infection, HIV/AIDS |
| DPI-3290 | | | U.S. 5,681,830 | Analgesic, other | Pain, general |
| DQ-113 | 5-Amino-7-[(3S,4R)-(1-aminocyclopropyl)-3-fluoropyrrolidin-1-yl]-1-[(1R,2S)-2-fluoro-1-cyclopropyl]-1,4-dihydro-8-methyl-4-oxo-3-quinolinecarboxylic acid | | | Quinolone antibacterial | Infection, general |
| Drofenine | | 1679-76-1 | | | |
| Droloxifene | | 82413-20-5 | | | |
| Drometrizole | | 2440-22-4 | | | |
| Dromo-stanolone | | 58-19-5 | | | |
| dronabinol | 6H-Dibenzo[b,d]pyran-1-ol, 6a,7,8,10a-tetrahydro-6,6,9-trimethyl-3-pentyl-, (6aR-trans)-[CAS] | 1972-08-3 | | Antiemetic | Chemotherapy-induced nausea and vomiting |
| dronedarone | 2-n-Butyl 3-[4-(3-di-n-butylamino-propoxy)benzoyl]5-methylsulfonamidobenzofuran | | | Antiarrhythmic | Arrhythmia, general |
| Droperidol | | 548-73-2 | | | |
| Droprenilamine | | 57653-27-7 | | | |
| Dropropizine | | 17692-31-8 | | | |
| Drospirenone | | 67392-87-4 | | | |
| Drotaverine | | 14009-24-6 | | | |
| Drotebanol | | 03/02/3176 | | | |
| droxicam | 2H,5H-1,3-Oxazino[5,6-c][1,2]benzothiazine-2,4(3H)-dione, 5-methyl-3-(2-pyridinyl)-, 6,6-dioxide [CAS] | 90101-16-9 | EP 99770 | Anti-inflammatory | Inflammation, general |
| droxidopa | L-Tyrosine, β,3-dihydroxy-, threo-[CAS] | 23651-95-8 | EP 128684 | Antiparkinsonian | Parkinson's disease |
| Droxidopa | | 23651-95-8 | | | |
| DU-125530 | 1,2-Benzisothiazol-3(2H)-one, 2-[4-[4-(7-chloro-2,3-dihydro-1,4-benzodioxin-5-yl)-1-piperazinyl]butyl]-, 1,1-dioxide [CAS] | 161611-99-0 | EP 633260 | Anxiolytic | Anxiety, general |
| duloxetine | 2-Thiophenepropanamine, N-methyl-Gamma-(1-naphthalenyloxy)-, hydrochloride, (S)-[CAS] | 136434-34-9 116539-59-4 | U.S. 5,362,886 | Antidepressant | Depression, general |
| duramycin | | | WO 9428726 | Formulation, inhalable, solution | Cystic fibrosis |
| Durapatite | | 1306-06-5 | | | |
| dutasteride | 4-Azaandrost-1-ene-17-carboxamide, N-(2,5-bis(trifluoromethyl)phenyl)-3-oxo-, (5Alpha,17β)-[CAS] | 164656-23-9 | U.S. 5,565,467 | Prostate disoders | Benign prostatic hyperplasia |
| DW-1141 | N,N-diisopropyl-4-[4-(3-aminobenzo[d]isoxazol-6-yloxy)butoxy]-3-methoxybenzamide | | | Osteoporosis treatment | Osteoporosis |
| DW-286a | (R)-(−)-7-((4-aminomethyl-4-methyl-3-(Z)-methyloxyimino)pyrrolidin-1-yl)-1-cyclopropyl-6-fluoro-4-oxo-1,4-dihydro[1,8]naphthyridine-3-carboxylic acid | | | Quinolone antibacterial | Infection, general |
| DW-471 | | | U.S. 5,922,871 | Antiviral, other | Infection, hepatitis-B virus |
| DX-9065a | 2-Naphthalenepropanoic acid, 7-(aminoiminomethyl)-Alpha-[4-[[1-(1-iminoethyl)-3-pyrrolidinyl]oxy]phenyl]-, monohydrochloride, pentahydrate, (S-(R*,R*)]-[CAS] | 155204-81-2 | | Antithrombotic | Thrombosis |
| DY-9760e | 1H-Indazole, 3-[2-[4-(3-chloro-2-methylphenyl)-1-piperazinyl]ethyl]-1-(1H-imidazol-4-ylmethyl)-5,6-dimethoxy [CAS] | 160522-00-9 | U.S. 5,681,954 | Neuroprotective | Ischaemia, cerebral |
| Dyclonine | | 586-60-7 | | | |
| Dydrogesterone | | 152-62-5 | | | |
| Dymanthine | | 124-28-7 | | | |
| Dyphylline | | 479-18-5 | | | |

TABLE 3-continued

| API Generic Name | API Chemical Name | CAS No. | Patent Reference | Example of Therapeutic Use | Example of Indication |
|---|---|---|---|---|---|
| E-1010 | 1-Azabicyclo[3.2.0]hept-2-ene-2-cerboxylic acid, 6-[(1R)-1-hydroxyethyl]-3-[((3S,5S)-5-[(R)-hydroxy(3R)-3-pyrrolidinylmethyl]-3-pyrrolidinyl]thio]-4-methyl-7-oxo-, monohydrochionde, (4R,5S,6S)-[CAS] | 186319-97-1 | | Beta-lactam antibiotic | Infection, general |
| E-2101 | N-Ethyl-(1-[1-(2-fluorophenethyl)pipendin-4-yl]-1H-indol-6-yl)acetamide | | | Muscle relaxant | Muscle spasm, general |
| E2F antagonists | | | WO | 9606943 Anticancer, other | Cancer, general |
| E-3620 | Benzamide, 4-amino-5-chloro-N-(8-methyl-8-azabicyclo[3.2.1]oct-3-yl)-2-[(1-methyl-2-butynyl)oxy]-, monohydrochloride, [3(S)-endo]-. [CAS] | 151213-86-4 | EP | 554794 Antacid/Antiflatulent | Dyspepsia |
| E-5564 | Alpha-D-Glucopyranose, 3-O-decyl-2-deoxy-6-O-(2-deoxy-3-O-((3R)-3-methoxydecyl)-6-O-methyl-2-(((11Z)-1-oxo-11-octadecenyl)amino)-4-O-phosphono-β-D-glucopyranosyl)-2-((1,3-dioxotetradecyl)amino)-1-(dihydrogen phosphate), tetrasodium salt [CAS] | 185954-98-7 | EP | 536969 Septic shock treatment | Sepsis |
| E-5842 | Pyridine, 4-(4-fluorophenyl)-1,2,3,6-tetrahydro-1-[4-(1H-1,2,4-triazol-1-yl)butyl]-, 2-hydroxy-1,2,3-propanetncarboxylate (1:1) [CAS] | 220120-14-9 | | Neuroleptic | Schizophrenia |
| E-6259 | 1-(4-Aminosulfonylphenyl)-5-(2,4-difluorophenyl)-4,5-dihydro-3-trifluoromethyl-1-H-pyrazole | | | Antiarthritic, other | Unspecified |
| EAA-90 | [2-(8,9-Dioxo-2,6-diazabicyclo[5.2.0]non-1(7)-en-2-yl)-ethyl]phosphonic acid | | | Analgesic, other | Pain, neuropathic |
| e-Acetamido-caproic Acid | | 57-08-9 | | | |
| e-Aminocaproic Acid | | 60-32-2 | | | |
| ebastine | 1-Butanone, 1-[4-(1,1-dimethylethyl)phenyl]-4-[4-(diphenylmethoxy)-1-piperidinyl]-[CAS] | 90729-43-4 | EP | 134124 Antiallergic, non-asthma | Rhinitis, allergic, seasonal |
| eberconazole | 1H-Imidazole, 1-(2,4-dichloro-10,11-dihydro-5H-dibenzo[a,d]cyclohepten-5-yl)-[CAS] | 128326-82-9 130104-32-4 | ES | 2012297 Antifungal | Infection, dermatological |
| ebrotidine | Benzenesulfonamide, N-[[[2-[[[2-[(aminoiminomethyl)amino]-4-thiazoly]methyl]thio]ethyl]amino]methylene]-4-bromo-[CAS] | 100981-43-9 | EP | 159012 Antiulcer | Ulcer, duodenal |
| ebselen | 1,2-Benzisoselenazol-3(2H)-one, 2-phenyl-[CAS] | 60940-34-3 | EP | 44971 Neuroprotective | Haemorrhage, subarachnoid |
| Eburnamonine | | 474-00-0 | | | |
| Ecabapide | | 104775-36-2 | | | |
| ecabet | 1-Phenanthrenecarboxylic acid, 1,2,3,4,4a,9,10,10a-octahydro-1,4a-dimethyl-7-(1-methylethyl)-6-sulfo-, [1R-(1Alpha,4aβ,10aAlpha)]-[CAS] | 33159-27-2 86408-72-2 | DE | 3239172 Antiulcer | Ulcer, gastric |
| ecadotril | Glycine, N-[2-[(acetylthio)methyl]-1-oxo-3-phenylpropyl]-,phenylmethyl ester, (S)-[CAS] | 112573-73-6 | EP | 318377 Antihypertensive, other | Hypertension, general |
| Ecgonidine | | 484-93-5 | | | |
| Ecgonine | | 481-37-8 | | | |
| Echothiophate | | 513-10-0 | | | |
| Econazole | | 27220-47-9 | | | |
| ecopipam | 5H-Benzo[d]naphth[2,1-b]azepin-12-ol, 11-chloro-6,6a,7,8,9,13b-hexahydro-7-methyl-, (6aS-trans)-[CAS] | 112108-01-7 | EP | 230270 Anorectic/Antiobesity | Obesity |
| ecraprost | Prosta-8,13-dien-1-oic acid, 11,15-dihydroxy-9-(1-oxobutoxy)-, butyl ester, (11Alpha,13E,15S)-[CAS] | 136892-64-3 | EP | 423697 Vasodilator, peripheral | Peripheral vascular disease |
| Ectylurea | | 95-04-5 | | | |
| ED-71 | 9,10-Secocholesta-5,7,10(19)-triene-1,3,25-triol, 2-(3-hydroxypropoxy)-, (1Alpha,2β,3β,5Z,7E)-[CAS] | 104121-92-8 | EP | 184206 Osteoporosis treatment | Osteoporosis |
| edaravone | 3H-Pyrazol-3-one, 2,4-dihydro-5-methyl-2-phenyl-[CAS] | 89-25-8 | JP | 62108814 Neuroprotective | Infarction, cerebral |
| Edatrexate | | 80576-83-6 | | | |

TABLE 3-continued

| API Generic Name | API Chemical Name | CAS No. | Patent Reference | Example of Therapeutic Use | Example of Indication |
|---|---|---|---|---|---|
| Edetate Galcium Disodium | | 62-33-9 | | | |
| Edetate Disodium | | 139-33-3 | | | |
| Edetate Sodium | | 64-02-8 | | | |
| Edetate Trisodium | | 150-38-9 | | | |
| edonentan | Butanamide,N-[[2'-[[4,5-dimethyl-3-isoxazoyl)amino]sulfonyl]-4-(2-oxazolyl)[1,1'-biphenyl]-2-yl]methyl]-N,3,3-trimethyl-, monohydrate | 210891-04-6 | | Cardiostimulant | Heart failure |
| edotreotide | [N-[2-[4,7-Bis[(carboxy-kappaO)methyl] 10-(carboxymethyl)-1,4,7,10-tetraazacyclododec-1-yl-kappaN1,kappaN4,kappaN10]acetyl]-D-phenylalanyl-L-cysteinyl-L-tyrosyl-D-tryptophyl-L-lysyl-L-threonyl-L-cysteinyl-L-threoninol cyclic (2-7)-disulfidato(3-)] yttrium | 204318-14-9 | U.S. | 6,183,721 Anticancer, hormonal | Cancer, lung, small cell |
| edoxudine | Uridine, 2'-deaxy-5-ethyl-[CAS] | 15176-29-1 | GB | 1170565 Antiviral, other | Infection, herpes virus, general |
| Edrecolomab | | 156586-89-9 | | | |
| Edrophonium | | 116-38-1 | | | |
| Efalith | Butanedioic acid, lithium salt [CAS] | 16090-09-8 | | Antipruritic/inflamm, allergic | Eczema, seborrhoeic |
| efaproxiral | Propanoic acid, 2-[4-[2-[(3,5-dimethylphenyl)amino]-2-oxoethyl]phenoxy]-2-methyl-[CAS] | 131179-95-8 | U.S. | 5,705,521 Radio/chemosensitizer | Cancer, brain |
| efavirenz | 2H-3,1-Benzoxazin-2-one, 6-chloro-4-(cyclopropylethynyl)-1,4-dihydro-4-(trifluoromethyl)-, (S)-[CAS] | 154598-52-4 | WO | 9403440 Antiviral, anti-HIV | Infection, HIV/AIDS |
| efletirizine | [2-4-[Bis(p-fluorophenyl)methyl]-1-piperazinyl]ethoxylacetic acid | 150756-35-7 | GB | 2311940 Antiallergic, non-asthma | Allergy, general |
| eflornithine | DL-Ornithine, 2-(difluoromethyl)-[CAS] | 70052-12-9 67037-37-0 | U.S. | 4,413,141 Protozoacide, dermal, topical | Infection, trypanosomiasis, African, Hirsutism |
| Efloxate | | 119-41-5 | | | |
| eflucimibe | Benzeneacetamide, Alpha-(dodecylthio)-N-(4-hydroxy-2,3,5-trimethylphenyl)- (S)-[CAS] | 202340-45-2 | | Hypolipaemic/ Antitherosclerosis | Hyperlipidaemia, general |
| efonidipine | 3-pyridinecarboxylic acid, 5-(5,5-dimethyl-1,3,2-dioxaphosphorinan-2-yl) 1,4-dihydro-2,6-dimethyl-4-(3-nitrophenyl)-, 2-(phenyl(phenylmethyl)amino)ethyl ester, P-oxide [CAS] | 111011-53-1 111011-63-3 111011-76-8 | EP | 230944 Antihypertensive, other | Hypertension, general |
| EGIS-7229 | 5-Chloro-4-[3-[N-2-(3,4-dimethoxyphenyl)ethyl]-N-methylaminolpropylamino]- 3(2H)-pyridazinone fumarate [CAS] | 150800-12-7 190333-92-7 | DE | 4243381 Antiarrhythmic | Arrhythmia, general |
| eglumegad | Bicyclo[3.1.0]hexane-2,6-dicarboxylic acid, 2-amino-, (1S,2S,5R,6S)-[CAS] | 176199-48-7 209216-09-1 | | Anxiolytic | Anxiety, general |
| egualen | 1-Azulenesulfonic acid, 3-ethyl-7-(1-methylethyl)-, | 97683-31-3 99287-30-6 | EP | 147915 Antiulcer | Ulcer, gastric |
| Eicosa-pentaenoic Acid | | 10417-94-4 | | | |
| elarofiban | 3-Pyridinepropanoic acid, β-[((3R)-1-[1-oxo-3-(4-piperidinyl)propyl]-3-piperidinyl]carbonyl]amino]-, (βS)-[CAS] | 198958-88-2 | WO | 9741102 Antithrombotic | Thrombosis, general |
| Elcatonin | | 60731-46-6 | | | |
| Eledoisin | | 69-25-0 | | | |
| eletriptan | 1H-Indole, 3-((1-methyl-2-pyrrolidinyl)methyl)-5-(2-(phenylsulfonyl)ethyl)- (R)-[CAS] | 143322-58-1 | U.S. | 5,607,951 Antimigraine | Migraine |
| Elgodipine | | 119413-55-7 | | | |
| Ellagic Acid | | 476-66-4 | | | |
| Elliptinium | | 58337-35-2 | | | |
| Eltoprazine | | 98224-03-4 | | | |
| elvucitabine | β-L-2',3'-Didehydro-2,3'-dideoxy-5-fluorocytidine | 181785-84-2 | | Antiviral, other | Infection, hepatitis-B virus |

TABLE 3-continued

| API Generic Name | API Chemical Name | CAS No. | Patent Reference | Example of Therapeutic Use | Example of Indication |
|---|---|---|---|---|---|
| elzasonan | (2Z)-4-(3,4-dichlorophenyl)-2-[2-(4-methylpiperazin-1-yl)benzylidene]thiomorpholin-3-one monohydrochloride-[CAS] | 220322-05-4 361343-20-6 | | Antidepressant | Depression, general |
| Embelin | | 550-24-3 | | | |
| Embramine | | 3565-72-8 | | | |
| emedastine | 1H-Benzimidazole, 1-(2-ethoxyethyl)-2-(hexahydro-4-methyl-1H-1,4-diazepin-1-yl)-, (E)-2-butenedioate (1:2) [CAS] | 87233-61-2 87233-62-3 | EP | 79545 Antiallergic, non-asthma | Rhinitis, allergic, general |
| Emepronium | | 3614-30-0 | | | |
| Emetine | | 483-18-1 | | | |
| Emitefur | | 110690-43-2 | | | |
| EMM-210525 | 17Alpha-Acetoxy-6Alpha-methyl-1 9-nor 1β,2β-dihydrocyclopropa[1,2']pregn-4-ene-3,20-dione+Estra-1,3,5(10)-triene-3,17-diol(17β) | | | Formulation, fixed-dose combinations | Hormone replacement therapy |
| Emodin | | 518-82-1 | | | |
| emorfazone | 3(2H)-Pyridazinone, 4-ethoxy-2-methyl-5-(4-morpholinyl)-[CAS] | 38957-41-4 | JP | 7224030 Anti-inflammatory | |
| EMR-62203 | | | WO | 9806722 Male sexual dysfunction | Impotence |
| emtricitabine | 2(1H)-Pyrimidinone, 4-amino-5-fluoro-1 (2-(hydroxymethyl)-1,3-oxathiolan-5-yl)-, (2R-cis)-[CAS] | 143491-57-0 | WO | 9214743 Antiviral, anti-HIV | Infection, HIV/AIDS |
| Emylcamate | | 78-28-4 | | | |
| enalapril | L-Proline, 1-[N-[1-(ethoxycarbonyl)-3-phenylpropyl]-L-alanyl]-, (S)-, (Z)-2-butenedioate [CAS] | 76095-16-4 | U.S. | 4,374,829 Antihypertensive, renin systetm | |
| Enalaprilat | | 76420-72-9 | | | |
| Enallyl-propymal | | 1861-21-8 | | | |
| Encainide | | 66778-36-7 | | | |
| Enciprazine | | 68576-86-3 | | | |
| End ralazine | | 39715-02-1 | | | |
| enfenamic acid | Benzoic acid, 2-[(2-phenylethyl)amino]-[CAS] | 23049-93-6 | IN | 103066 Anti-inflammatory | |
| enflurane | Ethane, 2-chloro-1-(difluoromethoxy)-1,1,2-trifluoro-[CAS] | 13838-16-9 | U.S. | 3,469,011 Anaesthetic, inhalation | Anaesthesia |
| Enilconazole | | 35554-44-0 | | | |
| Eniluracil | | 59989-18-3 | | | |
| ENMD-0995 | S-3-amino-phthalidoglutarimide | | U.S. | 5,712,291 Anticancer, other | Cancer, myeloma |
| Enocitabine | | 55726-47-1 | | | |
| Enol-3-IPA | 1H-Indole-3-propanoic acid, Alpha-oxo-[CAS] | 392-12-1 | EP | 106813 Hypnotic/Sedative | Insomnia |
| enoxacin | 1,8-Naphthyridine-3-carboxylic acid, 1-ethyl-6-fluoro-1,4-dihydro-4-oxo-7-(1-piperazinyl)-[CAS] | 74011-58-8 | U.S. | 4,359,578 Quinolone antibacter | Infection, general |
| enoxaparin | Heparin, [CAS] | 9005-49-6 9041-08-1 | EP | 40144 Antithrombotic | Thrombosis, venous |
| enoximone | 2H-Imidazol-2-one, 1,3-dihydro-4-methyl-5-[4-(methylthio)benzoyl]-[CAS] | 77671-31-9 | EP | 59948 Cardiostimulant | Heart failure |
| Enoxolone | | 471-53-4 | | | |
| enprostil | 4,5-Heptadienoic acid, 7-[3-hydroxy-2-(3-hydroxy-4-phenoxy-1-butenyl)-5-oxocyclopentyl]-, methyl ester, [1Alpha,2β(1E,3R*),3Alpha]-[CAS] | 73121-56-9 | GB | 2025431 Prostaglandin | Ulcer, duodenal |
| enrasentan | 1H-Indene-2-carboxylic acid, 1-(1,3-benzodioxol-5-yl)-2,3-dihydro-3-(2-(2-hydroxyethoxy)-4-methoxyphenyl)-5-propoxy-, (1S-(lAlpha,2β,3Alpha))-[CAS] | 167256-08-8 | U.S. | 5,817,693 Antihypertensive, other | Hypertension, pulmonary |
| entacapone | 2-Propenamide, 2-cyano-3-(4,5-dihydroxy-3-nitrophenyl)-N,N-diethyl-[CAS] | 130929-57-6 | EP | 426468 Antiparkinsonian | Parkinson's disease |
| entecavir | 6H-Purin-6-one, 2-amino-1,9-dihydro-9 ((1S,3R,4S)-4-hydroxy-3-(hydroxymethyl)-2-methylenecyclopentyl]-[CAS] | 142217-69-4 | EP | 481754 Antiviral, other | Infection, hepatitis-B virus |
| Enviomycin | | 33103-22-9 | | | |
| epalrestat | 3-Thiazolidineacetic acid, 5-(2-methyl-3 phenyl-2-propenylidene)-4-oxo-2-thioxo-, (E,E)-[CAS] | 82159-09-9 | EP | 47109 Symptomatic antidiabetic | Neuropathy, diabetic |
| Epavir | L-lysine-cis-5,8,11,14,17-eicosapentanoate with L-lysine-cis-4,7,10,13,16,19-doahexanoate | | | Antiviral, other | Infection, herpes simplex virus |

TABLE 3-continued

| API Generic Name | API Chemical Name | CAS No. | Patent Reference | | Example of Therapeutic Use | Example of Indication |
|---|---|---|---|---|---|---|
| EPC-K1 | L-ascorbic acid 2-[3,4-dihydro-2,5,7,8-tetramethyl-2-(4,8,12-trimethyltridecyl)-2H-1-benzopyran-6-yl-hydrogen phosphate]potassium-[CAS] | 127061-56-7 | EP | 127471 | Neuroprotective | Infarction, cerebral |
| eperisone | 1-Propanone, 1-(4-ethylphenyl)-2-methyl-3-(1-pipendinyl)-[CAS] | 64840-90-0 | U.S. | 3,995,047 | Muscle relaxant | Spastic paralysis |
| epervudine | Uridine, 2'-deoxy-5-(1-methylethyl)-[CAS] | 60136-25-6 | DE | 2918260 | Antiviral, other | Infection, herpes simplex virus |
| Ephedrine | | 299-42-3 | | | | |
| Epiclilin | | 26774-90-3 | | | | |
| Epimestrol | | 7004-98-0 | | | | |
| epinastine | 1H-Dibenz[c,f]imidazo[1,5-a]azepin-3-amine, 9,13b-dihydro-[CAS] | 80012-43-7 | DE | 3008944 | Antiasthma | Asthma |
| epinephrine | (R)-4-[1-hydroxy-2-(methylamino)-ethyl]-1,2-benzenediol | 51-43-4 | | | Formulation, inhalable, dry powder | Anaphylaxis |
| Epinzole | | 18694-40-1 | | | | |
| epirubicin | 5,1 2-Naphtacenedione, 1 0-[(3-amino-2,3,6-trideoxy-Alpha-L-arabino-hexopyranosyl)oxy]-7,8,9,10-tetrahydro 6,8,11-trihydroxy-8-(hydroxyacetyl)-1-methoxy-, (8S-cis)-[CAS] | 56390-09-1 56420-45-2 | GB | 1457632 | Anticancer, antibiotic | |
| Epitiostanol | | 2363-58-8 | | | | |
| eplerenone | Pregn-4-ene-7,21-dicarboxylic acid, 9,11-epoxy-17-hydroxy-3-oxo-,Gamma lactone, methyl ester (7Alpha,11Alpha,17Alpha)-[CAS] | 107724-20-9 | EP | 122232 | Antihypertensive, diuretic | Hypertension, general |
| eplivanserin | 1-Propanone,1-(2-fluorophenyl)-3-(4-hydroxyphenyl)-, O-(2-(dimethylamino)ethyl)oxime, (Z)-, (E)-2-butenedloate (2:1) (salt) [CAS] | 130580-02-8 | EP | 373998 | Anxiolytic | Schizophrenia |
| epoprostenol | Prosta-5,13-dien-1-oic acid, 6,9-epoxy-11,15-dihydroxy-, (5Z,9Alpha,11Alpha,13E,15S)-[CAS] | 35121-78-9 61849-14-7 | DE | 2720999 | Prostaglandin | Hypertension, pulmonary |
| Epostane | | 80471-63-2 | | | | |
| Eprazinone | | 10402-90-1 | | | | |
| Epristeride | | 119169-78-7 | | | | |
| eprosartan | 3-[2-Butyl-1-(4-carboxybenzyl)-1H-imidazol-5-yl]-2-(2-thienylmethyl)-2-(E)-propenoic acid | 133040-01-4 | EP | 403159 | Antihypertensive, renin system | Hypertension, general |
| Eprozinol | | 32665-36-4 | | | | |
| eptapirone | 4-methyl-2-[4-(4-(pyrimidin-2-yl)-piperazino)-butyl]-2H,4H-1,2,4-triazin-3,5-dione | 179756-85-5 | | | Antidepressant | Depression, general |
| eptaplatin | Platinum, [(4R,5R)-2-(1-methylethyl)-1,3-dioxolane-4,5-dimethanamine-kappaN4',kappaN5][propanedioato(2-)-kappaO1,kappaO3]-, (SP-4-2)-[CAS] | 146665-77-2 | WO | 9216539 | Anticancer, alkylating. | Cancer, lung, small cell |
| Eptastigmine | | 101246-68-8 | | | | |
| eptazocine | 1,6-Methano-1H-4-benzazonin-10-ol, 2,3,4,5,6,7-hexahydro-1,4-dimethyl-, (1S)-[CAS] | 72522-13-5 | U.S. | 4,082,744 | Analgesic, other | |
| Eptifibatide | | 188627-80-7 | | | | |
| Equilenin | | 517-09-9 | | | | |
| Equilin | | 474-86-2 | | | | |
| ERA-923 | ERA 923 [CAS] | 352233-89-7 | EP | 802183 | Female contraceptive | Contraceptive, female |
| erdosteine | Acetic acid, [[2-oxo-2-[(tetrahydro-2-oxo-3-thienyl)amino]ethyl]thio]-[CAS] | 84611-23-4 | EP | 61386 | Respiratory | Respiratory disease, general |
| Ergocornine | | 564-36-3 | | | | |
| Ergocorninine | | 564-37-4 | | | | |
| Ergoloid Mesylates | | 8067-24-1 | | | | |
| Ergonovine | | 60-79-7 | | | | |
| Ergosterol | | 57-87-4 | | | | |
| ergotamine | (5'Alpha)-12'-Hydroxy-2'methyl-(phenylmethyl)ergotaman-3',6', 18-trione | 113-15-5 | | | Formulation, inhhalable, systemic | Migraine |
| Eritadenine | | 23918-98-1 | | | | |
| erlotinib | 4-Quinazolinamine, N-(3-ethynylphenyl)-6,7-bis(2-methoxyethoxy)-, monohydrochloride [CAS] | 183319-69-9 | WO | 9630347 | Anticancer, other | Cancer, lung, non-small cell |
| ertapenem | 1-Azabicyclo[3.2.0]hept-2-ene-2-carboxylic acid, 3-[[(3S,5S)-5-[[(3- | 153773-82-1 153832-46-3 | WO | 9315078 | Beta-lactam antibiotic | Infection, GI tract |

TABLE 3-continued

| API Generic Name | API Chemical Name | CAS No. | Patent Reference | | Example of Therapeutic Use | Example of Indication |
|---|---|---|---|---|---|---|
| | carboxyphenyl)amino]carbonyl]-3-pyrrolidinyl]thio]-6-[(1R)-1-hydroxyethyl]-4-methyl-7-oxo-, [CAS] | | | | | |
| Erythrityl Tetranitrate | | 7297-25-8 | | | | |
| Erythro-centaurin | | 50276-98-7 | | | | |
| erythromycin acistrate | Erythromycin, 2'-acetate, octadecanoate (salt) [CAS] | 96128-89-1 | U.S. | 4,599,326 | Macrolide antibiotic | Infection, general |
| Erythromycin Estolate | | 3521-62-8 | | | | |
| Erythromycin Glucoheptonate | | 23067-13-2 | | | | |
| Erythromycin Lactobionate | | 3847-29-8 | | | | |
| Erythromycin Propionate | | 134-36-1 | | | | |
| Erythromycin Stearate | | 643-22-1 | | | | |
| erythromycin stinoprate | Erythromycin, 2'-propanoate, compd. with N-acetyl-L-cysteine (1:1) [CAS] | 84252-03-9 | EP | 57489 | Macrolide antibiotic | Infection, respiratory tract, lower |
| erythromycin | Erythromycin [CAS] | 114-07-8 | | | Formulation, dermal, topical | Acne |
| Erythrophleine | | 36150-73-9 | | | | |
| Esaprazole | | 64204-55-3 | | | | |
| escitalopram | 5-Isobenzofurancarbonitrile, 1-[3-(dimethylamino)propyl]-1-(4-fluorophenyl)-1,3-dihydro-, (S)-[CAS] | 128196-01-0 | EP | 347066 | Antidepressant | Depression, general |
| Esculin | | 531-75-9 | | | | |
| Eseridine | | 25573-43-7 | | | | |
| esmolol | Benzenepropanoic acid, 4-[2-hydroxy-3-[(1-methylethyl)amino]propoxy]-, methyl ester, (+/−)-[CAS] | 81147-92-4 | US | 4,387,103 | Antihypertensive, adrenergic | Tachycardia, supraventricular |
| esomeprazole | bis (5-methoxy-2-(((4-methoxy-3,5-dimethyl-2-pyridinyl)methyl)sulfinyl)-1H-benzimidazolato) | 161 973-10-0 | US | 5,877,192 | Antispasmodic | Gastro-oesophageal reflux |
| estazolam | 4H-[1,2,4]Triazolo[4,3-a][1,4]benzodiazepine, 8-chloro-6-phenyl-[CAS] | 29975-16-4 | US | 3,987,052 | Hypnotic/Sedative | |
| estradiol | Androst-4-en-3-one, 17-hydroxy-, (17β) [CAS] | 58-22-0 | U.S. | 5,460,820 | Formulation, transdermal, patch | Sexual dysfunction, female |
| estradiol | Estra-1,3,5(10)-triene-3,17-diol (17β)-[CAS] | 50-28-2 | EP | 430491 | Formulation, transdermal, systemic | Menopausal symptoms, general |
| estramustine | Estra-1,3,5(10)-triene-3,17-diol (17β)-, 3-[bis(2-chloroethyl)carbamate] 17-[CAS] | 2998-57-4 4891-15-0 52205-73-9 | | | Anticancer, alkylating | Cancer, prostate |
| Estriol | | 50-27-1 | | | | |
| estrogen | | | WO | 9924041 | Menopausal disorders | Menopausal symptoms, general |
| Estrone | | 53-16-7 | | | | |
| eszopiclone | 1-Piperazinecarboxylic acid, 4-methyl-6-(5-chloro-2-pyridinyl)-6,7-dihydro-7-oxo-5H-pyrrolo(3,4-b)pyrazin-5-yl ester (S)-[CAS] | 138729-47-2 | U.S. | 5,786,357 | Hypnotic/Sedative | Insomnia |
| Etafedrine | | 7681-79-0 | | | | |
| Etafenone | | 90-54-0 | | | | |
| Etamiphyllin | | 314-35-2 | | | | |
| Etanercept | | 185243-69-0 | | | | |
| Etanidazole | | 22668-01-5 | | | | |
| Etaqualone | | 7432-25-9 | | | | |
| Eterobarb | | 27511-99-5 | | | | |
| Ethacridine | | 442-16-0 | | | | |
| Ethacrynic Acid | | 58-54-8 | | | | |
| Ethadione | | 520-77-4 | | | | |
| Ethambutol | | 74-55-5 | | | | |
| Ethamivan | | 304-84-7 | | | | |
| Ethamsylate | | 2624-44-4 | | | | |
| Ethanolamine | | 141-43-5 | | | | |
| Ethaverine | | 486-47-5 | | | | |
| Ethchlorvynol | | 113-18-8 | | | | |
| Ethenzamide | | 938-73-8 | | | | |
| Ethiazide | | 1824-58-4 | | | | |
| Ethinamate | | 126-52-3 | | | | |
| Ethinyl Estradiol | | 57-63-6 | | | | |

TABLE 3-continued

| API Generic Name | API Chemical Name | CAS No. | Patent Reference | | Example of Therapeutic Use | Example of Indication |
|---|---|---|---|---|---|---|
| ethinyl estradiol | 19-Norpregna-1,3,5(10)-trien-20-yne-3,17-diol, 3-(2-propanesulfonate), (17Alpha)-[CAS] | 28913-23-7 | DE | 1949095 | Formulation, modified-release, >24 hr | Cancer, prostate |
| Ethionamide | | 536-33-4 | | | | |
| Ethisterone | | 434-03-7 | | | | |
| Ethoheptazine | | 77-15-6 | | | | |
| Ethopropazine | | 522-00-9 | | | | |
| Ethosuximide | | 77-67-8 | | | | |
| Ethotoin | | 86-35-1 | | | | |
| Ethoxzolamide | | 452-35-7 | | | | |
| Ethybenztropine | | 524-83-4 | | | | |
| Ethyl Alcohol | | 64-17-5 | | | | |
| Ethyl Biscoumacetate | | 548-00-5 | | | | |
| Ethyl Chloride | | 75-00-3 | | | | |
| Ethyl Dibunate | | 5560-69-0 | | | | |
| Ethyl Ether | | 60-29-7 | | | | |
| ethyl icosapentate | 5,8,11,14,17-Eicosapentaenoic acid, ethyl ester, (all-Z)-[CAS] | 86227-47-6 | JP | 61043143 | Antithrombotic | Peripheral vascular disease |
| ethyl loflazepate | 1H-1,4-Benzodiazepine-3-carboxylic acid, 7-chloro-5-(2-fluorophenyl)-2,3-dihydro-2-oxo-, ethyl ester [CAS] | 29177-84-2 | U.S. | 3,657,223 | Anxiolytic | Anxiety, general |
| Ethyl Loflazepate | | 29177-84-2 | | | | |
| Ethylamine | | 75-04-7 | | | | |
| Ethylene | | 74-85-1 | | | | |
| Ethylestrenol | | 965-90-2 | | | | |
| Ethylidene Dicoumarol | | 1821-16-5 | | | | |
| Ethylmethyl-thiambutene | | 441-61-2 | | | | |
| Ethylmorphine | | 76-58-4 | | | | |
| Ethylnore-pinephrine | | 536-24-3 | | | | |
| Ethynodiol | | 1231-93-2 | | | | |
| ethynylcytidine | Uridine, 3'-C-ethynyl-[CAS] | 180300-49-6 | WO | 9618636 | Anticancer, antimetabolite | Cancer, general |
| Etidocaine | | 36637-18-0 | | | | |
| etidronate | Phosphonic acid, (1-hydroxyethylidene)bis-, [CAS] | 2809-21-4 7414-83-7 | U.S. | 4,137,309 | Osteoporosis treatment | Osteoporosis |
| Etidronic Acid | | 2809-21-4 | | | | |
| Etifelmin | | 341-00-4 | | | | |
| etifoxine | 4H-3,1-Benzoxazin-2-amine, 6-chloro-N-ethyl-4-methyl-4-phenyl-[CAS] | 21715-46-8 | U.S. | 3,725,404 | Anxiolytic | |
| Etilefrin | | 709-55-7 | | | | |
| etilevodopa | L-Tyrosine, 3-hydroxy-, ethyl ester [CAS] | 37178-37-3 | U.S. | 5,354,885 | Antiparkinsonian | Parkinson's disease |
| etiprednol | androsta-1,4-diene-17-carboxylic acid, 17-[(dichloroacetyl)oxy]-11-hydroxy-3-oxo-, ethyl ester, (11β,17Alpha)- | 199331-40-3 | | | GI inflammatory/bowel disorders | Crohn's disease |
| Etiroxate | | 17365-01-4 | | | | |
| Etizolam | | 40054-69-1 | | | | |
| etodolac | Pyrano[3,4-b]indole-1-acetic acid, 1,8-diethyl-1,3,4,9-tetrahydro-[CAS] | 41340-25-4 | U.S. | 3,939,178 | Antiarthritic, other | Arthritis, osteo |
| Etodroxizine | | 17692-34-1 | | | | |
| etofenamate | Benzoic acid, 2-[[3-(trifluoromethyl)phenyl]amino]-, 2-(2-hydroxyethoxy)ethyl ester [CAS] | 30544-47-9 | GB | 1285400 | Anti-inflammatory, topical | Inflammation, general |
| etofibrate | 3-Pyridinecarboxylic acid, 2-[2-(4-chlorophenoxy)-2-methyl-1-oxopropoxy]ethyl ester [CAS] | 31637-97-5 | U.S. | 3,723,446 | Hypolipaemic/Antiatherosclerosis | |
| Etofylline | | 519-37-9 | | | | |
| etofylline clofibrate | Propanoic acid, 2-(4-chlorophenoxy)-2-methyl-, 2-(1,2,3,6-tetrahydro-1,3-dimethyl-2,6-dioxo-7H-purin-7-yl)ethyl ester [CAS] | 54504-70-0 | DE | 2308826 | Hypolipaemic/Antiatherosclerosis | |
| Etofylline Nicotinate | | 13425-39-3 | | | | |
| Etoglucid | | 1954-28-5 | | | | |
| Etomidate | | 33125-97-2 | | | | |
| Etomidoline | | 21590-92-1 | | | | |
| Etonitazene | | 911-65-9 | | | | |
| etonogestrel | 18,19-Dinorpregn-4-en-20-yn-3-one, 13-ethyl-17-hydroxy-11-methylene, (17Alpha)-[CAS] | 54048-10-1 | | | Formulation, implant | Contraceptive, female |

TABLE 3-continued

| API Generic Name | API Chemical Name | CAS No. | Patent Reference | Example of Therapeutic Use | Example of Indication |
|---|---|---|---|---|---|
| Etoperidone | | 52942-31-1 | | | |
| etoposide | Furo[3',4':6,7]naphtho[2,3-d]-1,3-dioxol-6(5aH)-one, 9-[(4,6-O-ethylidene-β-D-glucopyranosyl)oxy]-5,8,8a,9-tetrahydro-5-(4-hydroxy-3,5-dimethoxyphenyl)-, [5R-[5Alpha,5aβ,8aAlpha,9β(R*)]]-[CAS] | 33419-42-0 | GB 1205966 | Anticancer, other | Cancer, testicular |
| etoposide phosphate | Furo[3',4':6,7]naphtho[2,3-d]-1,3-dioxol-6(5aH)-one, 5-[3,5-dimethoxy-4-(phosphonooxy)phenyl]-9-[(4,6-0-ethylidene-β-D-glucopyranosyl)oxy]-5,8,8a,9-tetrahydro-, [5R-[5Alpha,5aβ,8aAlpha,9β(R*)]]-[CAS] | 117091-64-2 | EP 302473 | Anticancer, other | Cancer, testicular |
| etoricoxib | 2,3-Bipyridine, 5-chloro-6'-methyl-3-(4-(methylsulfonyl)phenyl) [CAS] | 202409-33-4 | WO 9803484 | Antiarthritic, other | Arthritis, osteo |
| Etoxadrol | | 28189-85-7 | | | |
| Etozolin | | 73-09-6 | | | |
| etretinate | 2,4,6,8-Nonatetraenoic acid, 9-(4-methoxy-2,3,6-trimethylphenyl)-3,7-dimethyl-, ethyl ester, (all-E)-[CAS] | 54350-48-0 | U.S. 4,215,215 | Antipsoriasis | |
| Etryptamine | | 2235-90-7 | | | |
| Etymemazine | | 523-54-6 | | | |
| Eucatropine | | 100-91-4 | | | |
| Eugenol | | 97-53-0 | | | |
| EUK-134 | Manganese, chloro[[2,2'-[1,2-ethanediylbis[(nitrilo-kappaN)methylidyne]]bis(6-methoxyphenolato-kappaO]]]-, (SP-5-13)-[CAS] | 81065-76-1 | U.S. 6,046,188 | Cardiovascular | Unspecified |
| EUK-189 | | | U.S. 6,046,188 | Radio/chemoprotective | Chemotherapy-induced injury, general |
| Evan's Blue | | 314-13-6 | | | |
| everolimus | Rapamycin, 42-O-(2-hydroxyethyl)-[CAS] | 159351-69-6 | WO 9409010 | Immunosuppressant | Transplant rejection, general |
| exalamide | Benzamide, 2-(hexyloxy)-[CAS] | 53370-90-4 | GB 726786 | Antifungal | Infection, fungal, general |
| Exametazime | | 105613-48-7 | | | |
| exatecan | 10H,13H-Benzo[de]pyrano[3',4':6,7]indolizino[1,2-b]quinoline-10,13-diane, 1-amino-9-ethyl-5-fluoro-1,2,3,9,12,15-hexahydro-9-hydroxy-4-methyl-, (1S,9S)-, [CAS] | 171335-80-1 | | Anticancer, other | Cancer, pancreatic |
| exemestane | Androsta-1,4-diene-3,17-diane, 6-methylene-[CAS] | 107868-30-4 | DE 3622841 | Anticancer, hormonal | Cancer, breast |
| Exifone | | 52479-85-3 | | | |
| exisulind | 1H-Indene-3-acetic acid 5-fluora-2-methyl-1-((4-(methylsulfonyl)phenyl)methylene)-, (Z)-[CAS] | 59973-80-7 | | Anticancer, other | Polyp |
| Exosurf | | 99732-49-7 | | | |
| ezetimibe | 2-Azetidinone, 1-(4-fluorophenyl)-3-[(3S)-3-(4-fluorophenyl)-3-hydroxypropyl]-4-(4-hydroxyphenyl)-, (3R,4S)-[CAS] | 163222-33-1 | U.S. 5,846,966 | Hypolipaemic/Antiatherosclerosis | Hypercholesterol-aemia |
| Factor IX | | 9001-28-9 | | | |
| Factor VIII | | 9001-27-8 | | | |
| Factor XIII | | 9013-56-3 | | | |
| fadolmidine | 1H-Inden-5-ol, 2,3-dihydro-3-(1H-imidazol-4-ylmethyl)-, monohydrochloride [CAS] | 189353-32-0 | WO 9712874 | Analgesic, other | Pain, general |
| Fadrozole | | 102676-47-1 | | | |
| falecalcitriol | 9,10-Secocholesta-5,7,10(19)-triene-1,3,25-triol, 26,26,26,27,27,27-hexafluoro-, (1Alpha,3β,5Z,7E)-[CAS] | 83805-11-2 | JP 03099022 | Osteoporosis treatment | Hyperparathyroidism |
| famciclovir | 1,3-Propanediol, 2-[2-(2-amino-9H-purin-9-yl)ethyl]-, diacetate (ester)-[CAS] | 104227-87-4 | JP 61085388 | Antiviral, other | Infection, gynaecological |
| famotidine | Propanimidamide, 3-[[[2-[(aminoiminomethyl)amino]-4-thiazolyl]methyl]thio]-N-(aminosulfonyl)-[CAS] | 76824-35-6 | U.S. 4,283,408 | Antiulcer | Ulcer, duodenal |
| fampridine | 4-pyridinamine | 504-24-5 | | Neuroprotective | Spinal cord injury |
| fandofloxacin | 3-Quinolinecarboxylic acid, 6-fluoro-1-(5-fluoro-2-pyridinyl)-1,4-dihydro-7-(4-methyl-1-piperazinyl)-4-oxo, [CAS] | 164150-85-0 164150-99-6 | U.S. 5,496,947 | Quinolone antibacterial | Infection, urinary tract |

TABLE 3-continued

| API Generic Name | API Chemical Name | CAS No. | Patent Reference | Example of Therapeutic Use | Example of Indication |
|---|---|---|---|---|---|
| Fantofarone | | 114432-13-2 | | | |
| faropenem daloxate | (5R,6S)-6-[1(R)-Hydroxyethyl]-2-[2(R)-tetrahydrofuryl]-2-penem-3-carboxylic acid-5-methyl-2-oxo-1,3-dioxol-4-ylmethyl ester | | | Beta-lactam antibiotic | Infection, general |
| faropenem | 4-Thia-1-azabicycio[3.2.0]hept-2-ene-2-carboxylic acid, 6-(1-hydroxyethyl)-7-oxo-3-(tetrahydro-2-furanyl)-, [5R-[3(R*),5Alpha,6Alpha(R*)]]-[CAS] | 122547-49-3 | EP | 410727 Beta-lactam antibiotic | Infection, ocular |
| fasidotril | L-Alanine, N-[(2S)-3-(acetylthio)-2-(1,3-benzodioxol-5-ylmethyl)-1-oxopropyl]-, phenylmethyl ester [CAS] | 135038-57-2 | EP | 419327 Antihypertensive, renin system | Hypertension, general |
| fasudil | 1H-1,4-Diazepine, hexahydro-1-(5-isoquinolinylsulfonyl)-[CAS] | 103745-39-7 105628-07-7 | EP | 187371 Neuroprotective | Vasospasm, general |
| Fazadinium Bromide | | 49564-56-9 | | | |
| febarbamate | 2,4,6(1H,3H,5H)-Pyrimidinetrione, 1-[2-[(aminocarbonyl)oxy]-3-butoxypropyl]-5 ethyl-5-phenyl-[CAS] | 13246-02-1 | U.S. | 3,075,983 Psychostimulant | |
| Febuprol | | 3102-00-9 | | | |
| febuxostat | 5-Thiazolecarboxylic acid, 2-[3-cyano-4 (2-methylpropoxy)phenyl]-4-methyl-[CAS] | 144060-53-7 | WO | 9209279 Antigout | Hyperuricaemia |
| Fedotozine | | 123618-00-8 | | | |
| felbamate | 1,3-Propanediol, 2-phenyl-, dicarbamate [CAS] | 25451-15-4 | U.S. | 4,868,327 Antiepileptic | Epilepsy, general |
| felbinac | [1,1'-Biphenyl]-4-acetic acid [CAS] | 5728-52-9 | EP | 127840 Anti-inflammatory, topical | |
| felodipine | 3,5-Pyridinedicarboxylic acid, 4-(2,3-dichlorophenyl)-1,4-dihydro-2,6-dimethyl-, ethyl methyl ester [CAS] | 72509-76-3 | U.S. | 4,264,611 Antihypertensive, other | Hypertension, general |
| Felypressin | | 56-59-7 | | | |
| Femoxetine | | 59859-58-4 | | | |
| Fenbenicillin | | 1926-48-3 | | | |
| fenbufen | [1,1-Biphenyl]-4-butanoic acid, Gamma-oxo-[CAS] | 36330-85-5 | U.S. | 3,784,701 Anti-inflammatory | |
| Fenbutrazate | | 4378-36-3 | | | |
| Fencamfamine | | 1209-98-9 | | | |
| Fencamine | | 28947-50-4 | | | |
| Fenclozic Acid | | 17969-20-9 | | | |
| Fendiline | | 13042-18-7 | | | |
| Fendosal | | 53597-27-6 | | | |
| Fenethylline | | 3736081 | | | |
| Fenfluramine | | 458-24-2 | | | |
| Fenipentol | | 583-03-9 | | | |
| fenofibrate | Propanoic acid, 2-[4-(4-chlorobenzoyl)phenoxy]-2-methyl-, 1-methylethyl ester [CAS] | 26129-32-8 49562-28-9 | | Formulation, modified-release <=24 hr | Hyperlididaemia, general |
| fenoldopam | 1H-3-Benzazepine-7,8-diol, 6-chloro-2,3,4,5-tetrahydro-1-(4-hydroxyphenyl)-[CAS] | 67227-56-9 67227-57-0 | EP | 22330 Antihypertensive, other | Hypertension, general |
| Fenoprofen | | 31879-05-7 | | | |
| Fenoterol | | 13392-18-2 | | | |
| fenoverine | 10H-Phenothiazine, 10-[[4-(1,3-benzodioxol-5-ylmethyl)-1-piperazinyl]acetyl]-[CAS] | 37561-27-6 | FR | 2092639 Antispasmodic | |
| Fenoxazoline | | 4846-91-7 | | | |
| Fenoxedil | | 54063-40-0 | | | |
| Fenozolone | | 15302-16-6 | | | |
| Fenpentadiol | | 15687-18-0 | | | |
| Fenpiprane | | 3540-95-2 | | | |
| Fenpiverinium Bromide | | 125-60-0 | | | |
| Fenproporex | | 15686-61-0 | | | |
| Fenquizone | | 20287-37-0 | | | |
| fenretinide | Retinamide, N-(4-hydroxyphenyl)-[CAS] | 65646-68-6 | BE | 847942 Anticancer, other | Cancer, breast |
| Fenspiride | | 5053066 | | | |
| fentanyl | Propanamide, N-phenyl-N-[1-(2-phenylethyl)-4-piperidinyl]-[CAS] | 437-38-7 | | Formulation, transmucosal, systemic | Anaesthesia, adjunct |
| Fentiazac | | 18046-21-4 | | | |
| Fenticlor | | 97-24-5 | | | |
| fenticonazole | 1H-Imidazole, 1-[2-(2,4-dichlorophenyl)-2-[[4-(phenylthio)phenyl]methoxy]ethyl]-[CAS] | 72479-26-6 73151-29-8 | U.S. | 4,221,803 Antifungal | Infection, gynaecological |

TABLE 3-continued

| API Generic Name | API Chemical Name | CAS No. | Patent Reference | | Example of Therapeutic Use | Example of Indication |
|---|---|---|---|---|---|---|
| Fentonium Bromide | | 5868064 | | | | |
| fepradinol | Benzenemethanol, Alpha-[[(2-hydroxy-1,1-dimethylethyl)amino]methyl]-, (+/−)-[CAS] | 36981-91-6 67704-50-1 63075-47-8 | | | Anti-inflammatory, topical | |
| Feprazone | | 30748-29-9 | | | | |
| Ferric Sodium Edetate | | 15708-41-5 | | | | |
| ferrioxamine B | | | WO | 9426263 | Septic shock treatment | Respiratory distress syndrome, adult |
| Ferrocholinate | | 1336-80-7 | | | | |
| Ferrous Gluconate | | 299-29-6 | | | | |
| ferumoxytol | Polyglucose sorbitol carboxymethyl ether-coated non-stoichiometric magnetite Imaging agent | | | | Imaging agent | Diagnosis, cancer |
| fesoterodine | 2-((1R)-3-(bis(1-methylethyl)amino)-1-phenylpropyl)-4-(hydroxymethyl)Phenyl ester, (2E)-2-butenedioate (1:1) (Salt) - [CAS] | 286930-03-8 | | | Urological | Incontinence |
| fexofenadine | Benzeneacetic acid, 4-[1-hydroxy-4-[4(hydroxydiphenylmethyl)-1-pipendinyl]butyl]-Alpha,Alpha-dimethyl-, [CAS] | 153439-40-8 83799-24-0 138452-21-8 | U.S. | 5,375,693 | Antiallergic, non-asthma | Rhinitis, allergic, seasonal |
| Fibrostat | | | CA | 2132416 | Vulnerary | Wound healing |
| fidarestat | Spiro(4H-1-benzopyran-4,4-imidazolidine)-2-carboxamide, 6-fluoro-2,3-dihydro-2',5'-dioxo-, (2S-cis)-, [CAS] | 136087-85-9 | EP | 418834 | Symptomatic antidiabetic | Neuropathy, diabetic |
| fiduxosin | 8-Phenyl-3-[4-[(3aR,9bR)-1,3a,4,9b-tetrahydro-9-methoxy[1]benzopyrano[3,4-c]pyrrol-2(3H)-yl]butyl]pyrazino[2',3':4,5]thieno[3,2-d]pyrimidine-2,4(1H,3H)-dione | 208993-54-8 | | | Prostate disorders | Benign prostatic hyperplasia |
| finasteride | 4-Azaandrost-1-ene-17-carboxamide, N-(1,1-dimethylethyl)-3-oxo-, (5Alpha,17β)-[CAS] | 98319-26-7 | EP | 155096 | Prostate disorders | Benign prostatic hyperplasia |
| finrozole | Benzonitrile, 4-(3-(4-fluorophenyl)-2-hydroxy-1-(1H-1,2,4-triazol-1-yl)-propyl) [CAS] | 160146-16-7 | EP | 476944 | Urological | Urinary retention |
| Fipexide | | 34161-24-5 | | | | |
| FK-960 | N-(4-Acetyl-1-piperazinyl)-4-fluorobenzamide monohydrate-[CAS] | 133920-70-4 | WO | 9101979 | Cognition enhancer | Alzheimer's disease |
| Flavopiridol | | 146426-40-6 | | | | |
| flavoxate | 4H-1-Benzopyran-8-carboxylic acid, 3-methyl-4-oxo-2-phenyl-, 2-(1-piperidinyl)ethyl ester [CAS] | 15301-69-6 3717-88-2 | U.S. | 2,921,070 | Urological | |
| flecainide | Benzamide,N-(2-piperidinylmethyl)-2,5-bis(2,2,2-trifluoroethoxy)-,[CAS] | 54143-55-4 54143-56-5 | | | Formulation, modified-release <=24 hr | Fibrillation, atrial |
| fleroxacin | 3-Quinolinecarboxylic acid, 6,8-difluoro-1-(2-fluoroethyl)-1,4-dihydro-7-(4-methyl-1-piperazinyl)-4-oxo-[CAS] | 79660-53-0 79660-72-3 | U.S. | 4,398,029 | Quinolone antibacterial | Infection, general |
| Flesinoxan | | 98206-10-1 | | | | |
| flibanserin | 2H-Benzimidazol-2-one, 1,3-dihydro-1-(2-(4-(3-(trifluoromethyl)phenyl)-1-piperazinyl)ethyl)-[CAS] | 167933-07-5 | | | Reproductive/gonadal, general | Sexual dysfunction, female |
| floctafenine | Benzoic acid, 2-[[8-(trifluoromethyl)-4-quinoiinyl]amino]-, 2,3-dihydroxypropyl ester [CAS] | 23779-99-9 | U.S. | 3,644,368 | Analgesic, NSAID | |
| flomoxef | 5-Oxa-1-azabicyclo[4.2.0]oct-2-ene-2-carboxylic acid, 7-[[[(difluoromethyl)thio]acetyl]amino]-3-[[[1-(2-hydroxyethyl)-1H-tetrazol-5-yl]thio]methyl]-7-methoxy-8-oxo-, (6R-cis)-[CAS] | 92823-03-5 99665-00-6 | EP | 128536 | Cephalosporin, injectable | Infection, general |
| Flopropione | | 2295-58-1 | | | | |
| Florantyrone | | 519-95-9 | | | | |
| Flosequinan | | 76568-02-0 | | | | |
| Floxacillin | | 5250-39-5 | | | | |
| Floxuridine | | 50-91-9 | | | | |
| Fluacizine | | 30223-48-4 | | | | |
| Fluanisone | | 1480-19-9 | | | | |
| fluasterone | Androst-5-en-17-one, 16-fluoro-, (16Alpha)-[CAS] | 112859-71-9 | EP | 246650 | Cardiovascular | Keratosis |

TABLE 3-continued

| API Generic Name | API Chemical Name | CAS No. | Patent Reference | Example of Therapeutic Use | Example of Indication |
|---|---|---|---|---|---|
| fluazacort | 5'H-Pregna-1,4-dieno[17,16-d]oxazole-3,20-dione, 21-(acetyloxy)-9-fluoro-11-hydroxy-2'-methyl-, (11β,16β)-[CAS] | 19888-56-3 | U.S. 3,461,119 | Antipruritic/inflamm, non-allergic | |
| Flucloronide | | 3693-39-8 | | | |
| flucloxacillin | | 1847-24-1 34214-51-2 | | Formulation, other | Infection, general |
| fluconazole | 1H-1,2,4-Triazole-1-ethanol, Alpha-(2,4-difluorophenyl)-Alpha-(1H-1,2,4-triazol-1-ylmethyl)-[CAS] | 86386-73-4 | EP 96569 | Antifungal | Infection, dermatological |
| Flucytosine | | 2022-85-7 | | | |
| fludarabine | 9H-Purin-6-amine, 2-fluoro-9-(5-O-phosphono-β-D-arabinofuranosyl)-[CAS] | 75607-67-9 21679-14-1 | U.S. 4,357,324 | Anticancer, antimetabolite | Cancer, leukaemia, chronic lymphocytic |
| Fludeoxy-glucose F1B | | 105851-17-0 | | | |
| Fludiazepam | | 3900-31-0 | | | |
| Fludrocortisone | | 127-31-1 | | | |
| Flufenamic Acid | | 530-78-9 | | | |
| Fluindione | | 957-56-2 | | | |
| flumazenil | 4H-Imidazo[1,5-a][1,4]benzodiazepine-3-carboxylic acid, 8-fluoro-5,6-dihydro-5-methyl-6-oxo-, ethyl ester [CAS] | 78755-81-4 | EP 27214 | Neurological | |
| Flumecinol | | 56430-99-0 | | | |
| Flumequine | | 42835-25-6 | | | |
| Flumethasone | | 2 135-17-3 | | | |
| Flumethiazide | | 148-56-1 | | | |
| flunarizine | Piperazine, 1-[bis(4-fluorophenyl)methyl]-4-(3-phenyl-2-propenyl)-,(E)-[CAS] | 30484-77-6 52468-60-7 27848-84-6 | GB 1268710 | Antimigraine | |
| flunisolide | Pregna-1,4-diene-3,20-dione, 6-fluoro-11,21-dihydroxy-16,17-[(1-methylethylidene)bis(oxy)]-, (6Alpha,11β,16Alpha)-[CAS] | 3385-03-3 | U.S. 3,124,571 | Antiasthma | Rhinitis, allergic, general |
| flunitrazepam | 2H-1,4-Benzodiazepin-2-one, 5-(2-fluorophenyl)-1,3-dihydro-1-methyl-7-nitro-[CAS] | 1622-62-4 | U.S. 3,116,203 | Hypnotic/Sedative | |
| Flunoxaprofen | | 66934-18-7 | | | |
| Fluocinolone Acetonide | | 67-73-2 | | | |
| Fluocinonide | | 356-12-7 | | | |
| Fluocortin Butyl | | 41767-29-7 | | | |
| Fluocortolone | | 152-97-6 | | | |
| Fluorescein | | 2321-07-5 | | | |
| Fluoresone | | 2924-67-6 | | | |
| Fluoro-metholone | | 426-13-1 | | | |
| Fluorosalan | | 4776061 | | | |
| fluorouracil | 2,4(1H,3H)-Pyrimidinedione, 5-fluoro-[CAS] | 51-21-8 | | Formulation, transdermal, enhanced | Keratosis |
| fluoxetine | Benzenepropanamine, N-methyl Gamma-[4-(trifluoromethyl)phenoxy]-, (+/−)-[CAS] | 54910-89-3 56296-78-7 | U.S. 4,314,081 | Antidepressant | Depression, general |
| Fluoxymesterone | | 76-43-7 | | | |
| Flupentixol | | 2709-56-0 | | | |
| Fluperolone | | 2119-75-7 | | | |
| Fluphenazine | | 69-23-8 | | | |
| flupirtine | Carbamic acid, [2-amino-6-[[(4-fluorophenyl)methyl]amino]-3-pyridinyl]-, ethyl ester [CAS] | 33400-45-2 56995-20-1 75507-68-5 | U.S. 4,481,205 | Analgesic, other | Pain, post-operative |
| Fluprednidene Acetate | | 1255-35-2 | | | |
| Fluprednisolone | | 53-34-9 | | | |
| Fluproquazone | | 40507-23-1 | | | |
| Flurandrenolide | | 1524-88-5 | | | |
| Flurazepam | | 17617-23-1 | | | |
| flurbiprofen | [1,1-Biphenyl]-4-acetic acid, 2-fluoro-Alpha-methyl-[CAS] | 5104-49-4 | U.S. 3,793,457 | Anti-inflammatory | |
| flurithromycin | Erythromycin, 8-fluoro-mono(ethyl butanedioate) (ester)-[CAS] | 82730-23-2 | EP 56291 | Macrolide antibiotic | Infection, respitory tract, lower |
| Flurogestone | | 2529-45-5 | | | |
| Flurothyl | | 333-36-8 | | | |
| Fluroxene | | 406-90-6 | | | |
| Fluspirilene | | 1841-19-6 | | | |

TABLE 3-continued

| API Generic Name | API Chemical Name | CAS No. | Patent Reference | Example of Therapeutic Use | Example of Indication |
|---|---|---|---|---|---|
| flutamide | Propanamide, 2-methyl-N-[4-nitro-3-(trifluoromethyl)phenyl]-[CAS] | 13311-84-7 | U.S. 4,329,364 | Anticancer, hormonal | |
| flutazolam | Oxazolo[3,2-d][1,4]benzodiazepin-6(SH)-one, 10-chloro-11b-(2-fluorophenyl)-2,3,7,11b-tetrahydro-7-(2 hydroxyethyl)-[CAS] | 27060-91-9 | U.S. 3,905,956 | Anxiolytic | |
| fluticasone | Androsta-1,4-diene-17-carbothioic acid, 6,9-difluoro-11,17-dihydroxy-16-methyl-3-oxo-, S-(fluoromethyl) ester, (6Alpha, 11β, 16Alpha, 17Alpha)-[CAS] | 80474-14-2 90566-53-3 | | Formulation, inhalable, solution | Asthma |
| flutoprazepam | 2H-1,4-Benzodiazepin-2-one, 7-chloro-1-(cyclopropylmethyl)-5-(2-fluorophenyl)-1,3-dihydro-[CAS] | 25967-29-7 | GB 1253368 | Anxiolytic | Psychosis, general |
| flutrimazole | 1H-Imidazole, 1-[(2-fluorophenyl)(4-fluorophenyl)phenylmethyl]-[CAS] | 119006-77-8 | EP 352352 | Antifungal | Infection, dermatological |
| Flutropium Bromide | | 63516-07-4 | | | |
| fluvastatin | 6-Heptenoic acid, 7-[3-(4-fluorophenyl)-1-(1-methylethyl)-1H-indol-2-yl]-3,5-dihydroxy-, monosodium salt, [R*,S*-(E)]-(±)-[CAS] | 93957-55-2 93957-54-1 | EP 114027 | Hypolipaemic/ Antiantherosclerosis | Hypercholesterol-aemia |
| fluvoxamine | 1-Pentanone, 5-methoxy-1-[4-(trifluoromethyl)phenyl]-O-(2-aminoethyl)oxime, (E)-[CAS] | 61718-82-9 54739-18-3 | GB 1535226 | Antidepressant | Depression, general Obsessive-compulsive disorder |
| Folic Acid | | 59-30-3 | | | |
| Folinic Acid | | 58-05-9 | | | |
| Fomepizole | | 7554-65-6 | | | |
| fominoben | Benzamide, N-[3-chloro-2-[[methyl[2-(4 morpholinyl)-2-oxoethyl]amino]methyl]phenyl]-[CAS] | 18053-31-1 24600-36-0 | U.S. 3,661,903 | Respiratory stimulant | Eczema, general |
| Fomivirsen | | 144245-52-3 | | | |
| Fomocaine | | 17692-39-6 | | | |
| Fonazine | | 7456-24-8 | | | |
| fondaparinux | Alpha-D-Glucopyranoside, methyl 0-2-deoxy-6-O-sulfo-2-(sulfoamino)-Alpha-D-glucopyranosyl-(1-4)-O-β-D-glucopyranuronosyl-(1-4)-O-2-deoxy-3,6-di-O-sulfo-2-(sulfoamino)-Alpha-D-glucopyranosyl-(1-4)-O-2-O-sulfo-Alpha-L-idopyranuronosyl-(1-4)-2-deoxy-2-(sulfoamino)-,6-(hydrogen sulfate) [CAS] | 104993-28-4 114870-03-0 | | Anticoagulant | Thrombosis, venous |
| Formebolone | | 2454117 | | | |
| formestane | Androst-4-ene-3, 17-dione, 4-hydroxy-[CAS] | 566-48-3 | EP 346953 | Anticancer, hormonal | Cancer, breast |
| Formocortal | | 2825-60-7 | | | |
| formoterol | Formamide, N-[2-hydroxy-5-[1-hydroxy 2-[[2-(4-methoxyphenyl)-1-methylethyl]amino]ethyl]phenyl]-, (R*,R*)-(+/−)-[CAS] | 43229-80-7 73573-87-2 | GB 1415256 | Antiasthma | Asthma |
| fosamprenavir | Carbamic acid, ((1S,2R)-3-(((4-aminophenyl)sulfonyl)(2-methylpropyl)amino)-1-(phenylmethyl)-2-(phosphonooxy)propyl)-C-((3S)-tetrahydro-3-furanyl ester, [CAS] | 226700-81-8 | | Antiviral, anti-HIV | Infection, HIV/AIDS |
| foscarnet | Phosphinecarboxylic acid, dihydroxy-, oxide, trisodium salt [CAS] | 34156-56-4 4428-95-9 63585-09-1 | U.S. 4,839,445 | Antiviral, other | Infection, cytomegalovirus |
| Fosfestrol | | 522-40-7 | | | |
| fosfluconazole | 2,4-difluoro-Alpha,Alpha-bis(1H-1,2,4-triazol-1-ylmethyl)benzyl alcohol, dihydrogen phosphate (ester) | 194798-83-9 | | Antifungal | Infection, fungal, general |
| fosfomycin | Phosphonic acid, (3-methyloxiranyl)-, (2R-cis)-[CAS] | 23155-02-4 26016-98-8 | GB 1223923 | Antibiotic, other | Infection, general |
| fosfomycin trometamol | Phosphonic acid, (3-methyloxiranyl)-, (2R-cis)-, compd. with 2-amino-2-(hydroxymethyl)-1,3-propanediol (1:1)-[CAS] | 78964-85-9 | EP 27597 | Antibiotic, other | Infection, urinary tract |
| Fosfosal | | 6064-83-1 | | | |
| fosinopril | L-Proline, 4-cyclohexyl-1-[[[2-methyl-1-(1-oxopropoxy)propoxy] (4-phenylbutyl)phosphinyl]acetyl]-, (2Alpha,4β)-[CAS] | 88889-14-9 98048-97-6 | EP 63896 | Antihypertensive, renin system | Hypertension, general |

TABLE 3-continued

| API Generic Name | API Chemical Name | CAS No. | Patent Reference | | Example of Therapeutic Use | Example of Indication |
|---|---|---|---|---|---|---|
| fosphenytoin | 2,4-Imidazolidinedione, 5,5-diphenyl-3-[(phosphonooxy)methyl]-[CAS] | 92134-98-0 93390-81-9 | U.S. | 4,260,769 | Antiepileptic | Epilepsy, generalized, tonic-clonic |
| fotemustine | Phosphonic acid, [1-[[[(2-chloroethyl)nitrosoamino]carbonyl]amino] ethyl]-, diethyl ester [CAS] | 92118-27-9 | EP | 117959 | Anticancer, alkylating | Cancer, melanoma |
| Fropenem | | 106560-14-9 | | | | |
| frovatriptan | 1H-Carbazole-6-carboxamide, 2,3,4,9-tetrahydro-3-(methylamino)-, (R)-[CAS] | 158747-02-5 | WO | 9922730 | Antimigraine | Migraine |
| Fructose | | 57-48-7 | | | | |
| Fructose-1,6-diphosphate | | 488-69-7 | | | | |
| FTC | 2(1H)-Pyrimidinone, 4-amino-5-fluoro-1-(2-(hydroxymethyl)-1,3-oxathiolan-5-yl)-(4R) | | | | Antiviral, anti-HIV | Infection, HIV/AIDS |
| FTY-720 | 1,3-Propanediol, 2-amino-2-(2-(4-octylphenyl)ethyl)-,hydrochloride [CAS] | 162359-56-0 | WO | 9408943 | Immunosuppressant | Transplant rejection, general |
| fudosteine | Alanine, 3-((3-hydroxypropyl)thio)-[CAS] | 13189-98-5 | U.S. | 5,047,428 | Antitussive | Cough |
| fulvestrant | Estra-1,3,5(10)-triene-3,17-diol, 7-[9-[(4,4,5,5,5-pentafluoropentyl)sulfinyl]nonyl]-, (7Alpha,17β)-[CAS] | 129453-61-8 | EP | 346014 | Anticancer, hormonal | Cancer, breast |
| fumagiline | 2,4,6,8-Decatetraenedioic acid, mono[5-methoxy-4-[2-methyl-3-(3-methyl-2-butenyl)oxiranyl]-1-oxaspiro[2.5]oct-6-yl] ester, [3R-(3Alpha,4Alpha(2R*,3R*),5β,6β(all-E)]]-[CAS] | 23110-15-8 | | | Protozoacide | Infection, GI tract |
| Fumagillin | | 23110-15-8 | | | | |
| Furaltadone | | 139-91-3 | | | | |
| Furazabol | | 1239-29-8 | | | | |
| Furazolidone | | 67-45-8 | | | | |
| Furazolium Chloride | | 5118-17-2 | | | | |
| Furonazide | | 3460-67-1 | | | | |
| furosemide | Benzoic acid, 5-(aminosulfonyl)-4-chloro-2-[(2-furanylmethyl)amino]-[CAS] | 54-31-9 | | | Formulation, modified-release, other | Hypertension, general |
| Fursultiamine | | 804-30-8 | | | | |
| Furtrethonium | | 7618-86-2 | | | | |
| Fusidic Acid | | 06/03/6990 | | | | |
| G1, YM BioSciences | 1-(5-bromofur-2-yl)-2-bromo-2-nitroethene | | | | Antifungal | Infection, gynaecological |
| G25 | | | WO | 9804252 | Antimalarial | Infection, malaria |
| GABA-A Alpha5 inverse agonist,Mer | | | WO | 0206285 | Cognition enhancer | Alzheimer's disease |
| gabapentin | Cyclohexaneacetic acid, 1-(aminomethyl)-[CAS] | 60142-96-3 | U.S. | 4,152,326 | Antiepileptic | Epilepsy, general |
| gabexate | Benzoic acid, 4-[[6-[(aminoiminomethyl)amino]-1-oxohexyl]oxy]-, ethyl ester, monomethanesulfonate [CAS] | 39492-01-8 56974-61-9 | U.S. | 3,751,447 | GI inflammatory/bowel disorders | Pancreatitis |
| gaboxadol | Isoxazolo[5,4-c]pyridin-3(2H)-one, 4,5,6,7-tetrahydro-[CAS] | 64603-91-4 | CA | 1125288 | Hypnotic/Sedative | Sleep disorder, general |
| Gadobenate Dimeglumine | | 127000-20-8 | | | | |
| Gadobutrol | | 138071-82-6 | | | | |
| Gadodiamide | | 131410-48-5 | | | | |
| Gadopentetic Acid | | 80529-93-7 | | | | |
| Gadoteridol | | 120066-54-8 | | | | |
| Gadoversetamide | | 131069-91-5 | | | | |
| Gadoxetic Acid | | 135326-11-3 | | | | |
| galantamine | (4aS,6R,8aS)-6-Hydroxy-3-methoxy-11-methyl-5,6,9,10,11,12-hexahydro-4aH-benzofuro[3a,3,2-e,f][2]benzazepine | | | | Formulation, modified-release, other | Alzheimer's disease |
| Galanthamine | | 357-70-0 | | | | |
| galarubicin | β-Alanine, 2-[4-[(2,6-dideoxy-2-fluoro-Alpha-L-talopyranosyl)oxy]-1,2,3,4,6,11-hexahydro-2,5,12-trihydroxy-7-methoxy-6,11-dioxo-2-naphthacenyl]-2-oxoethyl ester, [CAS] | 140637-82-7 140637-86-1 | EP | 424899 | Anticancer, antibiotic | Cancer, breast |

TABLE 3-continued

| API Generic Name | API Chemical Name | CAS No. | Patent Reference | Example of Therapeutic Use | Example of Indication |
|---|---|---|---|---|---|
| Gallamine Triethiodide | | 65-29-2 | | | |
| Gallic Acid | | 149-91-7 | | | |
| gallium maltolate | 4H-Pyran-4-one, 3-hydroxy-2-methyl-, gallium complex | | | Anticancer, other | Cancer, myeloma |
| gallium nitrate | Nitric acid, gallium salt [CAS] | 13494-90-1 | U.S. 4,529,593 | Osteoporosh | Hypercalcaemia of malignancy |
| gallopamil | Benzeneacetonitrile, Alpha-[3-[[2-(3,4-dimethoxyphenyl)ethyl]methylamino]propyl]-3,4,5-trimethoxy-Alpha-(1-methylethyl)-[CAS] | 16662-47-8 | GB 1367677 | Antianginal | Angina, general |
| g-Aminobutyric Acid | | 56-12-2 | | | |
| Ganaxolone | | 38398-32-2 | | | |
| ganciclovir | 6H-Purin-6-one, 2-amino-1,9-dihydro-9[[2-hydroxy-1-(hydroxymethyl)ethoxy]methyl]-[CAS] | 107910-75-8 82410-32-0 | EP 49072 | Antiviral, other | Infection, cytomegalovirus |
| ganirelix | [N-Ac-D-NaI,D-pCl-Phe,D-Pal,D-hArg(Et)2,hArg(Et)2,D-Ala]GnRH-[CAS] | 124904-93-4 | EP 312052 | Releasing hormones | infertility, female |
| ganstigmine | Carbamic acid, (2-ethylphenyl)-, (3aS,8aS)-1,2,3,3a,8,8a-hexahydro-1,3a,8-trimethylpyrrolo[2,3-b]indol-5-yl ester, | 223585-99-7 | EP 1023297 | Cognition enhancer | Alzheimer's disease |
| gantofiban | 1-Piperazineacetic acid, 4-[[(5R)-3-[4-[imino[(methoxycarbonyl)amino]methyl]phenyl]-2-oxo-5-oxazolidinyl]methyl]-, ethylester [CAS] | 183547-57-1 | EP 741133 | Antithrombotic | Thrombosis, general |
| garenoxacin | 3-Quinolinecarboxylic acid, 1-cyclopropyl-8-(difluoromethoxy)-7-((1R)2,3-dihydro-1-methyl-1H-isoindol-5-yl)-1,4-dihydro-4-oxo-monomethanesulfonate [CAS] | 223652-82-2 | | Quinolone antibacterial | Infection, respiratory tract, lower |
| gamocestim | 5-73-macrophage inflammatory protein 2Alpha (human gene gro2)-[CAS] | 246861-96-1 | | Radio/chemoprotective | Chemotherapy-induced injury, bonemarrow, neutropenia |
| gatifloxacin | 3-Quinolinecarboxylic acid, 1-cyclopropyl-6-fluoro-1,4-dihydro-8-methoxy-7-(3-methyl-1-piperazinyl)-4-oxo-, (+/−)-[CAS] | 112811-59-3 | EP 230295 | Quinolone antibacterial | Infection, respiratory tract, general |
| Gefarnate | | 51-77-4 | | | |
| gefitinib | 4-Quinazolinamine, N-(3-chloro-4-fluorophenyl)-7-methoxy-6-(3-(4-morpholinyl)propoxy) [CAS] | 184475-35-2 | WO 9633980 | Anticancer, other | Cancer, lung, non-small cell |
| gemcabene | 6,6'-oxybis(2,2-dimethylhexanoate) | 209789-08-2 | | Hypolipaemic/Antitherosclerosis | Hyperlipidaemia, general |
| gemcitabine | Cytidine, 2'-deoxy-2', 2'-difluoro-, [CAS] | 122111-03-9 95058-81-4 | GB 2136425 | Anticancer, antimetabolite | Cancer, pancreatic |
| gemeprost | Prosta-2,13-dien-1-oic acid, 11,15-dihydroxy-16,16-dimethyl-9-oxo-, methyl ester, (2E,11Alpha,13E,15R)-[CAS] | 64318-79-2 | GB 1540427 | Prostaglandin | |
| gemfibrozil | Pentanoic acid, 5-(2,5-dimethylphenoxy)-2,2-dimethyl-[CAS] | 25812-30-0 | U.S. 3,674,836 | Hypolipaemic/Antiatherosclerosis | Hyperlipidaemia, general |
| gemifloxacin | 1,8-Naphthyridine-3-carboxylic acid, 7-(3-(aminomethyl)-4-(methoxyimino)-1-pyrrolidinyl)-1-cyclopropyl-6-fluoro-1,4-dihydro-4-oxo-[CAS] | 175463-14-6 | U.S. 5,869,670 | Quinolone antibacterial | Infection, respitory tract, general |
| gentamicin | Gentamicin [CAS] | 1403-66-3 | | Formulation, implant | Infection, general |
| Gentian Violet | | 548-62-9 | | | |
| Gentiopicrin | | 20831-76-9 | | | |
| Gentisic Acid | | 490-79-9 | | | |
| Gepef rifle | | 18840-47-6 | | | |
| gepirone | 2,6-Piperidinedione, 4,4-dimethyl-1-[4-[4-(2-pyrimidinyl)-1-piperazinyl]butyl]-[CAS] | | | Formulation, modified-release, other | Depression, general |
| gestodene | 18,19-Dinorpregna-4,15-dien-20-yn-3-one, 13-ethyl-17-hydroxy-, (17Alpha)-[CAS] | 109852-02-0 60282-87-3 | GB 1569135 | Formulation, fixed-dose combinations | Contraceptive, female |
| gestodene + ethinylest | 18,19-Dinorpregna-4,15-dien-20-yn-3-one, 13-ethyl-17-hydroxy-, (17Alpha) mixt with 19-Norpregna-1,3,5(10)-trien-20-yne-13,17-diol (17Alpha) | | | Formulation, modified-release, >24 hr | Contraceptive, female |
| Gestonorone Caproate | | 1253-28-7 | | | |

TABLE 3-continued

| API Generic Name | API Chemical Name | CAS No. | Patent Reference | Example of Therapeutic Use | Example of Indication |
|---|---|---|---|---|---|
| Gestrinone | | 16320-04-0 | | | |
| g-Hydroxy-butyrate | | 591-81-1 | | | |
| gimatecan | dimethylethoxy)imino]methyl]-4-ethyl-4-hydroxy-1-12-dihydro-14H-pyrano[3,4':6,7]indolizino[1,2-b]quinoline-3,14(4H)-dione | 292618-32-7 | | Anticancer, other | Cancer, brain |
| Giractide | | 24870-04-0 | | | |
| Gitoxin | | 4562-36-1 | | | |
| GL-406349 | N,N'-Bis[2-[N-[2-(N2,N5-dimethyl-DL-Iysylamino)-ethyl]carbamoyl]1H-indol-6-yl]-1H-indole-2,5-dicarboxamide | | | Antifungal | Infection, fungal, general |
| Glafenine | | 3820-67-5 | | | |
| glatiramer | L-Glutamic acid, polymer with L-alanine, L-lysine and L-tyrosine, [CAS] | 147245-92-9 28704-27-0 | WO | 5800808 Multiple sclerosis treatment | Multiple sclerosis, relapsing-remitting |
| Glibornuride | | 26944-48-9 | | | |
| gliclazide | Benzenesulfonamide, N-[[(hexahydrocyclopenta[c]pyrrol-2(1H)yl]amino]carbonyl]-4-methyl-[CAS] | 21187-98-4 | GB | 1153982 Antidiabetic | Diabetes, Type II |
| glimepiride | 1H-Pyrrole-1-carboxamide, 3-ethyl-2,5-dihydro-4-methyl-N-[2-[4-[[[[(4-methylcyclohexyl)amino]carbonyl]amino]sulfonyl]phenyl]ethyl]-2-oxo-[CAS] | 93479-97-1 | WO | 9303724 Antidiabetic | Diabetes, Type II |
| g-Linolenic Acid | | 506-26-3 | | | |
| glipizide | Pyrazinecarboxamide, N-[2-[4-[[[(cyclohexylamino)carbonyl]amino]sulfonyl]phenyl]ethyl]-5-methyl-[CAS] | 29094-61-9 | U.S. | 3,669,966 Antidiabetic | |
| gliquidone | Benzenesulfonamide, N-[(cyclohexylamino)carbonyl]-4-[2-(3,4-dihydro-7-methoxy-4,4-dimethyl-1,3-dioxo-2(1H)-isoquinolinyl)ethyl]-[CAS] | 33342-05-1 | GB | 1277847 Antidiabetic | Diabetes, general |
| glisolamide | 3-Isoxazolecarboxamide, N-[2-[4-[[[(cyclohexylamino)carbonyl]amino]sulfonyl]phenyl]ethyl]-5-methyl-[CAS] | 24477-37-0 | | Antidiabetic | Diabetes, general |
| Glisoxepid | | 25046-79-1 | | | |
| Glucametacin | | 52443-21-7 | | | |
| Glucoheptonic Acid | | 87-74-1 | | | |
| Gluconic Acid | | 526-95-4 | | | |
| glucosamine | D-Glucose, 2-amino-2-deoxy-, [CAS] | 29031-19-4 3416-24-8 | DE | 1953689 Antiarthritic, other | Arthritis, osteo |
| Glucosulfone | | 554-18-7 | | | |
| glufosfamide | β-D-Glucopyranose, 1-(N,N'-bis(2-chloroethyl)phosphorodiamidate)-[CAS] | 132682-98-5 | DE | 3835772 Anticancer, alkylating | Cancer, general |
| Glutamic Acid | | 56-86-0 | | | |
| Glutaraldehyde | | 111-30-8 | | | |
| Glutethimide | | 77-21-4 | | | |
| Giyburide | | 10238-21-8 | | | |
| Glybuthiazol(e) | | 535-65-9 | | | |
| Glybuzole | | 1492-02-0 | | | |
| Glycerol | | 56-81-5 | | | |
| Glycocyamine | | 352-97-6 | | | |
| Glycol Salicylate | | 87-28-5 | | | |
| Glyconiazide | | 3691-74-5 | | | |
| Glycopyrrolate | | 596-51-0 | | | |
| Glyhexamide | | 451-71-8 | | | |
| Glymidine | | 339-44-6 | | | |
| Glypinamide | | 1228-19-9 | | | |
| GMDP | N-acetylglucosaminyl-N-acetylmuramyl dipeptide | | | Anti-infective, | Infection, general |
| Gold Sodium Thiomalate | | 12244-57-4 | | | |
| Gold Sodium Thiosulfate | | 10233-88-2 | | | |
| goserelin | Luteinizing hormone-releasing factor (pig), 6-[O-(1,1-dimethylethyl)-D-serine]10-deglycinamide-, 2-(aminocarbonyl)hydrazide [CAS] | 65807-02-5 | U.S. | 4,100,274 Releasing hormones | Cancer, prostate |
| GPI-1485 | L-Proline, 1-(3,3-dimethyl-1,2-dioxopentyl)-, 3-(3-pyridinyl)propyl ester [CAS] | 186452-09-5 | | Antiparkinsonian | Parkinson's disease |
| GPI-5693 | 2-(Phosphonomethyl)pentanedioic acid | | U.S. | 5,672,592 Anagesic, other | Pain, neuropathic |

TABLE 3-continued

| API Generic Name | API Chemical Name | CAS No. | Patent Reference | Example of Therapeutic Use | Example of Indication |
|---|---|---|---|---|---|
| Graftskin | | | | | |
| granisetron | 1H-Indazole-3-carboxamide, 1-methyl-N-(9-methyl-9-azabicycio[3.3.1]non-3-yl)-, endo-[CAS] | 107007-99-8 109889-09-0 | EP 200444 | Antiemetic | Chemotherapy-induced nausea and vomiting |
| Grepafloxacin | | 119914-60-2 | | | |
| griseofulvin | Spiro[benzofuran-2(3H), 1'-[2]cyclohexane]-3,4-dione, 7-chloro-2',4,6-trimeth-oxy-6'methyl-, (1'S-trans) [CAS] | 126-07-8 | | Formulation, dermal, topical | Infection, dermatological |
| Guaiacol | | 90-05-1 | | | |
| Guaiapate | | 852-42-6 | | | |
| Guaiazulene | | 489-84-9 | | | |
| Guaifenesin | | 93-14-1 | | | |
| guaimesal | 4H-1,3-Benzodioxin-4-one, 2-(2-methoxyphenoxy)-2-methyl-[CAS] | 81674-79-5 | GB 2098201 | Anti-inflammatory | |
| Guamecycline | | 16545-11-2 | | | |
| Guanabenz | | 5051-62-7 | | | |
| Guanadrel | | 40580-59-4 | | | |
| Guanethidine | | 55-65-2 | | | |
| Guanfacine | | 29110-47-2 | | | |
| Guanoxabenz | | 24047-25-4 | | | |
| Guanoxan | | 2165-19-7 | | | |
| gugulipid | Pregna-4,17(20)-diene-3,16-dione [CAS] | 95975-55-6 | EP 447706 | Hypolipaemic/ Antiantherosclerosis | |
| Gusperimus | | 104317-84-2 | | | |
| GW-280430A | (Z)-2-Chlorofumaric acid 1-[3-[-[6,7-dimethoxy-2(S)-methyl-1 (R)-(3,4,5-trimethoxybenzyl)-1,2,3,4-tetrahydroisoquinolinium-2-yl]propyl] | | | Muscle relaxant | Anaesthesia, adjunct |
| GW-320659 | [2S,3S,5R]-2-[3,5-difluorophenyl]-3,5-dimethyl-2-morpholinol | | | Anorectic/Antiobesity | Obesity |
| GYKI-16084 | (+)-R-2-{3-[N-(2-Benzo[1,4]dioxanylmethyl)amino]-1-propyl}-3(2H)-pyndazinone hydrochloride | | U.S. 6,194,411 | Prostate disorders | Benign prostatic hyperplasia |
| Hachimycin | | 1394-02-1 | | | |
| Halazepam | | 23092-17-3 | | | |
| Halcinonide | | 3093-35-4 | | | |
| halobetasol | Pregna-1,4-diene-3,20-dione, 21-chloro-6,9-difluoro-11-hydroxy-16-methyl-17-(1-oxopropoxy)-, (6Alpha,11β,16β)-[CAS] | 66852-54-8 | U.S. 4,619,921 | Antipsoriasis | Psoriasis |
| halofantrine | 9-Phenanthrenemethanol, 1,3-dichloro-Alpha-[2-(dibutylamino)ethyl]-6-(trifluoromethyl)-[CAS] | 36167-63-2 69756-53-2 | EP 138374 | Antimalarial | Infection, malaria |
| halometasone | Pregna-1,4-diene-3,20-dione, 2-chloro-6,9-difluoro-11,17,21-trihydroxy-16-methyl-, (6Alpha,11β,16Alpha)-[CAS] | 50629-82-8 | U.S. 4,076,737 | Antipruritic/inflamm, allergic | |
| Haloperidol | | 52-86-8 | | | |
| Halopredone | | 57781-14-3 | | | |
| Haloprogin | | 777-11-7 | | | |
| Halopropane | | 679-84-5 | | | |
| Halothane | | 151-67-7 | | | |
| Haloxazolam | | 59128-97-1 | | | |
| harkoseride | 2(R)-Acetamido-N-benzyl-3-methoxypropionamide | | WO 9733861 | Antiepileptic | Epilepsy, general |
| HE-2000 | 16Alpha-Bromo-3β-hydroxy-5Alpha-androstane-17-one | | | Antiviral, anti-HIV | Infection, HIV/AIDS |
| Healos | | | WO 9714376 | Musculoskeletal | Regeneration, bone |
| Hematoporphyrin | | 14459-29-1 | | | |
| Hepronicate | | 7237-81-2 | | | |
| Heptabarbital | | 509-86-4 | | | |
| Heptaminol | | 372-66-7 | | | |
| Hetacillin | | 3511-16-8 | | | |
| Hetastarch | | 9004-62-0 | | | |
| Hexachlorophene | | 70-30-4 | | | |
| Hexadimethrine Bromide | | 28728-55-4 | | | |
| Hexafluorenium Bromide | | 317-52-2 | | | |
| Hexamethonium | | 60-26-4 | | | |
| Hexamidine | | 3811-75-4 | | | |
| Hexapropymate | | 358-52-1 | | | |
| Hexedine | | 5980-31-4 | | | |

TABLE 3-continued

| API Generic Name | API Chemical Name | CAS No. | Patent Reference | Example of Therapeutic Use | Example of Indication |
|---|---|---|---|---|---|
| Hexestrol | | 84-16-2 | | | |
| Hexestrol Bis(b-diethylamino-ethyl ether) | | 2691-45-4 | | | |
| Hexethal | | 144-00-3 | | | |
| Hexetidine | | 141-94-6 | | | |
| Hexobarbital | | 56-29-1 | | | |
| Hexobendine | | 54-03-5 | | | |
| Hexocyclium Methyl Sulfate | | 115-63-9 | | | |
| Hexoprenaline | | 3215-70-1 | | | |
| Hextend | Hextend [CAS] | 235746-51-7 | U.S. 5,407,428 | Plasma substitute | Surgery adjunct |
| Hexylcaine | | 532-76-3 | | | |
| HF-0299 | 11b-hydroxy androstenedione | | | Osteoporosis treatment | Osteoporosis |
| HGP-2 | Benzeneacetic acid, 4-[2-hydroxy-3-[(1-methylethyl)amino]propoxy]-, 2-tricyclo[3.3.1.13,7]dec-1-ylethyl ester, (2Z)-2-butenedioate (1:1) (salt) [CAS] | 121009-31-2 | | Antiglaucoma | Glaucoma |
| HGP-6 | 8-Azoniabicyclo[3.2.1]octane, 3-(3-ethoxy-1,3-dioxo-2-phenylpropoxy)-8,8-dimethyl-, (3-endo)-, methyl sulfate [CAS] | 113932-41-5 | | Antiepileptic | Epilepsy, general |
| hidrosmin | Hydrosmin-[CAS] | 120250-44-4 | | Vasoprotective, systemic | |
| histamine | histamine | 51-45-6 | EP 0493468 | Anticancer, immunological | Cancer, melanoma |
| Histapyrrodine | | 493-80-1 | | | |
| histrelin | Luteinizing hormone-releasing factor (pig), 6-[1-(phenylmethyl)-D-histidine]-9-(N-ethyl-L-prolinamide)-10-deglycinamide-[CAS] | 76712-82-8 | EP 217659 | Releasing hormones | Precocious puberty |
| HM-101 | HM 101 [CAS] | 217311-70-1 | | Osteoporosis treatment | Osteoporosis |
| HMN-214 | (E)-4-[2-[2-(p-methoxybenzenesulfonamide)-phenyl]ethenyl]pyridine-1-oxide | | | Anticancer, other | Cancer, general |
| Homatropine | | 87-00-3 | | | |
| Homocamfin | | 535-86-4 | | | |
| Homo-chlorcyclizine | | 848-53-3 | | | |
| Hopantenic Acid | | 18679-90-8 | | | |
| HP-228 | Glycinamide, N-acetyl-L-norleucyl-L-glutaminyl-L-histidyl-D-phenylalanyl-L-arginyl-D-tryptophyl-[CAS] | 172617-89-9 | EP 759770 | Analgesic, other | Pain, post-operative |
| Huperzine A | | 102518-79-6 | | | |
| hyaluronan | Hyaluronic acid [CAS] | 9004-61-9 | | Formulation, other | Restenosis |
| Hycanthone | | 3105-97-3 | | | |
| Hydnocarpic Acid | | 459-67-6 | | | |
| Hydralazine | | 86-54-4 | | | |
| Hydrastine | | 118-08-1 | | | |
| Hydrastinine | | 6592-85-4 | | | |
| Hydrochloro-thiazide | | 58-93-5 | | | |
| hydrocodone | Morphinan-6-one, 4,5-epoxy-3-hydroxy-17-methyl-,(5Alpha)-[CAS] | 466-99-9 | | Formulation, modified-release, other | Pain, general |
| | | 125-29-1 | | | |
| Hydrocortamate | | 76-47-1 | | | |
| hydrocortisone | Pregn-4-ene-3,20-dione, 21-(acetyloxy) 11-hydroxy-17-(1-oxopropoxy)-, (11β)-[CAS] | 74050-20-7 | DE 2826257 | Dermatological | Unspecified |
| | | 50-23-7 | | | |
| hydrocortisone butyrate propio | Pregn-4-ene-3,20-dione, 11-hydroxy-17-(1-oxobutoxy)-21-(1-oxopropoxy)-, (11β)-[CAS] | 72590-77-3 | DE 2910899 | Antipruritic/inflamm, allergic | |
| Hydroflume-thiazide | | 135-09-1 | | | |
| hydromorphone | Morphinan-6-one,4,5-epoxy-3-hydroxy-17-methyl-,(5Alpha)-, mixt with acetamide, N-(4-hydroxyphenyl)-, mixt with morphinan-6-one,17-(cyclopropylmethyl)-4,5-epoxy-3,14-dihydroxy-, (5Alpha)- | 103-90-2 | | Formulation, fixed-dose combinations | Pain, general |
| | | 16590-41-3 | | | |
| | | 466-99-9 | | | |
| Hydroquinidine | | 1435-55-8 | | | |
| Hydroquinine | | 522-66-7 | | | |
| Hydroquinone | | 123-31-9 | | | |
| Hydroxocob-alamin | | 13422-51-0 | | | |

TABLE 3-continued

| API Generic Name | API Chemical Name | CAS No. | Patent Reference | | Example of Therapeutic Use | Example of Indication |
|---|---|---|---|---|---|---|
| Hydroxy-amphetamine | | 1518-86-1 | | | | |
| Hydroxy-chloroquane | | 118-42-3 | | | | |
| Hydroxydione | | 53-10-1 | | | | |
| Hydroxy-pethidine | | 468-56-4 | | | | |
| Hydroxy-phenamate | | 50-19-1 | | | | |
| Hydroxypropyl Cellulose | | 9004-64-2 | | | | |
| Hydroxystil-bamidine | | 495-99-8 | | | | |
| Hydroxy-tetraceine | | 490-98-2 | | | | |
| Hydroxyzine | | 68-88-2 | | | | |
| Hylan G-F 20 | | | | | | |
| Hymecromone | | 90-33-5 | | | | |
| hyoscyamine | benzeneacetic acid, Alpha(hydroxymethyl)-, 8-methyl-B-azabicyclo [3.2.1.]oct-3-yl ester, [3(S)-endo], | 101-31-5 | | | Formulation, oral, orally-disintegrating | Ulcer, GI, general |
| hypericin | Phenanthro[1,10,9,8-opqra]perylene-7,14-dione, 1,3,4,6,8,13-hexahydroxy-10,11-dimethyl-[CAS] | 548-04-9 | | | Anticancer, other | Cancer, brain |
| IACFT | | 180468-34-2 | | | | |
| ibandronic acid | Phosphonic acid, [1-hydroxy-3-(methylpentylamino)propylidene] bis-[CAS] | 114084-78-5 | EP | 252504 | Osteoporosis treatment | Hypercalcaemia of malignancy |
| ibopamine | Propanoic acid, 2-methyl-, 4-12-(methylamino)ethyl]-1,2-phenylene ester-[CAS] | 66195-31-1 | GB | 1551661 | Cardiostimulant | Heart failure |
| ibopamine | Propanoic acid, 2-methyl-, 4-[2-(methylamino)ethyl]-12-phenylene ester-[CAS] | 66195-31-1 | | | Formulation, mucosal, topical | Surgery adjunct |
| Ibritumomab Tiuxetan | | 206181-63-7 | | | | |
| ibrolipim | Phosphonic acid, [[4-[[(4-bromo-2-cyanophenyl)amino]carbonyl]phenyl] methyl.).-, diethyl ester [CAS] | 133208-93-2 | EP | 402033 | Hypolipaemic/Antiatherosclerosis | Hypertri-glyceridaemia |
| ibudilast | 1-Propanone, 2-methyl-1-[2-(1-methylethyl)pyrazolo[1,5-a]pyridin-3-yl]-[CAS] | 50847-11-5 | EP | 215438 | Antiasthma | Asthma |
| Ibufenac | | 1553-60-2 | | | | |
| ibuprofen piconol | Benzeneacetic acid, Alpha-methyl-4-(2-methylpropyl)-, 2-pyridinylmethyl ester [CAS] | 64622-45-3 | DE | 2658610 | Antipruritic/inflamm, non-allergic | Eczema, contact |
| ibuprofen | Benzeneacetic acid, Alpha-methyl-4-(2-methylpropyl)-[CAS] | 15687-27-1 | | | Formulation, modified-release, other | Inflammation, general |
| Ibuproxam | | 53648-05-8 | | | | |
| ibutilide | Methanesulfonamide, N-[4-[4-(ethylheptylamino)-1-hydroxybutyl]phenyl]-, (+/−)-, [CAS] | 122647-31-8 122647-32-9 | JP | 60239458 | Antiarrhythmic | Fibrillatioin, atrial |
| ICA-17043 | | | U.S. | 6,288,122 | Antisickling | Anaemia, sickle cell |
| icodextrin | Dextrin-[CAS] | 9004-53-9 | | | Urological | Renal failure |
| idarubicin | 5,1 2-Naphthacenedione, 9-acetyl-7-[(3-amino-2,3,6-trideoxy-Alpha-L-lyxo-hexopyranosyl)oxy]-7,8,9,10-tetrahydro-6,9,11-trihydroxy-, (7S-cis)-[CAS] | 58957-92-9 86189-66-4 | U.S. | 4,471,052 | Anticancer, antibiotic | Cancer, leukaemia, acute lymphocytic |
| Idazoxan | | 79944-58-4 | | | | |
| IdB-1016 | 2-(2,3-dihydro-2-(4-hydroxy-3-methoxyphenyl)-3-(hydroxymethyl)-1,4-benzodioxin-6-yl)-2,3-dihydro-3,5,7-trihydroxy-4H-1-benzopyran-4-one phosphatidylcholine complex | 134499-06-2 | EP | 209038 | Anticancer, hormonal | Cancer, ovarian |
| idebenone | 2,5-Cyclohexadiene-1,4-dione, 2-(10-hydroxydecyl)-5,6-dimethoxy-3-methyl-[CAS] | 58186-27-9 | EP | 58057 | Neuroprotective | Ischaemia, cerebral |
| IDN-5109 | 4-Hexenoic acid, 3-[[(1,1-dimethylethoxy)carbonyl]amino]-2-hydroxy-5-methyl-, (3aS,4R,7R,8aS,9S,10aR,12aS,12bR,13S,13aS)-7,12a-bis(acetyloxy)-13-(benzoyloxy)-3a,4,7,8,8a,9,10,10a,12,12a,12b,13- | 186348-05-0 | U.S. | 5,264,591 | Anticancer, other | Cancer, colorectal |

TABLE 3-continued

| API Generic Name | API Chemical Name | CAS No. | Patent Reference | Example of Therapeutic Use | Example of Indication |
|---|---|---|---|---|---|
| | dodecahydro-9-hydroxy-5,8a,14,14-tetramethyl-2,8-dioxo-6,13a-methano-13aH-oxeto [2",3",5',6'] benzo[1,2:4,5] cyclodeca [1,2-d] dioxyl-4-yl ester, 2R,3S) [CAS} | | | | |
| Idoxifene | | 116057-75-1 | | | |
| idraparinux | Alpha-D-Glucopyranoside, methyl O-2,3,4-tri-O-methyl-6-O-sulfo-Alpha-D-glucopyranosyl-(1-4)-O-2,3-di-O-methyl β-D-glucopyranuronosyl-(1-4)-O-2,3,6-tri-O-sulfo-Alpha-D-glucopyranosyl-(1-4)-O-2,3-di-O-methyl-Alpha-L-idopyranuronosyl-(1-4)-, tris(hydrogen sulfate) nonasodium salt [CAS] | 149920-56-9 | AU | 698456 Antithrombotic | Thrombosis, venous |
| idrocilamide | 2-Propenamide, N-(2-hydroxyethyl)-3-phenyl-[CAS] | 6961-46-2 | U.S. | 3,659,014 Anti-inflammatory, topical | |
| ifenprodil | (7)-2-(4-benzyl piperidino)-1-p-hydroxyphenylpropanol tartrate | 23210-58-4 23210-56-2 | U.S. | 3,509,164 Neuroprotective | |
| ifosfamide | 2H-1,3,2-Oxazaphosphonn-2-amine, N,3-bis(2-chloroethyl)tetrahydro-,2-oxide [CAS] | 3778-73-2 | U.S. | 3,732,340 Anticancer, alkylating | Cancer, lung, general |
| iguratimod | N-[3-(Formylamino)-4-oxo-6-phenoxy-4H-chromen-7-yl] methanesulfonamide | 123663-49-0 | DE | 3834204 Antiarthritic, other | Arthritis, rheumatoid |
| ilaprazole | 1H-Benzimidazole, 2-(((4-methoxy-3-methyl-2-pyridinyl) methyl)sulflnyl)-5-(1H-pyrrol-1-yl)-[CAS] | 172152-36-2 | U.S. | 5,703,097 Antiulcer | Ulcer, GI, general |
| ilomastat | Butanediamide, N4-hydroxy-N1-(1-(1H-indol-3-ylmethyl)-2-(methylamino)-2-oxoethyl)-2-(2-methylpropyl)-, (S-(R*, S*))-[CAS] | 142880-36-2 | U.S. | 5,892,112 COPD treatment | Emphysema, smoking-related |
| iloperidone | Ethanone, 1-[4-[3-[4-(6-fluoro-1,2-benzisoxazol-3-yl)-1-piperidinyl]propoxy]-3-methoxyphenyl]-[CAS] | 133454-47-4 | U.S. | 5,776,963 Neuroleptic | Schizophrenia |
| iloprost trometamol | Pentanoic acid, 5-[hexahydro-5-hydroxy-4-(3-hydroxy-4-methyl-1-octen-6-ynyl)-2(1H)-pentalenylidene]-[CAS] | 78919-13-8 | DE | 3,417,638 Prostaglandin | Peripheral vascular disease |
| ILX23-7553 | 1Alpha,25-Hydroxy-16-yne vitamin D3 | | | Anticancer, other | Cancer, general |
| imatinib | 4-((Methyl-1-piperazinyl)methyl)-N-[4-methyl-3-[[4-(3-pyridinyl)-2-pyrimidinyl]amino]-phenyl]benzamide methanesulfonate | 152459-95-5 | U.S. | 5,521,184 Anticancer, other | Cancer, leukaemia, chronic myelogenous |
| imidapril | 4-Imidazolidinecarboxylic acid, 3-[2-[[1-(ethoxycarbonyl)-3-phenylpropyl]amino] 1-oxopropyl]-1-methyl-2-oxo-, [4S-[3[R*(R*)],4R*]]-[CAS] | 89371-37-9 89396-94-1 | EP | 95163 Antihypertensive, renin system, Musculoskeletal | Hypertension, general, Cachexia |
| imidazole salicylate | Benzoic acid, 2-hydroxy-, compd. with 1H-imidazole (1:1) [CAS] | 36364-49-5 | U.S. | 4,329,340 Anti-inflamatory | Pain, general |
| imipenem | 1-Azabicyclo[3.2.0]hept-2-ene-2-carboxylic acid, 6-(1-hydroxyethyl)-3-[[2-[(iminomethyl)amino]ethyl]thio]-7-oxo-, [5R-[5Alpha,6Alpha(R* )]]-[CAS] | 64221-86-9 74431-23-5 81129-83-1 | GB | 1570990 Beta-lactam antibiotic | infection, general |
| Imipramine | | 50-49-7 | | | |
| Imipramine N-Oxide | | 6829-98-7 | | | |
| imiquimod | 1H-Imidazo[4,5-c]quinolin-4-amine, 1-(2-methylpropyl)-[CAS] | 99011-02-6 | EP | 145340 Antiviral, other | Infection, human papilloma virus |
| Imolamine | | 318-23-0 | | | |
| implitapide | Benzeneacetamide, Alpha-cyclopentyl-4-((2,4-dimethyl-9H-pyrido(2,3-b)indol-9-yl)methyl)-N-((1R)-2-hydroxy-1-phenylethyl)- (AlphaS)-[CAS] | 177469-96-4 | EP | 705831 Hypolipaemic/Antiatherosclerosis | Atherosclerosis |
| Improsulfan | | 13425-98-4 | | | |
| Inaperisone | | 99323-21-4 | | | |
| incadronate | Phosphonic acid, [(cycloheptylamino)methylene]bis-, [CAS] | 138330-18-4 | | Musculoskeletal | Hypercalcaemia of malignancy |
| Incadronic Acid | | 124351-85-5 | | | |
| Indalpine | | 63758-79-2 | | | |
| Indanazoline | | 40507-78-6 | | | |
| indapamide | 4-chloro-N-(2-methylindolin-1-yl)-3-sulfamoylbenzamide | 26807-65-8 | GB | 1203691 Antihypertensice, diuretic | Hypertension, general |
| Indecainide | | 74517-78-5 | | | |
| indeloxazine | Morptioline, 2-[(1H-inden-7-yloxy)methyl]-[CAS] | 60929-23-9 65043-22-3 | JP | 52083773 Cognition enhancer | Alzheimer's disease |

TABLE 3-continued

| API Generic Name | API Chemical Name | CAS No. | Patent Reference | Example of Therapeutic Use | Example of Indication |
|---|---|---|---|---|---|
| Indeloxazine | | 65043-22-3 | | | |
| indenolol | 2-Propanol, 1-[1H-inden-4(or 7)-yloxy]-3-[(1-methylethyl)amino]-[CAS] | 30190-87-5 60607-68-3 68906-88-7 | GB | 1290343 Antihypertensive, adrenergic | |
| indinavir | D-erythro-Pentonamide, 2,3,5-trideoxy-N-(2,3-dihydro-2-hydroxy-1H-inden-1-dimethylethyl)amino)carbonyl)-4-(3-pyridinylmethyl)-1-piperazinyl)-2-(phenylmethyl), [1S-[1Alpha(R*),2Alpha]]-, [CAS] | 150378-17-9 157810-81-6 | EP | 0541168 Antiviral, anti-HIV | Infection, HIV/AIDS |
| indiplon | Acetamide, N-methyl-N-(3-(3-(2-thienylcarbonyl)pyrazolo(1,5-a)pyrimidin-7-yl)phenyl)-[CAS] | 325715-02-4 | US | 6,399,621 Hypnotic/Sedative | Insomnia |
| indisetron | 1H-Indazole-3-carboxamide, N-(3,9-dimethyl-3,9-diazabicyclo(3.3.1)non-7-yl)-, diendo-[CAS] | 160472-97-9 | | Antiemetic | Nausea and vomiting, general |
| indisulam | 1,4-Benzenedisulfonamide, N-(3-chloro-IH-indoi-7-yl)-[CAS] | 165668-41-7 | | Anticancer, other | Cancer, lung, non-small cell |
| Indobufen | | 63610-08-2 | | | |
| Indocyanine Green | | 3599-32-4 | | | |
| indometacin | 1H-Indole-3-acetic acid, 1-(4-chlorobenzoyl)-5-methoxy-2-methyl-[CAS] | 53-86-1 | | Formulation, modified-release, other | Inflammation, general |
| Indoprofen | | 31842-01-0 | | | |
| indoramin | Benzamide, N-[1-[2-(1H-indol-3-yl)ethyl]-4-pipendinyl]-[CAS] | 26844-12-2 38821-52-2 | GB | 1218570 Antihypertensive, adrenergic | |
| Inducterm | | | U.S. | 5,993,810 Labour inducer | Labour, induction |
| Infliximab | | 170277-31-3 | | | |
| Inosine Pranobex | | 36703-88-5 | | | |
| Inositol | | 87-89-8 | | | |
| Inositol Niacinate | | 6556112 | | | |
| Iobenguane | | 80663-95-2 | | | |
| Iobenzamic Acid | | 3115057 | | | |
| Iobitridol | | 136949-58-1 | | | |
| Iocarmic Acid | | 10397-75-8 | | | |
| Iocetamic Acid | | 16034-77-8 | | | |
| Iodamide | | 440-58-4 | | | |
| Iodine | Iodine [CAS] | 7553-56-2 | | Formulation, oral, other | Fibrocystic breast disorder |
| Iodipamide | | 606-17-7 | | | |
| Iodixanol | | 92339-11-2 | | | |
| Iodoalphionic Acid | | 577-91-3 | | | |
| iodochlor-hydroxyquin | 5-Chloro-7-iodo-8-quinolinol | 130-26-7 | | Cognition enhancer | Alzheimer's disease |
| Iodoform | | 75-47-8 | | | |
| Iodopyracet | | 300-37-8 | | | |
| Iodopyrrole | | 87-58-1 | | | |
| Iodoquinol | | 83-73-8 | | | |
| Iofetamine 123I | | 75917-92-9 | | | |
| Ioglycamic Acid | | 2618-25-9 | | | |
| Iohexol | | 66108-95-0 | | | |
| Iomeglamic Acid | | 25827-76-3 | | | |
| Iomeprol | | 78649-41-9 | | | |
| Iopamidol | | 60166-93-0 | | | |
| Iopanoic Acid | | 96-83-3 | | | |
| Iopentol | | 89797-00-2 | | | |
| Iophendylate | | 99-79-6 | | | |
| Iophenoxic Acid | | 96-84-4 | | | |
| Iopromide | | 73334-07-3 | | | |
| Iopronic Acid | | 41473-08-9 | | | |
| Iopydol | | 5579-92-0 | | | |
| Iopydone | | 5579-93-1 | | | |
| Iothalamic Acid | | 2276-90-6 | | | |
| Iotrolan | | 79770-24-4 | | | |

TABLE 3-continued

| API Generic Name | API Chemical Name | CAS No. | Patent Reference | | Example of Therapeutic Use | Example of Indication |
|---|---|---|---|---|---|---|
| Ioversol | | 87771-40-2 | | | | |
| Ioxaglic Acid | | 59017-64-0 | | | | |
| Ioxilan | | 107793-72-6 | | | | |
| IP-751 | (3R,4R)-(delta6)-THC-DMH-11-oic acid | | WO | 9401429 | Analgesic, other | Pain, neuropathic |
| Ipidacrine | | 62732-44-9 | | | | |
| IPL-576092 | Stigmastan-15-one, 22,29-epoxy-3,4,6,7,29-pentahydroxy-, (3Alpha,4β,5Alpha,6Alpha,7β,14β,22S)-[CAS] | 137571-30-3 | U.S. | 6,046,185 | Antiasthma | Asthma |
| Ipodate | | 5587-89-3 | | | | |
| ipratropium bromide | | 66985-17-9 22254-24-6 | | | Formulation, inhalable, solution | Chronic obstructive pulmonary disease |
| ipratropium | (endo,syn)-(±)-3-(3-Hydroxy-1-oxo-2-phenylpropoxy)-8-methyl-8-(1-methylethyl)-8-azoniabicyclo(3.2.1)octane | | | | Formulation, inhalable, topical | Asthma |
| iprazochrome | Hydrazinecarboxamide, 2-[1,2,3,6-tetrahydro-3-hydroxy-1-(1-methylethyl)-6-oxo-5H-indol-5-ylidene]-[CAS] | 7248-21-7 | | | Haemostatic | |
| ipriflavone | 4H-1-Benzopyran-4-one, 7-(1-methylethoxy)-3-phenyl-[CAS] | 35212-22-7 | EP | 214647 | Osteoporosis treatment | Osteoporosis |
| Iprindole | | 5560-72-5 | | | | |
| Iproclozide | | 3544-35-2 | | | | |
| Iproniazid | | 54-92-2 | | | | |
| Ipsapirone | | 95847-70-4 | | | | |
| irbesartan | 2-n-butyl-4-spirocyclopentane-1-[((2'-tetrazol-5-yl)biphenyl-4-yl)methyl]-2-imidazolin-5-one | 138402-11-6 | WO | 9114679 | Antihypertensive, renin system | Hypertension, general |
| IRFI-042 | Butanedioic acid, mono[2-[2-(acetylthio)ethyl]-2,3-dihydro-4,6,7-trimethyl-5-benzofuranyl] ester, (+/−)-[CAS] | 134867-62-2 | U.S. | 5,114,966 | Cardiovascular | Antherosclerosis |
| IRFI-165 | N-Cyclopentyl-1-methylimidazo[1,2-a]quinoxalin-4-amine | 191349-26-5 | EP | 865442 | Antidepressant | Depression, general |
| Iridomyrmecin | | 485-43-8 | | | | |
| irindalone | -Imidazolidinone, 1-[2-[4-[3-(4-fluorophenyl)-2,3-dihydro-1H-inden-1-yl]-1-piperazinyl]ethyl]-, (1R-trans)-[CAS] | 104113-57-7 96478-43-2 | EP | 183349 | Antidepressant | Depression, general |
| Irinotecan | | 97682-44-5 | | | | |
| irofulven | Spiro[cyclopropane-1,5-[5H]inden]-7'(6'H)-one, 6'-hydroxy-2',4',6-trimethyl, (R)-[CAS] | 125392-76-9 | U.S. | 5,563,176 | Anticancer, other | Cancer, prostate |
| Iron Sorbitex | | 1338-16-5 | | | | |
| irsogladine | 1,3,5-Triazine-2,4-diamine, 6-(2,5-dichlorophenyl)-[CAS] | 57381-26-7 57381-28-9 57381-33-6 | U.S. | 4,657,907 | Antihypertensive, diuretic | Hypertension, general |
| IS-741 | Cyclohexanecarboxamide, N-[2-[(ethylsulfonyl)amino]-5-(trifluoromethyl)-3-pyridinyl]-[CAS] | 141283-87-6 | EP | 465913 | GI inflammatory/bowel disorders | Pancreatitis |
| isaglitazone | 2,4-Thiazolidinedione, 5-[[6-[(2-fluorophenyl)methoxy]-2-naphthalenyl]methyl]-[CAS] | 161600-01-7 | U.S. | 5594016 | Antidiabetic | Diabetes, Type II |
| ISAtx-247 | | | NZ | 502362 | Immunosuppressant | Transplant rejection, general |
| Isbogrel | | 89667-40-3 | | | | |
| isepamicin | D-Streptamine, O-6-amino-6-deoxy-Alpha-D-glucopyranosyl-(1-4)-O-[3-deoxy-4-C-methyl-3-(methylamino)-β-L arabinopyranosyl-(1-6)1-N1-(3-amino-2-hydroxy-1-oxopropyl)-2-deoxy-, (S)-[CAS] | 58152-01-5 58152-03-7 | U.S. | 4,029,882 | Aminoglycoside antibiotic | Infection, fungal, general |
| Isoaminile | | 77-51-0 | | | | |
| Isobutyl p-Aminobenzoate | | 94-14-4 | | | | |
| Isocarboxazid | | 59-63-2 | | | | |
| isoconazole | 1-[2-(2-6-dichlorobenzyloxy)-2-(2-,4-dichlorophenyl)ethyl] | 24168-96-5 27523-40-6 | GB | 1244530 | Antifungal | Infection, fungal, general |
| Isoetharine | | 530-08-5 | | | | |
| isofloxythepin | 1-Piperazineethanol, 4-[3-fluoro-10,11-dihydro-8-(1-methylethyl)dibenzo[b,f]thiepin-10-yl]-[CAS] | 106819-39-0 106819-41-4 70931-18-9 | GB | 2010843 | Neuroleptic | |
| isoflurane | Ethane, 2-chloro-2-(difluoromethoxy)-1,1,1-trifluoro-[CAS] | 26675-46-7 | U.S. | 3,535,388 | Anaesthetic, inhalation | Anaesthesia |
| Isoflurophate | | 55-91-4 | | | | |

TABLE 3-continued

| API Generic Name | API Chemical Name | CAS No. | Patent Reference | | Example of Therapeutic Use | Example of Indication |
|---|---|---|---|---|---|---|
| Isoladol | | 530-34-7 | | | | |
| Isomethadone | | 466-40-0 | | | | |
| Isometheptene | | 503-01-5 | | | | |
| Isoniazid | | 54-85-3 | | | | |
| Isonixin | | 57021-61-1 | | | | |
| Isopromethazine | | 303-14-0 | | | | |
| Isopropamide Iodide | | 71-81-8 | | | | |
| Isopropyl Alcohol | | 67-63-0 | | | | |
| isopropyl unoprostone | 5-Heptenoic acid, 7-(3,5-dihydroxy-2-(3 oxodecyl)cyclopentyl)-, 1-methylethylester, (1R-(1Alpha(Z), 2β,3Alpha,5Alpha))-[CAS] | 120373-24-2 | EP | 289349 | Prostaglandin | Glaucoma |
| Isoproterenol | | 7683-59-2 | | | | |
| Isosorbide | | 652-67-5 | | | | |
| isosorbide dinitrate | D-Glucitol, 1,4:3,6-dianhydro-, dinitrate [CAS] | 87-33-2 | | | Formulation, modified-release, other | Angina, general |
| isosorbide mononitrate | D-Glucitol, 1,4:3,6-dianhydro-, 5-nitrate [CAS] | 16051-77-7 | | | Formulation, modified-release, other | Angina, general |
| Isothipendyl | | 482-15-5 | | | | |
| isotretinoin | Retinoic acid, 13-cis-[CAS] | 4759-48-2 | U.S. | 4,843,096 | Antiacne | Acne |
| Isovaleryl Diethylamide | | 533-32-4 | | | | |
| Isoxepac | | 55453-87-7 | | | | |
| Isoxicam | | 34552-84-6 | | | | |
| Isoxsuprine | | 395-28-8 | | | | |
| isradipine | 3,5-Pyridinedicarboxylic acid, 4-(4-benzofurazanyl)-1,4-dihydro-2,6-dimethyl-, methyl 1-methylethyl ester [CAS] | 75695-93-1 | GB | 2037766 | Antihypertensive, other | Hypertension, generation |
| israpafant | 6H-Thienol3,2-f][l,2,4]triazolo[4,3-a][1,4]diazepine, 4-(2-chlorophenyl)-6,9-dimethyl-2-[2-[4-(2-methylpropyl)phenyl]ethyl]-[CAS] | 117279-73-9 | EP | 268242 | Antiasthma | Asthma |
| ISV-403 | | | U.S. | 5,447,926 | Formulation, mucosal, topical | Conjunctivitis |
| Itasetron | | 123258-84-4 | | | | |
| ITF-282 | ITF 282 [CAS] | 93615-44-2 | GB | 2115821 | Antianaemic | Anaemia, general |
| itopride | Benzamide, N-[[4-[2-(dimethylamino)ethoxy]phenyl]methyl]-3,4-dimethoxy-, monohydrochloride [CAS] | 122892-31-3 | EP | 306827 | Gastroprokinetic | Gastritis |
| itraconazole | 3H-1,2,4-Triazol-3-one, 4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-2,4-dihydro-2-(1-methylpropyl)-[CAS] | 84625-61-6 | EP | 6711 | Antifungal | Infection, fungal, general |
| Itramin | | 13445-63-1 | | | | |
| itriglumide | 1-Naphthalenepropanoic acid, β-[2-[[2-(8-azaspiro[4.5]dec-8-ylcarbonyl)-4,6-dimethylphenyl]amino]-2-oxoethyl]-, (βR)-[CAS] | 201605-51-8 | WO | 9800404 | Anxiolytic | Anxiety, general |
| iturelix | D-Alaninamide N-acetyl-3-(2-naphthalenyl)-D-alanyl-4-chloro-D-phenylalanyl-3-(3-pyridinyl)-D-alanyl-L-seryl-N6-(3-pyridinylcarbonyl)-L-lysyl-N6-(3-pyridinylcarbonyl)-D-lysyl-L-leucyl-N6-(1-methylethyl)-L-lysyl-L-prolyl-[CAS] | 112568-12-4 | WO | 8901944 | Fertility enhancer | Infertility, female |
| ivabradine | 7,8-dimethoxy-3-(3-[[(1S)(4,5-dimethoxybenzocyclobutan-1-yl)methyl]methylamino]propyl)-1,3,4,5-tetrahydro-2H-benzazepin-2-one | | | | Antianginal | Anginal, general |
| ixabepilone | 17-Oxa-4-azabicyclo(14.1.0)heptadecane-5,9-dione, 7,11-dihydroxy-8,8,10,12,16-pentamethyl-3-(1-methyl-2-(2-methyl-4-thiazolyl)ethenyl, (1R,3S,7S,10R,11S,12S,16R) [CAS] | 219989-84-1 | | | Anticancer, other | Cancer, breast |
| J-104132 | 5H-Cyclopenta[b]pyridine-6-carboxylic acid, 5-(1,3-benzodioxol-5-yl)-2-butyl-7-[2[(2S)-2-carboxypropyl]-4-methoxyphenyl]-6,7-dihydro-, (5S,6R,7R)-[CAS] | 198279-45-7 | WO | 9737665 | Antihypertensive, other | Heart failure |

TABLE 3-continued

| API Generic Name | API Chemical Name | CAS No. | Patent Reference | | Example of Therapeutic Use | Example of Indication |
| --- | --- | --- | --- | --- | --- | --- |
| J-107088 | 5H-Indolo(2,3-a)pyrrolo(3,4-c)carbazole-5,7(6H)-dione, 12-β-D-glucopyranosyl-12,13-dihydro-2,10-dihydroxy-6-((2-hydroxy-1-(hydroxymethyl)ethyl)amino-[CAS] | 174402-32-5 | | | Anticancer, other | Cancer, bladder |
| J-113397 | 1-[(3R,4R)-1-Cyclooctylmethyl-3-hydroxymethyl-4-piperidyl]-3-ethyl-1,3-dihydro-2H-benzimidazole-2-one | | | | Analgesic, other | Pain, general |
| Janex-1 | Phenol, 4-[(6,7-dimethoxy-4-quinazolinyl)amino]-[CAS] | 202475-60-3 | | | Anticancer, other | Cancer, leukaemia, general |
| josamycin | Leucomycin V, 3-acetate 4B-(3-methylbutanoate) [CAS] | 16846-24-5 | JP | 41021759 | Macrolide antibiotic | Infection, general |
| JTV-519 | 1,4-Benzothiazepine, 2,3,4,5-tetrahydro-7-methoxy-4-[1-oxo-3-[4-(phenylmethyl)-1-piperidinyl]propyl]-[CAS] | 145903-06-6 | WO | 9212148 | Cardiovascular | Infarction, myocardial |
| K-777 | | | U.S. | 6,287,840 | Protozoacide | Infection, trypanosomiasis, American |
| Kainic Acid | | 487-79-6 | | | | |
| Kalimate | Kalimate-[CAS] | 92354-70-6 | | | Urological | |
| Kallidin | | 342-10-9 | | | | |
| KB-130015 | Acetic acid (2,6-diiodo-4-((2-methyl-3-benzofuranyl)methyl)phenoxy)-[CAS] | 147030-48-6 | | | Antiarrhythmic | Arrhythmia, general |
| KCB-328 | Methanesulfonamide, N-[3-amino-4-[2-[[2-(3,4-dimethoxyphenyl)ethyl]methylamino]ethoxy]phenyl]-, monohydrochloride [CAS] | 177596-55-3 | WO | 9604231 | Antiarrhythmic | Arrythmia, general |
| Kebuzone | | 853-34-9 | | | | |
| ketamine | 2-(2-Chlorophenyl)-2-(methylamino)-cyclohexanone hydrochloride | 6740-88-1 | | | Formulation, transmucosal, nasal | Pain, post-operative |
| ketanserin | 2,4(1H,3H)-Quinazolinedione, 3-[2-[4-(4-fluorobenzoyl)-1-piperidinyl]ethyl]-[CAS] | 74050-98-9 83846-83-7 | EP | 13612 | Antihypertensive, other | Hypertension, general |
| ketazolam | 4H-[1,3]Oxazino[3,2-d][1,4]benzodiazepine-4,7(6H)-dione, 11-chloro-8,12b-dihydro-2,8-dimethyl-12b-phenyl-[CAS] | 27223-35-4 | GB | 1222294 | Anxiolytic | |
| Kethoxal | | 27762-78-3 | | | | |
| Ketobemidone | | 469-79-4 | | | | |
| ketoconazole | Piperazine, 1-acetyl-4-[4-[[2-(2,4-dichlorophenyl)-2-(1H-imidazol-1-ylmethyl)-1,3-dioxolan-4-yl]methoxy]phenyl]-, cis-[CAS] | 65277-42-1 | U.S. | 4,335,125 | Antifungal | Infection, fungal, general |
| ketoprofen | mono(3-benzoyl-Alpha-methylbenzeneacetate) [CAS] | 173011-11-5 | EP | 502502 | Formulation, transdermal, systemic | Pain, general |
| ketorolac | 1H-Pyrrolizine-1-carboxylic acid, 5-benzoyl-2,3-dihydro-, (+/−)-[CAS] | 74103-06-3 74103-07-4 | EP | 53021 | Analgesic, NSAID | |
| Ketorolac Tromethamine | | | | | | |
| ketotifen | 10-H-Benzo[4,5]cyclohepta[1,2-b]thiophen-10-one, 4,9-dihydro-4-(1-methyl-4-piperidinylidene)-, (E)-2-butenedioate (1:1)-[CAS] | 34580-13-7 34580-14-8 | GB | 1355539 | Antiasthma | |
| Khellin | | 82-02-0 | | | | |
| kinetin | | 9001-29-0 | | | Dermatological | Photodamage |
| KNI-272 | 4-Thiazolidinecarboxamide, N-(1,1-dimethylethyl)-3-[2-hydroxy-3-[[2-[[(5-isoquinolinyloxy)acetyl]amino]-3-(methylthio)-1-oxopropyl]amino]-1-oxo-4-phenylbutyl]-, [4R-[3[2S*,3S*(R*)],4R*]]-[CAS] | 147318-81-8 | U.S. | 5,644,028 | Antiviral, anti-HIV | Infection, HIV/AIDS |
| KP-103 | (R,R)-2-(2,4-Difluorophenyl)-3-(4-methylenepiperidin-1-yl)-1-(1,2,4-triazol-1-yl)-2-butanol | | | | Antifungal | Infection, general |
| KP-157 | | | U.S. | 6,110,961 | Antidepressant | Depression, general |
| KP-544 | | | WO | 9919305 | Cognition enhancer | Unspecified |
| KRN-5500 | L-glycero-β-L-manno-Heptopyranosylamine, 4-deoxy-4-[[[[(2E,4E)-1-oxo-2,4-tetradecadienyl]amino]acetyl]amino]-N-1H-purin-6-yl-[CAS] | 151276-95-8 | WO | 9015811 | Anticancer, antibiotic | Cancer, colorectal |

TABLE 3-continued

| API Generic Name | API Chemical Name | CAS No. | Patent Reference | Example of Therapeutic Use | Example of Indication |
|---|---|---|---|---|---|
| KT-136 | Alpha-D-Glucopyranoside, β-D-fructofuranosyl, mixt. with 1-ethenyl-2-pyrrolidinone homopolymer compd. with iodine [CAS] | 121602-88-8 | | Formulation, dermal, topical | Ulcer, decubitus |
| KUL7211 | (−)-2-[(2S)-1,2,3,4-tetrahydro-2-[[(2R)-2 hydroxy-2-(4-hydroxphenyl)ethyl]amino]naphthalen-7-yloxy]-N,N-dimethylacetamide hydrochloride monohydrate | | | Urological | Urinary calculus |
| KW-2170 | 6H-Pyrazolo[4,5,1-de]acridin-6-one,5-[(3-aminopropyl)amino]-7,10-dihydroxy-2-[[(2-hydroxyethyl)amino]methyl]-, dihydrochloride [CAS] | 207862-44-0 | | Anticancer, alkylating | Cancer, lung, non-small cell |
| KW-6002 | 1H-Purine-2,6-dione, 8-(2-(3,4-dimethoxyphenyl)ethenyl)-1,3-diethyl-3,7-dihydro-7-methyl- (E)-[CAS] | 155270-99-8 | | Antiparkinsonian | Parkinson's disease |
| KW-71 58 | 3,3,3-Trifluoro-2-hydroxy-2-methyl-N-(10-oxo-4,10-dihydrothieno[3,2-C][1]benzothiepin-9-yl)propanamide 5,5 dioxide | | | Urological | Incontinence |
| L-365260 | Urea, N-(2,3-dihydro-1-methyl-2-oxo-5-phenyl-1H-1,4-benzodiazepin-3-yl)-N'-(3-methylphenyl)-, (R)-[CAS] | 118101-09-0 | EP 284256 | Anticancer, other | Cancer, general |
| L-5-hydroxy-tryptophan | L-Tryptophan, 5-hydroxy-[CAS] | 4350-09-8 | | Metabolic and enzyme disorders | Unspecified |
| L-745337 | Methanesulfonamide, N-[6-[(2,4-difluorophenyl)thio]-2,3-dihydro-1-oxo-1H-inden-5-yl]-[CAS] | 158205-05-1 | WO 9413635 | Analgesic, NSAID | Pain, general |
| L-758298 | Phosphonic acid, [3-fl(2R,3S)-2-.(.(1R)1-[3,5-bis(trifluoromethyl)phenyl]ethoxy]-3-(4-fluorophenyl)-4-morpholinyl]methyl]-2,5-dihydro-5-oxo-1H-1,2,4-triazol-1-yl]-[CAS] | 172673-20-0 | WO 9523798 | Antiemetic | Chemotherapy-induced nausea and vomiting |
| L-826141 | | | WO 9722585 | Antiasthma | Unspecified |
| labetalol | 5-[1-hydroxy-2-[(1-methyl-3-phenylpropyl)amino]ethyl]salicylamide HCl | 32780-64-6 36894-69-6 | U.S. 4,012,444 | Antihypertensive, adrenergic | |
| lacidipine | 3,5-Pyridinedicarboxylic acid, 4-[2-[3-(1,1-dimethylethoxy)-3-oxo-1-propenyl]phenyl]-1,4-dihydro-2,6-dimethyl-, diethyl ester, (E)-[CAS] | 103890-78-4 | GB 2164336 | Antihypertensive, other | Hypertension, general |
| Lactic Acid | | | | | |
| lactitol | D-Glucitol, 4-O-β-D-galactopyranosyl-[CAS] | 585-86-4 | | Hepatoprotective | Infection, neurological |
| Lactulose | | 46 18-18-2 | | | |
| lafutidine | Acetamide, 2-[[(2-furanylmethyl)sulfinyl]-N-[4-[[4-(1-pipendinylmethyl)-2-pyridinyl]oxy]-2-butenyl]-, (Z)-[CAS] | 118288-08-7 169899-19-8 | EP 282077 | Antiulcer | Ulcer, gastric |
| Lamifiban | | 1444 12-49-7 | | | |
| lamivudine | 2(1H)-Pyrimidinone, 4-amino-1-[2-(hydroxymethyl)-1,3-oxathiolan-5-yl]-, (2R-cis)-[CAS] | 134678-17-4 | EP 513917 | Antiviral, anti-HIV | Infection, HIV/AIDS |
| lamotrigine | 1,2,4-Triazine-3,5-diamine, 6-(2,3-dichlorophenyl)-[CAS] | 84057-84-1 | EP 21121 | Antiepileptic | Epilepsy, partial (focal, local) |
| landiolol | Benzenepropanoic acid, 4-[2-hydroxy-3-morpholinylcarbonyl)amino]ethyl]amino]propoxy]-, (2,2-dimethyl-1,3-dioxolan-4-yl)methyl ester, [S-(R*,R*)]- HCL | 133242-30-5 | EP 397031 | Antiarrhythmic | Tachycardia, general |
| lanicemine | (S)-Alpha-phenyl-2-pyridine ethanamine dihydrochloride | 153322-05-5 | | Neurological | Unspecified |
| laniquidar | Methyl 6,11-dihydro-11-11-[2-[4-(-2-quinolylmethoxy)phenyl]ethyl]-4-piperidinylidene]-5H-imidazo[2,1-b][3]benzazepine-3-carboxylate | 197509-46-9 | WO 9734897 | Radio/chemosensitizer | Cancer, general |
| lanoconazole | 1H-Imidazole-1-acetonitrile, Alpha-[4-(2 chlorophenyl)-1,3-dithiolan-2-ylidene]-, (E)-(±)-[CAS] | 101530-10-3 | U.S. 4,738,976 | Antifungal | Infection, fungal, general |
| Lanoteplase | | 171870-23-8 | | | |
| Lanreotide | | 108736-35-2 | | | |
| lansoprazole | 1H-Benzimidazole, 2-[[[3-methyl-4-(2,2,2-trifluoroethoxy)-2-pyridyl]methyl]sulfinyl]-[CAS] | 103577-45-3 | EP 174726 | Antiulcer | Ulcer, duodenal |
| lanthanum carbonate | Carbonic acid, lanthanum(3+) salt (3:2)[CAS] | 587-26-8 | U.S. 5,968,976 | Urological | Hyperphosphataemia |

TABLE 3-continued

| API Generic Name | API Chemical Name | CAS No. | Patent Reference | | Example of Therapeutic Use | Example of Indication |
|---|---|---|---|---|---|---|
| lapatinib | 4-Quinazolinamine, N-[3-chloro-4-[(3-fluorobenzyl)methoxy phenyl]-6-[5-[[[2-[methylsulfonyl]ethyl]amino]methyl]furan-2-yl] | 388082-78-8 | | | Anticancer, other | Cancer, breast |
| laquinimod | | 248281-84-7 | | | Multiple sclerosis treatment | Multiple sclerosis, general |
| lasofoxifene | 2-Naphthalenol, 5,6,7,8-tetrahydro-6-phenyl-5-(4-(2-(1-pyrrolidinyl)ethoxy)phenyl-(5R-cis)-, (5-(R*, R*))-2,3-dihydroxybutanedioate [CAS] | 190791-29-8 | WO | 9716434 | Menopausal disorders | Hormone replacement therapy |
| latamoxef | 5-Oxa-1-azabicyclo[4.2.0]oct-2-ene-2-carboxylic acid, 7-[[carboxy(4-hydroxyphenyl)acetyl]amino]-7-methoxy-3-[[(1-methyl-1H-tetrazol-5-yl)thio]methyl]-8-oxo-[CAS] | 64952-97-2 64953-12-4 | GB | 1547351 | Beta-lactam antibiotic | Infection, general |
| latanoprost | 5-Heptenoic acid, 7-(3,5-dihydroxy-2-(3-hydroxy-5-phenylpentyl)cyclopentyl)-, 1 methylethyl ester, (1R-(1Alpha(Z),2β(R*),3Alpha,5Alpha))-[CAS] | 130209-82-4 | WO | 9002553 | Prostaglandin | Glaucoma |
| Lauroguadine | | 135-43-3 | | | | |
| Laurolinium Acetate | | 146-37-2 | | | | |
| Lawsone | | 83-72-7 | | | | |
| LAX-111 | 1-(Z,Z,Z,Z,Z-eicosa-5,8,11,14,17-pentaenoyloxy)-3-(Z,Z,Z,Z,Z-eicosa-5,8,11,14,17-pentaenoyloxy)-propane | | | | Neuroleptic | Schizophrenia |
| Lazabemide | | 103878-84-8 | | | | |
| LB-30057 | Benzenecarboximidic acid, 4-[(2S)-3-(cyclopentylmethylamino)-2-[(2-naphthalenylsulfonyl)amino]-3-oxopropyl]-, hydrazide [CAS] | | WO | 9749673 | Antithrombotic | Thrombosis, venous |
| L-Cystine | | | | | | |
| Lefetamine | | 7262-75-1 | | | | |
| leflunomide | 4-Isoxazolecarboxamide, 5-methyl-N-[4-(trifluoromethyl)phenyl]-[CAS] | 75706-12-6 | EP | 13376 | Antiarthritic, immunological | Arthritis, rheumatoid |
| leflunomide | 4-Isoxazolecarboxamide, 5-methyl-N-[4-(trifluoromethyl)phenyl]-[CAS] | 104981-93-3 75706-12-6 | U.S. | 5,610,173 | Anticancer, other | Cancer, ovarian |
| Leiopyrrole | | 5633-16-9 | | | | |
| lenampicillin | 4-Thia-1-azabicyclo[3.2.0]heptane-2-carboxylic acid, 6-[(aminophenylacetyl)amino]-3,3-dimethyl-7-oxo-, (5-methyl-2-oxo-1,3-dioxol-4-yl)methyl ester, [2S-[2Alpha,5Alpha,6β(S*)]]-[CAS] | 80734-02-7 86273-18-9 | EP | 61206 | Penicillin, oral | Infection, general |
| lentinan | Lentinan [CAS] | 37339-90-5 | | | Anticancer, immunological | Cancer, stomach |
| Lepirudin | | | | | | |
| lercanidipine | 3,5-Pyridinedicarboxylic acid, 1,4-dihydro-2,6-dimethyl-4-(3-nitrophenyl)-, 2-[(3,3-diphenylpropyl)methylamino]-1,1-dimethylethyl methyl ester-, hydrochloride [CAS] | 100427-26-7 132866-11-6 | U.S. | 4,705,797 | Antihypertensive, other | Hypertensive, general |
| lerisetron | 1H-Benzimidazole, 1-(phenylmethyl)-2-(1-piperazinyl)-[CAS] | 143257-98-1 | U.S. | 5,256,665 | Antiemetic | Nausea and vomiting general |
| Lesopitron | | 132449-46-8 | | | | |
| leteprinim | Benzoic acid, 4-((3-(1,6-dihydro-6-oxo-9H-purin-9-yl)-1-oxopropyl)amino)-, monopotassium salt [CAS] | 138117-50-7 | U.S. | 6,338,963 | Antiparkinsonian | Parkinson's disease |
| letosteine | 4-Thiazolidinecarboxylic acid, 2-[2-[(2-ethoxy-2-oxoethyl)thio]ethyl]-[CAS] | 53943-88-7 | U.S. | 4,032,534 | COPD treatment | Bronchitis, chronic |
| letrozole | Benzonitrile, 4,4'-(1H-1,2,4-triazol-1-ylmethylene)bis-[CAS] | 112809-51-5 | EP | 236940 | Anticancer, hormonal | Cancer, breast |
| Leucocyanidin | | 480-17-1 | | | | |
| Leuprolide | | 53714-56-0 | | | | |
| leuprolide acetate | Luteinizing hormone-releasing factor (pig), 6-D-leucine-9-(N-ethyl-L-prolinamide)-10-deglycinamide-, monoacetate (salt) [CAS] | 53714-56-0 74381-53-6 | | | Formulation, implant | Cancer, prostate |
| leuprorelin | Luteinizing hormone-releasing factor (pig), 6-D-leucine-9-(N-ethyl-L-prolinamide)-10-deglycinamide-[CAS] | 53714-56-0 | | | Formulation, implant | Cancer, prostate |
| Levallorphan | | 152-02-3 | | | | |
| levamisole | Imidazo[2,1-b]thiazole, 2,3,5,6-tetrahydro-6-phenyl-, (S)-[CAS] | 14769-73-4 16595-80-5 | U.S. | 4,584,305 | Anthelmintic | Infection, helminth, general |

TABLE 3-continued

| API Generic Name | API Chemical Name | CAS No. | Patent Reference | Example of Therapeutic Use | Example of Indication |
|---|---|---|---|---|---|
| Levcromakalim | | 94535-50-9 | | | |
| levetiracetam | 1-Pyrrolidineacetamide, Alpha-ethyl-2-oxo-, (S)-[CAS] | 102767-28-2 | EP 162036 | Antiepileptic | Epilepsy, general |
| levobetaxolol | 2-Propanol, 1-(4-(2-(cyclopropylmethoxy)ethyl)phenoxy)-3-((1-methylethyl)amino) hydrochloride [CAS] | 116209-55-3 | | Formulation, mucosal, topical | Glaucoma |
| levobunolol | 1(2H)-Naphthalenone, 5-[3-[(1,1-dimethylethyl)amino]-2-hydroxypropoxy]-3,4-dihydro-, (S)-[CAS] | 27912-14-7 47141-42-4 | U.S. 3,641,152 | Formulation, mucosal, topical | Glaucoma |
| levobupivacaine | 2-Piperidinecarboxamide, 1-butyl-N-(2,6-dimethylphenyl)-, (S)-[CAS] | 27262-47-1 | WO 9510276 | Anaesthetic, injectable | Anaesthesia |
| levocabastine | 4-Piperidinecarboxylic acid, 1-[4-cyano-4-(4-fluorophenyl)cyclohexyl]-3-methyl-4-phenyl-, [3S-[1(cis),3Alpha,4β]]-[CAS] | 79449-98-2 79516-68-0 79547-78-7 | U.S. 4,369,184 | Antiallergic, non-asthma | Rhinitis, allergic, general |
| levocetirizine | Acetic acid, (2-(4-((4-chlorophenyl)phenylmethyl)-1-piperazinyl)ethoxy)-, (R)-[CAS] | 130018-77-8 | WO 9406429 | Antiallergic, non-asthma | Allergy, general |
| Levodopa | | 59-92-7 | | | |
| levodropropizine | 1,2-Propanediol, 3-(4-phenyl-1-piperazinyl)-, (S)-[CAS] | 99291-25-5 | EP 147847 | Antitussive | Cough |
| levofloxacin | 7H-Pyrido[1,2,3-de]-1,4-benzoxazine-6 carboxylic acid, 9-fluoro-2,3-dihydro-3-methyl-10-(4-methyl-1-piperazinyl)-7-oxo-, (S)-[CAS] | 100986-85-4 138199-71-0 | EP 206283 | Quinolone antibacterial | Infection, respiratory tract, lower |
| Levomethadyl Acetate | | 1477-40-3 | | | |
| levomoprolol | 2-Propanol, 1-(2-methoxyphenoxy)-3-[(1-methylethyl)amino]-, (S)-[CAS] | 27058-84-0 5741-22-0 77164-20-6 | EP 15418 | Antihypertensive, adrenergic | |
| levonorgestrel | 18,19-Dinorpregn-4-en-20-yn-3-one, 13-ethyl-17-hydroxy-, (17Alpha)-[CAS] | 797-63-7 | | Formulation, implant | Contraceptive, female |
| Levophace-toperane | | 24558-01-8 | | | |
| Levopro-poxyphene | | 2338-37-6 | | | |
| Levorphanol | | 77-07-6 | | | |
| levosimendan | Propanedinitrile, (14-(1,4,5,6-tetrahydro-4-methyl-6-oxo-3-pyridazinyl)phenyl]hydrazono]-, (R)-[CAS] | 131741-08-7 141505-33-1 | EP 383449 | Cardiostimulant | Heart failure |
| levosulpiride | Benzamide, 5-(aminosulfonyl)-N-[(1-ethyl-2-pyrrolidinyl)methyl]-2-methoxy-, (S)-[CAS] | 23672-07-3 | GB 2014990 | Antiemetic | Dyspepsia |
| Levothyroxine | | | | | |
| levovirin | 1-β-L-ribofuranosyl-1,2,4-triazole-3-carboxamide | | | Antiviral, other | Infection, hepatitis-C virus |
| lexipafant | L-Leucine, N-methyl-N-[[4-[(2-methyl-1H-imidazo[4,5-c]pyridin-1-yl)methyl]phenyl]sulfonyl]-, ethyl ester-[CAS] | 139133-26-9 | WO 9203423 | Neurological | Dementia, AIDS-related |
| LF-15-0195 | | | WO 9624579 | Immunosuppressant | Lupus erythematosus, general |
| LF-16-0687 | 2-Pyrrolidinecarboxamide, N-[3-[[4-(aminoiminomethyl)benzoyl]amino]propyl]-1-[[2,4-dichloro-3-[[(2,4-dimethyl-8-quinolinyl)oxy]methyl]phenyl]sulfonyl]-, (2S)-[CAS] | 209733-45-9 | FR 2756562 | Neuroprotective | Head trauma |
| LGD-1550 | 2,4,6-Octatrienoic acid, 7-(3,5-bis(1,1-dimethylethyl)phenyl)-3-methyl-(2E,4E,6E)-[CAS] | 178600-20-9 | | Anticancer, other | Cancer, cervical |
| LH | | 9002-67-9 | | | |
| LH-RH | | 9034-40-6 | | | |
| liarozole | 1H-Benzimidazole, 5-[(3-chlorophenyl)-1H-imidazol-1-ylmethyl]-[CAS] | 115575-11-6 | | Formulation, other | Psoriasis |
| licofelone | 1H-Pyrrolizine-5-acetic acid, 6-(4-chlorophenyl)-2,3-dihydro-2,2-dimethyl-7-phenyl-[CAS] | 156897-06-2 | | Antiarthritic, other | Arthritis, osteo |
| Licostinel | | 153504-81-5 | | | |
| lidadronate | Phosphonic acid, [1-amino-3-(dimethylamino)propylidene]bis-[CAS] | 63132-38-7 | WO 9702827 | Urological | Unspecified |

TABLE 3-continued

| API Generic Name | API Chemical Name | CAS No. | Patent Reference | Example of Therapeutic Use | Example of Indication |
|---|---|---|---|---|---|
| Lidamidine | | 66871-56-5 | | | |
| lidocaine | Acetamide, 2-(diethylamino)-N-(2,6-dimethylphenyl)-[CAS] | 137-58-6 | | Formulation, transdermal, patch | Pain, post-herpetic |
| Lidofenin | | 59160-29-1 | | | |
| Lidoflazine | | 3416-26-0 | | | |
| limaprost | Prosta-2,13-dien-1-oic acid, 11,15-dihydroxy-17,20-dimethyl-9-oxo-, (2E,11Alpha,13E,15S,17S)-, [CAS] | 74397-12-9 | GB 2041368 | Prostaglandin | Buerger's syndrome |
| Lincomycin | | 154-21-2 | | | |
| Lindane | | 58-89-9 | | | |
| linezolid | Acetamide, N-((3-(3-fluoro-4-(4-morpholinyl)phenyt)-2-oxo-5-oxazolidinyl)methyl)-, (S)-[CAS] | 165800-03-3 | WO 9507271 | Antibiotic, other | Infection, dermatological |
| Linoleic Acid | | 60-33-3 | | | |
| Linolenic Acid | | 463-40-1 | | | |
| Liothyronine | | 6893023 | | | |
| Lipase | | 9001-62-1 | | | |
| Lipo-dexamethasone palmitate | Pregna-1,4-diene-3,20-dione, 9-fluoro-11,17-dihydroxy-16-methyl-21-[(1-oxohexadecyl)oxy]-, (11β, 16Alpha)-[CAS] | 14899-36-6 | | Formulation, optimized, microemulsion | Arthritis, rheumatoid |
| lipo-flurbiprofen | [1,1'-Biphenyl]-4-acetic acid, 2-fluoro-Alpha-methyl-, 1-(acetyloxy)ethyl ester [CAS] | 91503-79-6 | JP 60208910 | Formulation, optimized, microemulsion | Pain, cancer |
| Lipogel HA | | | EP 525655 | Formulation, optimized,, liposomes | Unspecified |
| LiquiVent | perfluorooctylbromide | 423-55-2 | U.S. 5,437,272 | Lung Surfactant | Respiratory distress syndrome, adult |
| liranaftate | Garbamothioic acid, (6-methoxy-2-pyridinyl)methyl-, O-(5,6,7,8-tetrahydro-2-naphthalenyl) ester [CAS] | 88678-31-3 | GB 2124617 | Antifungal | Infection, dermatological |
| lisinopril | L-Proline, 1-[N2-(1-carboxy-3-phenylpropyl)-L-lysyl]-, (5)-[CAS] | 76547-98-3 83915-83-7 | EP 12401 | Antihypertensive, renin system | Hypertension, general |
| Lisofylline | | 100324-81-0 | | | |
| lisuride | Urea, N'-[(8Alpha)-9,10-didehydro-6-methylergolin-8-yl]-N,N-diethyl-, [CAS] | 19875-60-6 305-13-5 18016-80-3 | | Antiprolactin | Acromegaly |
| Lithium Citrate | | 919-16-4 | | | |
| lithium | Carbonic acid, dilithium salt [CAS] | 554-13-2 | | Formulation, modified-release <=24 hr | Depression, bipolar |
| lixivaptan | Benzamide, N-[3-chloro-4-(5H-pyrrolo[2,1-c][1,4]benzodiazepin-10(11H)-ylcarbonyl)phenyl]-5-fluoro-2-methyl-[CAS] | 168079-32-1 | U.S. 5,736,540 | Cardiovascular | Heart failure |
| LJP-1082 | | | U.S. 6,207,160 | Immunosuppressant | Thrombosia, venous |
| LLUAlpha | S-2,7,8-Tnmethyl-6-(11-carboxyethyl)-6-hydroxychroman | | | Antihypertensive, other | Hypertension, general |
| LMP-160 | | | U.S. 5,643,893 | Antiasthma | Asthma |
| LMP-420 | | | U.S. 5,643,893 | Antiarthritic, other | Arthritis, rheumatoid |
| lobaplatin | Platinum, (1,2-cyclobutanedimethanamine-N,N')[2-hydroxypropanoato(2-)-O1,O2]-, [SP-4-3-(S),(trans)]-[CAS] | 135558-11-1 | DE 4115559 | Anticancer, alkylatin | |
| Lobeline | | 90-69-7 | | | |
| Lobenzarit | | 63329-53-3 | | | |
| lodoxamide | 2,2'-((2-chloro-5-cyano-1,3-phenylene)diimino)bis(2-oxoacetate):2-amino-2-(hydroxymethyl)-1,3-propanediol (1:2) | 63610-09-3 53882-12-5 | U.S. 4,439,445 | Antiasthma | Asthma |
| Lofentanil | | 61380-40-3 | | | |
| lofepramine | Ethanone, 1-(4-chlorophenyl)-2-[[3-(10,11-dihydro-5H-dibenz[b,f]azepin-5-yl)propyl]methylamino]-[CAS] | 23047-25-8 26786-32-3 | GB 1177525 | Antidepressant | |
| lofexidine | 1H-Imidazole, 2-[1-(2,6-dichlorophenoxy)ethyl]-4,5-dihydro-[CAS] | 31036-80-3 | GB 1181356 | Antihypertensive, adrenergic | Hypertension, general |
| Loflucarban | | 790-69-2 | | | |
| lomefloxacin | 3-Quinolinecarboxylic acid, 1-ethyl-6,8-difluoro-1,4-dihydro-7-(3-methyl-1-piperazinyl)-4-oxo-[CAS] | 98079-51-7 98079-52-8 | EP 140116 | Quinolone antibacterial | Infection, respitory tract, lower |
| lomerizine | Piperazine, 1-[bis(4-fluorophenyl)methyl]-4-[(2,3,4-trimethoxyphenyl)methyl]-, [CAS] | 101477-54-7 101477-55-8 | EP 159566 | Antimigraine | Migraine |

TABLE 3-continued

| API Generic Name | API Chemical Name | CAS No. | Patent Reference | Example of Therapeutic Use | Example of Indication |
|---|---|---|---|---|---|
| lomifylline | 7-(5-oxohexyl)theophylline | 10226-54-7 | DE 2207860 | Neurological | |
| lomustine | Urea, N-(2-chloroethyl)-N'-cyclohexyl-N-nitroso-[CAS] | 13010-47-4 | JP 48075526 | Anticancer, alkylating | |
| lonafarnib | 1-Piperidinecarboxamide, 4-[2-[4-[(11R)-3,10-dibromo-8-chloro-6,11-dihydro-5H-benzo[5,6]cyclohepta[1,2-b]pyridin-11-yl]-1-piperidinyl]-2-oxoethyl]-[CAS] | 193275-84-2 | U.S. 5,874,442 | Anticancer, other | Cancer, lung, l non-small cel |
| Lonapalene | | 91431-42-4 | | | |
| Lonazolac | | 53808-88-1 | | | |
| lonidamine | 1H-Indazole-3-carboxylic acid, 1-[(2,4-dichlorophenyl)methyl]-[CAS] | 50264-69-2 | DE 2310031 | Radio/chemosensitizer | Cancer, breast |
| loperamide | 4-(p-chlorophenyl)-4-hydroxy-N,N-dimethyl-Alpha,Alpha-diphenyl-1-piperidine butyramide HCl | 34552-83-5 53179-11-6 | U.S. 3,714,159 | Antidiarrhoeal | Diarrhoea, general |
| loperamide oxide | 1-Piperidinebutanamide, 4-(4-chlorophenyl)-4-hydroxy-N,N-dimethyl-Alpha,Alpha-diphenyl-, 1-oxide, trans-[CAS] | 106900-12-3 | EP 219898 | Antidiarrhoeal | Diarrhoea, general |
| loprazolam | 1H-Imidazo[1,2-a][1,4]benzodiazepin-1 one, 6-(2-chlorophenyl)-2,4-dihydro-2-[(4-methyl-1-piperazinyl)methylene]-8-nitro-[CAS] | 61197-73-7 61197-93-1 70111-54-5 | GB 1496426 | Hypnotic/Sedative | |
| Loprinone | | 106730-54-5 | | | |
| loracarbef | 1-Azabicyclo[4.2.0]oct-2-ene-2-carboxylicacid, 7-[(aminophenylacetyl)amino]-3-chloro-8-oxo-, [6R-[6Alpha,7β,(R*)]]-[CAS] | 76470-66-1 121961-22-6 | EP 14475 | Cephalosporin, oral | Infection, respitory tract, lower |
| Lorajmine | | 47562-08-3 | | | |
| loratadine | 1-Pipendinecarboxylic acid, 4-(8-chloro 5,6-dihydro-11H-benzo[5,6]cyclohepta[1,2-b]pyridin-11-ylidene)-, ethyl ester-[CAS] | 79794-75-5 | EP 42544 | Antiallergic, non-asthma | Rhinitis, allergic, general |
| lorazepam | 2H-1,4-Benzodiazepin-2-one, 7-chloro-5-(2-chlorophenyl)-1,3-dihydro-3-hydroxy- | 846-49-1 | | Formulation, oral, orally-disintegrating | Epilepsy, general |
| lorcainide | Benzeneacetamide, N-(4-chlorophenyl) N-[1-(1-methylethyl)-4-piperidinyl]-[CAS] | 58934-46-6 59729-31-6 | DE 2642856 | Antiarrhythmic | |
| lormetazepam | 2H-1,4-Benzodiazepin-2-one, 7-chloro-5-(2-chlorophenyl)-1,3-dihydro-3-hydroxy-1-methyl-[CAS] | 848-75-9 | U.S. 3,296,249 | Hypnotic/Sedative | Insomnia |
| lornoxicam | 2H-Thieno[2,3-e]-1,2-thiazine-3-carboxamide, 6-chloro-4-hydroxy-2-methyl-N-2-pyridinyl-, 1,1-dioxide-[CAS] | 70374-39-9 | EP 313935 | Analgesic, NSAID | Pain, post-operative |
| losartan | 1H-Imidazole-5-methanol, 2-butyl-4-chloro-1-[[2'-(1H-tetrazol-5-yl)[1,1'-biphenyl]-4-yl]methyl]-, [CAS] | 124750-99-8 114798-26-4 | EP 253310 | Antihypertensive, renin system | Hypertension, general |
| loteprednol | Androsta-1,4-diene-17-carboxylic acid, 17-[(ethoxycarbonyl)oxy]-11-hydroxy-3-oxo-, chloromethyl ester, (11β,17Alpha)-[CAS] | 82034-46-6 | GB 2079755 | Anti-inflammatory, topical | Uveitis |
| Lotrafiban | | 171049-14-2 | | | |
| Lovastatin | | 75330-75-5 | | | |
| Loxapine | | 10/02/1977 | | | |
| loxiglumide | Pentanoic acid, 4-[(3,4-dichlorobenzoyl)amino]-5-[(3-methoxypropyl)pentylamino]-5-oxo-, (±)-[CAS] | 107097-80-3 | WO 8703869 | GI inflammatory/bowel disorders | Pancreatitis |
| loxoprofen | Benzeneacetic acid, Alpha-methyl-4-[(2 oxocyclopentyl)methyl]-[CAS] | 68767-14-6 80382-23-6 87828-36-2 | EP 55588 | Antiarthritic, other | Arthritis, rheumatoid |
| Lu-35-138 | 1-[3[[2-[5-chloro-1-(4-fluorophenyl)-3-1H-indolyl]ethyl]methylamino]propyl]-2-imidazolidinone hydrochloride | | WO 9516684 | Neuroleptic | Psychosis, general |
| Lubeluzole | | 144665-07-6 | | | |
| lubiprostone | (−)-7-[(2R,4aR,5R,7aR)-2-(1,1-difluoropentyl)-2-hydroxy-6-oxooctahydrocyclopenta[b]pyran-5-yl]heptanoic acid | 136790-76-6 | | Laxative | Constipation |
| lucanthone | Thioxanthen-9-one, 1-((2-(diethylamino)ethyl)amino-4-methyl-[CAS] | 479-50-5 | | Radio/chemosensitizer | Cancer, brain |
| Lucanthone | | 548-57-2 | | | |
| Lumefantrine | | 82186-77-4 | | | |

TABLE 3-continued

| API Generic Name | API Chemical Name | CAS No. | Patent Reference | Example of Therapeutic Use | Example of Indication |
|---|---|---|---|---|---|
| lumiracoxib | Benzeneacetic acid, 2-((2-chloro-6-fluorophenyl)amino)-5-methyl-[CAS] | 220991-20-8 | | Analgesic, NSAID | Pain, general |
| lurtotecan | 11H-1,4-Dioxino[2,3-g]pyrano[3,4:6,7]indolizino[1,2-b]quinoline-9,12[8H,14H]-dione, 8-ethyl 2,3-dihydro-8-hydroxy-15-[[4-methyl-1-piperazinyl]methyl]-, [CAS] | 155773-58-3 | | Formulation, optimized, liposomes | Cancer, ovarian |
| lutetium texaphyrin | Lutetium, bis(acetato-O)[9,10-diethyl-20,21-bis-[2-[2-(2-methoxyethoxy)ethoxy]ethoxy]-4,15-dimethyl-8,11-imino-3,6:16,13-dinitrilo-1,18-benzodiazacycloeicosine-5,14-dipropanolato-N1,N18,N23,N24,N25]-, (PB-7-11-233'2'4)-[CAS] | 156436-90-7 | WO 9906411 | Radio/chemosensitizer | Anthersclerosis |
| LV-216 | Zinc[2-(2,6-dichloroanilino)phenyl]acetate | | | Anti-inflammatory | Arthritis, rheumatoid |
| LX-104 | Hexadecanamide, N-[4-[[2-[2-[2-[[O-(N-acetyl-Alpha-neuraminosyl)-(2-3)-O-β-D-galactopyranosyl-(1-4)-O-[6-deoxy-Alpha-L-galactopyranosyl-(1-3)]-β-D-glucapyranosyl]oxy]ethoxy]ethoxy]ethoxy]methyl]phenyl]-2-tetradecyl-[CAS] | 158792-45-1 | | Cognition enhancer | Dementia, senile, general |
| LY-156735 | β-methyl-6-chloromelatonin | | EP 655243 | Hypnotic/Sedative | Sleep disorder, general |
| LY-293111 | Benzoic acid, 2-[3-[3-[(5-ethyl-4-fluoro-2-hydroxy[1,1'-biphenyl]-4-yl)oxy]propoxy]-2-propylphenoxy]-[CAS] | 161172-51-6 | | Anticancer, other | Cancer, melanoma |
| LY-293558 | 3-Isoquinolinecarboxylic acid, decahydro-6-[2-(1H-tetrazol-5-yl)ethyl]-, [3S-(3Alpha.,4aAlpha,6β,8aAlpha.)]-[CAS] | 154652-83-2 | | Analgesic, other | Pain, neuropathic |
| LY-355703 | 1,4-Dioxa-8,11-diazacyclohexadec-13-ene-2,5,9,12-tetrone, 10-[(3-chloro-4-methoxyphenyl)methyl]-6,6-dimethyl-3-(2-methylpropyl)-16-[(1S)-1-[(2S,3R)-3-phenyloxiranyl]ethyl]-, (3S,10R,13E,16S)-[CAS] | 18256-67-7 | WO 9707798 | Anticancer, other | Cancer, lung, non-small cell |
| Lyapolate | | 25053-27-4 | | | |
| Lymecycline | | 992-21-2 | | | |
| Lynestrenol | | 52-76-6 | | | |
| Lypressin | | 50-57-7 | | | |
| Lysine Acetylsalicylate | | 62952-06-1 | | | |
| lysine salicylate | L-Lysine, 2-hydroxybenzoate [CAS] | 59535-08-9 | WO 9624331 | Analgesic, NSAID | |
| lysophospholipids | | | WO 9843093 | Diagnostic | Diagnosis, cancer |
| M-40403 | Dichloro[(4aR,13aR,17aR,21aR)-1,2,3,4,4a,5,6,12,13,13a,14,15,16,17,17a,18,19,20,21,21a-eicosahydro-1,7-nitrilo-7H-dibenzo[b,h][1,4,7,10]tetraazacyclo-heptadecine-kappaN5,kappaN13,kappaN18,kappaN21,kappaN22]manganese | | U.S. 6,180,620 | Anticancer, other | Unspecified |
| mabuprofen | Benzeneacetamide, N-(2-hydroxyethyl) Alpha-methyl-4-(2-methylpropyl)-, (+/−)-[CAS] | 82821-47-4 | DE 3121595 | Anti-inflammatory | |
| Mabuterol | | 56341-08-3 | | | |
| Macrophage Colony-Stimulating Factor | | 81627-83-0 | | | |
| MADU | | 840-50-6 | | | |
| mafenide | Benzenesulfonamide, 4-(aminomethyl)-monoacetate [CAS] | 13009-99-9 138-39-6 | | Vulnerary | Burns |
| mafosfamide | Ethanesulfonic acid, 2-[[2-[bis(2-chloroethyl)amino]tetrahydro-2H-1,3,2-oxazaphosphorin-4-yl]thio]-, P-oxide, cis-(±)-[CAS] | 88859-04-5 98845-64-8 | EP 393575 | Anticancer, alkylating | Cancer, renal |
| magaldrate | Aluminum magnesium hydroxide sulfate (Al5Mg10(OH)31(SO4)2), hydrate [CAS] | 74978-16-8 | U.S. 2,923,660 | Antacid/Antiflatulent | |
| Magenta I | | 632-99-5 | | | |
| Magnesium Acetylsalicylate | | 132-49-0 | | | |
| Magnesium | | 39409-82-0 | | | |

TABLE 3-continued

| API Generic Name | API Chemical Name | CAS No. | Patent Reference | Example of Therapeutic Use | Example of Indication |
|---|---|---|---|---|---|
| Carbonate Hydroxide magnesium chloride | Magnesium chloride (MgCl2) [CAS] | 7786-30-3 | | Formulation, oral, enteric-coated | Nutrition |
| Magnesium Citrate | | 3344-18-1 | | | |
| magnesium gluconate | D-Gluconic acid, magnesium salt (2:1) [CAS] | 3632-91-5 | | Formulation, other | Hypertension, general |
| Magnesium Lactate | | 18917-93-6 | | | |
| Magnesium Salicylate | | 18917-89-0 | | | |
| Malathion | | 121-75-5 | | | |
| Malotilate | | 59937-28-9 | | | |
| Mandelic Acid | | 90-64-2 | | | |
| Mandelic Acid Isoamyl Ester | | 5421045 | | | |
| Mangafodipir | | 118248-94-5 (free acid); 155319-91-8 (hexahydrogen) | | | |
| manidipine | 3,5-Pyridinedicarboxylic acid, 1,4-dihydro-2,6-dimethyl-4-(3-nitrophenyl)-, 2-[4-(diphenylmethyl)-1-piperazinyl]ethyl methyl ester [CAS] | 89226-50-6 89226-75-5 | EP | 94159 Antihypertensive, other | Hypertension, general |
| Mannomustine | | 551-74-6 | | | |
| mannose-6-phosphate | mannose-6-phosphate | | | Vulnerary | Wound healing |
| Maprotiline | | 10262-69-8 | | | |
| maribavir | 1H-Benzimidazol-2-amine, 5,6-dichloro N-(1-methylethyl)-1-β-L-ribofuranosyl-[CAS] | 176161-24-3 | | Antiviral, other | Cancer, pancreatic |
| marimastat | N-[2,2-Dimethyl-1(S)-(N-methylcarbamoyl)propyl]-N,3(S)-dihydroxy-2(R)-isobutytsuccinamide | 154039-60-8 | WO | 9402447 Anticancer, other | Cancer, pancreatic |
| maxacalcitol | 1,3-Cyclohexanediol, 4-methylene-5-(2(octahydro-1-(1-(3-hydroxy-3-methylbutoxy)ethyl)-7a-methyl-4H-inden-4-ylidene)ethylidene)-, (1S-(1Alpha(R*),3aβ,4E(1S*,3R*,5Z),7aAlpha))-[CAS] | 103909-75-7 | U.S. | 4,891,364 Hormone | Hyperarathyroidism |
| mazindol | 3H-Imidazo[2,1-a]isoindol-5-ol, 5-(4-chlorophenyl)-2,5-dihydro-[CAS] | 22232-71-9 | U.S. | 3,763,178 Anorectic/Antiobesity | Obesity |
| Mazipredone | | 13085-08-0 | | | |
| MC-5723 | | | U.S. | 6,043,259 Cardiovascular | Unspecified |
| MCC-478 | (2-amino-6-(4-methoxyphenylthio)-9-[2-(phosphonomethoxy)ethyl]purine bis(2,2,2-trifluoroethyl) ester) | | | Antiviral, other | Infection, hepatitis-B virus |
| MCI-154 | 3(2H)-Pyridazinone, 4,5-dihydro-6-[4-(4-pyridinylamino)phenyl]-, monohydrochioride [CAS] | 98326-32-0 98326-33-1 | EP | 145019 Cardiostimulant | Heart failure |
| m-Cresyl Acetate | | 122-46-3 | | | |
| MDAM | Gamma-Methylene-10-deazaaminopterin | | | Anticancer, antimetabolite | Cancer, general |
| MDI-101 | | | U.S. | 4,885,311 Antiacne | Acne |
| MDI-403 | | 403849-94-5 | U.S. | 4,677,120 Antiacne | Acne |
| MDL-100907 | 4-Piperidinemethanol, Alpha-(2,3-dimethoxyphenyl)-1-(2-(4-fluorophenyl)ethyl)-, (R)-[CAS] | 139290-65-6 | | Hypnotic/Sedative | Sleep disorder, general |
| mebendazole | methyl-5-benzoylbenzimidazole-2-carbamate | 31431-39-7 | GB | 1307306 Anthelmintic | |
| mebeverine | Benzoic acid, 3,4-dimethoxy-, 4-[ethyl[2-(4-methoxyphenyl)-1-methylethyl]amino]butyl ester [CAS] | 3625-06-7 | | Antispasmodic | Irritable bowel syndrome |
| Mebhydroline | | 524-81-2 | | | |
| Mebrofenin | | 78266-06-5 | | | |
| Mebutamate | | 64-55-1 | | | |
| mecamylamine | Bicyclo(2.2.1)heptan-2-amine, N,2,3,3-tetramethyl-[CAS] | 60-40-2 | | Neurological | Unspecified |
| Mechlorethamine | | 51-75-2 | | | |
| Mechlorethamine Oxide | | 302-70-5 | | | |

TABLE 3-continued

| API Generic Name | API Chemical Name | CAS No. | Patent Reference | | Example of Therapeutic Use | Example of Indication |
|---|---|---|---|---|---|---|
| mecillinam | 4-Thia-1-azabicyclo[3.2.0]heptane-2-carboxylic acid, 6-[[(hexahydro-1H-azepin-1-yl)methylene]amino]-3,3-dimethyl-7-oxo-, [2S-(2Alpha,5Alpha,6.beta.)]-[CAS] | 32887-01-7 32887-03-9 | GB | 1293590 | Penicillin, injectable | Infection, general |
| Meclizine | | 569-65-3 | | | | |
| Meclocycline | | 2013-58-3 | | | | |
| meclofenamate | Benzoic acid, 2-[(2,6-dichloro-3-methylphenyl)amino]-, monosodium salt [CAS] | 6385-02-0 644-62-2 | | | Antiarthritic, other | Arthritis, osteo |
| Meclofenamic Acid | | 644-62-2 | | | | |
| Meclofenoxate | | 51-68-3 | | | | |
| Mecloqualone | | 340-57-8 | | | | |
| Mecysteine | | 18598-63-5 | | | | |
| Medazepam | | 12/06/2898 | | | | |
| medifoxamine | Ethanamine, N,N-dimethyl-2,2-diphenoxy-[CAS] | 32359-34-5 | FR | M5498 | Antidepressant | |
| Medrogestone | | 977-79-7 | | | | |
| Medronic Acid | | 1984-15-2 | | | | |
| medroxyprogesterone | Pregn-4-ene-3,20-dione, 17-(acetyloxy)-6-methyl-,(6Alpha) | 71-58-9 520-85-4 | | | Formulation, fixed-dose combinations | Contraceptive, female |
| Medrysone | | 2668-66-8 | | | | |
| Mefenamic Acid | | 61-68-7 | | | | |
| Mefenorex | | 17243-57-1 | | | | |
| Mefexamide | | 1227-61-8 | | | | |
| mefloquine | 4-Quinolinemethanol, Alpha-2-piperidinyl-2,8-bis(trifluoromethyl)-, (R*,S*)-(±)-[CAS] | 51773-92-3 53230-10-7 69191-18-0 | GB | 1594282 | Antimalarial | |
| Mefruside | | 7195-27-9 | | | | |
| Megestrol | | 595-33-5 | | | | |
| Meglumine | | 22154-43-4 131-49-7 | | | | |
| meglutol | 2-hydroxy-2-methyl-,3-propandicarboxylic acid | 503-49-1 | U.S. | 3,629,449 | Hypolipaemic/Antiatherosclerosis | Hyperlipidaemia, general |
| melagatran | Glycine, N-[(1R)-2-[(2S)-2-[[[[4-(aminoiminomethyl)phenyl]methyl]amino]carbonyl]-1-azetidinyl]-1-cyclohexyl-2-oxoethyl]-[CAS] | 159776-70-2 | WO | 9616671 | Antithrombotic | Thrombosis, general |
| melanocortin-4 agonist | N-[(3R)-1,2,3,4-Tetrahydroisoquinolinium-3-ylcarbonyl]-(1R)-1-(4-chlorobenzyl)-2-[4-cyclohexyl-4-(1H-1,2,4-triazol-1-ylmethyl)piperidin-1-yl]-2-oxoethylamine(1) | | | | Anorectic/Antiobesity | Obesity |
| Melarsoprol | | 494-79-1 | | | | |
| Melengestrol | | 5633-18-1 | | | | |
| melevodopa | Alanine, 3-(3,4-dihydroxyphenyl)-methylester [CAS] | 7101-51-1 | EP | 252290 | Antiparkinsonian | Parkinson's disease |
| Melinamide | | 14417-88-0 | | | | |
| Melitracen | | 5118-29-6 | | | | |
| meloxicam | 2H-1,2-Benzothiazine-3-carboxamide, 4-hydroxy-2-methyl-N-(5-methyl-2-thiazolyl)-, 1,1-dioxide-[CAS] | 71125-38-7 | U.S. | 4,233,299 | Antiarthritic, other | Arthritis, rheumatoid |
| melperone | 1-Butanone, 1-(4-fluorophenyl)-4-(4-methyl-1-piperidinyl)-[CAS] | 1622-79-3 3575-80-2 | BE | 651144 | Neuroleptic | |
| Metphalan | | 148-82-3 | | | | |
| meluadrine | Benzenemethanol, 2-chloro-Alpha-(((1,1-dimethylethyl)amino)methyl)-4-hydroxy-, (R)-, (R*,R*))-2,3-dihydroxybutanedjoate (1:1) (salt) [CAS] | 134865-37-5 | EP | 420120 | Labour inhibitor | Labour, preterm |
| memantine | Tricyclo[3.3.1.13,7]decan-1-amine, 3,5-dimethyl [CAS] | 41100-52-1 19982-08-2 | EP | 392059 | Cognition enhancer | Dementia, AIDS-related |
| MEN-10700 | Acetamide, 2-[[[(5R,6S)-6-[(1R)-1-hydroxyethyl]-2-methyl-7-oxo-4-thia-1-azabicyclo[3.2.0]hept-2-en-3-yl]methyl]methylamino]-[CAS] | 195874-55-6 | WO | 9406803 | Beta-lactam antibiotic | Infection, general |
| MEN-10755 | 5,12-Naphthacenedione, 7-[[4-O-(3-amino-2,3,6-trideoxy-Alpha-L-lyxo-hexopyranosyl)-2,6-dideoxy-Alpha-L-lyxo-hexopyranosyl]oxy]-7,8,9,10-tetrahydro-6,9,11-trihydroxy-9-(hydroxyacetyl)-, hydrochloride, (7S,9S)-[CAS] | 169317-77-5 | WO | 9509173 | Anticancer, antibiotic | Cancer, breast |

TABLE 3-continued

| API Generic Name | API Chemical Name | CAS No. | Patent Reference | Example of Therapeutic Use | Example of Indication |
|---|---|---|---|---|---|
| Menadiol | | 481-85-6 | | | |
| Menadione | | 58-27-5 | | | |
| Menadoxime | | 573-01-3 | | | |
| Menbutone | | 3562-99-0 | | | |
| Menogaril | | 71628-96-1 | | | |
| MENT | 7Alpha-Methyl-19-nortestosterone | | | Formulation, transdermal, systemic | Contraceptive, male |
| menthol | Cyclohexanol, 5-methyl-2-(1-methlethyl)-[CAS] | 1490-04-6 89-78-1 | | Formulation, dermal, topical | Puritus |
| Menthyl Valerate | | 89-47-4 | | | |
| Meobentine | | 46464-11-3 | | | |
| Meparfynol | | 77-75-8 | | | |
| mepartricin | Partricin, methyl ester [CAS] | 11121-32-7 | U.S. | 3,780,173 Antifungal | Infection, *Candida*, general |
| Mepazine | | 60-89-9 | | | |
| Mepenzolate Bromide | | 76-90-4 | | | |
| Meperidine | | 57-42-1 | | | |
| Mephenesin | | 59-47-2 | | | |
| Mephenoxalone | | 70-07-5 | | | |
| Mephentermine | | 100-92-5 | | | |
| Mephenytoin | | 50-12-4 | | | |
| Mephobarbital | | 115-38-8 | | | |
| Mepindolol | | 23694-81-7 | | | |
| Mepitiostane | | 21362-69-6 | | | |
| mepivacaine | N-(2,6-Dimethylphenyl)-1-methyl-2-piperidinecarboxamide | 96-88-8 | | Formulation, modified-release, >24 hr | Pain, post-operative |
| Mepixanox | | 17854-59-0 | | | |
| Meprednisone | | 1247-42-3 | | | |
| Meprobamate | | 57-53-4 | | | |
| meproscillarin | Bufa-4,20,22-trienolide, 3-[(6-deoxy-4-O-methyl-Alpha-L-mannopyranosyl)oxy]-14-hydroxy-, (3β) [CAS] | 33396-37-1 | DE | 1910207 Cardiostimulant | Heart failure |
| meptazinol | Phenol, 3-(3-ethylhexahydro-1-methyl-1H-azepin-3-yl)-[CAS] | 54340-58-8 59263-76-2 | GB | 1285025 Analgesic, other | Pain, general |
| mequitazine | 10H-Phenothiazine, 10-(1-azabicyclo[2.2.2]oct-3-ylmethyl)-[CAS] | 29216-28-2 | GB | 1250534 Antiallergic, non-asthma | |
| Meralein | | 4386-35-0 | | | |
| Meralluride | | 8069-64-5 | | | |
| Merbromin | | 129-16-8 | | | |
| Mercaptomerin | | 21259-76-7 | | | |
| Mercumallylic Acid | | 86-36-2 | | | |
| Mercuric Chloride, Ammoniated | | 10124-48-8 | | | |
| Mercuric Oleate | | 1191-80-6 | | | |
| Mercuric Oxycyanide | | 1335-31-5 | | | |
| merimepodib | Carbamic acid, ((3-((((3-methoxy-4-(5-oxazolyl)phenyl)amino)carbonyl)amino)phenyl)methyl)-(3S)-tetrahydro-3-furanyl ester [CAS] | 198821-22-6 | U.S. | 5,807,876 Antiviral, other | Infection, hepatitis-C virus |
| meropenem | 1-Azabicyclo[3.2.0]hept-2-ene-2-carboxylic acid, 3-[[5-[(dimethylamino)carbonyl]-3-pyrrolidinyl]thio]-6-(1-hydroxyethyl)-4-methyl-7-oxo-, [4R-[3(3S*,5S*),4Alpha,5β,6β(R*)]]-[CAS] | 96036-03-2 | EP | 126587 Beta-lactam antibiotic | Infection, respiratory tract, lower |
| Mersalyl | | 492-18-2 | | | |
| Mesalamine | | 89-57-6 | | | |
| mesalazine | Benzoic acid, 5-amino-2-hydroxy-[CAS] | 89-57-6 | WO | 5541170 Formulation, oral, other | Colitis, ulcerative |
| Mesna | | 19767-45-4 | | | |
| Mesoridazine | | 5588-33-0 | | | |
| Mestanolone | | 521-11-9 | | | |
| Mesterolone | | 1424-00-6 | | | |
| Mestranol | | 72-33-3 | | | |
| Mesulfen | | 135-58-0 | | | |
| Metaclazepam | | 84031-17-4 | | | |
| Metampicillin | | 6489-97-0 | | | |
| Metapramine | | 21730-16-5 | | | |

TABLE 3-continued

| API Generic Name | API Chemical Name | CAS No. | Patent Reference | Example of Therapeutic Use | Example of Indication |
|---|---|---|---|---|---|
| Metaproterenol | | 586-06-1 | | | |
| Metaraminol | | 54-49-9 | | | |
| Metazocine | | 3734-52-9 | | | |
| metergoline | Carbamic acid, [[(8β)-1,6-dimethylergolin-8-yl]methyl]-, phenylmethyl ester [CAS] | 17692-51-2<br>21631-37-8<br>2706-42-5 | GB | 1401935 Antiprolactin | Amenorrhoea |
| metformin | Imidodicarbonimidic diamide, N,N-dimethyl-[CAS] | 657-24-9 | | Formulation, modified-release, <=24 hr | Diabetes, Type II |
| Methacholine | | 62-51-1 | | | |
| Methacycline | | 914-00-1 | | | |
| Methadone | | 76-99-3 | | | |
| Methafurylene | | 531-06-6 | | | |
| Methamphetamine | | 537-46-2 | | | |
| Methandriol | | 521-10-8 | | | |
| Methandrostenolone | | 72-63-9 | | | |
| Methantheline | | 53-46-3 | | | |
| Methapyrilene | | 91-80-5 | | | |
| Methaqualone | | 72-44-6 | | | |
| Metharbital | | 50-11-3 | | | |
| Methazolamide | | 554-57-4 | | | |
| Methdilazine | | 1982-37-2 | | | |
| Methenamine | | 100-97-0 | | | |
| Methenolone | | 153-00-4 | | | |
| Methestrol | | 130-73-4 | | | |
| Methetoin | | 5696-06-0 | | | |
| Methicillin | | 132-92-3 | | | |
| Methimazole | | 60-56-0 | | | |
| Methiodal | | 126-31-8 | | | |
| Methionic Acid | | 503-40-2 | | | |
| Methionine | | 63-68-3 | | | |
| Methisazone | | 1910-68-5 | | | |
| Methitural | | 467-43-6 | | | |
| Methixene | | 02/02/4969 | | | |
| Methocarbamol | | 532-03-6 | | | |
| Methohexital | | 22151-68-4 | | | |
| methotrexate | L-Glutamic acid, N-[4-[[(2,4-diamino-6-ptendinyl)methyl]methylamino]benzoyl]-[CAS] | 59-05-2 | U.S. | 2,512,572 Anticancer, anmetabolite | Cancer, general |
| Methotnmeprazine | | 60-99-1 | | | |
| Methoxamine | | 390-28-3 | | | |
| Methoxsalen | | 298-81-7 | | | |
| Methoxyflurane | | 76-38-0 | | | |
| Methoxyphenamine | | 93-30-1 | | | |
| Methoxypromazine | | 61-01-8 | | | |
| Methscopolamine | | 155-41-9 | | | |
| Methsuximide | | 77-41-8 | | | |
| Methyclothiazide | | 135-07-9 | | | |
| Methyl Blue | | 28983-56-4 | | | |
| Methyl Nicotinate | | 93-60-7 | | | |
| Methyl Propyl Ether | | 557-17-5 | | | |
| Methyl Salicylate | | 119-36-8 | | | |
| Methyl tert-Butyl Ether | | 1634-04-4 | | | |
| Methylbenzethonium Chloride | | 25155-18-4 | | | |
| Methylcobalamin | | 13422-55-4 | | | |
| methyldopa | L-Tyrosine, 3-hydroxy-Alpha-methyl-[CAS] | 555-30-6 | | Formulation, modified-release, <=24 hr | Hypertension, general |
| Methylene Blue | | 61-73-4 | | | |
| Methylergonovine | 113-42-8 | | | | |
| Methylhexaneamine | | 105-41-9 | | | |

TABLE 3-continued

| API Generic Name | API Chemical Name | CAS No. | Patent Reference | Example of Therapeutic Use | Example of Indication |
|---|---|---|---|---|---|
| methylphenidate | 2-Piperidineacetic acid, Alpha-phenyl-, methyl ester [CAS] | 113-45-1 298-59-9 83-43-2 | | Formulation, modified-release, multi | Attention deficit disorder |
| Methyl-prednisolone | | | | | |
| methyl-prednisolone aceponate | Pregna-1,4-diene-3,20-dione, 21-(acetyloxy)-11-hydroxy-6-methyl-17-(1-oxopropoxy)-, (6Alpha,11β)-[CAS] | 86401-95-8 | EP | 72547 Antipruritic/inflamm, allergic | Pruritus |
| methyl-prednisolone suleptanate | Pregna-1,4-diene-3,20-dione, 11,17-dihydroxy-6-methyl-21-[[8-[methyl(2-sulfoethyl)amino]-1,8-dioxooctyl]oxy]-, monosodium salt, (6Alpha,11β)-[CAS] | 90350-40-6 | JP | 59137500 Antiasthma | Asthma |
| Methylthiouracil | | 56-04-2 | | | |
| Methyltrienolone | | 965-93-5 | | | |
| Methyprylon | | 125-64-4 | | | |
| Methysergide | | 361-37-5 | | | |
| Metiazinic Acid | | 13993-65-2 | | | |
| metipranolol | Phenol, 4-[2-hydroxy-3-[(1-methylethyl)amino]propoxy]-2,3,6-trimethyl-, 1-acetate [CAS] | 22664-55-7 | GB | 1206148 Antihypertensive, adrenergic | |
| metoclopramide | Benzamide, 4-amino-5-chloro-N-[2-(diethylamino)ethyl]-2-methoxy-[CAS] | 364-62-5 | | Formulation, modified-release, <=24 hr | Gastro-oesophageal reflux |
| Metocurine Iodide | | 7601-55-0 | | | |
| Metofenazate | | 388-51-2 | | | |
| metolazone | 6-Quinazolinesulfonamide, 7-chloro-1,2,3,4-tetrahydro-2-methyl-3-(2-methylphenyl)-4-oxo-[CAS] | 17560-51-9 | U.S. | 4,517,179 Antihypertensive, diuretic | |
| Metopimazine | | 14008-44-7 | | | |
| Metopon | | 143-52-2 | | | |
| metoprolol | 2-Propanol, 1-[4-(2-methoxyethyl)phenoxy]-3-[(1-methylethyl)amino]-, (+/−)-[CAS] | 51384-51-1 56392-17-7 37350-58-6 | | Formulation, modified-release, other | Hypertension, general |
| Metralindole | | 54188-38-4 | | | |
| Metnzamide | | 31112-62-6 | | | |
| Metrizoic Acid | | 1949-45-7 | | | |
| Metron S | | 13946-02-6 | | | |
| Metyrapone | | 54-36-4 | | | |
| Metyrosine | | 672-87-7 | | | |
| Mexazolam | | 31868-18-5 | | | |
| Mexenone | | 1641-17-4 | | | |
| Mexiletine | | 31828-71-4 | | | |
| mezlocillin | 4-Thia-1-azabicyclo[3.2.0]heptane-2-carboxylic acid, 3,3-dimethyl-6-[[[[[3-(methylsulfonyl)-2-oxo-1-imidazolidinyl]carbonyl]amino]phenylacetyl]amino]-7-oxo-, [2S-[2Alpha,5Alpha,6β(S*)]]-[CAS] | 42057-22-7 51481-65-3 72539-76-5 | GB | 1301961 Penicillin, injectable | Infection, general |
| MFH-244 | Benzenecarboximidic acid, 3,4,5-trihydroxy-, ethyl ester, hydrochloride | 95933-76-9 | U.S. | 4,623,659 Cardiovascular | Reperfusion injury |
| mianserin | Dibenzo[c,f]pyrazino[1,2-a]azepine, 1,2,3,4,10,14b-hexahydro-2-methyl-[CAS] | 21535-47-7 24219-97-4 | GB | 1173783 Antidepressant | Depression, general |
| Mibefradil | | 116644-53-2 | | | |
| Miboplatin | | 103775-75-3 | | | |
| Micafungin | | 235114-32-6 | | | |
| miconazole | 1H-Imidazole,1-(2,4-dichlorophenyl)-2[2,4-dichlorophenyl)methoxy]ethyl] | 22916-47-8 | | Formulation, modified-release, other | Infection, *Candida*, general |
| Micronomicin | | 52093-21-7 | | | |
| midaxifylline | 1H-Purine-2,6-dione, 8-(1-aminocyclopentyl)-3,7-dihydro-1,3-dipropyl-[CAS] | 151159-23-8 | U.S. | 5,378,844 Cardiovascular | Unspecified |
| midazolam | 4H-Imidazo[1,5-a][1,4]benzodiazepine, 8-chloro-6-(2-fluorophenyl)-1-methyl-[CAS] | 59467-70-8 59467-94-6 | U.S. | 4,280,957 Anaesthetic, injectable | |
| midecamycin | Leucomycin V, 3,4B-dipropanoate [CAS] | 35457-80-8 | U.S. | 3,761,588 Macrolide antibiotic | Infection, general |
| midecamycin acetate | Leucomycin V, 3B,9-diacetate 3,4B-dipropanoate [CAS] | 55881-07-7 | JP | 49124087 Macrolide antibiotic | Infection, general |
| midesteine | 2-Thiophenecarbothioic acid, S-[1-methyl-2-oxo-2-[(tetrahydro-2-oxo-3-thienyl)amino]ethyl] ester [CAS] | 94149-41-4 | EP | 120534 COPD treatment | Emphysema, general |
| midodrine | Acetamide, 2-amino-N-[2-(2,5-dimethoxyphenyl)-2-hydroxyethyl]-[CAS] | 42318-56-0 42794-76-3 | EP | 164571 Urological | Incontinence |

TABLE 3-continued

| API Generic Name | API Chemical Name | CAS No. | Patent Reference | Example of Therapeutic Use | Example of Indication |
|---|---|---|---|---|---|
| midostaurin | Benzamide, N-(2,3,10,11,12,13-hexahydro-10-methoxy-9-methyl-1-oxo 9,13-epoxy-1H,9H-diindolo[1.2,3-gh:3',2',1'-lm]pyrrolo[3,4-j][1,7]benzodiazonin-11-yl)-N-methyl-, (9Alpha,10β,11β,13Alpha)-[CAS] | 120685-11-2 | EP | 296110 Anticancer, other | Cancer, leukaemia, acute myelogenous |
| mifepristone | Estra-4,9-dien-3-one, 11-[4-(dimethylamino)phenyl]-17-hydroxy-17-(1-propynyl)-, (11β,17β)-[CAS] | 84371-65-3 | EP | 57115 Abortifacient | Abortion |
| miglitol | 3,4,5-Piperidinetnol, 1-(2-hydroxyethyl)-2-(hydroxymethyl)-, [2R-(2Alpha,3β,4Alpha,5β)]-[CAS] | 72432-03-2 | EP | 55431 Antidiabetic | Diabetes, Type I |
| miglustat | 3,4,5-Piperidinetriol, 1-butyl-2-(hydroxymethyl)-(2R-(2Alpha, 3B, 4Alpha, 5β)) [CAS] | 72599-27-0 | DE | 2758025 Metabolic and enzyme disorders | Gaucher's disease |
| mildronate | Hydrazinium, 2-(2-carboxyethyl)-1,1,1-trimethyl-, inner salt-[CAS] | 76144-81-5 | WO | 8001068 Cardiostimulant | Heart failure |
| milnacipran | Cyclopropanecarboxamide, 2-(aminomethyl)-N,N-diethyl-1-phenyl-, cis-(±)-[CAS] | 101152-94-7 92623-85-3 | U.S. | 4,478,836 Antidepressant | Depression, general |
| Miloxacin | | 37065-29-5 | | | |
| milrinone | [3,4'-Bipyridine]-5-carbonitrile, 1,6-dihydro-2-methyl-6-oxo-[CAS] | 78415-72-2 | U.S. | 4,313,951 Cardiostimulant | Heart failure |
| miltefosine | Ethanaminium, 2-[[(hexadecyloxy)hydroxyphosphinyl]oxy] N,N,N-trimethyl-, hydroxide, inner salt [CAS] | 53949-20-5 58066-85-6 | EP | 225608 Anticancer, other | Cancer, skin, general |
| minaprine | 4-Morpholineethanamine, N-(4-methyl-6-phenyl-3-pyridazinyl)-[CAS] | 25905-77-5 25953-17-7 | GB | 1345880 Antidepressant | Depression, general |
| minocycline | 2-Naphthacenecarboxamide, 4,7-bis(dimethylamino)-1,4,4a,5,5a,6,11,12a-octahydro-3,10,12,12a-tetrahydroxy-1,11-dioxo-, [4S-(4Alpha,4aAlpha,5a.alpha.,12aAlpha)]-[CAS] | 10118-90-8 | | Formulation, optimized, microparticles | Infection, oral |
| minodronic acid | Phosphonic acid, (1-hydroxy-2-imidazo(1,2-a)pyridin-3-ylethylidene)bis-, [CAS] | 180064-38-4 | EP | 354806 Anticancer, other | Cancer, myeloma |
| minoxidil | 2,4-Pyrimidinediamine, 6-(1-piperidinyl)-, 3-oxide [CAS] | 38304-91-5 | U.S. | 4,139,619 Vasodilator, peripheral | Hypertension, general |
| Miokamycin | | 55881-07-7 | | | |
| mirtazapine | Pyrazino[2,1-a] pyrido[2,3-c][2]benzazepine,1,2,3,4,10,14b-hexahydro-2-methyl-[CAS] | 85650-52-8 61337-67-5 | GB | 1543171 Antidepressant | Depression, general |
| misoprostol | Prost-13-en-1-oic acid, 11,16-dihydro 16-methyl-9-oxo-, methyl ester, (11Alpha,13E)-(±)-[CAS] | 59122-46-2 59122-48-4 | U.S. | 4,301,146 Prostaglandin | Ulcer, gastric |
| mitemcinal | Erythromycin, 8,9-didehydro-N-demethyl-9-deoxo-6,11-dideoxy-6,9-epoxy-12-O-methyl-N-(1-methylethyl)-11-oxo-, (2E)-2-butenedioate (2:1) [CAS] | 154802-96-7 | WO | 9324509 Gastroprokinetic | Gastro-oesophageal reflux |
| mitigilnide | Calcium (2S)-2-benzyl-3-(cis-hexahydro-2-isoindolinylcarbonyl)propionate, dihydrate-[CAS] | 145525-41-3 | EP | 507534 Antidiabetic | Diabetes, Type II |
| Mitobronitol | | 488-41-5 | | | |
| Mitoguazone | | 459-86-9 | | | |
| mitolactol | Galactitol, 1,6-dibromo-1,6-dideoxy-[CAS] | 10318-26-0 | U.S. | 3,993,781 Anticancer, alkylating | Cancer, cervical |
| mitomycin | Azirino[2',3':3,4]pyrrolo[1,2-a]indole-4,7-dione, 6-amino-8-[[(aminocarbonyl)oxy]methyl]-1,1a,2,8,8a,8b-hexahydro-8a-methoxy-5-methyl-, [1aS-(1aAlpha,8β,8aAlpha,8bAlpha)]-[CAS] | 50-07-7 | | Formulation, parenteral, other | Cancer, stomach |
| Mitotane | | 53-19-0 | | | |
| mito-xantrone | 9,10-Anthracenedione, 1,4-dihydroxy-5,8-bis[[2-[(2-hydroxyethyl)amino]ethyl]amino]-[CAS] | 65271-80-9 70476-82-3 | U.S. | 4,197,249 Anticancer, other | Cancer, breast |
| mito-xantrone | 9,10-Anthracenedione, 1,4-dihydroxy-5,8-bis[[2-[(2-hydroxyethyl)amino]ethyl]amino]-[CAS] | 65271-80-9 70476-82-9 | | Formulation, optimized, liposomes | Cancer, general |

TABLE 3-continued

| API Generic Name | API Chemical Name | CAS No. | Patent Reference | | Example of Therapeutic Use | Example of Indication |
|---|---|---|---|---|---|---|
| MIV-210 | (3-Fluoro-2'-3'-dideoxy guanosine) | | | | Antiviral, other | Infection, hepatitis-B virus |
| mivacurium | Isoquinolinium, 2,2'-[(1,8-dioxo-4-octene-1,8-diyl)bis(oxy-3,1-propanediyl)]bis[1,2,3,4-tetrahydro-6,7-dimethoxy-2-methyl-1-[(3,4,5-trimethoxyphenyl)methyl]-, dichloride, [R-[R*,R*-(E)]]]-[CAS] | 106861-44-3 | EP | 181055 | Muscle relaxant | Anaesthesia, adjunct |
| Mivazerol | | 125472-02-8 | | | | |
| mizolastine | 4(1H)-Pyrimidinone, 2-[[1-[1-[(4-fluorophenyl)methyl]-1H-benzimidazol 2-yl]-4-piperidinyl]methylamino]-[CAS] | 108612-45-9 | EP | 217700 | Antiallergic, non-asthma | Rhinitis, allergic, general |
| Mizoribine | | 50924-49-7 | | | | |
| MKC-733 | (R)-N-(3-quinuclidinyl)-7-oxo-4,7-dihydrothieno[3,2-b]pyridine-6-carboxamide hydrochloride | 194093-42-0 | JP | 09216888 | Gastroprokinetic | Gastro-oesophageal reflux |
| MLN-519 | 6-Oxa-2-azabicyclo[3.2.0]heptane-3,7-dione, 1-[(1S)-1-hydroxy-2-methylpropyl]-4-propyl-, (1R,4R,5S)-[CAS] | 211866-70-5 | WO | 9915183 | Neuroprotective | Ischaemia, cerebral |
| MLN.576 | 4-Methoxy-benzo[a]phenazine-11-carboxylic acid (2-(dimethylamino)-1-(R)-methylethyl)-amide | | | | Anticancer, other | Cancer, general |
| moclobemide | Benzamide, 4-chloro-N-[2-(4-morpholinyl)ethyl]-[CAS] | 71320-77-9 | EP | 326023 | Antidepressant | Depression, general |
| modafinil | Acetamide, 2-[(diphenylmethyl)sulfinyl]-[CAS] | 68693-11-8 | DE | 2809625 | Psychostimulant | Narcolepsy |
| moexipril | 3-Isoquinolinecarboxylic acid, 2-[2-[[1-(ethoxycarbonyl)-3-phenylpropyl]amino] 1-oxopropyl]-1,2,3,4-tetrahydro-6,7-dimethoxy- (3S-(2(R*(R*)),3R*))-[CAS] | 103775-10-6 103775-14-0 | U.S. | 4,344,949 | Antihypertensive, renin system | Hypertension, general |
| Mofarotene | | 125533-88-2 | | | | |
| Mofebutazone | | 2210-63-1 | | | | |
| Mofegiline | | 119386-96-8 | | | | |
| mofezolac | 5-Isoxazoleacetic acid, 3,4-bis(4-methoxyphenyl)-[CAS] | 78967-07-4 | EP | 26928 | Analgesic, NSAID | Pain, post-operative |
| MOL-6131 | N-[4-(aminomethyl)benzyl]-8(S)-[1-[4-[2 (4-aminophenyl)-acetamido]butyryl]piperidin-4-yl]-2-(naphthalen-1-ylmethyl)-1,3-dioxo-2,3,5,8-tetrahydro-1H-[1,2,4]triazolo[1,2-a]-pyridazine-5(R)-carboxamide | | | | Antiasthma | Asthma |
| Molindone | | 7416-34-4 | | | | |
| molsidomine | Sydnone imine, N-(ethoxycarbonyl)-3-(4-morpholinyl)-[CAS] | 25717-80-0 | U.S. | 3,769,283 | Vasodilator, coronary | |
| mometasone | Pregna-1,4-diene-3,20-dione, 9,21-dichloro-11,17-dihydroxy-16-methyl-, (11β,16Alpha)-[CAS] | 105102-22-5 83919-23-7 | EP | 57401 | Antipruritic/inflamm, allergic | Psoriasis |
| Monatepil | | 103377-41-9 | | | | |
| Monobenzone | | 103-16-2 | | | | |
| monolaurin | Dodecanoic acid, monoester with 1,2,3-propanetriol [CAS] | 27215-38-9 | U.S. | 4,885,282 | Dermatological | Ichthyosis |
| montelukast | Cyclopropaneacetic acid, 1-[[[1-[3-[2-(7 Chloro-2-quinolinyl)ethenyl]phenyl]-3-[2 (1-hydroxy-1-methylethyl)phenyl]propyl]thio]methyl]-, [CAS] | 151767-02-1 158966-92-8 | | | Antiasthma | Asthma |
| Monteplase | | 122007-85-6 | | | | |
| Moperone | | 1050-79-9 | | | | |
| Mopidamol | | 13665-88-8 | | | | |
| Moprolol | | 5741-22-0 | | | | |
| moracizine | Carbamic acid, [10-[3-(4-morpholinyl)-1 oxopropyl]-10H-phenothiazin-2-yl]-, ethyl ester [CAS] | 29560-58-5 31883-05-3 | U.S. | 3,864,487 | Antiarrhythmic | Tachycardia, ventricular |
| Morazone | | 6536-18-1 | | | | |
| Moricizine | | 31883-05-3 | | | | |
| Moroxydine | | 3731-59-7 | | | | |
| Morphazin-amide | | 952-54-5 | | | | |
| morphine | Morphinan-3,6-diol, 7,8-didehydro-4,5-epoxy-17-methyl- (5Alpha,6Alpha)-, [CAS] | 57-27-2 6055-06-7 64-31-3 | | | Formulation, parenteral, other | Pain, cancer |
| morphine-6-glucuronide | morphine-6-glucuronide | | | | Formulation, inhalable, systemic | Pain, general |
| mosapramine | Spiro[imidazo[1,2-a]pyridine-3(2H),4'- | 89419-40-9 | U.S. | 4,337,260 | Neuroleptic | |

TABLE 3-continued

| API Generic Name | API Chemical Name | CAS No. | Patent Reference | | Example of Therapeutic Use | Example of Indication |
|---|---|---|---|---|---|---|
| | piperidin]-2-one, 1'-[3-(3-chloro-10,11-dihydro-5H-dibenz[b,f]azepin-5-yl)propyl]hexahydro-, (+/−)-[CAS] | 98043-60-8 | | | | |
| mosapride | Benzamide, 4-amino-5-chloro-2-ethoxy N-((4-((4-fluorophenyl)methyl)-2-morpholinyl)methyl)-[CAS] | 112885-41-3 112885-42-4 | EP | 243959 | GI inflammatory/bowel disorders | Gastritis |
| motexafin gadolinium | Gadolinium, bis(acetetato-kappaO)(9,10-diethyl-20,21-bis(2-(2-(2-methoxy)ethoxy)ethoxy)-4,15-dimethyl-8,11-imino-3,16:16,13-dinitrilo-1,18-benzodiazacycloeicosine-5,14-dipropanalato-kappaN1, kappaN18, kappaN23, kappaN24, kappaN25), (PB-7-11-233'2'4) [CAS] | 246252-06-2 | | | Radio/chemosensitizer | Cancer, brain |
| Motretinide | | 56281-36-8 | | | | |
| Moveitipril | | 85856-54-8 | | | | |
| Moxalactam | | 64952-97-2 | | | | |
| Moxastine | | 3572-74-5 | | | | |
| Moxaverine | | 10539-19-2 | | | | |
| Moxestrol | | 34816-55-2 | | | | |
| moxifloxacin | 3-Quinolinecarboxylic acid, 1-cyclopropyl-6-fluoro-1,4-dihydro-8-methoxy-7-(octahydro-6H-pyrrolo(3,4-b)pyridin-6-yl)-4-oxo-, hydrochloride (4aS-cis)-[CAS] | 186826-86-8 151096-09-2 | DE | 19546249 | Quinolone antibacterial | Infection, respiratory tract, general |
| moxisylyte | Phenol, 4-[2-(dimethylamino)ethoxy]-2-methyl-5-(1-methylethyl)-, acetate (ester), [CAS] | 964-52-3 54-32-0 | | | Male sexual dysfunction | Impotence |
| moxonidine | 5-Pyrimidinamine, 4-chloro-N-(4,5-dihydro-1H-imidazol-2-yl)-6-methoxy-2-methyl-[CAS] | 75438-57-2 | DE | 2849537 | Antihypertensive, other | Hypertension, general |
| M-PGA | (−)-(S)-2-Methyl-2-(1-oxo-2,3-dihydro-1H-isoindol-2-yl)pentanedioic acid | | U.S. | 5,712,291 | Anticancer, other | Cancer, general |
| MPI-5010 | Platinum diamminedichloro-, (SP-4-2) + (R)-4-[1-hydroxy-2-(methylamino)-ethyl]-1,2-benzenediol | | U.S. | 6,224,883 | Formulation, parenteral, other | Cancer, head and neck |
| MPI-5020 | 2,4(1H,3H)-Pyrimidinedione, 5-fluoro-[CAS] | 51-21-8 | U.S. | 5,750,146 | Formulation, parenteral, other | Cancer, breast |
| MPL | | 198076-81-2 | | | Immunostimulant, other | Vaccine adjunct |
| MRS-1754 | | | U.S. | 6,060,481 | Antiasthma | Asthma |
| MS-209 | 1-Piperazineethanol, 4-(diphenylacetyl) Alpha-[(5-quinolinyloxy)methyl]-, (2E)-2 butenedioate(2:3) (salt) [CAS] | 158681-49-3 | | | Radio/chemosensitizer | Cancer, breast |
| MS-275 | N-(2-Aminophenyl)-4-[N-(pyridin-3-yl-methoxycarbonyl)aminomethyl]benz-amide | | | | Anticancer, antimetabolite | Cancer, lung, general |
| MS-325 | | 201688-00-8 | | | | |
| MS-377 | | | EP | 839805 | Neuroleptic | Schizophrenia |
| Mupirocin | | 12650-69-0 | | | | |
| Muscarine | | 300-54-9 | | | | |
| Muzolimine | | 55294-15-0 | | | | |
| MX-101 3 | | | U.S. | 6,153,591 | Hepatoprotective | Unspecified |
| myco-phenolate mofetil | 4-Hexenoic acid, 6-(1,3-dihydro-4-hydroxy-6-methoxy-7-methyl-3-oxo-5-isobenzofuranyl)-4-methyt-, 2-(4-morpholinyl)ethyl ester, (E)-[CAS] | 116680-01-4 128794-94-5 | WO | 9119498 | Immunosuppressant | Transplant rejection, general |
| myco-phenolic acid | 4-hexanoic acid, 6-(1,3-dihydro-4-hydroxy-6-methoxy-7-methyl-3-oxo-5-isobenzofuranyl)-4-methyl-, | 37415-62-6 24280-93-1 | | | Formulation, oral, enteric-coated | Transplant rejection, general |
| Myrophine | | 467-18-5 | | | | |
| N-(Hydroxy-methyl) nicotinamide | | 3569-99-1 | | | | |
| N,N,N¢,N¢-Tetraethyl-phthalamide | | 83-81-8 | | | | |
| N2-Formyl-sulfisomidine | | 795-13-1 | | | | |
| N4-b-D-Glucosyl-sulfanilamide | | 53274-53-6 | | | | |
| N4-Sulfanilyl-sulfanilamide | | 547-52-4 | | | | |
| Nabilone | | 51022-71-0 | | | | |
| nabumetone | 2-Butanone, 4-(6-methoxy-2-naphthalenyl)-[CAS] | 42924-53-8 | GB | 1476721 | Anti-inflammatory | Arthritis, osteo |

TABLE 3-continued

| API Generic Name | API Chemical Name | CAS No. | Patent Reference | Example of Therapeutic Use | Example of Indication |
| --- | --- | --- | --- | --- | --- |
| N-acetyl-cysteine | L-Cysteine, N-acetyl-[CAS] | 616-91-1 | | Anticancer, other | Cancer, general |
| N-Acetyl-methionine | | 65-82-7 | | | |
| nadifloxacin | 1H,5H-Benzo[ij]quinolizine-2-carboxylic acid, 9-fluoro-6,7-dihydro-8-(4-hydroxy-1-piperidinyl)-5-methyl-1-oxo-, (+/−)-[CAS] | 124858-35-1 | U.S. | 4,399,134 Quinolone antibacterial | Acne |
| nadolol | 2,3-Naphthalenediol, 5-[3-[(1,1-dimethylethyl)amino]-2-hydroxypropoxy]-1,2,3,4-tetrahydro-[CAS] | 42200-33-9 | U.S. | 4,346,106 Antihypertensive, adrenergic | |
| Nadoxolol | | 54063-51-3 | | | |
| nafamostat | Benzoic acid, 4-[(aminoiminomethyl)amino]-, 6-(aminoiminomethyl)-2-naphthalenyl ester-[CAS] | 80251-32-7 81525-10-2 82956-11-4 | EP | 450232 GI inflammatory/ bowel disorders | Pancreatitis |
| nafarelin | Luteinizing hormone-releasing factor (pig), 6-[3-(2-naphthalenyl)-D-alanine]-[CAS] | 76932-56-4 86220-42-0 | EP | 21234 Releasing hormones | Endometriosis |
| Nafcillin | | 147-52-4 | | | |
| Nafronyl | | 31329-57-4 | | | |
| naftidrofuryl | 2-Furanpropanoic acid, tetrahydro-Alpha-(1-naphthalenylmethyl)-, 2-(diethylamino)ethyl ester | 31329-57-4 | | Formulation, modified-release, other | Unspecified |
| naftifine | 1-Naphthalenemethanamine, N-methyl-N-(3-phenyl-2-propenyl)-, (E)-[CAS] | 65472-88-0 65473-14-5 | U.S. | 4,282,251 Antifungal | Infection, dermatological |
| naftopidil | 1-Piperazineethanol, 4-(2-methoxyphenyl)-Alpha-[(1-naphthalenyloxy)methyl]-[CAS] | 57149-07-2 | U.S. | 3,997,666 Antihypertensive, adrenergic | Hypertension, general |
| nalbuphine | Morphinan-3,6,14-triol, 17-(cyclobutylmethyl)-4,5-epoxy-, (5Alpha,6Alpha)-[CAS] | 20594-83-6 23277-43-2 | U.S. | 3,393,197 Analgesic, other | Pain, general |
| Nalidixic Acid | | 389-08-2 | | | |
| nalmefene | Morphinan-3,14-diol, 17-(cyclopropylmethyl)-4,5-epoxy-6-methylene-,(5Alpha)-[CAS] | 55096-26-9 | JP | 56167687 Dependence treatment | Poisoning, drug |
| Nalorphine | | 62-67-9 | | | |
| naloxone | Morphinan-6-one, 17-allyl-4,5Alpha-epoxy-3,14-dihydroxy-, hydrochloride [CAS] | 357-08-4 465-65-6 | | Septic shock treatment | |
| naltrexone | Morphinan-6-one, 17-(cyclopropylmethyl)-4,5-epoxy-3,14-dihydroxy-, (SAlpha)-[CAS] | 16590-41-3 16676-29-2 | U.S. | 3,332,950 Dependence treatment | Addiction, narcotic/ opiate |
| NAMI | Imidazolium trans(imidazole)(dimethylsulfoxide)tetra chlororuthenate (III) | | | Anticancer, other | |
| naminidil | Guanidine, N-cyano-N'-(4-cyanophenyl)-N''-[(1R)-1,2,2-trimethylpropyl]-[CAS] | 220641-11-2 | | Dermatological | Alopecia, general |
| Nandrolone | | 434-22-0 | | | |
| Naphazoline | | 835-31-4 | | | |
| Naphthalene | | 91-20-3 | | | |
| naproxen betainate | Methanaminium, 1-carboxy-N, N, N-trimethyl- salt with (R)-6-methoxy-Alpha-methyl-2-naphthaleneacetic acid (1:1), sodium salt [CAS] | 104124-26-7 | U.S. | 4,672,077 Antiarthritic, other | Arthritis, rheumatoid |
| naproxen | 2-Naphthaleneacetic acid, 6-methoxy-Alpha-methyl-, [CAS] | 26159-34-2 22204-53-1 | GB | 1,211,134 Analgesic, NSAID | Pain, general |
| naratriptan | 1H-Indole-5-ethanesulfonamide, N-methyl-3-(1-methyl-4-piperidinyl)-[CAS] | 121679-13-8 | EP | 303507 Antimigraine | Migraine |
| Narceine | | 131-28-2 | | | |
| Narcobarbital | | 125-55-3 | | | |
| Natamycin | | 7681-93-8 | | | |
| nateglinide | D-phenylalanine, N-((4-(1-methylethyl)cyclohexyl)carbonyl)-, trans [CAS] | 105816-04-4 | EP | 196222 Antidiabetic | Diabetes, Type II |
| N-Butyldeo-xynojirimycin | | 72599-27-0 | | | |
| N-Butylsco-polammonium Bromide | | 149-64-4 | | | |
| NC-503 | | | U.S. | 5,643,562 Anti-inflammatory | Amyloidosis |
| NC-531 | | | U.S. | 5,643,562 Cognition enhancer | Alzheimer's disease |

TABLE 3-continued

| API Generic Name | API Chemical Name | CAS No. | Patent Reference | Example of Therapeutic Use | Example of Indication |
|---|---|---|---|---|---|
| NCX-1000 | | | WO 0061604 | Hepatoprotective | Cirrhosis, hepatic |
| NGX-4016 | Benzoic acid, 2-(acetyloxy)-, 2-((nitrooxy)methyl)phenyl ester [CAS] | 175033-36-0 | WO 9716405 | Symptomatic antidiabetic | Insulin-related metabolic syndrome |
| NGX-456 | Benzoic acid, 5-amino-2-hydroxy-, 4-(nitrooxy)butyl ester [CAS] | 256499-26-0 | | GI inflammatory/bowel disorders | Inflammatory bowel disease |
| NCX-950 | Alpha'-[[(1,1-dimethylethyl)amino]methyl]-4-hydroxyl 1,3-benzenedimethanol nitrate | | | Antiasthma | Asthma |
| n-Docosanol | | 661-19-8 | | | |
| NE-100 | Benzeneethanamine, 4-methoxy-3-(2-phenylethoxy)-N,N-dipropyl-, hydrochloride [CAS] | 149409-57-4 | WO 9307113 | Neuroleptic | Schizophrenia |
| Nealbarbital | | 561-83-1 | | | |
| nebivolol | 2H-1-Benzopyran-2-methanol, Alpha,Alpha' [iminobis(methylene)]bis[6-fluoro-3,4-dihydro]-, (2R*(R*(R*(S))))-(1+)-[CAS] | 118457-14-0 99200-09-6 | EP 145067 | Antihypertensive, adrenergic | Hypertension, general |
| nebostinel | N1-(4,4-Dimethylcyclohexyl)-L-isoglutamine | 163000-63-3 | EP 0688312 | Cognition enhancer | Unspecified |
| Nebracetam | | 97205-34-0 | | | |
| nedaplatin | Platinum, diammine[hydroxyacetato(2−)-O1,O2]-, (SP-4-3)-[CAS] | 95734-82-0 | EP 216362 | Anticancer, alkylating | |
| nedocromil | 4H-Pyrano[3,2-g]quinoline-2,8-dicarboxylic acid, 9-ethyl-6,9-dihydro-4,6-dioxo-10-propyl-[CAS] | 69049-73-6 69049-74-7 | EP 555718 | Antiasthma, Ophthalmological | Rhinitis, allergic, general, Ocular disorder, general |
| nefazodone | 3H-1,2,4-Triazol-3-one, 2-[3-[4-(3-chlorophenyl)-1-piperazinyl]propyl]-5-ethyl-2,4-dihydro-4-(2-phenoxyethyl)-, [CAS] | 82752-99-6 83366-66-9 | U.S. 4,338,317 | Antidepressant | Depression, general |
| nefiracetam | 1-Pyrralidineacetamide, N-(2,6-dimethylphenyl)-2-oxo-[CAS] | 77191-36-7 | U.S. 4,341,790 | Cognition enhancer | Dementia, senile, general |
| nefopam | 1H-2,5-Benzoxazocine, 3,4,5,6-tetrahydro-5-methyl-1-phenyl-[CAS] | 13669-70-0 23327-57-3 | U.S. 3,487,153 | Analgesic, NSAID | |
| Negamycin | | 33404-78-3 | | | |
| netfinavir | 3-Isoquinolinecarboxamide, N-(1,1-dimethylethyl)decahydro-2-(2-hydroxy-3-((3-hydroxy-2-methylbenzoyl)amino)-4-(phenylthio)butyl)-, (3S-(2(2S*,3S*),3Alpha,4aβ,8aβ))-, [CAS] | 159989-65-8 159989-64-7 | | Antiviral, anti-HIV | Infection, HIV/AIDS |
| Nemonapride | | 75272-39-8 | | | |
| Neostigmine | | 59-99-4 | | | |
| nepadutant | Cyclo[3-amino-L-alanyl-L-leucyl-N-[2-(acetylamino)-2-deoxy-β-D-glucopyranosyl]-L-asparaginyl-L-Alpha-aspartyl-L-tryptophyl-L-phenylalanyl], (4 1)-lactam [CAS] | 183747-35-5 | WO 9628467 | Antiasthma | Asthma |
| neramexane | 1,3,3,5,5-pentamethylcyclohexylamine | 202807-80-5 219810-59-0 | | Dependence treatment | Addiction, alcohol |
| neridronic acid | Phosphonic acid, (6-amino-1-hydroxyhexylidene)bis-[CAS] | 79778-41-9 | | Musculoskeletal | Osteogenesis imperfecta |
| Neriifolin | | 466-07-9 | | | |
| N-Ethyl-amphetamine | | 457-87-4 | | | |
| neticonazole | 1H-Imidazole, 1-[2-(methylthio)-1-[2-(pentyloxy)phenyl]ethenyl]-, monohydrochloride, (E)-[CAS] | 130773-02-3 130726-68-0 | EP 445540 | Antifungal | Infection, Candida, general |
| netilmicin | D-Streptamine, O-3-deoxy-4-C-methyl-3-(methylamino)-B-L-arabinopyranosyl-(1-6)-O-[2,6-diamino-2,3,4,6-tetradeoxy-Alpha-D-glycero-hex-4-enopyranosyl-(1-4)]-2-deoxy-N1-ethyl-[CAS] | 56391-56-1 56391-57-2 | GB 1473733 | Aminoglycoside antibiotic | Infection, general |
| nevirapine | 6H-Dipyrido[3,2-b:2',3'-e][1,4]diazepin-6-one, 11-cyclopropyl-5,11-dihydro-4-methyl-[CAS] | 129618-40-2 | EP 429987 | Antiviral, anti-HIV | Infection, HIV/AIDS |
| NGD-98-2 | | | WO 9635689 | Anxiolytic | Anxiety |
| Nialamide | | 51-12-7 | | | |
| Niaprazine | | 27367-90-4 | | | |
| Nicametate | | 3099-52-3 | | | |
| nicaraven | 3-Pyndinecarboxamide, N,N-(1-methyl 1,2-ethanediyl)bis-[CAS] | 79455-30-4 | EP 29602 | Neuroprotective | Haemorrhage, subarachnoid |

TABLE 3-continued

| API Generic Name | API Chemical Name | CAS No. | Patent Reference | Example of Therapeutic Use | Example of Indication |
|---|---|---|---|---|---|
| nicardipine | 3,5-Pyridinedicarboxylic acid, 1A-dihydro-2,6-dimethyl-4-(3-nitrophenyl)-, methyl 2-[methyl(phenylmethyl)amino]ethyl ester [CAS] | 54527-84-3 55985-32-5 | U.S. 3,985,758 | Neuroprotective | Hypertension, general |
| nicergoline | Ergoline-8-methanol, 10-methoxy-1,6-dimethyl-, (8/b)-, 5-bromo-3-pyridinecarboxylate(ester) | 27848-84-6 | | Formulation, modified-release, other | Unspecified |
| Nicentrol | | 5868053 | | | |
| Niclosamide | | 50-65-7 | | | |
| Nicoclonate | | 10571-59-2 | | | |
| Nicofuranose | | 15351-13-0 | | | |
| Nicomol | | 27959-26-8 | | | |
| Nicomorphine | | 639-48-5 | | | |
| nicorandil | 3-Pyridinecarboxamide, N-[2-(nitrooxy)ethyl]-[CAS] | 65141-46-0 | U.S. 4,792,564 | Vasodilator, coronary | Hypertension, general |
| Nicotinamide | | 98-92-0 | | | |
| nicotine | Pyridine, 3-(1-methyl-2-pyrrolidinyl)-, (S)-[CAS] | 54-11-5 | | Formulation, inhalable, other | Addiction, nicotine |
| Nicotinic Acid | | 59-67-6 | | | |
| Nicotinic Acid Benzyl Ester | | 94-44-0 | | | |
| Nicotinyl Alcohol | | 100-55-0 | | | |
| nifedipine | 4-(2'-nitrophenyl)-2,6-dimethyl-3,5-dicarbomethoxy-1,4-dihydropyridine | 21829-25-4 | GB 1173862 | Vasodilator, coronary | Hypertension, general |
| nifekalant | 2,4(1H,3H)-Pyrimidinedione, 6-[[2-[(2-hydroxyethyl)[3-(4-nitrophenyl)propyl]amino]ethyl]amino]-1,3-dimethyl-, [CAS] | 130636-43-0 130656-51-8 | EP 369627 | Antiarrhythmic | Arrhythmia, general |
| Nifenalol | | 7413-36-7 | | | |
| Niflumic Acid | | 4394-00-7 | | | |
| Nifuratel | | 4936-47-4 | | | |
| Nifurfoline | | 3363-58-4 | | | |
| Nifuroxazide | | 965-52-6 | | | |
| Nifuroxime | | 6236051 | | | |
| Nifurpirinol | | 13411-16-0 | | | |
| Nifurprazine | | 1614-20-6 | | | |
| Nifurtimox | | 23256-30-6 | | | |
| Nifurtoinol | | 1088-92-2 | | | |
| nifurzide | 2-Thiophenecarboxylic acid, 5-nitro-, [3 (5-nitro-2-furanyl)-2-propenylidene]hydrazide [CAS] | 39978-42-2 | U.S. 3,847,911 | Antidiarrhoeal | Infection, GI tract |
| NIK-254 | Gentamicin, sulfate (salt) [CAS] | 1405-41-0 | | Formulation, other | Infection, general |
| Nikethamide | | 59-26-7 | | | |
| nilutamide | 2,4-Imidazolidinedione, 5,5-dimethyl-3-(4-nitro-3-(trifluoromethyl)phenyl)-[CAS] | 63612-50-0 | U.S. 4,472,382 | Anticancer, hormonal | Cancer, prostate |
| nilvadipine | 3,5-Pyridinedicarboxylic acid, 2-cyano-1,4-dihydro-6-methyl-4-(3-nitrophenyl)-, 3-methyl 5-(1-methylethyl) ester [CAS] | 75530-68-6 | U.S. 4,338,322 | Antihypertensive, other | Hypertension, general |
| nimesulide | Methanesulfonamide, N-(4-nitro-2-phenoxyphenyl)-[CAS] | 51803-78-2 | U.S. 3,840,597 | Anti-inflammatory | Pain, general |
| Nimetazepam | | 2011-67-8 | | | |
| nimodipine | 3,5-Pyridinedicarboxylic acid, 1,4-dihydro-2,6-dimethyl-4-(3-nitrophenyl)-, 2-methoxyethyl 1-methylethyl ester [CAS] | 66085-59-4 | EP 533014 | Neuroprotective | |
| Nimorazole | | 6506-37-2 | | | |
| nimustine | Urea, N'-[(4-amino-2-methyl-5-pyrimidinyl)methyl]-N-(2-chloroethyl)-N-nitroso-[CAS] | 103745-00-2 42471-28-3 55661-38-6 | GB 1374344 | Anticancer, alkylating | Cancer, brain |
| Ninopterin | | 2179-16-0 | | | |
| NIP-142 | N-[4(S)-(Cyclopropylamino)-3-(R)-hydroxy-2,2-dimethyl-7-nitro-3,4-dihydro-2H-1-benzopyran-6-yl]-4-methoxybenzeneacetamide | | WO 9804542 | Antiarrhythmic | Fibrillation, atrial |
| NIP-531 | N'-[3,5-Bis(trifluoromethyl)benzyl]-N-[3-[N-(1-(4-fluorobenzyl)benzimidazol-2-yl) amino]propyl-N-methylurea hydrochloride | | | Antipruritic/inflamm, allergic | Eczema, atopic |
| niperotidine | [(dimethylamino)methyl]furfuryl]thio] ethyl]-2-nitro-N'-piperonyl-1,1-ethenediamine | 84845-75-0 | GB 2104071 | Antiulcer | Ulcer, GI, general |

TABLE 3-continued

| API Generic Name | API Chemical Name | CAS No. | Patent Reference | | Example of Therapeutic Use | Example of Indication |
|---|---|---|---|---|---|---|
| nipradilol | 2H-1-Benzopyran-3-ol, 3,4-dihydro-8-[2 hydroxy-3-[(1-methylethyl)amino]propoxy]-, 3-nitrate [CAS] | 81486-22-8 86247-86-1 | EP | 42299 | Formulation, mucosal, topical | Glaucoma |
| Niridazole | | 61-57-4 | | | | |
| nisoldipine | 3,5-Pyridinedicarboxylic acid, 1,4-dihydro-2,6-dimethyl-4-(2-nitrophenyl)-, methyl 2-methylpropyl ester-[CAS] | 63675-72-9 | GB | 1516793 | Antihypertensive, other | Hypertension, general |
| nitazoxanide | Benzamide, 2-(acetyloxy)-N-(5-nitro-2-thiazolyl)-[CAS] | 55981-09-4 | U.S. | 5,387,598 | Protozoacide | Infection, GI tract |
| nitisinone | 1,3-Cyclohexanedione, 2-[2-nitro-4-(trifluoromethyl)benzoyl]-[CAS] | 104206-65-7 | EP | 186118 | Metabolic and enzyme disorders | Cirrhosis |
| nitracrine | 1,3-Propanediamine, N,N-dimethyl-N'-(1-nitro-9-acridinyl)-[CAS] | 4533-39-5 6514-85-8 | FR | 1458183 | Anticancer, other | Cancer, ovarian |
| Nitrazepam | | 146-22-5 | | | | |
| nitrendipine | 3,5-Pyridinedicarboxylic acid, 1,4-dihydro-2,6-dimethyl-4-(3-nitrophenyl)-, ethyl methyl ester-[CAS] | 39562-70-4 | GB | 1358951 | Antihypertensive, other | Hypertension, general |
| nitroflurbi-profen | (1,1'-Biphenyl)-4-acetic acid, 2-fluoro-Alpha-methyl-, 4-(nitrooxy)butyl ester [CAS] | 158836-71-6 | EP | 670825 | Urological | Incontinence |
| Nitrofurantoin | | 67-20-9 | | | | |
| Nitrofurazone | | 59-87-0 | | | | |
| nitroglycerin | 1,2,3-Propanetriol, trinitrate [CAS] | 55-63-0 | | | Formulation, transdermal, patch | Angina, general |
| Nitromersol | | 133-58-4 | | | | |
| nitronaproxen | 2-Napthaleneacetic acid, 6-methoxy-Alpha-methyl 4-(nitrooxy)butyl ester (AlphaS)-[CAS] | 163133-43-5 | WO | 9509831 | Analgesic, NSAID | Pain, post-operative |
| nitroxazepine | Dibenz[b,f][1,4]oxazepin-11(10H)-one, 10-(3-(dimethylamino)propyl]-2-nitro-, monohydrochloride [CAS] | 16398-39-3 | NL | 6608671 | Antidepressant | |
| Nitroxoline | | 4008-48-4 | | | | |
| nizatidine | 1,1-Ethenediamine, N-[2-[[[2-[(dimethylamino)methyl]-4-thiazolyl]methyl]thio]ethyl]-N'-methyl-2-nitro-[CAS] | 76963-41-2 | EP | 49618 | Antiulcer | Ulcer, duodenal |
| Nizofenone | | 54533-85-6 | | | | |
| NM-3 | 3-(2-methylcarboxymethyl)-6-methoxy-8-hydroxy-isocoumarin | | JP | 08176138 | Anticancer, other | Cancer, general |
| NM-702 | 4-Bromo-5-(3-pyridylmethylamino)-6-[3 (4-chlorophenyl)propoxy]-3(2H)pyridazinone hydrochloride | | | | Antithrombotic | Peripheral vascular disease |
| N-Methyle-phedrine | | 552-79-4 | | | | |
| N-Methyle-pinephrine | | 554-99-4 | | | | |
| N-Methyl-glucamine | | 6284-40-8 | | | | |
| NN-414 | 6-chloro-3-(1-methylcyclopropylamino)-4H-thieno[3,2-e]-[1,2,4]thiadiazine-1,1-dioxide | | | | Antidiabetic | Diabetes, Type II |
| NNC-05-1869 | (R)-1-(3-(10,11-dihydro-5H-dibenzo[a,d]cyclohepten-5-ylidene)-1-propyl)-3-piperidine carboxylic acid | | | | Symptomatic antidiabetic | Neuropathy, diabetic |
| Nogalamycin | | 1404-15-5 | | | | |
| nolatrexed | 4(1H)-Quinazolinone, 2-amino-6-methyl-5-(4-pyridinylthio)-, [CAS] | 152946-68-4 147149-76-6 | WO | 9320055 | Anticancer, antimetabolite | Cancer, liver |
| nolomirole | Propanoic acid, 2-methyl-, 5,6,7,8-tetrahydro-6-(methylamino)-1,2-naphthalenediyl ester, hydrochloride, (+/−)-[CAS] | 138531-51-8 | WO | 9529147 | Cardiostimulant | Heart failure |
| nolpitantium | 1-Azoniabicyclo[2.2.2]octane, 1-[2-[3-(3,4-dichlorophenyl)-1-[[3-(1-methylethoxy)phenyl]acetyl]-3-piperidinyl]ethyl]-4-phenyl-, chloride, (S)-[CAS] | 153050-21-6 | EP | 591040 | GI inflammatory/bowel disorders | Inflammatory bowel disease |
| nomegestrol | 19-Norpregna-4,6-diene-3,20-dione, 17 (acetyloxy)-6-methyl-[CAS] | 58652-20-3 | DE | 2522533 | Menstruation disorders | Menstrual disorder, general |
| Nomifensine | | 24526-64-5 | | | | |
| Noprylsulfamide | | 576-97-6 | | | | |
| Norbolethone | | 1235-15-0 | | | | |
| Nordazepam | | 1088-11-5 | | | | |
| Nordefrin | | 6539-57-7 (unspecified); 74812-63-8 | | | | |

TABLE 3-continued

| API Generic Name | API Chemical Name | CAS No. | Patent Reference | | Example of Therapeutic Use | Example of Indication |
|---|---|---|---|---|---|---|
| Nordihydro-guaiaretic Acid | | (R*,S*)-(±)-form 27686-84-6 (mesa-form); 500-38-9 (unspecified) | | | | |
| Norelgestramin, Ethinyl Estradial | | | | | | |
| Norepinephrine | | 51-41-2 | | | | |
| Norethandrolone | | 52-78-8 | | | | |
| Norethindrone | | 68-22-4 | | | | |
| Norethynodrel | | 68-23-5 | | | | |
| Norfenefrine | | 536-21-0 | | | | |
| norfioxacin | 3-Quinolinecarboxylic acid, 1-ethyl-6-fluoro-1,4-dihydro-4-oxo-7-(1-piperazinyl)-[CAS] | 68077-27-0 70458-96-7 | U.S. | 4,146,719 | Quinolone antibacterial | Infection, general |
| Norgesterone | | 13563-60-5 | | | | |
| Norgestimate | | 35189-28-7 | | | | |
| Norgestrel | | 6533-00-2 | | | | |
| Norgestnenone | | 848-21-5 | | | | |
| Norlevorphanol | | 1531-1 2-0 | | | | |
| Normethadone | | 467-85-6 | | | | |
| Normethandrone | | 514-61-4 | | | | |
| Normorphine | | 466-97-7 | | | | |
| Norphenazone | | 89-25-8 | | | | |
| Norpipanone | | 561-48-8 | | | | |
| Norpseudoe-phedrine | | 492-39-7 | | | | |
| Nortriptyline | | 72-69-5 | | | | |
| Norvinisterone | | 6795-60-4 | | | | |
| Noscapine | | 128-62-1 | | | | |
| Novembichin | | 1936-40-9 | | | | |
| Novobiocin | | 303-81-1 | | | | |
| Noxiptilin | | 3362-45-6 | | | | |
| Noxythiolin | | 15599-39-0 | | | | |
| NS-1209 | Butanoic acid, 2-[[[5-[4-[(dimethytamino)sulfonyl]phenyl] 1,2,6,7,8,9-hexahydro-8-methyl-2-oxo-3H-pyrrolo[3,2-h]isoquinolin-3-ylidene]amino]oxy]-3-hydroxy-[CAS] | 254751-28-5 | WO | 9426747 | Antiepileptic | Epilepsy, general |
| NS-1231 | 5-(4-chlorophenyl)-6,7,8,9-tetrahydro-1H-pyrolo-(3,2-h]naphthalene-2,3-dione-3-oxime | | | | Neuroprotective | Ischaemia, cerebral |
| NS-126 | | | U.S. | 5,063,222 | Antiallergic, non-asthma | Rhinitis, allergic, general |
| NS-220 | 2-Methyl-c-5-[4-[5-methyl-2-(4-methytphenyl)-4-oxazolyl]butyl]-1,3-dioxane-r-2-carboxylic acid | | | | Hypolipaemic/Antitherosclerosis | Antherosclerosis |
| NS-2330 | NS 2330 [CAS] | 402856-42-2 | | | Cognition enhancer | Alzheimer's disease |
| NS5A inhibitors | | | U.S. | 6,030,785 | Antiviral, other | Infection, hepatitis-C virus |
| NS-7 | Pyrimidine, 4-(4-fluorophenyl)-2-methyl 6-[[5-(1-piperidinyl)pentyl]oxy]-, monohydrochionde [CAS] | 178429-67-9 | WO | 9607641 | Neuroprotective | Ischaemia, cerebral |
| NS-8 | 2-Amino-5-(2-fluorophenyl)-4-methyl-1H-pyrrole-3-carbonitrile | | | | Urological | Incontinence |
| NSC-330507 | 17-Allylaminogeldanamycin | | | | Anticancer, antibiotic | Cancer, general |
| NSC-619534 | 2-chloroethyl phenyl selenone | | | | Anticancer, alkylating | Cancer, general |
| NSC-697726 | 2,5-diazinidinyl-3-[hydroxymethyl]6-methyl-1,4-benzoquinone | | | | Anticancer, antibiotic | Cancer, general |
| N-Sulfanilyl-3,4-xylamide | | 120-34-3 | | | | |
| NU-6027 | 2,4-Pyrimidinediamine, 6-(cyclohexylmethoxy)-5-nitroso-[CAS] | 220036-08-8 | | | Anticancer, other | Cancer, general |
| NV-07 | 2,4,6(1H,3H,5H)-Pyrimidinetnone, 5-ethyl-5-sec-pentyl-, 2-oxime [CAS] | 53745-16-7 | U.S. | 6,455,032 | Antipruritic/inflamm, non-allergic | Keratosis |
| NVP-SRA880 | ([3R,4aR,10aR]-1,2,3,4,4a,5,10,10a-Octahydro-6-methoxy-1-methyl-benz[g]quinoline-3-carboxylic acid-4-(4-nitrophenyl)piperazine amide, hydrogen maleate | | | | Neurological | Unspecified |
| NW-1029 | (S)-(+)-2-[4-(2-fluorobenzyloxy)benzylamino] propanamide methansulfonate | | | | Analgesic, other | Pain, general |

TABLE 3-continued

| API Generic Name | API Chemical Name | CAS No. | Patent Reference | Example of Therapeutic Use | Example of Indication |
|---|---|---|---|---|---|
| NXY-059 | CPI 22 [CAS] | 168021-79-2 | U.S. 5,780,510 | Neuroprotective | Ischaemia, cerebral |
| Nylidrin | | 447-41-6 | | | |
| NZ-314 | 1-Imidazolidineacetic acid, 3-[(3-nitrophenyl)methyt]-2,4,5-trioxo-[CAS] | 128043-99-2 | EP 353198 | Symptomatic antidiabetic | Neuropathy, diabetic |
| NZ-419 | 5-hydroxy-1-methylimidazolidine-2,4-dione | | EP 412940 | Urological | Renal failure |
| Obidoxime Chloride | | 114-90-9 | | | |
| OC-108 | OC 108 [CAS] | 162602-62-2 | | Vasoprotective, topical | Venous insufficiency |
| ocinaplon | Methanone, 2-pyridinyl[7-(4-pyridinyl)pyrazolo[1,5-a]pyrimidin-3-yl]-[CAS] | 96604-21-6 | EP 129847 | Anxiolytic | Generalized anxiety disorder |
| Octabenzone | | 1843-05-6 | | | |
| Octacaine | | 13912-77-1 | | | |
| Octamoxin | | 4684-87-1 | | | |
| Octavenne | | 549-68-8 | | | |
| octenidine | 1-Octanamine, N,N-(1,10-decanediyldi-1(4H)-pyridinyl-4-ylidene)bis-[CAS] | 70775-75-6 71251-02-0 86767-75-1 | WO 8705501 | Stomatological | Periodontitis |
| Octodrine | | 543-82-8 | | | |
| Octopamine | | 104-14-3 | | | |
| Octotiamine | | 137-86-0 | | | |
| octreotide | L-Cysteinamide, D-phenylalanyl-L-cysteinyl-L-phenylalanyl-D-tryptophyl-L-lysyl-L-threonyl-N-[2-hydroxy-1-(hydroxymethyl)propyl]-, cyclic (2-7)-disulfide, [R-(R*,R)]-[CAS] | 83150-76-9 | | Formulation, fixed-dose combinations | Cancer, general |
| Octyl Methoxy-cinnamate | | 5466-77-3 | | | |
| ofloxacin | 7H-Pyrido[1,2,3-de]-l,4-benzoxazine-6-carboxylic acid, 9-fluoro-2,3-dihydro-3-methyl-10-(4-methyl-l-piperazinyl)-7-oxo-, (+/−)-[CAS] | 82419-36-1 | EP 47005 | Quinolone antibacterial | |
| o-lodohippurate | | 133-17-5 | | | |
| olanzapine | 10H-Thieno(2,3-b)(1,5)benzodiazepine, 2-methyl-4-(4-methyl-1-piperazinyl)-[CAS] | 132539-06-1 | EP 454436 | Neuroleptic | Schizophrenia |
| Oleandrin | | 465-16-7 | | | |
| Oleic Acid | | 112-80-1 | | | |
| olmesartan medoxomil | 1H-Imidazole-5-carboxylic acid, 4-(1-hydroxy-1-methylethyl)-2-propyl-1-((2-(1H-tetrazol-5-yl)(1,1'-biphenyl)-4-yl)methyl)-, (5-methyl-2-oxo-1,3-dioxol-4-yl) methyl ester [CAS] | 144689-63-4 | EP 503785 | Antihypertensive, renin system | Hypertension, general |
| olopatadine | 11-[(Z)-3-(Dimethylamino)propylidene]-6,11-dihydrodibenz[b,e]oxepin-2-acetic acid, monohydrochloride | 113806-05-6 140462-76-6 | EP 235796 | Ophthalmological | Conjuctivitis |
| olpadronic acid | Monosodium 3-dimethylamino-1-(hydroxypropylidene)-1,1-bisphosphonate | 63132-39-8 | WO 9619998 | Osteoporosis treatment | Osteoporosis |
| olsalazine | Benzoic acid, 3,3'-azobis[6-hydroxy-[CAS] | 15722-48-2 53200-51-4 | U.S. 4,559,330 | GI inflammatory/bowel disorders | Colitis, ulcerative |
| oltipraz | 3H-1,2-Dithiole-3-thione, 4-methyl-5-pyrazinyl-[CAS] | 64224-21-1 | DE 2705641 | Anticancer, other | Cancer, general |
| OM-294DP | 2-[3(R)-(Dodecanoytoxy)tetradecanamido]-N-[4 [3(R)-hydroxytetradecanamido]-5-(phosphonooxy)pentyl]-4-(phosphonooxy)butyramide. | | | Anticancer, immunological | Unspecified |
| Omacor | ethyl (5Z,8Z,11Z,14Z,17Z)-eicosa-5,8,11,14,17-pentaenoate + ethyl (4Z,7Z,10Z,13Z,16Z,19Z)-docosa-4,7,10,13,16,19-hexaenoate | 81926-94-5 86227-47-6 | | Hypolipaemic/Antiherosclerosis | Hypertri-glyceridaemia |
| omapatrilat | 7H-Pyrido(2,1-b)(1,3)thiazepine-7-carboxylic acid, octahydro-4-((2-mercapto-1-oxo-3-phenylpropyl)amino) 5-oxo, (4S-(4Alpha(R*),7Alpha, 10aβ))-[CAS] | 167305-00-2 | U.S. 5,508,272 | Antihypertensive, renin system | Hypertension, general |
| omeprazole | 1H-Benzimidazole, 5-methoxy-2-[[(4-methoxy-3,5-dimethyl-2-pyridinyl)methyl]sulfinyl]-[CAS] | 73590-58-6 | U.S. 4,255,431 | Antiulcer | Ulcer, GI, general |
| omiloxetine | Ethanone, 2-[(3R,45)-3-[(1,3-benzodioxol-5-yloxy)methyl]-4-(4-fluorophenyl)-1-piperidinyl]-1-(4-fluorophenyl)-, rel-[CAS] | 176894-09-0 | | Antidepressant | Depression, general |

TABLE 3-continued

| API Generic Name | API Chemical Name | CAS No. | Patent Reference | Example of Therapeutic Use | Example of Indication |
|---|---|---|---|---|---|
| omoconazole | 1H-Imidazole, 1-[2-[2-(4-chlorophenoxy)ethoxy]-2-(2,4-dichlorophenyl)-1-methylethenyl]-, (Z)-[CAS] | 74512-12-2 | EP 8804 | Antifungal | Infection, dermatological |
| Onapristone | | 96346-61-1 | | | |
| ondansetron | 4H-Carbazol-4-one, 1,2,3,9-tetrahydro-9-methyl-3-[(2-methyl-1H-imidazol-1-yl)methyl]-[CAS] | 99614-01-4 99614-02-5 | U.S. 4,847,281 | Antiemetic | Chemotherapy-induced nausea and vomiting |
| ONO-3403 | Benzoic acid, 4-[(1E)-3-[(2-ethoxy-2-oxoethyl)-2-propenylamino]-2-methyl-3-oxo-1-propenyl]-, 4-(aminoiminomethyl)phenyl ester, monomethanesulfonate [CAS] | 181586-07-2 | | GI inflammatory/bowel disorders | Unspecified |
| ONO-4128 | 1,4,9-Triazaspiro(5.5)undecane-2,5-dione, 1-butyl-3-(cyclohexytmethyl)-9-((2,3-dihydro-1,4-benzodioxin-6-yl)methyl-[CAS] | 342394-93-8 | | Antiviral, anti-HIV | Infection, HIV/AIDS |
| ONO-8815 Ly | L-lysine (Z)-7-[(1R,2R,3R,5R)-5-chloro-3-hydroxy-2-[(E)-(S)-4-(1-ethylcyclobutyl)-4-hydroxy-1-butenyl]cyclopentyl]-5-heptenoate | | | Labour inhibitor | Labour, preterm |
| ONT-093 | | | U.S. 5,756,527 | Radio/chemosensitizer | Cancer, general |
| OPC-14523 | 2(1H)-Quinolinone, 1-[3-[4-(3-chlorophenyl)-1-piperazinyl]propyl]-3,4-dihydro-5-methoxy-[CAS] | 145969-30-8 | EP 512525 | Antidepressant | Depression, general |
| OPC-31260 | Benzamide, N-[4-[[5-(dimethylamino)-2,3,4,5-tetrahydro-1H-1-benzazepin-1-yl]carbonyl]phenyl]-2-methyl- | 137975-06-5 | WO 9105549 | Unspecified | |
| OPC-51803 | (5R)-2-[1-(2-chloro-4-(1-pyrolidinyl)benzoyl)-2,3,4,5-tetrahydro-1H-1-benzazepin-5-yl]-N-isopropytacetamide | | | Antidiabetic | Diabeters, insipidus |
| OPC-6535 | 2-Pyridinecarboxylic acid, 6-[2-(3,4-diethoxyphenyl)-4-thiazolyl]-[CAS] | 145739-56-6 | WO 9209586 | GI inflammatory/bowel disorders | Inflammatory bowel disease |
| Opiniazide | | 2779-55-7 | | | |
| opioid analgesics | 2-(4-trifluoromethylphenyl)-N-methyl-[1-phenyl-2-(1-pyrolidinyl)ethylacetamide | | | Analgesic, other | Pain, general |
| Opipramol | | 315-72-0 | | | |
| Orazamide | | 2574-78-9 | | | |
| orazipone | 2,4-Pentanedione, 3-((4-methylsulfonyl)phenyl)methylene)-[CAS] | 137109-78-5 | EP 440324 | Antiasthma | Unspecified |
| Org-12962 | Piperazine, 1-[6-chloro-5-(trifluoromethyl)-2-pyridinyl]-, monohydrochionde [CAS] | 210821-63-9 | | Antidepressant | Depression, general |
| Org-24448 | | | U.S. 6,166,008 | Neuroleptic | Schizophrenia |
| oritavancin | Vancomycin, 22-O-(3-amino-2,3,6-trideoxy-3-C-methyl-Alpha-L-arabino-hexopyranosyl)-N3''-[(4'-chloro[1,1'-biphenyl]-4-yl)methyl]-,(4''R)-[CAS] | 171099-57-3 | U.S. 5,840,684 | Peptide antibiotic | Infection, dermatological |
| orlistat | L-Leucine, N-formyl-, 1-[(3-hexyl-4-oxo-2-oxetanyl)methyl]dodecyl ester, [2S-[2Alpha(R*),3β,]]-[CAS] | 96829-58-2 | EP 129748 | Anorectic/Antiobesity | Obesity |
| ormeloxifene | Pyrrolidine, 1-[2-(p-(7-methoxy-2,2-dimethyl-3-phenyl-4-chromanyl)phenoxy)ethyl]-, trans-[CAS] | 31477-60-8 | DE 2329201 | Female contraceptive | Contraceptive, female |
| Omidazole | | 16773-42-5 | | | |
| Omipressin | | 3397-23-7 | | | |
| Ornithine | | 70-26-8 | | | |
| ornoprostil | Prost-13-en-1-oic acid, 11,15-dihydro 17,20-dimethyl-6,9-dioxo-, methyl ester, (11Alpha,13E,15S,17S)-[CAS] | 70667-26-4 | U.S. 4,278,688 | Prostaglandin | Ulcer, gastric |
| Orotic Acid | | 65-86-1 | | | |
| Orphenadrine | | 83-98-7 | | | |
| Orthocaine | | 536-25-4 | | | |
| Osalmid | | 526-18-1 | | | |
| osanetant | Acetamide, N-[1-[3-[(3R)-1-benzoyl-3-(3,4-dichlorophenyl)-3-piperidinyl]propyl]-4-phenyl-4-piperidinyl]-N-methyl-[CAS] | 160492-56-8 | EP 673928 | Neuroleptic | Schizophrenia |
| osaterone | 2-Oxapregna-4,6-diene-3,20-dione, 17-(acetyloxy)-6-chloro-[CAS] | 105149-00-6 | EP 193871 | Prostate disorders | Benign prostatic hyperplasia |
| oseltamivir | 1-Cyclohexene-1-carboxylic acid, 4-(acetylamino)5-amino-3-(1- | 196618-13-0 | WO 9626933 | Antiviral, other | Infection, influenza virus |

TABLE 3-continued

| API Generic Name | API Chemical Name | CAS No. | Patent Reference | Example of Therapeutic Use | Example of Indication |
|---|---|---|---|---|---|
| OSI-7836 | ethylpropoxy)-, ethyl ester, (3R-(3Alpha,(4β,5Alpha))-[CAS] 4'-Thio-β-D-arabinofuranosylcytosine | | | Anticancer, antimetabolite | Cancer, general |
| OSI-7904 | Pentanedioic acid, 2-[5-[[(l,2-dihydro-3-methyl-1-oxobenzo[f]quinazolin-9-yl)methyl]amino]-1,3-dihydro-l-oxo-2H-isoindol-2-yl]-, (S)-[CAS] | 139987-54-5 | WO 9119700 | Formulation, optimized, liposomes | Cancer, general |
| ospemifene | Ethanol, 2-[4-[(1Z)-4-chloro-1,2-diphenyl-1-butenyl]phenoxy]-[CAS] | 128607-22-7 | WO 9607402 | Menopausal disorders | Osteoporosis |
| otilonium bromide | Ethanaminium, N,N-diethyl-N-methyl-2-[[4-[[2-(octyloxy)benzoyl]amino]benzoyl]oxy]-, bromide [CAS] | 26095-59-0 | GB 1181406 | Antispasmodic | Irritable bowel syndrome |
| Ouabain | | 630-60-4 | | | |
| Oxaceprol | | 33996-33-7 | | | |
| Oxacillin | | 66-79-5 | | | |
| Oxaflozane | | 26629.87-8 | | | |
| oxaliplatin | Platinum, (1,2-cyclohexanediamine-N,N')[ethanedioato(2–)-O,O']-, [SP-4-2-(1R-trans)]-[CAS] | 61825-94-3 | EP 393575 | Anticancer, alkylating | Cancer, colorectal |
| Oxalyt-C | 1,2,3-Propanetricarboxylic acid, 2-hydroxy-, potassium sodium salt [CAS] | 28060-67-5 | DE 2249274 | Urological | |
| Oxamarin | | 15301-80-1 | | | |
| Oxametacine | | 27035-30-9 | | | |
| Oxamniquine | | 21738-42-1 | | | |
| oxandrolone | 2-Oxaandrostan-3-one, 17-hydroxy-17-methyl-, (5Alpha,17β)-[CAS] | 53-39-4 | U.S. 3,128,283 | Reproductive/gonad | Sexchromosome abnormality, Turner's syndrome |
| Oxantel | | 36531-26-7 | | | |
| Oxapropanium | | 541-66-2 | | | |
| oxaprozin | 2-Oxazolepropanoic acid, 4,5-diphenyl-[CAS] | 21256-18-8 | GB 1206403 | Antiarthritic, other | Arthritis, osteo |
| oxatomide | 2H-Benzimidazol-2-one, 1-[3-[4-(diphenylmethyl)-1-piperazinyl]propyl]-1,3-dihydro-[CAS] | 60607-34-3 | GB 1579365 | Antiallergic, non-asthma | Rhinitis, allergic, general |
| oxazepam | 7-Chloro-1,3-dihydro-3-hydroxy-5-phenyl-2H-1,4-benzodiazepin-2-one | 604-75-1 | | Formulation, oral, orally-disintegrating | Anxiety, general |
| oxazolam | Oxazolo[3,2-d][1,4]benzodiazepin-6(5H)-one, 10-chloro-2,3,7,11b-tetrahydro-2-methyl-11b-phenyl-[CAS] | 27167-30-2 | U.S. 3,772,371 | Anxiolytic | |
| oxcarbazepine | 5H-Dibenz[b,f]azepine-5-carboxamide, 10,11-dihydro-10-oxo-[CAS] | 28721-07-5 29331-92-8 | DE 2011087 | Antiepileptic | Epilepsy, general |
| Oxeladin | | 468-61-1 | | | |
| Oxendolone | | 33765-68-3 | | | |
| Oxethazaine | | 126-27-2 | | | |
| Oxetorone | | 26020-55-3 | | | |
| oxiconazole | Ethanone, 1-(2,4-dichlorophenyl)-2-(1H-imidazol-1-yl)-, O-[(2,4-dichlorophenyl)methyl]oxime, (Z)-[CAS] | 64211-45-6 | GB 1514870 | Antifungal | Infection, fungal, general |
| Oxidronic Acid | | 15468-10-7 | | | |
| Oxiniacic Acid | | 2398-81-4 | | | |
| Oxiracetam | | 62613-82-5 | | | |
| oxitropium | 3-Oxa-9-azoniatricyclo[3.3.1.02,4]nonane, 9-ethyl-7-(3-hydroxy-1-oxo-2-phenylpropoxy)-9-methyl-, bromide, [7(S)-(1Alpha,2β,4β,5Alpha,7β)]-[CAS] | 30286-75-0 | GB 1178305 | Antiasthma | |
| Oxolamine | | 959-14-8 | | | |
| Oxolinic Acid | | 14698-29-4 | | | |
| Oxophen-arsine | | 538-03-4 | | | |
| Oxprenolol | | 6452-71-7 | | | |
| Oxybenzone | | 131-57-7 | | | |
| oxybutynin | Benzeneacetic acid, Alpha-cyclohexyl-Alpha-hydroxy-, 4-(diethylamino)-2-butynyl ester-[CAS] | 5633-20-5 | | Formulation, modified-release, othe | Incontinence |
| Oxycinchophen | | 485-89-2 | | | |
| oxycodone | Morphinan-6-one, 4,5-epoxy-14-hydroxy-3-methoxy-1 7-methyl-, (5Alpha)- | 76-42-6 | | Formulation, transmucosal, nasal | Pain, general |

TABLE 3-continued

| API Generic Name | API Chemical Name | CAS No. | Patent Reference | Example of Therapeutic Use | Example of Indication |
|---|---|---|---|---|---|
| Oxyfedrine | | 15687-41-9 | | | |
| Oxygent | Octane, 1-bromo-1,1,2,2,3,3,4,4,5,5,6,6,7,7,8,8,8-heptadecafluoro-[CAS] | 423-55-2 | | Haematological | Surgery adjunct |
| Oxymesterone | | 145-12-0 | | | |
| Oxymetazoline | | 1491-59-4 | | | |
| oxymetholone | Androstan-3-one, 17-hydroxy-2-(hydroxymethylene)-17-methyl-, (5Alpha,17β)-[CAS] | 434-07-1 | | Hormone | Anaemia, general |
| Oxymethurea | | 140-95-4 | | | |
| oxymorphone | (5Alpha)-4,5-Epoxy-3,14-dihydroxy-17-methylmorphinan-6-one [CAS] | 76-41-5 | | Formulation, modified-release, immediate | Pain, general |
| Oxypendyl | | 5585-93-3 | | | |
| Oxypertine | | 153-87-7 | | | |
| Oxyphenbutazone | | 129-20-4 | | | |
| Oxyphencyclimine | | 125-53-1 | | | |
| Oxyphenisatin | | 115-33-3 | | | |
| Oxyphenonium | | 50-10-2 | | | |
| Oxypinocemphone | | 10136-65-9 | | | |
| oxypurinol | 1H-Pyrazolo[3,4-d]pyrimidine-4,6(5H,7H)-dione [CAS] | 2465-59-0 | | Antigout | Hyperuricaemia |
| Oxytetracycline | | 79-57-2 | | | |
| ozagrel | 2-Propenoic acid, 3-[4-(1H-imidazol-1-ylmethyl)phenyl]-, (E)-[CAS] | 78712-43-3 82571-53-7 536-95-8 | GB | 2025946 Antithrombotic | Vasospasm, cerebral |
| p-(Benzylsulfonamido) benzoic Acid | | | | | |
| P-100 | | | U.S. | 6,313,177 Antiviral, anti-HIV | Infection, HIV/AIDS |
| P-1202 | Pentanoic acid, 5-amino-4-oxo, methyl ester, hydrochloride [CAS] | 79416-27-6 | U.S. | 6,034,267 Dermatological | Keratosis |
| P32/98 | Di-(3N-[(2S,3S)-2-amino-3-methyl-pentanoyl]-1,3-thiazolidine)fumarate | | | Antidiabetic | Diabetes, Type II |
| PA-824 | | | WO | 9701562 Antimycobacteria | Infection, tuberculosis |
| PACAP 38 | Pituitary adenylate cyclase-activating peptide-38 [CAS] | 128606-20-2 | U.S. | 5,128,242 Neuroprotective | Nerve injury, general |
| paclitaxel | 5β,20-Epoxy-1,2Alpha,4,7β,10β,13Alpha-hexahydroxytax-11-en-9-one-4,10-diacetate-2-benzoate-13-(Alpha-phenylhippurate) | 33069-62-4 | | Formulation, optimized, nanoparticles | Cancer, breast |
| PADRE | | | U.S. | 6,413,935 Immunostimulant, other | Vaccine adjunct |
| pagoclone | 1H-Isoindol-1-one, 2-(7-chloro-1,8-naphthyridin-2-yl)-2,3-dihydro-3-(5-methyl-2-oxohexyl)- (R)-[CAS] | 133737-32-3 | U.S. | 4,960,779 Anxiolytic | Panic disorder |
| PAI inhibs | | | WO | 9404512 Antithrombotic | |
| palindore | 8H-1,4-dioxino[2,3-e]indol-8-one,2,3,7,9-tetrahydro-2-[(phenylmethyl)amino]methyl]-, 2(5)-, (2E)-2-butendioate (1:1) | 189681-71-8 | | Neuroleptic | Schizophrenia |
| Palivizumab | | 188039-54-5 | | | |
| palonosetron | 3a5-2-[(S)-1-Azabicyclo[2.2.2]oct-3-yl]-2,3,3a,4,5,6-hexahydro-1-oxo-1H-benz[de]isoquinoline hydrochloride | 135729-62-3 | U.S. | 5,202,333 Antiemetic | Chemotherapy-induced nausea and vomiting |
| Pamabrom | | 606-04-2 | | | |
| Pamaquine | | 491-92-9 | | | |
| pamicogrel | 1H-Pyrrole-1-acetic acid, 2-[4,5-bis(4-methoxyphenyl)-2-thiazolyl]-, ethyl ester [CAS] | 101 001-34-7 | EP | 159677 Antithrombotic | Thrombosis, cerebral |
| pamidronate | (3-Amino-1-hydroxypropylidene)diphosphonic acid-[CAS] | 40391-99-9 | | Formulation, implant | Hypercalcaemia of malignancy |
| p-Aminobenzoic Acid | | 150-13-0 | | | |
| p-Aminohippuric | | 61-78-9 | | | |

TABLE 3-continued

| API Generic Name | API Chemical Name | CAS No. | Patent Reference | Example of Therapeutic Use | Example of Indication |
|---|---|---|---|---|---|
| Acid p-Amino-propiophenone | | 70-69-9 | | | |
| p-Amino-salicylic Acid | | 65-49-6 | | | |
| Panavir | 4,4'-isopropylidenedithiobis-2,6-di-t-butylphenol | | | Neuroprotective | Vasospasm, cerebral |
| Pancuronium | | 15500-66-0 | | | |
| Panipenem | | 87726-17-8 | | | |
| Pantethine | | 16816-67-4 | | | |
| pantoprazole | 1H-Benzimidazole, 5-(difluoromethoxy)-2-[[(3,4-dimethoxy-2-pyridinyl)methyl]sulfinyl]-[CAS] | 102625-70-7 | EP | 166287 Antiulcer | Ulcer, duodenal |
| Pantothenic Acid | | 79-83-4 | | | |
| Papain | | | | | |
| Papaverine | | 58-74-2 | | | |
| paracetamol | Acetamide, N-(4-hydroxyphenyl)-[CAS] | 103-90-2 | | Formulation, oral, other, modified-release | Pain, general |
| Paraflutizide | | 1580-83-2 | | | |
| Paraldehyde | | 123-63-7 | | | |
| Paramethadione | | 115-67-3 | | | |
| Paramethasone | | 53-33-8 | | | |
| Paranyline | | 1729-61-9 | | | |
| Parathyroid Hormone | | 9002-64-6 | | | |
| parecoxib | Propanamide, N-((4-(5-methyl-3-phenyl-4-isoxazolyl)phenyl)sulfonyl)-, sodium salt [CAS] | 198470-85-8 | WO | 9738986 Analgesic, NSAID | Pain, post-operative |
| Parethoxycaine | | 94-23-5 | | | |
| Pargyline | | 555-57-7 | | | |
| paricalcitol | 19-Nor-9,10-secoergosta-5,7,22-triene-1,3,25-triol, (1Alpha,3β,7E,22E)-[CAS] | 131918-61-1 | EP | 387077 Hormone | Hyperparathyroidism |
| paromomycin | O-2-Amino-2-deoxy-Alpha-D-glucopyranosyl-(1-4)-O-[O-2,6-diamino-2,6-dideoxy-β-L-idopyranosyl-(1-3)-β-D-ribofuranosyl-(1-5)]-2-deoxy-D-streptamine | 7542-37-2 | | Protozoacide | Infection, leishmaniasis |
| paroxetine | Piperidine, 3-((l,3-benzodioxol-5-yloxy)methyl]-4-(4-fluorophenyl)-, (3S-trans)-[CAS] | 61869-08-7 | EP | 223403 Antidepressant, formulation, oral, orally-disintegrating | Depression, general |
| Paroxypropione | | 70-70-2 | | | |
| Parsalmide | | 30653-83-9 | | | |
| PaTrin-2 | 4-Bromothenylguanine | | | Radio/chemosensitizer | Cancer, melanoma |
| Pazinaclone | | 103255-66-9 | | | |
| pazufloxacin | 7H-Pyrido[1.2,3-de]-1,4-benzoxazine-6-carboxylic acid, 10-(1-aminocyclopropyl)-9-fluoro-2,3-dihydro-3-methyl-7-oxo-, (S)-[CAS] | 127045-41-4 127046-45-1 136905-87-8 | DE | 3913245 Quinolone antibacterial | Infection, general |
| p-Bromo-acetanilide | | 103-88-8 | | | |
| PC-NSAIDs | | | U.S. | 4,918,063 Formulation, other | Arthritis, general |
| PD-0166285 | 6-(2,6-Dichlorophenyl)-2-[4-(diethylamino-ethoxy)-phenylamino]-8-pyrido[2,3-D]pyrimidine-7-one Anticancer, other | | | | |
| Pecilocin | | 19504-77-9 | | | |
| pefloxacin | 3-Quinolinecarboxylic acid, 1-ethyl-6-fluoro-1,4-dihydro-7-(4-methyl-1-piperazinyl)-4-oxo-[CAS] | 70458-92-3 | GB | 1598915 Quinolone antibacterial | Infection, urinary tract |
| pegvisomant | Somatotropin (18-aspartic acid, 21-asparagine, 120-lysine, 167-asparagine, 168-alanine, 171-serine, 172-arginine, 174-serine, 179-threonine (human), pegylated [CAS] | 218620-50-9 | | Somatostatin | Acromegaly |
| Pelletierine | | 4396-1-4 | | | |
| pemetrexed | L-Glutamic acid, N-[4-[2-(2-amino-4,7-dihydro-4-oxo-1H-pyrrolo[2,3-d]pyrimidin-5-yl)ethyl]benzoyl]-, disodium salt [CAS] | 137281-23-3 150399-23-8 | U.S. | 5,248,775 Anticancer, antimetabolite | Cancer, mesothelioma |
| pemirolast | 4H-Pyrido[1,2-a]pyrimidin-4-one, 9-methyl-3-(1H-tetrazol-5-yl)-[CAS] | 100299-08-9 69372-19-6 | U.S. | 4,457,932 Antiasthma | Asthma |
| Pemoline | | 2152-34-3 | | | |
| Pempidine | | 79-55-0 | | | |

TABLE 3-continued

| API Generic Name | API Chemical Name | CAS No. | Patent Reference | Example of Therapeutic Use | Example of Indication |
|---|---|---|---|---|---|
| PEN-203 | | | U.S. 5,955,446 | Antiviral, other | Infection, human papilloma virus |
| Penamecillin | | 983-85-7 | | | |
| penbutolol | 2-Propanol, 1-(2-cyclopentylphenoxy)-3 [(1,1-dimethylethyl)amino]-,(S)-, sulfate (2:1) (salt) [CAS] | 38363-32-5 38363-40-5 | GB 1215751 | Antihypertensive, adrenergic | |
| penciclovir | 6H-Purin-6-one, 2-amino-1,9-dihydro-9 [4-hydroxy-3-(hydroxymethyl)butyl]-[CAS] | 39809-25-1 | JP 60058982 | Antiviral, other | Infection, herpes simplex virus |
| Penetha mate | | 808-71-9 | | | |
| penfluridol | 4-Piperidinol, 1-[4,4-bis(4-fluorophenyl)butyl]-4-[4-chloro-3-(trifluoromethyl)phenyl]-[CAS] | 26864-56-2 | DE 2040231 | Neuroleptic | |
| Penicillamine | | 52-67-5 | | | |
| Penicillin G | | 61-33-6 | | | |
| Penicillin G Benzathine | | 1538-09-6 | | | |
| Penicillin G Procaine | | 6130-64-9 | | | |
| Penicillin N | | 525-94-0 | | | |
| Penicillin O | | 87-09-2 | | | |
| Penicillin V | | 87-08-1 | | | |
| Penimepicycline | | 4599-60-4 | | | |
| Penntuss | | | U.S. 4,221,778 | Formulation, modified-release, other | Rhinitis, allergic, general |
| Pentaerythritol Chloral | | 78-12-6 | | | |
| Pentaerythritol Dichlorohydrin | | 2209-86-1 | | | |
| Pentaerythritol | | 597-71-7 | | | |
| Pentagastrin | | 5534-95-2 | | | |
| Pentagestrone | | 7001-56-1 | | | |
| PentaLyte | Starch, 2-hydroxyethyl ether [CAS] | 9005-27-0 | U.S. 5,407,428 | Plasma substitute | Surgery adjunct |
| Pentamethonium | | 541-20-8 | | | |
| pentamidine | Benzenecarboximidamide, 4,4-[1,5-pentanediylbis(oxy)]bis-[CAS] | 100-33-4 | | Formulation, inhalable, systemic | Infection, Pneumocystis jiroveci prophylaxis |
| Pentazocine | | 359-83-1 | | | |
| Pentetate | | 12111-24-9 | | | |
| Pentetic Acid | | 67-43-6 | | | |
| Pentetreotide | | 138661-02-6 | | | |
| Penthienate | | 60-44-6 | | | |
| Pentifylline | | 1028-33-7 | | | |
| Pentigetide | | 62087-72-3 | | | |
| Pentisomide | | 78833-03-1 | | | |
| Pentobarbital | | 76-74-4 | | | |
| Pentolinium | | 52-62-0 | | | |
| Pentorex | | 434-43-5 | | | |
| pentosan | Xylan, [CAS] | 37319-17-8 | U.S. 5,180,715 | Urological | Inflammation, urinary tract |
| pentostatin | Imidazo[4,5-d][1,3]diazepin-8-ol, 3-(2-deoxy-I1-D-erythro-pentofuranosyl)-3,6,7,8-tetrahydro-, (R)-[CAS] | 53910-25-1 | U.S. 3,923,785 | Anticancer, anticancer, antimetabolite | Cancer, leukaemia, hairy cell |
| pentoxifylline | 1H-Purine-2,6-dione, 3,7-dihydro-3,7-dimethyl-1-(5-oxohexyl)-[CAS] | | | Neuroprotective | Amyotrophic lateral sclerosis |
| Pentoxyl | | 147-61-5 | | | |
| Pentrinitrol | | 1607-17-6 | | | |
| Pentylenetetrazole | | 54-95-5 | | | |
| peplomycin | Bleomycinamide, N1-[3-[(1-phenylethyl)amino]propyl]-, (S)-[CAS] | 68247-85-8 | U.S. 4,195,018 | Anticancer, antibiotic | |
| Perazine | | 84-97-9 | | | |
| Perflubron | | 423-55-2 | | | |
| Perfosfamide | | 62435-42-1; 39800-16-3 (unspecified) | | | |
| pergolide | Ergoline, 8-[(methylthio)methyl]-6-propyl-, (8β)-, monomethanesulfonate-[CAS] | 66104-22-1 66104-23-2 | U.S. 4,797,405 | Antiparkinsonian | Parkinson's disease |
| Perhexiline | | 6621-47-2 | | | |
| Pencyazine | | 2622-26-6 | | | |
| perifosine | Piperidinium, 4-[[hydroxy(octadecyloxy)phosphinyl]oxy]-1,1-dimethyl-, inner salt [CAS] | 157716-52-4 | EP 594999 | Anticancer, other | Cancer, prostrate |
| perillyl | 1-Cyclohexene-1-methanol, 4-(1- | 536-59-4 | U.S. 5,110,832 | Anticancer, other | Cancer, breast |

TABLE 3-continued

| API Generic Name | API Chemical Name | CAS No. | Patent Reference | Example of Therapeutic Use | Example of Indication |
|---|---|---|---|---|---|
| alcohol | methylethenyl)-[CAS] | | | | |
| Penmethazine | | 13093-88-4 | | | |
| perindopril | 1H-Indole-2-carboxylic acid, 1-[2-[[1-(ethoxycarbonyl)butyl],amino]-1-oxopropyl]octahydro-, [2S-[1[R*(R*)],2Alpha,3aβ,7aβ]]-, compd. with 2-methyl-2-propanamine (1:1) [CAS] | 107133-36-8 82834-16-0 95153-31-4 | EP | 49658 Antihypertensive, renin system | Hypertension, general |
| Periodyl | | 53586-99-5 | | | |
| perisoxal | 1-Piperidineethanol, Alpha-(5-phenyl-3-isoxazolyl)-, 2-hydroxy-1,2,3-propanetncarboxylate (2:1) (salt) [CAS] | 2139-25-5 2055-44-9 | JP | 04217925 Anti-inflammatory | |
| Pertapine | | 1977-11-3 | | | |
| Permethnn | | 52645-53-1 | | | |
| perospirone | 1H-Isoindole-1,3(2H)-dione, 2-[4-[4-(1,2-benzisothiazol-3-yl)-1-piperazinyl]butyl]hexahydro-, cis-[CAS] | 129273-38-7 150915-41-6 | CA | 2167004 Neuroleptic | Schizophrenia |
| Perphenazine | | 58-39-9 | | | |
| Petroleum Benzin | | 8030-30-6 | | | |
| PH-b | | | U.S. | 6,331,286 Antipsoriasis | Psoriasis |
| Phanquinone | | 84-12-8 | | | |
| Pharmaprojects No. 4994 | | | WO | 9638482 Immunological | Unspecified |
| Pharmaprojects No. 5325 | | | WO | 9703986 Neuroleptic | Schizophrenia |
| Pharmaprojects No. 5972 | | | WO | 0204426 Antiasthma | Asthma |
| Pharmaprojects No. 6362 | | | U.S. | 6,057,346 Antiviral, anti-HIV | Infection, HIV/AIDS |
| Pharmaprojects No. 6446 | (R)-N-[4-[2-[[2-Hydroxy-2-(3-pyridinyl)ethyl]amino]ethyl]phenyl]-4-(4-[4-(trifluoromethyl)phenyl]thiazol-2-yl]benzenesulfonamide | | | Anorectic/Antiobesity | Obesity |
| Pharmaprojects No. 6590 | | | WO | 0206223 Psychostimulant | Attention deficit disorder |
| Pharmaprojects No. 6656 | | | U.S. | 6,455,026 Genomics-based drug discovery | Cancer, brain |
| Pharmaprojects No. 6691 | | | U.S. | 6,299,900 Formulation, other | Pain, general |
| Pharmaprojects No. 6743 | 3-(6-Aminopyndin-3-yl)-N-methyl-N-[(1-methyl-1H-indol-2-yl)methyl]acrylamide | | | Antibacterial, other | Infection, general |
| Pharmaprojects No. 6748 | 1,2,3,4,10,14b-Hexahydro-6-methoxy-2-methyldibenzo[c,f]pyrazino[1,2-a]azepin | | | Antidepressant | Depression, general |
| Phenacaine | | 620-99-5 | | | |
| Phenacemide | | 63-98-9 | | | |
| Phenacetin | | 62-44-2 | | | |
| Phenadoxone | | 467-84-5 | | | |
| Phenallymal | | 115-43-5 | | | |
| Phenamet | | 3819-34-9 | | | |
| Phenazocine | | 127-35-5 | | | |
| Phenazopyridine | | 136-40-3 | | | |
| Phenbutamide | | 3149-00-6 | | | |
| Phencyclidine | | 77-10-1 | | | |
| Phendimetrazine | | 634-03-7 | | | |
| Phenelzine | | 51-71-8 | | | |
| Phenesterine | | 3546-10-9 | | | |
| Phenetharbital | | 357-67-5 | | | |
| Phenethicillin | | 132-93-4 | | | |
| Phenetunde | | 90-49-3 | | | |
| Phenformin | | 114-86-3 | | | |
| Phenglutanmide | | 1156-05-4 | | | |
| Phenindamine | | 82-88-2 | | | |
| Phenindione | | 83-12-5 | | | |
| Pheniprazine | | 55-52-7 | | | |
| Pheniramine | | 86-21-5 | | | |
| Phenmetrazine | | 134-49-6 | | | |
| Phenobarbital | | 50-06-6 | | | |
| Phenobutiodil | | 554-24-5 | | | |
| Phenocoll | | 103-97-9 | | | |
| Phenoctide | | 78-05-7 | | | |
| Phenolphthalein | | 77-09-8 | | | |
| Phenolphthalol | | 81-92-5 | | | |
| Phenolsulfon-phthalein | | 143-74-8 | | | |

TABLE 3-continued

| API Generic Name | API Chemical Name | CAS No. | Patent Reference | Example of Therapeutic Use | Example of Indication |
|---|---|---|---|---|---|
| Phenoltetra-chlorophthalein | | 639-44-1 | | | |
| Phenopendine | | 562-26-5 | | | |
| Phenosulfazole | | 515-54-8 | | | |
| Phenoxy-benzamine | | 59-96-1 | | | |
| Phenoxy-propazine | | 3818-37-9 | | | |
| Phenprobamate | | 673-31-4 | | | |
| Phenprocoumon | | 435-97-2 | | | |
| phenserine | Pyrrolo(2,3-b)indol-5-ol, 1,2,3,3a,8,8a-hexahydro-1,3a,8-trimethyl-, phenylcarbamate (ester), (3aS-cis)-[CAS] | 101246-66-6 | | Cognition enhancer | Alzheimer's disease |
| Phensuximide | | 86-34-0 | | | |
| Phentermine | | 122-09-8 | | | |
| Phentetiothalein | | 18265-54-8 | | | |
| phentolamine | Phenol, 3-(((4,5-dihydro-1H-imidazol-2-yl)methyl)(4-methylphenyl)amino)-, monomethanesulfonate (salt) [CAS] | 65-28-1 50-60-2 | | Formulation, oral, other | Impotence |
| Phenyl Acetylsalicylate | | 134-55-4 | | | |
| Phenyl Aminosalicylate | | 133-11-9 | | | |
| Phenyl Salicylate | | 118-55-8 | | | |
| Phenylbutazone | | 50-33-9 | | | |
| Phenylephrine | | 61-76-7 | | | |
| Phenyl-ethanolamine | | 7568-93-6 | | | |
| Phenylmercury | | 102-98-7 | | | |
| Phenylmethyl-barbituric Acid | | 76-94-8 | | | |
| phenyl-propanolamine | Benzenemethanol, Alpha-(1-aminoethyl)-, (R*,S*)-(+/−)-[CAS] | 14838-15-4 | | Anorectic/Antiobesity, formulation, optimized, microparticles | |
| Phenylpropyl-methylamine | | 93-88-9 | | | |
| Phenylto-loxamine | | 92-12-6 | | | |
| Phenyramidol | | 553-69-5 | | | |
| phenytoin | 2,4-Imidazolidinedione, 5,5-diphenyl-[CAS] | 57-41-0 | | Formulation, oral, other | Epilepsy, general |
| Phethenylate | | 510-34-9 | | | |
| Phloroglucinol | | 108-73-6 | | | |
| Pholcodine | | 509-67-1 | | | |
| Pholednne | | 370-14-9 | | | |
| Phospho-creatine | | 67-07-2 | | | |
| Phospho-cysteamine | | 5746-40-7 | | | |
| Phospho-rylcholine | | 107-73-3 | | | |
| Phthalyl-sutfacetamide | | 131-69-1 | | | |
| Phthalyl-sutfathiazole | | 85-73-4 | | | |
| p-Hydroxy-ephedrine | | 365-26-4 | | | |
| Phylloquinone | | 84-80-0 | | | |
| Physostigmine | | 57-47-6 | | | |
| Phytic Acid | | 83-86-3 | | | |
| PI-88 | D-Mannose, O-6-O-phosphono-Alpha-D-mannopyranosyl-(1-3)-O-Alpha-D-mannopyranosyl-(1-3)-O-Alpha-D-man nopyranosyl-(1-3)-O-Alpha-D-mannopyranosyl-(1-2)- hydrogen sulphate [CAS] | 185077-23-0 | | Anticancer, other | Cancer, melanoma |
| Piberaline | | 39640-15-8 | | | |
| pibaserod | 2H-(1,3)Oxazino(3,2-a)indole-10-carboxamide, N-((1-butyl-4-piperidinyl)methyl)-3,4-dihydro-[CAS] | 152811-62-6 | WO 9318036 | Antiarrhythmic | Fibrillation, atrial |
| Picilorex | | 62510-56-9 | | | |
| Picloxydine | | 5636-92-0 | | | |
| Picopenne | | 21755-66-8 | | | |
| Picosulfate | | 10040-45-6 | | | |

TABLE 3-continued

| API Generic Name | API Chemical Name | CAS No. | Patent Reference | | Example of Therapeutic Use | Example of Indication |
|---|---|---|---|---|---|---|
| Picotamide | | 32828-81-2 | | | | |
| Picumast | | 39577-19-0 | | | | |
| pidotimod | 4-Thiazolidinecarboxylic acid, 3-[(5-oxo-2-pyrrolidinyl)carbonyl]-[CAS] | 121808-62-6 | EP | 276752 | Immunomodulator, anti-infective | Infection, respiratory tract lower |
| Pifarnine | | 56208-01-6 | | | | |
| piketoprofen | Benzeneacetamide, 3-benzoyl-Alpha-methyl-N-(4-methyl-2-pyridinyl)-[CAS] | 60576-13-8 | GB | 1436502 | Anti-inflammatory, topical | |
| Pildralazine | | 64000-73-3 | | | | |
| pilocarpine | 2(3H)-Furanone, 3-ethyldihydro-4-[(1-methyl-1H-imidazol-5-yl)methyl]-, (3S-cis)-[CAS] | 92-13-7 | | | Formulation, implant, Stomatological | |
| Piloplex | 2-Propenoic acid, 2-methyl-, dodecyl ester, polymer with 2-propenoicacid, compd. with (3S-cis)-3-ethyldihydro-4-[(1-methyl-1H-imidazol-5-yl)methyl]-2(3H)-furanone [CAS] | 62783-28-2 | DE | 2636559 | Formulation, mucosal, topical | Glaucoma |
| pilsicainide | 1H-Pyrrolizine-7a(5H)-acetamide, N-(2,6-dimethylphenyl)tetrahydro-, monohydrochloride [CAS] | 88069-49-2 88069-67-4 | U.S. | 4,564,624 | Antiarrhythmic | Arrhythmia, general |
| Pimeclone | | 534-84-9 | | | | |
| pimecrolimus | 15,19-Epoxy-3H-pyrido(2,1-c)(1,4)oxaazacyclotricosine-1,7,20,21(4H,23H)-tetrone, 3-(2-(4-chloro-3-methoxycyclohexyl)-1-methyletheny)-8-ethyl-5,6,8,11,12,13,14,15,16,17,18,19,24,25,26,26a-hexadecahydro-5,19-dihydroxy-14,16-dimethoxy-4,10,12,18-tetramethyl-(3S-(3R*E(1S*,3S*,4R*)),4S*,5R*,8S*,9E*,12R*,14R*,5S*,16R*,18S8,19S*,26aR*))-[CAS] | 137071-32-0 | EP | 626385 | Antipruritic/inflamm, allergic | Eczema, atopic |
| Pimefylline | | 10001-43-1 | | | | |
| pimilprost | Acetic acid, [2-[octahydro-5-hydroxy-6-(3-hydroxy-5-methyl-1-nonenyl)-2-pentalenyl]ethoxy]-, methyl ester, [2R-[2Alpha,3Alpha,4Alpha(1E,3S,5S),5β,6aAlpha]]-[CAS] | 139403-31-9 | | | Dermatological | Ulcer, general |
| Piminodine | | 13495-09-5 | | | | |
| Pimobendan | | 74150-27-9 | | | | |
| pimozide | 2H-Benzimidazol-2-one, 1-[1-[4,4-bis(4-fluorophenyl)butyl]-4-piperidinyl]-1,3-dihydro-[CAS] | 2062-78-4 | FR | M3695 | Neuroleptic | |
| Pinacidil | | 85371-64-8 | | | | |
| pinaverium | Morpholinium, 4-[(2-bromo-4,5-dimethoxyphenyl)methyl]-4-[2-[2-(6,6-dimethylbicyclo[3.1.1]hept-2-yl)ethoxy]ethyl]-, [CAS] | 53251-94-8 59995-65-2 | EP | 406743 | Antispasmodic | Irritable bowel syndrome |
| pinazepam | 2H-1,4-Benzodiazepin-2-one, 7-chloro-1,3-dihydro-5-phenyl-1-(2-propynyl)-[CAS] | 52463-83-9 | DE | 2339790 | Anxiolytic | |
| Pindolol | | 13523-86-9 | | | | |
| pioglitazone | 2,4-Thiazolidinedione, 5-[[4-[2-(5-ethyl-2-pyridinyl)ethoxy]phenyl]methyl]-, monohydrochloride (+/−)-[CAS] | 111025-46-8 112529-15-4 | EP | 193256 | Antidiabetic | Diabetes, Type II |
| Pipacycline | | 1110-80-1 | | | | |
| Pipamazine | | 84-04-8 | | | | |
| Pipamperone | | 1893-33-0 | | | | |
| Pipazethate | | 2167-85-3 | | | | |
| Pipebuzone | | 27315-91-9 | | | | |
| Pipecurium | | 52212-02-9 | | | | |
| pipecuronium | Piperazinium, 4,4'-[(2β,3Alpha,5Alpha,16β,17β)-3,17-bis(acetyloxy)androstane-2,16-diyl]bis[1,1]-dimethyl-, [CAS] | 52212-02-9 68399-57-5 | GB | 1398050 | Muscle relaxant | Anaesthesia, adjunct |
| pipemidic acid | Pyrido[2,3-d]pyrimidine-6-carboxylic acid, 8-ethyl-5,8-dihydro-5-oxo-2-(1-piperazinyl)-[CAS] | 51940-44-4 | GB | 1451911 | Antibacterial, other | Infection, urinary tract |
| Pipenzolate Bromide | | 125-51-9 | | | | |
| Piperacetazine | | 3819-00-9 | | | | |
| piperacillin | 4-Thia-1-azabicyclo[3.2.0]heptane-2-carboxylic acid, 6-[[[[(4-ethyl-2,3-dioxo-1-piperazinyl)carbonyl]amino]phenylacetyl]amino]-3,3-dimethyl-7-oxo-,[2S-[2Alpha,5Alpha,6β(S*)]]-[CAS] | 59703-84-3 61477-96-1 | GB | 1508062 | Penicillin, injectable | Infection, general |

TABLE 3-continued

| API Generic Name | API Chemical Name | CAS No. | Patent Reference | Example of Therapeutic Use | Example of Indication |
|---|---|---|---|---|---|
| Piperazine Adipate | | 142-88-1 | | | |
| Piperidione | | 77-03-2 | | | |
| Piperidolate | | 82-98-4 | | | |
| Pipenlate | | 4546-39-8 | | | |
| pipenne analogues | | | WO | 002544 Dermatological | Vitiligo |
| Piperocaine | | 136-82-3 | | | |
| Piperonal | | 120-57-0 | | | |
| Piperoxan | | 59-39-2 | | | |
| Piperylone | | 25 31-4-6 | | | |
| Pipobroman | | 54-91-1 | | | |
| Piposulfan | | 2608-24-4 | | | |
| pipotiazine | Hexadecanoic acid, 2-[1-[3-[2-[(dimethylamino)sulfonyl]-10H-phenothiazin-10-yl]propyl]-4-piperidinyl]ethyl ester [CAS] | 37517-26-3 39860-99-6 | U.S. | 4,782,077 Neuroleptic | |
| Pipoxolan | | 18174-58-8 | | | |
| Pipradrol | | 467-60-7 | | | |
| piprozolin | Acetic acid, [3-ethyl-4-oxo-5-(1-piperidinyl)-2-thiazolidinylidene]-, ethyl ester [CAS] | 17243-64-0 | U.S. | 3,971,794 GI inflammatory/bowel disorders | Moltility dysfunction, GI, general |
| Piracetam | | 7491-74-9 | | | |
| pirarubicin | 5,12-Naphthacenedione, 10-[[3-amino-2,3,6-trideoxy-4-O-(tetrahydro-2H-pyran-2-yl)-Alpha-L-lyxo-hexopyranosyl]oxy]-7,8,9,10-tetrahydro-6,8,11-trihydroxy-8-(hydroxyacetyl)-1-methoxy-, [8S-[8Alpha,10Alpha(S*)]]-[CAS] | 72496-41-4 | U.S. | 4,303,785 Anticancer, antibiotic | Cancer, breast |
| Pirazolac | | 71002-09-0 | | | |
| pirbuterol | 2,6-Pyridinedimethanol, Alpha6-[[(1,1-dimethylethyl)amino]methyl]-3-hydroxy-, monoacetate (salt) [CAS] | 38029-10-6 38677-81-5 65652-44-0 | U.S. | 3,786,160 Antiasthma | Asthma |
| Pirenoxine | | 1043-21-6 | | | |
| pirenzepine | 6H-Pyrido[2,3-b][1,4]benzodiazepin-6-one, 5,11-dihydro-11-[(4-methyl-1-piperazinyl)acetyl]-[CAS] | 28797-61-7 29868-97-1 | FR | 1505795 Antiulcer | |
| piretanide | Benzoic acid, 3-(aminosulfonyl)-4-phenoxy-5-(1-pyrrolidinyl)-[CAS] | 55837-27-9 | U.S. | 4,010,273 Antihypertension, diuetic | Hypertension, general |
| pirfenidone | 2(1H)-Pyridinone, 5-methyl-1-phenyl-[CAS] | 53179-13-8 | | Respiratory | Fibrosis, pulmonary |
| piribedil | Pyrimidine, 2-(4-(1,3-benzodioxol-5-ylmethyl)-1-piperazinyl]-[CAS] | 3605-01-4 | U.S. | 3,299,067 Vasodilator, peripheral | Parkinson's disease |
| Piridocaine | | 87-21-8 | | | |
| Pirifibrate | | 55285-45-5 | | | |
| Piritramide | | 302-41-0 | | | |
| Piritrexim | | 72732-56-0 | | | |
| pirlindole | 1H-Pyrazino[3,2,1-jk]carbazole, 2,3,3a,4,5,6-hexahydro-8-methyl-[CAS] | 16154-78-2 60762-57-4 | SU | 276060 Antidepressant | Depression, general |
| pirmenol | (2-Pyndinemethanol, Alpha-[3-(2,6-dimethyl-1-piperidinyl)propyl]-.Alpha.phenyl-, cis-(+)-[CAS] | 61477-94-9 68252-19-7 | U.S. | 4,112,103 Antiarrhythmic | Tachycardia, supraventricular |
| Piroctone | | 50650-76-5 | | | |
| Piroheptine | | 16378-21-5 | | | |
| Piromidic Acid | | 19562-30-2 | | | |
| piroxicam | 2H-1,2-Benzothiazine-3-carboxamide, 4-hydroxy-2-methyl-N-2-pyridinyl-, 1,1-dioxide [CAS] | 36322-90-4 | U.S. | 3,862,319 Anti-inflammatory | |
| piroxicam betadex | (β-Cyclodextrin, compd. with 4-hydroxy-2-methyl-N-2-pyndinyl-2H-1,2-benzothiazine-3-carboxamide 1,1-dioxide-[CAS] | 121696-62-6 96684-39-8 | EP | 153998 Formulation, other | Pain, musculoskeletal |
| piroxicam cinnamate | 2-Propenoic acid, 3-phenyl-, 2-methyl-3-[(2-pyridinylamino)carbonyl]-2H-1,2-benzothiazin-4-yl ester, 5,5-dioxide [CAS] | 87234-24-0 | EP | 79639 Antiarthritic, other | Inflammation, general |
| Pirozadil | | 54110-25-7 | | | |
| Pirprofen | | 31793-07-4 | | | |
| pitavastatin | 6-Heptenoic acid, 7-[2-cyclopropyl-4-(4 fluorophenyl)-3-quinolinyl]-3,5-dihydroxy-, calcium salt (2:1), [S-[R*,S*-(E)]]-[CAS] | 147526-32-7 | EP | 304063 Hypolipaemic/Antiatherosclerosis | Hyperlipidaemia, general |
| pivagabine | N-trimethylacetyl-4-aminobutyric acid | 69542-93-4 | | Neurological | Anxiety, general |

TABLE 3-continued

| API Generic Name | API Chemical Name | CAS No. | Patent Reference | Example of Therapeutic Use | Example of Indication |
|---|---|---|---|---|---|
| pivaloyloxymethyl | Butanoic acid, (2,2-dimethyl-1-oxopropoxy)methyl ester [CAS] | 122110-53-6 | EP 302349 | Anticancer, other | Cancer, lung, non-small cell |
| Pivalylbenzhydrazine | | 306-19-4 | | | |
| Pivampicillin pivampiciiiin/ pivmecillinam | | 33817-20-8 98445-47-7 | | Penicillin, oral | Infection, general |
| Pivcefalexin | | 63836-75-9 | | | |
| pivmecillinam | 4-Thia-1-azabicyclo[3.2.0]heptane-2-carboxylic acid, 6-[[(hexahydro-1H-azepin-1-yl)methylene]amino]-3,3-dimethyl-7-oxo-, (2,2-dimethyl-1-oxopropoxy)methyl ester, [2S-(2Alpha,5Alpha,6β)]-[CAS] | 32886-97-8 | GB 1293590 | Penicillin, oral | Infection, general |
| pixantrone | Benz[g]isoquinoline-5,10-diane, 6,9-bis[(2-aminoethyl)amino]-, (2Z)-2-butenedioate(1 :2) [CAS] | 144675-97-8 | EP 503537 | Anticancer, other | Cancer, lymphoma, non-Hodgkin's |
| pizotifen | 4-(9,10-dihydro-4H-benzo[4,5]cyclohepta[1,2-b]thien-4-ylidene)-1-methylpiperidine | 15574-96-6 | DE 2346747 | Antimigraine | |
| Pizotyline | | 15574-96-6 | | | |
| PKI-166 | Phenol, 4-(4-(((1R)-1-phenylethyl)amino)-1H-pyrrolo(2,3-d)pyrimidin-6-yl)-[CAS] | 187724-61-4 | | Anticancer, other | Cancer, general |
| p-Lactophenetide | | 539-08-2 | | | |
| Plafibride | | 63394-05-8 | | | |
| plasminogen activator | Plasminogen activator [CAS] | 105913-11-9 | EP 151996 | Fibrinolytic | Infarction, myocardial |
| Plasmocid | | 551-01-9 | | | |
| Platonin | | 3571-88-8 | | | |
| Plaunotol | | 64218-02-6 | | | |
| PLD-118 | Cyclopentanecarboxylic acid, 2-amino-4-methylene-, (1R,2S)-[CAS] | 198022-65-0 | EP 805145 | Antifungal | Infection, *Candida*, general |
| PLD-147 | (OC-6-43)-Bis(acetato)(1-adamantylamine)ammine-dichloro-platinum (IV) | | | Anticancer, alkylating | Cancer, general |
| pleconaril | 1,2,4-Oxadiazole, 3-(3,5-dimethyl-4-(3-(3-methyl-5-isoxazolyl)propoxy)phenyl)-5-(trifluoromethyl)-[CAS] | 153168-05-9 | U.S. 5,464,848 | Antiviral, other | Infection, respiratory tract, general |
| Plicamycin | | 18378-89-7 | | | |
| p-Methyldiphenhydramine | | 19804-27-4 | | | |
| PMS-601 | | | WO 0001677 | Antiviral, anti-HIV | Infection, HIV/AIDS |
| Pneumococcal Vaccine, Diphtheria Conjugate | | | | | |
| Pneumococcal Vaccine, Polyvalent | | | | | |
| PNU-288034 | N-[[(5s)-3[4[(1,1-dioxido-4-thiomorpholinyl)3,5-difluorophenyl]-2-oxo-5-oxazolidinyl]methyl]acetamide] | | | Antibiotic, other | Infection, general |
| Podophyllotoxin | | 518-28-5 | | | |
| polaprezinc | Zinc, bis(N-β-alanyl-L-histidinato-N3,OAlpha)-, (T-4)-[CAS] | 107667-60-7 | EP 303380 | Antiulcer | Ulcer, duodenal |
| Poldine Methylsulfate | | 545-80-2 | | | |
| Policresulen | | 9011-2-3 | | | |
| Polidexide | | 9064-92-0 | | | |
| polidocanol | Polyethylene glycol monododecyl ether | 3055-99-0 9002-92-0 | | Vasoprotective, systemic | Venous insufficiency |
| Poliovirus Vaccine Inactivated | | | | | |
| poty-ADPRT inhibitors | | | WO 9845253 | Anticancer, other | Cancer, general |
| Polyestradiol Phosphate | | 28014-46-2 | | | |
| Polyphenon E | Polyphenon E [CAS] | 188265-33-0 | | Antiviral, other | Infection, human papilloma virus |

TABLE 3-continued

| API Generic Name | API Chemical Name | CAS No. | Patent Reference | | Example of Therapeutic Use | Example of Indication |
|---|---|---|---|---|---|---|
| Polythiazide | | 346-18-9 | | | | |
| porfimer | Photofrin [CAS] | 87806-31-3 | U.S. | 4,882,234 | Anticancer, other | Cancer, lung, non-small cell |
| Porfiromycin | | 801-52-5 | | | | |
| posaconazole | D-threo-Pentitol, 2,5-anhydro-1,3,4-trideoxy-2-C-(2,4-difluorophenyl)-4-((4-(4-(4-(1(1S,2S)-1-ethyl-2-hydroxypropyl)-1,5-dihydro-5-oxo-4H-1,2,4-triazol-4-yl)phenyl)-1-piperazinyl)phenoxy)methyl)-1-(1H-1,2,4-triazol-1-yl)-[CAS] | 171228-49-2 | U.S. | 5,714,490 | Antifungal | Infection, fungal, general |
| Posatirelin | | 78664-73-0 | | | | |
| potassium chloride | Potassium chloride (KCl) [CAS] | 7447-40-7 | | | Formulation, oral, enteric-coated | |
| Potassium Gluconate | | 299-27-4 | | | | |
| Potassium Guaiacol-sulfonate | | 1321-14-8 | | | | |
| Potassium p-Aminobenzoate | | 138-84-1 | | | | |
| Potassium Pemianganate | | 7722-64-7 | | | | |
| Povidone | | 9003-39-8 | | | | |
| Povidone-Iodine | | 25655-41-8 | | | | |
| PP-117 | 3-Pyridinemethanol, hydrofluoride [CAS] | 62756-44-9 | DE | 2633028 | Formulation, oral, other | Unspecified |
| PR-2699 | (−)-(E)-[4-(2,4-dichlorophenyl)-1,3-dithiolan-2-ylidene]-1-imidazolylacetonitrile | | | | Antifungal | Infection, fungal, general |
| PR-608 | (S)-(−)-1-[4,4-bis(4-fluorophenyl)butyl]-4-(2-hydroxy-3-phenylaminopropyl)piperazine trihydrochloride | | | | Antiparkinsonian | Parkinson's disease |
| Practolol | | 6673-35-4 | | | | |
| Prajmaline | | 35080-11-6 | | | | |
| Pralidoxime | | 51-15-0 | | | | |
| pralnacasan | 6H-Pyridazino(1,2-a)(1,2)diazepine-1-carboxamide, N-((2R,3S)-2-ethoxytetrahydro-5-oxo-3-furanyl)octahydro-9-((1-isoquinolinylcarbonyl)amino)-6,10-dioxo-, (1S,9S)-[CAS] | 192755-52-5 | | | Antiarthritic, immunological | Arthritis, rheumatoid |
| pramipexole | 2,6-Benzothiazolediamine, 4,5,6,7-tetrahydro-N6-propyl-, (S)-[CAS] | 104632-26-0 | EP | 186087 | Antiparkinsonian | Parkinson's disease |
| pramiracetam | 1-Pyrrolidineacetamide, N-[2-[bis(1-methylethyl)amino]ethyl]-2-oxo-, monohydrochloride [CAS] | 68497-62-1 72869-16-0 75733-50-5 | U.S. | 4,145,347 | Cognition enhancer | Amnesia |
| Pramiverin | | 14334-40-8 | | | | |
| pramlintide | 1,2-Dithia-5,8,11,14,17-pentaazacycloeicosane, cyclic peptide deriv. [CAS] | 151126-32-8 | U.S. | 5,124,314 | Antidiabetic | Diabetes, Type I |
| Pramoxine | | 140-65-8 | | | | |
| pranidipine | 3,5-Pyridinedicarboxylic acid, 1,4-dihydro-2,6-dimethyl-4-(3-nitrophenyl)-, methyl 3-phenyl-2-propenyl ester, (E)-[CAS] | 99522-79-9 | EP | 173126 | Antihypertensive, other | Hypertension, general |
| Pranlukast | | 103177-37-3 | | | | |
| pranoprofen | 5H-[1]Benzopyrano[2,3-b]pyridine-7-acetic acid, Alpha-methyl-[CAS] | 52549-17-4 | | | Formulation, mucosal, topical | Ocular disorder, general |
| prasterone | Androst-5-en-17-one, 3-hydroxy-, (3β)-[CAS] | 53-43-0 | | | Labour inducer | |
| pratosartan | 4(3H)-Cycloheptimidazolone, 5,6,7,8-tetrahydro-2-propyl-3-[[2'-(1H-tetrazol-5-yl)[1,1'-biphenyl]-4-yl]methyl]-[CAS] | 153804-05-8 | U.S. | 5,409,947 | Antihypertensive, | |
| pravastatin | 1-Naphthaleneheptanoic acid, 1,2,6,7,8,8a-hexahydro-β,delta,6-trihydroxy-2-methyl-8-(2-methyl-1-oxobutoxy)-, monosodium salt, [1S-[1Alpha(βS*,deltaS*),2Alpha,6Alpha,8β(R*),8aAlpha]]-[CAS] | 81093-37-0 81131-70-6 | U.S. | 4,346,227 | Hypolipaemic/ Antiatherosclerosis | Anthersclerosis |
| Prazepam | | 2955-38-6 | | | | |
| praziquantel | 4H-Pyrazino[2,1-a]isoquinolin-4-one, 2-(cyclohexylcarbonyl)-1,2,3,6,7,11b-hexahydro-[CAS] | 55268-74-1 | U.S. | 4,001,411 | Schistosomicide | |

TABLE 3-continued

| API Generic Name | API Chemical Name | CAS No. | Patent Reference | Example of Therapeutic Use | Example of Indication |
|---|---|---|---|---|---|
| prazosin | Piperazine, 1-(4-amino-6,7-dimethoxy-2-quinazolinyl)-4-(2-furanylcarbonyl)-[CAS] | 19216-56-9<br>19237-84-4 | U.S. 4,092,315 | Antihypertensive, adrenergic | Hypertension, general |
| Prednicarbate | | 73771-04-7 | | | |
| prednimustine | Pregna-1,4-diene-3,20-dione, 21-[4-[4-[bis(2-chloroethyl)amino]phenyl]-1-oxobutoxy]-11,17-dihydroxy-, (11β)-[CAS] | 29069-24-7 | GB 1272841 | Anticancer, alkylating | |
| Prednisolone | | 50-24-8 | | | |
| Prednisolone 21-Diethyl-aminoacetate | | 5626-34-6 | | | |
| prednisolone farnesil | Pregna-1,4-diene-3,20-dione, 11,17-dihydroxy-21-[(3,7,11-trimethyl-1-oxo 2,6,10-dodecatrienyl)oxy]-, [11β,21(2E,6E)]-[CAS] | 118244-44-3 | EP 332143 | Antiarthritic, other | Arthritis, rheumatoid |
| Prednisolone Sodium Phosphate | | 125-02-0 | | | |
| Prednisone | | 53-03-2 | | | |
| Prednival | | 15180-00-4 | | | |
| Prednylidene | | 599-33-7 | | | |
| pregabalin | Hexanoic acid, 3-(aminomethyl)-5-methyl, (S)-[CAS] | 148553-50-8 | | Antiepileptic | Epilepsy, general |
| Pregnan-3a-ol-20-one | | 128-20-1 | | | |
| Premarin + trimegestone | Estra-4,9-dien-3-one, 17-(2-hydroxy-1-oxopropyl)-1 7-methyl-, [1711 (S)]-[CAS] | 74513-62-5 | | Menopausal disorders | Hormone replacement therapy |
| prenalterol | Phenol, 4-[2-hydroxy-3-[(1-methylethyl)amino]propoxy]-, hydrochloride, (S)-[CAS] | 57526-81-5<br>61260-05-7 | GB 1470039 | Cardiostimulant | |
| Prenoxdiazine | | 982-43-4 | | | |
| Prenylamine | | 390-64-7 | | | |
| prezatide | Cuprate(1-), (N2-(N-glycyl-L-histidyl)-L-lysinato)(N2-(N-glycyl-L-histidyl)-L-lysinato(2-))-, hydrogen, [CAS] | 130120-57-9 | | Vulnerary | Wound healing |
| Pridinol | | 511-45-5 | | | |
| Prifinium | | 4630-95-9 | | | |
| Prilocaine | | 721-50-6 | | | |
| Primaquine | | 90-34-6 | | | |
| Primidone | | 125-33-7 | | | |
| Prinomastat | | 192329-42-3 | | | |
| PRO-2000 | | | U.S. 5,614,599 | Antiviral, anti-HIV | Infection, HIV prophylaxis |
| Probenecid | | 57-66-9 | | | |
| Probucol | | 23288-49-5 | | | |
| procainamide | Benzamide, 4-amino-N-[2-(diethylamino)ethyl]-[CAS] | 51-06-9<br>614-39-1 | | Formulation, other | Arrhythmia, general |
| Procaine | | 59-46-1 | | | |
| Procarbazine | | 671-16-9 | | | |
| procaterol | 2(1H)-Quinolinone, 8-hydroxy-5-[1-hydroxy-2-[(1-methylethyl)amino]butyl]-, monohydrochloride [CAS] | 59828-07-8<br>60443-17-6<br>72332-33-3 | GB 1496766 | Antiasthma | |
| prochlorperazine | 10H-Phenothiazine,2-chloro-10-[3-(4-methyl-1-piperazinyl)propyl]-, (Z)-2-butenedioate | 58-38-8<br>84-02-6 | | Formulation, oral, other | Nausea and vomiting, general |
| procodazol | 1H-Benzimidazole-2-propanoic acid [CAS] | 23249-97-0 | ES 407882 | Anticancer, immunological | Cancer, general |
| Procyclidine | | 77-37-2 | | | |
| Procymate | | 13931-64-1 | | | |
| Prodipine | | 31314-38-2 | | | |
| Proflavine | | 92-62-6 | | | |
| Progabide | | 62666-20-0 | | | |
| progesterone | Pregn-4-ene-3,20-dione [CAS] | 57-83-0 | | Formulation, transmucosal, systemic | Amenorrhoea |
| proglumetacin | 1H-Indole-3-acetic acid, 1-(4-chlorobenzoyl)-5-methoxy-2-methyl-, 2-(4-(3-((4-(benzoylamino)-5-(dipropylamino)-1,5-dioxopentyl)oxy)propyl)-1-piperazinyl)ethylester, (+/-)-[CAS] | 57132-53-3<br>59209-40-4 | GB 1467568 | Anti-inflammatory | Inflammation, general |
| proglumide | Pentanoic acid, 4-(benzoylamino)-5-(dipropylamino)-5-oxo-, (+/-)-[CAS] | 6620-60-6 | DE 1518125 | Antiulcer | Ulcer, gastric |
| Proheptazine | | 77-14-5 | | | |
| Prolactin | | 9002-62-4 | | | |

TABLE 3-continued

| API Generic Name | API Chemical Name | CAS No. | Patent Reference | Example of Therapeutic Use | Example of Indication |
|---|---|---|---|---|---|
| Prolintane | | 493-92-5 | | | |
| Prolonium | | 123-47-7 | | | |
| Promazine | | 58-40-2 | | | |
| Promedol | | 64-39-1 | | | |
| Promegestone | | 34184-77-5 | | | |
| promestriene | Estra-1,3,5(10)-triene, 17-methoxy-3-propoxy-, (17β)-[CAS] | 39219-28-8 | GB 1337198 | Reproductive/gonadal, general | Acne |
| Promethazine | | 60-87-7 | | | |
| Pronethalol | | 54-80-8 | | | |
| propacetamol | Glycine, N,N-diethyl-, 4-(acetylamino)phenyl ester [CAS] | 66532-85-2 66532-86-3 | U.S. 4,127,671 | Formulation, parenteral, other | |
| propafenone | 1-Propanone, 1-[2-[2-hydroxy-3-(propylamino)propoxy]phenyl]-3-phenyl [CAS] | 54063-53-5 | GB 1307455 | Antiarrhythmic | Fibrillation, ventricular |
| Propagermanium | | 12758-40-6 | | | |
| Propallylonal | | 545-93-7 | | | |
| Propamidine | | 104-32-5 | | | |
| propane-1,2-diol | 1,2-propanediol | 57-55-6 | | Formulation, dermal, topical | Infection, fungal, general |
| Propanidid | | 1421-14-3 | | | |
| Propantheline | | 50-34-0 | | | |
| Proparacaine | | 499-67-2 | | | |
| Propatyl | | 2921-92-8 | | | |
| propenidazole | ethyl trans-Alpha-acetyl-1-methyl-5-nitroimidazole-2-acrylate | 76448-31-2 | | Antifungal | Infection, trichomoniasis |
| propentofylline | 1H-Purine-2,6-dione, 3,7-dihydro-3-methyl-1-(5-oxohexyl)-7-propyl-[CAS] | 55242-55-2 | GB 1470220 | Neuroprotective | Ischaemia, cerebral |
| Propicillin | | 551-27-9 | | | |
| Propiomazine | | 362-29-8 | | | |
| Propionic Acid | | 79-09-4 | | | |
| propionyt L-carnitine | 1-Propanaminium, 3-carboxy-N,N,N-trimethyl-2-(1-oxopropoxy)-, chloride, (R)-[CAS] | 119793-66-7 20084-19-1 | GB 2008578 | Vasodilator, peripheral | Peripheral vascular disease |
| Propipocaine | | 3670-68-6 | | | |
| Propiram | | 15686-91-6 | | | |
| propiverine | 2,2-diphenyl-2-(1-propoxy)acetic acid (1-methylpiperid-4-yl) ester54556-98-8 hydrochloride | 60569-19-9 | | Urological | Incontinence |
| Propizepine | | 10321-12-7 | | | |
| propofol | Phenol, 2,6-bis(1-methylethyl)-[CAS] | 2078-54-8 | U.S. 4,056,635 | Anaesthetic, injectable | Anaesthesia |
| Propoxycaine | | 550-83-4 | | | |
| Propoxyphene | | 469-62-5 | | | |
| propranolol | 2-Propanol, 1-[(1-methylethyl)amino]-3-(1-naphthalenyloxy)-[CAS] | 318-98-9 525-66-6 | | Formulation, modified-release, <=24 hr | Hypertension, general |
| Propylhexednne | | 101-40-6 | | | |
| Propyliodone | | 587-61-1 | | | |
| Propylthiouracil | | 51-52-5 | | | |
| Propyphenazone | | 479-92-5 | | | |
| Proquazone | | 22760-18-5 | | | |
| Proscillaridin | | 466-06-8 | | | |
| Prostacyclin | | 35121-78-9 | | | |
| Prostaglandin E1 | | 745-65-3 | | | |
| Prostaglandin E2 | | 363-24-6 | | | |
| Prostaglandin F2a | | 551-11-1 | | | |
| Prosultiamine | | 59-58-5 | | | |
| Protein C | | 60202-16-6 | | | |
| Protheobromine | | 50-39-5 | | | |
| Prothipendyl | | 303-69-5 | | | |
| Protiofate | | 58416-00-5 | | | |
| Protionamide | | 14222-60-7 | | | |
| protizinic acid | 10H-Phenothiazine-2-acetic acid, 7-methoxy-Alpha,10-dimethyl-, (+/−)-[CAS] | 13799-03-6 | U.S. 3,450,698 | Anti-inflammatory | |
| Protoanemonin | | 108-28-1 | | | |
| Protokytol | | 136-70-9 | | | |
| Protoporphyrin IX | | 553-12-8 | | | |
| Protriptytine | | 438-60-8 | | | |
| Pro-Urokinase | | 82657-92-9 | | | |
| Proxazole | | 5696-9-3 | | | |
| Proxibarbal | | 2537-29-3 | | | |
| proxigermanium | Propanoic acid, 3,3-(1,3-dioxo-1,3-digermoxanediyl)bis-[CAS] | 12758-40-6 | FR 2005110 | Antiviral, other | Infection, hepatitis-B virus |
| Proxyphylline | | 603-00-9 | | | |
| Prozapine | | 3426-8-2 | | | |
| Prucalopride | | 179474-81-8 | | | |

TABLE 3-continued

| API Generic Name | API Chemical Name | CAS No. | Patent Reference | Example of Therapeutic Use | Example of Indication |
|---|---|---|---|---|---|
| prulifloxacin | 1H,4H-[1,3]Thiazeto[3,2-a]quinoline-3-carboxylic acid, 6-fluoro-1-methyl-7-[4-[(5-methyl-2-oxo-1,3-dioxol-4-yl)methyl]1-piperazinyl]-4-oxo-[CAS] | 123447-62-1 | EP 315828 | Quinolone antibacterial | Infection, respiratory tract, general |
| Pseudocacaine | | 478-73-9 | | | |
| pseudoephedrine + triprolidine | Benzenemethanol, Alpha-[1-(methylamino)ethyl]-, hydrochloride, [S-(R*,R*)]-, mixt. with (E)-2-[1-(4-methylphenyl)-3-(1-pyrrolidinyl)-1-propenylipyndine monohydrochloride [CAS] | | | Formulation, modified-release, other | Rhinitis, allergic, general |
| pseudoephedrine | Benzenemethanol, Alpha-[1-(methylamino)ethyl]-, [S-(R*,R*)]-[CAS] | 90-82-4, 8054-271, 345-78-8 | | Formulation, oral, other | Infection, respiratory tract, general |
| Psilocybin | | 520-52-5 | | | |
| PSK-3841 | Benzonitrile, 4-[3-(4-hydroxybutyl)-4,4-dimethyl-2,5-dioxo-1-imidazolidinyl]-2-(trifluoromethyl)-[CAS] | 154992-24-2 | | Dermatological | Alopecia, general |
| p-Sulfanilyl-benzylamine | | 4393-19-5 | | | |
| PT-141 | | | U.S. 6,051,555 | Male sexual dysfunction | Impotence |
| Pteropterin | | 89-38-3 | | | |
| Puromycin | | 53-79-2 | | | |
| PX-12 | 1-Methylpropyl 2-mercaptoimidazolyl disulfide | | | Anticancer, other | Cancer, general |
| Pyrantel | | 15686-83-6 | | | |
| Pyrazinamide | | 98-96-4 | | | |
| Pyridinol Carbamate | | 1882-26-4 | | | |
| Pyridostigmine Bromide | | 101-26-8 | | | |
| Pyridoxal 5-Phosphate | | 54-47-7 | | | |
| Pyridoxine | | 58-56-0 | | | |
| Pyrilamine | | 91-84-9 | | | |
| Pyrimethamine | | 58-14-0 | | | |
| Pyrinoline | | 1740-22-3 | | | |
| Pyrisuccideanol | | 33605-94-6 | | | |
| Pynthione | | 1121-30-8 | | | |
| Pyrithyldione | | 77-04-3 | | | |
| Pyritinol | | 1098-97-1 | | | |
| Pyrocatechol | | 120-80-9 | | | |
| Pyrogallol | | 87-66-1 | | | |
| Pyronandine | | 74847-35-1 | | | |
| Pyrovalerone | | 3563-49-3 | | | |
| Pyroxylin | | 9004-70-0 | | | |
| Pyrrobutamine | | 91-82-7 | | | |
| Pyrrocaine | | 2210-77-7 | | | |
| Pyrrolnitnn | | 1018-71-9 | | | |
| Pyrvinium Pamoate | | 3546-41-6 | | | |
| quazepam | 2H-1,4-Benzodiazepine-2-thione, 7-chloro-5-(2-fluorophenyl)-1,3-dihydro-1-(2,2,2-trifluoroethyl)-[CAS] | 36735-22-5 | U.S. 3,845,039 | Hypnotic/Sedative | Insomnia |
| Quercetin | | 117-39-5 | | | |
| quetiapine | Ethanol, 2-[2-(4-dibenzo[b,f][1,4]thiazepin-11-yl-1-piperazinyt)ethoxy]-, (E)-2-butenedloate (2:1) (salt)[CAS] | 111974-69-7 111974-72-2 | EP 240228 | Neuroleptic | Schizophrenia |
| Quinacillin | | 1596-63-0 | | | |
| quinacnne | N-(6-Chloro-2-methoxy-9-acridinyl)-N,N diethyl-1,4-pentanediamine + 10H-Phenothiazine-10-propanamine, 2-chloro-N,N-dimethyl | 83-89-6 | | Neurological | Creutzfeidt-Jakob disease |
| quinagolide | Sulfamide, N,N-diethyl-N'-(1,2,3,4,4a,5,10,10a-octahydro-6-hydroxy-1-propylbenzo[g]quinolin-3-yl)-, (3Alpha,4aAlpha,10aβ)- (+/−)-[CAS] | 87056-78-8 94424-50-7 97805-49-7 | EP 77754 | Antiprolactin | Hyperprolactinaemia |
| quinapril | 3-Isoquinolinecarboxylic acid, 2-[2-[[1-(ethoxycarbonyl)-3-phenylpropyl]amino]1-oxopropyl]-1,2,3,4-tetrahydro-, [3S-[2(R*(R*)],3R*]]-[CAS] | 82586-55-8 85441-61-8 90243-99-5 | EP 49605 | Antihypertensive, renin system | Hypertension, general |

TABLE 3-continued

| API Generic Name | API Chemical Name | CAS No. | Patent Reference | | Example of Therapeutic Use | Example of Indication |
|---|---|---|---|---|---|---|
| quinaprilat | 3-Isoquinolinecarboxylic acid, 2-[2-[(1-carboxy-3-phenylpropyl)amino]-1-oxopropyl]-1,2,3,4-tetrahydro-, [3S-[2[R*(R*)],3R*]]-[CAS] | 82768-85-2 | EP | 46953 | Antihypertensive, renin system | Hypertension, general |
| Quinapyramine | | 20493-41-8 | | | | |
| Quinbolone | | 2487-63-0 | | | | |
| Quinestradiol | | 1169-79-5 | | | | |
| Quinestrol | | 152-43-2 | | | | |
| Quinethazone | | 73-49-4 | | | | |
| quinfamide | 2-Furancarboxylic acid, 1-(dichloroacetyl)-1,2,3,4-tetrahydro-6-quinolinyl ester [CAS] | 62265-68-3 | U.S. | 3,997,542 | Amoebicide | |
| quinidine | Cinchonan-9-ol, 6'-methoxy-, (9S)-, sulfate (1:1) (salt) [CAS] | 747-45-5<br>56-54-2 | | | Formulation, modified-release, other | Arrhythmia, general |
| Quinine | | 130-95-0 | | | | |
| Quinocide | | 525-61-1 | | | | |
| Quinupramine | | 31721-17-2 | | | | |
| Quinupristin | | 120138-50-3 | | | | |
| R-107500 | cis-2,3,3a,8-tetrahydro-N,N-dimethyldibenz[c,f]isoxazolo[2,3-a]azepine-2-methanamine | | WO | 9614320 | Anxiolytic | Anxiety, general |
| R-667 | | | WO | 0204439 | COPD treatment | Emphysema, general |
| rabeprazole | 1H-Benzimidazole, 2-[[[4-(3-methoxypropoxy)-3-methyl-2-pyridinyl]methyl]sulfinyl]-, sodium salt-[CAS] | 117976-89-3<br>117976-90-6 | EP | 268956 | Antiulcer | Ulcer, gastric |
| racecadotril | Glycine, N-[2-[(acetylthio)methyl]-1-oxo 3-phenylpropyl]-, phenylmethyl ester, (+/−)-[CAS] | 112573-72-5<br>81110-73-8 | EP | 38758 | Antidiarrhoeal | Diarrhoea, general |
| Racemethorphan | | 510-53-2 | | | | |
| raloxifene | Methanone, [6-hydroxy-2-(4-hydroxyphenyl)benzo[b]thien-3-yl][4-[2-(1-piperidinyl)ethoxy]phenyl]-, hydrochloride [CAS] | 82640-04-8<br>84449-90-1 | EP | 62503 | Osteoporosis treatment | Osteoporosis |
| raltitrexed | L-glutamic acid, N-[[5-[[(1,4-dihydro-2-methyl-4-oxo-6-quinazolinyl)methyl]methylamino]-2-thienylicarbonyl]-[CAS] | 112887-68-0 | EP | 239362 | Anticancer, antimetabolite | Cancer, colorectal |
| ramatroban | 9H-Carbazole-9-propanoic acid, 3-[[(4-fluorophenyl)sulfonyl]amino]-1,2,3,4-tetrahydro-, (R)-[CAS] | 116649-85-5 | EP | 242518 | Antiallergic, non-asthma | Rhinitis, allergic, perennial |
| Ramifenazone | | 3615-24-5 | | | | |
| ramipril | Cyclopenta[b]pyrrole-2-carboxylic acid, 1-[2-[[1-(ethoxycarbonyl)-3-phenylpropyl]amino]-1-oxopropyl]octahydro-, [2S-[1[R*(R)],2Alpha,3aβ,6aβ]]-[CAS] | 87269-97-4<br>87333-19-5 | EP | 79022 | Antihypertensive, renin system | Heart failure |
| ramosetron | Methanone, (1-methyl-1H-indol-3-yl)(4,5,6,7-tetrahydro-1H-benzimidazol-5-yl)-, monohydrochloride, (R)-[CAS] | 132907-72-3<br>132036-88-5 | EP | 381422 | Antiemetic | Nausea and vomiting, general |
| Ramot project No. 1097 | | | U.S. | 5,730,992 | Dermatological | Unspecified |
| Ranimustine | | 58994-96-0 | | | | |
| ranitidine | 1,1-Ethenediamine, N-[2-([[5-[(dimethylamino)methyl]-2-furanyl]methyl]thio]ethyl]-N'-methyl-2-nitro-[CAS] | 66357-35-5 | U.S. | 4,128,658 | Antiulcer | Ulcer, duodenal |
| ranitidine bismuth citrate | 1,2,3-Propanetricarboxylic acid, 2-hydroxy-bismuth(3+) salt (1:1), compd. with N-(2-(((5-((dimethylamino)methyl)-2-furanyl)methyl)thio)ethyl)-N'-methyl-2 ni1-ethenediamine (1:1)-[CAS] | 128345-62-0 | EP | 533281 | Antiulcer | Ulcer, duodenal |
| ranolazine | 1-Piperazineacetamide, N-(2,6-dimethylphenyl)-4-(2-hydroxy-3-(2-methoxyphenoxy)propyl]-, (+/−)-[CAS] | 95635-55-5<br>95635-56-6 | EP | 126449 | Antianginal | Angina, general |
| Ranpirnase | | 133737-96-9 | | | | |
| Rapacuronium | | 156137-99-4 | | | | |
| rasagiline | 1H-Inden-1-amine, 2,3-dihydro-N-2-propynyl-, (R)-, [CAS] | 161735-79-1 | U.S. | 5,457,133 | Antiparkinsonian | Parkinson's disease |
| Raubasine | | 483-04-5 | | | | |
| ravuconazole | Benzonitrile, 4-[2-[(1R,2R)-2-(2,4-difluorophenyl)-2-hydroxy-1-methyl-3-(1H-1,2,4-triazol-1-yl)propyl]-4-thiazolyl]-[CAS] | 182760-06-1 | | | Antifungal | Infection, meningitis, general |

TABLE 3-continued

| API Generic Name | API Chemical Name | CAS No. | Patent Reference | Example of Therapeutic Use | Example of Indication |
|---|---|---|---|---|---|
| raxofeiast | 2-Benzofuranacetic acid, 5-(acetyloxy)-2,3-dihydro-4,6,7-trimethyl-, (+)-[CAS] | 128232-14-4 | U.S. 4,999,350 | Symptomatic antidiabetic | Nephropathy, diabetic |
| razoxane | 2,6-Piperazinedione, 4,4'-(1-methyl-1,2-ethanediyl)bis-[CAS] | 21416-67-1, 21416-87-5 | GB 1234935 | Anticancer, other | Cancer, general |
| RC-529 | Tetradecanoic acid (1R)-1-(2-((2-((2-deoxy-3-O-((3R)-1-oxo-3-((1-oxotetradecyl)oxy)tetradecyl)amino-4-O-phosphono-β-D-glucopyranosyl)oxy)ethyl)amino)-2-oxoethyl)dodecyl ester, compd. with N,N-diethylethanamine (1:1) [CAS] | 216014-46-9 | | Immunostimulant, other | Vaccine adjunct |
| rebamipide | 4-Quinolinepropanoic acid, Alpha-[(4-chlorobenzoyl)amino]-1,2-dihydro-2-oxo-[CAS] | 90098-04-7 | DE 3324034 | Antiulcer | |
| rebimastat | L-Valinamide, N-((2S)-2-mercapto-1-oxo-4-(3,4,4-trimethyl-2,5-dioxo-1-imidazolidinyl)butyl)-L-leucyl-N,3-dimethyl-[CAS] | 259188-38-0 | | Anticancer, other | Cancer, lung, non-small cell |
| reboxetine | Morpholine, 2-[(2-ethoxyphenoxy)phenylmethyl]-, (R*,S*)-[CAS] | 71620-89-8, 98769-81-4 | U.S. 4,229,449 | Antidepressant | Depression, general |
| Remacemide | | 128298-28-2 | | | |
| remifentanil | 1-Piperidinepropanoic acid, 4-(methoxycarbonyl)-4-((1-oxopropyl)phenylamino)-methyl ester-[CAS] | 132539-07-2, 132875-61-7 | EP 383579 | Analgesic, other | Pain, general |
| reminertant | Tricyclo[3.3.1.13,7]decane-2-carboxylic acid, 2-[[[1-(7-chloro-4-quinolinyl)-5-(2,6-dimethoxyphenyl)-1H-pyrazol-3-yl]carbonyl]amino]-[CAS] | 146362-70-1 | EP 699438 | Neuroleptic | Schizophrenia |
| Remoxipride | | 80125-1 4-0 | | | |
| renzapride | Benzamide, 4-amino-N-1-azabicyclo[3.3.1]non-4-yl-5-chloro-2-methoxy-[CAS] | 109872-41-5, 88721-77-1 | JP 58188885 | Gastroprokinetic | Irratable bowel syndrome |
| repaglinide | Benzoic acid, 2-ethoxy-4-[2-[[3-methyl-1-[2-(1-piperidinyl)phenyl]butyl]amino]-2-oxoethyl]-, (S)-[CAS] | 135062-02-1 | WO 9300337 | Antidiabetic | Diabetes, Type II |
| repertaxin L-lysine salt | 2(R)-Isobutylphenylpropionyl methanesulfonamide L-lysine salt | | WO 0024710 | Cardiovascular | Reperfusion injury |
| repinotan | 1,2-Benzisothiazol-3(2H)-one, 2-(4-(((3,4-dihydro-2H-1-benzopyran-2-yl)methyl)amino)butyl)-, 1,1-dioxide, monohydrochloride [CAS] | 144980-29-0, 144980-77-8 | U.S. 5,137,901 | Neuroprotective | Ischaemia, cerebral |
| repirinast | 4H-Pyrano[3,2-c]quinoline-2-carboxylic acid, 5,6-dihydro-7,8-dimethyl-4,5-dioxo-, 3-methylbutyl ester [CAS] | 73080-51-0 | U.S. 4,298,610 | Antiasthma | |
| Reposal | | 3625-25-0 | | | |
| reproterol | 1H-Purine-2,6-dione, 7-[3-[[2-(3,5-dihydroxyphenyl)-2-hydroxyethyl]amino]propyl]-3,7-dihydro-1,3-dimethyl-[CAS] | 13055-82-8, 54063-54-6 | FR M5969 | Antiasthma | Asthma |
| Rescimetol | | 73573-42-9 | | | |
| Rescinnamine | | 24815-24-5 | | | |
| Reserpiline | | 131-02-2 | | | |
| Reserpine | | 50-55-5 | | | |
| Resibufogenin | | 465-39-4 | | | |
| resiquimod | 1H-Imidazo(4,5-c)quinoline-1-ethanol(ethoxymethyl)-Alpha, Alpha-dimethyl-[CAS] | 144875-48-9 | U.S. 5,389,640 | Antiviral, other | Infection, hepatitis-C virus |
| Resorcinol | | 108-46-3 | | | |
| Reteplase | | 133652-38-7 | | | |
| retigabine | Carbamic acid, (2-amino-4-(((4-fluorophenyl)methyl)amino)phenyl)-, ethyl ester [CAS] | 150812-12-7 | DE 4200259 | Antiepileptic | Epilepsy, general |
| retinoic acid | Retinoic acid [CAS] | 302-79-4 | | Formulation, parental, other | Cancer, leukaemia, acute myelogenous |
| Revimid | | | U.S. 6,281,230 | Anticancer, other | Cancer, myeloma |
| R-flurbiprofen | [1,1-Biphenyl]-4-acetic acid, 2-fluoro-Alpha-methyl | 5104-49-4 | | Anticancer, other | Cancer, prostate |
| Rho (D) Immune Globuhn (Human) | | | | | |
| Rho-kinase inhibitors | | | WO 0156988 | Antiasthma | Unspecified |

TABLE 3-continued

| API Generic Name | API Chemical Name | CAS No. | Patent Reference | Example of Therapeutic Use | Example of Indication |
| --- | --- | --- | --- | --- | --- |
| ribavirin | 1H-1,2,4-Triazole-3-carboxamide, 1-β-D-ribofuranosyl-[CAS] | 36791-04-5 | U.S. | 4,211,771 Antiviral, other | Infection, haemorrhagic fever |
| Riboflavin | | 146-17-8 | | | |
| ribostamycin | D-Streptamine, O-2,6-diamino-2,6-dideoxy-Alpha-D-glucopyranosyl-(1-4)-O-(β-D-ribofuranosyl-(1-5)]-2-deoxy-[CAS] | 25546-65-0 | GB | 1254883 Aminoglycoside antibiotic | Infection, general |
| Ricinoleic Acid | | 141-22-0 | | | |
| Ridogrel | | 110140-89-1 | | | |
| rifabutin | Rifamycin XIV, 1',4-didehydro-1-deoxy-1,4-dihydro-5'-(2-methylpropyl)-1-oxo-[CAS] | 72559-06-9 | U.S. | 4,219,478 Antimycobacterial | Infection, *Mycobacterium avium* complex |
| rifalazil | Rifamycin VIII, 1',4-didehydro-1-deoxy-1,4-dihydro-3'-hydroxy-5'-(4-(2-methylpropyl)-1-piperazinyt]-1-oxo-[CAS] | 129791-92-0 129791-94-2 133633-12-2 | EP | 366914 Antimycobacterial | Infection, tuberculosis |
| rifametane | Rifamycin, 3-[[[1-(diethylamino)ethylidene]hydrazono]methyl]-[CAS] | 94168-98-6 | EP | 119571 Antimycobacterial | Infection, general |
| Rifamide | | 2750-76-7 | | | |
| rifampicin + trimethoprim | Rifamycin, 3-[[(4-methyl-1-piperazinyl)imino]methyl]-, mixt. with 5-[(3,4,5-trimethoxyphenyl)methyl]-2,4-pyrimidinediamine [CAS] | 61498-94-0 | | Formulation, fixed-dose combinations | Infection, general |
| Rifampin | | 13292-46-1 | | | |
| Rifamycin SV | | 6998-60-3 | | | |
| rifapentine | Rifamycin, 3-[[(4-cyclopentyl-1-piperazinyl)imino]methyl]-[CAS] | 61379-65-5 | DE | 2608218 Antibiotic, other | Infection, tuberculosis |
| rifaximin | Epoxypentadeca[1,11,13]trienimino) benzofuro[4,5-e]-pyrido[1,2-a]benzimidazole-1,15(2H)-dione, 25-(acetyloxy)-5,6,21,23-tetrahydroxy-27-methoxy-2,4,11,16,20,22,24,26-octamethyl-, [25-(2R*,16Z,18E,20R*,22S*,23S*,24S*,25R*,26S*,27R*,28E)] | 80621-81-4 | GB | 2079270 Antibiotic, other | Infection, GI tract |
| rifaximine cream | 4-deoxy-4'-methylpyrido[1',2'-1,2]imidoazo[5,4-c]rifamycin SV | 80621-81-4 | BE | 888895 Formulation, dermal, topical | Infection, dermatological |
| Rilmazafone | | 99593-25-6 | | | |
| rilmenidine | 2-Oxazolamine, N-(dicyclopropylmethyl)-4,5-dihydro-[CAS] | 54187-04-1 54249-57-9 | DE | 2362754 Antihypertensive, adrenergic | Hypertension, general |
| riluzole | 2-Benzothiazolamine, 6-(trifluoromethoxy)-[CAS] | 1744-22-5 | EP | 50551 Neuroprotective | Amyotrophic lateral sclerosis |
| Rimantadine | | 13392-28-4 | | | |
| rimazolium | 4H-Pyrido[1,2-a]pyrimidinium, 3-(ethoxycarbonyl)-6,7,8,9-tetrahydro-1,6-dimethyl-4-oxo-, [CAS] | 28610-84-6 35615-72-6 | DE | 2461349 Analgesic, NSAID | |
| rimexolone | Androsta-1,4-dien-3-one,11-hydroxy-16,17-dimethyl-17-(1-oxopropyl)-, (11β,16Alpha,17β)-[CAS] | 49697-38-3 | DE | 2301317 Ophthalmological | Inflammation, ocular |
| Rimiterol | | 32953-89-2 | | | |
| rimonabant | 1H-Pyrazole-3-carboxamide, 5-(4-chlorophenyl)-1-(2,4-dichlorophenyl)-4-methyl-N-1-piperidinyl-, monohydrochloride [CAS] | 158681-13-1 | U.S. | 5,624,941 Anorectic/Antiobesity | Obesity |
| riodoxol | 1,3-Benzenediol, 2,4,6-triiodo-[CAS] | 19403-92-0 | U.S. | 3,755,251 Antiviral, other | |
| Rioprostil | | 77287-05-9 | | | |
| risedronate | Phosphonic acid, (1-hydroxy-2-(3-pyridinyl)ethylidene)bis-, monosodium salt | 115436-72-1 | EP | 304961 Osteoporosis treatment | Paget's disease |
| Risedronic Acid | | 105462-24-6 | | | |
| risperidone | 4H-Pyrido[1,2-a]pyrimidin-4-one, 3-[2-[4-(6-fluoro-1,2-benzisoxazol-3-yl)-1-piperidinyl]ethyl]-6,7,8,9-tetrahydro-2-methyl-[CAS] | 106266-06-2 | EP | 196132 Neuroleptic, formulation, optimized, microencapsulate | Schizophrenia |
| Ritanserin | | 87051-43-2 | | | |
| Ritipenem | | 84845-57-8 | | | |
| ritodrine | Benzenemethanol, 4-hydroxy-Alpha-[1-[[2-(4-hydroxyphenyl)ethyl]amino]ethyl]-, (R*,S*)-[CAS] | 23239-51-2 26652-09-5 | U.S. | 3,410,944 Labour inhibitor | Labour, preterm |
| ritonavir | 2,4,7,12-Tetraazatridecan-13-oic acid, 10-hydroxy-2-methyt-5-(1-methylethyl)-1-(2-(1-methylethyl)-4-thiazolyl)-3,6- | 155213-67-5 | WO | 9414436 Antiviral, anti-HIV | Infection, HIV/AIDS |

TABLE 3-continued

| API Generic Name | API Chemical Name | CAS No. | Patent Reference | Example of Therapeutic Use | Example of Indication |
|---|---|---|---|---|---|
| | dioxo-8,11-bis(phenylmethyl)-, 5-thiazolyl-methyl ester, (5S-(5R*,8R*,10R*,11R*))-[CAS] | | | | |
| Rituximab | | 174722-31-7 | | | |
| rivastigmine | Carbamic acid, ethylmethyl-, 3-[1-(dimethylamino)ethyl]phenyl ester, (S)-[CAS] | 123441-03-2 129101-54-8 | DE 3805744 | Cognition enhancer | Alzheimer's disease |
| rizatriptan | 1H-Indole-3-ethanamine, N,N-dimethyl-5-(1H-1,2,4-triazol-1-ylmethyl)-, [CAS] | 145202-66-0 159776-67-7 144034-80-0 | EP 497512 | Antimigraine | Migraine |
| RJR-2403 | 3-Buten-1-amine, N-methyl-4-(3-pyridinyl)-, (3E)-, (2E)-2-butenedioate (1:1) [CAS] | 183288-99-5 | | Cognition enhancer | Alzheimer's disease |
| RNA Stealth Nucleosides | 5-Formyluridine | | | Antiviral, other | Infection, hepatitis-C virus |
| Ro-0094889 | 2',3'-Di-O-acetyl-5'-vinylcytidine | | | Anticancer, antimetabolite | Cancer, general |
| Ro-61-1790 | 2-Pyridinesulfonamide, N-[6-(2-hydroxyethoxy)-5-(2-methoxyphenoxy)-2-[2-(1H-tetrazol-5-yl)-4-pyridinyl]-4-pyrimidinyl]-5-methyl-[CAS] | 180384-56-9 | WO 9619459 | Cardiovascular | Haemorrhage, subarachnoid |
| Rociverine | | 53716-44-2 | | | |
| rocuronium | Pyrrolidinium, 1-[(2β,3Alpha,5Alpha, 16β, 17β,)-17-(acetyloxy)-3-hydroxy-2-(4-morpholinyl)androstan-16-yl]-1-(2-propenyl)-, bromide-[CAS] | 104855-17-6 104884-91-5 119302-91-9 143558-00-3 | EP 287150 | Muscle relaxant | Muscle spasm, general |
| rofecoxib | 2(5H)-Furanone, 4-(4-(methylsulfonyl)phenyl)-3-phenyl-[CAS] | 162011-90-7 | U.S. 5,474,995 | Analgesic, NSAID | Arthritis, osteo |
| roflumilast | Benzamide, 3-(cyclopropylmethoxy)-N-(3,5-dichloro-4-pyridinyl)-4-(difluoromethoxy)-[CAS] | 162401-32-3 | WO 9501338 | COPD treatment | Chronic obstructive pulmonary disease |
| rokitamycin | Leucomycin V, 4B-butanoate 3B-propanoate [CAS] | 74014-51-0 | U.S. 4,242,504 | Macrolide antibiotic | Infection, general |
| Rolipram | | 61413-54-5 | | | |
| Rolitetracycline | | 751-97-3 | | | |
| Romurtide | | 78113-36-7 | | | |
| Ronifibrate | | 42597-57-9 | | | |
| ropinirole | 2H-Indol-2-one, 4-[2-(dipropylamino)ethyl]-1,3-dihydro-, monohydrochloride-[CAS] | 91374-20-8 91374-21-9 | EP 266033 | Antiparkinsonian | Parkinson's disease |
| ropivacaine | 2-Piperidinecarboxamide, N-(2,6-dimethylphenyl)-1-propyl-, (S)-[CAS] | 84057-95-4 98717-15-8 | EP 239710 | Anaesthetic, local | Anaesthesia |
| Roquinimex | | 84088-42-6 | | | |
| rosaprostol | Cyclopentaneheptanoic acid, 2-hexyl-5-hydroxy-[CAS] | 56695-65-9 | GB 1523355 | Prostaglandin | |
| Rosaramicin | | 35834-26-5 | | | |
| Rose Bengal | | 632-68-8 | | | |
| rosiglitazone | 2,4-Thiazolidinedione, 5-((4-(2-(methyl-2-pyridinylamino)ethoxy)phenyl)methyl)-, (Z)-2-butenedioate (1:1) [CAS] | 122320-73-4 155141-29-0 | U.S. 5,002,953 | Antidiabetic | Diabetes, Type II |
| rosoxacin | 3-Quinolinecarboxylic acid, 1-ethyl-1,4-dihydro-4-oxo-7-(4-pyridinyl)-[CAS] | 40034-42-2 | U.S. 3,753,993 | Quinolone antibacterial | Infection, gonorrhoea |
| rostaporfin | Tin, dichloro[ethyl 3,4,20,21-tetradehydro-4,9,14,19-tetraethyl-18,19 dihydro-3,8,13,18-tetramethyl-20-phorbinecarboxylato(2-)-kappaN23,kappaN24,kappaN25,kappa N26]-, (OC-6-13)-[CAS] | 114494-17-6 | | Ophthalmological | Macular degeneration |
| rosuvastatin | 6-Heptenoic acid, 7-(4-(4-fluorophenyl) 6-(1-methylethyl)-2-(methyl(methylsulfonyl)amino)-5-pyrimidinyl)-3,5-dihydroxy- (S-(R*, S*-(E))) [CAS] | 147098-20-2 | JP 2648897 | Hypolipaemic/ Antiatherosclerosis | Hyperlipidaemia, general |
| rotigotine | 1-Naphthalenol, 5,6,7,8-tetrahydro-6-[propyl[2-(2-thienyl)ethyl]amino]-, (S)-[CAS] | 99755-59-6 | U.S. 4,564,628 | Antiparkinsonian | Parkinson's disease |
| Rotraxate | | 92071-51-7 | | | |
| Roxarsone | | 121-19-7 | | | |
| roxatidine | Acetamide, 2-(acetyloxy)-N-[3-[3-(1-piperidinylmethyl)phenoxy]propyl]-, [CAS] | 78628-28-1 93793-83-0 | EP 24510 | Antiulcer | Ulcer, gastric |
| roxifiban | L-Alanine, 3-(((3-(4-(aminoiminomethyl)phenyl)-4,5-dihydro 5-isoxazolyl)acetyl)amino)-N- | 176022-59-6 | U.S. 5,849,736 | Antithrombotic | Thrombosis, general |

TABLE 3-continued

| API Generic Name | API Chemical Name | CAS No. | Patent Reference | Example of Therapeutic Use | Example of Indication |
|---|---|---|---|---|---|
| | (butoxycarbonyl)-, methyl ester, (R)-, [CAS] | | | | |
| Roxindole | | 112192-04-8 | | | |
| roxithromycin | Erythromycin, 9-[O-[(2-methoxyethoxy)methyl]oxime] [CAS] | 80214-83-1 80214-86-4 | EP 33255 | Macrolide antibiotic | Infection, general |
| RPR-109881A | Benzenepropanoic acid, β-(((1,1-dimethylethoxy)carbonyl)amino)-Alpha-hydroxy-(1S,2S,4S,7R,8aR,9aS,10aR,12aS,12bR)-7,12a-bis(acetyloxy)-1-(benzoyloxy)-1,3,47,8,9,9a,10,10a,12,12a,12b-dodecahydro-2-hydroxy-5,13,13-trimethyl-8-oxo-2,6-methano-2H-cyclodeca(3,4) cyclopropa (4,5) benz (1,2-b) oxet-4-yl ester, dihydrate Alpha R, betaS [CAS] | 192573-38-9 | | Anticancer, other | Cancer, lung, general |
| RPR-130401 | 4,9-Ethano-3aH-benz[f]isoindole-3a-carboxylicacid, 1,2,3,4,9,9a-hexahydro-2-[2-(2-methoxyphenyl)-1-oxo-2-propenyl]-9-(4-methylphenyl)-, (3aR,4S,9S,9aR)-rel-[CAS] | 210282-69-2 | WO 9829390 | Anticancer, other | Cancer, general |
| R-roscovitine | | | U.S. 6,316,456 | Anticancer, other | Cancer, lung, non-small cell |
| RS-0406 | N'N'-bis(3-hydroxyphenyl)pyridazine-3,6-diamine | | | Neuroprotective | Alzheimer's disease |
| RSR-13 | | 131179-95-8 | | | |
| Rubijervine | | 79-58-3 | | | |
| rubitecan | 1H-Pyrano(3',4':6,7)indoiizino(1,2-b)quinoline-3,14(4H,12H)-dione, 4-ethyl-4-hydroxy-10-nitro-, (S)-[CAS] | 91421-42-0 | U.S. 6,485,514 | Anticancer, other | Cancer, pancreatic |
| ruboxistaurin | 9H,18H-5,21:12,17-Dimethenodibenzo(e,k)pyrrolo(3,4-h)(1,4,13)oxadiazacyclohexadecine-18,20(19H)-dione,9-((dimethylamino)methyl)-6,7,10,11-tetrahydro-, (S)-[CAS] | 169939-94-0 | | Symptomatic antidiabetic | Retinopathy, diabetic |
| Rufinamide | | 106308-44-5 | | | |
| rufloxacin | 7H-Pyrido[1,2,3-de]-1,4-benzothiazine-6-carboxylic acid, 9-fluoro-2,3-dihydro-10-(4-methyl-1-piperazinyl)-7-oxo-[CAS] | 101363-10-4 102052-47-1 106017-08-7 | EP 165375 | Quinolone antibacterial | Infection, general |
| rupatadine | 5H-Benzo[5,6]cyclohepta[1,2-b]pyridine, 8-chloro-6,11-dihydro-11-[1-[(5-methyl-3-pyridinyl)methyl]-4-piperidinylidene]-, trihydrochloride-[CAS] | 156611-76-6 | EP 0577957 | Antiallergic, non-asthma | Rhinitis, allergic, seasonal |
| Rutin | | 153-18-4 | | | |
| RWJ-54428 | 5-Thia-1-azabicyclo[4.2.0]oct-2-ene-2-carboxylic acid, 7-[[(2Z)-(2-amino-5-chloro-4-thiazolyl)(hydroxyimino)acetyl]amino]-3-[(3-[[(2-aminoethyl)thio]methyl]-4-pyridinyl]thio-8-oxo-, (6R,7R)-[CAS] | 189448-35-9 | WO 9713772 | Cephalosporin, injectable | Infection, beta-lactamase resistant |
| S-0139 | Olean-12-en-28-oic acid, 27-[[3-[5-hydroxy-2-[(4-methoxy-1,4-dioxo-2-butenyl)amino]phenyl]-1-oxo-2-propenyl]oxy]-3-oxo-[CAS] | 193969-54-9 | WO 9727314 | Cardiovascular | Ischaemia, cerebral |
| S-15535 | Piperazine, 1-(2,3-dihydro-1,4-benzodioxin-5-yl)-4-(2,3-dihydro-1H-inden-2-yl)-[CAS] | 146998-34-7 | | Cognition enhancer | Cognitive disorder, general |
| S-18886 | 1-Napthalenepropanoic acid, 6-(((4-chlorophenyl)sulfonyl)amino)-5,6,7,8-tetrahydro-2-methyl [CAS] | 165537-73-5 | | Antithrombotic | Thrombosis, general |
| S-34730 | 7-chloro-6-sulfamoyl-2-(1H)-quinoleinone-3-phosphonic acid | | | Neuroprotective | Unspecified |
| S-3578 | 7β-[2-(5-amino-1,2,4-thiadiazol-3-yl)-2(Z)-ethoxyiminoacetamido]-3-(1-(N-methylaminopropyl)-1H-imidazo[4,5-b]pyridinium-4-methyl-3-cephem-4-carboxytate monosulfate | | | Cephalosporin, injectable | Infection, general |
| S-36496 | 2-{N-[4-(4-Chlorophenylsulfonylamino)butyl]-N-{3-[(4-isopropylthiazol-2-yl)methyloxy]benzyl}sulfamoyl}benzoic acid | | | Antiasthma | Asthma |

TABLE 3-continued

| API Generic Name | API Chemical Name | CAS No. | Patent Reference | | Example of Therapeutic Use | Example of Indication |
|---|---|---|---|---|---|---|
| S-36527 | 2-{N-[4-(4-Chlorophenylsulfonylamino)butyl]-N-{3-[2-(4-cyclobutylthiazol-2-yl)ethyl]benzyl}sulfamoyl}benzoic acid | | | | Antiasthma | Asthma |
| S-5751 | (1R,2R,3S,5S)-7-[2-(5-Hydroxybenzothiophen-3-ylcarboxamido)-6,6-dimethylbicyclo[3.1.1]hept-3yl]-5(Z)-heptenoic acid | | | | Antiallergic, non-asthma | Allergy, general |
| S-8510 | Imidazo[4,5-d]pyrano[4,3-b]pyridine, 1,6,7,9-tetrahydro-2-(3-isoxazolyl)-, phosphate (1:1) [CAS] | 151466-23-8 | EP | 556008 | Cognition enhancer | Alzheimer's disease |
| S-8921 | 2-Naphthalenecarboxylic acid, 1-(3,4-dimethoxyphenyl)-3-(3-ethyl-1-oxopentyl)-4-hydroxy-6,7,8-trimethoxy-, methyl ester [CAS] | 151165-96-7 | WO | 9308155 | Hypolipaemic/ Antiatherosclerosis | Hypercholesterol-aemia |
| Sabcomeline | | 159912-53-5 | | | | |
| Sabeluzole | | 104383-17-7 | | | | |
| S-Adenosyl-methionine | | 29908-03-0 | | | | |
| safinamide | (S)-(+)-2-[4-(3-fluorobenzyloxy)benzylamino] propanamide methansulfonate | 133865-89-1 | AU | 711309 | Antiepileptic | Epilepsy, general |
| Salacetamide | | 487-48-9 | | | | |
| Salazo-sulfadimidine | | 2315-8-4 | | | | |
| salbutamol | 1,3-Benzenedimethanol,Alphal-[[(1,1-dimethylethyl)amino]methyl]-4-hydroxy- [CAS] | 18559-94-9 | EP | 451745 | Formulation, inhalable, topical, dry powder | Asthma |
| Salicin | | 138-52-3 | | | | |
| Salicyl Alcohol | | 90-01-7 | | | | |
| Salicyamide | | 65-45-2 | | | | |
| Salicytamide O-Acetic Acid | | 25395-22-6 | | | | |
| Salicylanilide | | 87-17-2 | | | | |
| Salicylic Acid | | 69-72-7 | | | | |
| Salicylsulfuric Acid | | 89-45-2 | | | | |
| Salinazid | | 495-84-1 | | | | |
| salmeterol | 1,3-Benzenedimethanol, 4-hydroxy-Alpha 1-[[[6-(4-phenylbutoxy)hexyl]amino]methyl]-, (±)-1-hydroxy-2-naphthalenecarboxylate [CAS] | 89365-50-4 94749-08-3 | WO | 9006775 | Antiasthma | Asthma |
| Salsalate | | 552-94-3 | | | | |
| Salverine | | 6376-26-7 | | | | |
| Samarium 153Sm Lexidronam | | 154427-83-5 | | | | |
| sampatrilat | L-Tyrosine, N2-(methylsulfonyl)-L-lysyl-1-[(2S)-3-amino-2-carboxypropyl]cyclopentanecarbonyl- [CAS] | 129981-36-8 | EP | 358398 | Antihypertensive, renin system | Hypertension, general |
| Sancycline | | 808-26-4 | | | | |
| Saperconazole | | 110588-57-3 | | | | |
| sapropterin | 4(1H)-Pteridinone, 2-amino-6-(1,2-dihydroxypropyl)-5,6,7,8-tetrahydro-, dihydrochloride, [6R-[6R*(1R*,2S*)]]- [CAS] | 69056-38-8 62989-33-7 | EP | 191335 | Antidepressant | Hyperphenyl-alaninaemia |
| saquinavir | Butanediamide, N1-[3-[3-[[(1,1-dimethylethyl)amino]carbonyl]octahydro-2(1H)-isoquinolinyl]-2-hydroxy-1-(phenylmethyl)propyl]-2-[(2-quinolinylcarbonyl)amino]-, [3S- [CAS] | 127779-20-8 | EP | 432695 | Antiviral, anti-HIV | Infection, HIV/AIDS |
| Saralasin | | 34273-10-4 | | | | |
| saredutant | Benzamide, N-[4-[4-(acetylamino)-4-phenyl-1-piperidinyl]-2-(3,4-dichlorophenyl)butyl]-N-methyl-, (S)- [CAS] | 142001-63-6 | EP | 474561 | Antiasthma | Asthma |
| sarizotan | 3-Pyridinemethanamine, N-((3,4-dihydro-2H-1-benzopyran-2-yl)methyl)-5-(4-fluorophenyl)- [CAS] | 177975-08-5 | | | Antiparkinsonian | Parkinson's disease |
| sarpogrelate | Butanedlaic acid, mono[2-(dimethylamino)-1-[[2-[2-(3- | 125926-17-2 | EP | 398326 | Antithrombotic | |

TABLE 3-continued

| API Generic Name | API Chemical Name | CAS No. | Patent Reference | | Example of Therapeutic Use | Example of Indication |
|---|---|---|---|---|---|---|
| | methoxyphenyl)ethyl]phenoxy]methyl] ethyl] ester [CAS] | | | | | |
| Satigrel | | 111753-73-2 | | | | |
| satraplatin | Platinum, bis(acetato-O)amminedichloro(cyclohexanamine)-, (OC-6-43)-[CAS] | 129580-63-8 | EP | 328274 | Anticancer, alkylating | Cancer, prostate |
| Satumomab | | 144058-40-2 | | | | |
| SB-237376 | N-[3-[[2-(3,4-dimethoxyphenyt)ethyl]amino]propyl]-4-nitrobenzamide, HCl | | | | Antiarrhythmic | Fibrillation, atrial |
| SB-238039 | (5(-2-phenylamino-4-pyrimidinyl)-4-)(4-fluorophenyl)-1-(4-piperidinyl)imidazole | | | | Anticancer, other | Cancer, general |
| SB-277011 | trans-N-[4-[2-(6-Cyano-1,2,3,4-tetrahydroisoquinolin-2-yl)ethyl]cyclohexyl]-4-quinolinecarboxamide | | | | Neuroleptic | Schizophrenia |
| Scarlet Red | | 85-83-6 | | | | |
| SCH-00013 | Benzonitrile, 4-[2-[3,6-dihydro-4-(1,4,5,6-tetrahydro-6-oxo-3-pyridazinyl)-1(2H)-pyridinyl]-1-hydroxyethyl]-[CAS] | 217963-18-3 | EP | 618204 | Cardiostimulant | Heart failure |
| Sch-23863 | (2-[10,11-Dihydro-5-ethoxy-5H-dibenzo [a,d] cyclohepten-S-yl]-N, N-dimethyl-ethanamine | | | | Immunosuppressant | Inflammation, general |
| Sch-57790 | 1-Piperazineacetonitrile, 4-cyclohexyl-alpha-[4-[(S)-(4-methoxyphenyl)sulfinyl]phenyl]-[CAS] | 221660-80-6 | | | Cognition enhancer | Alzheimer's disease |
| Sch-63390 | 7H-Pyrazolo[4,3-e][1,2,4]tnazolo[1.5-c]pyrimidin-5-amine, 2-(2-furanyl)-7-(3-phenylpropyl)-[CAS] | 174648-45-4 | | | Antiparkinsonian | Parkinson's disease |
| Scillarenin | | 465-22-5 | | | | |
| Scopolamine | | 51-34-3 | | | | |
| Scopolamine N-Oxide | | 97-75-6 | | | | |
| scopolamine | Benzeneacetic acid, Alpha-(hydroxymethyl)-, 9-methyl-3-oxa-9-azatricyclo[3.3.1.02,4]non-7-yl ester, [7(S)-(1Alpha,2β,4β,5Alpha,7β)]-[CAS] | 51-34-3 | U.S. | 4,262,003 | Formulation, transdermal, other | Nausea and vomiting, general |
| SGS technology | | | U.S. | 6,046,188 | Antiasthma | Unspecified |
| secalciferol | 9,10-Secocholesta-5,7,10(19)-triene-3,24,25-triol, (3β,5Z,7E,24R)-[CAS] | 55721-11-4 | EP | 301167 | Osteoporosis treatment | Osteodystrophy |
| secnidazole | 1H-lmidazole-1-ethanol, Alpha,2-dimethyl-5-nitro-[CAS] | 3366-95-8 | FR | M3270 | Protozoacide | Infection, trichomoniasis |
| Secobarbital | | 309-43-3 | | | | |
| selegiline | Benzeneethanamine, N,Alpha-dimethyl N-2-propynyl-, (R)-[CAS] | 14611-51-9 | GB | 1153578 | Antiparkinsonian | |
| Seleno-methionine | | 1464-42-2 | | | | |
| Sematilide | | 101526-83-4 | | | | |
| Semotiadil | | 116476-13-2 | | | | |
| seocalcitol | 1,3-Cyclohexanediol, 5-((1-(6-ethyl-6-hydroxy-1-methyl-2,4-octadienyl)octahydro-7a-methyl-4H-inden-4-ylidene)ethylidene)-4-methylene-, (1R-(1Alpha(1R*,2E,4E),3aβ,4E(1R*,3S*,5Z),7aAlpha))-[CAS] | 134404-52-7 | WO | 9100855 | Anticancer, other | Cancer, liver |
| Sepimostat | | 103926-64-3 | | | | |
| seratrodast | Benzeneheptanoic acid, zeta-(2,4,5-tnmethyl-3,6-dioxo-1,4-cyclohexadien-yl)-, (+/−)-[CAS] | 1103187-07-1 112665-43-7 | EP | 232089 | Antiasthma | Asthma |
| sertaconazole | 1H-Imidazole, 1-[2-[(7-chlorobenzo[b]thien-3-yl)methoxy]-2-(2,4-dichlorophenyl)ethyl]-[CAS] | 99592-32-2 | EP | 151477 | Antifungal | Infection, dermatological |
| sertindole | 2-Imidazolidinone, 1-[2-[4-[5-chloro-1-(4-fluorophenyl)-1H-indol-3-yl]-1-pipendinyl]ethyl]-[CAS] | 106516-24-9 | EP | 392959 | Neuroleptic | Schizophrenia |
| sertraline | 1-Naphthalenamine, 4-(3,4-dichlorophenyl)-1,2,3,4-tetrahydro-N-methyl-, (1S-cis)-[CAS] | 79559-97-0 79617-96-2 7961 7-97-3 | EP | 30081 | Antidepressant | Depression, general |
| Setastine | | 64294-95-7 | | | | |
| sevelamer | 2-Propen-1-amine polymer with (chloromethyl)oxirane, hydrochloride [CAS] | 152751-57-0 52757-95-6 | U.S. | 5,496,545 | Urological | Renal failure |
| sevoflurane | Propane, 1,1,1,3,3,3-hexafluoro-2-(fluoromethoxy)-[CAS] | 28523-86-6 | DE | 1954268 | Anaesthetic, inhalation | Anaesthesia |

TABLE 3-continued

| API Generic Name | API Chemical Name | CAS No. | Patent Reference | Example of Therapeutic Use | Example of Indication |
|---|---|---|---|---|---|
| SG-210 | 2H-1,4-Benzothiazine-2-acetic acid, 3,4-dihydro-3-oxo-4-((4,5,7-trifluro-2-benzothiazolyl)methyl)-[CAS] | 143162-65-6 | | Symptomatic antidiabetic | Neuropathy, diabetic |
| sibutramine | Cyclobutanemethanamine, 1-(4-chlorophenyl)-N,N-dimethyl-Alpha-(2-methylpropyl)-[CAS] | 106650-56-0 84485-00-7 | GB 2098602 | Anorectic/Antiobesity | Obesity |
| siccanin | (4aS-(4aAlpha,6aAlpha,11bAlpha,13aR*,13b Alpha))-l,2,3,4,4a,5,6a,11b,13b-decahydro-4,4,6a,9-tetramethyl-13H-benzo[a]furo[2,3,4-mn]xanthen-11-ol | 22733-60-4 | JP 37003548 | Antifungal | |
| sildenafil | Piperazine, 1-((3-(4,7-dihydro-1-methyl-7-oxo-3-propyl-1H-pyrazolo(4,3-d)pyrimidin-5-yl)-4-ethoxyphenyl)sulfonyl)-4-methyl, 2-hydroxy-1,2,3-propanetricarboxylate-(1:1) [CAS] | 171599-83-0 139755-83-2 | WO 9428902 | Male sexual dysfunction | Impotence |
| silodosin | 1H-Indale-7-carboxamide, 2,3-dihydro-1-(3-hydroxypropyl)-5-[(2R)-2-[[2-[2-(2,2,2-trifluoroethoxy)phenoxy]ethyl]amino] propyl]-[CAS] | 160970-54-7 | EP 600675 | Urological | Dysuria |
| Silver Lactate | | 128-00-7 | | | |
| Silver Picrate | | 146-84-9 | | | |
| silver sulfadiazine | N'-2-pyrimidinylsulfanilamide monosilver salt | 22199-08-2 68-35-9 | | Anti-infective | Infection, general |
| Simetride | | 154-82-5 | | | |
| Simfibrate | | 14929-11-4 | | | |
| simvastatin | Butanoic acid, 2,2-dimethyl-, 1,2,3,7,8,8a-hexahydro-3,7-dimethyl-8-[2-(tetrahydro-4-hydroxy-6-oxo-2H-pyran-2-yl)ethyl]-1-naphthalenyl ester, [1S-[1Alpha,3Alpha,7β,8β(2S*,4S*),8aβ]]-[CAS] | 79902-63-9 | U.S. 4,444,784 | Hypolipaemic/ Antiatherosclerosis | Hyperlipidaemia, general |
| Sincalide | | 25126-32-3 | | | |
| Sintropium Bromide | | 79467-19-9 | | | |
| Sisomicin | | 32385-11-8 | | | |
| sitafloxacin | 3-Quinolinecarboxylic acid, 7-(7-amino-5-azaspiro[2.4]hept-5-yl)-8-chloro-6-fluoro-1-(2-fluorocyclopropyl)-1,4-dihydro-4-oxo-, [1R-[1Alpha(S*),2Alpha]]-, hydrate | 127254-12-0 | EP 341493 | Quinolone antibacterial | Infection, general |
| sitamaquine | 1,6-Hexanediamine, N,N-diethyl-N'-(6-methoxy-4-methyl-8-quinolinyl)-[CAS] | 5330-29-0 57695-04-2 | | Protozoacide | Infection, leishmaniasis |
| sitaxsentan | N-(4-Chloro-3-methyl-5-isoxazolyl)-2-[[4,5-(methylenedioxy)-o-tolyl]acetyl]-3-thiophenesulfonamide | 184036-34-8 | U.S. 5,464,853 | Antihypertensive, other | Hypertension, pulmonary |
| sivelestat | Glycine, N-[2-D[4-(2,2-dimethyl-1-oxopropoxy)phenyl]sulfonyl]amino] benzoyl]-[CAS] | 127373-66-4 | EP 347168 | Respiratory | Systemic inflammatory response syndrome |
| SJA-6017 | Butanamide, 2-[[(4-fluorophenyt)sulfonyl]amino]-N-[(1S)-1-formyl-3-methylbutyl.).-3-methyl-, (2S)-[CAS] | 190274-53-4 | EP 771565 | Ophthalmological | Cataract |
| SL-65-1498 | 6-Fluoro-9-methyl-2-phenyl-4-pyrrolidin-1-ylcarbonyl)-2,9-dihydro-1H-pyrido[3,4 b]indole-1-one | | EP 607076 | Anxiolytic | Anxiety, general |
| SLV-306 | (3S,2'R)-3-[1-[2'-(Ethoxycarbonyl)-4'-phenyl-butyl-]-cyclopentan-1-carbonylamino]-2,3,4,5-tetra-hydro-2-oxo-1H-benzapin-1-acetic acid | | | Antihypertensive, diuretic | Hypertension, general |
| SLV-308 | 2(3H)-Benzoxazolone, 7-(4-methyl-1-piperazinyl)-, monohydrochloride | 269718-83-4 | | Antiparkinsonian | Parkinson's disease |
| Sm153 lexidronam | Samarate(5-)-153Sm, (((1,2-ethanediylbis(nitrilobis(methylene))) tetrakis(phosphonato))(8-)-N,N',OP,OP',OP'',OP''')-, pentasodium, (OC-6-21)-[CAS] | 160369-78-8 | | Analgesic, other | Pain, cancer |
| S-Methyl-methionine | | 4727-40-6 | | | |
| SMP-300 | N-(Aminoiminomethyl)-11-chloro-5,6,7,8-tetrahydro-8-oxo-4H-pyrrolo[3,2,1-kl][1]benzazocine-2- | | | Antianginal | Angina, general |

TABLE 3-continued

| API Generic Name | API Chemical Name | CAS No. | Patent Reference | | Example of Therapeutic Use | Example of Indication |
|---|---|---|---|---|---|---|
| SN-38 | carboxamide monomethanesulfonate monohydrate (4S)-4,7,11-tnethyl-3,4,12,14-tetrahydro-4, 10-dihydroxy-3,14-dioxo-1H-pyrano[3',4':6,7]indolizino[1,2-b]quindin-9-yl | 100286-90-6 | | | Formulation, optimized, liposomes | Cancer, colorectal |
| SNAP-7941 | ((+)-methyl (4S)-3-{[(3-{4-[3-(acetylamino)phenyl]-1-piperidinyl}propyl)amino] carbonyl}-4-(3,4-difluorophenyl)-6-(methoxymethyl) 2-oxo-1,2,3,4-tetrahydro-5-pyrimidinecarboxylate hydrochloride) | | | | Anxiolytic | Anxiety, general |
| SOA-132 | 2-Naphthalenecarboxamide, N-[2-[4-(diphenylmethoxy)-1-piperidinyl]ethyl]-3 hydroxy-5-(3-pyridinylmethoxy)-[CAS] | 143964-80-1 | | | Formulation, inhalable, topical | Asthma |
| soblidotin | L-valinamide, N,N-dimethyl-L-valyl-N-[2-methoxy-4-L2-[1-methoxy-2-methyl-3-oxo-3-[(2-phenylethyl)amino]propyl]-1-pyrrolidinyl]-1-(2-methylpropyl)-4-oxobutyl]-N-methyl-, [2S-[1[1R*(R*),2S*],2R*(1S*,2S*)]]-[CAS] | 149606-27-9 | WO | 9303054 | Anticancer, other | Cancer, lung, non-small cell |
| Sobrerol | | 498-71-5 | | | | |
| sobuzoxane | Carbonic acid, 1,2-ethanediylbis[(2,6-dioxo-4,1-piperazinediyl)methylene]bis(2-methylpropyl) ester [CAS] | 98631-95-9 | EP | 140327 | Anticancer, other | Cancer, lymphoma, T-cell |
| Sodium Arsanilate | | 127-85-5 | | | | |
| Sodium Arsphenamine | | 1936-28-3 | | | | |
| Sodium Chloride | | | | | | |
| Sodium Dibunate | | 14992-59-7 | | | | |
| Sodium Folate | | 6484-89-5 | | | | |
| Sodium Formaldehydesulfoxylate | | 149-44-0 | | | | |
| Sodium Glycerophosphate | | 1334-74-3 | | | | |
| Sodium Hyaluronate | | | | | | |
| Sodium Iodomethamate | | 519-26-6 | | | | |
| Sodium Nitrite | | 7632-00-0 | | | | |
| Sodium Nitroprusside | | 14402-89-2 | | | | |
| sodium oxybate | Butync acid, 4-hydroxy monosodium salt [CAS] | 502-85-2 | | | Psychostimulant | Narcolepsy |
| Sodium Phenolsulfonate | | 1300-51-2 | | | | |
| sodium phenylbutyrate | Butyric acid, 4-phenyl-, sodium salt-[CAS] | 1716-12-7 | | | Formulation, other | Hyperammon-aemia |
| sodium phosphate | Sodium phosphate monobasic monohydrate + sodium phosphate dibasic anhydrous | | U.S. | 6,162,464 | Formulation, oral, other | Surgery adjunct |
| sodium prasterone sulfate | 3B-hydroxy-5-androsten-17-one(sodium sulfate dihydrate) | | EP | 380036 | Formulation, mucosal, topical | Labour, induction |
| Sodium Propionate | | 137-40-6 | | | | |
| sodium salicylate | Benzoic acid, 2-hydroxy-, monosodium salt [CAS] | 54-21-7 | | | Formulation, oral, solubility-enhanced | Pain, general |
| Sodium Tetradecyl Sulfate | | 139-88-8 | | | | |
| sofalcone | Acetic acid, [5-((3-methyl-2-butenyl)oxy)-2-[3-[4-[(3-methyl-2-butenyl)oxy]phenyl]-1-oxo-2-propenyl]phenoxy]-[CAS] | 64506-49-6 | GB | 1523241 | Antiulcer | |
| Solasulfone | | 133-65-3 | | | | |
| solifenacin | Butanedioic acid compd with (1S)-(3R)-1-azabicyclo(2.2.2)oct-3-yl 3,4-dihydro-1-phenyl-2(1H)-isoquinolinecarboxylate (1:1) [CAS] | 242478-38-2 | | | Urological | Overactive bladder |

TABLE 3-continued

| API Generic Name | API Chemical Name | CAS No. | Patent Reference | | Example of Therapeutic Use | Example of Indication |
|---|---|---|---|---|---|---|
| Sorbinicate | D-Glucitol, hexa-3-pyridinecarboxylate [CAS] | 6184-06-1 | BE | 883352 | Hypolipaemic/ Antiatherosclerosis | |
| Sorbitol | | 50-70-4 | | | | |
| Sorivudine | | 77181-69-2 | | | | |
| sotalol | Methanesulfonamide, N-[4-[1-hydroxy-2-[(1-methylethyl)amino]ethyl]phenyl]-[CAS] | 3930-20-9 959-24-0 | | | Antiarrhythmic | |
| Soterenol | | 13642-52-9 | | | | |
| Sozojodolic Acid | | 554-71-2 | | | | |
| spaglumic acid | L-Glutamic acid, N-(N-acetyl-L-Alpha-aspartyl)-[CAS] | 3106-85-2 80619-64-3 | | | Formulation, mucosal, topical | Conjuctivitis |
| sparfloxacin | 3-Quinolinecarboxylic acid, 5-amino-1-cyclopropyl-7-(3,5-dimethyl-1-piperazinyl)-6,8-difluoro-1,4-dihydro-4-oxo-, cis-[CAS] | 110871-86-8 | EP | 221463 | Quinolone antibacterial | |
| Sparteine | | 90-39-1 | | | | |
| SPA-S-843 | Candicin D, 18-decarboxy-40-demethyl-3,7-dideoxo-N3'-((dimethylamino)acetyl)-18-(((2-(dimethylamino)ethyl)amino)carbonyl)-3,7-dihydroxy-N47-methyl-5-oxo cyclic 15,19-hemiacetal, comp with L-ascorbic acid (1:2) [CAS] | 202748-83-2 | U.S. | 5,298,495 | Antifungal | Infection, fungal, general |
| Spasmolytol | | 25333-96-4 | | | | |
| SPD-754 | 2(1H)-Pyrimidinone, 4-amino-1-(2-(hydroxymethyl)-1,3-oxathiolan-4-yl-(2R-cis)- | 160707-69-7 | U.S. | 6,228,860 | Antiviral, anti-HIV | Infection, HIV/AIDS |
| Spectinomycin | | 1695-77-8 | | | | |
| SPI-339 | 4-[3-(4-Oxo-4,5,6,7-tetrahydroindol-yl)propionylamino]benzoic acid ethyl ester | | | | Cognition enhancer | Alzheimer's disease |
| Spiperone | | 749-02-0 | | | | |
| spirapril | 1,4-Dithia-7-azaspiro[4.4]nonane-8-carboxylic acid, 7-[2-[[1-(ethoxycarbonyl)-3-phenylpropyl]amino]1-oxopropyl]-, [8S-[7[R*(R*)],8R*]]-[CAS] | 83647-97-6 | EP | 50800 | Antihypertensive, renin system | Hypertension, general |
| Spirogermanium | | 41992-23-8 | | | | |
| spironolactone | Pregn-4-ene-21-Carboxylic acid, 7-(acetylthio)-17-hydroxy-3-oxo-,Gamma-lactone,(7Alpha, 17Alpha)-[CAS] | 52-01-7 | EP | 124147 | Formulation, dermal, topical | Acne |
| SR-121463 | Benzamide, N-(1,1-dimethylethyl)-4-[[cis-5'-ethoxy-4-[2-(4-morpholinyl)ethoxy]-2'-oxospiro[cyclohexa ne-1,3'-[3H]indol]-1'(2H)-yl]sulfonyl]-3-methoxy-[CAS] | 185913-78-4 | WO | 9715556 | Cardiostimulant | Heart failure |
| SR-144190 | Morpholine, 4-benzoyl-2-(3,4-difluorophenyl)-2-[2-[4-[[(dimethylamino)carbonyl]amino]-4-phenyl-1-piperidinyl]ethyl]-, (2R)-[CAS] | 201152-86-5 | WO | 9623787 | Anxiolytic | Anxiety, general |
| SR-146131 | 1H-Indole-1-acetic acid, 2-[[[4-(4-chloro-2,5-dimethoxyphenyl)-5-(2-cyclohexytethyl)-2-thiazolyl]amino]carbonyl]-5,7-dimethyl-[CAS] | 221671-61-0 | WO | 9915525 | Anorectic/Antiobesity | Obesity |
| SR-271425 | N-[1-[2-(diethylamino)ethylamino]-7-methoxy-9-oxo-9H-thioxanthen-4-ylmethyl]formamide | | | | Anticancer, alkylating | Cancer, general |
| SR-27897 | 1H-Indole-1-acetic acid, 2-[[[4-(2-chlorophenyl)-2-thiazolyl]amino]carbonyl]-[CAS] | 136381-85-6 | EP | 432040 | Anticancer, other | Cancer, pancreatic |
| SR-31747 | Cyclohexanamine, N-(3-chloro-4-cyclohexylphenyl)-2-propenyl)-N-ethyl-, hydrochloride, (Z)-[CAS] | 132173-07-0 | EP | 376850 | Anticancer, other | Cancer, myeloma |
| SR-58611 | Acetic acid, [[(7S)-7-[[(2R)-2-(3-chlorophenyl)-2-hydroxyethyl]amino]-5,6,7;8-tetrahydro-2-naphthalenyl]oxy]-, ethyl ester, hydrochloride [CAS] | 121524-09-2 | EP | 303546 | GI inflammatory/bowel disorders | Irritable bowel syndrome |
| SS732 | | | U.S. | 5,385,900 | Formulation, mucosal, topical | Infection, ocular |
| SS-750 | (R)-(−)-2-(2,4-difluorophenyl)-1-(ethylsulfonyl)-1,1-difluoro-3-(1H-1,2,4-triazol-1-yl)-2-propanol | | U.S. | 6,083,968 | Antifungal | Infection, fungal, general |
| β-alethine | Propanamide, N, N(dithiodi-2,1-ethanediyl)bis(3-amino)-[CAS] | 646-08-2 | | | Anticancer, immunological | Cancer, myeloma |

TABLE 3-continued

| API Generic Name | API Chemical Name | CAS No. | Patent Reference | | Example of Therapeutic Use | Example of Indication |
|---|---|---|---|---|---|---|
| SSR-149415 | (2S,4R)-1-[5-chloro-1-[(2,4-dimethoxyphenyl)sulfonyl]-3-(2-methoxy-phenyl)-2-oxo-2,3-dihydro-1H-indol-3-yl]-4-hydroxy-N,N-dimethyl-2-pyrrolidine carboxamide | | WO | 0155130 | Antidepressant | Depression, general |
| SSR-180575 | 2-(7-chloro-5-methyl-4-oxo-3-phenyl-4,5-dihydro-3H-pyridazino[4,5-6]indol-1-yl)-N,N-dimethylacetamide | | | | Neuroprotective | Unspecified |
| SSR-181507 | (3-Exo)-8-benzoyl-N-[[(2S)-7-chloro-2,3-dihydro-1,4-benzodioxin-2-yl]methyl]-8-azabicyclo[3.2.1]octane-3-methanamine HCl | | U.S. | 6,221,879 | Neuroleptic | Schizophrenia |
| SSR-591813 | (5aS,8S,10aR)-5a,6,9,1 0-tetrahydro, 7H,11H-8,10a-methanopyrido[2',3':5,6]pyrano[2,3-d]azepine | | | | Dependence, treatment | Addiction, nicotine |
| SST-101 | D-Glucitol, 1,4:3,6-dianhydro-, dinitrate [CAS] | 87-33-2 | | | Formulation, transdermal, other | Angina, general |
| SSY-726 | (−)-(R)-3-Methyl-3-(methylsuifonyl)-1-(1,2,4-triazol-1-yl)-2-[4-(trifluoromethyl)phenyl]-2-butanol | | U.S. | 5,147,886 | Antifungal | Infection, fungal, general |
| ST-200 | 1-Propanaminium, 2-(acetyloxy)-3-carboxy-N,N,N-trimethyl-, chloride, (R)-[CAS] | 5080-50-2 | DE | 3015635 | Cognition enhancer | Dementia, senile, general |
| stachyflin | | | WO | 9711947 | Antiviral, other | Infection, influenza virus |
| Stallimycin | | 636-47-5 | | | | |
| Stampidine | | | U.S. | 6,350,736 | Antiviral, anti-HIV | Infection, HIV/AIDS |
| Stannous Pyrophosphate | | 15578-26-4 | | | | |
| stannsoporfin | (OC-6-13)-Dihydrogen dichloro[7,12-diethyl-3,8,13,17-tetramethyl-21H,23H-porphine-2,18-dipropanoato(4-)-N21,N22,N23,N24]stannate(2-) | 106344-20-1 | | | Hepatoprotective | Hyperbilirubin-aemia |
| Stanolone | | 521-18-6 | | | | |
| Stanozolol | | 10418-03-8 (2¢Hform); 302-96-5 (1¢H form) | | | | |
| Staph aureus ther | | | U.S. | 6,376,652 | Genomics-based drug discovery | Infection, MRSA |
| STAT4 inhibitors | | | WO | 9629341 | Immunosuppressant | Unspecified |
| stavudine | Thymidine, 2',3-didehydro-3'-deoxy-[CAS] | 3056-17-5 | EP | 501511 | Antiviral, anti-HIV | Infection, HIV/AIDS |
| Stenbolone | | 5197-58-0 | | | | |
| stepronin | Glycine, N-[1-oxo-2-[(2-thienylcarbonyl)thio]propyl]-[CAS] | 72324-18-6 | U.S. | 4,242,354 | Antitussive | Cough |
| Stibocaptate | | 27279-76-1 | | | | |
| Stibophen | | 15489-16-4 | | | | |
| Stiibamidine | | 122-06-5 | | | | |
| stiripentol | 1-Penten-3-ol, 1-(1,3-benzodioxol-5-yl)-4,4-dimethyl-[CAS] | 49763-96-4 | | | Antiepileptic | Epilepsy, general |
| Streptodornase | | 37340-82-2 | | | | |
| Streptomycin | | 57-92-1 | | | | |
| Streptonicozid | | 5667-71-0 | | | | |
| Streptonigrin | | 3930-19-6 | | | | |
| Streptozocin | | 18883-66-4 | | | | |
| strontium ranelate | 3-Thiopheneacetic acid, 5-[bis(carboxymethyl)amino]-2-carboxy-4-cyano-, strontium salt (1:2)-[CAS] | 135459-87-9 | EP | 415850 | Osteoporosis treatment | Osteoporosis |
| strontium-89 chloride | Strontium chloride (89SrC12) [CAS] | 38270-90-5 | | | Analgesic, other | Pain, cancer |
| Succimer | | 304-55-2 | | | | |
| Succinimide | | 123-56-8 | | | | |
| Succinylcholine | | 55-94-7 | | | | |
| Succinylcholine | | 71-27-2 | | | | |
| Succinyl-sulfathiazole | | 116-43-8 | | | | |
| Succisulfone | | 5934-14-5 | | | | |
| Suclofenide | | 30279-49-3 | | | | |
| sucralfate | Aluminium, hexadeca-μ-hydroxytetracosahydroxy(μ8-(1,3,4,6-tetra-O-sulfo-β-D-fructofuranosyl-Alpha-D-glucopyranoside tetrakis(hydrogen sulfato)(8-)))hexadeca-[CAS] | 54182-58-0 | JP | 58208233 | Antiulcer, Formulation, oral, other | Ulcer, general |

TABLE 3-continued

| API Generic Name | API Chemical Name | CAS No. | Patent Reference | Example of Therapeutic Use | Example of Indication |
|---|---|---|---|---|---|
| sufentanil | Propanamide, N-[4-(methoxymethyl)-1-[2-(2-thienyl)ethyl]-4-pipendinyl]-N-phenyl-[CAS] | 56030-54-7 | U.S. 3,998,834 | Analgesic, other, formulation implant | Pain, general |
| sulbactam | 4-Thia-1-azabicyclo[3.2.0]heptane-2-carboxylic acid, 3,3-dimethyl-7-oxo-, 4,4-dioxide, (2S-cis)-[CAS] | 68373-14-8 | GB 2000138 | Antibiotic, other | Infection, general |
| sulbactam + ampicillin | | 117060-71-6 | U.S. 4,234,579 | Antibiotic, other | Infection, general |
| sulbenicillin | 4-Thia-1-azabicyclo[3.2.0]heptane-2-carboxylic acid, 3,3-dimethyl-7-oxo-6-[(phenylsulfoacetyl)amino]-, [2S-[2Alpha,5Alpha,6a(S*)]]-[CAS] | 28002-18-8 41744-40-5 | GB 1289358 | Penicillin, injectable | Infection, pseudomonal |
| Sulbentine | | 350-12-9 | | | |
| sulbutiamine | Propanoic acid, 2-methyl-, dithiobis[3-[1-[[(4-amino-2-methyl-5-pyrimidinyl)methyl]formylamino]ethylidene]-3,1-propanediyl] ester [CAS] | 3286-46-2 67-16-3 | | Neurological | Unspecified |
| sulconazole | 1H-Imidazole, 1-[2-[[(4-chlorophenyl)methyl]thio]-2-(2,4-dichlorophenyl)ethyl]-, (+/−)-[CAS] | 61318-90-9 61318-91-0 | U.S. 4,055,652 | Antifungal | Infection, fungal, general |
| Sulesomab | | 167747-19-5 | | | |
| Sulfabenzamide | | 127-71-9 | | | |
| Sulfacetamide | | 144-80-9 | | | |
| Sulfachlorpyridazine | | 80-32-0 | | | |
| Sulfachrysoidine | | 485-41-6 | | | |
| Sulfacytine | | 17784-12-2 | | | |
| Sulfadiazine | | 68-35-9 | | | |
| Sulfadicramide | | 115-68-4 | | | |
| Sulfadimethoxine | | 122-11-2 | | | |
| Sulfadoxine | | 2447-57-6 | | | |
| Sulfaethidole | | 94-19-9 | | | |
| Sulfaguanidine | | 57-67-0 | | | |
| Sutfaguanole | | 27031-08-9 | | | |
| Sulfalene | | 152-47-6 | | | |
| Sulfaloxic Acid | | 14376-16-0 | | | |
| Sulfamerazine | | 127-79-7 | | | |
| Sulfameter | | 651-06-9 | | | |
| Sulfamethazine | | 57-68-1 | | | |
| Sulfamethizole | | 144-82-1 | | | |
| Sulfamethomidine | | 3772-76-7 | | | |
| Sulfamethoxazole | | 723-46-6 | | | |
| Sulfamethoxypyridazine | | 80-35-3 | | | |
| Sulfametrole | | 32909-92-5 | | | |
| Sulfamidochrysoidine | | 103-12-8 | | | |
| Sulfamoxole | | 729-99-7 | | | |
| Sulfanilamide | | 63-74-1 | | | |
| Sulfanilic Acid | | 121-57-3 | | | |
| Sulfanilylurea | | 547-44-4 | | | |
| Sulfaperine | | 599-88-2 | | | |
| Sulfaphenazole | | 526-08-9 | | | |
| Sulfaproxyline | | 116-42-7 | | | |
| Sulfapyrazine | | 116-44-9 | | | |
| Sutfapyndine | | 144-83-2 | | | |
| Sulfarside | | 1134-98-1 | | | |
| Sulfarsphenamine | | 618-82-6 | | | |
| sulfasalazine | Benzoic acid, 2-hydroxy-5-[[4-[(2-pyridinylamino)sulfonyl]phenyl]azo]-[CAS] | 599-79-1 | | Formulation, oral, enteric-coated | Arthritis, rheumatoid |
| Sulfasomizole | | 632-00-8 | | | |
| Sulfasymazine | | 1984-94-7 | | | |
| Sulfathiazole | | 72-14-0 | | | |
| Sulfathiourea | | 515-49-1 | | | |
| Sulfinalol | | 66264-77-5 | | | |
| Sulfinpyrazone | | 57-96-5 | | | |
| Sulfiram | | 95-05-6 | | | |
| Sulfisomidine | | 515-64-0 | | | |
| Sulfisoxazole | | 127-69-5 | | | |
| Sulfobromophthalein | | 71-67-0 | | | |
| Sulfonethylmethane | | 76-20-0 | | | |
| Sulfoniazide | | 3691-81-4 | | | |
| Sulfonmethane | | 115-24-2 | | | |

TABLE 3-continued

| API Generic Name | API Chemical Name | CAS No. | Patent Reference | Example of Therapeutic Use | Example of Indication |
|---|---|---|---|---|---|
| Sulforidazine | | 14759-06-9 | | | |
| Sulfoxone | | 144-75-2 | | | |
| sulindac | cis-5-fluoro-2-methyl-1-[(p-methylsulfinyl)benzylidene]indene-3-acetic acid | 38194-50-2 | U.S. 3,725,548 | Anti-inflammatory | Inflammation, general |
| Sulisatin | | 54935-03-4 | | | |
| Sulisobenzone | | 4065-45-6 | | | |
| Sulmarin | | 29334-07-4 | | | |
| Sulmazole | | 73384-60-8 | | | |
| Suloctidil | | 54063-56-8 | | | |
| Sulphan Blue | | 129-17-9 | | | |
| sulpiride | Benzamide, 5-(aminosulfonyl)-N-[(1-ethyl-2-pyrrolidinyl)methyl]-2-methoxy-[CAS] | 15676-16-1 | | Alimentary/Metabolic, other | |
| sulprostone | 5-Heptenamide, 7-[3-hydroxy-2-(3-hydroxy-4-phenoxy-1-butenyl)-5-oxocyclopentyl]-N-(methylsulfonyl)-, [1R-[1Alpha(Z),2β(1E,3R*),3Alpha]]-[CAS] | 60325-46-4 | U.S. 4,024,179 | Prostaglandin | Abortion |
| sultamicillin | 4-Thia-1-azabicyclo(3.2.0)heptane-2-carboxylic acid, 6-((aminophenylacetyl)amino)-3,3-dimethyl-7-oxo-, (((3,3-dimethyl-7-oxo-4-thia-1-azabicyclo(3.2.0)hept-2-yl)carbonyl)oxy)methyl ester, 5, 5-dioxide, (2S-(2.alpha.(2R*,5S*),5,alpha.,6.beta.(S*)))-[CAS] | 117060-71-6 76497-13-7 | GB 2044255 | Penicillin, oral | Infection, general |
| Sulthiame | | 61-56-3 | | | |
| sultopride | Benzamide, N-((1-ethyl-2-pyrrolidinyl)methyl]-5-(ethylsulfonyl)-2-methoxy-[CAS] | 53583-79-2 | FR M5916 | Neuroleptic | Psychosis, general |
| Sultosilic Acid | | 57775-26-5 | | | |
| sumanirole | 4H-Imidazo[4,5,1-ij]quinolin-2(1H)-one, 5,6-dihydro-5-(methylamino)-, (5R)-, (2Z)-2-butenedioate (1:1) [CAS] | 179386-44-8 | WO 9514020 | Antiparkinsonian | Parkinson's disease |
| sumatriptan | 1H-Indole-5-methanesulfonamide, 3-[2 (dimethylamino)ethyl]-N-methyl-, butanedioate (1:1)-[CAS] | 103628-46-2 103628-48-4 | EP 147107 | Antimigraine | Migraine |
| SUN-N8075 | 1-(4-amino-2,3,5-trimethylphenoxy)-3-{4-[4-(4-fluorobenzyl)phenyl]piperazin-1-yl}propan-2(s)-ol dimethanesulfonate | | | Neuroprotective | Infarction, cerebral |
| suplatast | Sulfonium, (3-[[4-(3-ethoxy-2-hydroxypropoxy)phenyl]amino]-3-oxopropyl]dimethyl-, [CAS] | 94055-76-2 | JP 59167564 | Antiasthma | Asthma |
| Suprofen | | 40828-46-4 | | | |
| Suramin | | 129-46-4 | | | |
| surfactant TA | Beractant [CAS] | 108778-82-1 | WO 9117766 | Lung Surfactant | Respiratory distress syndrome, general |
| Suriclone | | 53813-83-5 | | | |
| Suxibuzone | | 27470-51-5 | | | |
| SYM-1010 | | | U.S. 5,830,998 | Antiepileptic | Epilepsy, general |
| SYM-2081 | L-Glutamic acid, 4-methyl-, (4R)-[CAS] | 31137-74-3 | | Analgesic, other | Pain, general |
| SYM-2207 | 4-(Aminophenyl)-1-methyl-6,7-(methylenedioxy)-N-butyl-1,2-dihydrophthalazine-2-carboxamide | | | Neuroprotective | Ischaemia, cerebral |
| Symclosene | | 87-90-1 | | | |
| Syn-1253 | 1-cyclopropyl-6-fluoro-8-methoxy-7-[3-(4-methyl-1,2,3-triazol-1-yl)pyrrolidin-1-yl]-4-oxo-1,4-dihydroquinoline 3-carboxylic acid | | | Quinolone antibacterial | Infection, peritoneum |
| Syn-2190 | 1-Azetidinesulfonic acid, 3-[[(2E)-[[(1,4-dihydro-1,5-dihydroxy-4-oxo-2-pyridinyl)methoxy]imino]-2-thienylacetyl]amino]-2-methyl-4-oxo, (2S,3S)-[CAS] | 214963-75-4 | WO 9847895 | Antibacterial, other | Infection, general |
| Syn-2869 | 3H-1,2,4-Triazol-3-one, 4-(4-(4-((1R,2R)-2-(2,4-difluorophenyl)-2-hydroxy-1-methyl-3-(1H-1,2,4-triazol-1-yl)propyl)-1-piperazinyl)phenyl)-2,4-dihydro-2((4-(trifluoromethoxy)phenyl)methyl)-[CAS] | 210562-98-4 | U.S. 6,153,616 | Antifungal | Infection, Aspergillus |

TABLE 3-continued

| API Generic Name | API Chemical Name | CAS No. | Patent Reference | | Example of Therapeutic Use | Example of Indication |
|---|---|---|---|---|---|---|
| Synephrine | | 94-07-5 | | | | |
| Syrosingopine | | 84-36-6 | | | | |
| T-1095 | 1-Propanone, 3-(5-benzofuranyl)-1-(2-hydroxy-6-((6-O-methoxycarbonyl)-B-D-glucopyranosyl)oxy)-4-methylphenyl-[CAS] | 209746-59-8 | EP | 850948 | Antidiabetic | Diabetes, general |
| T-1249 | L-Phenylalaninamide, N-acetyl-L-tryptophyl-L-glutaminyl-L-Alpha-glutamyl-L-tryptophyl-L-Alpha-glutamyl-L-glutaminyl-L-lysyl-L-isoleucyl-L-threonyl-L-alanyl-L-leucyl-L-leucyl-L-Alpha-glutamyt-L-glutaminyl-L-alanyl-L-glutaminyl-L-isoleucyl-L-glutaminyl-L-glutaminyl-L-Alpha-glutamyl-L-lysyl-L-Alpha-glutamyl-asparaginyl-L-tyrosyl-L-Alpha-glutamyl-L-leucyl-L-glutaminyl-L-lysyl-L-leucyl-L-Alpha-aspartyl-L-lysyl-I-trytophyl-L-ananyl-L-seryl-L-leucyl-L-trytophyl-L-Alpha-glutamyl-L-tryptophyl [CAS] | 251562-00-2 | WO | 9959615 | Antiviral, anti-HIV | Infection, HIV/AIDS |
| T-3912 | 1-cyclopropyl-8-methyl-7-[5-methyl-6-(methylamino)-3-pyridinyl]-4-oxo-1,4-dihydro-3-quinolinecarboxylic acid | | | | Quinolone antibacterial | Infection, dermatological |
| T-588 | Benzo(b)thiophene-5-methanol, Alpha-((2-(diethylamino)ethoxy)methyl)-, hydrochloride; (R)-[CAS] | 142935-03-3 | EP | 565965 | Cognition enhancer | Alzheimer's disease |
| T-67 | Benzenesulfonamide, 2,3,4,5,6-pentafluoro-N-(3-fluoro-4-methoxyphenyl)-[CAS] | 195533-53-0 | | | Anticancer, other | Cancer, liver |
| T-82 | | | U.S. | 5,190,951 | Cognition enhancer | Alzheimer's liver |
| TA-2005 | 2(1H)-Quinolinone, 8-hydroxy-5-[1-hydroxy-2-[[2-(4-methoxyphenyl)-1-methylethyl]amino]ethyl]-, monohydrochloride, [R-(R*,R*)]-[CAS] | 137888-11-0 | U.S. | 4,579,854 | Antiasthma | Asthma |
| TA-2005 | 2(1H)-Quinolinone, 8-hydraxy-5-[1-hydraxy-2-[[2-(4-methoxyphenyl)-1-methylethyl]amina]ethyl]-, manahydrochlaride, [R-(R*,R*)]-[CAS] | | WO | 189480 | Formulation, inhalable, solution | Asthma |
| TA-993 | 1,5-Benzathiazepin-4(5H)-one, 3-(acetyloxy)-5-[2-(dimethylamino)ethyl]-2,3-dihydra-8-methyl-2-(4-methylphenyl)-, (2R,3R)-rel-(−)-, (2Z)-2-butenedioate [CAS] | 122024-98-0 | JP | 01045376 | Antithrombotic | Peripheral vascular disease |
| tabimorelin | (R)-Alpha-[(E)-5-Amino-N,5-dimethyl-2-hexenamido]-N-methyl-N-[(R)-Alpha-(methylcarbamoyl)phenethyl]-2-napthaleneprapianamide | 193079-69-5 170851-70-4 | | | Releasing hormones | Growth hormone deficiency |
| tacalcitol | 9,10-Secachalesta-5,7,10(19)-triene-1,3,24-trial, (1Alpha,3β,5Z,7E,24R)-[CAS] | 57333-96-7 93129-94-3 | EP | 129003 | Antipsoriasis | Keratosis |
| tacedinaline | Benzamide, 4-(acetylamina)-N-(2-aminophenyl)-[CAS] | 112522-64-2 | DE | 3613571 | Anticancer, other | Cancer, pancreatic |
| tacrine | 9-Acridinamine, 1,2,3,4-tetrahydro-[CAS] | 1684-40-8 321-64-2 | EP | 332147 | Cognition enhancer | Alzheimer'disease |
| Tacralimus | | 104987-11-3 | | | | |
| tadalafil | Pyrazina(1',2':1,6)pyrida(3,4-b)indole1,4-dione, 6-(1,3-benzadiaxal-5yl)-2,3,6,7,12,12a-hexahydro-2-methyl-, (6R-trans) [CAS] | 171596-29-5 | U.S. | 6,143,746 | Male sexual dysfunction | Impotence |
| tafenoquine | 1,4-Pentanediamine, N4-[2,6-dimethaxy-4-methyl-5-[3-(trifluaramethyl)phenoxy]-8-quinalinyl]-[CAS] | 106635-80-7 106635-81-8 80065-55-0 | U.S. | 4,617,394 | Antimalarial | Infection, malaria |
| taflupaside | | 179067-42-6 | WO | 9612727 | Anticancer, other | Cancer, general |
| TAK-375 | (S)-N-[2-(1,6,7,8-Tetrahydro-2H-indeno[5,4-bifuran-8-yl)]propionamide | | | | Hypnotic/Sedative | Insomnia |
| TAK-427 | 2-[6-[[3-[4-(Diphenylmethoxy)-piperidino]imidazo[1,2-b]pyridazin-2-yl]-2-methylpropionic acid dihydrate | | | | Antipruritic/inflamm, allergic | Eczema, atopic |
| TAK-559 | (E)-4-{4-(5-Methyl-2-phenyl-13-oxazol-4-yl)methoxy]benzyloxylmino}-4-phenylbutyric acid | | | | Antidiabetic | Diabetes, general |
| Taka-Diastase | | 9001-19-8 | | | | |
| talampanel | 7H-1,3-Dioxolo[4,5-h][2,3]benzodiazepine,7-acetyl-5-(4- | 161832-65-1 | U.S. | 5,639,751 | Antiepileptic | Epilepsy, general |

TABLE 3-continued

| API Generic Name | API Chemical Name | CAS No. | Patent Reference | Example of Therapeutic Use | Example of Indication |
|---|---|---|---|---|---|
| | aminophenyl)-8,9-dihydro-8-methyl-, (8R)-[CAS] | | | | |
| Talampicillin | | 47747-56-8 | | | |
| talaporfin | N-[[(2S,3S)-18-Carboxy-2-(2-carboxyethyl)-13-ethyl-2,3-dihydro-3,7,12,17-tetramethyl-8-vinyl porphyrin-20-yl]acetyl]-L-aspartic acid | 220201-34-3 | | Radia/chemosensitizer | Cancer, lung, general |
| Talastine | | 16188-61-7 | | | |
| Talbutal | | 115-44-6 | | | |
| Talinolol | | 57460-41-0 | | | |
| talipexole | 4H-Thiazolo[4,5-d]azepin-2-amine, 5,6,7,8-tetrahydro-6-(2-propenyl)-[CAS] | 101626-70-4 36085-73-1 | DE | 3503963 Antiparkinsonian | Schizophrenia |
| talnetant | 4-Quinolinecarboxamide, 3-hydroxy-2-phenyl-N-[(1S)-1-phenylpropyl]-[CAS] | 174636-32-9 | WO | 9532948 GI inflammatory/bowel disorders | Irritable bowel syndrome |
| talniflumate | 3-Pyridinecarboxylic acid, 2-[[3-(trifluoromethyl)phenyl]amino]-, 1,3-dihydro-3-oxo-1-isobenzofuranyl ester [CAS] | 66898-62-2 | BE | 858864 Anti-inflammatory | Inflammation, ocular |
| taltirelin | L-Prolinamide, N-[(hexahydro-1-methyl 2,6-dioxo-4-pynmidinyl)carbonyl]-L-histidyl-, (S)-[CAS] | 103300-74-9 | JP | 61033197 Neurological | Dyskinesia, general |
| tamoxifen | Ethanamine, 2-[4-(1,2-diphenyl-1-butenyl)phenoxy]-N,N-dimethyl-, (Z) [CAS] | 10540-29-1 | U.S. | 4,536,516 Anticancer, hormonal | |
| tamsulosin | Benzenesulfonamide, 5-12-[[2-(2-ethoxyphenoxy)ethyl]amino]propyl]-2-methoxy-, (R)-[CAS] | 106133-20-4 80223-99-0 | EP | 34432 Prostate disorders | Benign prostatic hyperplasia |
| tandospirone | 4,7-Methano-1H-isoindole-1,3(2H)-dione, hexahydro-2-[4-[4-(2-pyrimidinyl)1-piperazinyl]butyl]-, (3aAlpha,4β,7β,7aAlpha)-, 2-hydroxy-1,2,3-propanetricarboxylate (1:1) [CAS] | 112457-95-1 87760-53-0 | EP | 82402 Anxiolytic | Anxiety, general |
| Tannoform | | 9010-29-1 | | | |
| Taprostene | | 108945-35-3 | | | |
| tariquidar | 3-Quinolinecarboxamide, N-(2-[[[4-[2-(3,4-dihydro-6,7-dimethoxy-2(1H)-isoquinolinyl)ethyl]phenyl]amino]carbonyl]-4,5-dimethoxyphenyl]-[CAS] | 206873-63-4 | WO | 9817648 Radio/chemosensitizer | Cancer, lung, non-small cell |
| TAS-103 | 6-[[2-(Dimethyl-amino)ethyl]amino]-3-hydroxy-7H-indeno[2,1-c]quinolin-7-one dihydrochloride | 174634-09-4 | WO | 9532187 Anticancer, other | Cancer, lung, non-small cell |
| Tasosartan | | 145733-36-4 | | | |
| Taurocholic Acid | | 81-24-3 | | | |
| Taurolidine | | 19388-87-5 | | | |
| tazanolast | Acetic acid, oxo[[3-(1H-tetrazol-5-yl)phenyl]amino]-, butyl ester [CAS] | 82989-25-1 | U.S. | 4,778,816 Antiasthma | |
| tazarotene | 3-Pyridinecarboxylic acid, 6-[(3,4-dihydro-4,4-dimethyl-2H-1-benzothiopyran-6-yl)ethynyl]-, ethyl ester [CAS] | 118292-40-3 | EP | 284288 Antipsoriasis | Psoriasis |
| Tazobactam | | 89786-04-9 | | | |
| tazobactam + piperacillin | | | JP | 58225091 Antibiotic, other | Infection, general |
| TBC-3711 | | 374680-51-0 | | Cardiovascular | Heart failure |
| TCH-346 | N-Methyl-N-propargyl-10-aminomethyl-dibenzo(b,f)oxepin | | | Neuroprotective | Amyotrophic lateral sclerosis |
| tebipenem | 5-Hexenoic acid, 4-hydroxy-, polymer with 4-ethenyl-1H-imidazole [CAS] | 82200-24-6 | | Beta-lactam antibiotic | Infection, streptococcal |
| tecadenoson | Adenosine, N-[(3R)-tetrahydro-3-furanyl]-[CAS] | 204512-90-3 | WO | 9808855 Antiarrhythymic | Tachycardia, supraventricular |
| tecastemizole | 1H-Benzimidazol-2-amine, 1-((4-fluorophenyl)methyl)-N-4-pipendinyl-[CAS] | 75970-99-9 | U.S. | 4,219,559 Antiallergic, non-asthma | Rhinitis, allergic, seasonal |
| Technetium 99mTc Bicisate | | 121281-41-2 | | | |
| Technetium 99mTc Mertiatide | | 125224-05-7; 104348-91-6 | | | |
| Technetium 99mTc Sestamibi | | 109581-73-9 | | | |
| Technetium 99mTc Teboroxime | | 104716-22-5 | | | |

TABLE 3-continued

| API Generic Name | API Chemical Name | CAS No. | Patent Reference | Example of Therapeutic Use | Example of Indication |
|---|---|---|---|---|---|
| Teclothiazide | | 4267-5-4 | | | |
| Teclozan | | 5560-78-1 | | | |
| tedisamil | Spirolcyclopentane-1,9-[3,7]diazabicyclo[3.3.1]nonane], 3',7'-bis(cyclopropylmethyl)-[CAS] | 90961-53-8 | EP 102833 | Antiarrhythmic | Fibrillation, atrial |
| Teflurane | | 124-72-1 | | | |
| tegafur | 2,4(1H,3H)-Pyrimidinedione, 5-fluoro-1-(tetrahydro-2-furanyl)-[CAS] | 17902-23-7 | GB 1168391 | Anticancer, antimetabolite | Cancer, general |
| tegafur + uracil | 2,4(1H,3H)-Pyrimidinedione, 5-fluoro-1-(tetrahydro-2-furanyl)-, mixt. with 2,4(1H,3H)-pyrimidinedione-[CAS] | 74578-38-4 | EP 224885 | Anticancer, antimetabolite | Cancer, breast |
| tegaserod | Hydrazinecarboximidamide, 2-((5-methoxy-1H-indol-3-yl)methylene)-N-pentyl-, (Z)-2-butenedioate [CAS] | 189188-57-6 145158-71-0 | | GI inflammatory/bowel disorders | Irritable bowel syndrome |
| Teicoplanin | | 61036-64-4 | | | |
| telbivudine | β-L-2-deoxythymidine | 3424-98-4 | | Antiviral, other | Infection, hepatitis-B virus |
| Telenzepine | | 80880-90-6 | | | |
| telithromycin | 3-De((2,6-dideoxy-3-C-methyl-3-O-methyl-Alpha-L-ribo-hexopyranosyl)oxy)-11,12-dideoxy-6-O-methyl-3-oxo-12,11-(oxycarbonyl((4-(4-(3-pyridinyl)-1H-imidazol-1-yl)butyl)imino))-[CAS] | 191114-48-4 | EP 680967 | Macrolide antibiotic | Infection, respiratory tract, general |
| telmesteine | 3,4-Thiazolidinedicarboxylic acid, 3-ethyl ester, (R)-[CAS] | 122946-43-4 | | COPD treatment | Bronchitis, chronic |
| telmisartan | (1,1-Biphenyl)-2-carboxylic acid, 4'-((1,4-dimethyl-2'-propyl(2,6'-bi-1H-benzimidazol)-1'-yl)methyl)-[CAS] | 144701-48-4 | EP 502314 | Antihypertensive, renin system | Hypertension, general |
| telomerase inhibs | | | WO 9941261 | Anticancer, other | Cancer, general |
| temazepam | 7-chloro-1,3-dihydro-3-hydroxy-1-methyl-5-phenyl-2H-1,4-benzodiazepin-2-one | 846-50-4 | U.S. 3197467 | Hypnotic/Sedative | Insomnia |
| temiverine | Benzeneacetic acid, Alpha-cyclohexyl-Alpha-hydroxy-, 4-(diethylamino)-1,1-dimethyl-2-butynyl ester, [CAS] | 129927-33-9 | GB 2222828 | Urological | Pollakisuria |
| temocapril | 1,4-Thiazepine-4(5H)-acetic acid, 6-[[1-(ethoxycarbonyl)-3-phenylpropyl]amino]tetrahydro-5-oxo-2-(2-thienyl)-, [2S-[2Alpha,6β(R*)]]-[CAS] | 102090-90-4 110221-44-8 111902-57-9 | U.S. 4,495,188 | Antihypertensive, renin system | Hypertension, general |
| Temocillin | | 66148-78-5 | | | |
| temoporfin | Phenol, 3,3',3''',3''''-(2,3-dihydro-21H,23H-porphine-5,10,15,20-tetrayl)tetrakis-[CAS] | 122341-38-2 | EP 337601 | Radio/chemosensitizer | Cancer, head and neck |
| temozolomide | Imidazo[5,1-d]-1,2,3,5-tetrazine-8-carboxamide, 3,4-dihydro-3-methyl-4-oxo-[CAS] | 85622-93-1 | DE 3231255 | Anticancer, alkylating | Cancer, brain, general |
| tenatoprazole | 1H-Imidazo(4,5-b)pyndine, 5-methoxy-2-(((4-methoxy-3,5-dimethyl-2-pyridinyl)methyl)sulfinyl)-[CAS] | 113712-98-4 | U.S. 4,808,596 | Antiulcer | Ulcer, gastric |
| Tenecteplase | | 191588-94-0 | | | |
| Tenidap | | 120210-48-2 | | | |
| teniposide | Furo[3',4':6,7]naphtho[2,3-d]-1,3-dioxol6(5aH)-one, 5,8,8a,9-tetrahydro-5-(4-hydroxy-3,5-dimethoxyphenyl)-9-[[4,6-O-(2-thienylmethylene)-β-D-glucopyranosyl]oxy]-, [5R-[5Alpha,5aβ,8aAlpha,9β(R*)]]-[CAS] | 29767-20-2 | U.S. 3524844 | Anticancer, other | Cancer, lymphoma, non-Hodgkin's |
| tenofovir | Phosphonic acid, (((1R)-2-(6-amino-9H-purin-9-yl)-1-methylethoxy)methyl)-[CAS] | 147127-20-6 | | Antiviral, anti-HIV | Infection, HIV/AIDS |
| tenofovir disoproxil | 2,4,6,8-tetraoxa-5-phosphanonanedioic acid, 5-(2-(6-amino-9H-purin-9-yl)-1-methylethoxymethyl) bis(1-methylethyl)ester, 5-oxide (R)-, (E)-2-butenedioate | 202138-50-9 | | Antiviral, anti-HIV | Infection, HIV/AIDS |
| Tenonitrozole | | 3810-35-3 | | | |
| tenoxicam | 2H-Thieno[2,3-e]-1,2-thiazine-3-carboxamide, 4-hydroxy-2-methyl-N-2-pyridinyl-, 1,1-dioxide [CAS] | 59804-37-4 | GB 1519811 | Antiarthritic, other | |
| Tenuazonic Acid | | 610-88-8 | | | |
| teprenone | 5,9,13,17-Nonadecatetraen-2-one, 6,10,14,18-tetramethyl-[CAS] | 3796-63-2 6809-52-5 | | Antiulcer | |

TABLE 3-continued

| API Generic Name | API Chemical Name | CAS No. | Patent Reference | Example of Therapeutic Use | Example of Indication |
|---|---|---|---|---|---|
| terazosin | Piperazine, 1-(4-amino-6,7-dimethoxy-2-quinazolinyl)-4-[(tetrahydro-2-furanyl)carbonyl]-[CAS] | 63074-08-8 63590-64-7 70024-40-7 | U.S. 4,112,097 | Antihypertensive, adrenergic | Hypertension, general |
| terbinafine | 1-Naphthalenemethanamine, N-(6,6-dimethyl-2-hepten-4-ynyl)-N-methyl-, (E)-[CAS] | 78628-80-5 91161-71-6 | EP 24587 | Antifungal | Infection, dermatological |
| terbutaline | 1,3-Benzenediol, 5-[2-[(1,1-dimethylethyl)amino]-1-hydroxyethyl]-[CAS] | 23031-25-6 | | Formulation, mucosal, topical | Dysmenorrhoea |
| terconazole | Piperazine, 1-[4-[[2-(2,4-dichlorophenyl)-2-(1H-1,2,4-triazol-1-ylmethyl)-1,3-dioxolan-4-yl]methoxy]phenyl]-4-(1-methylethyl)-, cis-[CAS] | 67915-31-5 | U.S. 4,358,449 | Antifungal | Vaginitis |
| terfenadine | 1-Pipendinebutanol, Alpha-[4-(1,1-dimethylethyl)phenyl]-4-(hydroxydiphenylmethyl)-[CAS] | 50679-08-8 | U.S. 3,878,217 | Antiallergic, non-asthma | |
| terguride | Urea, N,N-diethyl-N-[(8Alpha)-6-methylergolin-8-yl]-[CAS] | 37686-84-3 | EP 159522 | Antiprolactin | Hyperprolactinaemia |
| Terlipressin | | 14636-12-5 | | | |
| Terodiline | | 15793-40-5 | | | |
| Terofenamate | | 29098-15-5 | | | |
| Terpin | | 80-53-5 | | | |
| tertatolol | 2-Propanol, 1-[(3,4-dihydro-2H-1-benzothiopyran-8-yl)oxy]-3-[(1,1-dimethylethyl)amino]-, hydrochloride, (+\−)-[CAS] | 33580-30-2 83688-84-0 34784-64-0 | GB 1308191 | Antihypertensive, adrenergic | Hypertension, general |
| tert-Pentyl Alcohol | | 75-85-4 | | | |
| tesaglitazar | (2S)-2-ethoxy-3-[4-[2-[4-[(methylsulfonyl)oxy]phenyl]ethoxy]phenyl] propanoic acid | | | Antidiabetic | Diabetes, Type II |
| tesmilifene | Ethanamine, N,N-Diethyl-2-(4-(phenylmethyl)phenoxy)-[CAS] | 92981-78-7 | | Radio/chemosensitizer | Cancer, breast |
| Testolactone | | 968-93-4 | | | |
| Testosterone | androst-4-en-3-one, 17-hydroxy-, (17β)-[CAS] | 58-22-0 5949-44-0 | | Formulation, transdermal, systemic | Hormone replacement therapy |
| tetrabamate | | 60763-47-5 | DE 2748794 | Anxiolytic | Addictioin, alcohol |
| Tetrabarbital | | 76-23-3 | | | |
| Tetrabenazine | | 58-46-8 | | | |
| Tetracaine | | 136-47-0 | | | |
| Tetrachloro-ethylene | | 127-18-4 | | | |
| tetracine | Benzoic acid, 4-(butylamino)-, 2-(dimethylamino)ethyl ester [CAS] | 94-24-6 | | Formulation, transdermal, systemic | Pain, general |
| tetracycline | 2-Naphthacenecarboxamide, 4-(dimethylamino)-1,4,4a,5,5a,6,11,12a-octahydro-3,6,10,12,12a-pentahydroxy-6-methyl-1,11-dioxo-, [4S-(4Alpha,4aAlpha,5aAlpha,6β,12aAlpha)]-[CAS] | 60-54-8 | | Formulation, oral, other | Infection, oral |
| Tetrahy-drozoline | | 84-22-0 | | | |
| Tetrandrine | | 518-34-3 | | | |
| Tetrantoin | | 52094-70-9 | | | |
| Tetrazepam | | 10379-14-3 | | | |
| Tetrofosmin | | 127502-06-1 | | | |
| tetroxoprim | 2,4-Pyrimidinediamine, 5-[[3,5-dimethoxy-4-(2-methoxyethoxy)phenyl]methyl]-[CAS] | 53808-87-0 74515-38-1 | U.S. 3,992,379 | Trimethoprim and analogues | Infection, general |
| Tevenel ® | | 4302-95-8 | | | |
| tezacitabine | Cytidine, 2'-deoxy-2'-(fluoromethylene)-, (2E)-[CAS] | 130306-02-4 | U.S. 5,616,702 | Anticancer, antimetabolite | Cancer, general |
| tezosentan | 2-Pyridinesulfonamide, N-(6-(2-hydroxyethoxy)-5-(2-methoxyphenoxy)-2-(2-(1H-tetrazol-5-yl)-4-pyridinyl)-4-pyrimidinyl)-5-(1-methylethyl)-[CAS] | 180384-57-0 | | Cardiostimulant | Oedema, general |
| thalidomide | 1H-Isoindole-1,3(2H)-dione, 2-(2,6-dioxo-3-piperidinyl)-[CAS] | 50-35-1 | | Dermatological | Infection, dermatological |
| Thenaldine | | 86-12-4 | | | |
| Thenyldiamine | | 91-79-2 | | | |
| Theobromine | | 83-67-0 | | | |
| Theofibrate | | 54504-70-0 | | | |
| theophylline | 1H-Purine-2,6-dione, 3,7-dihydro-1,3-dimethyl-[CAS] | 58-55-9 5967-84-0 | | Formulation, modified-release, other | Asthma |
| Thiabendazole | | 148-79-8 | | | |

TABLE 3-continued

| API Generic Name | API Chemical Name | CAS No. | Patent Reference | | Example of Therapeutic Use | Example of Indication |
|---|---|---|---|---|---|---|
| Thiacetazone | | 104-06-3 | | | | |
| thiacymsenne | Carbamic acid, [4-(1-methylethyl)phenyl]-, (3aS,8aS)-3,3a,8,8a-tetrahydro-3a,8-dimethyl-2H-thieno[2,3-b]indol-5-yl ester [CAS] | 145209-51-4 | | | Cognition enhancer | Alzheimer's disease |
| Thialbarbital | | 467-36-7 | | | | |
| Thiamine | | 59-43-8 | | | | |
| Thiamine | | 154-87-0 | | | | |
| Thiamine | | 67-16-3 | | | | |
| Thiamiprine | | 5581-52-2 | | | | |
| Thiamphenicol | | 15318-45-3 | | | | |
| Thiamylal | | 77-27-0 | | | | |
| Thiazesim | | 5845-26-1 | | | | |
| Thiazinamium | | 58-34-4 | | | | |
| Thiazolino-butazone | | 54749-86-9 | | | | |
| Thiazolsulfone | | 473-30-3 | | | | |
| Thibenzazoline | | 6028-35-9 | | | | |
| Thiethylperazine | | 1420-55-9 | | | | |
| Thimerfonate | | 5964249 | | | | |
| Thimerosal | | 54-64-8 | | | | |
| Thiobarbital | | 77-32-7 | | | | |
| Thiobutabarbital | | 2095-57-0 | | | | |
| Thiocarbamizine | | 91-71-4 | | | | |
| Thiocarbarsone | | 120-02-5 | | | | |
| Thiocolchicine | | 2730-71-4 | | | | |
| Thiocresol | | 26445-03-4 | | | | |
| Thioctic Acid | | 62-46-4 | | | | |
| Thioglycerol | | 96-27-5 | | | | |
| Thioguanine | | 154-42-7 | | | | |
| Thioimreg | L-Thiotyrosinyl-glycinyl-glycine | | | | Anticancer, immunological | Cancer, general |
| Thiopental | | 71-73-8 | | | | |
| Thiopropazate | | 84-06-0 | | | | |
| Thioproperazine | | 316-81-4 | | | | |
| Thioridazine | | 50-52-2 | | | | |
| Thiothixene | | 5591-45-7 | | | | |
| Thiovir | Thiophosphonoformic acid | | | | Antiviral, anti-HIV | Infection, HIV/AIDS |
| Thiphenamil | | 82-99-5 | | | | |
| Thiram | | 137-26-8 | | | | |
| Thonzylamine | | 63-56-9 | | | | |
| Thozalinone | | 655-05-0 | | | | |
| Thromboplastin | | 9035-58-9 | | | | |
| Thurfyl Nicotinate | | 70-19-9 | | | | |
| thymectacin | | | U.S. | 6,245,750 | Anticancer, other | Cancer, colorectal |
| Thymol | | 89-83-8 | | | | |
| Thymopentin | | 69558-55-0 | | | | |
| Thymyl N-Isoamylcarbamate | | 578-20-1 | | | | |
| Thyropropic Acid | | 51-26-3 | | | | |
| Thyroxine | | 51-48-9 | | | | |
| Tiadenoi | | 6964-20-1 | | | | |
| tiagabine | 3-Piperidinecarboxylic acid, 1-[4,4-bis(3 methyl-2-thienyl)-3-butenyl]-, (R) [CAS] | 115103-54-3 | WO | 8700171 | Antiepileptic | Epilepsy, general |
| Tiamenidine | | 31428-61-2 | | | | |
| tianeptine | Heptanoic acid, 7-[(3-chloro-6,11-dihydro-6-methyldibenzo[c,f][1,2]thiazepin-11-yl)amino]-, 5,5-dioxide [CAS] | 72797-41-2 66981-73-5 | GB | 1269551 | Antidepressant | Depression, general |
| tiapride | Benzamide, N-[2-(diethylamino)ethyl]-2-methoxy-5-(methylsulfonyl)-[CAS] | 51012-32-9 | GB | 1394563 | Neuroleptic | |
| tiaprofenic acid | 2-Thiopheneacetic acid, 5-benzoyl-Alpha-methyl-[CAS] | 33005-95-7 | GB | 1331505 | Antiarthritic, other | |
| Tiaramide | | 32527-55-2 | | | | |
| tiazofurin | 4-Thiazolecarboxamide, 2-β-D-ribofuranosyl-[CAS] | 60084-10-8 | EP | 54432 | Anticancer, antimetabolite | Cancer, leukaemia, chronic myelogenous |
| Tibezonium | | 54663-47-7 | | | | |
| tibolone | 19-Norpregn-5(10)-en-20-yn-3-one, 17-hydroxy-7-methyl-, (7Alpha,17Alpha)-[CAS] | 5630-53-5 | EP | 389035 | Menopausal disorders | Hormone replacement therapy |

TABLE 3-continued

| API Generic Name | API Chemical Name | CAS No. | Patent Reference | Example of Therapeutic Use | Example of Indication |
|---|---|---|---|---|---|
| Ticarcillin | | 34787-01-4 | | | |
| ticlopidine | Thieno[3,2-c]pyridine, 5-[(2-chlorophenyl)methyl]-4,5,6,7-tetrahydro-[CAS] | 53885-35-1 55142-85-3 | GB 1554424 | Antithrombotic | |
| Ticrynafen | | 40180-04-9 | | | |
| tiemonium | 4-(3-hydroxy-3-phenyl-3-thien-2-yl-propyl)-4-methylmorpholinium | 6252-92-2 144-12-7 | | Antispasmodic | |
| tigecycline | 2-Naphthacenecarboxamide, 4,7-bis(dimethylamino)-9-[[[(1,1-dimethylethyl)amino]acetyl]amino]-1,4,4a,5,5a,6,11,12a-octahydro-3,10,12,12a-tetrahydroxy-1,11-dioxo-, (4S,4aS,5aR,12aS)-[CAS] | 220620-09-7 | EP 582829 | Tetracycline | Infection, general |
| Tigemonam | | 102507-71-1 | | | |
| Tigloidine | | 495-83-0 | | | |
| Tilidine | | 20380-58-9 | | | |
| Tilisolol | | 85136-71-6 | | | |
| tilmacoxib | Benzenesulfonamide, 4-(4-cyclohexyl-2-methyl-5-oxazolyl)-2-fluoro-[CAS] | 180200-68-4 | WO 9619463 | Alimentary/Metabolic, other | Polyp |
| tiludronic acid | Phosphonic acid, [[(4-chlorophenyl)thio]methylene]bis-[CAS] | 89987-06-4 | EP 100718 | Osteoporosis treatment | Paget's disease |
| Timentin | | 86482-18-0 | | Antibiotic, other | Infection, general |
| timepidium | Piperidinium, 3-(di-2-thienylmethylene)-5-methoxy-1,1-dimethyl-, [CAS] | 35035-05-3 | GB 1358446 | Antispasmodic | |
| Timiperone | | 57648-21-2 | | | |
| timolol | (−)-1-(t-butylamino)-3-[(4-morpholino-1,2,5-thiadiazol-3-yl)oxy]-2-propanolmaleate (1:1) salt | 26839-75-8 26921-17-5 | GB 1253709 | Antihypertensive, adrenergic antiglaucoma | |
| Timonacic | | 444-27-9 | | | |
| Tin Ethyl Etiopurpurin | | 113471-15-1 | | | |
| tinazoline | 1H-Indole, 3-[(4,5-dihydro-1H-imidazol-2-yl)thio]-[CAS] | 62882-99-9 | U.S. 3,376,311 | Vasodilator, peripheral | |
| Tinidazole | | 19387-91-8 | | | |
| Tinondine | | 24237-54-5 | | | |
| Tiocarlide | | 910-86-1 | | | |
| Tioclomarol | | 22619-35-8 | | | |
| tioconazole | 1H-Imidazole, 1-[2-[(2-chloro-3-thienyl)methoxy]-2-(2,4-dichlorophenyl)ethyl]-[CAS] | 61675-64-7 65899-73-2 | U.S. 4,062,966 | Antifungal | Infection, fungal, general |
| tiopronin | Glycine, N-(2-mercapto-1-oxopropyl)-[CAS] | 1953-02-2 | U.S. 3,246,025 | Urological | Homocystinuria |
| tiotropium | 3-Oxa-9-azoniatricyclo(3.3.1.02,4)nonane, 7-((hydroxydi-2-thienylacetyl)oxy)-9,9-dimethyl-, [CAS] | 136310-93-5 | EP 418716 | COPD treatment | Chronic obstructive pulmonary disease |
| Tioxolone | | 4991-65-5 | | | |
| Tipepidine | | 5169-78-8 | | | |
| tipifarnib | 2(1H)-Quinolone, 6-(amino(4-chlorophenyl)(1-methyl-1H-imidazol-5-yl)methyl)-4-(3-chlorophenyl)-1-methyl [CAS] | 192185-68-5 192185-72-1 | WO 9716443 | Anticancer, other | Cancer, breast |
| tipranavir | N-[3-[1(R)-[4-Hydroxy-2-oxo-6(R)-(2-phenylethyl)-6-propyl-5,6-dihydro-2H-pyran-3-yl]propyl]phenyl]-5-(trifluoromethyl)pyridine-2-sulfonamide | 174484-41-4 | | Antiviral, anti-HIV | Infection, HIV/AIDS |
| tiquizium | 2H-Quinolizinium, 3-(di-2-thienylmethylene)octahydro-5-methyl-, [CAS] | 71731-58-3 | U.S. 4,205,074 | Antispasmodic | |
| tirapazamine | 1,2,4-Benzotriazin-3-amine, 1,4-dioxide [CAS] | 20028-80-2 27314-97-2 5424-06-6 | DE 2204574 | Radio/chemosensitizer | Cancer, lung, non-small cell |
| Tiratricol | | 51-24-1 | | | |
| tirilazad | Pregna-1,4,9(11)-triene-3,20-dione, 21-[4-(2,6-di-1-pyrrolidinyl-4-pyrimidinyl)-1-piperazinyl]-16-methyl-, (16Alpha)-, [CAS] | 110101-65-0 110101-67-2 110101-66-1 | WO 8701706 | Neuroprotective | Haemorrhage, subarachnoid |
| tirofiban | L-Tyrosine, N-(butylsulfonyl)-O-[4-(4-piperidinyl)butyl]-, [CAS] | 142373-60-2 144494-65-5 | EP 478363 | Antithrombotic | Infarction, myocardial |
| tiropramide | Benzenepropanamide, Alpha-(benzoylamino)-4-[2-(diethylamino)ethoxy]-N,N-dipropyl-, (+\−)-[CAS] | 55837-29-1 | DE 2503992 | Antispasmodic | Muscle spasm, general |

TABLE 3-continued

| API Generic Name | API Chemical Name | CAS No. | Patent Reference | Example of Therapeutic Use | Example of Indication |
|---|---|---|---|---|---|
| Titanium Sulfate | | 13825-74-6 | | | |
| tixocortol | Pregn-4-ene-3,20-dione, 21-[(2,2-dimethyl-1-oxopropyl)thio]-11,17-dihydroxy-, (11β)-[CAS] | 55560-96-8 61951-99-3 | GB 1475795 | Antiallergic, non-asthma, mucosal, topical | Rhinitis, allergic, general |
| tizanidine | 2,1,3-Benzothiadiazol-4-amine, 5-chloro-N-(4,5-dihydro-1H-imidazol-2-yl)-[CAS] | 51322-75-9 | GB 1429926 | Muscle relaxant | Spastic paralysis |
| TLK-199 | Glycine, L-Gamma-glutamyl-S-(phenylmethyl)-L-cysteinyl-2-phenyl-, diethyl ester, (2R)-[CAS] | 168682-53-9 | U.S. 5,679,643 | Immunostimulant, other | Myelodysplastic syndrome |
| TLK-286 | Glycine, L-Gamma-glutamyl-3-[[2-([bis[bis(2-chloroethyl)amino]phosphinyl]oxy)ethyl]sulfonyl]-L-alanyl-2-phenyl-, (2R)-[CAS] | 158382-37-7 | U.S. 5,545,621 | Anticancer, other | Cancer, ovarian |
| TNF-β, analogue | | | RU 2035185 | Anticancer, immunological | Cancer, general |
| TNP-470 | | 129298-91-5 | | | |
| TO-186 | Pregna-1,4-diene-3,20-dione, 9-fluoro-11β,17,21-trihydroxy-16.beta.-methyl-, 17-butyrate 21-propionate [CAS] | 5534-02-1 | | Antipruritic/inflamm, allergic | |
| tobramycin | O-3-amino-3-deoxy-Alpha-D-glucopyranosyl-(1,6)-O-(2,6-diamino-2,3,6-trideoxy-Alpha-D-ribo-hexopyranosyl-(1-4)-2-deoxy-[CAS] | 32986-56-4 | | Formulation, inhalable, topical | Infection, respiratory tract, general |
| tocainide | Propanamide, 2-amino-N-(2,6-dimethylphenyl)-[CAS] | 41708-72-9 | U.S. 4,218,477 | Antiarrhythmic | Fibrillation, ventricular |
| Tocamphyl | | 5634-42-4 | | | |
| tocladesine | 8-Chloroadenosine 3'5'-cyclic phosphate | 41941-56-4 | | Anticancer, other | Cancer, colorectal |
| Tocoretinate | | 40516-48-1 | | | |
| Todralazine | | 14679-73-3 | | | |
| Tofenacin | | 15301-93-6 | | | |
| tofimilast | 5H-Pyrazolo[3,4-c]-1,2,4-triazolo[4,3-a]pyridine,9-cyclopentyl-7-ethyl-6,9-dihydro-3-(2-thienyl)- | 185954-27-2 | | Antiasthma | Asthma |
| tofisopam | 5H-2,3-Benzodiazepine, 1-(3,4-dimethoxyphenyl)-5-ethyl-7,8-dimethoxy-4-methyl-[CAS] | 22345-47-7 | GB 1334271 | Anxiolytic | Anxiety, general |
| Tolazamide | | 1156-19-0 | | | |
| Tolazoline | | 59-98-3 | | | |
| Tolbutamide | | 64-77-7 | | | |
| tolcapone | Methanone, (3,4-dihydroxy-5-nitrophenyl)(4-methylphenyl)-[CAS] | 134308-13-7 | EP 237929 | Antiparkinsonian | Parkinson's disease |
| tolciclate | Carbamothioic acid, methyl(3-methylphenyl)-, O-(1,2,3,4-tetrahydro-1,4-methanonaphthalen-6-yl) ester [CAS] | 50838-36-3 | GB 1364407 | Antifungal | Infection, dermatological |
| Tolcyclamide | | 664-95-9 | | | |
| tolevamer | Benzenesulfonic acid, 4-ethenyl-, homopolymer, | 28038-50-8 | | Antibacterial, other | Infection, Clostridium, general |
| tolfenamic acid | Benzoic acid, 2-[(3-chloro-2-methylphenyl)amino]-[CAS] | 13710-19-5 | DE 1543295 | Anti-inflammatory | Inflammation, general |
| Tolindate | | 27877-51-6 | | | |
| Toliprolol | | 2933-94-0 | | | |
| Tolmetin | | 26171-23-3 | | | |
| Tolnaftate | | 2398-96-1 | | | |
| Tolonidine | | 4201-22-3 | | | |
| Tolonium | | 92-31-9 | | | |
| toloxatone | 2-Oxazolidinone, 5-(hydroxymethyl)-3-(3-methylphenyl)-[CAS] | 29218-27-7 | GB 1250538 | Antidepressant | |
| Tolperisone | | 728-88-1 | | | |
| Tolpropamine | | 5632-44-0 | | | |
| Tolrestat | | 82964-04-3 | | | |
| tolserine | Carbamic acid, (2-methylphenyl)-, (3aS,8aR)-1,2,3,3a,8,8a-hexahydro-1,3a,8-trimethylpyrrolo[2,3-b]indol-5-yl ester [CAS] | 145209-30-9 | | Cognition enhancer | Alzheimer's disease |
| tolterodine | Phenol, 2-(3-(bis(1-methylethyl)amino)-1-phenylpropyl)-4-methyl-, (R)-[CAS] | 124937-51-5 | EP 325571 | Urological | Incontinence |
| tolvaptan | Benzamide, N-[4-[(7-chloro-2,3,4,5-tetrahydro-5-hydroxy-1H-1-benzazepin-1-yl)carbonyl]-3-methylphenyl]-2-methyl-[CAS] | 150683-30-0 | EP 450097 | Cardiovascular | Heart failure |

TABLE 3-continued

| API Generic Name | API Chemical Name | CAS No. | Patent Reference | Example of Therapeutic Use | Example of Indication |
|---|---|---|---|---|---|
| Tolycaine | | 3686-58-6 | | | |
| Topiramate | Beta-D-Fructopyranose, 2,3:4,5-bis-O-(1-methylethylidene)-, sulfamate [CAS] | 97240-79-4 | EP 533483 | Antiepileptic | Epilepsy, generalized, tonic-clonic |
| topoisomerase inhibitors | | | U.S. 5,733,880 | Anticancer, other | Cancer, general |
| topotecan | 1H-Pyrano[3',4':6,7]indolizino[1,2-b]quinoline-3,14(4H, 12H)-dione, 9-[(dimethylamino)methyl]-4-ethyl-4,10-dihydroxy-, (S)-[CAS] | 123948-87-8 | EP 321122 | Anticancer, other | Cancer, ovarian |
| torasemide | 3-Pyridinesulfonamide, N-[[(1-methylethyl)amino]carbonyl]-4-[(3-methylphenyl)amino]-[CAS] | 56211-40-6 | U.S. 4,018,929 | Antihypertertensive, diuretic | Hypertension, general |
| torcetrapib | ethyl (2R,4S)-4-[[3,5-bis(trifluoromethyl)benzyl](methoxycarbonyl)amino]-2-ethyl-6-(trifluoromethyl)-3,4-dihydroquinoline-1(2H)-carboxylate | 262352-17-0 | | Hypolipaemic/Antiatherosclerosis | Atherosclerosis |
| torcitabine | β-L-2'Deoxycytidine | | | Antiviral, other | Infection, hepatitis-B virus |
| toremifene | Ethanamine, 2-[4-(4-chloro-1,2-diphenyl-1-butenyl)phenoxy]-N,N-dimethyl-, (Z)-[CAS] | 89778-26-7 89778-27-8 | EP 95875 | Anticancer, hormonal | Cancer, breast |
| Torsemide | | 56211-40-6 | | | |
| Tositumomab | | 208921-02-2 | | | |
| tosufloxacin | 1,8-Naphthyridine-3-carboxytic acid, 7-(3-amino-1-pyrrolidinyl)-1-(2,4-difluorophenyl)-6-fluoro-1,4-dihydro-4-oxo-, [CAS] | 100490-36-6 115964-29-9 | U.S. 4,704,459 | Quinolone antibacterial | Infection, urinary tract |
| tramadol | Cyclohexanol, 2-[(dimethylamino)methyl]-1-(3-methoxyphenyl)-, cis-(+/−)-[CAS] | 27203-92-5 36282-47-0 | | Analgesic, other | Pain, general |
| Tramazoline | | 1082-57-1 | | | |
| trandolapril | 1H-Indole-2-carboxylic acid, 1-[2-[(1-carboxy-3-phenylpropyl)amino]-1-oxopropyl]octahydro-, [2S-[1[R*(R*)],2Alpha,3aAlpha,7aβ]]-[CAS] | 87679-71-8 87679-37-6 52-53-9 | DE 3151690 | Antihypertensive, renin system | Hypertension, general |
| tranexamic acid | Cyclohexanecarboxylic acid, 4-(aminomethyl)-, trans-[CAS] | 1197-18-8 | U.S. 3,950,405 | Antifibrinolytic | Menstrual disorder, general |
| tranilast | Benzoic acid, 2-[[3-(3,4-dimethoxyphenyl)-1-oxo-2-propenyl]amino]-[CAS] | 53902-12-8 | U.S. 3,940,422 | Vulnerary | Wound healing |
| trans-retinoic acid | Retinoic acid[CAS] | 302-79-4 | | Anticancer, other | Cancer, general |
| Tranylcypromine | | 155-09-9 | | | |
| trapidil | [1,2,4]Triazolo[1,5-a]pyrimidin-7-amine, N,N-diethyl-5-methyl-[CAS] | 15421-84-8 | DD 55956 | Vasodilator, coronary | |
| Trastuzumab | | 180288-69-1 | | | |
| travoprost | 5-Heptenoic acid, 7-(3,5-dihydroxy-2-(3-hydroxy-4-(3-(trifluoromethyl)phenoxy)-1-butenyl)cyclopentyl)-, 1-methylethylester (1R(1Alpha(Z),2B(1E,3R*),3Alpha,5Alpha) [CAS] | 157283-68-6 | | Formulation, mucosal, topical | Glaucoma |
| Traxanox | | 58712-69-9 | | | |
| traxoprodil | 1-Piperidineethanol, 4-hydroxy-Alpha-(4-hydroxyphenyl)-β-methyl-4-phenyl-, (AlphaS,βS)-[CAS] | 134234-12-1 188591-67-5 | | Analgesic, other | Pain, general |
| trazodone | 1,2,4-Triazolo[4,3-a]pyridin-3(2H)-one, 2-[3-[4-(3-chlorophenyl)-1-piperazinyl]propyl]-[CAS] | 19794-93-5 25332-39-2 | U.S. 4,215,104 | Antidepressant | |
| Tremacamra | | 155576-45-7 | | | |
| Trenbolone | | 10161-33-8 | | | |
| Trengestone | | 5192-84-7 | | | |
| treosulfan | 1,2,3,4-Butanetetrol, 1,4-dimethanesutfonate, [S-(R*,R*)]-[CAS] | 299-75-2 | WO 8401506 | Anticancer, alkylating | |
| trepibutone | Benzenebutanoic acid, 2,4,5-triethoxy-Gamma-oxo-[CAS] | 41826-92-0 | GB 1387733 | Antispasmodic | |
| treprostinol | Prosta-5,13-dien-1-oic acid, 6,9-epoxy-11,15-dihydroxy-, [5Z,9Alpha, 11Alpha, 13E, 15S]-[CAS] | 35121-78-9 61849-14-7 | U.S. 6,054,486 | Formulation, parenteral, other | Hypertension, pulmonary |
| tretinoin | Retinoic acid [CAS] | 302-79-4 | | Formulation, dermal, topical | Acne |

TABLE 3-continued

| API Generic Name | API Chemical Name | CAS No. | Patent Reference | Example of Therapeutic Use | Example of Indication |
|---|---|---|---|---|---|
| tretoquinol | 6,7-Isoquinolinediol, 1,2,3,4-tetrahydro-1-[(3,4,5-trimethoxyphenyl)methyl]-, (S) [CAS] | 18559-59-6 30418-38-3 21650-42-0 | ZA 6802416 | Antiasthma | |
| TRH | | 24305-27-9 | | | |
| TRI-50b | TRI 50b [CAS] | 226214-49-9 | | Antithrombotic | Thrombosis, general |
| Triacetin | | 102-76-1 | | | |
| Triamcinolone Acetonide | | 76-25-5 | | | |
| Triamcinolone Benetonide | | 31002-79-6 | | | |
| Triamcinolone Hexacetonide | | 5611-51-8 | | | |
| triamcinolone | Pregna-1,4-diene-3,20-dione, 9-fluoro-11,21-dihydroxy-16,17-[(1-methylethylidene)bis(oxy)]-, (11β, 16Alpha)-[CAS] | 76-25-5 124-94-7 | | Formulation, inhalable, topical | Asthma |
| Triamterene | | 396-01-0 | | | |
| triapine | Triapine [CAS] | 236392-56-6 | U.S. 6,458,816 | Anticancer, antimetabolite | Cancer, leukaemia, general |
| Triaziquone | | 68-76-8 | | | |
| triazolam | 8-chloro-6-(2-chlorophenyl)-1-methyl-4H-[1,2,4]-triazolo[4,3-a][1,4]benzodiazepine | 28911-01-5 | U.S. 3,980,790 | Hypnotic/Sedative | Insomnia |
| Tribenoside | | 10310-32-4 | | | |
| Trichlorfon | | 52-68-6 | | | |
| Trichlormethiazide | | 133-67-5 | | | |
| Trichlormethine | | 555-77-1 | | | |
| Trichloroethylene | | 79-01-6 | | | |
| Triclobisonium | | 79-90-3 | | | |
| Triclocarban | | 101-20-2 | | | |
| Triclofenol Piperazine | | 5714-82-9 | | | |
| Triclofos | | 306-52-5 | | | |
| Triclosan | | 3380-34-5 | | | |
| Tricromyl | | 85-90-5 | | | |
| Tridihexethyl Iodide | | 125-99-5 | | | |
| trientine | 1,2-Ethanediamine, N,N2-bis(2aminoethyl)-, [CAS] | 38260-01-4 112-24-3 | | Metabolic and enzyme | Wilson's disease |
| Triethanolamine | | 102-71-6 | | | |
| Triethylene-melamine | | 51-18-3 | | | |
| Triethylene-phosphoramide | | 545-55-1 | | | |
| Tnethylenethio-phosphoramide | | 52-24-4 | | | |
| Trifluoperazine | | 117-89-5 | | | |
| Trifluperidol | | 749-13-3 | | | |
| Triflupromazine | | 146-54-3 | | | |
| trifluridine | Thymidine, Alpha,Alpha,Alpha-trifluoro-[CAS] | 70-00-8 | U.S. 3,201,387 | Antiviral, other | Infection, herpes virus, general |
| triflusal | Benzoic acid, 2-(acetyloxy)-4-(trifluoromethyl)-[CAS] | 322-79-2 | U.S. 4,096,252 | Antithrombotic | Thrombosis, general |
| Trihexyphenidyl | | 52-49-3 | | | |
| trilostane | Androst-2-ene-2-carbonitrile, 4,5-epoxy-3,17-dihydroxy-, (4Alpha,5Alpha, 17β)-[CAS] | 13647-35-3 | U.S. 3,296,255 | Anticancer, hormonal | Cancer, breast |
| Trimazosin | | 35795-16-5 | | | |
| trimebutine | Benzoic acid, 3,4,5-trimethoxy-, 2-(dimethylamino)-2-phenylbutyl ester, (Z)-2-butenedioate (1:1) [CAS] | 34140-59-5 39133-31-8 | DE 2151716 | Antispasmodic | |
| Trimecaine | | 616-68-2 | | | |
| Trimeprazine | | 84-96-8 | | | |
| Trimetazidine | | 5011-34-7 | | | |
| Trimethadione | | 127-48-0 | | | |
| Trimethaphan | | 68-91-7 | | | |
| Trimetho-benzamide | | 138-56-7 | | | |
| Trimethoprim | | 738-70-5 | | | |
| Trimetozine | | 635-41-6 | | | |
| trimetrexate | 2,4-Quinazolinediamine, 5-methyl-6-[[(3,4,5-trimethoxyphenyl)amino]methyl]-[CAS] | 52128-35-5 82952-64-5 | U.S. 4,391,809 | Antifungal | Infection, Pneumocystis jiroveci |

TABLE 3-continued

| API Generic Name | API Chemical Name | CAS No. | Patent Reference | Example of Therapeutic Use | Example of Indication |
|---|---|---|---|---|---|
| trimipramine | 5H-Dibenz[b,f]azepine-5-propanamine, 10,11-dihydro-N,N,t1-trimethyl-, (Z)-2-butenedioate (1:1) [CAS] | 521-78-8 739-71-9 | | Antidepressant | |
| Trimoprostil | | 69900-72-7 | | | |
| Trioxsalen | | 3902-71-4 | | | |
| tripamide | Benzamide, 3-(aminosulfonyl)-4-chloro-N-(octahydro-4,7-methano-2H-isoindol-2-yl-, (3aAlpha,4Alpha,7Alpha,7aAlpha)-[CAS] | 73803-48-2 | JP | 7305585 Antihypertensive, diuretic | Hypertension, general |
| Triparanol | | 78-41-1 | | | |
| Tripelennamine | | 91-81-6 | | | |
| Triprolidine | | 486-12-4 | | | |
| triptorelin | Luteinizing hormone-releasing factor (pig), 6-D-tryptophan-[CAS] | 124508-66-3 57773-63-4 | U.S. | 4,010,125 Releasing hormones | Cancer, prostate |
| tritiozine | Morpholine, 4-[thioxo(3,4,5-trimethoxyphenyl)methyl]-[CAS] | 35619-65-9 | U.S. | 3,862,138 Antiulcer | |
| Tritoqualine | | 14504-73-5 | | | |
| TRK-530 | Phosphonic acid, [[[4-(methylthio)phenyl]thio]methylene]bis-, disodium salt [CAS] | 151425-92-2 | WO | 9410181 Antiarthritic, other | Arthritis, rheumatoid |
| TRK-820 | 2-Propenamide, N-[(5Alpha,6β)-17-(cyclopropylmethyl)-4,5-epoxy-3,14-dihydroxymorphinan-6-yl]-3-(3-furanyl)-N-methyl-, monohydrochloride, (2E)-[CAS] | 152658-17-8 | WO | 9315081 Antipruritic/inflamm, non-allergic | Pruritus |
| Troclosene | | 2244-21-5 | | | |
| trofosfamide | 3-2-(chloroethyl)-2-[bis(2-chloroethyl)amino]tetrahydro-2H-1,3,2-oxazaphosphorin 2-oxide | 22089-22-1 | GB | 1188159 Anticancer, alkylating | |
| Troglitazone | | 97322-87-7 | | | |
| Troleandomycin | | 2751-9-9 | | | |
| Trolnitrate | | 588-42-1 | | | |
| tromantadine | N-(1-adamantyl)-2-(2-dimethylamine ethoxy)acetamide | 53783-83-8 | DE | 1941218 Antiviral, other | Infection, herpes simplex virus |
| Tromethamine | | 77-86-1 | | | |
| Tropacine | | 6878-98-4 | | | |
| Tropesin | | 65189-78-8 | | | |
| Tropicamide | | 1508-75-4 | | | |
| tropine | 1H-Indole-3-acetic acid, 1-(4-chlorobenzoyl)-5-methoxy-2-methyl-, 2-carboxy-2-phenylethyl ester, (+/−)-[CAS] | 65189-78-8 | | Antiarthritic, other | |
| tropisetron | 1H-Indole-3-carboxylic acid, 8-methyl-8 azabicyclo[3.2.1]oct-3-yl ester, endo-[CAS] | 89565-68-4 | GB | 2125398 Antiemetic | Chemotherapy-induced nausea and vomiting |
| Trospectomycin | | 88669-04-9 | | | |
| trospium | 3Alpha-Hydroxyspiro[1AlphaH,5AlphaH-nortropane-8,1'-pyrrolidinium] benzilate | 10405-02-4 | | Urological | Pollakisuria |
| trovafloxacin | 1,8-Naphthyridine-3-carboxylic acid, 7-(6-amino-3-azabicyclo[3.1.0]hex-3-yl)-1-(2,4-difluorophenyl)-6-fluoro-1,4-dihydro-4-oxo-, (1Alpha,5Alpha,6Alpha)-, [CAS] | 147059-72-1 147059-75-4 | U.S. | 5,164,402 Quinolone antibacterial | Infection, respiratory tract, general |
| troxacitabine | 2(1H)-Pyrimidinone, 4-amino-1-(2-(hydroxymethyl)-1,3-dioxolan-4-yl)-, (2S-cis)-[CAS] | 145918-75-8 | | Anticancer, other | Cancer, leukaemia, acute myelogenous |
| Troxerutin | | 7085-55-4 | | | |
| troxipide | Benzamide, 3,4,5-trimethoxy-N-3-piperidinyl-, (+/−)-[CAS] | 30751-05-4 99777-81-8 | U.S. | 3,647,805 Antiulcer | Ulcer, gastric |
| Trypan Red | | 574-64-1 | | | |
| Tryparsamide | | 554-72-3 | | | |
| Tryptophan | | 73-22-3 | | | |
| TSH | | 9002-71-5 | | | |
| TSN-09 | 6,14-Ethenomorphinan-7-methanol, 17-(cyclopropylmethyl)-Alpha-(1,1-dimethylethyl)-,5-epoxy-18,19-dihydro-3-hydroxy-6-methoxy-Alpha-methyl-, [5Alpha,7Alpha,(S)]-[CAS] | 52485-79-7 | | Formulation, transdermal, patch | Pain, cancer |
| TU-2100 | Nonanedioic acid, bis[(2-(ethoxycarbonyl)phenyl] ester | | U.S. | 6,180,669 Antiacne | Acne |
| Tuaminoheptane | | 123-82-0 | | | |
| Tubercidin | | 69-33-0 | | | |
| Tubocurarine Chloride | | 57-94-3 | | | |

TABLE 3-continued

| API Generic Name | API Chemical Name | CAS No. | Patent Reference | Example of Therapeutic Use | Example of Indication |
|---|---|---|---|---|---|
| tulobuterol | Benzenemethanol, 2-chloro-Alpha-[[(1,1-dimethylethyl)amino]methyl]-[CAS] | 41570-61-0 | DE 2244737 | Antiasthma | Asthma |
| TV-3326 | N-(Propargyl-(3R)aminoindan-5-yl)-ethyl methyl carbamate | | | Cognition enhancer | Alzheimer's disease |
| TY-11223 | Acetic acid, [2-[2,3,3a,6,7,7a-hexahydro-2-hydroxy-6-(3-hydroxy-4,4-dimethyl-1,6-nonadiynyl)-1H-inden-5-yl]ethoxy]-, [1S-[1Alpha(R*),2β,3aAlpha,7aAlpha]]-[CAS] | 140694-43-5 | U.S. 4,837,342 | Antithrombotic | Unspecified |
| TY-12533 | 6,7,8,9-Tetrahydro-2-methyl-5H-cyclohepta[b]pyridine-3-carbonylguanidine maleate | | U.S. 6,258,829 | Antiarrhythmic | Unspecified |
| TYB-3215 | D-Glucitol, 1,4:3,6-dianhydro-, dinitrate [CAS] | 87-33-2 | | Formulation, modified-release, other | Angina, general |
| Tybamate | | 4268-36-4 | | | |
| tyloxapol | 4-(1,1,3,3-Tetramethylbutyl)phenol polymer with formaldehyde and oxirane [CAS] | 25301-02-4 | | Formulation, inhalable, topical | |
| Tymazoline | | 24243-97-8 | | | |
| Tyramine | | 51-67-2 | | | |
| Tyropanoate | | 7246-21-1 | | | |
| Ubenimex | | 58970-76-6 | | | |
| ufenamate | Benzoic acid, 2-[[3-(trifluoromethyl)phenyl]amino]-, butyl ester [CAS] | 67330-25-0 | BE 861852 | Antipruritic/inflamm, non-allergic | |
| Undecylenic Acid | | 112-38-9 | | | |
| Unoprostone | | 120373-36-6 | | | |
| UR-8880 | 4-[4-Chloro-5-(3-fluoro-4-methoxyphenyl)imidazol-1-imidazol-1-yl]benzenesulfonamide-[CAS] | | | Anti-inflammatory | Inflammation, general |
| Uracil Mustard | | 66-75-1 | | | |
| Uralyt-U | 1,2,3-Propanetricarboxylic acid, 2-hydroxy-, potassium sodium salt (5:6:6), hydrate [CAS] | 55049-48-4 | U.S. 4,400,535 | Urological | |
| urapidil | 2,4(1H,3H)-Pyrimidinedione, 6-[[3-[4-(2-methoxyphenyl)-1-piperazinyl]propyl]amino]-1,3-dimethyl-[CAS] | 34661-75-1 | GB 1309324 | Antihypertensive, adrenergic | Hypertension, general |
| urea | Urea [CAS] | 57-13-6 | | Antipsoriasis | |
| Uredepa | | 302-49-8 | | | |
| Urethan | | 51-79-6 | | | |
| Uridine 5¢-Triphosphate | | 63-39-8 | | | |
| Urinastatin | | 80449-31-6 | | | |
| ursodeoxycholic acid | 3Alpha,7β-dihydroxy-5β-cholan-24-oic acid [CAS] | 128-13-2 | | Formulation, other, Cirrhosis primary biliary, hepatic dysfunction biliary calcalus | Cirrhosis, primary biliary |
| Ursodiol | | 128-13-2 | | | |
| Ushercell | | | U.S. 6,063,773 | Formulation, mucosal, topical | Contraceptive, female |
| Uzarin | | 20231-81-6 | | | |
| valaciclovir | L-Valine, 2-[(2-amino-1,6-dihydro-6-oxo-9H-purin-9-yl)methoxy]ethyl ester [CAS] | 124832-26-4 | EP 308065 | Antiviral, other | Infection, herpes simplex virus |
| Valacyclovir | | 124832-26-4 | | | |
| valdecoxib | Benzenesulfonamide, 4-(5-methyl-3-phenyl-4-isoxazolyl)-[CAS] | 181695-72-7 | U.S. 5859257 | Antiarthritic, other | Arthritis, rheumatoid |
| Valdetamide | | 512-48-1 | | | |
| Valethamate | | 90-22-2 | | | |
| valganciclovir | L-Valine, 2-((2-amino-1,6-dihydro-6-oxo-9H-purin-9-yl)methoxy)-3-hydroxypropyl ester [CAS] | 175865-59-5 175865-60-8 | EP 694547 | Antiviral, other | Infection, cytomegalovirus |
| Valnoctamide | | 4171-13-5 | | | |
| valomaciclovir | L-Valine (3R)-3-((2-amino-1,6-dihydro-6-oxo-9H-purin-9-yl)methyl)-4-((1-oxooctadecyl)oxy)butyl ester [CAS] | 1951 56-77-5 | | Antiviral, other | Infection, herpes simplex virus |
| valproate | Pentanoic acid, 2-propyl-, [CAS] | 76584-70-8 1069-66-5 | U.S. 4,988,731 | Antiepileptic | Epilepsy, generalized, tonic-clonic |
| Valproic Acid | | 99-66-1 | | | |
| Valpromide | | 2430-27-5 | | | |

TABLE 3-continued

| API Generic Name | API Chemical Name | CAS No. | Patent Reference | | Example of Therapeutic Use | Example of Indication |
|---|---|---|---|---|---|---|
| valrocemide | Pentanamide, N-(2-amino-2-oxoethyl)-2-propyl-[CAS] | 92262-58-3 | U.S. | 5,585,358 | Antiepileptic | Epilepsy, general |
| valrubicin | Pentanoic acid, 2-(1,2,3,4,6,11-hexahydro-2,5,12-trihydroxy-7-methoxy 6,11-dioxo-4-((2,3,6-trideoxy-3-((trifluoroacetyl)amino)-Alpha-L-lyxo-hexopyranosyl)oxy)-2-naphthacenyl)-2-oxoethyl ester (2S-cis)-[CAS] | 56124-62-0 | U.S. | 4,035,566 | Anticancer, antibiotic | Cancer, bladder |
| valsartan | L-Valine, N-(1-oxopentyl)-N-[[2'-(1H-tetrazol-5-yl)[1,1'-biphenyl]-4-yl]methyl]-[CAS] | 137862-53-4 | EP | 443983 | Antihypertensive, renin system | Hypertension, general |
| Valspodar | | 121584-18-7 | | | | |
| vardenafil | Piperazine, 1-(3-(1,4-dihydro-5-methyl(-4-oxo-7-propylimidazo(5,1-f)(1,2,4)-triazin-2-yl)-4-ethoxyphenyl)sulfonyl)-4-ethyl-[CAS] | 224785-90-4 | | | Male sexual dysfunction | Sexual dysfunction, male, general |
| varespladib | Acetic acid, ((3-(aminooxoacetyl)-2-ethyl-1-(phenylmethyl)-1H-indol-4-yl)oxy)-[CAS] | 172732-68-2 172733-42-5 | EP | 675110 | Septic shock treatment | Sepsis |
| Varicella Virus Vaccine | | | | | | |
| vatanidipine | 3,5-Pyridinedicarboxylic acid, 1,4-dihydro-2,6-dimethyl-4-(3-nitrophenyl)-, 2-[4-[4-(diphenylmethyl)-1-piperazinyl]phenyl]ethyl methyl ester, [CAS] | 116308-55-5 133743-71-2 | EP | 257616 | Neuroprotective | Hypertension, general |
| VEA | | | U.S. | 6,007,817 | Radio/chemosensitizer | Cancer, general |
| vecuronium | Piperidinium, 1-bis(acetyloxy)-2-(1-piperidinyl)androstan-16-yl]-1-methyl-, [CAS] | 50700-72-6 | U.S. | 4,237,126 | Muscle relaxant | Anaesthesia, adjunct |
| Velnacrine | | 104675-29-8 | | | | |
| venlafaxine | Cyclohexanol, 1-[2-(dimethylamino)-1-(4-methoxyphenyl)ethyl]-, [CAS] | 93413-69-5 99300-78-4 | GB | 2227743 | Antidepressant | Depression, general |
| Veralipride | | 66644-81-3 | | | | |
| verapamil | Benzeneacetonitrile, Alpha-[3-[[2-(3,4-dimethoxyphenyl)ethyl]methylamino]propyl]-3,4-dimethoxy-Alpha-(1-methylethyl)-[CAS] | 52-53-9 | | | Formulation, modified-release, other | Hypertension, general |
| verteporfin | 23H,25H-Benzo[b]porphine-9,13-dipropanoic acid, 18-ethenyl-4,4a-dihydro-3,4-bis(methoxycarbonyl)-4a,8,14,19-tetramethyl-, monomethyl ester, trans-[CAS] | 129497-78-5 | U.S. | 5,238,940 | Ophthalmological | Macular degeneration |
| vesnarinone | Piperazine, 1-(3,4-dimethoxybenzoyl)-4-(1,2,3,4-tetrahydro-2-oxo-6-quinolinyl)-[CAS] | 81840-15-5 | GB | 2086896 | Cardiostimulant | Heart failure |
| Vetrabutine | | 3735-45-3 | | | | |
| VF-233 | Benzene carboximidamide, N,3,4,5-tetrahydroxy-[CAS] | 95933-74-7 | U.S. | 4,623,659 | Cardiovascular | Reperfusion injury |
| VI-0134 | | | U.S. | 6,403,597 | Male sexual dysfunction | Premature ejaculation |
| vidarabine | 9H-Purin-6-amine, 9-β-D-arabinofuranosyl-[CAS] | 24356-66-9 5536-17-4 | GB | 1159290 | Antiviral, other | Infection, herpes virus, general |
| vigabatrin | 5-Hexenoic acid, 4-amino-[CAS] | 68506-86-5 60643-86-9 | GB | 1472525 | Antiepileptic | Epilepsy, partial (focal, local) |
| vilazodone | 2-Benzofurancarboxamide, 5-[4-[4-(5-cyano-1H-indol-3-yl)butyl]-1-piperazinyl]-[CAS] | 163521-12-8 | EP | 648767 | Antidepressant | Depression, general |
| Viloxazine | | 46817-91-8 | | | | |
| Viminol | | 21363-18-8 | | | | |
| Vinbarbital | | 125-44-0 | | | | |
| Vinblastine | | 865-21-4 | | | | |
| vinburnine | Eburnamenin-14(15H)-one, (3Alpha,16Alpha)-[CAS] | 474-00-0 4880-88-0 | DE | 1932245 | Cognition enhancer | |
| Vincamine | | 1617-90-9 | | | | |
| Vinconate | | 70704-03-9 | | | | |
| vincristine | Vincaleukoblastine, 22-oxo-, sulfate (1:1) (salt) [CAS] | 2068-78-2 57-22-7 | EP | 207831 | Formulation, parenteral, other | Cancer, general |
| vindesine | Vincaleukoblastine, 3-(aminocarbonyl)-O4-deacetyl-3-de(methoxycarbonyl)-[CAS] | 53643-48-4 59917-39-4 | GB | 1463575 | Anticancer, other | Cancer, leukaemia, acute lymphocytic |
| vinflunine | Aspidospermidine-3-carboxylic acid, 4-(acetyloxy)-6,7-didehydro-15- | 162652-95-1 | FR | 2707988 | Anticancer, other | Cancer, general |

TABLE 3-continued

| API Generic Name | API Chemical Name | CAS No. | Patent Reference | Example of Therapeutic Use | Example of Indication |
|---|---|---|---|---|---|
| | [(2R,4R,6S,8S)-4-(1,1-difluoroethyl)-1,3,4,5,6,7,8,9-octahydro-8-(methoxycarbonyl)-2,6-methano-2H-azecino[4,3-b]indol-8-yl]-3-hydroxy-16-methoxy-1-methyl-, methyl ester, (2β,3β,4β,5Alpha,12β,19Alpha)-[CAS] | | | | |
| vinorelbine | C'-Norvincaleukoblastine, 3,4'-didehydro-4'-deoxy-[CAS] | 71486-22-1 | EP 10458 | Anticancer, other | Cancer, lung, non-small cell |
| vinpocetine | Ebumamenine-14-carboxylic acid, ethyl ester, (3Alpha,l6Alpha)-[CAS] | 42971-09-5 | GB 1405127 | Cognition enhancer | Cognitive disorder, general |
| Vinyl Ether | | 109-93-3 | | | |
| Vinylbital | | 2430-49-1 | | | |
| Viquidil | | 84-55-9 | | | |
| Viridin | | 3306-52-3 | | | |
| Visnadine | | 477-32-7 | | | |
| Vitamin A | | 68-26-8 | | | |
| vitamin B12 | Vitamin B12 [CAS] | 68-19-9 | | Formulation, transmucosal, nasal | Anaemia, general |
| vitamin C | L-Ascorbic acid [CAS] | 50-81-7 | | Formulation, modified-release, <=24 hr | Nutrition |
| Vitamin D2 | | 50-14-6 | | | |
| Vitamin D3 | | 67-97-0 | | | |
| Vitamin KS | | 83-70-5 | | | |
| Vitamins, Prenatal | | | | | |
| VLA-4 antagonists | ((R,S)-4-(4-(Amino-imino-methyl)-phenyl)-3-((4-biphenylyl)-methyl)-4-methyl-2,5-dioxoimidazolidin-1-yl)-acetyl-L-N-methyl-aspartyl-L-phenylglycine | | EP 842943 | Antiasthma | Asthma |
| VNP-40101M | 1,2-Bis(methylsulfonyl)-1-(2-chloroethyl)-2-(methylamino)carbonylhydrazine | | U.S. 6,040,338 | Anticancer, alkylating | Cancer, general |
| voglibose | D-epi-Inositol, 3,4-dideoxy-4-[[2-hydroxy-1-(hydroxymethyl)ethyl]amino]-2-C-(hydroxymethyl)-[CAS] | 83480-29-9 | EP 56194 | Antidiabetic | Diabetic, Type II |
| vonconazole | 4-Pyrimidineethanol, Alpha-(2,4-difluorophenyl)-5-fluoro-β-methyl-Alpha-(1H-1,2,4-triazol-1-ylmethyl)-, (R-(R*,S*))-[CAS] | 137234-62-9 | EP 440372 | Antifungal | Infection, fungal, general |
| Vorozole | | 129731-10-8 | | | |
| VUF-K-8788 | 7-[3-[4-(2-Quinolinylmethyl)-1-piperazinyl]propoxy]-3,4-dihydro-2H-1,4-benzothiazine-3-one | | | Antiasthma | Asthma |
| Warfarin | | 81-81-2 | | | |
| WF-10 | Tetrachlorodecaoxide [CAS] | 92047-76-2 | | Radio/chemoprotective | Chemotherapy-induced injury, bone marrow, general |
| WMC-79 | 2-(3-[4-[3-(6-oxo-6H-2,10b-diaza-aceanthrenylen-5-ylamino)propyl]-piperazin-1-yl]propyl)-5-nitro-2-aza-phenalene-1,3-dione | | | Anticancer, other | Cancer, colorectal |
| wound healing matrix | | | U.S. 5,897,880 | Formulation, transdermal, patch | Ulcer, diabetic |
| WP-170 | | | U.S. 6,531,121 | Cytokine | Unspecified |
| xaliproden | Pyridine, 1,2,3,6-tetrahydro-1-[2-(2-naphthalenyl)ethyl]-4-(3-(trifluoromethyl)phenyl]-, [CAS] | 135354-020-8 90494-79-4 | EP 101381 | Neuroprotective | Amyotrophic lateral sclerosis |
| xamoterol | 4-Morpholinecarboxamide, N-[2-[[2-hydroxy-3-(4-hydroxyphenoxy)propyl]amino]ethyl]-, (+/−)-[CAS] | 73210-73-8 81801-12-9 | GB 2002748 | Cardiostimulant | Heart failure |
| Xanomeline | | 131986-45-3 | | | |
| Xanthinol Niacinate | | 437-74-1 | | | |
| Xemilofiban | | 149820-74-6 | | | |
| Xenbucin | | 959-10-4 | | | |
| Xibenolol | | 81584-06-7 | | | |
| xibornol | Phenol, 4,5-dimethyl-2-(1.7,7-trimethylbicyclo[2.2.1]hept-2-yl)-, exo-[CAS] | 13741-18-9 | GB 1206774 | Antibacterial, other | Infection, general |

TABLE 3-continued

| API Generic Name | API Chemical Name | CAS No. | Patent Reference | Example of Therapeutic Use | Example of Indication |
|---|---|---|---|---|---|
| ximelagatran | Glycine, N-((R)-cyclohexyl-2-((2S)-2-((((4-(hydroxyamino)iminomethyl)phenyl)methyl)amino)carbonyl)-1-azetidinyl)2-oxoethyl ethyl ester [CAS] | 192939-46-1 | | Antithrombotic | Thrombosis, venous |
| Ximoprofen | | 56187-89-4 | | | |
| xipamide | Benzamide, 5-(aminosulfonyl)-4-chloro-N-(2,6-dimethylphenyl)-2-hydroxy-[CAS] | 14293-44-8 | U.S. | 3,567,777 Antihypertensive, diuretic | |
| xorphanol | Morphinan-3-ol, 17-(cyclobutylmethyl)-8-methyl-6-methylene-, (8β)-[CAS] | 77287-89-9 | | Analgesic, other | Pain, cancer |
| XR-5118 | 2,5-Piperazinedione, 3-[[5-[[2-(dimethylamino)ethyl]thio]-2-thienyl]methylene]-6-(phenylmethylene), monohydrochlonde, (3Z,6Z)-[CAS] | 174766-49-5 | WO | 9532190 Anticancer, other | Cancer, general |
| XR-5944 | N,N'-(1,2-Ethanediyl)bis(imino-2,1-ethanediyl)bis(9-methylphenazine-1-carboxamide) | | EP | 934278 Anticancer, other | Cancer, general |
| Xylometazoline | | 526-36-3 | | | |
| Xylose | | 58-86-6 | | | |
| YH-1885 | 2-Pyrimidinamine, 4-(3,4-dihydro-1-methyl-2(1H)-isoquinolinyl)-N-(4-fluorophenyl)-5,6-dimethyl-, monohydrochloride [CAS] | 178307-42-1 | WO | 9605177 Antiulcer | Ulcer, GI, general |
| YM-511 | Benzonitrile, 4-[[(4-bromophenyl)methyl]-4H-1,2,4-triazol-4-ylamino]-[CAS] | 148869-05-0 | WO | 9305027 Anticancer, hormonal | Cancer, breast |
| YM-598 | potassium(E)-N-[6-methoxy-5-(2-methoxyphenoxy)-2-(pyrimidin-2-yl)pyrimidin-4-yl]-2-phenylethenesulfonamidate | | | Anticancer, other | Cancer, prostate |
| Yahimbine | | 146-48-5 | | | |
| YT-146 | Adenosine, 2-(1-octynyl)-[CAS] | 90596-75-1 | U.S. | 5,270,304 Anti-inflammation, general | |
| Z-321 | Thiazolidine, 3-((2,3-dihydro-1H-inden-2-yl)acetyl)-4-(1-pyrrolidinylcarbonyl)-, (R)-[CAS] | 130849-58-0 | EP | 372484 Cognition enhancer | Dementia, senile, general |
| Z-335 | (1H-Indene-5-acetic acid, 2[[[(4-chlorophenyl)sulfonyl]amino]methyl]-2,3-dihydro, monosodium salt) [CAS] | 146731-14-8 | JP | 92506077 Antithrombotic | Peripheral vascular disease |
| zafirtukast | Carbamic acid, [3-[[2-methoxy-4-[[[(2-methylphenyl)sulfonyl]amino]carbonyl]phenyl]methyl]-1-methyl-1H-indol-5-yl]-, cyclopentyl ester [CAS] | 107753-78-6 | EP | 199543 Antiasthma | Asthma |
| zalcitabine | Cytidine, 2',3'-dideoxy-[CAS] | 7481-89-2 | U.S. | 4,879,277 Antiviral, anti-HIV | Infection, HIV/AIDS |
| Zaldaride | | 109826-26-8 | | | |
| zaleplon | Acetamide, N-[3-(3-cyanopyrazolo[1,5-a]pynmidin-7-yl)phenyl]-N-ethyl-[CAS] | 151319-34-5 | EP | 776898 Hypnotic/Sedative | Insomnia |
| zaltoprofen | Dibenzo[b,f]thiepin-2-acetic acid, 10,11-dihydro-Alpha-methyl-10-oxo-[CAS] | 74711-43-6 | JP | 55053282 Anti-inflammatory | |
| zanamivir | 5-Acetamido-2,6-anhydro-3,4,5-trideoxy-4-guanidino-D-glycero-D-galacto-non-2-enonic acid [CAS] | 139110-80-8 | WO | 9116320 Antiviral, other | Infection, influenza virus |
| zanapezil | 1-Propanone, 3-(1-(phenylmethyl)-4-piperidinyl)-1-(2,3,4,5-tetrahydro-1H-1-benzazepin-8-yl)-[CAS] | 142852-50-4 | EP | 487071 Cognition enhancer | Alzheimer's disease |
| Zatebradine | | 85175-67-3 | | | |
| ZD-0473 | Platinum, amminedichloro(2-methylpyridine)- (SP-4-3)-[CAS] | 181630-15-9 | EP | 727430 Anticancer, alkylating | Cancer, ovarian |
| ZD-0947 | | | WO | 9528388 Urological | Overactive bladder |
| ZD-6126 | N-acetylcolchinol-O-phosphate | | | Anticancer, other | Cancer, general |
| ZD-9331 | 1H-Tetrazole-5-butanoic acid, Alpha-((4-(((1,4-dihydro-2,7-dimethyl-4-oxo-6-quinazolinyl)methyl)-2-propynylamino)-2-fluorobenzoyl)amino) (S)-[CAS] | 153537-73-6 | GB | 2264946 Anticancer, antimetabolite | Cancer, pancreatic |
| zebularine | 2(1H)-Pyrimidinone, 1-β-D-ribofuranosyl-[CAS] | 3690-10-6 | | Anticancer, other | Cancer, general |
| zelandopam | 7,8-Isoquinolinediol, 4-(3,4-dihydroxyphenyl)-1,2,3,4-tetrahydro-, [CAS] | 138086-00-7 | JP | 03190818 Vasodilator, renal | Hypertension, general |
| Zenarestat | | 112733-06-9 | | | |
| Ziconotide | | 107452-89-1 | | | |
| zidovudine | Thymidine, 3'-azido-3'-deoxy-[CAS] | 30516-87-1 | U.S. | 4,724,232 Antiviral, anti-HIV | Infection, HIV/AIDS |
| zileuton | Urea, N-(1-benzo[b]thien-2-ylethyl)-N-hydroxy-[CAS] | 111406-87-2 | EP | 279263 Antiasthma | Asthma |

TABLE 3-continued

| API Generic Name | API Chemical Name | CAS No. | Patent Reference | Example of Therapeutic Use | Example of Indication |
|---|---|---|---|---|---|
| Zimeldine | | 56775-88-3 | | | |
| zinc acetate | hexakis(\m-acetato)-\m4-oxotetrazinc | 12129-82-7 | | Antiviral, other virus prophylaxis | Infection, herpes simplex |
| zinc acexamate | Hexanoic acid, 6-(acetylamino)-, zinc salt (2:1)-[CAS] | 70020-71-2 | EP 369088 | Antiulcer | Ulcer, duodenal |
| zinc ibuprofenate | | 78416-80-5 | | Anti-inflammatory, topical | Inflammation, dermal |
| Zinc p-Phenolsulfonate | | 127-82-2 | | | |
| Zinc Salicylate | | 16283-36-6 | | | |
| Zinostatin | | 9014-2-2 | | | |
| zinostatin stimalamer | | 123760-07-6 | EP 136791 | Anticancer, antibiotic | Cancer, liver |
| Zipeprol | | 34758-83-3 | | | |
| ziprasidone | 2H-Indol-2-one, 5-(2-(4-(1,2-benzisothiazol-3-yl)-1-piperazinyl)ethyl) 6-chloro-1,3-dihydro-[CAS] | 122883-93-6 146939-27-7 | EP 281309 | Neuroleptic | Schizophrenia |
| zofenopril | L-Proline, 1-[3-(benzoylthio)-2-methyl-1-oxopropyl]-4-(phenylthio)-, [1(R*),2Alpha,4Alpha]-[CAS] | 75176-37-3 81872-10-8 81938-43-4 | GB 2028327 | Antihypertensive, renin system | Hypertension, general |
| zofenopril + HCTZ | L-Proline, 1-[3-(benzoylthio)-2-methyl-1-oxopropyl]-4-(phenylthio)-, [1(R*),2Alpha,4Alpha]- + 6-Chloro-3,4-dihydro-2H-1,2,4-benzothiazide-7-sulfonamide 1,1-dioxide [CAS] | | | Formulation, fixed-dose combinations | Hypertensions, general |
| zoledronic acid | Phosphonic acid, [1-hydroxy-2-(1H-imidazol-1-yl)ethylidene]bis-[CAS] | 118072-93-8 165800-06-6 | EP 531253 | Osteoporosis treatment | Hypercalcaemia of malignancy |
| zolimidine | 2-(p-methylsulfonylphenyl)imidazo[1,2-a]pyridine | 1222-57-7 | U.S. 3,318,880 | Antiulcer | Gastritis |
| zolmitriptan | 2-Oxazolidinone, 4-((3-(2-(dimethylamino)ethyl)-1H-indol-5-yl)methyl)-, (5)-[CAS] | 139264-17-8 | WO 9118897 | Antimigraine | Migraine |
| zolpidem | Imidazo[1,2-a]pyridine-3-acetamide, N,N,6-trimethyl-2-(4-methylphenyl)-(R-(R*,R*))-2,3-dihydroxybutanediotade (2:1) [CAS] | 99294-93-6 82626-48-0 | EP 50563 | Hypnotic/Sedative | Insomnia |
| Zomepirac | | 33369-31-2 | | | |
| zonampanel | 1(2H)-Quinoxalineacetic acid, 3,4-dihydro-7-(1H-imidazol-1-yl)-6-nitro-2,3 dioxo-[CAS] | 210245-80-0 | | Neuroprotective | Ischaemia, cerebral |
| zoniporide | 1H-pyrazole-4-carboxamide,N-(aminoimino methyl)-5-cyclopropyl-1-(5-quinolinyl)-, | 249296-45-5 | | Cardiovascular | Unspecified |
| zonisamide | 1,2-Benzisoxazole-3-methanesulfonamide [CAS] | 68291-97-4 68291-98-5 | GB 2025931 | Antiepileptic | Epilepsy, generalized, tonic-clonic |
| zopiclone | 1-Piperazinecarboxylic acid, 4-methyl-, 6-(5-chloro-2-pyridinyl)-6,7-dihydro-7-oxo-5H-pyrrolo[3,4-b]pyrazin-5-yl ester [CAS] | 43200-80-2 | GB 1358680 | Hypnotic/Sedative | Insomnia |
| Zopolrestat | | 110703-94-1 | | | |
| Zorubicin | | 54083-22-6 | | | |
| zosuquidar | 1-Piperazineethanol, 4-(1,1-difluoro-1,1a,6,10b-tetrahydrodibenzo[a,e]cyclopropa[c] cyclohepten-6-yl)-Alpha-[(5-quinolinyloxy)methyl]-, [6(R)-(1aAlpha,6Alpha,10bAlpha)]-[CAS] | 167465-36-3 | | Radio/chemosensitizer | Cancer, leukaemia, acute myelogenous |
| zotepine | Ethanamine, 2-1(8-chlorodibenzo[b,t]thiepin-10-yl)oxy]-N,N-dimethyl-[CAS] | 26615-21-4 | GB 1247067 | Neuroleptic | Schizophrenia |
| ZP-123 | | | WO 0162775 | Antiarrhythmic | Arrhythmia, general |
| Z-tamoxifen | Ethanamine, 2-[4-(1,2-diphenyl-1-butenyl)phenoxy]-N,N-dimethyl-, (Z)-[CAS] | 10540-29-1 | | Anticancer, hormonal | Cancer, colorectal |
| zuclopenthixol | 1-Piperazineethanol, 4-[3-(2-chloro-9H-thioxanthen-9-ylidene)propyl]-, (Z)-[CAS] | 53772-83-1 982-24-1 85721-05-7 64053-00-5 | EP 270282 | Neuroleptic | Psychosis, general |

The invention claimed is:

1. A propylene glycol solvate of a sodium salt of celecoxib having a stoichiometric ratio of 1 celecoxib: 1 sodium: 1 propylene glycol.

2. A propylene glycol solvate of celecoxib sodium trihydrate having a stoichiometric ratio of 1 celecoxib: 1 sodium: 1 propylene glycol: 3 hydrate.

3. A propylene glycol solvate of celecoxib selected from:
   a) a propylene glycol solvate of celecoxib sodium trihydrate characterized by a thermogravimetric analysis of FIG. 18 or FIG. 20, said propylene glycol solvate of celecoxib sodium trihydrate having a stoichiometric ratio of 1 celecoxib: 1 sodium: 1 propylene glycol: 3 hydrate; or
   b) a propylene glycol solvate of a sodium salt of celecoxib characterized by a thermogravimetric analysis of FIG. 1, said propylene glycol solvate of a sodium salt of celecoxib having a stoichiometric ratio of 1 celecoxib: 1 sodium: 1 propylene glycol.

4. The propylene glycol solvate of celecoxib according to claim 3, wherein the form is a propylene glycol solvate of celecoxib sodium trihydrate characterized by a thermogravimetric analysis of FIG. 18, said propylene glycol solvate of celecoxib sodium trihydrate having a stoichiometric ratio of 1 celecoxib: 1 sodium: 1 propylene glycol: 3 hydrate.

5. The propylene glycol solvate of celecoxib according to claim 3, wherein the form is a propylene glycol solvate of celecoxib sodium trihydrate characterized by a thermogravimetric analysis of FIG. 20, said propylene glycol solvate of celecoxib sodium trihydrate having a stoichiometric ratio of 1 celecoxib: 1 sodium: 1 propylene glycol: 3 hydrate.

6. The propylene glycol solvate of celecoxib according to claim 3, wherein the form is a propylene glycol solvate of a sodium salt of celecoxib characterized by a thermogravimetric analysis of FIG. 1, said propylene glycol solvate of a sodium salt of celecoxib having a stoichiometric ratio of 1 celecoxib: 1 sodium: 1 propylene glycol.

7. A propylene glycol solvate of celecoxib selected from:
   a) a propylene glycol solvate of celecoxib sodium trihydrate characterized by the PXRD pattern of FIG. 19 or FIG. 21, said propylene glycol solvate of celecoxib sodium trihydrate having a stoichiometric ratio of 1 celecoxib: 1 sodium: 1 propylene glycol: 3 hydrate; or
   b) a propylene glycol solvate of a sodium salt of celecoxib characterized by a PXRD pattern of FIG. 2A, 2B, 2C or 2D, said propylene glycol solvate of a sodium salt of celecoxib having a stoichiometric ratio of 1 celecoxib: 1 sodium: 1 propylene glycol.

8. The propylene glycol solvate according to claim 7, wherein said propylene glycol solvate is a propylene glycol solvate of celecoxib sodium trihydrate characterized by the PXRD pattern of FIG. 19 and having a stoichiometric ratio of 1 celecoxib: 1 sodium: 1 propylene glycol: 3 hydrate.

9. The propylene glycol solvate according to claim 7, wherein said propylene glycol solvate is a propylene glycol solvate of celecoxib sodium trihydrate characterized by the PXRD pattern of FIG. 21 and having a stoichiometric ratio of 1 celecoxib: 1 sodium: 1 propylene glycol: 3 hydrate.

10. The propylene glycol solvate according to claim 7, wherein said propylene glycol solvate is a propylene glycol solvate of a sodium salt of celecoxib, said propylene glycol solvate of a sodium salt of celecoxib characterized by a PXRD pattern of FIG. 2A, 2B, 2C or 2D and having a stoichiometric ratio of 1 celecoxib: 1 sodium: 1 propylene glycol.

11. The propylene glycol solvate according to claim 7, wherein said propylene glycol solvate is a propylene glycol solvate of a sodium salt of celecoxib and said composition is characterized by the PXRD pattern of FIG. 2A.

12. The propylene glycol solvate according to claim 7, wherein said propylene glycol solvate is a propylene glycol solvate of a sodium salt of celecoxib and said composition is characterized by the PXRD pattern of FIG. 2B.

13. The propylene glycol solvate according to claim 7, wherein said propylene glycol solvate is a propylene glycol solvate of a sodium salt of celecoxib and said composition is characterized by the PXRD pattern of FIG. 2C.

14. The propylene glycol solvate according to claim 7, wherein said propylene glycol solvate is a propylene glycol solvate of a sodium salt of celecoxib and said composition is characterized by the PXRD pattern of FIG. 2D.

15. A pharmaceutical composition comprising an excipient and a form of a propylene glycol solvate of celecoxib selected from:
   a) a propylene glycol solvate of celecoxib sodium trihydrate characterized by the PXRD pattern of FIG. 19 or FIG. 21, said propylene glycol solvate of celecoxib sodium trihydrate having a stoichiometric ratio of 1 celecoxib: 1 sodium: 1 propylene glycol: 3 hydrate; or
   b) a propylene glycol solvate of a sodium salt of celecoxib characterized by a PXRD pattern of FIG. 2A, 2B, 2C or 2D, said propylene glycol solvate of a sodium salt of celecoxib having a stoichiometric ratio of 1 celecoxib: 1 sodium: 1 propylene glycol.

16. The composition according to claim 15, wherein said form is a propylene glycol solvate of celecoxib sodium trihydrate characterized by the PXRD pattern of FIG. 19 or FIG. 21 and having a stoichiometric ratio of 1 celecoxib: 1 sodium: 1 propylene glycol: 3 hydrate.

17. The composition according to claim 15, wherein said form is a propylene glycol solvate of a sodium salt of celecoxib, said propylene glycol solvate of a sodium salt of celecoxib characterized by a PXRD pattern of FIG. 2A, 2B, 2C or 2D and having a stoichiometric ratio of 1 celecoxib: 1 sodium: 1 propylene glycol.

18. The composition according to claim 17, wherein said form is a propylene glycol solvate of a sodium salt of celecoxib and said composition is characterized by the PXRD pattern of FIG. 2A.

19. The composition according to claim 17, wherein said form is a propylene glycol solvate of a sodium salt of celecoxib and said composition is characterized by the PXRD pattern of FIG. 2B.

20. The composition according to claim 17, wherein said form is a propylene glycol solvate of a sodium salt of celecoxib and said composition is characterized by the PXRD pattern of FIG. 2C.

21. The composition according to claim 16, wherein said form is a propylene glycol solvate of celecoxib sodium trihydrate characterized by the PXRD pattern of FIG. 19 and having a stoichiometric ratio of 1 celecoxib: 1 sodium: 1 propylene glycol: 3 hydrate.

22. The composition according to claim 16, wherein said form is a propylene glycol solvate of celecoxib sodium trihydrate characterized by the PXRD pattern of FIG. 21 and having a stoichiometric ratio of 1 celecoxib: 1 sodium: 1 propylene glycol: 3 hydrate.

23. The composition according to claim 17, wherein said form is a propylene glycol solvate of a sodium salt of celecoxib and said composition is characterized by the PXRD pattern of FIG. 2D.

* * * * *

UNITED STATES PATENT AND TRADEMARK OFFICE
CERTIFICATE OF CORRECTION

PATENT NO. : 7,790,905 B2
APPLICATION NO. : 10/747742
DATED : September 7, 2010
INVENTOR(S) : Mark Tawa, Orn Almarsson and Julius F. Remenar It is certified that error appears in the above-identified patent and that said Letters Patent is hereby corrected as shown below:

Column 3,
Line 60, "if their were" should read --if there were--.

Column 22,
Line 16, "((⁸1995-2002, Materials Data, Inc." should read
    --(⁸1995-2002, Materials Data, Inc.)--.
Line 63, "(D 2001" should read -© 2001--.

Column 24,
Line 24, "gly solvate" should read --glycol solvate--.

Column 27, Table 3,
Column "API Chemical Name", Row "(-)-amlodipine",
    "3-ethyl-S-methyl ester" should read --3-ethyl-5-methyl ester--.

Column 30, Table 3,
Column "Example of Indication", Row "5-azacitidine",
    "Mylodysplastic" should read --Myelodysplastic--.

Column 31, Table 3,
Column "CAS No.", Row "AC-5216",
    "2627-69-2" should read --blank--.

Signed and Sealed this
Nineteenth Day of April, 2011

David J. Kappos
*Director of the United States Patent and Trademark Office*

CERTIFICATE OF CORRECTION (continued)
U.S. Pat. No. 7,790,905 B2

Column 33, Table 3,
Column "API Chemical Name", Row "acrivastine + pseudoephedrine",
  "[S-(R*,R)]-" should read --[S-(R*,R*)]- --.
Column "API Chemical Name", Row "Adenoscan",
  "6-Amino-9-ß-D-nbofuranosyl-9H-purine [CAS]" should read
  --6-Amino-9-ß-D-ribofuranosyl-9H-purine [CAS]--.

Column 37, Table 3,
Column "API Chemical Name", Row "alizapride",
  "1H-Benzotriazoie-5-carboxamide, 6-methoxy-N-[[1-(2-propenyl)-2-
  pyrrolidinyl)methyl]- [CAS]" should read
  --1H-Benzotriazole-5-carboxamide, 6-methoxy-N-[[1-(2-propenyl)-2-
  pyrrolidinyl]methyl]- [CAS]--.
Column "API Chemical Name", Row "alprazolam",
  "4H-[1,2,4]Triazolo[4,3-al][1,4]benzodiazepine" should read
  --4H-[1,2,4]Triazolo[4,3-a][1,4]benzodiazepine--.

Column 38, Table 3,
Column "Example of Therapeutic Use", Row "alfuzosin",
  "modivied-release" should read --modified-release--.

Column 39, Table 3,
Column "API Generic Name", "Amdinociiiin Pivoxil" should read --Amdinocillin
  Pivoxil--.

CERTIFICATE OF CORRECTION (continued)

Column 40, Table 3,
Column "Example of Indication", Row "AMD-3100",
    "leocopenia" should read --leucopenia--.

Column 41, Table 3,
Row "Aminoguanidine",
"API Chemical Name   CAS No."    should read    --API Chemical Name   CAS No.--.
  79-17-4                                                                               79-17-4

Column 47, Table 3,
Column "API Chemical Name", Row "aprepitant",
    "5-[[(2R,3S)-2-[(1R)-1-[3,5-bis(trifluoromethyl)phenyl]ethoxy]-3-(4-
    fluorophenyl)-4-morpholinyl]methyl]-1,2-dihydro- [CAS]" should read
    --5-[[(2R,3S)-2-[(1R)-1-[3,5-bis(trifluoromethyl)phenyl]ethoxy]-3-(4-
    fluorophenyl)-4-morpholinyl]methyl]-1,2-dihydro- [CAS]--.

Column 49, Table 3,
Column "API Chemical Name", Row "artemotil",
    "12+62,12aR*)]-[CAS]" should read --12ß,12aR*)]- [CAS]--.

Column 50, Table 3,
Column "Example of Therapeutic Use", Row "atenolol",
    "Antihypeertensive" should read --Antihypertensive--.

Column 52, Table 3,
Column "Example of Indication", Row "AZD-4282",
    "Pain, neuronpathic" should read --Pain, neuropathic--.

Column 53, Table 3,
Column "API Generic Name", "aziocillin" should read --azlocillin--.
Column "API Chemical Name", Row "balofloxacin",
  "3-Quinolinecarboxylic acid, 1-cyclopropyl-6-fluoro-1,4-dihydro-8-methoxy-7-
  [3-(methylamino)-1-pipendinyl]-4-oxo-[CAS]" should read
  --3-Quinolinecarboxylic acid, 1-cyclopropyl-6-fluoro-1,4-dihydro-8-methoxy-7-
  [3-(methylamino)-1-piperidinyl]-4-oxo- [CAS]--.
Column "API Generic Name", "bamidipine" should read --barnidipine--.
Column "API Chemical Name", Row "betahistine",
  "2-Pyndineethanamine" should read --2-Pyridineethanamine--.

Column 58, Table 3,
Column "Example of Therapeutic Use", Row "benzydamine",
  "Stomatologic
   reproductive,
   inflammatory"
should read
  --Stomatologicical
   reproductive/gonoadal,
   anti-inflammatory--.
Column "Example of Therapeutic Use", Row "biapenem",
  "Beta-lactam antibic" should read --Beta-lactam antibiotic--.

Column 59, Table 3,
Column "API Generic Name", "Betamiverine" should read --Bietamiverine--.

Column 59, Table 3,
Column "API Chemical Name", Row "bimosiamose",
  "(1,1-Biphenyl)-3-acetic acid, 3',3'''-(1,6-hexanediyl)bis(6-Alpha-D-
  mannopyranosyloxy)-, [CAS]" should read
  --(1,1'-Biphenyl)-3-acetic acid, 3',3'''-(1,6-hexanediyl)bis(6'-Alpha-D-
  mannopyranosyloxy)-, [CAS]--.

Column 61, Table 3,
Column "API Chemical Name", Row "bosentan",
  "Benzenesulfonamide, 4-(1,1-dimethylethyl)-N-[6-(2-hydroxyethoxy)-5-(2-
  methoxyphenoxy)[2,2-bipynmidin]-4-yl]-[CAS]" should read
  --Benzenesulfonamide, 4-(1,1-dimethylethyl)-N-[6-(2-hydroxyethoxy)-5-(2-
  methoxyphenoxy)[2,2'-bipyrimidin]-4-yl]- [CAS]--.

Column 63, Table 3,
Column "API Chemical Name", Row "brivudin",
  "Uridine, 5-(2-bromoethenyl)-2-deoxy, (E)-[CAS]" should read
  --Uridine, 5-(2-bromoethenyl)-2'-deoxy, (E)- [CAS]--.

Column 66, Table 3,
Row "bunazosin",   "Example of              Example of Indication"
                   Therapeutic Use
                   Antihypertens
    should read    --Example of             Example of Indication--.
                   Therapeutic Use
                   Antihypertensive,        Hypertension, general
                   adrenergic Column 67, Table 3,
Column "API Generic Name",
    "Calciuhi Mesoxalate" should read --Calcium Mesoxalate--.

Column 69, Table 3,
Column "API Chemical Name", Row "camptothecin",
    "4-Ethyl-4-hydroxy-1H-pyrano-[13'4':6,7]indolizino[1,2-b;]quinoline-
    3,14(4H,12H)-dione microemulsion" should read
    --4-Ethyl-4-hydroxy-1H-pyrano-[13'4':6,7]indolizino[1,2-b;]quinoline-
    3,14(4H,12H)-dione--.

Column 71, Table 3,
Column "API Chemical Name", Row "carmustine",
    "Urea, N,N-bis(2-chloroethyl)-N-nitroso- [CAS]" should read
    --Urea, N,N'-bis(2-chloroethyl)-N-nitroso- [CAS]--.

Column 73, Table 3,
Column "API Chemical Name", Row "cefalexin",
    "5-Thia-1-azabicyclo[4.2.0]oct-2-ene-2-carboxylic acid, 7-
    [(aminophenylacetyl)amino]-3-methyl-oxo-, [CAS]" should read
    --5-Thia-1-azabicyclo[4.2.0]oct-2-ene-2-carboxylic acid, 7-
    [(aminophenylacetyl)amino]-3-methyl-8-oxo-, [CAS]--.
Column "CAS No.", Row "cefalexin", "8105879-42-3" should read --105879-42-3--.

Column 75, Table 3,
Column "API Chemical Name", Row "cefmetazole",
    "5-Thia-1-azabicyclo[4.2.0]oct-2-ene-2-carboxylic acid, 7-[[[(cyanomethyl)thio]
    acetyl]amino]-7-methoxy-3-[[(1-methyl-1H-tetrazol-5-yl)thso]methyl]-8-oxo-,
    (6R-cis)-[CAS]" should read
    --5-Thia-1-azabicyclo[4.2.0]oct-2-ene-2-carboxylic acid, 7-[[[(cyanomethyl)thio]
    acetyl]amino]-7-methoxy-3-[[(1-methyl-1H-tetrazol-5-yl)thio]methyl]-8-oxo-,
    (6R-cis)- [CAS]--.
Column "API Chemical Name", Row "cefonicid,
    "[6R-[6Alpha,7B(R)]]-[CAS]" should read --[6R-[6Alpha,7β(R*)]]- [CAS]--.
Column "API Chemical Name", Row "cefoperazone",
    "[6R-[6Alpha,7β(R*)]]]-[CAS]" should read --[6R-[6Alpha,7β(R*)]]- [CAS]--.

Column 75, Table 3,
Column "API Chemical Name", Row "cefpimizole",
"[6R-[6Alpha,7β4R*)]]-[CAS]" should read --[6R-[6Alpha,7ß(R*)]]- [CAS]--.

Column 77, Table 3,
Column "API Chemical Name", Row "cefpirome",
"[6R-[6Alpha,711(Z)]]-[CAS]" should read --[6R-[6Alpha,7ß(Z)]]- [CAS]--.
Column "API Chemical Name", Row "cefuroxime axetil",
"5-Thia-1-azabicyclo[4.2.0]oct-2-ene-2-carboxylic acid,
3-[[(aminocarbonyl)oxy]methyl]-7-[(2-furanyl(methoxyimino)acetyl]amino]-8-
oxo-," should read
--5-Thia-1-azabicyclo[4.2.0]oct-2-ene-2-carboxylic acid,
3-[[(aminocarbonyl)oxy]methyl]-7-[[2-furanyl(methoxyimino)acetyl]amino]-8-
oxo-,--.

Column 78, Table 3,
Column "Patent Reference", Row "cefroxadine",
"143511" should read --1435111--.
Column "Patent Reference", Row "cefsulodin",
"138765" should read --1387656--.
Column "Patent Reference", Row "ceftazidime",
"202539" should read --2025398--.

Column 81, Table 3,
Column "API Generic Name", "Chiorproethazine" should read --Chlorproethazine--.
Column "API Generic Name", "Chiorquinaidol" should read --Chlorquinaldol--.

Column 83, Table 3,
Column "API Chemical Name", Row "choline-L-alfoscerate",
"Ethanaminium, 2-[[(2,3dihydroxypropoxy)hydroxyphosphinyl]xy]-N,N,N-
trimethyl-," should read
--Ethanaminium, 2-[[(2,3-dihydroxypropoxy)hydroxyphosphinyl]oxy]-N,N,N-
trimethyl-,--.

Column 85, Table 3,
Column "API Generic Name", "cispiatin" should read --cisplatin--.

Column 89, Table 3,
Column "API Chemical Name", Row "CMI-392",
"Trans-2-[3-methoxy-4-(2-p-chlorophenylthio)ethoxy-5-(N-methyl-N'-
hydroxyureidyl)methylphenyl]-5-(3,4,5-trimethoxyphenyl)tetrahydrofuran"
should read
--Trans-2-[3-methoxy-4-(2-p-chlorophenylthio)ethoxy-5-(N'-methyl-N'-
hydroxyureidyl)methylphenyl]-5-(3,4,5-trimethoxyphenyl)tetrahydrofuran--.
Column "API Chemical Name", Row "CMT-3",
"(4a5,5aR,12a5)-[CAS]" should read --(4aS,5aR,12aS)- [CAS]--.

CERTIFICATE OF CORRECTION (continued)

Column 89, Table 3,
Column "API Chemical Name", Row "CNI-1493",
    "Decanediamide, N,N-bis[3,5-bis[1-[(aminoiminomethyl)hydrazono]
    ethyl]phenyl]-, tetrahydrochloride [CAS]" should read
    --Decanediamide, N,N'-bis [3,5-bis[1-[(aminoiminomethyl)hydrazono]
    ethyl]phenyl]-, tetrahydrochloride [CAS]--.

Column 90, Table 3,
Column "Example of Indication", Row "clopidogrel",
    "myocardia" should read --myocardial--.

Column 91, Table 3,
Column "API Chemical Name", Row "CNS-5161",
    "N-[2-chloro-5-(methylthio)phenyl]-N-methyl-N-[3-methylthio)phenyl]guanidine
    [CAS]" should read
    --N'-[2-chloro-5-(methylthio)phenyl]-N-methyl-N-[3-methylthio)phenyl]guanidine
    [CAS]--.

Column 92, Table 3,

| Row "CP-461", | "Example of Therapeutic Use | Example of Indication" |
|---|---|---|
|  | Anticancer, other |  |
| should read | --Example of Therapeutic Use | Example of Indication--. |
|  | Anticancer, other | Cancer, prostate |

Column 92, Table 3,

| Row "CRL-5861", | "Example of Therapeutic Use | Example of Indication" |
|---|---|---|
|  | Antisickling |  |
| should read | --Example of Therapeutic Use | Example of Indication--. |
|  | Antisickling | Anaemia, sickle cell |

Column 95, Table 3,
Column "API Chemical Name", Row "cymserine",
    "(3aS,8aR)-1,2,3,3a,8,8a-hexahydro-1,3a,8-trimethylpyrrolo[2,3-blindol-5-yl
    ester [CAS]" should read
    --(3aS,8aR)-1,2,3,3a,8,8a-hexahydro-1,3a,8-trimethylpyrrolo[2,3-b]indol-5-yl
    ester [CAS]--.
Column "API Chemical Name", Row "cyproterone",
    "(1β,2β)-6-Chloro-1,2-dihydro-17-hydroxy-3H-cyclopropa[1,2]pregna-1,4,6-
    triene-3,20-dione [CAS]" should read
    --(1β,2β)-6-Chloro-1,2-dihydro-17-hydroxy-3'H-cyclopropa[1,2]pregna-1,4,6-
    triene-3,20-dione [CAS]--.

CERTIFICATE OF CORRECTION (continued)
U.S. Pat. No. 7,790,905 B2

Column 95, Table 3,
Column "API Chemical Name", Row "dalfopristin + quinupristin",
  "mixt with 4-(4-(dimethylamino)-N-methyl-L-phenylalanine)-5-(5-((1-
  azabicyclo(2.2.2)oct-3-ylthio)methyl)-4-oxo-L-2-pipendinecarboxylic acid)
  virginiamycin S1- [CAS]" should read
  --mixt with 4-(4-(dimethylamino)-N-methyl-L-phenylalanine)-5-(5-((1-
  azabicyclo(2.2.2)oct-3-ylthio)methyl)-4-oxo-L-2-piperidinecarboxylic acid)
  virginiamycin S1- [CAS]--.

Column 97, Table 3,
Row "DB-67",

| "API Generic Name | API Chemical Name" |
|---|---|
| DB-67 | 7-tert-Butyldimethylsiiyl-10-hydroxy-camptothecin | should read

| --API Generic Name | API Chemical Name--. |
|---|---|
| DB-67 | 7-tert-Butyldimethylsiyl-10-hydroxycamptothecin |

Column 99, Table 3,
Column "API Generic Name", "Delmadinane" should read --Delmadinone--.

Column 100, Table 3,
Row "dersalazine",

| "Example of Therapeutic Use | Example of Indication" |
|---|---|
| Anti-inflammatory | | should read

| --Example of Therapeutic Use | Example of Indication--. |
|---|---|
| Anti-inflammatory | Colitis, ulcerative |

Column 101, Table 3,
Column "API Chemical Name", Row "dexrazoxane",
  "2,6-Piperazinedione, 4,4'-(1-methyl-1,2-ethanediyl)bis-, (5)- [CAS]" should read
  --2,6-Piperazinedione, 4,4'-(1-methyl-1,2-ethanediyl)bis-, (S)- [CAS]--.
Column "API Chemical Name", Row "dextropropoxyphene",
  "[S-(R,S*)]-[CAS]" should read --[S-(R*,S*)]- [CAS]--.
Column "API Chemical Name", Row "dibekacin",
  "D-Streptamine, O-3-amino-3-deoxy-Alpha-D-glucopyranosyl-(1-6)-O-[2,6-
  diamino-2,3,4,6-tetradeoxy-Alpha-D-erythro-hexopyranosyl-(1-4)1-2-deoxy-,
  sulfate (salt)[CAS]" should read
  --D-Streptamine, O-3-amino-3-deoxy-Alpha-D-glucopyranosyl-(1-6)-O-[2,6-
  diamino-2,3,4,6-tetradeoxy-Alpha-D-erythro-hexopyranosyl-(1-4)]-2-deoxy-,
  sulfate (salt)[CAS]--.

Column 105, Table 3,
Column "API Generic Name", "Diisapropylamine" should read --Diisopropylamine--.
Column "API Chemical Name", Row "dinoprostone",
"Prosta-5,13-dien-1-oic acid, 11,15-dihydroxy-9-oxo-, (5Z, 11 Alpha, 13E, 15S)-[CAS]" should read
--Prosta-5,13-dien-1-oic acid, 11,15-dihydroxy-9-oxo-, (5Z,11Alpha,13E,15S)-[CAS]--.
Column "API Generic Name", "Dioxethednne" should read --Dioxethedrine--.

Column 107, Table 3,
Column "API Generic Name", "Dastigmine" should read --Distigmine--.
Column "API Chemical Name", Row "DK-507k",
"(-)-7-[(7S)-7-Amino-5-azaspiro[2,4]heptan-5-yl]-6-fluoro-1-[(1R,2S)-2-fluoro-1-cyclopropyl]-1,4-dihydro-8-methoxy-4-oxo-3-quinolinecarboxylic acid hydrochloride monohydrate" should read
--(-)-7-[(7S)-7-Amino-5-azaspiro[2,4]heptan-5-yl]-6-fluoro-1-[(1R,2S)-2-fluoro-1-cyclopropyl]-1,4-dihydro-8-methoxy-4-oxo-3-quinolinecarboxylic acid hydrochloride monohydrate--.
Column "API Chemical Name", Row "dofetilide",
"Methanesulfonamide, N-[4-[2-[methyl[2-[4[(methylsulfonyl)amino]phenoxy]ethyl]amino]ethyl]phenyq]-[CAS]" should read
--Methanesulfonamide, N-[4-[2-[methyl[2-[4[(methylsulfonyl)amino]phenoxy]ethyl]amino]ethyl]phenyl]- [CAS]--.

Column 108, Table 3,
Column "Example of Therapeutic Use", Row "docusate",
"Formulation, derm" should read --Formulation, dermal, topical--.

Column 109, Table 3,
Column "API Generic Name", "Domiodoi" should read --Domiodol--.
Column "API Generic Name", "darzolamide" should read --dorzolamide--.
Column "API Chemical Name", Row "dorzolamide + timolol",
"4H-Thieno(2,3-b)thiopyran-2-sulfonamide, 4-(ethylamino)-5,6-dihydro-6-methyl-7,7-dioxide (4S-trans) + ethyl 2-propanol, 1-[(1,1-dimethyl)amino]-3-[[4-(4-morpholinyl)-1,2,5-thiadiazol-3-yl]oxy]-, (5), (Z)-2-butenedioate (1:1) (salt) [CAS]" should read
--4H-Thieno(2,3-b)thiopyran-2-sulfonamide, 4-(ethylamino)-5,6-dihydro-6-methyl-7,7-dioxide (4S-trans) + ethyl 2-propanol, 1-[(1,1-dimethyl)amino]-3-[[4-(4-morpholinyl)-1,2,5-thiadiazol-3-yl]oxy]-, (S), (Z)-2-butenedioate (1:1) (salt) [CAS]--.

Column 113, Table 3,
Column "API Chemical Name", Row "E-1010",
"1-Azabicyclo[3.2.0]hept-2-ene-2-carboxylic acid, 6-[(1R)-1-hydroxyethyl]-3-[((3S,5S)-5-[(R)-hydroxy(3R)-3-pyrrolidinylmethyl]-3-pyrrolidinyl]thio]-4-methyl-7-oxo-, monohydrochionde, (4R,5S,6S)-[CAS]" should read
--1-Azabicyclo[3.2.0]hept-2-ene-2-carboxylic acid, 6-[(1R)-1-hydroxyethyl]-3-[((3S,5S)-5-[(R)-hydroxy(3R)-3-pyrrolidinylmethyl]-3-pyrrolidinyl]thio]-4-methyl-7-oxo-, monohydrochloride, (4R,5S,6S)- [CAS]--.

Column 113, Table 3,
Column "API Chemical Name", Row "E-2101",
"N-Ethyl-(1-[1-(2-fluorophenethyl)pipendin-4-yl]-1H-indol-6-yl)acetamide"
should read
--N-Ethyl-(1-[1-(2-fluorophenethyl)piperidin-4-yl]-1H-indol-6-yl)acetamide--.
Column "API Chemical Name", Row "E-5842",
"Pyridine, 4-(4-fluorophenyl)-1.2,3,6-tetrahydro-1-[4-(1H-1,2,4-triazol-1-yl)butyl]-, 2-hydroxy-1,2,3-propanetncarboxylate (1:1) [CAS]" should read
--Pyridine, 4-(4-fluorophenyl)-1,2,3,6-tetrahydro-1-[4-(1H-1,2,4-triazol-1-yl)butyl]-, 2-hydroxy-1,2,3-propanetricarboxylate (1:1) [CAS]--.

Column 115, Table 3,
Column "API Generic Name",
"Edetate Galcium Disodium" should read --Edetate Calcium Disodium--.

Column 116, Table 3,
Column "Example of Therapeutic Use", Row "eflucimibe",
"Hypolipaemic/Antitherosclerosis" should read
--Hypolipaemic/Antiatherosclerosis--.

Column 118, Table 3,
Column "Example of Therapeutic Use", Row "enoxacin",
"Quinolone antibacter" should read
--Quinolone antibacterial--.

Column 119, Table 3,
Column "API Chemical Name", Row "eperisone",
"1-Propanone, 1-(4-ethylphenyl)-2-methyl-3-(1-pipendinyl)- [CAS]" should read
--1-Propanone, 1-(4-ethylphenyl)-2-methyl-3-(1-piperidinyl)- [CAS]--.
Column "API Generic Name", "Epiclilin" should read --Epicillin--.
Column "API Generic Name", "Epinzole" should read --Epirizole--.
Row "Epitiostanol",

| "API Chemical Name | CAS No." |
|---|---|
| | 2363-58-8 | should read

| --API Chemical Name | CAS No.--. |
|---|---|
| | 2363-58-8 |

Column "API Chemical Name", Row "eptaplatin",
"Platinum, [(4R,5R)-2-(1-methylethyl)-1,3-dioxolane-4,5-dimethanamine-kappaN4',kappaN5][propanedioato(2-)-kappaO1,kappaO3]-, (SP-4-2)-[CAS]"
should read
--Platinum, [(4R,5R)-2-(1-methylethyl)-1,3-dioxolane-4,5-dimethanamine-kappaN4,kappaN5][propanedioato(2-)-kappaO1,kappaO3]-, (SP-4-2)- [CAS]--.

Column 119, Table 3,
Row "Eptastigmine",
    "API Chemical    CAS No."
    Name
    101246-68-8
should read
    --API Chemical    CAS No.--.
    Name
    101246-68-8

Column 121, Table 3,
Column "API Chemical Name", Row "escitalopram",
    "(5)- [CAS]" should read --(S)- [CAS]--.
Column "API Generic Name", "Etafedrine" should read --Etafedrine--.

Column 123, Table 3,
Column "API Generic Name", "Etilefnn" should read --Etilefrin--.

Column 125, Table 3,
Column "API Chemical Name", Row "exatecan",
    "10H,13H-Benzo[de]pyrano[3',4':6,7]indolizino[1,2-b]quinoline-10,13-diane, 1-
    amino-9-ethyl-5-fluoro-1,2,3,9,12,15-hexahydro-9-hydroxy-4-methyl-, (1S,9S)-,
    [CAS]" should read
    --10H,13H-Benzo[de]pyrano[3',4':6,7]indolizino[1,2-b]quinoline-10,13-dione, 1-
    amino-9-ethyl-5-fluoro-1,2,3,9,12,15-hexahydro-9-hydroxy-4-methyl-, (1S,9S)-,
    [CAS]--.

Column 125, Table 3,
Column "API Chemical Name", Row "exemestane",
    "Androsta-1,4-diene-3,17-diane, 6-methylene-[CAS]" should read
    --Androsta-1,4-diene-3,17-dione, 6-methylene- [CAS]--.
Column "API Chemical Name", Row "ezetimibe",
    "2-Azetidinone, 1-(4-fluorophenyl)-3-[(3S)-3-(4-fluorophenyl)-3-hydroxypropyl]-
    4-(4-hydroxyphenyl)-, (3R,4S)-[CAS]" should read
    --2-Azetidinone, 1-(4-fluorophenyl)-3-[(3S)-3-(4-fluorophenyl)-3-hydroxypropyl]-
    4-(4-hydroxyphenyl)-, (3R,4S)- [CAS]--.

Column 129, Table 3,
Column "API Generic Name", "Ferrous Giuconate" should read --Ferrous Gluconate--.
Column "API Chemical Name", Row "ferumoxytol",
    "Polyglucose sorbitol carboxymethyl ether-coated non-stoichiometric magnetite
       Imaging agent"
    should read
    --Polyglucose sorbitol carboxymethyl ether-coated non-stoichiometric
       magnetite--.
Column "API Chemical Name", Row "fexofenadine",
    "Benzeneacetic acid, 4-[1-hydroxy-4-[4(hydroxydiphenylmethyl)-1-
    pipendinyl]butyl]-Alpha,Alpha-dimethyl-, [CAS]" should read
    --Benzeneacetic acid, 4-[1-hydroxy-4-[4(hydroxydiphenylmethyl)-1-
    piperidinyl]butyl]-Alpha,Alpha-dimethyl-, [CAS]--.

CERTIFICATE OF CORRECTION (continued)
U.S. Pat. No. 7,790,905 B2

Column 129, Table 3,
Column "API Chemical Name", Row "fidarestat",
"Spiro(4H-1-benzopyran-4,4-imidazolidine)-2-carboxamide, 6-fluoro-2,3-dihydro-2',5'-dioxo-, (2S-cis)-, [CAS]" should read
--Spiro(4H-1-benzopyran-4,4'-imidazolidine)-2-carboxamide, 6-fluoro-2,3-dihydro-2',5'-dioxo-, (2S-cis)-, [CAS]--.

Column 131, Table 3,
Column "API Generic Name",
"Fludeoxyglucose F18" should read --Fludeoxyglucose F18--.
Column "API Chemical Name", Row "flurbiprofen",
"[1,1-Biphenyl]-4-acetic acid, 2-fluoro-Alpha-methyl-[CAS]" should read
--[1,1'-Biphenyl]-4-acetic acid, 2-fluoro-Alpha-methyl- [CAS]--.

Column 133, Table 3,
Column "API Chemical Name", Row "flutazolam",
"Oxazolo[3,2-d][1,4]benzodiazepin-6(5H)-one, 10-chloro-11b-(2-fluorophenyl)-2,3,7,11b-tetrahydro-7-(2-hydroxyethyl)-[CAS]" should read
--Oxazolo[3,2-d][1,4]benzodiazepin-6(5H)-one, 10-chloro-11b-(2-fluorophenyl)-2,3,7,11b-tetrahydro-7-(2-hydroxyethyl)- [CAS]--.

Column 135, Table 3,
Column "API Chemical Name", Row "fumagiline",
"[3R-(3Alpha,4Alpha(2R*,3R*),5β,6β(all-E)]]- [CAS]" should read
--[3R-[3Alpha,4Alpha(2R*,3R*),5ß,6ß(all-E)]]- [CAS]--.

Column 137, Table 3,
Column "API Generic Name", "Gepef rifle" should read --Gepefrine--.

Column 138, Table 3,
Column "Example of Therapeutic Use", Row "gallium nitrate",
"Osteoporosh" should read --Osteoporosis treatment--.

Column 139, Table 3,
Column "API Chemical Name", Row "gimatecan",
"dimethylethoxy)imino]methyl]-4-ethyl-4-hydroxy-1-12-dihydro-14H-pyrano[3,4':6,7]indolizino[1,2-b]quinoline-3,14(4H)-dione" should read
--(4S)-11-[(E)-[(1,1-dimethylethoxy)imino] methyl]-4-ethyl-4-hydroxy-1-12-dihydro-14H-pyrano[3',4':6,7]indolizino[1,2-b]quinoline-3,14(4H)-dione--.
Column "API Generic Name", "Giyburide" should read --Glyburide--.

Column 141, Table 3,
Column "API Generic Name", "griseofuivin" should read --griseofulvin--.
Column "API Chemical Name", Row "GYKI-16084",
"(+)-R-2-{3-[N-(2-Benzo[1,4]dioxanylmethyl)amino]-1-propyl}-3(2H)-pyndazinone hydrochloride" should read
--(+)-R-2-{3-[N-(2-Benzo[1,4]dioxanylmethyl)amino]-1-propyl}-3(2H)-pyridazinone hydrochloride--.

CERTIFICATE OF CORRECTION (continued)
U.S. Pat. No. 7,790,905 B2

Column 143, Table 3,
Column "API Generic Name", "HGP-6" should read --HGP-6^--.

Column 145, Table 3,
Column "API Generic Name",
   "Hydroxychloroquane" should read --Hydroxychloroquine--.
Column "API Chemical Name", Row "hyoscyamine",
   "benzeneacetic acid, Alpha(hydroxymethyl)-, 8-methyl-B-azabicyclo [3.2.1.]oct-3-yl ester, [3(S)-endo]," should read
   --benzeneacetic acid, Alpha(hydroxymethyl)-, 8-methyl-8-azabicyclo [3.2.1.]oct-3-yl ester, [3(S)-endo],--.
Column "API Chemical Name", Row "ibopamine",
   "Propanoic acid, 2-methyl-, 4-12-(methylamino)ethyl]-1,2-phenylene ester-[CAS]" should read
   --Propanoic acid, 2-methyl-, 4-[2-(methylamino)ethyl]-1,2-phenylene ester-[CAS]--.

Column 147, Table 3,
Column "API Chemical Name", Row "indeloxazine",
   "Morptioline" should read --Morpholine--.

Column 149, Table 3,
Column "API Chemical Name", Row "indinavir",
   "D-erythro-Pentonamide, 2,3,5-trideoxy-N-(2,3-dihydro-2-hydroxy-1H-inden-1-dimethylethyl)amino)carbonyl)-4-(3-pyridinylmethyl)-1-piperazinyl)-2-(phenylmethyl), [1S-[1Alpha(R*),2Alpha]]-, [CAS]" should read
   --D-erythro-Pentonamide, 2,3,5-trideoxy-N-(2,3-dihydro-2-hydroxy-1H-inden-1-yl)-5-(2-(((1,1-dimethylethyl)amino)carbonyl)-4-(3-pyridinylmethyl)-1-piperazinyl)-2-(phenylmethyl), [1S-[1Alpha(R*),2Alpha]]-, [CAS]--.
Column "API Chemical Name", Row "indisulam",
   "1,4-Benzenedisulfonamide, N-(3-chloro-1H-indoi-7-yl)-[CAS]"should read
   --1,4-Benzenedisulfonamide, N-(3-chloro-1H-indol-7-yl)- [CAS]--.

Column 151, Table 3,
Column "API Chemical Name", Row "irofulven",
   "Spiro[cyclopropane-1,5-[5H]inden]-7'(6'H)-one, 6'-hydroxy-2',4',6-trimethyl-, (R)-[CAS]" should read
   --Spiro[cyclopropane-1,5'-[5H]inden]-7'(6'H)-one, 6'-hydroxy-2',4',6'-trimethyl-, (R)- [CAS]--.
Column "API Chemical Name", Row "isepamicin",
   "D-Streptamine, O-6-amino-6-deoxy-Alpha-D-glucopyranosyl-(1-4)-O-[3-deoxy-4-C-methyl-3-(methylamino)-β-L-arabinopyranosyl-(1-6)1-N1-(3-amino-2-hydroxy-1-oxopropyl)-2-deoxy-, (S)- [CAS]" should read
   --D-Streptamine, O-6-amino-6-deoxy-Alpha-D-glucopyranosyl-(1-4)-O-[3-deoxy-4-C-methyl-3-(methylamino)-ß-L-arabinopyranosyl-(1-6)]-N1-(3-amino-2-hydroxy-1-oxopropyl)-2-deoxy-, (S)- [CAS]--.

CERTIFICATE OF CORRECTION (continued)
U.S. Pat. No. 7,790,905 B2

Column 152, Table 3,
Column "Example of Indication", Row "isepamicin",
  "Infection, fungal, general" should read --Infection, dermatological--.

Column 153, Table 3,
Column "API Chemical Name", Row "israpafant",
  "6H-Thieno13,2-f][1,2,4]triazolo[4,3-a][1,4]diazepine, 4-(2-chlorophenyl)-6,9-
  dimethyl-2-[2-[4-(2-methylpropyl)phenyl]ethyl]-[CAS]" should read
  --6H-Thieno[3,2-f][1,2,4]triazolo[4,3-a][1,4]diazepine, 4-(2-chlorophenyl)-6,9-
  dimethyl-2-[2-[4-(2-methylpropyl)phenyl]ethyl]-[CAS]--.

Column 155, Table 3,
Column "API Chemical Name", Row "JTV-519",
  "1,4-Benzothiazepine, 2,3,4,5-tetrahydro-7-methoxy-4-[1-oxo-3-[4-
  (phenylmethyl)-1-piperidinylipropyl]- [CAS]" should read
  --1,4-Benzothiazepine, 2,3,4,5-tetrahydro-7-methoxy-4-[1-oxo-3-[4-
  (phenylmethyl)-1-piperidinyl]propyl]- [CAS]--.
Column "API Chemical Name", Row "KCB-328",
  "Methanesulfonamide, N-[3-amino-4-[2-[[2-(3,4-dimethoxyphenyl)ethyl]
  methylamino]ethoxylphenyl]-, monohydrochloride [CAS]" should read
  --Methanesulfonamide, N-[3-amino-4-[2-[[2-(3,4-dimethoxyphenyl)ethyl]
  methylamino]ethoxy]phenyl]-, monohydrochloride [CAS]--.

Column 157, Table 3,
Column "API Generic Name", "KUL7211" should read --KUL-7211--.
Column "API Chemical Name", Row "L-758298",
  "Phosphonic acid, [3-fl(2R,3S)-2-.(.(1R)-1-[3,5-bis(trifluoromethyl)phenyl]
  ethoxy]-3-(4-fluorophenyl)-4-morpholinyl]methyl]-2,5-dihydro-5-oxo-1H-1,2,4-
  triazol-1-yl]-[CAS]" should read
  --Phosphonic acid, [3-[[(2R,3S)-2-.(.(1R)-1-[3,5-bis(trifluoromethyl)phenyl]
  ethoxy]-3-(4-fluorophenyl)-4-morpholinyl]methyl]-2,5-dihydro-5-oxo-1H-1,2,4-
  triazol-1-yl]-[CAS]--.
Column "API Chemical Name", Row "landiolol",
  "Benzenepropanoic acid, 4-[2-hydroxy-3-morpholinylcarbonyl)amino]ethyl]
  amino]propoxy]-, should read
  --Benzenepropanoic acid, 4-[2-hydroxy-3-[[2-[(4-Morpholinylcarbonyl)amino]
  ethyl]amino]propoxy]-,--.
Column "API Chemical Name", Row "laniquidar",
  "Methyl 6,11-dihydro-11-11-[2-[4-(-2-quinolylmethoxy)phenyl]ethyl]-4-
  piperidinylidene]-5H-imidazo[2,1-b][3]benzazepine-3-carboxylate" should read
  --Methyl 6,11-dihydro-11-[1-[2-[4-(-2-quinolylmethoxy)phenyl]ethyl]-4-
  piperidinylidene]-5H-imidazo[2,1-b][3]benzazepine-3-carboxylate--.

CERTIFICATE OF CORRECTION (continued)

Column 159, Table 3,
Column "API Chemical Name", Row "lasofoxifene",
"2-Naphthalenol, 5,6,7,8-tetrahydro-6-phenyl-5-(4-(2-(1-pyrrolidinyl)ethoxy)phenyl-(5R-cis)-, (5-(R*, R*))-2,3-dihydroxybutanedioate [CAS]" should read
--2-Naphthalenol, 5,6,7,8-tetrahydro-6-phenyl-5-(4-(2-(1-pyrrolidinyl)ethoxy)phenyl-(5R-cis)-, (S-(R*, R*))-2,3-dihydroxybutanedioate [CAS]--.
Column "API Chemical Name", Row "levamisole",
"Imidazo[2,1-b1thiazole, 2,3,5,6-tetrahydro-6-phenyl-, (5)-[CAS]" should read
--Imidazo[2,1-b]thiazole, 2,3,5,6-tetrahydro-6-phenyl-, (S)- [CAS]--.

Column 160, Table 3,
Column "Example of Therapeutic Use", Row "LAX-111",
"Neuroleleptic" should read --Neuroleptic--.

Column 161, Table 3,
Column "API Chemical Name", Row "levetiracetam",
"1-Pyrrolidineacetamide, Alpha-ethyl-2-oxo-, (5)-[CAS]" should read
--1-Pyrrolidineacetamide, Alpha-ethyl-2-oxo-, (S)- [CAS]--.
Column "API Chemical Name", Row "levobupivacaine",
"2-Piperidinecarboxamide, 1-butyl-N-(2,6-dimethylphenyl)-, (5)-[CAS]" should read
--2-Piperidinecarboxamide, 1-butyl-N-(2,6-dimethylphenyl)-, (S)- [CAS]--.

Column 161, Table 3,
Column "API Chemical Name", Row "levodropropizine",
"1,2-Propanediol, 3-(4-phenyl-1-piperazinyl)-, (5)-[CAS]" should read
--1,2-Propanediol, 3-(4-phenyl-1-piperazinyl)-, (S)- [CAS]--.
Column "API Chemical Name", Row "levofloxacin",
"7H-Pyrido[1,2,3-de]-1,4-benzoxazine-6-carboxylic acid, 9-fluoro-2,3-dihydro-3-methyl-10-(4-methyl-1-piperazinyl)-7-oxo-, (5)-[CAS]" should read
--7H-Pyrido[1,2,3-de]-1,4-benzoxazine-6-carboxylic acid, 9-fluoro-2,3-dihydro-3-methyl-10-(4-methyl-1-piperazinyl)-7-oxo-, (S)- [CAS]--.
Column "API Chemical Name", Row "levomoprolol",
"2-Propanol, 1-(2-methoxyphenoxy)-3-[(1-methylethyl)amino]-, (5)-[CAS]" should read
--2-Propanol, 1-(2-methoxyphenoxy)-3-[(1-methylethyl)amino]-, (S)- [CAS]--.
Column "API Chemical Name", Row "levosimendan",
"Propanedinitrile, (14-(1,4,5,6-tetrahydro-4-methyl-6-oxo-3-pyridazinyl)phenyl]hydrazono]-, (R)- [CAS]" should read
--Propanedinitrile, [[4-(1,4,5,6-tetrahydro-4-methyl-6-oxo-3-pyridazinyl)phenyl]hydrazono]-, (R)-[CAS]--.

Column 163, Table 3,
Column "API Chemical Name, Row "liranaftate",
"Garbamothioic acid" should read --Carbamothioic acid--.
Column "API Chemical Name, Row "lisinopril",
"(5)- [CAS]" should read --(S)- [CAS]--.

CERTIFICATE OF CORRECTION (continued)
U.S. Pat. No. 7,790,905 B2

Column 163, Table 3,
Column "API Chemical Name", Row "LLUAlpha",
    "S-2,7,8-Trimethyl-6-(11-carboxyethyl)-6-hydroxychroman" should read
    --S-2,7,8-Trimethyl-6-(ß-carboxyethyl)-6-hydroxychroman--.

Column 164, Table 3,
Row "lobaplatin",

| "Example of Therapeutic Use | Example of Indication" |
|---|---|
| Anticancer alkylatin | | should read

| --Example of Therapeutic Use | Example of Indication--. |
|---|---|
| Anticancer alkylating | Cancer, lung, small cell |

Column 165, Table 3,
Column "API Chemical Name", Row "loratadine",
    "1-Pipendinecarboxylic acid" should read
    --1-Piperidinecarboxylic acid--.

Column 167, Table 3,
Column "API Chemical Name", Row "lurtotecan",
    "11H-1,4-Dioxino[2,3-g]pyrano[3,4:6,7]indolizino[1,2-b]quinoline-
    9,12[8H,14H]-dione," should read
    --11H-1,4-Dioxino[2,3-g]pyrano[3',4':6,7]indolizino[1,2-b]quinoline-
    9,12[8H,14H]-dione,--.

Column 170, Table 3,
Column "Example of Indication", Row "maribavir",
"Cancer, pancreatic" should read --Infection, cytomegalovirus--.

Column 171, Table 3,
Column "API Chemical Name", Row "meluadrine",
"(R*,R*))-2,3-dihydroxybutanedjoate (1:1) (salt) [CAS]" should read
--(R*,R*))-2,3-dihydroxybutanedioate (1:1) (salt) [CAS]--.

Column 173, Table 3,
Column "API Generic Name", "mepartncin" should read --mepartricin--.
Column "API Generic Name", "Methotnmeprazine" should read --Methotrimeprazine--.

Column 175, Table 3,
Row "Methylergonovine",

| "API Chemical Name 113-42-8 | CAS No." | should read | --API Chemical Name | CAS No.-- 113-42-8 |
|---|---|---|---|---|

Column 177, Table 3,
Column "API Generic Name", "Metnzamide" should read --Metrizamide--.

Column 179, Table 3,
Column "API Chemical Name", Row "misoprostol",
"Prost-13-en-1-oic acid, 11,16-dihydro 16-methyl-9-oxo-," should read
--Prost-13-en-1-oic acid, 11,16-dihydroxy-16-methyl-9-oxo-,--.

CERTIFICATE OF CORRECTION (continued)
U.S. Pat. No. 7,790,905 B2

Column 183, Table 3,
Column "API Chemical Name", Row "mycophenolate mofetil",
"4-Hexenoic acid, 6-(1,3-dihydro-4-hydroxy-6-methoxy-7-methyl-3-oxo-5-
isobenzofuranyl)-4-methyt-," should read
--4-Hexenoic acid, 6-(1,3-dihydro-4-hydroxy-6-methoxy-7-methyl-3-oxo-5-
isobenzofuranyl)-4-methyl-,--.

Column 185, Table 3,
Column "API Chemical Name", Row "naltrexone",
"(SAlpha)-[CAS]" should read --(5Alpha)-[CAS]--.

Column 186, Table 3,
Row "NAMI",

| Example of | Example of |
| Therapeutic Use | Indication |
| Anticancer, other | | should read

| --Example of | Example of--. |
| Therapeutic Use | Indication |
| Anticancer, other | Cancer, general |

Column 187, Table 3,
Column "API Generic Name", "NGX-4016" should read --NCX-4016--.
Column "API Chemical Name", Row "nicaraven",
"3-Pyndinecarboxamide, N,N-(1-methyl-1,2-ethanediyl)bis-[CAS]" should read
--3-Pyridinecarboxamide, N,N'-(1-methyl-1,2-ethanediyl)bis- [CAS]--.

Column 189, Table 3,
Column "API Chemical Name", Row "nicorandil",
"3-Pyndinecarboxamide" should read --3-Pyridinecarboxamide--.
Column "API Chemical Name", Row "nicotine",
"Pyridine, 3-(1-methyl-2-pyrrolidinyl)-, (5)-[CAS]" should read
--Pyridine, 3-(1-methyl-2-pyrrolidinyl)-, (S)- [CAS]--.
Column "API Chemical Name", Row "niperotidine",
"[(dimethylamino)methyl]furfuryl]thio]ethyl]-2-nitro-N'-piperonyl-1,1-
ethenediamine" should read
--N-[2-[[5-[(dimethylamino)methyl]furfuryl]thio]ethyl]-2-nitro-N'-piperonyl-1,1-
ethenediamine--.

Column 191, Table 3,
Column "API Chemical Name", Row "NM-3",
"3-(2-methylcarboxymethyl)-6-methoxy-8-hydroxy-isocoumann" should read
--3-(2-methylcarboxymethyl)-6-methoxy-8-hydroxy-isocoumarin--.
Column "API Generic Name",
"N-Methylepinephnne" should read --N-Methylepinephrine--.

Column 192, Table 3,
Column "Example of Indication", Row "nitisinone",
"Cirrhosis" should read --Cirrhosis, hepatic--.

Column 193, Table 3,
Column "API Generic Name", "Norelgestramin, Ethinyl Estradial" should read
--Norelgestromin, Ethinyl Estradiol--.

CERTIFICATE OF CORRECTION (continued)
U.S. Pat. No. 7,790,905 B2

Column 193, Table 3,
Column "API Generic Name", "Norgestnenone" should read --Norgestrienone--.
Column "API Chemical Name", Row "NV-07",
 "2,4,6(1H,3H,5H)-Pyrimidinetnone, 5-ethyl-5-sec-pentyl-, 2-oxime [CAS]"
should read
 --2,4,6(1H,3H,5H)-Pyrimidinetrione, 5-ethyl-5-sec-pentyl-, 2-oxime [CAS]--.

Column 194, Table 3,
Column "Example of Therapeutic Use", Row "NS-220",
 "Hypolipaemic/Antitherosclerosis" should read
 --Hypolipaemic/Antiatherosclerosis--.

Column 195, Table 3,
Column "API Generic Name", "Octavenne" should read --Octaverine--.
Column "API Chemical Name", Row "octenidine",
 "1-Octanamine, N,N-(1,10-decanediyldi-1(4H)-pyridinyl-4-ylidene)bis-[CAS]"
should read
 --1-Octanamine, N,N'-(1,10-decanediyldi-1(4H)-pyridinyl-4-ylidene)bis- [CAS]--.
Column "API Chemical Name", Row "olmesartan medoxomil",
 "1H-Imidazole-5-carboxylic acid, 4-(1-hydroxy-1-methylethyl)-2-propyl-1-((2-
 (1H-tetrazol-5-yl)(1,1'-biphenyl)-4-yl)methyl)-," should read
 --1H-Imidazole-5-carboxylic acid, 4-(1-hydroxy-1-methylethyl)-2-propyl-1-((2'
 -(1H-tetrazol-5-yl)(1,1'-biphenyl)-4-yl)methyl)-,--.

Column 195, Table 3,
Column "API Chemical Name", Row "omiloxetine",
 "Ethanone, 2-[(3R,4S)-3-[(1,3-benzodioxol-5-yloxy)methyl]-4-(4-fluorophenyl)-
 1-piperidinyl]-1-(4-fluorophenyl)-, rel- [CAS]" should read
 --Ethanone, 2-[(3R,4S)-3-[(1,3-benzodioxol-5-yloxy)methyl]-4-(4-fluorophenyl)-
 1-piperidinyl]-1-(4-fluorophenyl)-, rel- [CAS]--.

Column 196, Table 3,
Column "Example of Therapeutic Use", Row "Omacor",
 "Hypolipaemic/Antitherosclerosis" should read
 --Hypolipaemic/Antiatherosclerosis--.

Column 197, Table 3,
Column "API Chemical Name", Row "OPC-51803",
 "(5R)-2-[1-(2-chloro-4-(1-pyrolidinyl)benzoyl)-2,3,4,5-tetrahydro-1H-1-
 benzazepin-5-yl]-N-isopropytacetamide" should read
 --(5R)-2-[1-(2-chloro-4-(1-pyrolidinyl)benzoyl)-2,3,4,5-tetrahydro-1H-1-
 benzazepin-5-yl]-N-isopropylacetamide--.
Column "API Chemical Name", Row "Org-12962",
 "Piperazine, 1-[6-chloro-5-(trifluoromethyl)-2-pyridinyl]-, monohydrochionde
 [CAS]" should read
 --Piperazine, 1-[6-chloro-5-(trifluoromethyl)-2-pyridinyl]-, monohydrochloride
 [CAS]--.

Column 197, Table 3,
Column "API Chemical Name", Row "ornoprostil",
"Prost-13-en-1-oic acid, 11,15-dihydro-17,20-dimethyl-6,9-dioxo-, methyl ester, (11Alpha,13E,15S,17S)-[CAS]" should read
--Prost-13-en-1-oic acid, 11,15-dihydroxy-17,20-dimethyl-6,9-dioxo-, methyl ester, (11Alpha,13E,15S,17S)- [CAS]--.

Column 198, Table 3,
Row "OPC-31260",

| "Example of Therapeutic Use | Example of" Indication |
|---|---|
| Unspecified | | should read

| --Example of Therapeutic Use | Example of--. Indication |
|---|---|
| Urological | Unspecified |

Column 200, Table 3,
Column "Example of Therapeutic Use", Row "oxandrolone",
"Reproductive/gonad" should read --Reproductive/gonadal, general--.

Column 201, Table 3,
Column "API Generic Name", "Oxypinocemphone" should read --Oxypinocamphone--.

Column 201, Table 3,
Column "API Chemical Name", Row "palindore",
"2(5)-, (2E)-2-butendioate (1:1)" should read
--2(S)-, (2E)-2-butendioate (1:1)--.
Column "API Chemical Name", Row "palonosetron",
"3a5-2-[(S)-1-Azabicyclo[2.2.2]oct-3-yl]-2,3,3a,4,5,6-hexahydro-1-oxo-1H-benz[de]isoquinoline hydrochloride" should read
--3aS-2-[(S)-1-Azabicyclo[2.2.2]oct-3-yl]-2,3,3a,4,5,6-hexahydro-1-oxo-1H-benz[de]isoquinoline hydrochloride--.

Column 202, Table 3,
Row "PAI inhibs",

| "Example of Therapeutic Use | Example of" Indication |
|---|---|
| Antithrombotic | | should read

| --Example of Therapeutic Use | Example of--. Indication |
|---|---|
| Antithrombotic | Thrombosis, venous |

Column 205, Table 3,
Column "API Chemical Name", Row "pentamidine",
"Benzenecarboximidamide, 4,4-[1,5-pentanediylbis(oxy)]bis-[CAS]" should read
--Benzenecarboximidamide, 4,4'-[1,5-pentanediylbis(oxy)]bis- [CAS]--.

CERTIFICATE OF CORRECTION (continued)
U.S. Pat. No. 7,790,905 B2

Column 205, Table 3,
Column "API Chemical Name", Row "peplomycin",
 "(5)-[CAS]" should read --(S)- [CAS]--.
Column "API Generic Name", "Pencyazine" should --Pericyazine--.

Column 206, Table 3,
Column "Example of Therapeutic Use", Row "pentostatin",
 "Anticancer, anticancer, antimetabolite" should read
 --Anticancer, antimetabolite--.

Column 207, Table 3,
Column "API Generic Name", "Penmethazine" should --Perimethazine--.
Column "API Chemical Name", Row "perisoxal",
 "1-Piperidineethanol, Alpha-(5-phenyl-3-isoxazolyl)-, 2-hydroxy-1,2,3-
 propanetricarboxylate (2:1) (salt) [CAS]" should read
 --1-Piperidineethanol, Alpha-(5-phenyl-3-isoxazolyl)-, 2-hydroxy-1,2,3-
 propanetricarboxylate (2:1) (salt) [CAS]--.
Column "API Generic Name", "Pertapine" should read --Perlapine--.
Column "API Generic Name", "Permethnn" should read --Permethrin--.
Column "API Generic Name", "PH-b" should read --PH-10--.
Column "API Generic Name", "Phenetunde" should read --Phencturide--.
Column "API Generic Name", "Phenglutanmide" should read --Phenglutarimide--.

Column 209, Table 3,
Column "API Generic Name", "Phenopendine" should read --Phenoperidine--.
Column "API Generic Name", "Pholednne" should read --Pholedrine--.
Column "API Generic Name", "pibaserod" should read --piboserod--.
Column "API Generic Name", "Picopenne" should read --Picoperine--.

Column 211, Table 3,
Column "API Chemical Name", Row "pimilprost",
 "Acetic acid, [2-[octahydro-5-hydroxy-6-(3-hydroxy-5-methyl-1-nonenyl)
 -2-pentalenyllethoxy]-, methyl ester, [2R-[2Alpha,3Alpha,4Alpha
 (1E,3S,5S),5β,6aAlpha]]-[CAS]" should read
 --Acetic acid, [2-[octahydro-5-hydroxy-6-(3-hydroxy-5-methyl-1-nonenyl)
 -2-pentalenyl]ethoxy]-, methyl ester,[2R-[2Alpha,3Alpha,4Alpha
 (1E,3S*,5S*),5β,6aAlpha]]- [CAS]--.
Column "API Chemical Name", Row "pioglitazone",
 "2,4-Thiazolidinedione, 5-[(4-[2-(5-ethyl-2-pyridinyl)ethoxy]phenyl]methyl[-,
 monohydrochlonde (+/-)-[CAS]" should read
 --2,4-Thiazolidinedione, 5-[[4-[2-(5-ethyl-2-pyridinyl)ethoxy]phenyl]methyl]-,
 monohydrochloride (+/-)- [CAS]--.

Column 213, Table 3,
Column "API Generic Name", "Pipenlate" should read --Piperilate--.
Column "API Generic Name", "pipenne analogues" should read --piperine analogues--.
Column "API Chemical Name", Row "pirmenol",
   "(2-Pyndinemethanol, Alpha-[3-(2,6-dimethyl-1-piperidinyl)propyl]-
   .Alpha.phenyl-, cis-(+)-[CAS]" should read
   --(2-Pyridinemethanol, Alpha-[3-(2,6-dimethyl-1-piperidinyl)propyl]-
   .Alpha.phenyl-, cis-(+)- [CAS]--.
Column "API Chemical Name", Row "piroxicam betadex",
   "(β-Cyclodextrin" should read --ß-Cyclodextrin--.
Column "API Chemical Name", Row "piroxicam cinnamate",
   "5,5-dioxide [CAS]" should read --S,S-dioxide [CAS]--.

Column 215, Table 3,
Column "API Generic Name",
   "pivampiciiiin/pivmecillinam" should read --pivampicillin/pivmecillinam--.
Column "API Chemical Name", Row "pivmecillinam",
   "[25-(2Alpha,5Alpha,6β)]-[CAS]" should read
   --[2S-(2Alpha,5Alpha,6ß)]- [CAS]--.

Column 217, Table 3,
Column "API Generic Name",
   "Potassium Pemianganate" should read --Potassium Permanganate--.
Column "API Chemical Name", Row "pramipexole",
   "(5)- [CAS]" should read --(S)- [CAS]--.

Column 218, Table 3,
Row "pratosartan",

| Example of | Example of |
| Therapeutic Use | Indication |
| Antithypertensive, | | should read

| --Example of | Example of--. |
| Therapeutic Use | Indication |
| Antihypertensive, | Hypertension, general |
| renin system | |

Column 219, Table 3,
Column "API Chemical Name", Row "pregabalin",
"Hexanoic acid, 3-(aminomethyl)-5-methyl, (5)-[CAS]" should read
--Hexanoic acid, 3-(aminomethyl)-5-methyl, (S)- [CAS]--.
Column "API Chemical Name", Row "Premarin + trimegestone",
"Estra-4,9-dien-3-one, 17-(2-hydroxy-1-oxopropyl)-1 7-methyl-, [1711 (5)]-[CAS]" should read
--Estra-4,9-dien-3-one, 17-(2-hydroxy-1-oxopropyl)-17-methyl-, [17ß (S)]-[CAS]--.

Column 221, Table 3,
Column "API Generic Name",
"propionyt L-carnitine" should read --propionyl L-carnitine--.

Column 221, Table 3,
Row "propiverine",

| "API Chemical | CAS No." |
| Name | |
| 2,2-diphenyl-2-(1-propoxy) | |
| acetic acid | 60569-19-9 |
| (1-methylpiperid-4-yl) | |
| ester54556-98-8 | |
| hydrochloride | | should read

| --API Chemical | CAS No.--. |
| Name | |
| 2,2-diphenyl-2-(1-propoxy) | 54556-98-8 |
| acetic acid | 60569-19-9 |
| (1-methylpiperid-4-yl) | |
| ester hydrochloride | |

Column "API Generic Name", "Propylhexednne" should read --Propylhexedrine--.
Column "API Chemical Name", Row "proxigermanium",
"Propanoic acid, 3,3-(1,3-dioxo-1,3-digermoxanediyl)bis-[CAS]" should read
--Propanoic acid, 3,3'-(1,3-dioxo-1,3-digermoxanediyl)bis- [CAS]--.

CERTIFICATE OF CORRECTION (continued)
U.S. Pat. No. 7,790,905 B2

Column 223, Table 3,
Column "API Chemical Name", Row "pseudoephedrine + triprolidine",
 "mixt. with (E)-2-[1-(4-methylphenyl)-3-(1-pyrrolidinyl)-1-propenylipynidine monohydrochloride [CAS]" should read
 --mixt. with (E)-2-[1-(4-methylphenyl)-3-(1-pyrrolidinyl)-1-propenyl]pyridine monohydrochloride [CAS]--.
Column "CAS No.", Row "pseudoephedrine",
 "90-82-4, 8054-271, 345-78-8" should read --90-82-4, 8054-27-1, 345-78-8--.
Row "PX-12",

| API Generic Name | API Chemical Name |
|---|---|
| PX-12 | 1-Methylpropyl 2-mercaptoimidazolyl disulfide | should read

| --API Generic Name | API Chemical Name--. |
|---|---|
| PX-12 | 1-Methylpropyl 2-mercaptoimidazolyl disulfide |

Column "API Generic Name", "Pynthione" should read --Pyrithione--.
Column "API Generic Name", "Pyronandine" should read --Pyronaridine--.
Column "API Generic Name", "Pyrrolnitnn" should read --Pyrrolnitrin--.

Column 223, Table 3,
Column "API Chemical Name", Row "quetiapine",
 "Ethanol, 2-[2-(4-dibenzo[b,f][1,4]thiazepin-11-yl-1-piperazinyt)ethoxy]-, (E)-2-butenedloate (2:1) (salt) [CAS]" should read
 --Ethanol, 2-[2-(4-dibenzo[b,f][1,4]thiazepin-11-yl-1-piperazinyl)ethoxy]-, (E)-2-butenedioate (2:1) (salt) [CAS]--.
Column "API Generic Name", "quinacnne" should read --quinacrine--.

Column 224, Table 3,
Column "Example of Indication", Row "quinacrine",
 "Creutzfeidt-Jakob disease" should read --Creutzfeldt-Jakob disease--.

Column 225, Table 3,
Column "API Chemical Name", Row "quinaprilat",
 "3-Isoquinolinecarboxylic acid, 2-[2-[(1-carboxy-3-phenylpropyl)amino]-1-oxopropyl]-1,2,3,4-tetrahydro-, [35-[2[R*(R*)],3R*]]-[CAS]" should read
 --3-Isoquinolinecarboxylic acid, 2-[2-[(1-carboxy-3-phenylpropyl)amino]-1-oxopropyl]-1,2,3,4-tetrahydro-, [3S-[2[R*(R*)],3R*]]- [CAS]--.
Column "API Chemical Name", Row "ramipril",
 "Cyclopenta[b]pyrrole-2-carboxylic acid, 1-[2-[[1-(ethoxycarbonyl)-3-phenylpropyl]amino]-1-oxopropytloctahydro-, [2S-[1[R*(R)],2Alpha,3aβ,6aβ]]-[CAS]" should read
 --Cyclopenta[b]pyrrole-2-carboxylic acid, 1-[2-[[1-(ethoxycarbonyl)-3-phenyl propyl]amino]-1-oxopropyl]octahydro-, [2S-[1[R*(R*)],2Alpha,3aß,6aß]]-[CAS]--.

CERTIFICATE OF CORRECTION (continued)
U.S. Pat. No. 7,790,905 B2

Column 225, Table 3,
Column "API Chemical Name", Row "ranitidine",
"1,1-Ethenediamine, N-[2-([[5-[(dimethylamino)methyl]-2-furanyl]methyl]thio]
ethyl]-N'-methyl-2-nitro-[CAS]" should read
--1,1-Ethenediamine, N-[2-[[[5-[(dimethylamino)methyl]-2-furanyl]methyl]thio]
ethyl]-N'-methyl-2-nitro- [CAS]--.
Column "API Chemical Name", Row "ranolazine",
"1-Piperazineacetamide, N-(2,6-dimethylphenyl)-4-(2-hydroxy-3-(2-
methoxyphenoxy)propyl]-, (+/-)-[CAS]" should read
--1-Piperazineacetamide, N-(2,6-dimethylphenyl)-4-[2-hydroxy-3-(2-
methoxyphenoxy)propyl]-, (+/-)- [CAS]--.

Column 227, Table 3,
Column "API Generic Name", "raxofeiast" should read --raxofelast--.
Column "API Chemical Name", Row "repaglinide",
"Benzoic acid, 2-ethoxy-4-[2-[[3-methyl-1-[2-(1-piperidinyl)phenyl]butyl]
amino]-2-oxoethyl]-, (S)-[CAS]" should read
--Benzoic acid, 2-ethoxy-4-[2-[[3-methyl-1-[2-(1-piperidinyl)phenyl]butyl]
amino]-2-oxoethyl]-, (S)- [CAS]--.
Column "API Chemical Name", Row "R-flurbiprofen",
"[1,1-Biphenyl]-4-acetic acid, 2-fluoro-Alpha-methyl" should read
--[1,1'-Biphenyl]-4-acetic acid, 2-fluoro-Alpha-methyl--.

Column 227, Table 3,
Column "API Generic Name",
"Rho (D) Immune Globuhn (Human)" should read
--Rho (D) Immune Globulin (Human)--.
Column "API Chemical Name", Row "rifaximin",
"[2S-(2R*,16Z,18E,20R*,22S*,23S*,24S*,25R*,26S*,27R*,28E)]" should read
--[2S-(2R*,16Z,18E,20R*,22S*,23S*,24S*,25R*,26S*,27R*,28E)]--.

Column 231, Table 3,
Column "API Chemical Name", Row "ropivacaine",
"2-Piperidinecarboxamide, N-(2,6-dimethylphenyl)-1-propyl-, (S)-[CAS]"
should read
--2-Piperidinecarboxamide, N-(2,6-dimethylphenyl)-1-propyl-, (S)- [CAS]--.
Column "API Chemical Name", Row "rotigotine",
"1-Naphthalenol, 5,6,7,8-tetrahydro-6-[propyl[2-(2-thienyl)ethyl]amino]-, (S)-
[CAS]" should read
--1-Naphthalenol, 5,6,7,8-tetrahydro-6-[propyl[2-(2-thienyl)ethyl]amino]-, (S)-
[CAS]--.

Column 233, Table 3,
Column "API Chemical Name", Row "rubitecan",
"1H-Pyrano(3',4':6,7)indoiizino(1,2-b)quinoline-3,14(4H,12H)-dione, 4-ethyl-4-
hydroxy-10-nitro-, (S)-[CAS]" should read
--1H-Pyrano(3',4':6,7)indolizino(1,2-b)quinoline-3,14(4H,12H)-dione, 4-ethyl-4-
hydroxy-10-nitro-, (S)- [CAS]--.

Column 235, Table 3,
Column "API Chemical Name", Row "saquinavir",
"Butanediamide, N1-[3-[3-[[(1,1-dimethylethyl)amino]carbonyl]octahydro-
2(1H)-isoquinolinyl]-2-hydroxy-1-(phenylmethyl)propyl]-2-[(2-
quinolinylcarbonyl)amino]-, [3S-[CAS]" should read
--Butanediamide, N1-[3-[3-[[(1,1-dimethylethyl)amino]carbonyl]octahydro-
2(1H)-isoquinolinyl]-2-hydroxy-1-(phenylmethyl)propyl]-2-[(2-
quinolinylcarbonyl)amino]-, [3S-[2[1R*(R*),2S*],3Alpha,4aß,8aß]]- [CAS]--.

Column 237, Table 3,
Column "API Chemical Name", Row "Sch-63390",
"7H-Pyrazolo[4,3-e][1,2,4]tnazolo[1,5-c]pyrimidin-5-amine, 2-(2-furanyl)-7-(3-
phenylpropyl)-[CAS]" should read
--7H-Pyrazolo[4,3-e][1,2,4]triazolo[1,5-c]pyrimidin-5-amine, 2-(2-furanyl)-7-(3-
phenylpropyl)- [CAS]--.
Column "API Generic Name", "SGS technology" should read --SCS technology--.

Column 237, Table 3,
Row "seratrodast",

| "API Chemical Name | CAS No." |
|---|---|
| Benzeneheptanoic acid, | 1103187-07-1 |
| zeta-(2,4,5-trimethyl-3,6- | 112665-43-7 |
| dioxo-1,4-cyclohexadien- | |
| -yl)-, (+/-)-[CAS] | | should read

| --API Chemical Name | CAS No.--. |
|---|---|
| Benzeneheptanoic acid, | 103187-07-1 |
| zeta-(2,4,5-trimethyl-3,6- | 112665-43-7 |
| dioxo-1,4-cyclohexadien- | |
| 1-yl)-, (+/-)- [CAS] | |

Column "API Chemical Name", Row "sertindole",
"2-Imidazolidinone, 1-[2-[4-[5-chloro-1-(4-fluorophenyl)-1H-indol-3-yl]-1-
pipendinyl]ethyl]-[CAS]" should read
--2-Imidazolidinone, 1-[2-[4-[5-chloro-1-(4-fluorophenyl)-1H-indol-3-yl]-1-
piperidinyl]ethyl]- [CAS]--.

Column 240, Table 3,
Column "Example of Therapeutic Use", Row "silver sulfadiazine",
"Anti-infective" should read --Anti-infective, other--.

CERTIFICATE OF CORRECTION (continued)
U.S. Pat. No. 7,790,905 B2

Column 239, Table 3,
Column "API Chemical Name", Row "sivelestat",
"Glycine, N-[2-D[4-(2,2-dimethyl-1-oxopropoxy)phenyl]sulfonyl]amino]
benzoyl]-[CAS]" should read
--Glycine, N-[2-[[[4-(2,2-dimethyl-1-oxopropoxy)phenyl]sulfonyl]amino]
benzoyl]- [CAS]--.

Column 241, Table 3,
Column "API Chemical Name", Row "SN-38",
"(4S)-4,7,11-tnethyl-3,4,12,14-tetrahydro-4, 10-dihydroxy-3,14-dioxo-1H-
pyrano[3',4':6,7]indolizino[1,2-b]quindin-9-yl" should read
--(4S)-4,7,11-triethyl-3,4,12,14-tetrahydro-4,10-dihydroxy-3,14-dioxo-1H-
pyrano[3',4':6,7]indolizino[1,2-b]quindin-9-yl--.
Column "API Chemical Name", Row "soblidotin",
"L-valinamide, N,N-dimethyl-L-valyl-N-[2-methoxy-4-L2-[1-methoxy-2-
methyl-3-oxo-3-[(2-phenylethyl)amino]propyl]-1-pyrrolidinyl]-1-(2-
methylpropyl)-4-oxobutyl]-N-methyl-, [2S-[1[1R*(R*),2S*],2R*(1S*,2S*)]]-
[CAS]" should read
--L-valinamide, N,N-dimethyl-L-valyl-N-[2-methoxy-4-[2-[1-methoxy-2-methyl-
3-oxo-3-[(2-phenylethyl)amino]propyl]-1-pyrrolidinyl]-1-(2-methylpropyl)-4-
oxobutyl]-N-methyl-, [2S-[1[1R*(R*),2S*],2R*(1S*,2S*)]]- [CAS]--.
Column "API Chemical Name", Row "sodium oxybate",
"Butync acid" should read --Butyric acid--.
Column "API Chemical Name", Row "sodium prasterone sulfate",
"3B-hydroxy-5-androsten-17-one(sodium sulfate dihydrate)" should read
--3ß-hydroxy-5-androsten-17-one(sodium sulfate dihydrate)--.

Column 241, Table 3,
Column "API Chemical Name", Row "sofalcone",
"Acetic acid, [5-((3-methyl-2-butenyl)oxy]-2-[3-[4-[(3-methyl-2-butenyl)oxy]phenyl]-1-oxo-2-propenyliphcnoxy]-[CAS]" should read
--Acetic acid, [5-[(3-methyl-2-butenyl)oxy]-2-[3-[4-[(3-methyl-2-butenyl)oxy]phenyl]-1-oxo-2-propenyl|phcnoxy]- [CAS]--.

Column 243, Table 3,
Column "API Chemical Name", Row "SR-146131",
"1H-Indole-1-acetic acid, 2-[[[4-(4-chloro-2,5-dimethoxyphenyl)-5-(2-cyclohexytethyl)-2-thiazolyl]amino]carbonyl]-5,7-dimethyl- [CAS]" should read
--1H-Indole-1-acetic acid, 2-[[[4-(4-chloro-2,5-dimethoxyphenyl)-5-(2-cyclohexylethyl)-2-thiazolyl|amino]carbonyl]-5,7-dimethyl- [CAS]--.
Column "API Chemical Name", Row "ß-alethine",
"Propanamide, N, N(dithiodi-2,1-ethanediyl)bis(3-amino)-[CAS]" should read
--Propanamide, N, N'(dithiodi-2,1-ethanediyl)bis(3-amino)- [CAS]--.

Column 245, Table 3,
Column "API Generic Name", "Stiibamidine" should read --Stilbamidine--.

Column 247, Table 3,
Column "API Chemical Name", Row "sufentanil",
"Propanamide, N-[4-(methoxymethyl)-1-[2-(2-thienyl)ethyl]-4-pipendinyl]-N-phenyl-[CAS]" should read
--Propanamide, N-[4-(methoxymethyl)-1-[2-(2-thienyl)ethyl]-4-piperidinyl]-N-phenyl- [CAS]--.

CERTIFICATE OF CORRECTION (continued)
U.S. Pat. No. 7,790,905 B2

Column 247, Table 3,
Column "API Chemical Name", Row "sulbenicillin",
    "4-Thia-1-azabicyclo[3.2.0]heptane-2-carboxylic acid, 3,3-dimethyl-7-oxo-6-
    [(phenylsulfoacetyl)amino]-, [2S-[2Alpha,5Alpha,6a(S*)]]-[CAS]"
should read
    --4-Thia-1-azabicyclo[3.2.0]heptane-2-carboxylic acid, 3,3-dimethyl-7-oxo-6-
    [(phenylsulfoacetyl)amino]-, [2S-[2Alpha,5Alpha,6ß(S*)]]- [CAS]--.
Column "API Generic Name", "Sutfaguanole" should read --Sulfaguanole--.
Column "API Generic Name", "Sutfapyndine" should read --Sulfapyridine--.

Column 249, Table 3,
Column "API Chemical Name", Row "sultamicillin",
    "5, 5-dioxide," should read --S, S-dioxide,--.
Column "API Chemical Name", Row "sultopride",
    "Benzamide, N-((1-ethyl-2-pyrrolidinyl)methyl]-5-(ethylsulfonyl)-2-methoxy-
    [CAS]" should read
    --Benzamide, N-[(1-ethyl-2-pyrrolidinyl)methyl]-5-(ethylsulfonyl)-2-methoxy-
    [CAS]--.

Column 251, Table 3,
Column "API Chemical Name", Row "T-1095",
    "1-Propanone, 3-(5-benzofuranyl)-1-(2-hydroxy-6-((6-O-methoxycarbonyl)-B-D-
    glucopyranosyl)oxy)-4-methylphenyl- [CAS]" should read
    --1-Propanone, 3-(5-benzofuranyl)-1-(2-hydroxy-6-((6-O-methoxycarbonyl)-ß-D-
    glucopyranosyl)oxy)-4-methylphenyl- [CAS]--.

Column 251, Table 3,
Column "API Chemical Name", Row "T-1249",
    "L-Phenylalaninamide, N-acetyl-L-tryptophyl-L-glutaminyl-L-Alpha-glutamyl-L-
    tryptophyl-L-Alpha-glutamyl-L-glutaminyl-L-lysyl-L-isoleucyl-L-threonyl-L-
    alanyl-L-leucyl-L-leucyl-L-Alpha-glutamyt-L-glutaminyl-L-alanyl-L-glutaminyl-
    L-isoleucyl-L-glutaminyl-L-glutaminyl-L-Alpha-glutamyl-L-lysyl-L-Alpha-
    glutamyl-asparaginyl-L-tyrosyl-L-Alpha-glutamyl-L-leucyl-L-glutaminyl-L-
    lysyl-L-leucyl-L-Alpha-aspartyl-L-lysyl-l-trytophyl-L-ananyl-L-seryl-L-leucyl-L-
    trytophyl-L-Alpha-glutamyl-L-tryptophyl [CAS]"
should read
    --L-Phenylalaninamide, N-acetyl-L-tryptophyl-L-glutaminyl-L-Alpha-glutamyl-
    L-tryptophyl-L-Alpha-glutamyl-L-glutaminyl-L-lysyl-L-isoleucyl-L-threonyl-L-
    alanyl-L-leucyl-L-leucyl-L-Alpha-glutamyl-L-glutaminyl-L-alanyl-L-glutaminyl-
    L-isoleucyl-L-glutaminyl-L-glutaminyl-L-Alpha-glutamyl-L-lysyl-L-Alpha-
    glutamyl-asparaginyl-L-tyrosyl-L-Alpha-glutamyl-L-leucyl-L-glutaminyl-L-
    lysyl-L-leucyl-L-Alpha-aspartyl-L-lysyl-l-trytophyl-L-ananyl-L-scryl-L-leucyl-L-
    trytophyl-L-Alpha-glutamyl-L-tryptophyl- [CAS]--.
Column "API Chemical Name", Row "TA-2005",
    "2(1H)-Quinolinone, 8-hydroxy-5-[1-hydraxy-2-[[2-(4-methoxyphenyl)-1-
    methylethyl]amina]ethyl]-, manahydrochlaride, [R-(R*,R*)]-[CAS]" should read
    --2(1H)-Quinolinone, 8-hydroxy-5-[1-hydroxy-2-[[2-(4-methoxyphenyl)-1-
    methylethyl]amino]ethyl]-, monohydrochloride, [R-(R*,R*)]- [CAS]--.

CERTIFICATE OF CORRECTION (continued)
U.S. Pat. No. 7,790,905 B2

Column 251, Table 3,
Column "API Chemical Name", Row "TA-993",
"1,5-Benzothiazepin-4(5H)-one, 3-(acetyloxy)-5-[2-(dimethylamino)ethyl]-2,3-dihydra-8-methyl-2-(4-methylphenyl)-, (2R,3R)-rel-(-)-, (2Z)-2-butenedioate [CAS]" should read
--1,5-Benzothiazepin-4(5H)-one, 3-(acetyloxy)-5-[2-(dimethylamino)ethyl]-2,3-dihydro-8-methyl-2-(4-methylphenyl)-, (2R,3R)-rel-(-)-, (2Z)-2-butenedioate [CAS]--.

Column "API Chemical Name", Row "tacalcitol",
"9,10-Secachalesta-5,7,10(19)-triene-1,3,24-trial, (1Alpha,3β,5Z,7E,24R)-[CAS]" should read
--9,10-Secocholesta-5,7,10(19)-triene-1,3,24-triol, (1Alpha,3β,5Z,7E,24R)-[CAS]--.

Column "API Chemical Name", Row "tacedinaline",
"Benzamide, 4-(acetylamina)-N-(2-aminophenyl)-[CAS]" should read
--Benzamide, 4-(acetylamino)-N-(2-aminophenyl)- [CAS]--.

Column "API Generic Name", "Tacralimus" should read --Tacrolimus--.

Column "API Chemical Name", Row "tadalafil",
"Pyrazina(1',2':1,6)pyrida(3,4-b)indole1,4-dione, 6-(1,3-benzodiaxal-5-yl)-2,3,6,7,12,12a-hexahydro-2-methyl-, (6R-trans) [CAS]" should read
--Pyrazino(1',2':1,6)pyrido(3,4-b)indole1,4-dione, 6-(1,3-benzodioxol-5-yl)-2,3,6,7,12,12a-hexahydro-2-methyl-, (6R-trans) [CAS]--.

Column 251, Table 3,
Column "API Chemical Name", Row "tafenoquine",
"1,4-Pentanediamine, N4-[2,6-dimethaxy-4-methyl-5-[3-(trifluaramethyl)phenoxy]-8-quinalinyl]- [CAS]" should read
--1,4-Pentanediamine, N4-[2,6-dimethoxy-4-methyl-5-[3-(trifluoromethyl)phenoxy]-8-quinolinyl]- [CAS]--.

Column "API Generic Name", "taflupaside" should read --tafluposide--.

Column "API Chemical Name", Row "TAK-375",
"(S)-N-[2-(1,6,7,8-Tetrahydro-2H-indeno-[5,4-bifuran-8-yl)]propionamide" should read
--(S)-N-[2-(1,6,7,8-Tetrahydro-2H-indeno-[5,4-b]furan-8-yl)]propionamide--.

Column 253, Table 3,
Column "API Chemical Name", Row "taltirelin",
"L-Prolinamide, N-[(hexahydro-1-methyl-2,6-dioxo-4-pynmidinyl)carbonyl]-L-histidyl-, (S)-[CAS]" should read
--L-Prolinamide, N-[(hexahydro-1-methyl-2,6-dioxo-4-pyrimidinyl)carbonyl]-L-histidyl-, (S)- [CAS]--.

Column "API Chemical Name", Row "tamsulosin",
"Benzenesulfonamide, 5-12-[[2-(2-ethoxyphenoxy)ethyl]amino]propyl]-2-methoxy-, (R)-[CAS]" should read
--Benzenesulfonamide, 5-[2-[[2-(2-ethoxyphenoxy)ethyl]amino]propyl]-2-methoxy-, (R)- [CAS]--.

Column 253, Table 3,
Column "API Chemical Name", Row "tecastemizole",
"1H-Benzimidazol-2-amine, 1-((4-fluorophenyl)methyl)-N-4-pipendinyl- [CAS]"
should read
--1H-Benzimidazol-2-amine, 1-((4-fluorophenyl)methyl)-N-4-piperidinyl-
[CAS]--.

Column 254, Table 3,
Column "Example of Therapeutic Use", Row "talaporfin",
"Radia/chemosensitizer" should read --Radio/chemosensitizer--.

Column 255, Table 3,
Column "API Chemical Name", Row "tedisamil",
"Spirolcyclopentane-1,9-[3,7]diazabicyclo[3.3.1]nonane],
3',7'-bis(cyclopropylmethyl)-[CAS]" should read
--Spiro[cyclopentane-1,9'-[3,7]diazabicyclo[3.3.1]nonane],
3',7'-bis(cyclopropylmethyl)- [CAS]--.
Column "API Chemical Name", Row "telbivudine",
"β-L-2-deoxythymidine" should read --ß-L-2'-deoxythymidine--.
Column "API Chemical Name", Row "telmisartan",
"(1,1-Biphenyl)-2-carboxylic acid" should read
--(1,1'-Biphenyl)-2-carboxylic acid--.

Column 255, Table 3,
Column "API Chemical Name", Row "tenatoprazole",
"1H-Imidazo(4,5-b)pyndine" should read --1H-Imidazo(4,5-b)pyridine--.
Column "API Chemical Name", Row "teniposide",
"Furo[3',4':6,7]naphthol2,3-d]-1,3-dioxol-6(5aH)-one, 5,8,8a,9-tetrahydro-5-(4-
hydroxy-3,5-dimethoxyphenyl)-9-[[4,6-O-(2-thienylmethylene)-β-D-
glucopyranosylloxy]-, [5R-[5Alpha,5aβ,8aAlpha,9β(R*)]]-[CAS]" should read
--Furo[3',4':6,7]naphtho[2,3-d]-1,3-dioxol-6(5aH)-one, 5,8,8a,9-tetrahydro-5-(4-
hydroxy-3,5-dimethoxyphenyl)-9-[[4,6-O-(2-thienylmethylene)-ß-D-
glucopyranosyl]oxy]-, [5R-[5Alpha,5aß,8aAlpha,9ß(R*)]]- [CAS]--.

Column 257, Table 3,
Column "API Chemical Name", Row "terfenadine",
"1-Pipendinebutanol, Alpha-[4-(1,1-dimethylethyl)phenyl]-4-
(hydroxydiphenylmethyl)-[CAS]" should read
--1-Piperidinebutanol, Alpha-[4-(1,1-dimethylethyl)phenyl]-4-
(hydroxydiphenylmethyl)- [CAS]--.
Column "API Chemical Name", Row "terguride",
"Urea, N,N-diethyl-N-[(8Alpha)-6-methylergolin-8-yl]-[CAS]" should read
--Urea, N,N-diethyl-N'-[(8Alpha)-6-methylergolin-8-yl]- [CAS]--.

Column 259, Table 3,
Column "API Generic Name", "thiacymsenne" should read --thiacymserine--.
Column "CAS No.", Row "Thimerfonate", "5964249" should read --5964-24-9--.
Column "API Generic Name", "Tiadenoi" should read --Tiadenol--.

CERTIFICATE OF CORRECTION (continued)

Column 259, Table 3,
Column "API Chemical Name", Row "tianeptine",
"5,5-dioxide [CAS]" should read --S,S-dioxide [CAS]--.

Column 261, Table 3,
Column "API Generic Name", "Tinondine" should read --Tinoridine--.

Column 265, Table 3,
Column "API Chemical Name", Row "travoprost",
"1-methylethylester (1R(1Alpha(Z),2B(1E,3R*),3Alpha,5Alpha) [CAS]"
should read
--1-methylethylester (1R(1Alpha(Z),2ß(1E,3R*),3Alpha,5Alpha) [CAS]--.
Column "API Chemical Name", Row "trazodone",
"1,2,4-Triazolo[4,3-a]pyridin-3(2H)-one, 2-[3-[4-(3-chlorophenyl)-1-
piperazinylipropyl]- [CAS]" should read
--1,2,4-Triazolo[4,3-a]pyridin-3(2H)-one, 2-[3-[4-(3-chlorophenyl)-1-
piperazinyl]propyl]- [CAS]--.

Column 269, Table 3,
Column "API Chemical Name", Row "trimipramine",
"5H-Dibenz[b,f]azepine-5-propanamine, 10,11-dihydro-N,N,t1-trimethyl-, (Z)-2-
butenedioate (1:1) [CAS]" should read
--5H-Dibenz[b,f]azepine-5-propanamine, 10,11-dihydro-N,N,ß-trimethyl-, (Z)-2-
butenedioate (1:1) [CAS]--.

Column 269, Table 3,
Column "API Chemical Name", Row "trofosfamide",
"3-2-(chloroethyl)-2-[bis(2-chloroethyl)amino]tetrahydro-2H-1,3,2-
oxazaphosphonn 2-oxide" should read
--3-2-(chloroethyl)-2-[bis(2-chloroethyl)amino]tetrahydro-2H-1,3,2-
oxazaphosphorin 2-oxide--.

Column 271, Table 3,
Row "Valnoctamide",
    "API Chemical    CAS No."
    Name
    4171-13-5
should read
    --API Chemical    CAS No.--.
    Name    4171-13-5

Column 271, Table 3,
Column "API Generic Name", "Vaiproic Acid" should read --Valproic Acid--.

Column 272, Table 3,
Row "tyloxapol",

"Example of           Example of
    Therapeutic Use      Indication
    Formulation, inhalable,
    topical should read --Example of          Example of--.
    Therapeutic Use      Indication
    Formulation, inhalable,    Cystic fibrosis
    topical Column 273, Table 3,
Column "API Chemical Name", Row "vecuronium",
    "Piperidinium, 1-bis(acetyloxy)-2-(1-piperidinyl)androstan-1 6-yl]-1-methyl-, [CAS]" should read
    --Piperidinium, 1-[(2ß,3Alpha,5Alpha,16ß,17ß)-3,17-bis(acetyloxy)-2-(1-piperidinyl)androstan-16-yl]-1-methyl-, [CAS]--.
Column "API Chemical Name", Row "venlafaxine",
    "Gyclohexanol, 1-[2-(dimethylamino)-1-(4-methoxyphenyl)ethyl]-, [CAS]"
should read
    --Cyclohexanol, 1-[2-(dimethylamino)-1-(4-methoxyphenyl)ethyl]-, [CAS]--.

Column 275, Table 3,
Column "API Chemical Name", Row "vinorelbine",
    "C'-Norvincaleukoblastine, 3,4'-didehydro-4'-deoxy-[CAS]" should read
    --C'-Norvincaleukoblastine, 3',4'-didehydro-4'-deoxy- [CAS]--.

Column 275, Table 3,
Column "API Chemical Name", Row "vinpocetine",
    "Eburnamenine-14-carboxylic acid, ethyl ester, (3Alpha,16Alpha)-[CAS]"
should read
    --Eburnamenine-14-carboxylic acid, ethyl ester, (3Alpha,16Alpha)- [CAS]--.
Column "API Generic Name", "vonconazole" should read --voriconazole--.

Column 277, Table 3,
Column "API Generic Name", "Yahimbine" should read --Yohimbine--.

Column 278, Table 3,
Row "YT-146",

"Example of           Example of
    Therapeutic Use      Indication
    Anti-inflammation,
    general should read --Example of          Example of--.
    Therapeutic Use      Indication
    Anti-inflammatory     Inflammation, general Column 280, Table 3,
Row "zinc acetate",

| "Example of Therapeutic Use | Example of" Indication |
|---|---|
| Antiviral, other | virus prophylaxis | should read

| --Example of Therapeutic Use | Example of--. Indication |
|---|---|
| Antiviral, other | Infection, herpes simplex virus prophylaxis |

Column 279, Table 3,
Column "API Chemical Name", Row "zolmitriptan",
"(5)-[CAS]" should read --(S)- [CAS]--.